(12) United States Patent
Logtenberg et al.

(10) Patent No.: US 9,951,124 B2
(45) Date of Patent: *Apr. 24, 2018

(54) ANTIBODY PRODUCING NON-HUMAN MAMMALS

(71) Applicant: MERUS N.V., Utrecht (NL)

(72) Inventors: Ton Logtenberg, Utrecht (NL); Rui Daniel Pinto, Utrecht (NL); Erwin Houtzager, Zeist (NL)

(73) Assignee: MERUS N.V., Utrecht (NL)

( * ) Notice: Subject to any disclaimer, the term of this patent is extended or adjusted under 35 U.S.C. 154(b) by 175 days.

This patent is subject to a terminal disclaimer.

(21) Appl. No.: 13/750,753

(22) Filed: Jan. 25, 2013

(65) Prior Publication Data
US 2013/0145484 A1 Jun. 6, 2013

Related U.S. Application Data

(63) Continuation of application No. 12/589,181, filed on Oct. 19, 2009, which is a continuation of application No. 12/459,285, filed on Jun. 29, 2009, now abandoned.

(60) Provisional application No. 61/133,274, filed on Jun. 27, 2008.

(51) Int. Cl.
*A01K 67/027* (2006.01)
*C12P 21/08* (2006.01)
*C07K 16/12* (2006.01)
*C07K 14/47* (2006.01)
*C07K 16/24* (2006.01)
*C12N 15/85* (2006.01)
*C12P 21/00* (2006.01)

(52) U.S. Cl.
CPC ........ *C07K 16/1282* (2013.01); *A01K 67/027* (2013.01); *A01K 67/0278* (2013.01); *C07K 14/47* (2013.01); *C07K 16/248* (2013.01); *C12N 15/8509* (2013.01); *C12P 21/00* (2013.01); *A01K 2207/15* (2013.01); *A01K 2217/052* (2013.01); *A01K 2217/075* (2013.01); *A01K 2217/15* (2013.01); *A01K 2217/206* (2013.01); *A01K 2227/105* (2013.01); *A01K 2267/01* (2013.01); *C07K 2317/24* (2013.01)

(58) Field of Classification Search
CPC .......... A01K 67/0278; A01K 2227/105; A01K 2267/01; A01K 67/027; A01K 67/0275
USPC ................................. 800/18, 13, 6
See application file for complete search history.

(56) References Cited

U.S. PATENT DOCUMENTS

| 5,565,332 | A | 10/1996 | Hoogenboom et al. |
|---|---|---|---|
| 5,614,396 | A | 3/1997 | Bradley et al. |
| 5,770,429 | A | 6/1998 | Lonberg et al. |
| 5,789,215 | A | 8/1998 | Berns et al. |
| 5,939,598 | A | 8/1999 | Kycherlapati et al. |
| 6,069,010 | A | 5/2000 | Choi |
| 6,114,598 | A | 9/2000 | Kucherlapati et al. |
| 6,596,541 | B2 | 7/2003 | Murphy et al. |
| 7,105,348 | B2 | 9/2006 | Murphy et al. |
| 7,262,028 | B2 | 8/2007 | Van Berkel et al. |
| 7,329,530 | B2 | 2/2008 | Houtzager et al. |
| 7,429,486 | B2 | 9/2008 | Van Berkel et al. |
| 7,579,446 | B2 | 8/2009 | Bakker et al. |
| 7,696,330 | B2 | 4/2010 | ter Meulen et al. |
| 7,740,852 | B2 | 6/2010 | Bakker et al. |
| 7,777,010 | B2 | 8/2010 | Logtenberg |
| 7,858,086 | B2 | 12/2010 | Geuijen et al. |
| 7,901,919 | B2 | 3/2011 | Houtzager et al. |
| 7,919,257 | B2 | 4/2011 | Hoogenboom et al. |
| 7,927,834 | B2 | 4/2011 | Van Berkel et al. |
| 7,932,360 | B2 | 4/2011 | Van Berkel et al. |
| 7,960,518 | B2 | 6/2011 | Throsby et al. |
| 7,968,092 | B2 | 6/2011 | Throsby et al. |
| 8,052,974 | B2 | 11/2011 | Throsby et al. |
| 8,106,170 | B2 | 1/2012 | ter Meulen et al. |
| 8,148,497 | B2 | 4/2012 | Bakker et al. |
| 8,192,927 | B2 | 6/2012 | van den Brink et al. |
| 8,211,431 | B2 | 7/2012 | Throsby et al. |
| 8,241,631 | B2 | 8/2012 | Throsby et al. |
| 8,268,756 | B2 | 9/2012 | Logtenberg et al. |
| 8,502,018 | B2 | 8/2013 | Murphy et al. |

(Continued)

FOREIGN PATENT DOCUMENTS

EP 0 814 159 8/1991
EP 0 469 025 8/1995

(Continued)

OTHER PUBLICATIONS de Wildt et al. (1999) J. Mol. Biol., vol. 285, 895-901.*

(Continued)

*Primary Examiner* — Anne Marie S Wehbe
(74) *Attorney, Agent, or Firm* — Morrison & Foerster LLP

(57) ABSTRACT

Described are transgenic, non-human animals comprising a nucleic acid encoding an immunoglobulin light chain, whereby the immunoglobulin light chain is human, human-like, or humanized. The nucleic acid is provided with a means that renders it resistant to DNA rearrangements and/or somatic hypermutations. In one embodiment, the nucleic acid comprises an expression cassette for the expression of a desired molecule in cells during a certain stage of development in cells developing into mature B cells. Further provided is methods for producing an immunoglobulin from the transgenic, non-human animal.

4 Claims, 82 Drawing Sheets
(3 of 82 Drawing Sheet(s) Filed in Color)

(56) References Cited

U.S. PATENT DOCUMENTS

| | | |
|---|---|---|
| 9,248,182 B2 | 2/2016 | De Kruif et al. |
| 2002/0138857 A1 | 9/2002 | Ghayur |
| 2003/0093820 A1 | 5/2003 | Green et al. |
| 2003/0096225 A1 | 5/2003 | Logtenberg |
| 2005/0170398 A1 † | 8/2005 | Van Berkel |
| 2006/0015949 A1 | 1/2006 | Lonberg et al. |
| 2006/0015957 A1* | 1/2006 | Lonberg et al. ............... 800/18 |
| 2006/0205077 A1 | 9/2006 | Schwenk et al. |
| 2006/0257397 A1 | 11/2006 | Throsby et al. |
| 2007/0280945 A1 | 12/2007 | Stevens et al. |
| 2008/0070799 A1 | 3/2008 | Bakker et al. |
| 2009/0054254 A1 | 2/2009 | Throsby et al. |
| 2009/0130652 A1 | 5/2009 | Throsby et al. |
| 2009/0181855 A1 | 7/2009 | Vasquez et al. |
| 2010/0069614 A1 | 3/2010 | Houtzager et al. |
| 2010/0146647 A1 | 6/2010 | Logtenberg et al. |
| 2010/0172917 A1 | 7/2010 | ter Meulen et al. |
| 2010/0297153 A1 | 11/2010 | Geuijen et al. |
| 2010/0310572 A1 | 12/2010 | Bakker et al. |
| 2010/0310586 A1 | 12/2010 | Dolcetti et al. |
| 2010/0331527 A1 | 12/2010 | Davis et al. |
| 2011/0177073 A1 | 7/2011 | Van Berkel et al. |
| 2011/0195454 A1 | 8/2011 | McWhirter |
| 2011/0268739 A1 | 11/2011 | Throsby et al. |
| 2012/0021409 A1 | 1/2012 | McWhirter |
| 2012/0039898 A1 | 2/2012 | Throsby et al. |
| 2012/0058907 A1 | 3/2012 | Logtenberg et al. |
| 2012/0076794 A1 | 3/2012 | Throsby et al. |
| 2012/0093823 A1 | 4/2012 | van den Brink et al. |
| 2012/0141493 A1 | 6/2012 | Throsby et al. |
| 2012/0177637 A1 | 7/2012 | Hoogenboom et al. |
| 2012/0192300 A1 | 7/2012 | Babb |
| 2012/0276115 A1 | 11/2012 | van den Brink et al. |
| 2012/0315278 A1 | 12/2012 | Throsby et al. |

FOREIGN PATENT DOCUMENTS

| | | | |
|---|---|---|---|
| EP | 0814159 A2 | | 12/1997 |
| EP | 1 204 740 | | 5/2002 |
| EP | 1349234 A2 | | 10/2003 |
| EP | 1 399 575 | | 3/2004 |
| EP | 1 439 234 | | 7/2004 |
| EP | 1 439 234 A1 | | 7/2004 |
| EP | 2 147 594 | | 1/2010 |
| JP | 2004-008218 | | 1/2004 |
| JP | 2006-109711 | | 4/2006 |
| WO | WO-90/04036 | | 4/1990 |
| WO | WO-90/12878 | | 11/1990 |
| WO | WO-91/00906 | | 1/1991 |
| WO | WO-92/03918 | | 3/1992 |
| WO | 94/02602 A1 | | 2/1994 |
| WO | WO-94/02602 | | 2/1994 |
| WO | WO-94/04667 | | 3/1994 |
| WO | WO-96/30498 | | 10/1996 |
| WO | WO-98/24893 | | 6/1998 |
| WO | WO-98/50431 | | 11/1998 |
| WO | WO 98 50431 | | 11/1998 |
| WO | WO 98/52976 | | 11/1998 |
| WO | WO-99/45962 | | 9/1999 |
| WO | WO-02/36789 | | 5/2002 |
| WO | 02/066630 A1 | | 8/2002 |
| WO | WO-02/066630 | | 8/2002 |
| WO | WO-03/47336 | | 6/2003 |
| WO | 2004/009618 A2 | | 1/2004 |
| WO | 2004106375 A1 † | | 5/2004 |
| WO | 20040106375 A1 † | | 12/2004 |
| WO | WO-04/106375 | | 12/2004 |
| WO | WO 2004/106375 A1 | | 12/2004 |
| WO | WO 2005/068622 A2 | | 7/2005 |
| WO | WO-06/68953 | | 6/2006 |
| WO | WO 02/066630 | * | 8/2006 |
| WO | 2006117699 A2 † | | 11/2006 |
| WO | 20060117699 A2 † | | 11/2006 |
| WO | WO-06/117699 | | 11/2006 |
| WO | 2008/054606 A2 | | 5/2008 |
| WO | WO-08/54606 | | 5/2008 |
| WO | 2008/076379 A2 | | 6/2008 |
| WO | WO-08/76379 | | 6/2008 |
| WO | WO-09/18411 | | 2/2009 |
| WO | WO-09/23540 | | 2/2009 |
| WO | WO 2009/157771 A2 | | 12/2009 |
| WO | WO-11/014469 | | 2/2011 |
| WO | WO 2011/097603 A1 | | 8/2011 |
| WO | WO-12/141798 | | 10/2012 |
| WO | WO-16/081923 | | 5/2016 |

OTHER PUBLICATIONS

O'Brien et al. (1987) Nature, vol. 326, 405-409.*

Peled et al.(2008) Annu. Rev. Immunol., vol. 26, 481-511.*

Davies, Nicholas P. et al., "Creation of Mice Expressing Human Antibody Light Chains by Introduction of a Yeast Artificial Chromosome Containing the Core Region of the Human Immunoglobulin kappa Locus," Bio/Technology, vol. 11:911-914 (1993).

Lonberg, Nils et al., "Antigen-specific human antibodies from mice comprising four distinct genetic modificaitons," Nature, vol. 368:856-859 (1994).

Taylor, Lisa D. et al., "A transgenic mouse that expresses a diversity of human sequence heavy and light chain immunoglobulins," Nucleic Acids Research, vol. 20(23):6287-6295 (1992).

Taylor, Lisa D. et al., "Human immunoglobulin transgenes undergo rearrangement, somatic mutation and class switching in mice that lack endogenous IgM," International Immunology, vol. 6(4):579-591 (1994).

Attaelmannan, Mohammed et al., "Understanding and Identifying Monoclonal Gammopathies," Clinical Chemistry, vol. 46(8B):1230-1238 (2000).

Carter, Paul, "Bispecific human IgG by design," Journal of Immunological Methods, vol. 248:7-15 (2001).

Dechiara, Thomas M. et al., "VelociMouse: Fully ES Cell-Derived F0-Generation Mice Obtained from the Injection of ES Cells into Eight-Cell-Stage Embryos," Gene Knockout Protocols: Second Edition, Ralf Kuhn (Ed.), Humana Press, vol. 530, Chapter 16, pp. 311-324 (2009).

Fecteau, Jessie F. et al., "A New Memory CD27 IgG+ B Cell Population in Peripheral Blood Expressing VH Genes with Low Frequency of Somatic Mutation," The Journal of Immunology, vol. 177:3728-3736 (2006).

GenBank Accession No. DQ187586-1, Protein ID ABA26122.1, Rabquer, B.J. et al., "Differential variable gene usage between pneumococcal polysaccharide specific B cells isolated 5-10 days and 4-6 weeks post-vaccination," 1 page (2005).

Kling, Jim, "Big Pharma vies for mice," Nature Biotechnology, vol. 25 (6):613 (2007).

Lie, Y.S. et al., "Advances in quantitative PCR technology: 5' nuclease assays," Curr. Opin. Biotechnol., vol. 9 (1):43-48 (1998).

Logtenberg, Ton, "Antibody cocktails: next-generation biopharmaceuticals with improved potency," Trends in Biotechnology, vol. 25(9):390-394 (2007).

Merus, "MeMo—the ingenious mouse, for improved antibody therapeutics," www.merus.nl, 3 pages (2011).

Murphy, Kenneth, "The Development and Survival of Lymphocytes," Janeway's Immunobioloby, 8th Edition, Taylor & Francis, Chapter 8, pp. 275-290 (2011).

Nagle, Mike, "Regeneron helps make Sanofi VelocImmune to its 'weak' pipeline," Outsourceing-Pharma.com, 2 pages (2007).

Nemazee, David, "Receptor editing in lymphocyte development and central tolerance," Nature, vol. 6(10):728-740 (2006).

Retter, Marc W. et al., "Receptor Editing Occurs Frequently during Normal B Cell Development," J. Exp. Med., vol. 188(7):1231-1238 (1998).

Sasaki, Yoshiteru et al., "Canonical NF-kB Activity, Dispensable for B Cell Development, Replaces BAFF-Receptor Signals and Promotes B Cell Proliferation upon Activation," Immunity, vol. 24:729-739 (2006).

Scott, Christopher Thomas, "Mice with a human touch," Nature Biotechnology, vol. 25:1075-1077 (2007).

(56) References Cited

OTHER PUBLICATIONS

Stevens, Sean, "Human Antibody Discovery, VelocImmune—A novel platform," Pharma Focus Asia, Issue 8, pp. 72-74 (2008).
Torres, Raul M. et al., Laboratory Protocols for Conditional Gene Targeting, Oxford University Press, Oxford, Chapters 10-11, pp. 42-53 (1997).
Van Doorn, S.T., Additional post-filing data and letter filed by the patentee, 1 page, dated Jun. 13, 2013.
Yang, X.W. et al., "Homologous recombination based modification in Escherichia coli and germline transmission in transgenic mice of a bacterial artificial chromosome," Nat. Biotechnol., vol. 15(9):859-865 (1997).
Australian Office Action for Application No. 2009263082, 8 pages, dated Mar. 18, 2014.
Canadian Protest and Submission of Prior Art for Application No. 2,729,095, 16 pages, dated Apr. 8, 2014.
International Preliminary Report on Patentability and Written Opinion for Application No. PCT/NL2009/050381, 11 pages, dated Jan. 5, 2011.
Third Party Observation for Application No. 09075279.1, 12 pages, dated Sep. 12, 2013.
Third Party Observation for Application No. 09075279.1, 4 pages, dated Oct. 10, 2013.
Third Party Observation for Application No. 2009263082, 25 pages, dated Oct. 28, 2013.
Third Party Observation for Application No. EP20090075279, 12 pages (2013).
Third Party Observations Against European Parent Application No. 09075279.1 in the Name of Merus BV, 3 pages, dated Jul. 1, 2013.
Statement of Facts and Arguments in Support of Opposition, Patent No. EP2147594 B1, 46 pages, dated Aug. 11, 2014.
Aucouturier et al., Monoclonal Ig L Chain and L Chain V Domain Fragment Crystallization in Myeloma-Associated Fanconi's Syndrome, The Journal of Immunology, Apr. 15, 1993, pp. 3561-3568, vol. 150, No. 8.
de Wildt et al., Analysis of Heavy and Light Chain Pairings Indicates that Receptor Editing Shapes the Human Antibody Repertoire, J. Mol. Biol., 1999, pp. 895-901, vol. 285.
Gonzales-Fernandez et al., Analysis of somatic hypermutation in mouse Peyer's patches using immunoglobulin κlight-chain transgenes, Proc. Natl. Acad. Sci., Nov. 1993, pp. 9862-9866, vol. 90.
Goyenechea et al., Modifying the sequence of an immunoglobulin V-gene alters the resulting pattern of hypermutation, Proc. Natl. Acad. Sci, 1996, pp. 13979-13984, vol. 93.
Hengstschlager et al., A λ1 transgene under the control of a heavy chain promoter and enhancer does not undergo somatic hypermutation, Eur. J. Immunol. 1994, pp. 1649-1656, vol. 24.
Jolly et al., Rapid methods for the analysis of immunoglobulin gene hypermutation: application to transgenic and gene targeted mice, Nucleic Acids Research, 1997, pp. 1913-1919, vol. 25, No. 10.
Klotz et al., Somatic Hypermutation of a $\lambda_2$ Transgene Under the Control of the λ Enhancer or the Heavy Chain Intron Enhancer, The Journal of Immunology, 1996, pp. 4458-4463, vol. 157.
Kong et al., A λ 3' Enhancer Drives Active and Untemplated Somatic Hypermutation of a $\lambda_1$ Transgene, The Journal of Immunology, 1998, pp. 294-301, vol. 161.
Mendez et al., Functional transplant of megabase human immunoglobulin loci recapitulates human antibody response in mice, Nature Genetics, 1997, pp. 146-156, vol. 15.
Nissim et al., Antibody fragments from a 'single pot' phage display library as immunochemical reagents, The EMBO Journal, 1994, pp. 692-698, vol. 13. No. 3.
Odegard et al., Targeting of somatic hypermutation, Nature Reviews, Immunology, Aug. 2006, pp. 573-583, vol. 6, No. 8.
Sharpe et al., Somatic hypermutation of immunoglobulin κ may depend on sequences 3' of $C_\kappa$ and occurs on passenger transgenes, The EMBO Journal, 1991, pp. 2139-2145, vol. 10, No. 8.
Sirac et al., Role of the monoclonal κ chain V domain and reversibility of renal damage in a transgenic model of acquired Fanconi syndrome, Blood, Jul. 15, 2006, pp. 536-543, vol. 108, No. 2.
De Kruif et al., Human Immunoglobulin Repertoires against Tetanus Toxoid Contain a Large and Diverse Fraction of High-Affinity Promiscuous $V_H$ Genes, J. Mol. Biol., 2009, pp. 548-558, vol. 387.
Homig-Holzel et al., Constitutive CD40 signaling in B cells selectively activates the noncanonical NF-κB pathway and promotes lymphomagenesis, J. Exp. Med., 2008, pp. 1317-1329, vol. 205, No. 6.
ImMunoGeneTics Information System, for analysed sequence CHEB VK, http://www.imgt.org/IMGT_vquest/vquest, at least as early as Apr. 25, 2012.
Jakobovits et al., From XenoMouse technology to panitumumab, the first fully human antibody product from transgenic mice, Nature Biotechnology, Oct. 2007, pp. 1134-1143, vol. 25, No. 10.
Kwaks et al., Employing epigenetics to augment the expression of therapeutic proteins in mammalian cells, Trends in Biotechnology, Mar. 1, 2006, pp. 137-142, vol. 24, No. 3, Elsevier Publications, Cambridge, GB.
Lonberg et al., Human antibodies from transgenic animals, Nature Biotechnology, Sep. 1, 2005, pp. 1117-1125, vol. 23, No. 9, Nature Publishing Group, New York, NY, US.
NCBI, Aucouturier et al., Monoclonal IgL Claim and L chain V domain fragment crystallization in myeloma-associated Fanconi's syndrome, <http://www.ncbi.nlm.nib/gov/nuccore/M87478, at least as early as Apr. 25, 2012.
PCT International Preliminary Report on Patentability, PCT/NL2009/050381 dated Jan. 5, 2011.
PCT International Search Report, PCT/NL2009/050381 dated Dec. 7, 2009.
Third Party Observations Under Article 115 EPC Against European Parent Application No. 09075279.1 in the name of Merus B.V., dated Oct. 25, 2012.
Third Party Observations Under Article 115 EPC Against European Parent Application No. 09075279.1 in the name of Merus B.V., dated Apr. 25, 2012.
European Patent Office Communication for Application No. 09075279.1 dated Nov. 5, 2012.
European Patent Office Communication for Application No. 09075279.1 dated May 8, 2012.
Bruggemann et al., A Repertoire of Monoclonal Antibodies with Human Heavy Chains from Transgenic Mice, Proc. Natl. Acad. Sci., Sep. 1989, pp. 6709-6713, vol. 86, USA.
Hochedlinger et al., Nature, 2002, pp. 1035-1038, vol. 415.
Meyer et al., N.A.R., 1990, 5609-15, vol. 18, No. 19.
Pelanda et al., A prematurely expressed Ig(kappa) transgene, but not V(kappa)J(kappa) gene segment targeted into the Ig(kappa) locus, can rescue B cell development in lambda5-deficient mice, Immunity, Sep. 1996, pp. 229-239, vol. 5, No. 3.
Popov et al., J. Exp. Med, 1999, pp. 1611-1619, vol. 189, No. 10.
Presta et al., Engineering of therapeutic antibodies to minimize immunogenicity and optimize function, Advanced Drug Delivery Reviews, Aug. 7, 2006, pp. 640-656, vol. 58, No. 5-6, Elsevier BV, Amsterdam, NL.
Smith-Gill et al., Contributions of immunoglobulin heavy and light chains to antibody specificity for lysozyme and two haptens, Journal of Immunology, Dec. 15, 1987, pp. 4135-4144, vol. 139, No. 12., Baltimore, MD, US.
Storb et al., J. Exp. Ed., 1986, pp. 627-641, vol. 164.
Weiner, et al., Abstract, Fully human therapeutic monoclonal antibodies, Journal of Immunotherapy, Jan. 1, 2006, pp. 1-9, vol. 29, No. 1, Lippincott Williams & Wilkins, Hagerstown, MD, US.
Winter et al., Insertion of 2 kb of bacteriophage DNA between an immunoglobulin promoter and leader exon stops somatic hypermutation in a kappa transgene, Molecular Immunology, Apr. 1997, pp. 359-366, vol. 34, No. 5.
Xiang et al., The Downstream Transcriptional Enhancer, Ed, positively regulates mouse Ig kappa gene expression and somatic hypermutation, Journal of Immunology, May 15, 2008, pp. 6725-6732, vol. 180, No. 10, Baltimore, MD.
U.S. Appl. No. 13/488,628, filed Jun. 5, 2012.

(56) References Cited

OTHER PUBLICATIONS

U.S. Appl. No. 14/266,540, filed Apr. 30, 2014, Ton Logtenberg.
U.S. Appl. No. 14/265,046, filed Apr. 29, 2014, Ton Logtenberg.
U.S. Appl. No. 12/589,181, Ton Logtenberg, filed Oct. 19, 2009, dated Sep. 24, 2014.
U.S. Appl. No. 14/266,540, Ton Logtenberg, filed Apr. 30, 2014, dated Aug. 29, 2014.
U.S. Appl. No. 14/265,046, Ton Logtenberg, filed Apr. 29, 2014, dated Aug. 29, 2014.
U.S. Appl. No. 12/589,181, filed Oct. 19, 2009, Ton Logtenberg.
U.S. Appl. No. 12/589,181, dated Jan. 17, 2014.
U.S. Appl. No. 12/589,181, dated Aug. 21, 2013.
U.S. Appl. No. 12/589,181, dated May 13, 2013.
U.S. Appl. No. 12/589,181, dated Apr. 16, 2012.
U.S. Appl. No. 12/589,181, dated Dec. 22, 2011.
U.S. Appl. No. 12/589,181, dated Oct. 31, 2011.
Bogen, Bjarne et al., "A rearranged lambda 2 light gene chain retards but does not exclude kappa and lambda 1 expression," Eur. J. Immunol., vol. 21:2391-2395 (1991).
Esposito, Gloria et al., "Phage display of a human antibody against Clostridium tetani toxin," Gene, vol. 148:167-168 (1994).
Goyenechea, Beatriz et al., "Cells strongly expressing Igk transgenes show clonal recruitment of hypermutation: a role for both MAR and the enhancers," The EMBO Journal, vol. 16(13):3987-3994 (1997).
Klohn, Peter-Christian et al., "IBC's 23rd Annual Antibody Engineering, 10th Annual Antibody Therapeutics International Conferences and the 2012 Annual Meeting of the Antibody Society," mAbs, vol. 5(2):178-201 (2013).
Mao, Xiaohong et al., "Activation of EGFP expression by Cre-mediated excision in a new ROSA26 reporter mouse strain," Blood, vol. 97(1):324-326 (2001).
Neuberger, M.S. et al., "Isotype exclusion and transgene down-regulation in immunoglobulin-lambda transgenic mice," Nature, vol. 338:350-352 (1989).
Peled, Jonathan U. et al., "The Biochemistry of Somatic Hypermutation," Annu. Rev. Immunol., vol. 26:481-511 (2008).
Rickert, Robert C. et al., "B lymphocyte-specific, Cre-mediated mutagenesis in mice," Nucleic Acids Research, vol. 25(6):1317-1318 (1997).
Roitt, A. , Immunology, Mir, Moscow, pp. 134, 214 (2000).
Singer, Maxine et al., "Transcription: The Transfer of DNA Sequence Information to RNA," Genes & Genomes, University Science Books, CA, Chapter 3.2, pp. 134-145 (1991).
Yarilin, A.A., Osnovy Immunologii, [Fundamentals of Immunology], Meditsina, Moscow, p. 194 (1999).
Yarilin, A.A., Osnovy Immunologii, [Fundamentals of Immunology], Meditsina, Moscow, p. 195 (1999).
Third Party Observations Against European Parent Application No. 09075279.1 in the Name of Merus BV, 8 pages, dated May 16, 2013.
Third Party Observation for Application No. EP20090075279, 16 pages, dated Jun. 14, 2013.
U.S. Appl. No. 12/589,181, dated Oct. 23, 2013.
Declaration of Robert Brink, Apr. 30, 2015, 34 pages.
Declaration of Anthony L. DeFranco, Dec. 21, 2014, 56 pages.
Declaration of Peter Hudson, May 1, 2015, 52 pages.
Declaration of Andrew Murphy, Dec. 19, 2014, 18 pages.
Declaration of David Tarlinton, Dec. 21, 2014, 40 pages.
Second Declaration of Robert Brink, Jun. 2, 2015, 38 pages.
Second Delaration of Peter Hudson, Jun. 2, 2015, 81 pages.
Pokorna et al., "DNA-vaccination via tattooing induces stronger humoral and cellular immune responses than intramuscular delivery supported by molecular adjuvants," Genetic Vaccines and Therapy (2008) 6:4.
Third Party Observations against EP 12186010.0, dated Mar. 13, 2017, 8 pages.
Mead et al., "Detection of Bence Jones myeloma and monitoring of myeloma chemotherapy using immunoassays specific for free immunoglobulin light chains," Clinical Laboratory (2003) 49(1-2):25-27.
Roebroek et al., "Mutant Lrp1 Knock-in mice generated by recombinase-mediated cassette exchange reveal differential importance of the NPXY motifs in the intracellular domain on LRP1 for normal fetal development," Molecular and Cellular Biology (2006) 26(2):605-616.
Shmerling et al., "Strong and ubiquitous expression of transgenes targeted into the beta-actin locus by Cre/lox cassette replacement," Genesis (2005) 42(4):229-235.
Toledo et al., "RMCE-ASAP: a gene targeting method for ES and somatic cells to accelerate phenotype analyses," Nucleic Acids Research (2006) 34(13):e92.
Protest under 37 CFR § 1.291 in Re-issue U.S. Appl. No. 15/158,543, filed Oct. 14, 2016, 45 pages.
Amendment for U.S. Appl. No. 12/932,719, filed Oct. 8, 2013, 12 pages.
Amendment under AFCP 2.0 for U.S. Appl. No. 12/932,719, filed Jun. 11, 2014, 12 pages.
Amendment for U.S. Appl. No. 12/932,719, filed Feb. 27, 2012, 10 pages.
Teaching of U.S. Appl. No. 12/589,181, presented May 24, 2012, 30 pages.
Notice of Opposition to a European Patent in EP 1360287 from Kymab Limited, filed Jun. 12, 2013, 8 pages.
Notice of Opposition to a European Patent in EP 1360287 from Merus B.V, filed Jun. 12, 2013, 8 pages.
Notice of Opposition to a European Patent in EP 1360287 from Merus B.V, filed Jun. 12, 2013, 4 pages.
Communication of a notice of opposition in EP 02709544.7, dated Jun. 12, 2013, 1 page.
Payment of fees and expenses in EP 02709544.7, filed Jun. 12, 2013, 1 page.
Authorisation for filing an opposition in EP 02709544.7, filed Jun. 11, 2013, 1 page.
Third party observations filed during prosecution (D12) in EP 02709544.7, filed Jun. 12, 2013, 20 pages.
Thykjaer et al., "Gene targeting approaches using positive-negative selection and large flanking regions," Plant Molecular Biology (1997) 35:523-530.
Deng et al., "Reexamination of gene targeting frequency as a function of the extent of homology between the targeting vector and the target locus," Mol Cell Biol (1992) 12(8):3365-3371.
Taki et al., "Targeted insertion of a variable region gene into the immunoglobulin heavy chain locus," Science (1993) 262:1268.
Zhang et al., "A new logic for DNA engineering using recombination in *Escherichia coli*," Nature Genetics (1998) (20):123-128.
Houldsworth et al., "Comparative genomic hybridization: an overview," AJP (1994) 145(6):1253-1260.
Shi et al., "The mapping of transgenes by fluorescence in situ hybridization on G-branded mouse chromosomes," Mammalian Genome (1994) 5:337-341.
Wilke et al., "Diagnosis of haploidy and triploidy based on measurement of gene copy number by real-time PCR," Human Mutation (2000) 16:431-436.
Bruggemann et al., "Strategies for expressing human antibody repertoires in transgenic mice," Immunol Today (1996) 17(8):391-397.
Zou et al., "Cre-loxP-mediated gene replacement: a mouse strain producing humanized antibodies," Current Biology (1994) 4:1099-1103.
Jessen et al., "Modification of bacterial artificial chromosomes through Chi-stimulated homologous recombination and its application in zebrafish transgenesis," Proc Natl Acad Sci USA (1998) 95:5121-5126.
IMGT Repertoire (IG and TR) Locus representation: Human (*Homo sapiens*) IGH, retrieved from http://www.imgt.org/IMGTrepertoire/index.php?section=LocusGenes&repertoire=locus&species=human&group=IGH on Apr. 2, 2012, 6 pages.
IMGT Repertoire (IG and TR) Locus representation: Human (*Homo sapiens*) IGL, retrieved from http://www.imgt.org/IMGTrepertoire/index.php?section=LocusGenes&repertoire=locus&species=human&group=IGL on Apr. 4, 2012, 3 pages.

(56) References Cited

OTHER PUBLICATIONS

Narayanan et al., "Efficient and precise engineering of a 200kb β-globin human/bacterial artificial chromosome in *E. coli* DH10B using an inducible homologous recombination system," Gene Therapy (1999) 6:442-447.
Muyrers et al., "Rapid modification of bacterial artificial chromosomes by ET-recombination," Nucleic Acids Research (1999) 27(6):1555-1557.
Schlake et al., "Use of mutated FLP recognition target (FRT) sites for the exchange of expression cassettes at defined chromosomal loci," Biochemistry (1994) 33:12746-12751.
Waterhouse et al., "Combinatorial infection and in vivo recombination: a strategy for making large phage antibody repertoires," Nucleic Acids Research (1993) 21(9):2265-2266.
Gu et al., "Independent control of immunoglobulin switch recombination at individual switch regions evidenced through Cre-loxP-Mediated gene targeting," Cell (1993) 73:1155-1164.
Mendez et al., "Functional transplant of megabase human immunoglobulin loci recapitulates human antibody response in mice," Nature Genetics (1997) 15:146-156.
Neuberger et al., "Isotype exclusion and transgene down-regulation in immunoglobulin-λ transgenic mice," Nature (1989) 338:350-352.
Bogen et al., "A rearranged λ2 light gene chain retards but does not exclude χ and λ1 expression," Eur J Immunol (1991) 24:2391-2395.
Davies et al., "Creation of mice expressing human antibody light chains by introduction of a yeast artificial chromosome containing the core region of the human immunoglobulin κ locus," Biotechnology (1993) 11:911-914.
Takeda et al., "Construction of chimaeric processed immunoglobulin genes containing mouse variable and human constant region sequences," Nature (1985) 314(4):452-454.
Taylor et al., "Human immunoglobulin transgenes undergo rearrangement, somatic mutation and class switching in mice that lack endogenous IgM," Int Immunol (1994) 6(4):579-591.
Bruggemann, "Human antibody expression in transgenic mice," Archivum Immunologiae et Therapiae Experimentalis (2001) 49:203-208.
Statement of Sean Stevens, PHD in EP 02709544.7, filed Aug. 7, 2009, 14 pages.
U.S. Appl. No. 09/732,234, filed Dec. 7, 2000, 57 pages.
U.S. Appl. No. 60/244,665, filed Oct. 31, 2000, 51 pages.
Appendix 1: The claims of the patent, dated Jun. 12, 2013, 5 pages.
List of evidence, dated Jun. 12, 2013, 2 pages.
Opposition against EP 1360287, dated Jun. 12, 2013, 2 pages.
Statement of facts and arguments, dated Jun. 12, 2013, 22 pages.
Statement of facts and arguments against EP 1360287, dated Jun. 12, 2013, 40 pages.
Acknowledgment of receipt for EP 1360287, dated Jun. 12, 2013, 2 pages.
Acknowledgment of receipt for EP 1360287, dated Jun. 12, 2013, 3 pages.
Submission in opposition proceedings in EP 1360287, dated Jun. 20, 2013, 2 pages.
Brief communication in EP1360287, dated Jun. 20, 2013, 1 page.
Smith et al., "Genomic analysis of transgenic animals," Methods in Molecular Biology (1993) 18:323-327.
Letter regarding the opposition procedure in EP 02709544.7, filed Jun. 14, 2013, 1 page.
Acknowledgment of receipt for EP 1360287, dated Jun. 20, 2013, 2 pages.
Communication of notices of opposition in EP 1360287, dated Jul. 18, 2013, 1 page.
Communication of further notices of opposition pursuant to Rule 79(2) EPC in EP 1360287, dated Jul. 18, 2013, 1 page (Stephen, Robert John).
Communication of further notices of opposition pursuant to Rule 79(2) EPC in EP 1360287, dated Jul. 18, 2013, 1 page (EP&C).
Letter accompanying subsequently filed items in EP 02709544.7, dated Sep. 16, 2013, 1 page.
Acknowledgment of receipt in EP 02709544.7, dated Sep. 16, 2013, 1 page.
Request for extension of time limit in EP 02709544.7, dated Sep. 16, 2013, 1 page.
Brief communication for EP 02709544.7, dated Sep. 17, 2013, 1 page (Stephen, Robert John).
Brief communication for EP 02709544.7, dated Sep. 17, 2013, 1 page (EP&C).
Grant of extension of time limit pursuant to Rule 132 EPC, dated Sep. 17, 2013, 1 page.
Submission in opposition proceedings in EP 02709544.7, dated Oct. 11, 2013, 2 pages.
Opposition proceedings for EP 1360287, dated Oct. 11, 2013, 1 page.
Acknowledgment of receipt in EP 02709544.7, dated Oct. 11, 2013, 1 page.
Brief communication for EP 02709544.7, dated Oct. 14, 2013, 1 page (Bentham, Andrew).
Brief communication for EP 02709544.7, dated Oct. 14, 2013, 1 page (EP&C).
Submission in opposition proceedings for EP 02709544.7, dated Jan. 28, 2014, 2 pages.
Letter accompanying subsequently filed items in EP 02709544.7, dated Jan. 28, 2014, 2 pages.
Brief communication for EP 02709544.7, dated Jan. 28, 2014, 1 page (Bentham, Andrew).
Brief communication for EP 02709544.7, dated Jan. 28, 2014, 1 page (Stephen, Robert John).
Bruggemann, "Human monoclonal antibodies from translocus mice," Molecular Biology of B Cells (2004) Chapter 34 pp. 547-561.
Honjo et al., "Molecular Biology of B Cells," $1^{st}$ Edition (2004) 1 page.
Open Monoclonal Technology, Inc, "OmniRat, OmniMouse and OmniFlic, Natually optimized human antibodies," (2013) 3 pages.
Ma et al., "Human antibody expression in transgenic rats: Comparison of chimeric IgH loci with human VH, D and JN but bearing different rat C-gene regions," J Immunol Methods (2013) 400-401:78-86.
Green et al., "Antigen-specific human monoclonal antibodies from mice engineered with human Ig heavy and light chain YACs," Nature Genetics (1994) 7:13-21.
Green et al., "Regulation of B cell development by variable gene complexity in mice reconstituted with human immunoglobulin yeast artificial chromosomes," J Exp Med (1998) 188(3):483-495.
Hansen, "Kymab: More mAb diversity," BioCentury (2012) 2 pages.
McCallister, "Still on the lookout," (2013) 21(48) pp. A1 and A13.
News in Brief, "Big Pharma vies for mice," Nature Biotechnology (2007) 25(6):613-614.
Nagle, "Regeneron helps make Sanofi VelocImmune to its "weak" pipeline," (2007) Retrieved on http://www.outsourcing-pharma.com/Preclinical-Research/Regeneron-helps-make-Sanofi-VelocImmune-to-its-weak-pipeline. Retrieved on Oct. 11, 2013.
"AstraZeneca licenses Regeneron's VelocImmune technology for discovering human monoclonal antibodies," (2007) Retrieved on https://www.drugs.com/news/astrazeneca-licenses-regeneron-s-velocimmune-technology-discovering-human-monoclonal-antibodies-5221.html. Retrieved on Jan. 23, 2014.
The Barnes Report, "A new target and technology have Regeneron's future looking bright," (2007) 1(4):1-2.
Business Wire, "Astellas licenses Regeneron's VelocImmune technology for discovering human monoclonal antibodies," (2007) Retrieved on http://www.businesswire.com/news/home/20070329006182/en/Astellas-Licenses-Regenerons-Velocimmune-Technology-Discovering-Human. Retrieved on Dec. 16, 2016.
Business Wire, "Regeneron and Columbia University enter into a strategic VelocImmune agreement to discover human monoclonal antibodies," (2008) Retrieved on http://www.businesswire.com/news/home/20080916005336/en/Regeneron-Columbia-University-Enter-Strategic-VelocImmune-Agreement. Retrieved on Jan. 23, 2014.

(56) References Cited

OTHER PUBLICATIONS

"Regeneron partners VelocImmune with University of Texas," Elsevier Business Intelligence (2009) 1 page.
Statement of Sue Klapholz, M.D., Ph.D, dated Jan. 27, 2014, 14 pages.
Jakobovits, "Production of fully human antibodies by transgenic mice," Current Opinion in Biotechnology (1995) 6:561-566.
Glanville et al., "Niave antibody gene-segment frequencies are heritable and unaltered by chronic lymphocyte ablation," PNAS (2011) 108(50):20066-20071.
Tomizuka et al., "Double trans-chromosomic mice: Maintenance of two individual human chromosome fragments containing Ig heavy and κ loci and expression of fully human antibodies," PNAS (2000) 97(2):722-727.
Green, "Antibody engineering via genetic engineering of the mouse: XenoMouse strains are a vehicle for the facile generation of therapeutic human monoclonal antibodies," Journal of Immunological Methods (1999) 231:11-23.
Statement of Andrew Murphy, dated Jan. 27, 2014, 33 pages.
First auxiliary request, dated Jan. 28, 2014, 8 pages.
Second auxiliary request, dated Jan. 28, 2014, 8 pages.
Amended claims (First auxiliary request), dated Jan. 28, 2014, 8 pages.
Amended claims (Second auxiliary request), dated Jan. 28, 2014, 8 pages.
Patentee's response to Oppositions in EP 1360287, dated Jan. 28, 2014, 1 page.
Patentee's response to Opposition in EP 1360287, dated Jan. 28, 2014, 47 pages.
Letter regarding Opposition proceedings in EP 1360287, dated Jan. 28, 2014, 1 page.
Acknowledgment of receipt in EP 02709544.7, dated Jan. 28, 2014, 1 page.
Acknowledgment of receipt in EP 02709544.7 by Andrew Bentham, dated Jan. 28, 2014, 2 pages.
Brief Communication in EP 027099544.7, dated Jan. 29, 2014, 1 page (Stephen, Robert & John).
Brief Communication in EP 027099544.7, dated Jan. 29, 2014, 1 page (EP&C).
Submission in opposition proceedings in EP 02709544.7, dated Feb. 10, 2014, 2 pages.
Tan et al., "A human-mouse chimeric immunoglobulin gene with a human variable region is expressed in mouse myeloma cell," The Journal of Immunology (1985) 135(5):3564-3567.
Kouskoff et al., "Cassette vectors directing expression of T cell receptor genes in transgenic mice," J Immunological Methods (1995) 180:273-280.
Fleischer et al., "Reactivity of mouse T-cell hybridomas expressing human Vbeta gene segments with staphylococcal and streptococcal superantigens," Infect Immun (1996) 64(3):987.
Vollmer et al., "Antigen contacts by Ni-reactive TCR: typical αβ chain cooperation versus α chain-dominated specificity," International Immunology (2000) 12(12):1723-1731.
Opposition against EP 1360287, dated Feb. 10, 2014, 6 pages.
Acknowledgment of receipt in EP 02709544.7, dated Feb. 10, 2014, 2 pages.
Brief Communication in EP 02709544.7, dated Feb. 11, 2014, 1 page (Bentham, Andrew).
Brief Communication in EP 02709544.7, dated Feb. 13, 2014, 1 page (EP&C).
Submission in opposition proceedings in EP 1360287, dated Feb. 11, 2014, 2 pages.
Letter accompanying subsequently filed items in EP 02709544.7, dated Feb. 12, 2014, 1 page.
Baker et al., "Adaptation of TCR expression vectors for the construction of mouse-human chimeric MBP-Specific TCR transgenes," Journal of Neuroscience Research (1996) 45:487-491.
Opposition against EP 1360287, dated Feb. 11, 2014, 1 page.
Request for acceleration of the opposition procedure in EP 1360287, dated Feb. 12, 2014, 2 pages.
Acknowledgement of receipt in EP 02709544.7, dated Feb. 12, 2014, 2 pages.
Acknowledgement of receipt in EP 02709544.7, dated Feb. 12, 2014, 1 page (James Nicholls).
Designation of inventor in EP 02709544.7, dated Feb. 24, 2014, 2 pages (Margaret Karow).
Designation of inventor in EP 02709544.7, dated Feb. 24, 2014, 2 pages (Lynn Macdonald).
Designation of inventor in EP 02709544.7, dated Feb. 24, 2014, 2 pages (Aris Economides).
Designation of inventor in EP 02709544.7, dated Feb. 24, 2014, 2 pages (Sean Stevens).
Designation of inventor in EP 02709544.7, dated Feb. 24, 2014, 2 pages (David Valenzuela).
Letter accompanying subsequently filed items in EP 02709544.7, dated Feb. 26, 2014, 1 page.
Letter concerning the inventors in EP 02709544.7, dated Feb. 26, 2014, 1 page.
Acknowledgement of receipt in EP 02709544.7, dated Feb. 26, 2014, 2 pages.
Preparation for oral proceedings in EP 02709544.7, dated Feb. 18, 2014, 2 pages.
Information concerning oral proceedings in EP 02709544.7, dated Apr. 30, 2014, 3 pages.
Summons to attend oral proceedings pursuant to Rule 115(1) in EP 02709544.7, dated Feb. 28, 2014, 1 page (Stephen, Robert John).
Summons to attend oral proceedings pursuant to Rule 115(1) in EP 02709544.7, dated Feb. 28, 2014, 1 page (EP&C).
Summons to attend oral proceedings pursuant to Rule 115(1) in EP 02709544.7, dated Feb. 28, 2014, 1 page (Bentham, Andrew).
Facts and Submissions in EP 02709544.7, dated Feb. 28, 2014, 7 pages.
Acknowledgement of receipt in EP 02709544.7, dated Feb. 28, 2014, 1 page (Stephen, Robert John).
Acknowledgement of receipt in EP 02709544.7, dated Feb. 28, 2014, 1 page (Andrew Bentham).
Acknowledgement of receipt in EP 02709544.7, dated Feb. 28, 2014, 1 page (EP&C).
Notification of the data mentioned in Rule 19(3) EPC in EP 02709544.7, dated Mar. 5, 2014, 1 page (Sean Stevens).
Notification of the data mentioned in Rule 19(3) EPC in EP 02709544.7, dated Mar. 5, 2014, 1 page (Margaret Karow).
Notification of the data mentioned in Rule 19(3) EPC in EP 02709544.7, dated Mar. 5, 2014, 1 page (David Valenzuela).
Notification of the data mentioned in Rule 19(3) EPC in EP 02709544.7, dated Mar. 5, 2014, 1 page (Lynn Macdonald).
Notification of the data mentioned in Rule 19(3) EPC in EP 02709544.7, dated Mar. 5, 2014, 1 page (Aris Economides).
Bibliographical data of European patent application No. 02709544.7, dated Feb. 28, 2014, 1 page.
Brief Communication in EP 02709544.7, dated Mar. 5, 2014, 1 page (Stephens, Robert John).
Brief Communication in EP 02709544.7, dated Mar. 5, 2014, 1 page (EP&C).
Brief Communication in EP 02709544.7, dated Mar. 5, 2014, 1 page (Andrew Bentham).
Acknowledgement of receipt of the document 2310 in EP 02709544.7, dated Feb. 28, 2014, 1 page (Stephen, Robert John).
Acknowledgement of receipt of the document 2310 in EP 02709544.7, dated Feb. 28, 2014, 1 page (EPC).
Letter accompanying subsequently filed items in EP 02709544.7, dated Mar. 10, 2014, 1 page.
Letter concerning inventor's name in EP 02709544.7, dated Mar. 10, 2014,1 page.
Acknowledgement of receipt in EP 02709544.7, dated Mar. 10, 2014, 1 page.
Bibliographical data of European patent application No. 02709544.7, dated Mar. 11, 2014, 1 page.
Brief Communication in EP 02709544.7, dated Mar. 14, 2014, 1 page (Andrew Bentham).
Brief Communication in EP 02709544.7, dated Mar. 14, 2014, 1 page (EP&C).

(56) References Cited

OTHER PUBLICATIONS

Brief Communication in EP 02709544.7, dated Mar. 14, 2014, 1 page (Stephens, Robert John).
Letter accompanying subsequently filed items in EP 02709544.7, dated Mar. 18, 2014, 1 page.
Letter concerning inventor's address in EP 02709544.7, dated Mar. 18, 2014, 1 page.
Advice of delivery in EP 02709544.7, dated Feb. 28, 2014, 2 pages.
Acknowledgement of receipt in EP 02709544.7, dated Mar. 18, 2014, 1 page.
Bibliographical data of European patent application No. 02709544.7, dated Mar. 19, 2014, 1 page.
Acknowledgement of receipt of the document 2310 in EP 02709544.7, dated Feb. 28, 2014, 1 page (Andrew Bentham).
Brief Communication in EP 02709544.7, dated Mar. 24, 2014, 1 page (Andrew Bentham).
Brief Communication in EP 02709544.7, dated Mar. 24, 2014, 1 page (Stephen, Robert John).
Brief Communication in EP 02709544.7, dated Mar. 24, 2014, 1 page (EPC).
Notice of Opposition to a European patent in EP 02709544.7, dated Apr. 3, 2014, 4 pages.
Cover sheet for fax transmission in EP 02709544.7, dated Apr. 3, 2014, 1 page.
Online fee payment in EP 02709544.7, dated Apr. 2, 2014, 1 page.
Notice of Intervention by Novo Nordisk in EP 02709544.7, dated Apr. 3, 2014, 13 pages.
Particulars of Infringement in EP 02709544.7, dated Apr. 3, 2014, 8 pages.
Soukharev et al., "Segmental genomic replacement in embryonic stem cells by double lox targeting," (1999) 27(18):e21.
Letter regarding Notice of Intervention in EP 02709544.7, dated Apr. 3, 2014, 1 page.
Notice of opposition to a European patent in EP 02709544.7, dated Apr. 4, 2014, 4 pages.
Brief Communication in EP 02709544.7, dated Apr. 10, 2014, 1 page (Andrew Bentham).
Brief Communication in EP 02709544.7, dated Apr. 10, 2014, 1 page (Stephen, Robert John).
Brief Communication in EP 02709544.7, dated Apr. 10, 2014, 1 page (EP&C).
Maintenance of oral proceedings in EP 02709544.7, dated Apr. 7, 2014, 2 pages.
Brief Communication in EP 02709544.7, dated Apr. 22, 2014, 1 page (Stephen, Robert John).
Brief Communication in EP 02709544.7, dated Apr. 22, 2014, 1 page (EP&C).
Brief Communication in EP 02709544.7, dated Apr. 22, 2014, 1 page (Andrew Bentham).
Preparation for oral proceedings in EP 02709544.7, dated Apr. 17, 2014, 2 pages.
Information concerning oral proceedings in EP 02709544.7, dated Jul. 16, 2014, 3 pages.
Summons to attend oral proceedings pursuant to Rule 115(1) in EP 02709544.7, dated Apr. 24, 2014, 1 page (Stephen, Robert John).
Summons to attend oral proceedings pursuant to Rule 115(1) in EP 02709544.7, dated Apr. 24, 2014, 1 page (EP&C).
Summons to attend oral proceedings pursuant to Rule 115(1) in EP 02709544.7, dated Apr. 24, 2014, 1 page (Bentham, Andrew).
Summons to attend oral proceedings pursuant to Rule 115(1) in EP 02709544.7, dated Apr. 24, 2014, 1 page (Thomas, Philip John Duval).
Facts and Submissions in EP 02709544.7, dated Apr. 24, 2014, 3 pages.
Acknowledgement of receipt of the document 2310 in EP 02709544.7, dated Apr. 24, 2014, 1 page (Andrew Bentham).
Acknowledgement of receipt of the document 2310 in EP 02709544.7, dated Apr. 24, 2014, 1 page (Stephen, Robert John).
Acknowledgement of receipt of the document 2310 in EP 02709544.7, dated Apr. 24, 2014, 1 page (EP&C).
Acknowledgement of receipt of the document 2310 in EP 02709544.7, dated Apr. 24, 2014, 1 page (Thomas, Philip John Duval).
Advice of delivery in EP 02709544.7, dated Apr. 24, 2014, 2 pages (Thomas, Philip John Duval).
Letter accompanying subsequently filed items in EP 02709544.7, dated May 2, 2014, 1 page.
Acknowledgement of receipt of the document 2310 in EP 02709544.7, dated May 2, 2014, 1 page.
Opposition to EP 1360287, dated Jul. 15, 2014, 3 pages.
Authorisation of representative in EP 1360287, dated Jul. 15, 2014, 1 page.
Letter accompanying subsequently filed items in EP 02709544.7, dated Jul. 16, 2014, 1 page.
First auxiliary request in EP 1360287, dated Jul. 16, 2014, 7 pages.
Second auxiliary request in EP 1360287, dated Jul. 16, 2014, 7 pages.
Third auxiliary request in EP 1360287, dated Jul. 16, 2014, 7 pages.
Fourth auxiliary request in EP 1360287, dated Jul. 16, 2014, 7 pages.
Fifth auxiliary request in EP 1360287, dated Jul. 16, 2014, 7 pages.
Sixth auxiliary request in EP 1360287, dated Jul. 16, 2014, 7 pages.
Seventh auxiliary request in EP 1360287, dated Jul. 16, 2014, 7 pages.
Eighth auxiliary request in EP 1360287, dated Jul. 16, 2014, 7 pages.
Ninth auxiliary request in EP 1360287, dated Jul. 16, 2014, 7 pages.
Tenth auxiliary request in EP 1360287, dated Jul. 16, 2014, 7 pages.
Eleventh auxiliary request in EP 1360287, dated Jul. 16, 2014, 7 pages.
Twelfth auxiliary request in EP 1360287, dated Jul. 16, 2014, 7 pages.
Thirteenth auxiliary request in EP 1360287, dated Jul. 16, 2014, 7 pages.
Fourteenth auxiliary request in EP 1360287, dated Jul. 16, 2014, 7 pages.
McMurry et al., "Enhancer control of local accessibility to V(D)J recombinase," Molecular and Cellular Biology (1997) 17(8):4553-4561.
Johnston et al., "Complete sequence assembly and characterization of the C57BL/6 mouse Ig heavy chain V region," J Immunol (2006) 176:4221-4234.
Xu et al., "Deletion of the Igκ light chain intronic enhancer/matrix attachment region impairs but does not abolish VκJκ Rearrangement," Immunity (1996) 4:377-385.
Meier et al., "Short DNA sequences inserted for gene targeting can accidentally interfere with off-target gene expression," The FASEB Journal (2010) 24:1714-1724.
Ren et al., "Targeted insertion results in a rhombomere 2-specific Hoxa2 knockdown and ectopic activation of Hoxa1 expression," Developmental Dynamics (2002) 225:305-315.
Tucker et al., "Mouse IgA heavy chain gene sequence: Implications for evolution of immunoglobulin hinge exons," Proc Natl Acad Sci USA (1981) 78(12):7684-7688.
Blankenstein et al., "Immunoglobulin $V_H$ region genes of the mouse are organized in overlapping clusters," Eur. J. Immunol. 1987.17: 1351-1357.
Rathbun et al., "Organization and expression of the mammalian heavy-chain variable-region locus," (1989) Chapter 4, 9 pages.
Amended claims (First auxiliary request), dated Jul. 16, 2014, 8 pages.
Amended claims (Second auxiliary request), dated Jul. 16, 2014, 8 pages.
Amended claims (Third auxiliary request), dated Jul. 16, 2014, 8 pages.
Amended claims (Fourth auxiliary request), dated Jul. 16, 2014, 8 pages.
Amended claims (Fifth auxiliary request), dated Jul. 16, 2014, 8 pages.
Amended claims (Sixth auxiliary request), dated Jul. 16, 2014, 8 pages.
Amended claims (Seventh auxiliary request), dated Jul. 16, 2014, 8 pages.

(56) References Cited

OTHER PUBLICATIONS

Amended claims (Eighth auxiliary request), dated Jul. 16, 2014, 8 pages.
Amended claims (Ninth auxiliary request), dated Jul. 16, 2014, 8 pages.
Amended claims (Tenth auxiliary request), dated Jul. 16, 2014, 8 pages.
Amended claims (Eleventh auxiliary request), dated Jul. 16, 2014, 8 pages.
Amended claims (Twelfth auxiliary request), dated Jul. 16, 2014, 8 pages.
Amended claims (Thirteenth auxiliary request), dated Jul. 16, 2014, 8 pages.
Amended claims (Fourteenth auxiliary request), dated Jul. 16, 2014, 8 pages.
Witness statement of Nicole Helen Dagg, dated Jan. 31, 2014, 5 pages.
Office action (third-party submission), dated Apr. 3, 2014, 17 pages.
Statement of Victor L J Tybulewicz, dated Jul. 15, 2014, 26 pages.
Statement of Daniel J. Capon, dated Jul. 7, 2014, 4 pages.
Documents list (D78-D107), dated Jul. 16, 2014, 1 page.
Curriculum Vitae Hidde L. Ploegh, dated Jul. 16, 2014, 33 pages.
Statement of Craig H. Bassing, dated Jul. 16, 2014, 34 pages.
Document 89, dated Jul. 16, 2014, 1 page.
Document 93 (ANNEX—MOA), dated Jul. 16, 2014, 6 pages.
Document 95a (Statement of Prof. Dr. Hendriks), dated Jul. 16, 2014, 21 pages.
Curriculum Vitae Prof. Dr. Rudi W. Hendriks, dated Jul. 16, 2014, 24 pages.
Response to substantive Examination Report in EP 02709544.7, dated Dec. 22, 2008, 6 pages.
D80 (Examination in EP 02709544.7), dated Jul. 16, 2014, 2 pages.
Kingzette et al., "Trans-chromosomal recombination within the Ig heavy chain switch region in B lymphocytes," Proc Natl Acad Sci USA (1998) 95:11840-11845.
Karu et al., "Recombinant antibody technology," ILAR Journal (1995) 37(3):132-141.
Giusti et al., "Hypermutation is observed only in antibody H chain V region transgenes that have recombined with endogenous immunoglobulin H DNA: Implications for the location of *cis*-acting elements required for somatic mutation," J Exp Med (1993) 177:797-809.
Bruggemann et al., "The immunogenicity of chimeric antibodies," J Exp Med (1989) 170:2153-2157.
Seidl et al., "Position-dependent inhibition of class-switch recombination by PGK-neor cassettes inserted into the immunoglobulin heavy chain constant region locus," Proc. Natl. Acad. Sci. USA (1999) 96:3000-3005.
Jakobovits, "The long-awaited magic bullets: therapeutic human monoclonal antibodies from transgenic mice," Exp Opin Invest Drugs (1998) 7(4):607-614.
Jakobovits et al., "From XenoMouse technology to panitumumab, the first fully human antibody product from transgenic mice," Nature Biotechnology (2007) 25(10):1134-1143.
Gavilondo et al., "Antibody engineering at the millennium," BioTechniques (2000) 29:128-145.
Clark, "IgG effector mechanisms," Chem Immunol Basel Karger (1997) 65:88-110.
Yang et al., "Homologous recombination based modification in *Esherichia coli* and germline transmission in transgenic mice of a bacterial artificial chromosome," Nature Biotechnology (1997) 15:859-865.
Thomas et al., "Site-directed mutagenesis by gene targeting in mouse embryo-derived stem cells," Cell (1987) 51:503-512.
Spanopoulou et al., "Functional immunoglobulin transgenes guide ordered B-cell differentiation in Rag-1-deficient mice," Genes & Development (1994) 8:1030-1042.
Monaco et al., "YACs, BACs, PACs and MACs: artificial chromosomes as research tools," TIB Tech (1994) 12:280-286.
Giraldo et al., "Size matters: use of YACs, BACs and PACs in transgenic animals," Transgenic Research (2001) 10:83-103.
Clark,"Antibody humanization: a case of the 'Emperor's new clothes'?" Immunology Today (2000) 21(8):397-402.
D82 (Summary of product characteristics), dated Jul. 16, 2014, 39 pages.
D83 (Summary of product characteristics), dated Jul. 16, 2014, 29 pages.
D84 (Summary of product characteristics), dated Jul. 16, 2014, 63 pages.
Muller et al., "Ten years of gene targeting: targeted mouse mutants, from vector design to phenotype analysis," Mechanisms of Development (1999) 82:3-21.
D86 (Gene Targeting), dated Jul. 16, 2014, 98 pages.
D78 (Datasheet for the decision of the Enlarged Board of Appeal of Apr. 6, 2009 for EP 94115175.5), dated Jul. 16, 2014, 25 pages.
U.S. Appl. No. 09/784,859, filed Feb. 16, 2001, 69 pages.
D91 (Datasheet for the decision of Sep. 12, 2012), dated Jul. 16, 2014, 28 pages.
D92 (European patent specification for EP 1 399 575), dated Jul. 16, 2014, 26 pages.
Opposition against EP 1360287, dated Jul. 16, 2014, 34 pages.
Letter regarding references part 1 dated Jul. 16, 2014, 1 page.
Letter regarding references part 2, dated Jul. 16, 2014, 1 page.
Letter regarding references part 3, dated Jul. 16, 2014, 1 page.
Submission in opposition proceedings in EP 1360287, dated Jul. 16, 2014, 2 pages (Olswang).
Submission in opposition proceedings in EP 1360287, dated Jul. 16, 2014, 2 pages (EPC).
Letter regarding Merus' written submission, dated Jul. 16, 2014, 2 pages, 2 pages.
The alleged invention, dated Jul. 16, 2016, 79 pages.
Response to the Summons to oral proceedings, dated Jul. 16, 2014, 24 pages.
Acknowledgement of receipt in EP 1360287, dated Jul. 16, 2014, 2 pages (Jane Hollywood).
Acknowledgement of receipt in EP 1360287, dated Jul. 16, 2014, 2 pages (Groeneveld).
Acknowledgement of receipt in EP 1360287, dated Jul. 16, 2014, 3 pages (Andrew Bentham).
Joyner, "Gene targeting", dated Jul. 17, 2014, 196 pages.
Letter regarding references part 4, dated Jul. 17, 2014, 1 page.
Letter regarding refereneces part 5, dated Jul. 17, 2014, 1 page.
Brief communication in EP 02709544.7, dated Jul. 21, 2014, 1 page (Andrew Bentham).
Brief communication in EP 02709544.7, dated Jul. 21, 2014, 1 page (Stephen, Robert John).
Brief communication in EP 02709544.7, dated Jul. 21, 2014, 1 page (EP&C).
Brief Communication in EP 02709544.7 (Letter from the opponent 01 of Jul. 16, 2014 with non patent literature only), dated Jul. 21, 2014, 1 page (Andrew Bentham).
Brief Communication in EP 02709544.7, dated Jul. 25, 2014, 1 page (Thomas, Philip John Duval).
Brief Communication in EP 02709544.7, dated Jul. 25, 2014, 1 page (Stephen, Robert John).
Brief Communication in EP 02709544.7, dated Jul. 25, 2014, 1 page (EP&C).
Brief Communication in EP 02709544.7, dated Jul. 28, 2014, 1 page (Andrew Bentham).
Brief Communication in EP 02709544.7, dated Jul. 28, 2014, 1 page (Thomas, Philip John Duval).
Brief Communication in EP 02709544.7, dated Jul. 28, 2014, 1 page (Stephen, Robert John).
Submission in opposition proceedings in EP 1360287, dated Aug. 12, 2014, 2 pages.
Consolidated document list for EP 1360287, dated Aug. 12, 2014, 11 pages.
Letter regarding consolidated document list for EP 1360287, dated Aug. 12, 2014, 1 page.
Acknowledgement of receipt for EP 1360287, dated Aug. 12, 2014, 2 pages.

(56) References Cited

OTHER PUBLICATIONS

Brief Communication in EP 02709544.7, dated Aug. 19, 2014, 1 page (Stephen, Robert John).
Brief Communication in EP 02709544.7, dated Aug. 19, 2014, 1 page (EP&C).
Brief Communication in EP 02709544.7, dated Aug. 19, 2014, 1 page (Thomas, Philip John Duval).
Authorisation in EP 1360287, dated Aug. 12, 2014, 1 page.
Submission in opposition proceedings in EP 1360287, dated Aug. 20, 2014, 2 pages.
Acknowledgement of receipt for EP 1360287, dated Aug. 20, 2014, 1 page (Jane Hollywood).
Letter accompanying subsequently filed items in EP 02709544.7, dated Aug. 22, 2014, 1 page.
Murphy et al., "Mice with megabase humanization of their immunoglobulin genes generate antibodies as efficiently as normal mice," PNAS (2014) 111(14):5153-5158.
MacDonald et al., "Precise and in situ genetic humanization of 6 Mb of mouse immunoglobulin genes," 111(14):5147-5152.
Letter with scientific publications, dated Aug. 22, 2014, 2 pages (Olswang).
Acknowledgement of receipt for EP 1360287, dated Aug. 22, 2014, 1 page (Jane Hollywood).
Brief Communication in EP 02709544.7, dated Aug. 28, 2014, 1 page (EP&C).
Brief Communication in EP 02709544.7, dated Aug. 28, 2014, 1 page (Thomas, Philip John Duval).
Brief Communication in EP 02709544.7, dated Aug. 28, 2014, 1 page (Andrew Bentham).
Letter accompanying subsequently filed items in EP 02709544.7, dated Sep. 2, 2014, 1 page.
Submission in opposition proceedings in EP 1360287, dated Sep. 2, 2014, 2 pages.
Practising Certificate (Dr James Richard Cleland Whyte), dated Apr. 1, 2014, 1 page.
Letter regarding practicing certificate, dated Sep. 2, 2014, 1 page.
Wuerffel et al., "S-S synapsis during class switch recombination is promoted by distantly located transcriptional elements and activation-induced deaminase," Immunity (2007) 27:711-722.
Seidl et al., "An expressed neo$^r$ cassette provides required functions of the ly2b exon for class switching," International Immunology (1998) 10(11):1683-1692.
Kenter et al., "Three-dimensional architecture of the IgH locus facilitates class switch recombination," Ann N.Y. Acad Sci (2012) 1267:86-94.
Kitamura et al., "A B cell-deficient mouse by targeted disruption of the membrane exon of the immunoglobulin μ chain gene," Nature (1991) 350:423-426.
Scapini et al., "Myeloid cells, BAFF, and IFN-$\gamma$, establish an inflammatory loop that exacerbates autoimmunity in Lyn-deficient mice," J Exp Med (2010) 207(8):1757-1773.
Geuijen, "Full length human IgG bispecific antibodies for cancer therapy," Merus-RABs and Bispecific Antibodies (2013) 33 pages.
Merus, "MeMo—the ingenious mouse for improved antibody therapeutics," Retrieved on Oct. 2011. Retrieved on www.merus.nl.
Merus, "MeMo transgenic mouse for improved antibody therapeutics," Retrieved on Sep. 2012. Retrieved on www.merus.nl.
Lee et al., "Complete humanization of the mouse immunoglobulin loci enables efficient therapeutic antibody discovery," Nature Biotechnology (2014) 32:356-363.
Second statement of Craig H. Bassing Ph.D., dated Sep. 2, 2014, 5 pages.
Written submissions in response to the summons to attend oral proceedings, dated Apr. 23, 2013, 24 pages.
Statement of Prof. Dr. Anthony Defranco, dated Sep. 2, 2014, 19 pages.
Letter regarding submissions made by opponents, dated Sep. 2, 2014, 8 pages.
Acknowledgement of receipt for EP 1360287, dated Sep. 2, 2014, 1 page (Jane Hollywood).
Acknowledgement of receipt for EP 1360287, dated Sep. 2, 2014, 1 page (Andrew Bentham).
Submission in opposition proceedings, dated Sep. 5, 2014, 2 pages.
Consolidated documents list for EP 1360287, dated Sep. 3, 2014, 12 pages.
Letter regarding consolidated documents, dated Sep. 5, 2014, 1 page.
Acknowledgement of receipt for EP 1360287, dated Sep. 5, 2014, 2 pages.
Brief Communication in EP 02709544.7, dated Sep. 8, 2014, 1 page (Stephen, Robert John).
Brief Communication in EP 02709544.7, dated Sep. 8, 2014, 1 page (Thomas, Philip John Duval).
Brief Communication in EP 02709544.7, dated Sep. 8, 2014, 1 page (EP&C).
Submission in opposition proceedings, dated Sep. 9, 2014, 2 pages.
Practising Certificate (Justin John Turner QC), dated Apr. 1, 2014, 1 page.
Letter regarding practicing certificate, dated Sep. 9, 2014, 1 page.
Acknowledgement of receipt for EP 1360287, dated Sep. 9, 2014, 2 pages.
Brief Communication in EP 02709544.7, dated Sep. 10, 2014, 1 page (Stephen, Robert John).
Brief Communication in EP 02709544.7, dated Sep. 10, 2014, 1 page (EP&C).
Brief Communication in EP 02709544.7, dated Sep. 10, 2014, 1 page (Thomas, Philip John Duval).
Letter accompanying subsequently filed items in EP 02709544.7, dated Sep. 11, 2014, 1 page.
Letter regarding attending oral proceedings, dated Sep. 11, 2014, 1 page.
Acknowledgement of receipt for EP 1360287, dated Sep. 11, 2014, 1 page.
Letter accompanying subsequently filed items in EP 02709544.7, dated Sep. 12, 2014, 1 page.
Brief Communication in EP 02709544.7, dated Sep. 15, 2014, 1 page (Stephen, Robert John).
Brief Communication in EP 02709544.7, dated Sep. 15, 2014, 1 page (EP&C).
Brief Communication in EP 02709544.7, dated Sep. 15, 2014, 1 page (Thomas, Philip John Duval).
Brief Communication in EP 02709544.7, dated Sep. 18, 2014, 1 page (Stephen, Robert John).
Brief Communication in EP 02709544.7, dated Sep. 18, 2014, 1 page (Bentham, Andrew).
Brief Communication in EP 02709544.7, dated Sep. 18, 2014, 1 page (Thomas, Philip John Duval).
Letter regarding Opposition proceedings, dated Sep. 15, 2014, 2 pages.
Acknowledgement of receipt for EP 1360287, dated Sep. 15, 2014, 1 page.
Information regarding oral proceedings, dated Sep. 18, 2014, 1 page.
Brief Communication in EP 02709544.7, dated Sep. 17, 2014, 1 page (Stephen, Robert John).
Brief Communication in EP 02709544.7, dated Sep. 17, 2014, 1 page (Andrew Bentham).
Brief Communication in EP 02709544.7, dated Sep. 17, 2014, 1 page (Thomas, Philip John Duval).
Letter regarding Notice of Appeal, dated Sep. 18, 2014, 2 pages.
Payment of fees and costs, dated Sep. 18, 2014, 1 page.
Communication for EP 02709544.7, dated Nov. 28, 2014,1 page.
Provision of the minutes in accordance with Rule 124(4) EPC, dated Nov. 28, 2014, 1 page.
Minutes of the oral proceedings before the opposition division, dated Nov. 28, 2014, 1 page.
Minutes of the oral proceedings before the opposition division sheet 2, dated Nov. 28, 2014, 1 page.
Decision revoking the European Patent (Art 101(3)(b) EPC), dated Nov. 28, 2014, 2 pages.
Revocation of the European Patent (Art 101(3)(b) EPC), dated Nov. 21, 2014, 1 page.
Appeal against the decision, dated Nov. 28, 2014, 2 pages.

(56) References Cited

OTHER PUBLICATIONS

Annex to the communication in EP 02709544.7, dated Nov. 28, 2014, 17 pages.
Facts and submissions in EP 02709544.7, dated Nov. 28, 2014, 25 pages.
Acknowledgement of receipt of the document 2331 in EP 02709544.7, dated Nov. 28, 2014, 1 page (Thomas, Philip John Duval).
Acknowledgement of receipt of the document 2331 in EP 02709544.7, dated Nov. 28, 2014, 1 page (EP&C).
Acknowledgement of receipt of the document 2331 in EP 02709544.7, dated Nov. 28, 2014, 1 page (Andrew Bentham).
Acknowledgement of receipt of the document 2331 in EP 02709544.7, dated Nov. 28, 2014, 1 page (Stephen, Robert John).
New sixth auxiliary request, dated Sep. 17, 2014, 11 pages.
New sixth auxiliary request (Annex), dated Sep. 17, 2014, 12 pages.
Advice of payment in EP 02709544.7, dated Apr. 12, 2014, 2 pages.
Letter accompanying subsequently filed items, dated Dec. 9, 2014, 1 page.
Acknowledgement of receipt for EP 1360287, dated Dec. 9, 2014, 1 page.
Commencement of proceedings before the Board of Appeal, dated Dec. 10, 2014, 4 pages.
Advice of payment in EP 02709544.7, dated Mar. 12, 2014, 2 pages (EP&C).
Appeal order for T2220/14-3.3.08, dated Dec. 12, 2014, 1 page.
Letter accompanying subsequently filed items, dated Dec. 23, 2016, 1 page.
Trial for 2015 from the Patents Court, dated Dec. 18, 2014, 15 pages.
Request for accelerated processing, dated Dec. 23, 2014, 5 pages.
Acknowledgement of receipt in EP 02709544.7, dated Dec. 9, 2014, 1 page.
Letter from Boards of Appeal for T2220/14-3.3.08, dated Jan. 9, 2015, 1 page (Stephen, Robert John).
Letter from Boards of Appeal for T2220/14-3.3.08, dated Jan. 9, 2015, 1 page (Thomas, Philip John Duval).
Letter from Boards of Appeal for T2220/14-3.3.08, dated Jan. 9, 2015, 1 page (EP&C).
Letter from Boards of Appeal for T2220/14-3.3.08, dated Jan. 20, 2015, 1 page (Andrew Bentham).
Letter accompanying subsequently filed items, dated Jan. 22, 2015, 1 page (Andrew Bentham).
Letter accompanying subsequently filed items, dated Jan. 22, 2015, 1 page (Jane Hollywood).
Letter in response to Communication, dated Jan. 22, 2015, 1 page (Andrew Bentham).
Letter in response to Communication from the Board of Appeal, dated Jan. 22, 2015, 1 page (Robert Stephen).
Acknowledgement of receipt in EP 02709544.7, dated Jan. 22, 2015, 1 page (Andrew Bentham).
Acknowledgement of receipt in EP 02709544.7, dated Jan. 22, 2015, 1 page (Jane Hollywood).
Letter from Boards of Appeal for T2220/14-3.3.08, dated Jan. 23, 2015, 1 page (Stephen, Robert John).
Letter from Boards of Appeal for T2220/14-3.3.08, dated Jan. 23, 2015, 1 page (Andrew Bentham).
Letter accompanying subsequently filed items, dated Jan. 30, 2015, 1 page (Andrew Bentham).
Letter accompanying subsequently filed items, dated Jan. 30, 2015, 1 page (Robert Stephen).
Explanation regarding documents disclosed in proceedings, dated Jan. 29, 2015, 2 pages.
Letter regarding acceleration of appeal proceedings, dated Jan. 30, 2015, 2 pages (EP&C).
Letter in response to the communication, dated Jan. 30, 2015, 2 pages (Robert Stephen).
Letter in response to the communication, dated Jan. 30, 2015, 2 pages (Philip Thomas).
Submission in opposition proceedings, dated Jan. 30, 2015, 2 pages (Philip Thomas).
Acknowledgement of receipt in EP 02709544.7, dated Jan. 30, 2015, 1 page (Olivier Brake).
Acknowledgement of receipt in EP 02709544.7, dated Jan. 30, 2015, 1 page (Stephen).
Acknowledgement of receipt in EP 02709544.7, dated Jan. 30, 2015, 1 page (Helen Stanbrook).
Letter from Boards of Appeal for T2220/14-3.3.08, dated Feb. 5, 2015, 3 pages.
Letter from Boards of Appeal for T2220/14-3.3.08, dated Feb. 5, 2015, 3 pages (with EP&C).
Letter accompanying subsequently filed items, dated Feb. 9, 2015, 1 page (Andrew Bentham).
Letter regarding acceleration of the proceedings, dated Feb. 9, 2015, 6 pages.
Acknowledgement of receipt in EP 02709544.7, dated Feb. 9, 2015, 1 page (Andrew Bentham).
Letter from Boards of Appeal for T2220/14-3.3.08, dated Feb. 13, 2015, 1 page (Stephen, Robert John).
Letter from Boards of Appeal for T2220/14-3.3.08, dated Feb. 13, 2015, 1 page (Thomas, Philip John Duval).
Letter from Boards of Appeal for T2220/14-3.3.08, dated Feb. 13, 2015, 1 page (EP&C).
Letter accompanying subsequently filed items, dated Feb. 15, 2015, 3 pages (Andrew Bentham).
Consolidated document list (D1-D155), dated Sep. 12, 2014, 12 pages.
Reichert, "Monoclonal antibodies in the clinic," Nature Biotechnology (2001) 19:819-822.
Jones et al., "Replacing the complementarity-determining regions in a human antibody with those from a mouse," Nature (1986) 321:522-525.
Hurle et al., "Protein engineering techniques for antibody humanization," Current Opinion in Biotechnology (1994) 5:428-433.
Xu et al., "Diversity in the CDR3 region of $V_H$ is sufficient for most antibody specificities," Immunity (2000) 13:37-45.
Figini et al., "Panning phage antibody libraries on cells: isolation of human fab fragments against ovarian carcinoma using guided selection," Cancer Research (1998) 58:991-996.
Mortuza et al., "Immunoglobulin heavy-chain gene rearrangement in adult acute lymphoblastic leukemia reveals preferential usage of $J_H$-proximal variable gene segments," Blood (2001) 97(9):2716-2726.
Fujieda et al., "Multiple types of chimeric germ-line Ig heavy chain transcript in human B cells: evidence for trans-splicing of human Ig RNA ," J Immunol (1996) 157(8):3450-3459.
Shimizu et al., "Trans-splicing as a possible molecular mechanism for the multiple isotype expression of the immunoglobulin gene," J. Exp. Med (1991) 173:1385-1393.
Yancopoulos et al., "Preferential utilization of the most $J_H$-proximal $V_H$ gene segments in pre-B-cell lines," Nature (1984) 311:727-733.
Letter regarding grounds of Appeal, dated Feb. 15, 2015, 41 pages.
Main Request, dated Feb. 15, 2015, 5 pages.
Auxiliary Request 1, dated Feb. 15, 2015, 5 pages.
Auxiliary Request 2, dated Feb. 15, 2015, 5 pages.
Auxiliary Request 3, dated Feb. 15, 2015, 5 pages.
Auxiliary Request 4, dated Feb. 15, 2015, 5 pages.
Auxiliary Request 5, dated Feb. 15, 2015, 5 pages.
Auxiliary Request 6, dated Feb. 15, 2015, 5 pages.
Auxiliary Request 7, dated Feb. 15, 2015, 5 pages.
Auxiliary Request 8, dated Feb. 15, 2015, 5 pages.
Auxiliary Request 9, dated Feb. 15, 2015, 5 pages.
Auxiliary Request 10, dated Feb. 15, 2015, 5 pages.
Auxiliary Request 11, dated Feb. 15, 2015, 5 pages.
Auxiliary Request 12, dated Feb. 15, 2015, 5 pages.
Auxiliary Request 13, dated Feb. 15, 2015, 5 pages.
Auxiliary Request 14, dated Feb. 15, 2015, 5 pages.
Auxiliary Request 15, dated Feb. 15, 2015, 5 pages.
Auxiliary Request 16, dated Feb. 15, 2015, 5 pages.
Auxiliary Request 17, dated Feb. 15, 2015, 5 pages.
Auxiliary Request 18, dated Feb. 15, 2015, 6 pages.
Auxiliary Request 19, dated Feb. 15, 2015, 4 pages.

(56) References Cited

OTHER PUBLICATIONS

Auxiliary Request 20, dated Feb. 15, 2015, 5 pages.
Auxiliary Request 21, dated Feb. 15, 2015, 5 pages.
Amended claims (main request), dated Feb. 15, 2015, 8 pages.
Amended claims (Auxiliary request 1), dated Feb. 15, 2015, 8 pages.
Amended claims (Auxiliary request 2), dated Feb. 15, 2015, 8 pages.
Amended claims (Auxiliary request 3), dated Feb. 15, 2015, 8 pages.
Amended claims (Auxiliary request 4), dated Feb. 15, 2015, 8 pages.
Amended claims (Auxiliary request 5), dated Feb. 15, 2015, 8 pages.
Amended claims (Auxiliary request 6), dated Feb. 15, 2015, 8 pages.
Amended claims (Auxiliary request 7), dated Feb. 15, 2015, 8 pages.
Amended claims (Auxiliary request 8), dated Feb. 15, 2015, 8 pages.
Amended claims (Auxiliary request 9), dated Feb. 15, 2015, 8 pages.
Amended claims (Auxiliary request 10), dated Feb. 15, 2015, 8 pages.
Amended claims (Auxiliary request 11), dated Feb. 15, 2015, 8 pages.
Amended claims (Auxiliary request 12), dated Feb. 15, 2015, 12 pages.
Amended claims (Auxiliary request 13), dated Feb. 15, 2015, 13 pages.
Amended claims (Auxiliary request 14), dated Feb. 15, 2015, 11 pages.
Amended claims (Auxiliary request 15), dated Feb. 15, 2015, 12 pages.
Amended claims (Auxiliary request 16), dated Feb. 15, 2015, 12 pages.
Amended claims (Auxiliary request 17), dated Feb. 15, 2015, 12 pages.
Amended claims (Auxiliary request 18), dated Feb. 15, 2015, 13 pages.
Amended claims (Auxiliary request 19), dated Feb. 15, 2015, 11 pages.
Amended claims (Auxiliary request 20), dated Feb. 15, 2015, 11pages.
Amended claims (Auxiliary request 21), dated Feb. 15, 2015, 8 pages.
Acknowledgement of receipt in EP 02709544.7, dated Feb. 15, 2015, 1 page (James Nicholls).
Letter accompanying subsequently filed items, dated Feb. 20, 2015, 1 page (Jane Hollywood).
Letter accompanying subsequently filed items, dated Feb. 20, 2015, 1 page (EP&C).
Letter from Boards of Appeal for T2220/14-3.3.08, dated Feb. 20, 2015, 1 page (Stephen, Robert John).
Letter from Boards of Appeal for T2220/14-3.3.08, dated Feb. 20, 2015, 1 page (Thomas, Philip John Duval).
Letter from Boards of Appeal for T2220/14-3.3.08, dated Feb. 20, 2015, 1 page (EP&C).
Letter regarding prior art documents, dated Feb. 20, 2015, 2 pages (Robert Stephen).
Letter regarding representation of Merus, dated Feb. 20, 2015, 1 page.
Letter regarding representation of Merus, dated Feb. 20, 2015, 3 pages (Raphael Bosl).
Acknowledgement of receipt in EP 02709544.7, dated Feb. 20, 2015, 1 page (Jane Hollywood).
Acknowledgement of receipt in EP 02709544.7, dated Feb. 20, 2015, 1 page (Olivier Ter Brake).
Letter from Boards of Appeal for T2220/14-3.3.08, dated Feb. 24, 2015, 1 page (Thomas, Philip John Duval).
Letter from Boards of Appeal for T2220/14-3.3.08, dated Feb. 24, 2015, 1 page (Fritz Lahrtz).
Letter from Boards of Appeal for T2220/14-3.3.08, dated Feb. 25, 2015, 1 page (Andrew Bentham).
Letter from Boards of Appeal for T2220/14-3.3.08 (Opponent 1), dated Feb. 26, 2015, 1 page (Andrew Bentham).
Letter from Boards of Appeal for T2220/14-3.3.08 (Opponent 1), dated Feb. 26, 2015, 1 page (Thomas, Philip John Duval).
Letter from Boards of Appeal for T2220/14-3.3.08 (Opponent 2), dated Feb. 26, 2015, 1 page (EP&C).
Letter from Boards of Appeal for T2220/14-3.3.08 (Opponent 2), dated Feb. 26, 2015, 1 page (Andrew Bentham).
Letter from Boards of Appeal for T2220/14-3.3.08 (Opponent 2), dated Feb. 26, 2015, 1 page (Thomas, Philip John Duval).
Letter from Boards of Appeal for T2220/14-3.3.08 (Opponent 2), dated Feb. 26, 2015, 1 page (Stephen, Robert John).
Letter from Boards of Appeal for T2220/14-3.3.08 (form 3575), dated Feb. 26, 2015, 1 page (Andrew Bentham).
Letter from Boards of Appeal for T2220/14-3.3.08 (form 3575), dated Feb. 26, 2015, 1 page (Thomas, Philip John Duval).
Letter from Boards of Appeal for T2220/14-3.3.08 (form 3575), dated Feb. 26, 2015, 1 page (Stephen, Robert John).
Communication of amended entries for T2220/14-3.3.08, dated Feb. 26, 2015, 1 page (Fritz Lahrtz).
Letter accompanying subsequently filed items, dated Mar. 2, 2015, 1 page (Fritz Lahrtz).
Letter accompanying subsequently filed items, dated Mar. 2, 2015, 1 page (Andrew Bentham).
Communication of the Board of Appeal for T2220/14-3.3.08, dated Mar. 2, 2015, 10 pages (Andrew Bentham).
Further to the Communication of the Board of Appeal, dated Mar. 2, 2015, 1 page (Fritz Lahrtz).
Letter regarding communication, dated Mar. 2, 2015, 1 page (Andrew Bentham).
Acknowledgement of receipt in EP 02709544.7, dated Mar. 2, 2015, 1 page (Verena Behre).
Acknowledgement of receipt in EP 02709544.7, dated Mar. 2, 2015, 1 page (Andrew Bentham).
Letter confirming proposed dates, dated Mar. 4, 2015, 2 pages (Philip Thomas).
Letter accompanying subsequently filed items, dated Mar. 9, 2015, 1 page (Robert Stephen).
Letter from Boards of Appeal for T2220/14-3.3.08 (Opponent 2), dated Mar. 9, 2015, 1 page (Andrew Bentham).
Letter from Boards of Appeal for T2220/14-3.3.08 (Opponent 2), dated Mar. 9, 2015, 1 page (Thomas, Philip John Duval).
Letter from Boards of Appeal for T2220/14-3.3.08 (Opponent 2), dated Mar. 9, 2015, 1 page (Stephen, Robert John).
Letter from Boards of Appeal for T2220/14-3.3.08 (Patent proprietor), dated Mar. 9, 2015, 1 page (Stephen, Robert John).
Letter from Boards of Appeal for T2220/14-3.3.08 (Patent proprietor), dated Mar. 9, 2015, 1 page (Thomas, Philip John Duval).
Letter from Boards of Appeal for T2220/14-3.3.08 (Patent proprietor), dated Mar. 9, 2015, 1 page (Fritz Lahrtz).
Letter from Boards of Appeal for T2220/14-3.3.08 (Opponent 3), dated Mar. 9, 2015, 1 page (Andrew Bentham).
Letter from Boards of Appeal for T2220/14-3.3.08 (Opponent 3), dated Mar. 9, 2015, 1 page (Fritz Lahrtz).
Letter from Boards of Appeal for T2220/14-3.3.08 (Opponent 3), dated Mar. 9, 2015, 1 page (Stephen, Robert John).
Letter in response to the EPO communication, dated Mar. 9, 2015, 1 page (Robert Stephen).
Acknowledgement of receipt in EP 02709544.7, dated Mar. 9, 2015, 1 page (Stephen).
Letter from Boards of Appeal for T2220/14-3.3.08 (Opponent 1), dated Mar. 16, 2015, 1 page (Andrew Bentham).
Letter from Boards of Appeal for T2220/14-3.3.08 (Opponent 1), dated Mar. 16, 2015, 1 page (Thomas, Philip John Duval).
Letter from Boards of Appeal for T2220/14-3.3.08 (Opponent 1), dated Mar. 16, 2015, 1 page (Fritz Lahrtz).
Authorisation for EP02709544.7, dated Mar. 8, 2015, 1 page.
Letter regarding power of attorney, dated Mar. 19, 2015, 1 page.

(56) References Cited

OTHER PUBLICATIONS

Letter accompanying subsequently filed items, dated Mar. 26, 2015, 2 pages (Andrew Bentham).
Letter from Boards of Appeal for T2220/14-3.3.08 (Opponent 2), dated Mar. 26, 2015, 1 page (Andrew Bentham).
Letter from Boards of Appeal for T2220/14-3.3.08 (Opponent 2), dated Mar. 26, 2015, 1 page (Thomas, Philip John Duval).
Letter from Boards of Appeal for T2220/14-3.3.08 (Opponent 2), dated Mar. 26, 2015, 1 page (Stephen, Robert John).
Letter regarding typographical errors, dated Mar. 26, 2015, 2 pages.
Auxiliary Request 15, dated Mar. 26, 2015, 5 pages.
Auxiliary Request 11, dated Mar. 26, 2015, 5 pages.
Auxiliary Request 10, dated Mar. 26, 2015, 5 pages.
Auxiliary Request 6, dated Mar. 26, 2015, 5 pages.
Auxiliary Request 1, dated Mar. 26, 2015, 5 pages.
Amend claims (Auxiliary Request 1), dated Mar. 26, 2015, 8 pages.
Amend claims (Auxiliary Request 6), dated Mar. 26, 2015, 8 pages.
Amend claims (Auxiliary Request 10), dated Mar. 26, 2015, 8 pages.
Amend claims (Auxiliary Request 11), dated Mar. 26, 2015, 8 pages.
Amend claims (Auxiliary Request 15), dated Mar. 26, 2015, 8 pages.
Acknowledgement of receipt in EP 02709544.7, dated Mar. 26, 2015, 2 pages (Andrew Bentham).
Letter from Boards of Appeal for T2220/14-3.3.08 (Patent proprietor), dated Apr. 1, 2015, 1 page (Stephen, Robert John).
Letter from Boards of Appeal for T2220/14-3.3.08 (Patent proprietor), dated Apr. 1, 2015, 1 page (Thomas, Philip John Duval).
Letter from Boards of Appeal for T2220/14-3.3.08 (Patent proprietor), dated Apr. 1, 2015, 1 page (Fritz Lahrtz).
Letter accompanying subsequently filed items, dated Jul. 2, 2015, 2 pages (Robert Stephen).
Rule 80 EPC document, dated Jul. 2, 2015, 8 pages.
Submission in response to EPO communication, dated Mar. 23, 2015, 3 pages.
Response to the examination report, dated Apr. 2, 2015, 7 pages (Andrew Bentham).
Opinion & Order, dated Nov. 21, 2014, 59 pages.
Document regarding lack of sufficiency, dated Jul. 2, 2015, 1 page.
Document regarding application documents in application 11728509.8, dated Mar. 4, 2015, 6 pages.
Document regarding application documents in application 10010741.6, dated May 30, 2014, 2 pages.
Submission in response to the third party observations, dated Jul. 1, 2014, 5 pages.
Letter regarding response to application, dated Jun. 23, 2015, 4 pages.
Bruggemann, "The preparation of human antibodies from mice harbouring human immunoglobulin loci," Transgenic animals: generation and use (1997) pp. 397-402.
Dougier et al., "Interallelic class switch recombination can reverse allelic exclusion and allow trans-complementation of an IgH locus switching defect," Eur J Immunol (2006) 36:2181-2191.
Gerstein et al., "Isotype switching of an immunoglobulin heavy chain transgene occurs by DNA recombination between different chromosomes," Cell (1990) 63:537-548.
Decision of technical board of appeal, dated Feb. 3, 2015, 21 pages.
Letter regarding grounds of appeal, dated Jul. 2, 2015, 1 page (Robert Stephen).
Acknowledgement of receipt in EP 02709544.7, dated Jul. 2, 2015, 2 pages.
Request and admissibility, dated Jul. 2, 2015, 64 pages.
Letter regarding a response to the grounds of appeal, dated Jul. 2, 2015, 19 pages (Philip Thomas).
Letter in response to Patentee's grounds of appeal, dated Jul. 2, 2015, 85 pages (Fritz Lahrtz).
Letter in response to Patentee's grounds of appeal, dated Jul. 2, 2015, 44 pages (Philip Thomas).
Letter from Boards of Appeal for T2220/14-3.3.08 (Opponent 1), dated Jul. 8, 2015, 1 page (Andrew Bentham).
Letter from Boards of Appeal for T2220/14-3.3.08 (Opponent 1), dated Jul. 8, 2015, 1 page (Thomas, Philip John Duval).
Letter from Boards of Appeal for T2220/14-3.3.08 (Opponent 1), dated Jul. 8, 2015, 1 page (Fritz Lahrtz).
Letter from Boards of Appeal for T2220/14-3.3.08 (Opponent 3), dated Jul. 8, 2015, 1 page (Andrew Bentham).
Letter from Boards of Appeal for T2220/14-3.3.08 (Opponent 3), dated Jul. 8, 2015, 1 page (Fritz Lahrtz).
Letter from Boards of Appeal for T2220/14-3.3.08 (Opponent 3), dated Jul. 8, 2015, 1 page (Stephen, Robert John).
Letter from Boards of Appeal for T2220/14-3.3.08 (Opponent 2), dated Jul. 9, 2015, 1 page (Andrew Bentham).
Letter from Boards of Appeal for T2220/14-3.3.08 (Opponent 2), dated Jul. 9, 2015, 1 page (Thomas, Philip John Duval).
Letter from Boards of Appeal for T2220/14-3.3.08 (Opponent 2), dated Jul. 9, 2015, 1 page (Stephen, Robert John).
Letter from Boards of Appeal for T2220/14-3.3.08 (Patent proprietor), dated Jul. 14, 2015, 1 page (Andrew Bentham).
Letter from Boards of Appeal for T2220/14-3.3.08 (Patent proprietor), dated Jul. 14, 2015, 1 page (Fritz Lahrtz).
Letter from Boards of Appeal for T2220/14-3.3.08 (Patent proprietor), dated Jul. 14, 2015, 1 page (Stephen, Robert John).
Letter accompanying subsequently filed items, dated Aug. 3, 2015, 1 page (Andrew Bentham).
Consolidated document list for appeal (D1-D168), dated Aug. 3, 2015, 14 pages.
Letter in response to grounds of appeal, dated Aug. 3, 2015, 1 page.
Acknowledgement of receipt in EP 02709544.7, dated Aug. 3, 2015, 1 page.
Letter from Boards of Appeal for T2220/14-3.3.08 (Patent proprietor), dated Aug. 7, 2015, 1 page (Stephen, Robert John ).
Letter from Boards of Appeal for T2220/14-3.3.08 (Patent proprietor), dated Aug. 7, 2015, 1 page (Thomas, Philip John Duval).
Letter from Boards of Appeal for T2220/14-3.3.08 (Patent proprietor), dated Aug. 7, 2015, 1 page (Fritz Lahrtz).
Document regarding oral proceedings, dated Aug. 13, 2015, 1 page.
Summons to oral proceedings pursuant to Rule 115(1) EPC, dated Aug. 14, 2015, 26 pages.
Acknowledgement of receipt of the document 3011, dated Aug. 17, 2015, 1 page (Fritz Lahrtz).
Tracking information, dated Aug. 17, 2015, 1 page.
Letter regarding transfer of all cases, dated Aug. 20, 2015, 2 pages.
Advice of delivery, dated Aug. 24, 2015, 2 pages (Thomas).
Letter accompanying subsequently filed items, dated Aug. 27, 2015, 1 page.
Acknowledgement of receipt of the document 3011, dated Aug. 14, 2015, 1 page.
Acknowledgement of receipt in EP 02709544.7, dated Aug. 27, 2015, 1 page.
Letter from Boards of Appeal for T2220/14-3.3.08 (Board's communication), dated Aug. 31, 2015, 1 page (Andrew Bentham).
Letter from Boards of Appeal for T2220/14-3.3.08 (Opponent 3 and Board's communication), dated Aug. 31, 2015, 1 page (Fritz Lahrtz).
Letter from Boards of Appeal for T2220/14-3.3.08 (Opponent 3 and Board's communication), dated Aug. 31, 2015, 1 page (Stephen, Robert John).
Acknowledgement of receipt of the document 3011, dated Aug. 14, 2015, 1 page (Stephen, Robert John).
Letter in relation to appeal proceedings, dated Sep. 8, 2015, 4 pages.
Velocimmune history narrative—from Drew's memory, dated Sep. 8, 2015, 6 pages.
Letter in relation to Appeal proceedings, dated Sep. 16, 2015, 2 pages.
Letter regarding representative of opponent 1, dated Sep. 21, 2015, 1 page.
Communication of the Board of Appeal, dated Sep. 22, 2015, 1 page (Andrew Bentham).
Communication of the Board of Appeal, dated Sep. 22, 2015, 1 page (Potter Clarkson LLP).

(56) References Cited

OTHER PUBLICATIONS

Communication of the Board of Appeal, dated Sep. 22, 2015, 1 page (Fritz Lahrtz).
Communication of the Board of Appeal, dated Sep. 22, 2015, 1 page (Stephen, Robert John).
Letter accompanying subsequently filed items, dated Sep. 25, 2015, 2 pages (Andrew Bentham).
Letter from Boards of Appeal for T2220/14-3.3.08 (Opponent 2), dated Sep. 25, 2015, 1 page (Andrew Bentham).
Letter from Boards of Appeal for T2220/14-3.3.08 (Opponent 2), dated Sep. 25, 2015, 1 page (Potter Clarkson LLP).
Letter from Boards of Appeal for T2220/14-3.3.08 (Opponent 2), dated Sep. 25, 2015, 1 page (Stephen, Robert John).
Letter in relation to Appeal Proceedings, dated Sep. 25, 2015, 19 pages.
Letter in response to the summons to oral proceedings pursuant to Rule 115(1) EPC, dated Sep. 25, 2015, 9 pages.
Main Request, dated Sep. 25, 2015, 5 pages.
Auxiliary Request 4, dated Sep. 25, 2015, 5 pages.
Auxiliary Request 5, dated Sep. 25, 2015, 5 pages.
Auxiliary Request 6, dated Sep. 25, 2015, 5 pages.
Auxiliary Request 8, dated Sep. 25, 2015, 5 pages.
Auxiliary Request 9, dated Sep. 25, 2015, 5 pages.
Auxiliary Request 10, dated Sep. 25, 2015, 5 pages.
Auxiliary Request 11, dated Sep. 25, 2015, 5 pages.
Auxiliary Request 7, dated Sep. 25, 2015, 5 pages.
Auxiliary Request 1, dated Sep. 25, 2015, 5 pages.
Auxiliary Request 2, dated Sep. 25, 2015, 5 pages.
Auxiliary Request 3, dated Sep. 25, 2015, 5 pages.
Amend claims (Main Request), dated Sep. 25, 2015, 8 pages.
Amend claims (Auxiliary Request 1), dated Sep. 25, 2015, 8 pages.
Amend claims (Auxiliary Request 2), dated Sep. 25, 2015, 8 pages.
Amend claims (Auxiliary Request 4), dated Sep. 25, 2015, 8 pages.
Amend claims (Auxiliary Request 5), dated Sep. 25, 2015, 8 pages.
Amend claims (Auxiliary Request 6), dated Sep. 25, 2015, 8 pages.
Amend claims (Auxiliary Request 7), dated Sep. 25, 2015, 8 pages.
Amend claims (Auxiliary Request 8), dated Sep. 25, 2015, 8 pages.
Amend claims (Auxiliary Request 9), dated Sep. 25, 2015, 8 pages.
Amend claims (Auxiliary Request 11), dated Sep. 25, 2015, 8 pages.
Amend claims (Auxiliary Request 10), dated Sep. 25, 2015, 8 pages.
Acknowledgement of receipt in EP 02709544.7, dated Sep. 25, 2015, 2 pages.
Letter from Boards of Appeal for T2220/14-3.3.08 (Patent proprietor), dated Oct. 1, 2015, 1 page (Stephen, Robert John).
Letter from Boards of Appeal for T2220/14-3.3.08 (Patent proprietor), dated Oct. 1, 2015, 1 page (Potter Clarkson LLP).
Letter from Boards of Appeal for T2220/14-3.3.08 (Patent proprietor), dated Oct. 1, 2015, 1 page (Fritz Lahrtz).
Further to the Submission of Sep. 21, 2015, dated Oct. 1, 2015, 3 pages.
Communication of the Board of Appeal, dated Oct. 2, 2015, 5 pages (Andrew Bentham).
Letter in relation to appeal, dated Oct. 5, 2015, 2 pages.
Letter from Boards of Appeal for T2220/14-3.3.08 (Patent proprietor), dated Oct. 9, 2015, 1 page (Stephen, Robert John).
Letter from Boards of Appeal for T2220/14-3.3.08 (Patent proprietor), dated Oct. 9, 2015, 1 page (Potter Clarkson LLP).
Letter from Boards of Appeal for T2220/14-3.3.08 (Patent proprietor), dated Oct. 9, 2015, 1 page (Fritz Lahrtz).
Letter accompanying subsequently filed items, dated Oct. 12, 2015, 1 page.
Letter from Boards of Appeal for T2220/14-3.3.08 (Opponent 2), dated Oct. 12, 2015, 1 page (Andrew Bentham).
Letter from Boards of Appeal for T2220/14-3.3.08 (Opponent 2), dated Oct. 12, 2015, 1 page (Potter Clarkson LLP).
Letter from Boards of Appeal for T2220/14-3.3.08 (Opponent 2), dated Oct. 12, 2015, 1 page (Stephen, Robert John).
Letter regarding issue of insufficiency, dated Oct. 9, 2015, 1 page.
Letter in relation to appeal, dated Oct. 12, 2015, 3 pages (Andrew Bentham).
Consolidated document list, dated Oct. 12, 2015, 13 pages.
Acknowledgement of receipt in EP 02709544.7, dated Oct. 12, 2015, 1 page.
Letter regarding Oral Proceedings, dated Oct. 13, 2015, 1 page (Fritz Lahrtz).
Letter from Boards of Appeal for T2220/14-3.3.08 (Opponent 1), dated Oct. 16, 2015, 6 pages (Andrew Bentham).
Letter from Boards of Appeal for T2220/14-3.3.08 (Patent Proprietor), dated Oct. 16, 2015, 6 pages (Stephen, Robert John).
Letter from Boards of Appeal for T2220/14-3.3.08 (Opponent 2), dated Oct. 16, 2015, 1 page (Andrew Bentham).
Letter from Boards of Appeal for T2220/14-3.3.08 (Opponent 2), dated Oct. 16, 2015, 1 page (Potter Clarkson LLP).
Letter from Boards of Appeal for T2220/14-3.3.08 (Opponent 2), dated Oct. 16, 2015, 1 page (Stephen, Robert John).
Letter in relation to Appeal proceedings, dated Oct. 22, 2015, 5 pages.
Notice of electronic filing, dated Oct. 25, 2015, 1 page.
Memorandum decision and order, dated Oct. 25, 2015, 11 pages.
Letter regarding decision in US proceedings, dated Oct. 25, 2015, 2 pages.
Letter from Boards of Appeal for T2220/14-3.3.08 (Opponent 2), dated Oct. 26, 2015, 5 pages (Andrew Bentham).
Letter enclosing D173 and D174, dated Oct. 26, 2015, 1 page.
Letter from Boards of Appeal for T2220/14-3.3.08 (Opponent 1), dated Oct. 27, 2015, 1 page (Andrew Bentham).
Letter from Boards of Appeal for T2220/14-3.3.08 (Opponent 1), dated Oct. 27, 2015, 1 page (Potter Clarkson LLP).
Letter from Boards of Appeal for T2220/14-3.3.08 (Opponent 1), dated Oct. 27, 2015, 1 page (Fritz Lahrtz).
Letter from Boards of Appeal for T2220/14-3.3.08 (Patent Proprietor), dated Oct. 28, 2015, 6 pages (Stephen, Robert John).
Letter in relation to appeal, dated Oct. 23, 2015, 3 pages (Andrew Bentham).
Oral proceedings notice, dated Oct. 30, 2015, 1 page.
Acknowledgement of receipt of the document 3011, dated Oct. 30, 2015, 1 page (Potter Clarkson LLP).
Acknowledgement of receipt of the document 3011, dated Oct. 30, 2015, 1 page (Fritz Lahrtz).
Acknowledgement of receipt of the document 3011, dated Oct. 30, 2015, 1 page (Stephen, Robert John).
Opinion and order, dated Nov. 2, 2015, 114 pages.
Letter regarding decision of the court (D175), dated Nov. 3, 2015, 41 pages.
Letter accompanying subsequently filed items, dated Nov. 4, 2015, 1 page (Andrew Bentham).
Summons to oral proceedings pursuant to Rule 115(1) EPC, dated Nov. 4, 2015, 12 pages.
Letter in preparation of the fourth day of oral proceedings, dated Nov. 4, 2015, 6 pages.
Letter regarding amendments, dated Nov. 4, 2015, 2 pages.
First Auxiliary Request, dated Nov. 3, 2015, 2 pages.
Main request, dated Oct. 28, 2015, 4 pages.
New first auxiliary request, dated Nov. 3, 2015, 5 pages.
Acknowledgement of receipt of the document 3011, dated Nov. 4, 2015, 2 pages (Andrew Bentham).
Letter from Boards of Appeal for T2220/14-3.3.08 (Opponent 2), dated Nov. 5, 2015, 5 pages (Andrew Bentham).
Letter from Boards of Appeal for T2220/14-3.3.08 (Patent proprietor), dated Nov. 5, 2015, 6 pages (Stephen, Robert John).
Tracking information, dated Nov. 4, 2015, 1 page.
Acknowledgement of receipt of the document 3011, dated Nov. 5, 2015, 1 page (Fritz Lahrtz).
Letter from Boards of Appeal for T2220/14-3.3.08 (Opponent 2), dated Nov. 6, 2015, 3 pages (Andrew Bentham).
Minutes of oral proceedings, dated Nov. 9, 2015, 11 pages.
Main request, dated Nov. 9, 2015, 5 pages.
Description of EP 1360287, date Nov. 9, 2015, 24 pages.
Advice of delivery, dated Nov. 16, 2015, 2 pages.
Minutes of the oral proceedings, dated Nov. 18, 2015, 4 pages.
Request for correction of minutes, dated Nov. 25, 2015, 2 pages.
Letter from Boards of Appeal for T2220/14-3.3.08 (Opponent 2), dated Dec. 3, 2015, 1 pages (Andrew Bentham).

(56) References Cited

OTHER PUBLICATIONS

Letter from Boards of Appeal for T2220/14-3.3.08 (Opponent 2), dated Dec. 3, 2015, 1 page (Potter Clarkson LLP).
Letter from Boards of Appeal for T2220/14-3.3.08 (Opponent 2), dated Dec. 3, 2015, 1 page (Stephen, Robert John).
Communication of the Board of Appeal, dated Dec. 4, 2015, 7 pages.
Datasheet for the decision, dated Nov. 9, 2015, 83 pages.
Decision, dated Mar. 11, 2016, 1 page (Andrew Bentham).
Decision, dated Mar. 11, 2016, 1 page (Potter Clarkson LLP).
Decision, dated Mar. 11, 2016, 1 page (Fritz Lahrtz).
Decision, dated Mar. 11, 2016, 1 page (Stephen, Robert John).
Tracking information, dated Mar. 11, 2016, 1 page (Fritz Lahrtz).
Acknowledgement of receipt of the document 3032, dated Mar. 14, 2016, 1 page (Fritz Lahrtz).
Acknowledgement of receipt of the document 3032, dated Mar. 14, 2016, 1 page (Stephen, Robert John).
Advice of delivery, dated Mar. 16, 2016, 2 pages.
Letter accompanying subsequently filed items, dated Mar. 21, 2016, 1 page (James R Nicholls).
Acknowledgement of receipt of the document 3032, dated Mar. 11, 2016, 1 page (Andrew Bentham).
Acknowledgement of receipt in EP 02709544.7, dated Mar. 21, 2016, 1 page (James Nicholls).
Notification of the communication, dated May 24, 2016, 1 page.
Communication pursuant to Article 101(1) and Rule 81(2) to (3) EPC, dated May 24, 2016, 2 pages (Andrew Bentham).
Application documents, dated May 24, 2016, 1 page.
Request for recordal, dated May 30, 2016, 1 page.
Deed of conversion and amendment of the articles of association, dated May 19, 2016, 53 pages.
Payment of fees and expenses, dated May 30, 2016, 1 page.
Communication of amended entries in register of European patents, dated Jun. 20, 2016, 2 pages (Fritz Lahrtz).
Brief Communication, dated Jun. 20, 2016, 3 pages (Andrew Bentham).
Brief Communication, dated Jun. 20, 2016, 3 pages (Potter Clarkson LLP).
Brief Communication, dated Jun. 20, 2016, 3 pages (Stephen, Robert John).
Submission in opposition proceedings, dated Sep. 19, 2016, 2 pages.
Comments on amendments (opponent 1), dated Sep. 19, 2016, 4 pages.
Response to communication, dated May 24, 2016, 1 page (Robert Stephen).
Acknowledgement of receipt in EP 02709544.7, dated Sep. 19, 2016, 2 pages.
Brief communication, dated Sep. 23, 2016, 1 page (Andrew Bentham).
Brief communication, dated Sep. 23, 2016, 1 page (Fritz Lahrtz).
Brief communication, dated Sep. 23, 2016, 1 page (Potter Clarkson LLP).
Submission in opposition proceedings, dated Sep. 30, 2016, 2 pages (James Nicholls).
Description of U.S. Appl. No. 09/784,859, dated Sep. 30, 2016, 21 pages.
Response to the Communication, dated Sep. 30, 2016, 2 pages.
Acknowledgement of receipt in EP 02709544.7, dated Sep. 30, 2016, 2 pages.
Submission in opposition proceedings, dated Oct. 3, 2016, 1 page (Philip Thomas).
Letter in response to communication, dated Oct. 3, 2016, 1 page (Philip Thomas).
Acknowledgement of receipt in EP 02709544.7, dated Oct. 3, 2016, 1 page (Rebecca Hamilton).
Brief communication, dated Oct. 7, 2016, 1 page (Stephen, Robert John).
Brief communication (enclosed letter from proprietor of the patent), dated Oct. 7, 2016, 1 page (Fritz Lahrtz).
Brief communication, dated Oct. 7, 2016, 1 page (Potter Clarkson LLP).
Brief communication, dated Oct. 7, 2016, 1 page (Andrew Bentham).
Brief communication (enclosed letter from opponent 3), dated Oct. 7, 2016, 1 page (Stephen, Robert John).
Brief communication (enclosed letter from opponent 3), dated Oct. 7, 2016, 1 page (Fritz Lahrtz).
Communication, dated Oct. 14, 2016, 1 page.
Communication pursuant to Article 101(1) and Rule 82(1) EPC, dated Oct. 14, 2016, 2 pages.
Information of the oral proceedings, dated Oct. 28, 2016, 1 page.
Decision on opposition, dated Sep. 7, 2016, 50 pages.
Abedi et al., "Green fluorescent protein as a scaffold for intracellular presentation of peptides," Nucleic Acids Res (1998) 26(2):623-630.
Abidor et al., "Studies of cell pellets: II. Osmotic properties, electroporation, and related phenomena: membrane interactions," Biophysical Joural (1994) 67:427-435.
Akerstrom et al., "On the interaction between single chain Fv antibodies and bacterial immunoglobulin-binding proteins," J Immunol Methods (1994) 177:151-163.
Alber et al., "Nucleotide sequence of the triose phosphate isomerase gene of *Saccharomyces cerevisiae*," J Mol Appl Genet (1982) 1(5):419-434.
Al-Lazikani et al., "Standard conformations for the Canonical structures of immunoglobulins," J Mol Biol (1997) 273:927-948.
Allen, "Ligand-targeted therapeutics in anticancer therapy," Nat Rev Cancer (2002) 2(10):750-763.
Almagro et al., "Humanization of antibodies," Front Biosci (2008) 13:1619-1633.
Ammerer, "Expression of Genes in Yeast Using the ADCI Promoter," Methods in Enzymology (1983) 101:192-201.
Antica et al., "Thymic Stem Cells in Mouse Bone Marrow," Blood (1994) 84(1):111-117.
Appel et al., "A new generation of information retrieval tools for biologists: the example of the ExPASy WWW server," Trends Biochem Sci (1994) 19(6):258-260.
Approved judgment, dated Feb. 1, 2016, 87 pages.
Arai et al., "Antibody responses induced by immunization with a Japanese rabies vaccine determined by neutralization test and enzyme-linked immunosorbent assay," Vaccine (2002) 20(19-20):2448-2453.
Aramda et al., "Nuclear Hormone Receptors and Gene Expression," Physiol Rev (2001) 81(3):1269-1304.
Arnold et al., "Development of B-1 cells: segregation of phosphatidyl choline-specific B cells to the B-1 population occurs after immunoglobulin gene expression," J Exp Med (1994) 179(5):1585-1595.
Attaelmannan et al., "Understanding and identifying monoclonal gammopathies," Clin Chem (2000) 46(8 Pt 2):1230-1238.
Atwell et al., "Stable Heterodimers from Remodeling the Domain Interface of a Homodimer using a Phage Display Library," J Mol Biol (1997) 270:26-35.
Aucouturier et al., "Monoclonal Ig L chain and L chain V domain fragment crystallization in myeloma-associated Fanconi's syndrome," J Immunol (1993) 150(8) 3561-3568.
Auerbach et al., "Angiogenesis Assays: A Critical Overview," Clin Chem (2003) 49(1):32-40.
Babcook et al., "A novel strategy for generating monoclonal antibodies from single, isolated lymphocytes producing antibodies of defined specificities," Proc Natl Acad Sci USA (1996) 93:7843-7848.
Banchereau et al., "Long-term human B cell lines dependent on interleukin-4 and antibody to CD40," Science (1991) 251(4989):70-72.
Barbas et al., "Assembly of combinatorial antibody libraries on phage surfaces: the gene III site," Proc Natl Acad Sci U S A (1991) 88(18):7978-7982.
Barnes et al., "Characterization of the Stability of Recombinant Protein Production in the GS-NS0 Expression System," Biotechnol Bioeng (2001) 73(4):261-270.
BD Biosciences, "CD Marker Handbook," (2010) 4 pages.

(56) References Cited

OTHER PUBLICATIONS

Bebbington et al., "High-level expression of a recombinant antibody from myeloma cells using a glutamine synthetase gene as an amplifiable selectable marker," Biotechnology (N Y) (1992) 10(2):169-175.
Bell et al., "Insulators and boundaries: versatile regulatory elements in the eukaryotic genome," Science (2001) 291(5503):447-450.
Bengig, "The production of foreign proteins in mammalian cells," Genet Eng (1988) 7:91-127.
Bertagnolli et al., "IL-12 augments antigen-dependent proliferation of activation lymphocytes," J Immunol (1992) 149:3778-3783.
Bertagnolli et al., "IL-4-Supported Induction of Cytolytic T Lymphocytes Requires IL-2 and IL-6," Cell Immunol (1991) 133:327-341.
Bertagnolli et al., "IL-7 supports the generation of cytotoxic T lymphocytes from thymocytes. Multiple lymphokines required for proliferation and cytotoxicity," J Immunol (1990) 145:1706-1712.
Betz et al., "Elements regulating somatic hypermutation of an immunoglobulin kappa gene: critical role for the intron enhancer/matrix attachment region," Cell (1994) 77(2):239-248 (Abstract).
Bhardwaj et al., "Influenza virus-infected dendritic cells stimulate strong proliferative and cytolytic responses from human CD8+ T cells," J Clin Invest (1994) 94(2):797-807.
Bins et al., "A rapid and potent DNA vaccination strategy defined by in vivo monitoring of antigen expression," Nature Medicine (2005) 11(8):899-904.
Binz et al., "Designing Repeat Proteins: Well-expressed, Soluble and Stable Proteins from Combinatorial Libraries of Consensus Ankyrin Repeat Proteins," J Mol Biol (2003) 332:489-503.
Birchmeier et al., "Met, metastasis, motility and more," Nat Rev Mol Cell Biol (2003) 4(12):915-925.
Bitter et al.,"Expression and secretion vectors for yeast," Methods Enzymol (1987) 153:516-544.
Bitter, "Heterologous gene expression in yeast," Methods Enzymol (1987) 152:673-684.
Bode et al., "The Hitchhiking principle: Optimizing episomal vectors for the use in gene therapy and biotechnology," Gene Ther Mol Biol (2001) 6:33-46.
Boder et al., "Yeast surface display for screening combinatorial polypeptide libraries," Nat Biotechnol (1997) 15(6):553-557.
Boel et al., "Functional human monoclonal antibodies of all isotypes constructed from phage display library-derived single-chain Fv antibody fragments," J Immunol Methods (2000) 239(1-2):153-166.
Bowman et al., "The cloning of CD70 and its identification as the ligand for CD27," J Immunol (1994) 152:1756-1761.
Brady et al., "Rapid specific amplification of rat antibody cDNA from nine hybridomas in the presence of myeloma light chains," J Immunol Methods (2006) 315(1-2):61-67.
Brezinsky et al., "A simple method for enriching populations of transfected CHO cells for cells of higher specific productivity," J Immunol Methods (2003) 277(1-2):141-155.
Brink et al., "Developing efficient strategies for the generation of transgenic cattle which produce biopharmaceuticals in milk," Theriogenology (2000) 53(1):139-148.
Broach et al., "Transformation in yeast: development of a hybrid cloning vector and isolation of the CAN1 gene," Gene (1979) 8(1):121-133.
Burger et al., "An integrated strategy for the process development of a recombinant antibody-cytokine fusion protein expressed in BHK cells," Appl Microbiol Biotechnol (1999) 52(3):345-353.
Burioni et al., Nonneutralizing human antibody fragments against hepatitis C virus E2 glycoprotein modulate neutralization of binding activity of human recombinant Fabs, Virology (2001) 288:29-335.
Campbell et al., "Sheep cloned by nuclear transfer from a cultured cell line," Nature (1996) 380(6569):64-66.
Cao et al., "Neutralizing monoclonal antibodies to hepatocyte growth factor/scatter factor (HGF/SF) display antitumor activity in animal models," Proc Natl Acad Sci U S A (2001) 98(13):7443-7448.
Carmack et al. "Influence of a V kappa 8 L chain transgene on endogenous rearrangements and the immune response to the HA(Sb) determinant on influenza virus," J Immunol (1991) 147(6):2024-2033.
Carter et al. "Humanization of an anti-p185HER2 antibody for human cancer therapy," Proc Natl Acad Sci U S A (1992) 89(10)4285-4289.
Carter, "Bispecific human IgG by design" J Immunol Methods (2001 248(1-2):7-15.
Cascalho et al., "A quasi-monoclonal mouse," Science (1996) 272(5268):1649-1652.
Casellas et al., "Contribution of receptor editing to the antibody repertoire" Science (2001) 291(5508):1541-1544.
Castelli et al., "HLA-DP4, the most frequent HLA II molecule, defines a new supertype of peptide-binding specificity," J Immunol (2002) 169(12):6928-6934.
Champion et al., "The development of monoclonal human rabies virus-neutralizing antibodies as a substitute for pooled human immune globulin in the prophylactic treatment of rabies virus exposure," J Immunol Methods (2000) 235(1-2):81-90.
Chan et al., "Genomic Organization of the T Cell Receptor," Cancer Detect Prev (1989) 14(2):261-267.
Chao et al., "Isolating and engineering human antibodies using yeast surface display," Nature Protocols (2006) 1(2):755-769.
Chen et al., "Selection and Analysis of an Optimized Anti-VEGF Antibody: Crystal Structure of an Affinity-matured Fab in Complex with Antigen," J Mol Biol (1999) 293(4):865-881.
Cheong et al., "Affinity enhancement of bispecific antibody against two different epitopes in the same antigen," Biochem Biophys Res Commun (1990) 173(3):795-800.
Cherrington et al., "New paradigms for the treatment of cancer: the role of anti-angiogenesis agents," Adv Cancer Res (2000) 79:1-38.
Chesnut et al., "Selective isolation of transiently transfected cells from a mammalian cell population with vectors expressing a membrane anchored single-chain antibody," J Immunol Methods (1996) 193(1):17-27.
Cheung et al., "A Recombinant Human Fab Expressed in *Escherichia coli* Neutralizes Rabies Virus," J Virol (1992) 66(11):6714-6720.
Chothia et al., "Canonical Structures for the Hypervariable Regions of Immunoglobulins," J Mol Biol (1987) 196:901-917.
Clackson et al., "Making antibody fragments using phage display libraries," Nature (1991) 352(6336):624-628.
Cobaugh et al., "Synthetic antibody libraries focused towards peptide ligands," J Mol Biol (2008) 378(3):622-633.
Cockett et al., "High level expression of tissue inhibitor of metalloproteinases in Chinese hamster ovary cells using glutamine synthetase gene amplification," Biotechnology (N Y) (1990) 8(7):662-667.
Conn et al., "Purification of a glycoprotein vascular endothelial cell mitogen from a rat glioma-derived cell line," Proc Natl Acad Sci U S A (1990) 87(4):1323-1327.
Conrath et al., "Camel Single-domain Antibodies as Modular Building Units in Bispecific and Bivalent Antibody Constructs," J Biol Chem (2001) 276(10):7346-7350.
Conrath et al., "Emergence and evolution of functional heavy-chain antibodies in Camelidae," Dev Comp Immunol (2003) 27(2):87-103.
Corsaro et al., "Enhancing the Efficiency of DNA-Mediated Gene Transfer in Mammalian Cells," Somatic Cell Genetics (1981) 7(5):603-616.
Crowe, "Recent advances in the study of human antibody responses to influenza virus using optimized human hybridoma approaches," Vaccine (2009) 27S:G47-51.
Cvetkovic et al., "Appropriate Tissue- and Cell-specific Expression of a Single Copy Human Angiotensinogen Transgene Specifically Targeted Upstream of the HPRT Locus by Homologous Recombination," J Biol Chem (2000) 275(2):1073-1078.
Dammacco et al., "Immunoglobulin secretion by peripheral blood and bone marrow B cells in patients with multiple myeloma. Studies by the reverse haemolytic plaque assay," Clin exp Immunol (1984) 87:743-751.

(56) References Cited

OTHER PUBLICATIONS

Darzynkiewicz et al., "Features of Apoptotic Cells Measured by Flow Cytometry," Cytometry (1992) 13:795-808.
Davies et al., "Antibody VH Domains as Small Recognition Units," Nature (1995) 13:475-479.
De Chiara et al., "Producing fully ES cell-derived mice from eight-cell stage embryo injections," Methods Enzymol (2010) 476:285-294.
Declaration of Andrew Murphy, dated Dec. 19, 2014, 18 pages.
Declaration of Anthony DeFranco, dated Aug. 24, 2016, 22 pages.
Declaration of Anthony DeFranco, dated Oct. 18, 2015, 31 pages.
Declaration of Christopher Goodnow, dated Oct. 16, 2015, 81 pages.
Declaration of David Tarlinton, dated Oct. 15, 2015, 24 pages.
Declaration of Joel Martin, dated May 18, 2016, 13 pages.
Declaration of John McWhirter, dated Aug. 2, 2016, 4 pages.
Declaration of Peter Hudson, dated Jun. 2, 2015, 7 pages.
Declaration of Peter Hudson, dated May 1, 2015, 52 pages.
Declaration of Robert Brink, dated Jun. 2, 2015, 38 pages.
Declaration of Robert Brink, dated Oct. 19, 2016, 19 pages.
Declaration of Robert Brink, dated Apr. 30, 2015, 34 pages.
Declaration of Ton Logtenberg, dated Sep. 15, 2015, 5 pages.
Second declaration of Ton Logtenberg, dated Dec. 18, 2015, 10 pages.
De Graaf et al., "Expression of scFvs and scFv Fusion Proteins in Eukaryotic Cells," Methods Mol Biol (2002) 178:379-387.
De Kruif et al., "Human immunoglobulin repertoires against tetanus toxoid contain a large and diverse fraction of high-affinity promiscuous V(H) genes," J Mol Biol (2009) 387(3):548-558.
De Kruif et al., "Rapid selection of cell subpopulation-specific human monoclonal antibodies from a synthetic phage antibody library," Proc. Natl. Acad. Sci. USA (1995) 92:3939-3942.
De Kruif et al., "Selection and Application of Human Single Chain Fv Antibody Fragments from a Semi-synthetic Phage Antibody Display Library with Designed CDR3 Regions," J Mol Biol (1995) 248:97-105.
Desmet et al., "Anchor profiles of HLA-specific peptides: analysis by a novel affinity scoring methods and experimental validation," Protein (2005) 58:53-69.
Desmet et al., "Computation of the binding of fully flexible peptides to proteins with flexible side chains," FASEB Journal (2016) 11(2):164-172.
Desmet et al., "Fast and accurate side-chain topology and energy refinement (FASTER) as a new method for protein structure optimization," Protein (2002) 48:31-43.
Desmet et al., "The dead-end elimination theorem and its use in protein side-chain positioning," Nature (1992) 356:539-542.
De Vries et al., "The Effect of Recombinant Mast Cell Growth Factor on Purified Murine Hematopoietic Stem Cells," J Exp Med (1991) 173(5):1205-1211.
De Wildt et al., "Analysis of Heavy and Light Chain Pairings Indicates that Receptor Editing Shapes the Human Antibody Repertoire," J Mol Biol (1999) 285:895-901.
Declaration of Christopher Carl Goodnow, Oct. 4, 2016, 13 pages.
Declaration of Prof Logtenberg, dated May 4, 2016, 7 pages.
Dejong et al., "Mammalian Artificial Chromosome Pilot Production Facility: Large-Scale Isolation of Functional Satellite DNA-Based Artificial Chromosomes," Cytometry (1999) 35:129-133.
Desmyter et al., "Crystal structure of a camel single-domain VH antibody fragment in complex with lysozyme," Nat Struct Biol (1996) 3(9):803-811.
Detailed results for the IMGT/V-QUEST analysed sequences, IMGT, (2016) 7 pages.
Dinnyes et al., "Somatic Cell Nuclear Transfer: Recent Progress and Challenges," Cloning Stem Cells (2002) 4(1):81-90.
Dumoulin et al., "A camelid antibody fragment inhibits the formation of amyloid fibrils by human lysozyme," Nature (2003) 424(6950):783-788.
Dumoulin et al., "Single-domain antibody fragments with high conformational stability," Protein Sci (2002) 11(3):500-515.
Eggan et al., "Hybrid vigor, fetal overgrowth, and viability of mice derived by nuclear cloning and tetraploid embryo complementation," PNAS (2001) 98(11):6209-6214.
Esposito et al., "Phage display of a human antibody against *Clostridium tetani* toxin," Gene (1994) 148:167-168.
Ettinger et al., "IL-21 induces differentiation of human naïve and memory B cells into antibody-secreting plasma cells," The Journal of Immunology (2005) 176:7867-7879.
Ewert et al., "Biophysical Properties of Camelid VHH Domains Compared to Those of Human VH3 Domains," Biochemistry (2002) 41:3628-3636.
Ewert et al., "Biophysical properties of human antibody variable domains," J Mol Biol (2003) 325:531-553.
Ezzell, "Molecular guided missiles called monoclonal antibodies were poised to shoot down cancer and a host of other diseases—until they crashed and burned. Now a new generation is soaring to market," Scientific American (2001) pp. 35-41.
Fasta, Immunoglobulin light chain variable region, partial [*Homo sapiens*] (2014) 1 page.
Fecteau et al., "A new memory $CD27^-IgG^+$ B cell population in peripheral blood expressing $V_H$ genes with low frequency of somatic mutation," The Journal of Immunology (2006) 177:3728-3736.
Feldhaus et al., "Flow-cytometric isolation of human antibodies from a nonimmune *Saccharomyces cerevisiae* surface display library," Natura Biotechnology (2003) 21:163-170.
Feige et al., "Anti-interleukin-1 and anti-tumor necrosis factor-alpha synergistically inhibit adjuvant arthritis in Lewis rats," Cell Mol Life Sci (2000) 57(10):1457-1470.
Ferrara, "Vascular endothelial growth factor: molecular and biological aspects," Curr Top Microbiol Immunol (1999) 237:1-30.
Figini et al., "In Vitro Assembly of Repertoires of Antibody Chains on the Surface of Phage by Renaturation," J Mol Biol (1994) 239(1):68-78.
Fine et al., "Interleukin-10 Enhances γδ T Cell Development in the Murine Fetal Thymus," Cellular Immunol (1994) 155:111-122.
Fischer, "Sequencing antibody repertoires: The next generation," mAbs (2011) 3:17-20.
Fishwild et al., "High-avidity human IgG kappa monoclonal antibodies from a novel strain of minilocus transgenic mice," Nat Biotechnol (1996) 14(7):845-851.
Flavell et al., "Systemic therapy with 3BIT, a triple combination cocktail of anti-CD19, -CD22, and -CD38-saporin immunotoxins, is curative of human B-cell lymphoma in severe combined immunodeficient mice," Cancer Res (1997) 57(21):4824-4829.
Flavell et al., "Therapy of human T-cell acute lymphoblastic leukaemia with a combination of anti-CD7 and anti-CD38-SAPORIN immunotoxins is significantly better than therapy with each individual immunotoxin," Br J Cancer (2001) 84(4):571-578.
Folkman, "Angiogenesis in cancer, vascular, rheumatoid and other disease," Nat Med (1995) 1(1):27-31.
Franconi et al., "Functional expression in bacteria and plants of an scFv antibody fragment against tospoviruses," Immunotechnology (1999) 4(3-4):189-201.
Freken et al., "Isolation of antigen specific Llama VHH antibody fragments and their high level secretion by *Saccharomyces cerevisiae*," J Biotechnol (2000) 78(1):11-21.
French et al., "Cooperative Mixtures of Bispecific F(ab')2 Antibodies for Delivering Saporin to Lymphoma in Vitro and in Vivo," Cancer Res (1991) 51:2353-2361.
Friedenson et al., "Immunoglobulin G antibodies from an individual rabbit in which several heavy chain variants are paired with one light chain sequence," J Biol Chem (1973) 248(20):7073-7079.
Frykman et al., "Quantitating secretion rates of individual cells: design of secretion assays," Biotechnol Bioeng (1998) 59(2):214-226.
Fuchs et al., "Targeting recombinant antibodies to the surface of *Escherichia coli*: fusion to a peptidoglycan associated lipoprotein," Biotechnology (N Y) (1991) 9(12):1369-1372.
Fussenegger et al., "Genetic optimization of recombinant glycoprotein production by mammalian cells," Trends Biotechnol (1999) 17(1):35-42.

(56) References Cited

OTHER PUBLICATIONS

Garber, "Biotech industry faces new bottleneck," Nat Biotechnol (2001) 19:183-185.
Garnick, "Peptide Mapping for Detecting Variants in Protein Products," Develop biol Standard (1992) 76:117-130.
Garrard et al., "Fab assembly and enrichment in a monovalent phage display system," Biotechnology (N Y) (1991) 9(12):1373-1377.
Gascan et al., "Human B cell clones can be induced to proliferate and to switch to IgE and IgG4 synthesis by interleukin 4 and a signal provided by activated CD4$^+$ T cell clones," J Exp Med (1991) 173:747-750.
Ge et al., "Rapid construction and characterization of synthetic antibody libraries without DNA amplification," Biotechnology and Bioengineering (2010) 106(3):347-357.
Genbank, ABA26122.1, dated Dec. 31, 2005, 1 page.
Genbank, DQ187586.1, dated Jul. 26, 2016, 1 page.
Genbank, M87478.1, dated Oct. 28, 1994, 1 page.
Gerstner et al., "Sequence Plasticity in the Antigen-binding Site of a Therapeutic Anti-HER2 Antibody," J Mol Biol (2002) 321:851-862.
Giddings et al., "Transgenic plants as factories for biopharmaceuticals," Nat Biotechnol (2000) 18(11):1151-1155.
Gluzman, "SV40-Transformed Simian Cells Support the Replication of Early SV40 Mutants," Cell (1981) 23:175-I 82.
Gonzalez-Fernandez et al., "Analysis of somatic hypermutation in mouse Peyer's patches using immunoglobulin κ light-chain transgenes," Proc Natl Acad Sci USA (1993) 90:9862-9866.
Good et al., "Kinetics of human B cell behavior and amplification of proliferative responses following stimulation with IL-21," J Immunol (2006) 177:5236-5247.
Gorczyca et al., "DNA strand breaks occurring during apoptosis: Their early in situ detection by the terminal deoxynucleotidyl transferase and nick translation assays and prevention by serine protease inhibitors," Int J Oncol (1992) 1(6):639-648.
Gorczyca et al., "Induction of DNA Strand Breaks Associated with Apoptosis during Treatment of Leukemias," Leukemia (1993) 7(5):659-670.
Gorman et al., "Site-specific gene targeting for gene expression in eukaryotes," Curr Opin Biotechnol (2000) 11(5):455-460.
Goyenechea et al., "Modifying the sequence of an immunoglobulin V-gene alters the resulting pattern of hypermutation," Proc Natl Acad Sci USA (1996) 93:13979-13984.
Goyenechea et al., "Cells strongly expressing Igκ transgenes show clonal recruitment of hypermutation: a role for both MAR and the enhancers," The EMBO Journal (1997) 16(13):3987-3994.
Graham et al., "A New Technique for the Assay of Infectivity of Human Adenovirus 5 DNA," Virology (1973) 52:456-467.
Gram et al., "In vitro selection and affinity maturation of antibodies from a naive combinatorial immunoglobulin library," Proc. Natl. Acad. Sci. USA (1992) 89:3576-3580.
Graslund et al., "Integrated strategy for selective expanded bed ion-exchange adsorption and site-specific protein processing using gene fusion technology," J Biotechnol (2002) 96(1):93-102.
Gray et al., "Secretion capture and report web: use of affinity derivatized agarose microdroplets for the selection of hybridoma cells," J Immunol Methods (1995) 182(2):155-63.
Greenberger et al., "Demonstration of permanent factor-dependent multipotential (erythroid/neutrophil/basophil) hematopoietic progenitor cell lines," Proc. Natl Acad. Sci. USA (1983) 80:2931-2935.
Griffiths et al., "Human anti-self antibodies with high specificity from phage display libraries," EMBO J (1993) 12(2):725-734.
Griffiths et al., "Isolation of high affinity human antibodies directly from large synthetic repertoires," EMBO J (1994) 13(14):3245-3260.
Groeneveld et al., "Bone morphogenetic proteins in human bone regeneration," Eur J Endocrinol (2000)142(1):9-21.
Grosveld, "Activation by locus control regions?" Curr Opin Genet Dev (1999) 9(2):152-7.
Guery et al., "Dendritic cells are the most efficient in presenting endogenous naturally processed self-epitopes to class II-restricted T cells," J Immunol (1995) 154(2):536-544.
Guilli et al., "Epidermal growth factor-induced apoptosis in A431 cells can be reversed by reducing the tyrosine kinase activity," Cell Growth and Differentiation (1996) 7:173-178.
Gunasekaran et al., "Enhancing antibody Fc heterodimer formation through electrostatic steering effects," Journal of Biological Chemistry (2010) 285(25):19637-19646 (enclosing supplementary tables and figures).
Hamers-Casterman et al., "Naturally occurring antibodies devoid of light chains," Nature (1993) 363(6428):446-8.
Hanes et al., "Picomolar affinity antibodies from a fully synthetic naive library selected and evolved by ribosome display," Nat Biotechnol (2000) 18(12):1287-92.
Hanes et al., "Selecting and evolving functional proteins in vitro by ribosome display," Methods Enzymol (2000) 328:404-430.
Harding et al., "The immunogenicity of humanize and fully human antibodies," mAbs (2010) 2:3:256-265.
Hardy et al., "B cell development pathways," Annu Rev Immunol (2001) 19:595-621.
Harjunpaa et al., "Rituximab (Anti-CD20) Therapy of B-Cell Lymphomas: Direct Complement Killing is Superior to Cellular Effector Mechanisms," Scand J Immunol (2000) 51(6):634-41.
Harvey et al., "Anchored periplasmic expression, a versatile technology for the isolation of high-affinity antibodies from *Escherichia coli*-expressed libraries," PNAS (2004) 101(25):9193-9198.
Hawkins et al., "Selection of Phage Antibodies by Binding Affinity Mimicking Affinity Maturation," J Mol Biol (1992) 226:889-896.
Hay et al., "Bacteriophage cloning and *Escherichia coli* expression of a human IgM Fab," Hum Antibod Hybridomas (1992) 3:81-85.
Heintges et al., "Cloning, bacterial expression and sequencing of human antibody fragments against hepatitis Virus NS3 by Phage display of a combinatorial Phagemid Library," Hepatology (1998) 28(4 Pt 2):227A.
Hengstchlager et al., "A λ1 transgene under the control of a heavy chain promoter and enhancer does not undergo somatic hypermutation," Eur J Immunol (1994) 24:1649-1656.
Hiatt et al., "Production of antibodies in transgenic plants," Nature (1989) 342(6245):76-8.
Hitzeman et al., "Isolation and Characterization of the Yeast 3-Phosphoglycerokinase Gene (PGK) by an Immunological Screening Technique" J Biol Chem (1980) 255(24):12073-12080.
Hochedlinger et al., "Monoclonal mice generated by nuclear transfer from mature B and T donor cells," Nature (2002) 415:1035-1038.
Holliger et al., ""Diabodies": Small bivalent and bispecific antibody fragments," Proc. Natl. Acad. Sci. USA (1993) 90:6444-6448.
Holmes et al., "Improved cell line development by a high throughput affinity capture surface display technique to select for high secretors," J Immunol Methods (1999) 230(1-2):141-147.
Holt et al., "Domain antibodies: proteins for Therapy," Trends Biotechnol (2003) 21(11):484-490.
Homig-Holzel et al., "Constitutive CD40 signaling in B cells selectively activates the noncanonical NF-κB pathway and promotes lymphomagenesis," J Exp Med (2008) 205(6):1317-1329.
Hoogenboom et al., "Antibody phage display technology and its applications," Immunotechnology (1998) 4(1):1-20.
Hoogenboom et al., "By-passing immunisation. Human antibodies from synthetic repertoires of germline VH gene segments rearranged in vitro," J Mol Biol (1992) 227(2):381-388.
Hoogenboom et al., "Multi-subunit proteins on the surface of filamentous phage: methodologies for displaying antibody (Fab) heavy and light chains," Nucleic Acids Research (1991) 19(15):4133-4137.
Hoogenboom et al., "Natural and designer binding sites made by phage display technology," Immunol Today (2000) 21(8):371-378.
Hoogenboom, "Designing and optimizing library selection strategies for generating high-affinity antibodies," Trends Biotechnol (1997) 15(2):62-70.
Hoogenboom, "Selecting and screening recombinant antibody libraries," Nature Biotechnology (2005) 23(9):1105-1116.

(56) References Cited

OTHER PUBLICATIONS

Hooper, "Rabies Virus," Manual of Clinical Laboratory Immunology (1997) 5:755-760.
Houshmand et al., "Use of bacteriophage T7 displayed peptides for determination of monoclonal antibody specificity and biosensor analysis of the binding reaction," Anal Biochem (1999) 268(2):363-370.
Houston Jr et al., "Use of a Conformationally Restricted Secondary Structural Element to Display Peptide Libraries: A Two-stranded α-Helical Coiled-coil Stabilized by Lactam Bridges," J Mol Biol (1996) 262:270-282.
Huang et al., "Role of Bone Marrow-Derived Cells in Presenting MHC Class I-Restricted Tumor Antigens," Science (1994) 264:961-965.
Hudziak et al., "p185$^{HER2}$ Monoclonal Antibody Has Antiproliferative Effects in Vitro and Sensitizes Human Breast Tumor Cells to Tumor Necrosis Factor," Mol Cell Biol (1989) 9(3):1165-1172.
Huls et al., "A recombinant, fully human monoclonal antibody with antitumor activity constructed from phage-displayed antibody fragments," Nat Biotechnol (1999) 17(3):276-281.
Huls et al., "Antitumor Immune Effector Mechanisms Recruited by Phage Display-derived Fully Human IgG1 and IgA1 Monoclonal Antibodies," (1999) Cancer Res 59:1778-5784.
Huse et al., "Generation of a Large Combinatorial Library of the Immunoglobulin Repertoire in Phage Lambda," Science (1989) 246(4935):1275-1281.
Huse et al., "Purification of antibodies by affinity chromatography," J Biochem Biophys Methods (2002) 51:217-231.
Hwang et al., "Immunogenicity of engineered antibodies," Methods (2005) 36:3-10.
Hynes, "Cell adhesion: old and new questions," Trends Cell Biol (1999) 9(12):M33-M37.
Inaba et al., "Dendritic Cells Pulsed with Protein Antigens in Vitro Can Prime Antigen-specific, MHC-restricted T Cells in Situ," J Exp Med (1990) 172:631-640.
Inaba et al., "Distinct Mechanisms of Neonatal Tolerance Induced by Dendritic Cells and Thymic B Cells," J Exp Med (1991) 173:549-559.
Important information regarding oral proceedings, dated Jul. 16, 2014, 3 pages.
Inlay et al., "Essential roles of the κ light chain intronic enhancer and 3' enhancer in κ rearrangement and demethylation," Nature Immunology (2002) 3-5:463-468.
Inlay et al., "Roles of the Ig κ light chain intronic and 3' enhancers in Igκ somatic hypermutation," Journal of Immunology (2006) 177:1146-1151.
Ishii et al., "TANK-binding kinase-1 delineates innate and adaptive immune responses to DNA vaccines," Nature (2008) 451:725-730.
Itoh et al., "The Polypeptide Encoded by the cDNA for Human Cell Surface Antigen Fas Can Mediate Apoptosis," Cell (1991) 66:233-243.
Jacob et al., "Activity of DNA vaccines encoding self or heterologous Her-2/neu in Her-2 or neu transgenic mice," Cellular Immunology (2006) 240:96-106.
Jacob et al., "Combining human and rat sequences in Her-2 DNA vaccines blunts immune tolerance and drives antitumor immunity," Cancer Research (2010) Cancer Res 70(1):119-128.
Jain et al., "Engineering antibodies for clinical applications," TRENDS in Biotechnology (2007) 25(7):309-316.
Jakobovits et al., "Analysis of homozygous mutant chimeric mice: Deletion of the immunoglobulin heavy-chain joining region blocks B-cell development and antibody production," Proc Natl Acad Sci USA (1993) 90:2551-2555.
Jakobovits et al., "From XenoMouse technology to panitumumab, the first fully human antibody product from transgenic mice," Nat Biotechnol (2007) 25(10):1134-1143.
Jakobovits et al., "Germ-line transmission and expression of a human-derived yeast artificial chromosome," Nature (1993) 362(6417):255-258.

Janeway, "Immuno biology the immune system in health and disease," 4$^{th}$ edition (1999) 21 pages.
Janeway, "The development and survival of lymphocytes," pp. 275-290.
Janeway's immunology, "Antigen presentation to T lymphocytes," (2012) 31 pages.
Jechlinger, "Optimization and delivery of plasmid DNA for vaccination," Expert Rev Vaccines (2006) 5(6):803-825.
Jeffers et al., "Enhanced Tumorigenicity and Invasion-Metastasis by Hepatocyte Growth Factor/Scatter Factor-Met Signalling in Human Cells Concomitant with Induction of the Urokinase Proteolysis Network," Mol Cell Biol (1996) 16(3):1115-1125.
Jespers et al., "Guiding the selection of human antibodies from phage display repertoires to a single epitope of an antigen," Biotechnology (N Y) (1994) 12(9):899-903.
Jiang et al., "A novel strategy for generation of monoclonal antibodies from single B cells using RT-RCR technique and in vitro expression," Biotechnol Prog (2006) 22(4):979-988.
Jin et al., "A rapid and efficient single-cell manipulation method for screening antigen-specific antibody-secreting cells from human peripheral blood," Nature Medicine (2009) 15(9):1088-1093.
Johansson et al., "Evidence for Involvement of Activin A and Bone Morphogenetic Protein 4 in Mammalian Mesoderm and Hematopoietic Development," Mol Cell Biol (1995) 15(1):141-151.
Jolly et al., "Rapid methods for the analysis of immunoglobulin gene hypermutation: application to transgenic and gene targeted mice," Nucleic Acids Research (1997) 25(10):1913-1919.
Jonasson et al., "Genetic design for facilitated production and recovery of recombinant proteins in *Escherichia coli*," Biotechnol Appl Biochem (2002) 35:91-105.
Jones et al., "High Level Expression of Recombinant IgG in the Human Cell Line PER.C6," Biotechnol Prog (2003) 19:163-168.
Kang et al., "Linkage of recognition and replication functions by assembling combinatorial antibody Fab libraries along phage surfaces," Proc Natl Acad Sci USA (1991) 88:4363-4366.
Kakitani et al., "A novel transgenic chimaeric mouse system for the rapid functional evaluation of genes encoding secreted proteins," Nucleic Acids Research (2005) 33(9):e85 8 pages.
Kasprzyk et al., "Therapy of an Animal Model of Human Gastric Cancer Using a Combination of Anti-erbB-2 Monoclonal Antibodies," Cancer Res (1992) 52:2771-2776.
Kato et al., "Cell activation by CpG ODN leads to improved electrofusion in hybridoma production," J Immunological Methods (2011) 373:102-110.
Kaufman et al., "Amplification and Expression of Sequences Cotransfected with a Modular Dihydrofolate Reductase Complementary DNA Gene," J Mol Biol (1982) 159:601-621.
Kaufman, "Overview of Vector Design for Mammalian Gene Expression," Mol Biotechnol (2000) 16(2):151-160.
Keller et al., "Hematopoietic Commitment during Embryonic Stem Cell Differentiation in Culture," Mol Cell Biol (1993) 13(1): 473-486.
Kelley et al., "Antigen binding thermodynamics and antiproliferative effects of chimeric and humanized anti-p185HER2 antibody Fab fragments," Biochemistry (1992) 31(24):5434-541.
Kim et al., "Characterization of chimeric antibody producing CHO cells in the course of dihydrofolate reductase-mediated gene amplification and their stability in the absence of selective pressure," Biotechnol Bioeng (1998) 58(1):73-84.
Kim et al., "Comparative analyses of complex formation and binding sites between human tumor necrosis factor-alpha and its three antagonists elucidate their different neutralizing mechanisms," J Mol Biol (2007) 374:1374-1388.
Kim et al., "Subspecialization of CXCR5$^+$T Cells: B helper activity is focused in a germinal center-localized subset of CXCR5$^+$ T cells," J Exp Med (2001) 193(12):1373-1381.
Klagsbrun et al., "Vascular endothelial growth factor and its receptors," Cytokine Growth Factor Rev (1996) 7(3):259-270.
Kling et al., "Big Pharma vies for mice," Nature Biotechnology (2007) 25:613-614.

(56) References Cited

OTHER PUBLICATIONS

Klitz et al., "New HLA haplotype frequency reference standards: High-resolution and large sample typing of HLA DR-DQ haplotypes in a sample of European Americans," Tissue Antigens (2003) 62:296-307.
Klohn et al., "IBC's 23$^{rd}$ annual antibody engineering, 10$^{th}$ annual antibody therapeutics international conferences and the 2012 annual meeting of the antibody society," mAbs (2013) 5(2):178-201.
Klotz et al., "Somatic hypermutation of a $\lambda_2$ transgene under the control of the λ enhancer or the heavy chain intron enhancer," Journal of Immunology (1996) 157:4458-4463.
Klotz et al., "Somatic hypermutation of an artificial test substrate within an Igκ transgene," The Journal of Immunology (1998) 161:782-790.
Kohler et al., "Continuous cultures of fused cells secreting antibody of predefined specificity," Nature (1975) 256:495-497.
Kong et al., "A λ3' enhancer drives active and untemplated somatic hypermutation of a $\lambda_1$ transgene," The Journal of Immunology (1998) 161:294-301.
Koide et al., "The Fibronectin Type III Domain as a Scaffold for Novel Binding Proteins," J Mol Biol (1998) 284:1141-1151.
Kontermann, "Dual targeting strategies with bispecific antibodies," MAbs (2012) 4(2):182-97.
Koochekpour et al., "Met and Hepatocyte Growth Factor/Scatter Factor Expression in Human Gliomas," Cancer Res (1997) 57:5391-5398.
Koopman et al., "Annexin V for Flow Cytometric Detection of Phosphatidylserine Expression on B Cells Undergoing Apoptosis," Blood (1994) 84(5):1415-1420.
Korndorfer et al., "Crystallographic analysis of an "anticalin" with tailored specificity for fluorescein reveals high structural plasticity of the lipocalin loop region," Proteins (2003) 53(1):121-129.
Korndorfer et al., "Structural Mechanism of Specific Ligand Recognition by a Lipocalin Tailored for the Complexation of Digoxigenin," J Mol Biol (2003) 330:385-396.
Kortt et al., "Dimeric and trimeric antibodies: high avidity scFvs for cancer targeting," Biomol Eng (2001) 18(3):95-108.
Kramer et al., "A novel helper phage that improves phage display selection efficiency by preventing the amplification of phages without recombinant protein," Nucleuic Acids Research (2003) 31(11):e59.
Krebs et al., "High-throughput generation and engineering of recombinant human antibodies," J Immunol Methods (2001) 254(1-2):67-84.
Krosen et al., "Bispecific antibodies for treatment of cancer in experimental animal models and man," Advanced Drug Delivery Reviews (1998) 31:105-129.
Kruse et al., "Tissue Culture, Methods and Applications," Academic Press, New York (1973) p. 868.
Ku et al, "Alternate protein frameworks for molecular recognition," Proc Natl Acad Sci USA (1995) 92:6552-6556.
Kuhlman et al., "Design of a Novel Globular Protein Fold with Atomic-Level Accuracy," Science (2003) 302:1364-1368.
Kunkel et al., "Rapid and efficient site-specific mutagenesis without phenotypic selection," Proc Natl Acad Sci USA (1985) 82:488-492.
Kwakkenbos et al., "Generation of stable monoclonal antibody-producing BCR+ human memory B cells by genetic programming," Nat Med (2010) 16(1):123-128.
Kwaks et al., "Employing epigenetics to augment the expression of the therapeutic proteins in mammalian cells," TRENDS in Biotechnology (2006) 24(3):137-142.
Kwaks et al., "Identification of anti-repressor elements that confer high and stable protein production in mammalian cells," Nat Biotechnol (2003) 21(5):553-558.
Lang et al., "Immunotherapy with Human Monoclonal Antibodies," J Immunol (1993) 151(1):466-472.
Larbouret et al., "In vivo therapeutic synergism of anti-epidermal growth factor receptor and anti-HER2 monoclonal antibodies against pancreatic carcinomas," Clin Cancer Res (2007) 13(11):3356-3362.
Larrick et al., "Producing proteins in transgenic plants and animals," Curr Opin Biotechnol (2001) 12(4):411-418.
Lazar et al., "A molecular immunology approach to antibody humanization and functional optimization," Molecular Immunology (2007) 44:1986-1998.
Lefranc et al., "Nomenclature of the human immunoglobulin kappa (IGK) genes," Exp Clin Immunogenet (2001) 18:161-174.
Lekkerkerker et al., "Phage antibodies against human dendritic cell subpopulations obtained by flow cytometry-based selection on freshly isolated cells," J Immunol Methods (1999) 231(1-2):53-63.
Lenz et al., "Expression of heterobispecific antibodies by genes transfected into producer hybridoma cells," Gene (1990) 87(2):213-218.
Li et al., "Stable expression of three genes from a tricistronic retroviral vector containing a picornavirus and 9-nt cellular internal ribosome entry site elements," J Virol Methods (2004) 115(2):137-144.
Lie et al., "Advances in quantitative PCR technology: 5' nuclease assays," Current Opinion in Biotechnology (1998) 9:43-48.
Lindhofer et al., "Preferential species-restricted heavy/light chain pairing in rat/mouse quadromas. Implications for a single-step purification of bispecific antibodies," J Immunol (1995) 55(1):219-225.
Ling et al., "Modulation of the murine immune response to human IgG by complexing with monoclonal antibodies," Immunology (1987) 62:1-6.
Little et al., "Human antibody libraries in *Escherichia coli*," J Biotechnol (1995) 41(2-3):187-195.
Little, "Recombinant Antibodies for Immunotherapy," Cambridge University Press (2009) 1$^{st}$ edition, 21 pages.
Lobato et al., "Intracellular antibodies and challenges facing their use as therapeutic agents," Trends Mol Med (2003) 9(9):390-396.
Lofgren et al., "Comparing ELISA and surface plasmon resonance for assessing clinical immunogenicity of panitumumab," The Journal of Immunology (2007) 178:7467-7472.
Logtenberg, "Antibody cocktails: next-generation biopharmaceuticals with improved potency," Trends Biotechnol (2007) 25(9):390-394.
Lonberg et al., "Antigen-specific human antibodies from mice comprising four distinct genetic modifications," Nature (1994) 368:856-859.
Lonberg, "Human antibodies from transgenic animals," Nature Biotechnology (2005) 23(9):1117-1125.
Lonberg, "Fully human antibodies from transgenic mouse and phage display platforms," Curr Opin Immunol (2008) 20(4):450-459.
Love et al., "A microengraving method for rapid selection of single cells producing antigen-specific antibodies," Nature Biotechnology (2006) 24(6):703-707.
Lu et al., "Acquired antagonistic activity of a bispecific diabody directed against two different epitopes on vascular endothelial growth factor receptor 2," J Immunol Methods (1999) 230(1-2):159-171.
Lu et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," Cancer Res (2001) 61:7002-7008.
Lu et al., "Identification of the Residues in the Extracellular Region of KDR Important for Interaction with Vascular Endothelial Growth Factor and Neutralizing Anti-KDR Antibodies," J Biol Chem (2000) 275(19):14321-14330.
Lu et al., "Selection of High Affinity Human Neutralizing Antibodies to VEGFR2 From a Large Antibody Phage Display Library for Antiangiogenesis Therapy," Int. J. Cancer (2002) 97:393-399.
Lucas et al., "High-level production of recombinant proteins in CHO cells using a dicistronic DHFR intron expression vector," Nucleic Acids Res (1996) 24(9):1774-1779.
Ma et al., "Assembly of monoclonal antibodies with IgGI and IgA heavy chain domains in transgenic tobacco plants," Eur J Immunol (1994) 24:131-138.

(56) References Cited

OTHER PUBLICATIONS

Macatonia et al., "Dendritic cells produce IL-12 and direct the development of Th1 cells from naive CD4+ T cells," J Immunol (1995) 154(10):5071-5079.
Macatonia et al., "Primary stimulation by dendritic cells induces antiviral proliferative and cytotoxic T cell responses in vitro," J Exp Med (1989) 169(4):1255-1264.
MacDonald et al., "Precise and in situ genetic humanization of 6 Mb of mouse immunoglobulin genes," Proc Natl Acad Sci U S A (2014) 111(14):5147-5152.
Macejak et al., "Internal initiation of translation mediated by the 5' leader of a cellular mRNA," Nature (1991) 353(6339):90-94.
Manen et al., "A sensitive reporter gene system using bacterial luciferase based on a series of plasmid cloning vectors compatible with derivatives of pBR322," Gene (1997) 186:197-200.
Manz et al., "Maintenance of serum antibody levels," Annu Rev Immunol (2005) 23:367-386.
Mao et al., "Activation of EGFP expression by cre-mediated excision in a new ROSA26 reporter mouse strain," Blood (2001) 97(1):324-326.
Marasco, "Intrabodies as antiviral agents," Curr Top Microbiol Immunol (2001) 260:247-270.
Marks et al., "By-passing Immunization Human Antibodies from V-gene Libraries Displayed on Phage," J Mol Biol (1991) 222:581-597.
Marks, "Deciphering antibody properties that lead to potent botulinum neurotoxin neutralization," Mov Disord (2004) 19(Suppl 8):S101-S108.
Marvin et al., "Recombinant approaches to IgG-like bispecific antibodies," Acta Pharmacol Sin (2005) 26(6):649-658.
Massengale et al., "CD20-negative relapse of cutaneous B-cell lymphoma after anti-CD20 monoclonal antibody therapy," J Am Acad Dermatol (2002) 46(3):441-443.
Matsuda et al., "The Complete Nucleotide Sequence of the Human Immunoglobulin Heavy Chain Variable Region Locus," J Exp Med (1998) 188(11):2151-2162.
Mattheakis et al., "An in vitro polysome display system for identifying ligands from very large peptide libraries," Proc Natl Acad Sci U S A (1994) 91:9022-9026.
Mayer, "A new set of useful cloning and expression vectors derived from pBlueScript," Gene (1995) 163(1):41-46.
McBurney et al., "Evidence for Repeat-Induced Gene Silencing in Cultured Mammalian Cells: Inactivation of Tandem Repeats of Transfected Genes," Exp Cell Res (2002) 274(1):1-8.
McCafferty et al., "Antibody engineering," (1996) Oxford University Press 178 pages.
McClanahan et al., "Hematopoietic Growth Factor Receptor Genes as Markers of Lineage Commitment During in Vitro Development of Hematopoietic Cells," Blood (1993) 81(11):2903-2915.
McConnell et al., "Tendamistat as a Scaffold for Conformationally Constrained Phage Peptide Libraries," J Mol Biol (1995) 250:460-470.
McGinnes et al., "B-Lineage colonies from normal, human bone marrow are initiated by B cells and their progenitors," Blood (1991) 77(5):961-970.
Meijer et al., "Isolation of human antibody repertoires with preservation of the natural heavy and light chain pairing," J Mol Biol (2006) 358:764-772.
Mendel et al., "The Angiogenesis Inhibitor SU5416 Has Long-lasting Effects on Vascular Endothelial Growth Factor Receptor Phosphorylation and Function," Clin Cancer Res (2000) 6:4848-4858.
Merchant et al., "An efficient route to human bispecific IgG," Nat Biotechnol (1998) 16(7):677-681.
Merus prior art P61090-/P6498-/P67824, dated Jul. 12, 2016, 4 pages.
Merus prior art P61090-/P6498-/P67824, dated Oct. 18, 2016, 39 pages.
Merus prior art P85261, dated Jul. 19, 2016, 4 pages.
Merus prior art P85261, dated Oct. 21, 2016, 17 pages.
Merus prior art P99390, dated Sep. 30, 2016, 9 pages.
Meyer et al., "The importance of the 3'-enhancer region in immunoglobulin χ gene expression," Nucleic Acids Research (1990) 18(19):5609-5615.
Meyer et al., "The Igκ 3'—enhancer triggers gene expression in early B lymphocytes but its activity is enhanced on B cell activation," International Immunology (1996) 8(10):1561-1568.
Middendorp et al., "Cellular maturation defects in Bruton's tyrosine kinase-deficient immature B cells are amplified by premature B cell receptor expression and reduced by receptor editing," The Journal of Immunology (2004) 172:1371-1379.
Middendorp et al., "Impaired precursor cell differentiation in Bruton's tyrosine kinase-deficient mice," The Journal of Immunology (2002) 168:2695-2703.
Mirick et al., A review of human anti-globulin antibody (HAGA, HAMA, HACA, HAHA) responses to monoclonal antibodies not four letter words, QJ Nucl Med Mol Imaging (2004) 48:251-257.
Mohapatra et al., "Designer monoclonal antibodies as drugs: the state of the art," Expert Rev Clin Immunol (2008) 4(3):305-307.
Morimoto et al., "High level expression of a human rabies virus-neutralizing monoclonal antibody by a rhabdovirus-based vector," J Immunol Methods (2001) 252(1-2):199-206 (Abstract).
Morrison, "Transfectomas Provide Novel Chimeric Antibodies," Science (1985) 229(4719):1202-1207.
Mostoslavsky et al., "Asynchronous replication and allelic exclusion in the immune system," Nature (2001) 414:221-225.
Murakami et al., "Splenic CD19 cd35$^+$B220$^+$ cells function as an inducer of follicular dendritic cell network formation," Blood (2007) 110(4):1215-1224.
Muyldermans, "Single domain camel antibodies: current status," J Biotechnol (2001) 74(4):277-302.
Nahta et al., "The HER-2-Targeting Antibodies Trastuzumab and Pertuzumab Synergistically Inhibit the Survival of Breast Cancer Cells," Cancer Res (2004) 64:2343-2346.
Nair et al., "Induction of Primary, Antiviral Cytotoxic, and Proliferative Responses with Antigens Administered via Dendritic Cells," J Virol (1993) 67(7):4062-4069.
Nanbru et al., "Alternative Translation of the Proto-oncogene c-myc by an Internal Ribosome Entry Site," J Biol Chem (1997) 272(51):32061-32066.
Nelson et al., "Development trends for human monoclonal antibody therapeutics," Nat Rev Drug Discov (2010) 9(10):767-774.
Nemazee, "Receptor Editing in B Cells," Advances in Immunology (2000)74:89-126.
Nemazee, "Receptor editing in lymphocyte development and central tolerance," Nat Rev Immunol (2006) 6(10):728-740.
Neufeld et al., "Vascular endothelial growth factor (VEGF) and its receptors," FASEB J (1999) 13(1):9-22.
Ngo et al., "Identification of functional synergism between monoclonal antibodies. Application to the enhancement of plasminogen activator inhibitor-1 neutralizing effects," FEBS (1997) 416:373-376.
Nicholson et al., "Antibody repertoires of four- and five-feature translocus mice carrying human immunoglobulin heavy chain and kappa and lambda light chain yeast artificial chromosomes," J Immunol (1999) 163(12):6898-6906.
Nikolic et al., "A subfraction of B220$^+$ cells in murine bone marrow and spleen does not belong to the B cell lineage but has dendritic cell characteristics," Eur J Immunol (2002) 32:686-692.
Nissim et al., "Antibody fragments from a 'single pot' phage display library as immunochemical reagents," EMBO J (1994) 13(3):692-698.
Nord et al., "A combinatorial library of an a-helical bacterial receptor domain," Protein Engineering (1995) 8(6):601-608.
Nord et al., "Recombinant human factor VIII-specific affinity ligands selected from phage-displayed combinatorial libraries of protein A," Eur J Biochem (2001) 268:4269-4277.
Norderhaug et al., "Balanced expression of single subunits in a multisubunit protein, achieved by cell fusion of individual transfectants," Eur J Biochem (2002) 269:3205-3210.
Novimmune SA, "Therapeutic Bispecific Antibodies, The Fully-Human Kappa-Lambda Body: Simple, Stable, Smart," (2013) 2 pages.

(56) References Cited

OTHER PUBLICATIONS

Novobrantseva et al., "Rearrangement and expression of immunoglobulin light chain genes can precede heavy chain expression during normal B cell development in mice," J Exp Med (1999) 189(1):75-87.
Nowakowski et al., "Potent neutralization of botulinum neurotoxin by recombinant oligoclonal antibody," Proc Natl Acad Sci U S A (2002) 99(17):11346-11350.
Nuemann et al., "Gene transfer into mouse lyoma cells by electroporation in high electric fields," EMBO J (1982) 1(7):841-845.
O'Brien et al., "Somatic hypermutation of an immunoglobulin transgene in κ transgenic mice," Nature (1987) 326:405-409.
Odegard et al., "Targeting of somatic hypermutation," Nat Rev Immunol (2006) 6(8):573-583.
Ogunniyi et al., "Screening individual hybridomas by microengraving to discover monoclonal antibodies," Nature Protocols (2009) 4(5):767-782.
Oh et al., "Homeotic gene Antennapedia mRNA contains 5'-noncoding sequences that confer translational initiation by internal ribosome binding," Genes Dev (1992) 6(9):1643-1653.
Opposition against European Patent in EP 2314629 from Merus B.V., filed May 18, 2013, 13 pages.
Orban et al., "Tissue- and site-specific DNA recombination in transgenic mice," Proc Natl Acad Sci USA (1992) 89:6861-6865.
Padlan, "A possible procedure for reducing the immunogenicity of antibody variable domains while preserving their ligand-binding properties," Molecular Immunology (1991) 28(4-5):489-498.
Pasqualucci et al., "BCL-6 mutations in normal germinal center B cells: Evidence of somatic hypermutation acting outside Ig loci," Proc Natl Acad Sci USA (1998) 95:11816-11821.
Patel et al., "An improved assay for antibody dependent cellular cytotoxicity based on time resolved fluorometry," J Immunol Methods (1995)184(1):29-38.
Pau et al., "The human cell line PER.C6 provides a new manufacturing system for the production of influenza vaccines," Vaccines (2001) 19:2716-2721.
Peeters et al., "Production of Antibodies and Antibody Fragments in Plants," Vaccine (2001) 19 (17-19):2756-2761.
Pelanda et al., "A prematurely expressed Igκ transgene, but not a VκJκ gene segment targeted into the Igκ locus, can rescue B cell development in λ5-deficient mice," Immunity (1996) 5:229-239.
Peled et al., "The biochemistry of somatic hypermutation," Annu Rev Immunol (2008) 26:481-511.
Perrin et al., "In vitro rabies vaccine potency appraisal by ELISA: advantages of the immunocapture method with a neutralizing anti-glycoprotein monoclonal antibody," Biologicals. (1990) 18(4):321-330.
Persic et al., "An integrated vector system for the eukaryotic expression of antibodies or their fragments after selection from phage display libraries," Gene (1997) 187(1):9-18.
Persson et al., "A focused antibody library for improved hapten recognition," J Mol Biol (2006) 357:607-620.
Phan et al., "High affinity germinal center B cells are actively selected into the plasma cell compartment," J Exp Med (2006) 203(11):2419-2424.
Phelps et al., "Expression and characterization of a chimeric bifunctional antibody with therapeutic applications," J Immunol (1990) 145(4):1200-1204.
Pluckthun et al., "In vitro selection and evolution of proteins," Adv Protein Chem (2000) 55:367-403.
Ponsel et al., "High Affinity, developability and functional size: the holy grail of combinatorial antibody library generation," Molecules (2011) 16:3675-3700.
Pollock et al., "Transgenic milk as a method for the production of recombinant antibodies," J Immunol Methods (1999) 231(1-2):147-157.
Popov et al., "A human immunoglobulin λ locus is similarly well expressed in mice and humans," J Exp Med (1999) 189(10):1611-1619.

Porgador et al., "Bone Marrow-generated Dendritic Cells Pulsed with a Class I-restricted Peptide Are Potent Inducers of Cytotoxic T Lymphocytes," J Exp Med (1995) 182(1): 255-260.
Poulsen et al., "Limits for antibody affinity maturation and repertoire diversification in hypervaccinated humans," The Journal of Immunology (2011) 187:4229-4235.
Prak et al., "Light chain replacement: A new model for antibody gene rearrangement," J Exp Med (1995) 182:541-548.
Presta et al., "Engineering of therapeutic antibodies to minimize immunogenicity and optimize function," Advanced Drug Delivery Reviews (2006) 58:640-656.
Queen et al., "A humanized antibody that binds to the interleukin 2 receptor," Proc Natl Acad Sci USA (1989) 86:10029-10033.
Radic et al., "Ig H and L chain contributions to autoimmune specificities," J Immunol (1991) 146(1):176-182.
Rajewsky et al., "Perspectives series: molecular medicine in genetically engineered animals," J Clin Invest (1996) 98(3):600-603.
Ravn et al., "By-passing in vitro screening—next generation sequencing technologies applied to antibody display and in silico candidate selection," Necleic Acids Research (2010) 38(21):e193.
Rebar et al., "Phage display methods for selecting zinc finger proteins with novel DNA-binding specificities," Methods Enzymol (1996) 267:129-149.
Reddy et al., "Monoclonal antibodies isolated without screening by analyzing the variable-gene repertoire of plasma cells," Nature Biotechnology (2010) 28(9):965-971.
Reddy et al., "Systems analysis of adaptive immunity by utilization of high-throughput technologies," Current Opinion in Biotechnology (2011) 22:584-589.
Rees et al., "Bicistronic Vector for the Creation of Stable Mammalian Cell Lines that Predisposes All Antibiotic-Resistant Cells to Express Recombinant Protein," BioTechniques (1996) 20:102-110.
Reiter et al., "An Antibody Single-domain Phage Display Library of a Native Heavy Chain Variable Region: Isolation of Functional Single-domain VH Molecules with a Unique Interface," J Mol Biol (1999) 290:685-698.
Repp et al., "Phase I clinical trial of the bispecific antibody MDX-H210 (anti-FcgammaRI x anti-HER-2/neu) in combination with Filgrastim (G-CSF) for treatment of advanced breast cancer," Br J Cancer (2003) 89(12):2234-2243.
Retter et al., "Receptor editing occurs frequently during normal B cell development," J Exp Med (1998) 188(7):1231-1238.
Retter et al., "Receptor editing: genetic reprogramming of autoreactive lymphocytes," Cell Biochemistry and Biophysics (1999) 31:81-88.
Riechmann et al., "Novel folded protein domains generated by combinatorial shuffling of polypeptide segments," Proc Natl Acad Sci U S A (2000) 97(18):10068-10073.
Rickert et al., "B lymphocyte-specific, cre-mediated mutagenesis in mice," Nucleic Acids Research (1997) 25(6):1317-1318.
Ritchie et al., "Allelic exclusion and control of endogenous immunoglobulin gene rearrangement in kappa transgenic mice," Nature (1984) 312(5994):517-520.
Roberts et al., "RNA-peptide fusions for the in vitro selection of peptides and proteins," Proc Natl Acad Sci USA (1997) 94:12297-12302.
Roholt et al., "Antibodies of limited heterogeneity: L chains of a single mobility," Immunochemistry (1970) 7(4):329-340.
Roitt et al., "Anti-idiotypes as surrogate antigens: structural considerations," Immunol Today (1985) 6(9):265-267.
Roitt, Immunology translation, (2000) 3 pages.
Rojas et al., "Phage antibody fragments library combining a single human light chain variable region with immune mouse heavy chain variable regions," J Biotechnol (2002) 94(3):287-298.
Rong et al., "Tumorigenesis induced by coexpression of human hepatocyte growth factor and the human met protooncogene leads to high levels of expression of the ligand and receptor," Cell Growth Differ (1993) 4(7):563-569.
Rong et al., "Tumorigenicity of the met Proto-Oncogene and the Gene for Hepatocyte Growth Factor," Mol Cell Biol (1992) 12(11):5152-5158.

(56) References Cited

OTHER PUBLICATIONS

Rosenberg et al., "T7Select® Phage Display System: A powerful new protein display system based on bacteriophage T7," (1996) 7 pages.
Rottgen et al., "A human pancreatic secretory trypsin inhibitor presenting a hypervariable highly constrained epitope via monovalent phagemid display," Gene (1995) 164:243-250.
Ruuls et al., "Novel human antibody therapeutics: The age of the Umabs," Biotechnol journal (2008) 3:1157-1171.
Sanger et al., "DNA sequencing with chain-terminating inhibitors," Proc Natl Acad Sci USA (1977) 74(12):5463-5467.
Santini et al., "Efficient Display of an HCV cDNA Expression Library as C-terminal Fusion to the Capsid Protein D of Bacteriophage Lambda," J Mol Biol (1998) 282:125-135.
Sasaki et al., "Canonical NF-κB activity, dispensable for B cell development, replaces BAFF-receptor signals and promotes B cell proliferation upon activation," Immunity (2006) 24:729-739.
Schaffitzel et al., "In Vitro Selection and Evolution of Protein-Ligand Interactions by Ribosome Display" Protein-Ligand Interactions and Ribosome Display (2001) 27:517-548.
Schaffitzel et al., "Ribosome display: an in vitro method for selection and evolution of antibodies from libraries," J Immunol Methods (1999) 231(1-2):119-135.
Schmidlin et al., "New insights in the regulation of human B cell differentiation," Trends Immunol (2009) 30(6):277-285.
Schlehuber et al., "Tuning ligand affinity, specificity, and folding stability of an engineered lipocalin variant—a so-called 'anticalin'—using a molecular random approach," Biophys Chem (2002) 96(2-3):213-328.
Schmitz et al., "Phage Display: A Molecular Tool for the Generation of Antibodies—A Review," Placenta (2000) 21(A):S106-112.
Schnieke et al., "Human factor IX transgenic sheep produced by transfer of nuclei from transfected fetal fibroblasts," Science (1997) 278(5346):2130-2133.
Schoonjans et al., "A new model for intermediate molecular weight recombinant bispecific and trispecific antibodies by efficient heterodimerization of single chain variable domains through fusion to a Fab-chain," Biomol Eng (2001) 17(6):193-202.
Scott, "Mice with a human touch," Nat Biotechnol (2007) 25(10):1075-1077.
Segal et al., "Introduction: bispecific antibodies," J Immunol Methods (2001) 248(1-2):1-6.
Seibler et al., "Rapid generation of inducible mouse mutants," Nucleic Acids Research (2003) 31(4):e12.
Shaffer et al., "In vivo occupancy of the κ light chain enhancer in primary pro- and pre-B cells: A model for κ locus activation," Immunity (1997) 6:131-143.
Sharpe et al., "Somatic hypermutation of immunoglobulin χ may depend on sequences 3' of Cχ and occurs on passenger transgenes," The EMBO Journal (1991) 10(8):2139-2145.
Shapiro-Shelef et al., "Regulation of plasma-cell development," Nature Review Immunol (2005) 5:230-242.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem (2001) 276(9):6591-6604.
Shvarts et al., "A senescence rescue screen identifies BCL6 as an inhibitor of anti-proliferative p19$^{ARF}$-P53 signaling," Genes & Development (2002) 16:681-686.
Sidhu et al., "Phage-displayed antibody libraries of synthetic heavy chain complementarity determining regions," J Mol Biol (2004) 338(2):299-310.
Simmons et al., "Expression of full-length immunoglobulins in *Escherichia coli*: rapid and efficient production of aglycosylated antibodies," J Immunol Methods (2002) 263(1-2):133-147.
Singer, "Genes & Genomes: A changing perspective," University Sceince Books (1991) pp. 134-145.
Sirac et al., "Light chain inclusion permits terminal B cell differentiation and does not necessarily result in autoreactivity," PNAS (2006) 103(20):7747-7752.
Sirac et al., "Role of the monoclonal κ chain V domain and reversibility of renal damage in a transgenic model of acquired Fanconi syndrome," Blood (2006) 108:536-543.
Sirac et al., "Toward understanding renal fanconi syndrome: step by step advances through experimental models," Contrib Nephrol (2011) 169:247-261.
Sjolander et al., "Integrated Fluid Handling System for Biomolecular Interaction Analysis," Anal Chem (1991) 63:2338-2345.
Skerra. "'Anticalins': a new class of engineered ligand-binding proteins with antibody-like properties," J Biotechnol (2001) 74(4):257-275.
Smith et al., "A novel, native-format bispecific antibody triggering T-cell killing of B-cells is robustly active in mouse tumor models and cynomolgus monkeys," Sci Rep (2015) 5:17943.
Smith et al., "Characterization of a murine lymphokine distinct from interleukin 2 and interleukin 3 (IL-3) possessing a T-cell growth factor activity and a mast-cell growth factor activity that synergizes with IL-3," Proc Natl Acad Sci USA (1986) 83:1857-1861.
Smith et al., "Small Binding Proteins Selected from a Combinatorial Repertoire of Knottins Displayed on Phage," J Mol Biol (1998) 277:317-332.
Smith et al., "Rapid generation of fully human monoclonal antibodies specific to a vaccinating antigen," Nature Protocols (2009) 4(3):372-385.
Smith-Gill et al., "Contributions of immunoglobulin heavy and light chains to antibody specificity for lysozyme and two haptens," J Immunol (1987) 139:4135-4144.
Soriano, "Generalized IacZ expression with the ROSA26 cre reporter strain," Nature Genetics (1999) 21:70-71.
Spillner et al., "Paratope-based protein identification by antibody and peptide phage display," Anal Biochem (2003) 321(1):96-104.
M70120EPEIN opposition documents (P22), dated Jun. 21, 2016, 108 pages.
Spiridon et al., "Targeting multiple her-2 epitopes with monoclonal antibodies results in improved antigrowth activity of a human breast cancer cell line in vitro and in vivo," Clin Cancer Research (2002) 8:1720-1730.
Srinivas et al., "Cre reporter strains produced by targeted insertion of EYFP and ECFP into the ROSA26 locus," BMC Developmental Biology (2001) 1:4 8 pages.
Stein et al., "Translation of vascular endothelial growth factor mRNA by internal ribosome entry: implications for translation under hypoxia," Mol Cell Biol (1998) 18(6):3112-3119.
Stevens, "Human Antibody Discovery, VelocImmune—A novel platform," Pharma Focus Asia (2008) 8:72-74.
Stevenson et al., "DNA vaccines to attack cancer," PNAS (2004) 101(sup 2):14646-14652.
Stijlemans et al., "Efficient Targeting of Conserved Cryptic Epitopes of Infectious Agents by Single Domain Antibodies," J Biol Chem (2004) 279(2):1256-1261.
Stoneley et al., "C-Myc 5' untranslated region contains an internal ribosome entry segment," Oncogene (1998) 16, 423-428.
Storb et al., "Transgenic mice with μ and κ genes encoding antiphosphorylcholine antibodies," J Exp Med (1986) 164:627-641.
Storb et al., "Immunoglobulin transgenes as targets for somatic hypermutation," Int J Dev Biol (1998) 42:977-982.
Story et al., "Profiling antibody responses by multiparametric analysis of primary B cells," PNAS (2008) 105(46):17902-17907.
Strelkauskas et al., "Human monoclonal antibody: 2. Simultaneous expression of IgG and IgM with similar binding specificities by a human hybrid clone," Hybridoma (1987) 6(5):479-487.
Struhl et al., "High-frequency transformation of yeast: Autonomous replication of hybrid DNA molecules," Proc Natl Acad Sci USA (1979) 76( 3):1035-1039.
Szabo et al., "Surface plasmon resonance and its use in biomolecular interaction analysis (BIA)," Curr Opin Struct Biol (1995) 5(5):699-705.
Tada et al., "Expression and characterization of a chimeric bispecific antibody against fibrin and against urokinase-type plasminogen activator," J Biotechnol (1994) 33(2):157-174.

(56) References Cited

OTHER PUBLICATIONS

Tajiri et al., "Cell-microarray analysis of antigen-specific B-cells: single cell analysis of antigen receptor expression and specificity," Cytometry (2007) 71A:961-967.
Takahashi et al., "Role of thrombospondin-1 in hypoxia-induced migration of human vascular smooth muscle cells," Yakugaku Zasshi (2008) 128(3):377-383 (English abstract included).
Takai et al., "B cell stimulatory factor-2 is involved in the differentiation of cytotoxic T lymphocytes," J Immunol (1988) 140(2):508-512.
Takai et al., "Requirement for three distinct lymphokines for the induction of cytotoxic T lymphocytes from thymocytes," J Immunol (1986) 137(11):3494-3500.
Tan et al., "Superhumanized" Antibodies: Reduction of immunogenic potential by complementarity-determining region grafting with human germline sequences: Application to anti-CD28, The Journal of Immunology (2002) 169:1119-1125.
Tanaka et al., "De novo production of diverse intracellular antibody libraries," Nucleic Acids Res (2003) 31(5):e23.
Tanha et al., "Selection by phage display of llama conventional $V_H$ fragments with heavy chain antibody $V_HH$ properties," J Immunol Methods (2002) 263:97-109.
Taylor et al., "A transgenic mouse that expresses a diversity of human sequence heavy and light chain immunoglobulins," Nucleic Acids Research (1992) 20(23):6287-6295.
Thiebe et al., "The variable genes and gene families of the mouse immunoglobulin χ locus," Eur J Immunol (1999) 29:2072-2081.
Thomassen et al., "Large-scale production of $V_{HH}$ antibody fragments by *Saccharomyces cerevisiae*," Enzyme and Microbial Technology (2002) 30:273-278.
Thotakura et al., "Glycoprotein hormones: glycobiology of gonadotrophins, thyrotrophin and free α subunit," Glycoblology (1995) 5(1):3-10.
Throbsy et al., "Isolation and characterization of human monoclonal antibodies from individuals infected with west nile virus §," Journal of Virology (2006) 80(14):6982-6992.
Tiller et al., "Efficient generation of monoclonal antibodies from single human B cells by single cell RT-PCR and expression vector cloning," Journal of Immunological Methods (2008) 329:112-124.
Toki et al., "Analyses of T-cell differentiation from hemopoietic stem cells in the $G_O$ phase by an in vitro method," Proc Natl Acad Sci USA (1991) 88:7548-7551.
Tokimitsu et al., "Single lymphocyte analysis with a Microwell array chip," Cytometry (2007) 71A:1003-1010.
Torres et al., "Laboratory protocols for conditional gene targeting," Oxford University Press (1997) 15 pages.
Traggai et al., "An efficient method to make human monoclonal antibodies from memory B cells: potent neutralization of SARS coronavirus," Nature Medicine (2004) 10(8):871-875.
Transue et al., "Camel single-domain antibody inhibits enzyme by mimicking carbohydrate substrate," Proteins (1998) 32(4):515-522.
Urlaub et al., "Isolation of Chinese hamster cell mutants deficient in dihydrofolate reductase activity," Proc Natl Acad Sci USA (1980) 77(7): 4216-4220.
Vagner et al., "Alternative Translation of Human Fibroblast Growth Factor 2 mRNA Occurs by Internal Entry of Ribosomes," Mol Cell Biol (1995) 15(1): 35-44.
Vajdos et al., "Comprehensive functional maps of the antigen-binding site of an anti-ErbB2 antibody obtained with shotgun scanning mutagenesis," J Mol Biol (2002) 320(2):415-428.
Valenzuela et al., "High-throughput engineering of the mouse genome coupled with high-resolution expression analysis," Nat Biotechnol (2003) 21(6):652-659.
Van Den Berg, "Formulation and delivery of dermal DNA vaccines," Gildeprint Drukkerijen B.V (2009) 160 pages.
Van Den Beunken et al., "Building Novel Binding Ligands to B7.1 and B7.2 Based on Human Antibody Single Variable Light Chain Domains," J Mol Biol (2001) 310:591-601.
Van Der Heijden et al., "Structural and functional studies on a unique linear neutralizing antigenic site (G5) of the rabies virus glycoprotein," J Gen Virol (1993) 74(Pt 8):1539-1545.
Van Der Vuurst De Vries et al., "Dissecting the human peripheral B-cell compartment with phage display-derived antibodies," Immunology (1999) 98:55-62.
Vaughan et al., "Human antibodies with sub-nanomolar affinities isolated from a large non-immunized phage display library," Nat Biotechnol (1996) 14(3):309-314.
Verma et al., "Antibody engineering: Comparison of bacterial, yeast, insect and mammalian expression systems," J Immunol Methods (1998) 216:165-181.
Wang et al., "A T cell-independent antitumor response in mice with bone marrow cells retrovirally transduced with an antibody/Fc-gamma chain chimeric receptor gene recognizing a human ovarian cancer antigen," Nat Med (1998) 4(2):168-172.
Ward et al., "Binding activities of a repertoire of single immunoglobulin variable domains secreted from *Escherichia coli*," Nature (1989) 341:544-546.
Warnaar et al., "Purification of Bispecific F(ab')2 from Murine Trinoma OC/TR with Specificity for CD3 and Ovarian Cancer," Hybridoma (1994) 13(6):519-526.
Weeratna et al., "CPG ODN allows lower dose of antigen against hepatitis B surface antigen in BALB/c mice," Immunology and Cell Biology (2003) 81:59-62.
Weinberger et al., "Cellular interactions in the generation of cytolytic T lymphocyte responses: Role of Ia-positive splenic adherent cells in presentation of H-2 antigen," Proc Natl Acad Sci USA (1980) 77(10):6091-6095.
Weinberger et al., "Cellular interactions in the generation of cytolytic T lymphocyte responses. Analysis of the helper T cell pathway," Eur J Immunol (1981) 11(5):405-411.
Weiner et al., "Fully human therapeutic monoclonal antibodies," J Immunother (2006) 29(1):1-9.
Wen et al., "Tricistronic viral vectors co-expressing interleukin-12 (IL-12) and CD80 (B7-1) for the immunotherapy of cancer: Preclinical studies in myeloma," Cancer Gene Ther (2001) 8(5):361-370.
Whittington et al., "DNA vaccination controls Her-2$^+$ tumors that are refractory to targeted therapies," Cancer Res (2008) 68(18):7502-7511.
Wigler et al., "Biochemical Transfer of Single-Copy Eucaryotic Genes Using Total Cellular DNA as Donor," Cell (1978) 14:725-731.
Wilmut et al., "Basic techniques for transgenesis," J Reprod Fertil Suppl (1991) 43:265-275.
Wilmut et al., "Viable offspring derived from fetal and adult mammalian cells," Nature (1997) 385(6619):810-813.
Winter et al., "Insertion of 2 KB of bacteriophage DNA between an immunoglobulin promoter and leader exon stops somatic hypermutation in a κ transgene," Molecular Immunology (1997) 34(5):359-366.
Wrammert et al., "Rapid cloning of high-affinity human monoclonal antibodies against influenza virus," Nature (2008) 453:667-672.
Wright et al., "Effect of glycosylation on antibody function: implications for genetic engineering," Trends Biotechnol (1997) 15(1):26-32.
Wu et al., "Simultaneous targeting of multiple disease mediators by a dual-variable-domain immunoglobulin," Nature Biotechnology (2007) 25(11):1290-1297.
Wunderlich et al., "Generation of inducible Cre systems for conditional gene inactivation in mice," der Universitat zu Koln (2004) 413 pages.
X59315 Annotation, "IMGT/LIGM-DB sequence," (2016) 13 pages.
Xiang et al., "The downstream transcriptional enhancer, Ed, positively regulates mouse Igκ gene expression and somatic hypermutation," The Journal of Immunology(2008) 180:6725-6732.
Yang et al., "Control of gene conversion and somatic hypermutation by immunoglobulin promoter and enhancer sequences," J Exp Med (2006) 203(13):2919-2928.
Yarlin, "Fundamentals of Immunology," Meditsina (1999) 2 pages.

(56) References Cited

OTHER PUBLICATIONS

Ye et al., "Ultrabithorax and Antennapedia 5' Untranslated Regions Promote Developmentally Regulated Internal Translation Initiation," Mol Cell Biol (1997) 17(3):1714-1721.
Yelverton et al., "Rabies virus glycoprotein analogs: biosynthesis in *Escherichia coli*," Science (1983) 219(4585):614-620.
Yu et al., "An optimized electrofusion-based protocol for generating virus-specific human monoclonal antibodies," Journal of Immunological Methods (2008) 336:142-151.
Yoo et al., "Structural Requirements for Polymeric Immunoglobulin Assembly and Association with J Chain," J Biol Chem (1999) 274(47): 33771-33777.
Yoshio-Hoshino et al., "Establishment of a new interleukin-6 (IL-6) receptor inhibitor applicable to the gene therapy for IL-6-dependent tumor," Cancer Res (2007) 67(3):871-875.
Zacharchuk et al., "Programmed T lymphocyte death. Cell activation- and steroid-induced pathways are mutually antagonistic," J Immunol (1990) 145(12):4037-4045.
Zamai et al., "Optimal Detection of Apoptosis by Flow Cytometry Depends on Cell Morphology," Cytometry (1993)14:891-897.
Zhan-Zabel et al., "Development of stable cell lines for production or regulated expression using matrix attachment regions," J Biotech (2001) 87:29-42.
Zhu et al., "Inhibition of tumor growth and metastasis by targeting tumor-associated angiogenesis with antagonists to the receptors of vascular endothelial growth factor," Invest New Drugs (1999) 17(3):195-212.
Zhu et al., "Inhibition of Vascular Endothelial Growth Factor-induced Receptor Activation with Anti-Kinase Insert Domain-containing Receptor Single-Chain Antibodies from a Phage Display Library," Cancer Res (1998) 58:3209-3214.
Zhu et al., "Remodeling domain interfaces to enhance heterodimer formation," Protein Science (1997) 6:781-788.
Zou et al., "Generation of mouse strain that produces immunoglobulin κ chains with human constant regions," Science (1993) 262:1271-1274.
Zubler et al., "Theoretical and practical aspects of B-cells activation: murine and human systems," Immunological Reviews (1987) 99:281-299.
Abstract of Japanese patent application 2006109711, dated Apr. 27, 2006, 1 page.
First witness statement of Andrew Joseph Murphy, dated Oct. 2, 2015, 19 pages.
Mazor et al., "Isolation of engineered, full-length antibodies from libraries expressed in *Escherichia coli*," Nature Biotechnology (2007) 25(5):563-565.
Documents cited in opposition to Merus B.V. AU application No. 2009263082 by Regeneron Pharmaceuticals, Inc, dated Oct. 10, 2016, 5 pages.
Opposition against Japanese Patent application 5749161, dated Jan. 15, 2016, 55 pages.
Notice of Reasons for Revocation for JP 5749161, dated Mar. 17, 2016, 8 pages.
Third party observations under article 115 EPC against European Parent Application No. 09075279.1 in the name of Merus BV, dated Apr. 25, 2012, 6 pages.
Third party observation against European Parent Application No. 09075279.1 in the name of Merus BV, dated Aug. 28, 2013, 11 pages.
Patent Oppositions Application No. 2009263082, dated May 4, 2015, 3 pages.
Information sheet for submitted publications for JP Application No. 2011-516168, dated Apr. 25, 2012, 3 pages.
Patent applicant's outline of submissions for Australian patent application 2009263082, dated Sep. 6, 2016, 49 pages.
Australian opposition procedure, dated Jun. 27, 2014, 1 page.
Communication pursuant to Rule 114(2) EPC, dated Nov. 5, 2012, 7 pages.
Notification of material filed under section 27, dated Apr. 1, 2014, 1 page.
Content of Arguments, dated Jun. 21, 2016, 25 pages.
Documents regarding Opposition (Declaration of Peter Hudson and Robert Brink), dated Jun. 2, 2015, 1 page.
Opponent's final supplementary submissions, dated Oct. 19, 2016, 4 pages.
Declaration of Christopher Goodnow, dated Oct. 16, 2016, 13 pages.
Opponent's initial supplementary submissions, dated Oct. 5, 2016, 7 pages.
Letter enclosing written submissions and fee, dated May 18, 2015, 1 page.
M70120EPEIN opposition documents (P1), dated Jun. 21, 2016, 80 pages.
M70120EPEIN opposition documents (P2), dated Jun. 21, 2016, 61 pages.
M70120EPEIN opposition documents (P3), dated Jun. 21, 2016, 71 pages.
M70120EPEIN opposition documents (P4), dated Jun. 21, 2016, 80 pages.
M70120EPEIN opposition documents (P5), dated Jun. 21, 2016, 100 pages.
M70120EPEIN opposition documents (P6), dated Jun. 21, 2016, 100 pages.
M70120EPEIN opposition documents (P7), dated Jun. 21, 2016, 60 pages.
M70120EPEIN opposition documents (P8), dated Jun. 21, 2016, 60 pages.
M70120EPEIN opposition documents (P9), dated Jun. 21, 2016, 60 pages.
M70120EPEIN opposition documents (P10), dated Jun. 21, 2016, 60 pages.
M70120EPEIN opposition documents (P11), dated Jun. 21, 2016, 60 pages.
M70120EPEIN opposition documents (P12), dated Jun. 21, 2016, 100 pages.
M70120EPEIN opposition documents (P13), dated Jun. 21, 2016, 100 pages.
M70120EPEIN opposition documents (P14), dated Jun. 21, 2016, 100 pages.
M70120EPEIN opposition documents (P15), dated Jun. 21, 2016, 100 pages.
M70120EPEIN opposition documents (P16), dated Jun. 21, 2016, 80 pages.
M70120EPEIN opposition documents (P17), dated Jun. 21, 2016, 70 pages.
M70120EPEIN opposition documents (P18), dated Jun. 21, 2016, 70 pages.
M70120EPEIN opposition documents (P19), dated Jun. 21, 2016, 100 pages.
M70120EPEIN opposition documents (P20), dated Jun. 21, 2016, 100 pages.
M70120EPEIN opposition documents (P21), dated Jun. 21, 2016, 80 pages.
M70120EPEIN Proprietor documents (P1), dated Jul. 27, 2016, 100 pages.
M70120EPEIN Proprietor documents (P2), dated Jul. 27, 2016, 100 pages.
M70120EPEIN Proprietor documents (P3), dated Jul. 27, 2016, 80 pages.
M70120EPEIN Proprietor documents (P4), dated Jul. 27, 2016, 57 pages.
M70120EPEIN Proprietor EPA document, dated Jan. 12, 2016, 51 pages.
M70121EPEIN Oppo EPA (P1), dated Jul. 27, 2016, 60 pages.
M70121EPEIN Oppo EPA (P2), dated Jul. 27, 2016, 60 pages.
M70121EPEIN Oppo EPA (P3), dated Jul. 27, 2016, 50 pages.
M70121EPEIN Oppo EPA (P4), dated Jul. 27, 2016, 60 pages.
M70121EPEIN Oppo EPA (P5), dated Jul. 27, 2016, 80 pages.
M70121EPEIN Oppo EPA (P6), dated Jul. 27, 2016, 90 pages.
M70121EPEIN Oppo EPA (P7), dated Jul. 27, 2016, 100 pages.
M70121EPEIN Oppo EPA (P8), dated Jul. 27, 2016, 80 pages.
M70121EPEIN Oppo EPA (P9), dated Jul. 27, 2016, 100 pages.
M70121EPEIN Oppo EPA (P10), dated Jul. 27, 2016, 120 pages.

(56) References Cited

OTHER PUBLICATIONS

M70121EPEIN Oppo EPA (P11), dated Jul. 27, 2016, 100 pages.
M70121 Epein Oppo EPA (P12), dated Jul. 27, 2016, 60 pages.
M70121 Epein Oppo EPA (P13), dated Jul. 27, 2016, 59 pages.
M70121EPEIN Proprietor document (P1), dated Aug. 31, 2016, 100 pages.
M70121EPEIN Proprietor document (P2), dated Aug. 31, 2016, 80 pages.
M70121EPEIN Proprietor document (P3), dated Aug. 31, 2016, 60 pages.
M70121EPEIN Proprietor document (P4), dated Aug. 31, 2016, 60 pages.
M70121EPEIN Proprietor document (P5), dated Aug. 31, 2016, 100 pages.
M70121EPEIN Proprietor document (P6), dated Aug. 31, 2016, 100 pages.
M70121EPEIN Proprietor document (P7), dated Aug. 31, 2016, 80 pages.
M70121EPEIN Proprietor document (P8), dated Aug. 31, 2016, 80 pages.
M70121EPEIN Proprietor document (P9), dated Aug. 31, 2016, 90 pages.
M70121EPEIN Proprietor document (P10), dated Aug. 31, 2016, 70 pages.
M70121 Epein Proprietor document (P11), dated Aug. 31, 2016, 58 pages.
Canada Office Action for CA 2,729,095, dated Nov. 10, 2015, 8 pages.
Response to Office Action for CA 2,729,095, dated May 10, 2016, 12 pages.
Documents to CA Patent Office, Sep. 16, 2015, 15 pages.
Voluntary Amendment, dated May 12, 2016, 2 pages.
M70121PCEPT1 documents(P1), dated Aug. 8, 2016, 100 pages.
M70121PCEPT1documents (P2), dated Aug. 8, 2016, 100 pages.
M70121PCEPT1 documents (P3), dated Aug. 8, 2016, 100 pages.
M70121PCEPT1 documents (P4), dated Aug. 8, 2016, 100 pages.
M70121PCEPT1 documents (P5), dated Aug. 8, 2016, 100 pages.
M70121PCEPT1 documents (P6), dated Aug. 8, 2016, 90 pages.
Roitt et al., "Really Essential Medical Immunology," Blackwell Science (2000) 17 pages.
Response to Communication, dated Sep. 29, 2014, 7 pages.
Declaration of Peter Hudson, dated Jun. 17, 2016, 15 pages.
Non-final Office Action for JP 2015-097258, dated Apr. 11, 2016, 7 pages.
Communication of notices of opposition (R. 79(1) EPC), dated Sep. 25, 2014, 1 page.
Notice of Opposition, dated Jun. 20, 2014, 1 page.
Notification for JP 2011-516168, dated May 20, 2014, 1 page.
Third Party Observations, dated Jun. 27, 2013, 16 pages.
Third Party Observations, dated May 16, 2013, 82 pages.
Letter regarding Notice of Opposition, dated Jun. 23, 2014, 1 page.
Opponent counter argument, dated Aug. 22, 2016, 19 pages.
Canada Office Action for CA 2,729,095, dated Apr. 16, 2014, 1 page (Protest section 10).
Canada Office Action for CA 2,729,095, dated Apr. 16, 2014, 1 page (Letter).
Correspondence from Canadian Patent Office, dated Apr. 8, 2014, 16 pages.
Correspondence from Canadian Patent Office, dated Sep. 16, 2015, 15 pages.
Statement of Grounds and Particulars, dated Sep. 22, 2014, 35 pages.
Information in EP 09075279.1, dated Oct. 28, 2016, 1 page.
Communication of a notice of opposition, dated Aug. 20, 2014, 1 page.
Response to Communication under Rule 79(1) EPC, dated Apr. 2, 2015, 32 pages.
Opposition against EP 2147594, dated Aug. 11, 2014, 55 pages.
Annexure PH-4 (P1), dated Jul. 13, 2009, 37 pages.
Annexure PH-4 (P2), dated Jul. 13, 2009, 37 pages.
Carrion et al., "Light chain inclusion permits terminal B cell differentiation and does not necessarily result in autoreactivity," PANS (2006) 103(20):7747-7752.
Patent applicant's outline of submissions, dated Sep. 16, 2016, 15 pages.
Letter regarding new prior art documents, dated Mar. 18, 2014, 8 pages.
Notification of Material filed under Section 27, dated Oct. 28, 2013, 25 pages.
Summary of submissions on behalf of Merus B.V, dated May 18, 2015, 6 pages.
Third party observation, dated May 9, 2014, 14 pages.
Communication pursuant to Rule 114(2) EPC, dated Oct. 10, 2013, 4 pages.
Office Action for U.S. Appl. No. 15/140,321, dated Sep. 2, 2016, 58 pages.
Translation of the pertinent portions of the Action, dated 2016, 11 pages.
Payment of fees and expenses, dated Nov. 10, 2016, 1 page.
Notice of Opposition in EP 2701499, dated Nov. 10, 2016, 27 pages.
Extension of time limit pursuant to Rule 132 EPC, dated Jul. 5, 2016, 6 pages.
Communication of further notices of opposition pursuant to Rule 79(2) EPC, dated Jun. 29, 2016, 1 page (Fritz Lahrtz).
Notice of Opposition in EP 2501817, dated May 25, 2016, 28 pages.
Payment of fees and expenses, dated May 25, 2016, 1 page.
Annex in EP 14163642.3, dated Jan. 29, 2016, 3 pages.
Third party observation for application EP 20120783456, dated Jun. 16, 2016, 3 pages.
Joint Stipulation and Proposed order of invalidity and non-infringement of U.S. Pat. No. 8,502,018, dated Feb. 24, 2015, 7 pages.
Documents filed by proprietor during opposition, dated Aug. 26, 2016, 8 pages.
Communication of further notices of opposition pursuant to Rule 79(2) EPC, dated Aug. 23, 2016, 100 pages (P1).
Communication of further notices of opposition pursuant to Rule 79(2) EPC, dated Aug. 23, 2016, 100 pages (P2).
Communication of further notices of opposition pursuant to Rule 79(2) EPC, dated Aug. 23, 2016, 100 pages (P3).
Communication of further notices of opposition pursuant to Rule 79(2) EPC, dated Aug. 23, 2016, 100 pages (P4).
Communication of further notices of opposition pursuant to Rule 79(2) EPC, dated Aug. 23, 2016, 120 pages (P5).
Communication of further notices of opposition pursuant to Rule 79(2) EPC, dated Aug. 23, 2016, 100 pages (P6).
Communication of further notices of opposition pursuant to Rule 79(2) EPC, dated Aug. 23, 2016, 100 pages (P7).
Communication of further notices of opposition pursuant to Rule 79(2) EPC, dated Aug. 23, 2016, 80 pages (P8).
Communication of further notices of opposition pursuant to Rule 79(2) EPC, dated Aug. 23, 2016, 80 pages (P9).
Communication of further notices of opposition pursuant to Rule 79(2) EPC, dated Aug. 23, 2016, 70 pages (P10).
Communication of further notices of opposition pursuant to Rule 79(2) EPC, dated Aug. 23, 2016, 100 pages (P11).
Communication of further notices of opposition pursuant to Rule 79(2) EPC, dated Aug. 23, 2016, 150 pages (P12).
Communication of further notices of opposition pursuant to Rule 79(2) EPC, dated Aug. 23, 2016, 150 pages (P13).
Communication of further notices of opposition pursuant to Rule 79(2) EPC, dated Aug. 23, 2016, 150 pages (P14).
Communication of further notices of opposition pursuant to Rule 79(2) EPC, dated Aug. 23, 2016, 100 pages (P15).
Communication of further notices of opposition pursuant to Rule 79(2) EPC, dated Aug. 23, 2016, 100 pages (P16).
Communication of further notices of opposition pursuant to Rule 79(2) EPC, dated Aug. 23, 2016, 50 pages (P17).
Communication of further notices of opposition pursuant to Rule 79(2) EPC, dated Aug. 23, 2016, 50 pages (P18).
Communication of further notices of opposition pursuant to Rule 79(2) EPC, dated Aug. 23, 2016, 50 pages (P19).
Communication of further notices of opposition pursuant to Rule 79(2) EPC, dated Aug. 23, 2016, 50 pages (P20).

(56) References Cited

OTHER PUBLICATIONS

Communication of further notices of opposition pursuant to Rule 79(2) EPC, dated Aug. 23, 2016, 100 pages (P21).
Communication of further notices of opposition pursuant to Rule 79(2) EPC, dated Aug. 23, 2016, 100 pages (P22).
Communication of further notices of opposition pursuant to Rule 79(2) EPC, dated Aug. 23, 2016, 100 pages (P23).
Communication of further notices of opposition pursuant to Rule 79(2) EPC, dated Aug. 23, 2016, 150 pages (P24).
Communication of further notices of opposition pursuant to Rule 79(2) EPC, dated Aug. 23, 2016, 100 pages (P25).
Communication of further notices of opposition pursuant to Rule 79(2) EPC, dated Aug. 23, 2016, 150 pages (P26).
Communication of further notices of opposition pursuant to Rule 79(2) EPC, dated Aug. 23, 2016, 139 pages (P27).
Communication of further notices of opposition pursuant to Rule 79(2) EPC, dated Aug. 23, 2016, 150 pages (Potter Clarkson LLP) (P1).
Communication of further notices of opposition pursuant to Rule 79(2) EPC, dated Aug. 23, 2016, 150 pages (Potter Clarkson LLP) (P2).
Communication of further notices of opposition pursuant to Rule 79(2) EPC, dated Aug. 23, 2016, 140 pages (Potter Clarkson LLP) (P3).
Communication of further notices of opposition pursuant to Rule 79(2) EPC, dated Aug. 23, 2016, 110 pages (Potter Clarkson LLP) (P4).
Communication of further notices of opposition pursuant to Rule 79(2) EPC, dated Aug. 23, 2016, 150 pages (Potter Clarkson LLP) (P5).
Communication of further notices of opposition pursuant to Rule 79(2) EPC, dated Aug. 23, 2016, 150 pages (Potter Clarkson LLP) (P6).
Communication of further notices of opposition pursuant to Rule 79(2) EPC, dated Aug. 23, 2016, 150 pages (Potter Clarkson LLP) (P7).
Communication of further notices of opposition pursuant to Rule 79(2) EPC, dated Aug. 23, 2016, 150 pages (Potter Clarkson LLP) (P8).
Communication of further notices of opposition pursuant to Rule 79(2) EPC, dated Aug. 23, 2016, 120 pages (Potter Clarkson LLP) (P9).
Communication of further notices of opposition pursuant to Rule 79(2) EPC, dated Aug. 23, 2016, 85 pages (Potter Clarkson LLP) (P10).
Request for exclusion of file inspection, dated Jul. 12, 2016, 3 pages.
Bruggemann et al., "A repertoire of monoclonal antibody with human heavy chains from transgenic mice," PNAS USA (1989) 86:6709-6713.
Smith et al., "Filamentous fusion phage: Novel expression factors that display cloned antigens on the Virion surface," Science (1985) 228:1315-1317.
Third party pre-issuance submission in U.S. Appl. No. 15/140,321, dated Feb. 10, 2017, 19 pages.
Third party pre-issuance submission in U.S. Appl. No. 15/090,505, dated Feb. 24, 2017, 30 pages.
Moldenhauer, "Bispecific antibodies from hybrid hybridoma," Bispecific Antibodies (2011) pp. 29-46.
Staerz et al., "Hybrid hybridoma producing a bispecific monoclonal antibody that can focus effector T-cell activity," Proc Natl Acad Sci USA (1986) 83(5):1453-1457.
Opinion of In re Chu, United States Court of Appeals for the Federal Circuit, decided on Sep. 14, 1995.
Reply letter of proprietor in response to the opposition proceedings against EP 2264163 B1, dated Dec. 30, 2016.
Osoegawa et al., "Bacterial Artificial Chromosome Libraries for Mouse Sequencing and Functional Analysis," Genome Research (2000) 10(1):116-28.
Herring, CD., "Vector-Hexamer PCR Isolation of All Insert Ends from a YAC Contig of the Mouse Igh Locus," Genome Research (1998) 8(6):673-81.
DNA Sequencing Core Website, dated Nov. 21, 2015.
Schedl et al., "Transgenic mice generated by pronuclear injection of a yeast artificial chromosome," Nucleic Acids Re (1992) 20(12):3073-3077.
Mejia et al., "Retrofitting Vectors for *Escherichia coli*-Based Artificial Chromosomes (PACs and BACs) with Markers for Transfection Studies," Genome Research (1997) 7(2):179-186.
Sambrook 3rd ed pp. 2.110-2.111 (2001).
Sambrook 3rd ed Chapter 5 Protocols 15 and 19.
NEB 1-Ceul datasheet and heat inactivation table.
Schindelhauer et al., "Efficient combination of large DNA in vitro: in gel site specific recombination (IGSSR) of PAC fragments containing a satellite DNA and the human HPRT gene locus," Nucleic Acids Research (1997) 25(11):2241-3.
Mejia et al., "The Assembly of Large BACs by in Vivo Recombination," Genomics (2000) 70(2):165-70.
Shizuya et al., "Cloning and stable maintenance of 300-kilobase-pair fragments of human DNA in *Escherichia coli* using an F-factor-based vector," Proc Natl Acad Sci U S A (1992) 89(18):8794-7.
Sambrook 3rd ed, vol. 1 p. 6.3.
Sambrook 3rd ed, Chapter 5, Protocol 13.
Sambrook 3rd ed, Chapter 6, Protocol 2.
Boren et al., "A Simple and Efficient Method for Making Site-directed Mutants, Deletions, and Fusions of Large DNA Such as PI and BAC Clones," Genome Res (1996) 6(11): 1123-30.
DNA Cloning 3, A Practical Approach, 2nd Ed, pp. 112-114.
Trucksis et al., "The Vibrio cholerae genome contains two unique circular chromosomes," Proc Natl Acad Sci U S A, (1998) 95(24): 14464-9.
Potter et al., "Enhancer-dependent expression of human Kc immunoglobulin genes introduced into mouse pre-B lymphocytes by electroporation," Proc Natl Acad Sci U S A, 1984, 81(22), 7161-5.
Sambrook 3rd ed, Chapter 16.34, protocol 5.
Bio-Rad Cat No. 165-2105—Gene Pulser® II Electroporation System Instruction Manual.
Potter et al., "Transfection by Electroporation," Curr Prot Mol Biol (2003) Chapter 9:Unit9.3. doi: 10.1002/0471142727.mb0903s92.
Yang et al., Site-specific gene targeting in mouse embryonic stem cells with intact bacterial artificial chromosomes, Nat Biotechnol., 2003, 21(4):447-51.
Glaser et al., Current issues in mouse genome engineering, Nat Genet (2005) 37(11):1187-1193.
Bethke et al., "Segmental genomic replacement by ere-mediated recombination: genotoxic stress activation of the p53 promoter in single-copy transformants," Nucleic Acids Res (1997) 25(14):2828-2834.
Mansour, SL., "Disruption of the proto-oncogene int-2 in mouse embryo-derived stem cells: a general strategy for targeting mutations to non-selectable genes," Nature (1988) 336(6197):348-352.
Muyrers et al., "ET-cloning: think recombination first," Genetic Engineering (2000) 22:77-98.
Orford et al., "Engineering EGFP reporter constructs into a 200 kb human beta-globin BAC clone using GET Recombination," Nucleic Acids Res (2000) 28(18): E84.
Nefedov et al., "Insertion of disease-causing mutations in BACs by homologous recombination in *E coli*," Nucleic Acids Res (2000) 28(17): E79.
Call et al., "A Cre-lox recombination system for the targeted integration of circular yeast artificial chromosomes into embryonic stem cells," Hum Mol Genet (2000) 9(12):1745-1751.
Sambrook 3rd ed Chapter 5.3.
Angrand, PO. et al; Simplified generation of targeting constructs using ET recombination, Nucleic Acids Res., 1999, 27(17), e16.
Sambrook 3rd ed Protocol 7 4.48-4.52.
Nagy., "Cre Recombinase: The Universal Reagent for Genome Tailoring," Genesis "2000" 26(2):99-109.
Fox et al., "Fluorescent in situ hybridization (FISH) to mouse chromosomes, Mouse Genetics and Transgenics: A practical approach," I.J. Jackson, C.M. Abbott (Eds.), Oxford University Press, London (2000), pp. 154-168.

(56) References Cited

OTHER PUBLICATIONS

Rideout et al., "Generation of mice from wild-type and targeted ES cells by nuclear cloning," Nat Genetics (2000) 24(2):109-110.
Ramirez-Solis, "Gene Targeting in Embryonic Stem Cells," Methods Enzymol (1993) 225:855-78.
Zhang et al., "DNA cloning by homologous recombination in *Escherichia coli*," Nat Biotechnol (2000) 18(12):1314-1317.
Eppig, "Mouse Genome Informatics (MGI): reflecting on 25 years," Mamm Genome (2015) 26(7-8):272-84. doi: 10.1007/s00335-015-9589-4. Epub Aug. 4, 2015.
Mouse Genetics and Transgenics: A Practical Approach. I. J. Jackson and C. M. Abbott (eds). Oxford University Press, Oxford. 2000, chapter 7.
Dietrich et al., "A comprehensive genetic map of the mouse genome," Nature (1996) vol. 380, pp. 149-152.
Nusbaum et al., "A YAC-based physical map of the mouse genome," Nature Genetics (1999) 22(4):388-93.
Van Etten et al., "Radiation hybrid map of the mouse genome," Nature Genetics (1999) 22(4):384-7.
Muyrers et al., "Point mutation of bacterial artificial chromosomes by ET recombination," EMBO Reports (2000) 1(3):239-43.
Lee et al., "A Highly Efficient *Escherichia coli*-Based Chromosome Engineering System Adapted for Recombinogenic Targeting and Subcloning of BAC DNA," Genomics (2001) 73(1):56-65.
Sambrook 3rd Ed Chapter 1.21.
Hill et al., "BAC Trimming: Minimizing Clone Overlaps," Genomics (2000) 64(1):111-3.
Sheng et al., "Transformation of *Escherichia coli* with large DNA molecules by electroporation," Nucleic Acids Res (1995) 23(11):1990-6.
NEB PI-ScеI datasheet.
NIH website—Mouse BAC end sequencing project.
Reyrat et al., "Counterselectable Markers: Untapped Tools for Bacterial Genetics and Pathogenesis," Infect Immun (1998) 66(9):4011-4017.
Yu et al., "An efficient recombination system for chromosome engineering in *Escherichia coli*," Proc Natl Acad Sci U S A (2000) 97(11):5978-83.
Murphy; KC., "Use of Bacteriophage Lambda Recombination Functions to Promote Gene Replacement in *Escherichia coli*," J Bacteriol (1998) 180(8):2063-71.
Mouse Genome Data available in public databases, Feb. 2001, NIH.
Zhao, S., "A Comprehensive BAC Resource," Nucleic Acids Research (2001) 29(1):141-3.
Knight, "Mouse genome effort 'on course'," Nature (2001) vol. 411, p. 121.
Waterston et al., "Initial sequencing and comparative analysis of the mouse genome," Nature (2002) 420(6915):520-62.
Herring et al., "Vector-Hexamer PCR Isolation of All Insert engds from a YAC Contig of the Mouse Igh Locus," Genome Research (1998) 8(6): 673-81.
Factsheet from Opponent1 re MeMo mouse dated 2012.
MeMo™ the ingenious mouse for improved antibody therapeutics, www.merus.nl.
Presentation by Cecile Geuijen, May 27, 2013: Full length human IgG bispecific antibodies for cancer therapy.
Feeney et al., "Dst4: a new, and probably the last, functional Dh gene in the BALB/c mouse," Immunogenetics (1993) 37(3):217-21.
Mainville et al., "Deletion al Mapping of Fifteen Mouse VH Gene Families Reveals a Common Organization for Three Igh Haplotypes," Journal of Immunology (1996) 156(3):1038-46.
D'Eustachio et al., "Mouse Chromosome 12," Mammalian Genome (1998) 8:S241-S257.
Weigert et al., "The genetic control of antibody variable regions in the mouse," Springer Seminars in Immunopathology (1978) 1:133-169.
Riblet et al., "Polymorphism and evolution of Igh-V gene families," Curr. Top. Microbial. Immunol. (1986) 127:168.
Thiebe et al., The variable genes and gene families of the mouse immunoglobulin kappa locus, Eur J Immunol (1999) 29(7):2072-81.
Richards-Smith, BA. et al., "Deletion mapping of the mouse ornithine decarboxylase-related locus Odc-rs8 within Igh-V," Mammalian Genom (1992) 3(10):568-74.
Extract from Fundamental Immunology, 4th Edition, Paul, W.E., Lippincott-Raven (1999).
Materials from examination of a European Patent Application No. 09075279.1 in the name of O1, Apr. 23, 2013.
Kawasaki et al., "Evolutionary dynamics of the human immunoglobulin k locus and the germ line repertoire of the Vk genes," Eur J Immunol (2001) 31(4):1017-28.
O'Connor et al., "Construction of Large DNA Segments in *Escherichia coli*," Science (1989) 244(4910):1307-12.
Red/ET Recombination guide (Gene Bridges).
Sambrook 3rd ed vol. 3 p. 16.54-16.57.
Zheng et al., "Engineering Mouse Chromosomes with Cre-IoxP: Range, Efficiency, and Somatic Applications," Mol Cel Bio (2000) 20(2):648-55.
Wade-Martins et al., "Long-term stability of large insert genomic DNA episomal shuttle vectors in human cells," Nucleic Acids Res (1999) 27(7):1674-82.
Macdonald et al., Poster 2006—Velocigene® Technology Extended to Humanization of Several Megabases of Complex.
Abstract to 2006 Macdonald poster (1st International Mugen Conference Sep. 2006, Athens).
Stevens et al., Poster 2006—VelocImmune™: Humanization of immunoglobulin loci using VelociGene® technology.
Abstract to 2006 Stevens poster (1st International Mugen Conference Sep. 2006, Athens).
Sambrook 3d Ed 4.82-4.85.
Sauer, "Inducible gene targeting in mice using the Cre/loxSystem", Methods (1998) 14(4):381-392.
Sambrook 3rd Ed 12.10-12.13, protocol 1.
Presentation by Open Monoclonal Technology, Inc (Nov. 3, 2013), http://www.openmonoclonaltechnology.com/downloads.html.
Lonberg, "Human Monoclonal Antibodies from Transgenic Mice," Handb Exp Pharmacol (2008) 181:69-97.
Vasicek et al., "B-less: a Strain of Profoundly B Cell-deficient Mice Expressing a Human lambda Transgene," J Exp Med (1992) 175(5):1169-80.
Declaration of Sir Martin Evans dated Dec. 23, 2016 in opposition proceedings EP2264163.
Declaration of Professor Kenan Murphy dated Dec. 29, 2016 in opposition proceedings EP2264163.
Declaration of Dr Werner Muller dated Dec. 22, 2016 in opposition proceedings EP2264163.
Declaration of Dr Andrew Murphy dated Dec. 21, 2016 in opposition proceedings EP2264163.
Declaration of Dr Lynn Macdonald dated Dec. 20, 2016 in opposition proceedings EP2264163.
Declaration of Professor Hidde Ploegh dated Dec. 23, 2016 in opposition proceedings EP2264163.
Declaration of Andrew Murphy originally submitted for the EP1360287 Opposition (including appendices), dated Jan. 27, 2014.
Declaration and CV of Anthony De Franco originally submitted for the EP1360287 Opposition, dated Sep. 2, 2014.
Statement of Professor Ishida submitted in the UK High Court, first witness statement in UK litigation (The High Court of Justice, Chancery Division, Patents Court, Case No. HP-2013-000001/HP-2014-000001 dated Sep. 3, 2015, Report relates to a patent owned by Regeneron Pharmaceuticals, Inc., EP 2264163).
Statement of Professor Anthony De Franco, first witness statement in UK litigation (The High Court of Justice, Chancery Division, Patents Court, Case No. HP-2013-000001/HP-2014-000001 dated Oct. 3, 2015, Report relates to a patent owned by Regeneron Pharmaceuticals, Inc., EP 2264163).
Statement of Dr Yancopoulos, first witness statement in UK litigation (The High Court of Justice, Chancery Division, Patents Court, Case No. HP-2013-000001/HP-2014-000001 dated Oct. 2, 2015, Report relates to a patent owned by Regeneron Pharmaceuticals, Inc., EP 2264163).

(56) References Cited

OTHER PUBLICATIONS

Hansen et al., "Crescendo's Cash Fragments," BioCentury, The BernsteinReport on BioBusiness, Dec. 23, 2013, p. A13.
Declaration and CV of Craig Bassing, originally submitted for the EP1360287 Opposition.
Honjo et al., (Eds), Immunoglobulin Genes, Academic Press: London, 2nd Edition, (1990) pp. 71, 74-76.
Declaration of Sue Klapholz, originally submitted for the EP1360287 Opposition (including appendicies), Jan. 27, 2014.
Second Declaration of Craig Bassing (Bassing II), originally submitted for the EP1360287 Opposition, dated Sep. 2, 2014.
Kirschbaum et al., The 3' part of the immunoglobulin kappa locus of the mouse, Eur J Immunol (1998) 28(5):1458-66.
Kirschbaum et al., "The central part of the mouse immunoglobulin kappa locus," Eur J Immunol (1999) 29(7):2057-64.
Roschenthaler et al., "The 5' part of the mouse immunoglobulin kappa locus as a continuously cloned structure," Eur J Immunol (2000) 30(12):3349-3354.
Roschenthaler et al., "The 5' part of the mouse immunoglobulin kappa locus," Eur J Immunol (1999) 29(7):2065-2071.
Sambrook 3rd Ed 8.95, Real time PCR.
Huetz et al., "Targeted disruption of the V(H) 81X gene: influence on the B cell repertoire," Eur J Immunol (1997) 27(1):307-314.
Fukita et al., "Somatic hypermutation in the heavy chain locus correlates with transcription," Immunity (1998) 9(1):105-114.
Gu et al., "Most Peripheral B Cells in Mice Are Ligand Selected," J Exp Med (1991) 173(6):1357-71.
The mouse genome, Nature 420, 510, Dec. 5, 2002, p. 510-511 (Nature Genome Timeline).
Lefranc et al., The Immunoglobulin Facts Book Academic press (2001) p. 52-58.
Kawasaki et al., "One-megabase sequence analysis of the human immunoglobulin lambda gene locus," Genome Res (1997) 7(3):250-261.
Carson and Wu (1989) A linkage map of the mouse immunoglobulin lambda light chain.
Bruggemann et al., "Human antibody production in transgenic mice: expression from 100 kb of the human IgH locus," Eur J Immunol (1991) 21(5):1323-1326.
Sambrook 3rd ed pp. 4.1-4.8 (2001).
Sambrook 3rd ed pp. 1.2-1.16 (2001).
Xu et al., "Structure of the bacteriophage lambda cohesive end site. Genetic analysis of the site (cosN) at which nicks are introduced by terminase," J Mol Biol (1991) 220(2):281-92.
Catalano et al., "Virus DNA packaging: the strategy used by phage lambda," Molecular Microbiology (1995) 16(6):1075-1086.
Aggarwal et al., "Novel site-specific DNA endonucleases," Curr Opin Struct Biol (1998) 8(1):19-25.
Frengen et al., "A modular, positive selection bacterial artificial chromosome vector with multiple cloning sites," Genomics (1999) 58(3):250-3.
Naryanan et al., "Efficient and precise engineering of a 200 kb beta-globin human/bacterial artificial chromosome in *E. coli* DH10B using an inducible homologous recombination system," Gene Ther (1999) 6(3):442-7.
Email relating to Gene Bridges course on RedET recombination.
GeneBridges course invitation, 2003.
Reply letter of proprietor in response to the opposition proceedings against EP 2501817 B1, dated Dec. 23, 2016.
Janeway et al., "Immunobiology: the immune system in health and disease," Current Biology Publications, 4th edition, 1999, chapter 3, pp. 79-113.
Rickert et al., "Impairment of T-cell-dependent B-cell responses and B-1 cell development in CD19-deficient mice," Nature (1995) 376(6538):352-355.
Mendez et al. (1997) Functional transplant of mega base human immunoglobulin loci recapitulates human antibody response in mice, Nature Genetics, 15:146-156.†
Sirac et al. (2006) Role of the monoclonal kappa chain V domain and reversibility of renal damage in a transgenic model of acquired Franconi syndrome, Blood 108:536-543.†

\* cited by examiner
† cited by third party

Fig. 12 human germline IGKV1-39/J DNA
```
  1  GAC ATC CAG ATG ACC CAG AGC CCC AGC AGC CTG AGC GCC AGC GTG GGC GAC AGA GTG ACC ATC ACC TGC AGA GCC AGC
 79  CAG AGC ATC AGC AGC TAC CTG AAC TGG TAT CAG CAG AAG CCC GGC AAG GCC CCC AAG CTG CTG ATC TAC GCC GCC AGC
157  TCC CTG CAG AGC GGC GTG CCC AGC AGA TTC AGC GGC TCC GGC AGC GGC ACC GAC TTC ACC CTG ACC ATC AGC AGC CTG
235  CAG CCC GAG GAC TTC GCC ACC TAC TGC CAG CAG AGC TAC AGC ACC CCC CAG CAG ACC TTC GGC CAG GGC ACC AAG GTG
313  GAG ATC AAG
``` human germline IGKV1-39/J Protein
```
  1  DIQMTQSPSS LSASVGDRVT ITCRASQSIS SYLNWYQQKP GKAPKLLIYA
 51  ASSLQSGVPS RFSGSGSGTD FTLTISSLQP EDFATYYCQQ SYSTPPTFGQ
101  GTKVEIK
``` human germline IGLV2-14/J DNA
```
  1  CAG TCT GCC CTG ACC CAG CCC TCT GTG TCT GGC AGC CCT GGC CAG AGC ATC ACC ATC AGC TGC ACC GGC ACC AGC
 79  AGC GAC GTG GGC GGC TAC AAC TAT GTG TCC TGG TAT CAG CAG CAC CCC GGC AAG GCC CCC AAG CTG ATG ATC TAC GAG
157  GTG TCC AAC AGA CCC AGC GGC GTG CCC AAC AGA TTC AGC GGC AGC AAG AGC GGC AAC ACC GCC AGC CTG ACC ATC AGC
235  GGC CTC CAG GCT GAG GAC GAG GCC GAC TAC TAC TGC AGC AGC TAC ACC AGC AGC AGC ACC CTG GTG TTT GGC GGC GGA
313  ACA AAG CTG ACC GTG CTG
``` human germline IGLV2-14/J Protein
```
  1  QSALTQPASV SGSPGQSITI SCTGTSSDVG GYNYVSWYQQ HPGKAPKLMI
 51  YEVSNRPSGV SNRFSGSKSG NTASLTISGL QAEDEADYYC SSYTSSSTLV
101  FGGGTKLTVL
```

Rat IGCK allele a DNA
```
  1  AGA GCC GAC GCC GCT GAC GCC CCC ACC GTG TCC ATC TTC CCC CCC AGC ATG GAA CAG CTG ACC TCT GGC GGA GCC ACC GTG GTC
 79  TGC TTC GTG AAC AAC TTC TAC CCC AGA GAC ATC AGC GTG AAG TGG AAG ATC GAC GGC AGC AGG CAG GAC GTG GTG
157  CTG GAC AGC AGG ACC GAC CAG GAC AGC AAG TAC GCC ACC TCC AGC ATG AGC AGC ACC CTG AGC ATG GAC GTG TCC AAG GTG CAG CGG
235  TAC GAG AGG CAC AAC AAC TAC ACC TGC GAG GTG GTG CAC AAG ACC TCC AGC AGC CCC GTG GTC AAG TCC TTC AAC CGG
313  AAC GAG TGT
```

Fig. 12, contd.

Rat IGCK allele a protein

```
  1  RADAAPTVSI FPPSMEQLTS GGATVVCFVN NFYPRDISVK WKIDGSEQRD
 51  GVLDSVTDQD SKDSTYSMSS TLSLTKVEYE RHNLYTCEVV HKTSSSPVVK
101  SFNRNEC
```

IGKV1-39/J-Ck

```
  1  GGT ACC GCG GCC GCC ACC ATG GAC ATG AGA GTG CCC CAG CTC CTG GGG CTC CTG CTA CTC TGG CTC CGA GGT AAG
 79  GAT GGA GAA CAC TAG GAA ATT TGT GGG CAA CCA GTT TCC AGT GAC ATT CAG ATG ACT CAG TCA CAT GAG AAG TTC TCT GAT AAC ATG
157  ATT AAT AGT GAG CCT GTT TAT CGT CGG CGA AGC CAA CTT CAC CGA GCC CTG GAT CAG CCA CAT GAG ATG CCA CTA CCT GAA CTG CAG
235  CAG CCT TCA GCA GAA CAG GAG CTA CAG ATT CAC CCT CGG CAC CCC CAG GGT AGC GAG TGC CAG CGT CGT GCC CAC CGC CAG CAG CTA
313  GTA TCA GCA CGG CAG GCA CGG CTA CAG CCC CGA CCC CAT GCA CCT GCA GGC GAT CAA GAG CTT GGA CGT GAG GTG CAG CTA CTA CTA
391  ATT CAG GCA GAG GTC CAT CCC CAG GAA CAT GAG CAG GCC CGA CAA GGT AGC GAG GGA CAC CGT CGT GCT GGT GTA CGA GAG CAA CTT
469  CTG CCA GCA GTC CAG AGA CAA GTG CAG CGT GGA GAG CAC CGG GCA GGA CGG CAA GGT CGT GGA GAG AAA CTT GAC CGT GAC CAA CCT
547  CAC CGT GTC CAT AGA CAT GGA GAA CAT CAG CTC CAC CCC CGT CAC CCT GAG CAT CGA GAG GAG CTG GCT GTA CGA GAG GCA CAA CCT
625  CTA CCC CAG CTC CAC CCT CAG GAC CTA CAA CTT GTA CGA GGT GGT CAA AGT ACC CGT CAA CCC CGT GAA CGG CAA CGA CAA CCT
703  CCA GGA CAC CCA GAT CAG GAC CTC GTA CAC CCC CGT GGT CAA CCT CTT CAA CCC CGA CGA GTG AGC TAG
781  GTA CAC CTG CGA GGT GGT CAA GCA GAC CTC GAG GTC CTT C
859  CGA GCT C
```

IGLV2-14/J-Ck

```
  1  GGT ACC GCG GCC GCC ACC ATG GAC ATG AGA GTG CCC CAG CTC CTG GGG CTC CTG CTA CTC TGG CTC CGA GGT AAG
 79  GAT GGA GAA CAC TAG GAA ATT TGT CCA GAG ATT ACT TTT GAT ACT CAG CCT TCA CTC TCT GTA TCT CCA GGG GAA ATG
157  ATT AAT AGT GAG CCT GTC TGG CCA GCA CCC TGG GTT GTA GGG ACA GAG CCA CCC TCC ATC TCA GTG TCT GCA GGG GAG
235  TGT GTC CTG GTA CCC CAG GCA CGG CTG GGC CAG ATC CTC AGG TGC CAG CGT CAA GCC CGC CTC
313  GTC CTG GTA ATT CAG GCA CGG CAG GCT CAG GGT GTT TGG CGG GAC CTA CGA ACC CAG CGG CGT GAG
391  CAA CAG CTA CTG TCC CAC CTT CCC CAG GGT AAA GCT CCA TGA GGA TGA CGA CGA CGG CGA
469  CGC CGC CAC CGT CCC CAG AGA CAT CAG CTC CCC CGT GAA GTG CAG GGA CAC GGA AGC GAG GCT GGT CTG CTT CGT
547  GAA CAA CTT CTA CCC CGA GGA CAT CAG CTC GTG AAG TGG AAG ATC GAT GGC AGC GAG GGA CCT GCT GGT CGT GGA CAG
625  CGT GAC CGA CCA GGA CAG CAA GGA CAG CAC CTA CAG CAT GAG CAG CCT GAC CCT CAA CCA CTA CAC GCA CCG GAA GAG
703  GCA GAC CTA CAA CCT GTA CAC CTG CGA AGT GGT CAA CAA CAC CAC AGT GAA CCG GAA GAT GGT GGA GAG
781  TTG AGC TAG CGA GCT C
```

Fig. 12, contd.

VkP-IGKV1-39/J-Ck

```
6241 TGG ACA AAG AAA ATG TTT ACA TCA AAG GTG AGG CCA TAT TTG TTA GGA ACA TAA CTT AAA AAC CAT TTT GGA TAA
6319 CTA ATG AAA AGC CAT TTT GTG TGC CTT GGC TCA GAT ACA AGC CCA TGC CTA AGC AGT CAG ATA GAT AGA CCT AAG CCT
6397 CAG AAG CAA GCC CCT GCC CAG CAA GCA ACA GCC AGT GAA CCA GCC AGC TAA ACC AGC AGC TAA CAG AGG CCA TGA TAT GCT AAT GAA
6475 CTA CCT TCA AGG TGG TGT ACA ATT GGA ACT TTG GAA CTT GTG GGA ATG GCT CTG TAT GCC TGG AAC CAC AAA GCT ACT GCC CAA
6553 AGA AAT TAT GTA TTG ATA GTC CCA AAC TGC GTC TAG AGC TAG AAG CTT TCT GGT GTG AAA CTT TCT TTA TGT GCC ATG GAC CCC TCT CTA
6631 TGT TTT TGT GTG AAT AAA CCA CAC AAT GCT CTC CAT ATA TTT CCT TTT TAA AAG CAA ATA TTT CAT AAT ATT ATA AGG AAT
6709 CTC TTT TGT GTG AAT AAA CCA CAC AAT GCT CTC CAT ATA TTT CCT TTT TAA AAG CAA ATA TTT CAT AAT ATT ATA AGG AAT
6787 GTT TAG TCC CAT GCT CTC ACT GAG AGT GCA CCA AGT GCA CAT TGT CTT TTG GCA CAT TGC TAA AAA GTT TAC AGC TAA
6865 TAG GGT AAT GCT CTC CAC AAT GCA AAG CCA AGT GCA GAG TCC AAA TTT GGA TCC ATA AGG TTG GGC ATC TTT ACA GAG AAG AAG ACA
6943 TTA AAA ATG AAG AGA CAT GCA AAG CCA AGT GCA GAG TCC AAA TTT GGA TCC ATA AGG TTG GGC ATC TTT ACA GAG AAG TCA AAG
7021 AGG ATT ATG TGC CTT GTT AAG GTA AGA CAT GCT ATC CCT ATT GTT CTA AGC CCC
7099 AAC CAA CCA ACA CCT GCT GTT AAG GTA AGA CTT GCC TTA AGA ACT GTG AGA AGG TAG TGA GTT TTC CAG
7177 AGT AGT ATG TGC CTT TAT TTT TGG TTT GGG TGT TGT TGG TGG TGT TGT TTG TGT TGT TTG CTT
7255 GCC CTT CCT GTT TTT GGT TTT GTT TTT TGG GGG CCC CTC CTG TAG TCA CAG GTT TGT TTT TGT TTC TAT CTC
7333 TGG GAA TGT TTT TGG TTT TTT GTT TTT TGG GGG CCC CTC CTG TAG TCA CAG GTT TGT TCC TTC TAT CTC
7411 T-T TAA TGT CTA CAT ACT TTA CTT GTA GAT GGG TCT GTT TTT GAT GTT CAT GAG GTT GAG AGT ATA ACT AAT
7489 TAA TGT CTA CAT ACT TTA CTT GTA GAT GGG TCT GTT TTT GAT GTT CAT GAG GTT GAG AGT ATA GCT GGG TCA ACC
7567 TAT TAT TTA CTT ACT AGA CTA CTG TGG CTG ATG AAG CTC CAC CCA TCA AGG TAG TCC ATT TTT AGC TCT TTT TGT TTT ACA AAT AAT AAA
7645 GAG GAG TTC CTG TGG CTG ATG AAG CTG CAC CCA TCA AGG AAT TAA AAA TTG CTT CTG GAG ACT TGA AAC TTT ACA AGT TAA ATA ATA
7723 ATG ATG TTC CTG TGG CAT GAA CTC CAG AAT AAT AGG AGA ACT CTC AGA GAT AAG GAT TAT ATG CTC ATG AAG TTT CAT CTT AIC TCC
7801 AAA GGG CAT TTT ATT GTA GAA AGC AGA AGC AGA TCC GAG AAT TTA CAA AGT AGT ACG AAT TTA AGT CAC CAG CAC TTG TCC
7879 ATT TCT TAT ATT GTA GAA AGC AGA AGC AGA TCC GAG AAT CTG GCC CTT GCC AAG GAA TAT ATG CTC ATG ACA CTG AGA TAT GCA CTT TGT TAT TGT TCA TCA ACT
7957 AGT AGT TAT ATT GTA GAA AGC AGA AGC AGA TCC GAG AAT CTG GCC CTT GCC AAG GAA AAT ATA TTA GGA ACC TCT GCC TCT CCT CTT AAA CTC AGA
8035 AGA GGA GGA AGC AGA AGC AGA ACA GTC TTT GCC TTT GCC CTT TGA CTT GCA CAT CAG GAC TCT GCC TCT GCC TCT GCC TCT GCC
8113 GGG TAT TTC GCC TAT CTG TCT GCC TCT GCC TCT GCC TCT GCC TCT TGG GAA CTC TCT GCC TCT GCC TCT GCC
8191 TGC CAA CTC TGT TTA TAA CTG GGT AAC TTT GTG AAG GAA AGG TTT TAA AGG TTT GCG TGT TAA AGC CGG AAA TTT TTA
8269 TTA TAG CAA TCC TGT TTA TAA CTG GGT AAC TTT GTG AAG GAA AGG TTT TAA AGG TTT GCG TGT TCT TGC TTT GCT AAA
8347 TAC AAA ATT ACT AAT TCT ATA TAT ATG AGT TTG TAC ATG TTT GCT TTG CTT GCT TTG CTT TGT GTT TTG CTT TGT GGT
8425 CAA GAT CGA GAC AGG TCT CTG TAT AGT TTG TAC ATG AAG AAT CTT ACT ATG AAG CTC TGA CTG TCC TGG CTC AAA CTC AGA
8503 TTT CGA GAC AGG TCT CTG TAT CTT GCC TCT GCC TCT GCC CTC GAA CTC AGA CTC CTC ACT ATA TCC CTC AAA CTC AGA
8581 AAC CTA CCT TCT GCC TCT GCC TCT GCC TCT GCC TCT TAA AAG GCA TAG ACA TAG ATA TCC ATG CCC AGA TAG GAT
8659 TCT GCC TCT GCC TCT GCC TCT GCC TCT GCC TCT TAA AAG GCA TAG ACA TAG ATA TCC ATG CCC AGA TAG TGA
8737 TCT GCC TCT GCC TCT GCC TCT GCC TCT TAA AAG GCA TTT GAC ATT GTT ACA TGA ATT ACA CAA AGA ACT AAT GTG
8815 AAC TTT ATA TAT GTC TCA TTC TAT TGT TGC TCA AGG CTG TGT TAA AGA CTG TGT GCT TTG CTT TGC TTT GCT AAA
8893 AGT AAT CGC AAG TTG CTT TGC TTT GCT TTG CTT TGT GTT TGC TTT TTT CCC AAG
8971 TTG CTT TGC TTT GCT TTG AGA AAG AAT CTT ACT ATG AAG CTC TGA CTG TCC TGG CTC CTG GAA CTC TAG ATC CCC AGA CTT GAT
9049 GGG GAG GGA TGG AGA GAT CTG AAG AAT ATG TCC CAA GTG CTG GGA GTA AAG GCA TAC ACC ATG CAA AGA ACT AAT GTG
9127 TCA ACT CAT GTT TTA GAT CTG AAA CCT TCT TCT GCC ATT GAC GTT AGA TAG ACA TGA ATT ACA ACA AGA ACT AAT GTG
9205 TCC CAA GTT TAC CTG AAA CTC TCT TCT ACT ACT ACT TTA TCA ACA ATT AAA TTA ACA TTT CCA GTG CCA TAG AGG CAC
9283 GAG TTT ACC TGA ATC GCA GTG TTT GCC ATG AGG CTT CAG TGC TGA AAG TTG GGG GCA ATA TTA CTC ATT
9361 CAT TCA ATG GCA GTG TTT GCC ATG AGG CTT CAG TGC TGA AAG TTG GGG GCA ATA TTA CTC ATT
```

```
2185 AGG AAA GGG TGA CTT ATT GGA GAT TTC AGA AAT AAA ATG CAT TTA TTA TAT TCC CTT ATT TTA ATT TTC TAT TAG
2263 GGA ATT AGA AAG GCA AAA GTC ATA AAC TGC TTT ATC CAG TGT ATT ATT AAA TAT ATG TAT AGG TAA AAT
2341 CTA CAG GTT CCA AAA TTA TAA ATT GTA AAT CTT TGA CTG AAC TCT CTA AAT ACT CCT CTA TAT TCA TAT TAA
2419 CTG AAT AAT TTA GCA ATA TGT GAC TTC CCA ATA GGT TTC TTT TCA TGC AAA AAT ATG ACT
2497 AAT AAA TTT TGA AAA CTA TAT ATT TGG CTA TTT TAA AGG ATG GAT AGA TTT AAC TCA AGT GCT ATT CTT GGA ATC
2575 CCA TAA TGA AGG AGA AAA TGA GAA TCT CTG TCT GCT CTT CAA TAT CCC ACT TGT CCC AAA CAT CAG AGT TGT CAG
2653 GAC AGG AGA AAA TGG TCT GAA CTT CAA AGG GTC TCT GAA GCA TGG GAA AAC TTA AGG GAA GAA TAG GAG AAG GAA
2731 ATA AAC TGA GAA TAT CTT CAA AGG GTC AGA CTC AGA CCT GGC AAT TTA CTT AAA GAA GTA TAG GGA ATA ACT TAG AAA
2809 GCC TGA CAA GAT TGT ATA TGT ACA CAT AAT CAT CCT GGC AGG TGC TAG GGA AAC TAG GCG TTT GTG TGT CTG
2887 CAA CAA ATA CAA CTG TTT ATA TAT ACA CTG TTT CTT GTT CTT CCT ATT GGT CTT CAT ACC CTC TGG CGG AGC TCC
2965 TAT ATA ACA TAA CTG TTT ACA CAT AAT ACA CTG AAA TGG AGC CCC CTG AAA GTC CAT GAC ATC CTC TGG CGA GCA GGA
3043 TTC CTC AGG GGC CTT CGA CGC TCC CAC CGC GTC CAT CTT CCC CCC CGT CAG CGA GCA CCT GAC GTC CAA
3121 CGT GGT CTG GGA CGT CAG CGT CAG CAT GGA CAT CAG GAT GAG CTC GGT CAC CAC CAG CCT CGT GAC GTC CAG
3199 CGG GTT GCC CTA AAA TCC CGG GCA CAA GAC CAA CCT CTA CAC CGA CTG GCA CAG GCA CAC CCC ATC CTC TCC CTT CTA
3277 GGT GGT GGA CGA CGA GTG AAG GCA CAA GTC AAG CGA ACT GCG AAA ATA TTC CAG AAA ATA TTC AAT GTG AGT CTT TGC ACT CTC
3355 CAA CCG GAA CCG TCT AAG CAC ACA AAG CGA CCT ACC GTG CAG ATA TTC AAT AAA CCC ATC GTG GTT AAA GAA GTT AAA TGT TTA
3433 AGG TCT CCC TTT CCT TGG CTT TTA TCA TGC TAA TAT TTG CAG AGT GTG AGT TCT CTT TGC ACT CTG GAT CTC
3511 CCT GTA TCT TAC TAA ATG GTA ATC AGT TGT TTT TCC ATC CTG GGT ACT TAC ACT ACA TGG CAG
3589 TGT GTT GCC CTA AAA TCC ACA CTT AAA AGA TAA ATA CCC CTC TGG CCT TGG CTG AGG GTC TCC ACT ACA TCC TAG
3667 GTT CTA TCC AGG TTC ACG AGT ACT AAG ATT ACT GGC GTA TTT ACA GTC AGG ACA TGT TCT GTA ATC TGA TTC AAC AGG AAA
3745 TCC TTT TCT CCT CTT AAG TCA AGA AAG TCC TGA AGG CAT TAT CTG ACA CAA CCT GTT TCA CAT CAC TAA TGT AGA
3823 TTT TCT AAA CCT CTT GGC TCA GCA AAG CAT CAT CAT ACA ACC TAC TTC AAG GAC TCT TAG ACC GTG ATC CTT GTA ATC CAG AAA TCT
3901 CCC AGT TGG AAG CCC ATC ATA GTA CTT GGA CTA CCC GAG AGC TAT CTG GAA ATT TTT CAT GGG GCT TGG GAT ACA CAG AAC AGT TAA AGA
3979 ATG TGC CAT TGG GAA TAC CAA AGC TTC CAA GCT GAG AGA CTC ATT TAC AAA ACA TTT CAT GGG GCT TGG GAT ACA ATG TCC AAC AGT TAA TCT
4057 ATC AAA ATT TGG GAA ACC AGT ATT TTG AGG TAG CAA AAC GAT AGC CTC ATG AAC TCT GGG GCT TGG GAT ACT CTC TGT GTA AAA CTT AAG AGA
4135 TAA ACA GCA TAA GTT TCA CAA TTG AGG TAG CAA AGA CTC TAT GAG AAC TCT GGG GCT TAT ATA TTC CAC CTA AAG AGC ATA GTT TAA TCT
4213 GAG ACA TGT ATT GTG GAA TAC ATT TGG AGC TAT CAT GGG TCT ATG ACT TCA AAG AGC ATA GTT TAA TCT
4291 ATT GAG ACA TGT ATT GTG GAA TAC ATT TGG AGC TAT CAT GGG GCT TAT ATA TTC CAC CTA AAG AGC AAA TAG AAA
4369 CAT GAG ACA TAA GTT ATT TTG AGG TAG CAA TTG AGC TAT TAC ATT GGG GCT AAT TAA ACT CTC TGG CCT GTA AAG AGT TAA TCT
4447 GAG ACA TAA GTT ATT GTG GAA TAC ATT TTG AGG TAG GAT TAT AAT GAG AAC TCT ATG TTC CAC CTA AAG AGT TAA TCT
4525 GTT ACT ATT GTG AGT CAA ATC GCA TAC ATA AAA GAG GAT ACA AGG TCT CTC TGT CTC GTA AAG AGT TAA TCT
4603 CTA ATA CCC AGT CAA ATC GAT CCC TCC CAC CTT GGG GAT ATA TAG ACA CCT CCT TCA GAA ATA TGC ATC TTG ATC AGA TAG AAG
4681 ATC CAG GAT CAT GAT CCC TCC TTG CAA AGA ATA TAG AGT GTA ATT CTC AGG TAT GAA GAG CTG GAG GCC CCT CAG TTT AGT CCC TCG TGG GCT
4759 CAA ACA CCT TCA ACA GGT TAA ACA CTA GTA ATT CTC AGT CAT TTT TGC GCA GAA ATT GTA GAA ATG CAT TGG CCT
4837 AGA CCT TCA ACA GGT TAA TAT GCA GAG ATA TAG ACT TTC AGC ATC TCC TAC ACT TTC AGA ATC CAC ATT GTG TGG GCT
4915 GGA AGG AGC CTC ACA CTT TAA CTA GTC CAG CTT CTC AGT ATC TCC TAC ACT TTC AGA ATC CAC ATT GTG TGG CCT
4993 CAT CCA CTG AGC ACA ACA CAT TTA CAT GCT TTG CCT TCC TCC TAC CTC TTG AGA TAC ATG TTC ATC ATA AGA AGA CTT
5071 TCC CAC AGT TAA GGA GAG GAG TTT TTT GTC TTT GTC ATT AGC ATC TTC CCT TTG AAT AGC ATG TTC ATC ATA AGA AGA CTT
5149 CAC CAA ATA GCT TTT AAT CTG ATT GCT CTT AAT ACA AAT ACA CCT ATA AAT TTG AAA CTT CTT
5227 TTA ATT GCT TAA TGA GAG GGC TAA TTT GTC TTT TCA ACA AGC ATG ATC CAT TTT GAA CCA TTA TCA ATC
5305 AAC AGT GCC TCT AAT CTG GCT ATT AAT ACA ATA TAT TAT GTT CGA GTC TTA TCT AAA ACA GAA
```

Fig. 12, contd.

```
5383 CCC ACA ATA AAA AAG AAA GAA TAC ATA TAA GCA TTT ATA TAA TTC TGA GCA ACC TTG TGC TTT GTG AAA AAA ATA
5461 TAA TCT AAT GTC ACA TGC TGT ATT CTT TTT ATT CTT TGG TGA AAT TAT AAG AGA GAC CTT AGA TCA
5539 CTG ATC CTA GGA TCT AGG GAT GTT ACA GTT GAG AAA GTG ACA AAG AGC TGT CAC AAG GAT CTT CAA GGT
5617 CAC AGA ATC GTC TTG ATT TCA GTG CTT AAT ATA ATA TGT TAA ATA TTG AAC TAT ATT CAT
5695 ATA TTG TAC CAA TGT CAA AGG TGA GGC CAT ATT TGC TCT AGA GAA CCC ATA TTG GAT AAC TAA TGA AAA GCC
5773 TGA TGT TTA CAT GCC TTG GCA GCA CAG GCC ATA AGA ACC CCC AAA ATT TGT TAG GAA CTC AGA AGC AAG CCC
5851 ATT CCC AGC AAG CTA GTG AAC CAG CCC CAA GCC ATA AGA TAG ATC AAT AGC ACA CAT ATG CTA ATG CTT CAA GGT
5929 CTG GGT GTT GCT GAC CTT TGG GAA TTC GCA TTT GCA GGA GAT CCT GAA AAT AGC ACA AAT GAT AAG GAA ATT ATA CAA
6007 AAA TTG GAA TCT AGA AGC TTC CAA AAC TTT CTC ACT GAA GGA TAT GTT GTG GAA GAT TCT TTT GCC CAA
6085 TAC CAG ACT GCT TCC CTC GTG TGA TAT CTG TTT TGC CCT AGC ATT GTT AGG ATG TTT GTG TGA ATA
6163 ACA CAA ACA CTG AAT TTT AAA AGC CCA AAT AAG TCC AAA AGC TTT ACA GCT AAT AGT CCC ATG CTC
6241 TCC ACA ATA CTG AGA AGA CAC CAT GTG CAC AAT AGC CCT GAG ACA GAA CAT GAA TTA AAA TGA AGA
6319 GAC ATG CAG AGA GTG AAG AGC CAA GAG GTA TGA AGT CTC AGA GTA TTC CTA TCT ATT TAT TAC TTA CTT
6397 TCC AGA AGC ATG GCT TAA GAC TTC TTG CCT AAC AAT AGG GAC AAA AGG ATA GCT GTT TTT GTT TTT GGC ATG AAG
6475 CTT TTT TTA AGG TAG AGT CAA GAA ACC AAT GGT GGT GTT TTT CCT TCT ATC TCT AAT GTC TAC ATC
6553 TTG ATT TTT TTG GTT TTT TTG GGT TTT GTT TTT CTG TAT AGC AGT CCT ATT TAT TAC TTA CTT
6631 GGG GTT TTG TTT TTG TGA GAC GGG ATC CTC TAG TTT CAA ATG AGC AGT GGG CAA CTC AAA CTC AGA ATT
6709 TCA GAG GGG ATC CTC TAG AGC AGT TTT CAA ATG AGC AGT GGG AAA GGA TAT AAT ACA CTC AAG AAA TTT TGA
6787 ATT TTT TTA AAA GGA TAT AAT ACA CAG GAG TCA GTT TCT TTG AGA GTT TAA AAA AGG GCA GAG ACT AGG
6865 ACT TAT TGG CAC TTT TTG ATA GAC CTT CAA ATA CAT ATG GAC CAG ACC AAA GAA ATA CTG AGA GAG TAG AAG
6943 TCA GAG GGA ATC CTC TAG AGC AGT TTT CAA ATG AGC AGT GGG AAA TAT ATA CTT CAA ATA TTT GAA
7021 ACT TAT TGT CTG TAG ATG GGG AAA GGA TAT AAT ACA CAG GAG TCA GTT TCT TTG AGA GTT TAA AAA AGG
7099 CAA TTG ATG CAC ACC CAG AAT GCA GAT AAA GAT AAG ATT CTG AGA GTA TAG GTT AAA ATT CTT TCC GGC
7177 TGA TGT CAC ACC CAG AAT GCA GAT AAA GAT AAG ATT CTG AGA GTA TAG GTT AAA ATT CTT TCC GGC
7255 CAA TTG ATG CAC ACC CAG AAT GCA GAT AAA GAT AAG ATT CTG AGA GTA TAG GTT AAA ATT CTT TCC GGC
7333 CTT AAA AAT AGG GTT CAA GGA GGA TTA GAA ATT CAA GAG AAC AAT CTT AAA ACT AAG CAA CTT AAA ACA TAA GTT TTG TAG
7411 AAA AAA AGG TAG AGA GGA GAA TTA AAG GAG ATA AGG ATA GGG GAA GAG ATG GGT ATT TCT TTG
7489 GCA GAA GCA ATG GCT GAT AGA CAC ATG GTC TTG GCA AGG TTC AAG GCT TGT GCC AAC TCA ACA
7567 CCT ATC TGT GAC TTG CAC GTC TTG ATA ACC AGG CCC AGT CGG GTC CTC TTA TCT CCT TAT AGC AAT CCT
7645 GAG TCT TTC ATA TTA ACC AGG CCC AGT CGG GTC CTC TTA TCT CCT TAT AGC AAT CCT
7723 GTT TAT AAC TGG GTA ACT TTG TAA ATA TAA ATT AAT ATT ATG AAC CTC AAG ATA CTA ATT
7801 AGA GTT TGT ACA ATG TGT GTT AAA TCA ATA TAT AAA ACT GTT CAC ATG CTT GTT ATT GTG AGA AGG ATA CTA
7879 CTA TAT CTC TGT ATA TGG GCC GCT GTC CTG CCC CTG CTG GAA ACC CTG CCT CCT TTA ACC CTG CTG TAT ATG
7957 TTT CTG CCT CCT CCT AGT GCT AGA TAG GGA ATT TGT GTA GAC CTG AAT GTG CTG TCA AAA CTA ATC GCA AGT
8035 TAT CTT CAT TCT CAT ATT TCT ATT GCT GCT AGA TGG GGA CTT CTA TAT CTT CAT TCT CAT
8113 CTG CCT CCT CCT CCT CCT CCT AGT GCT AGA TAG GGA TTC CCA ATA TAT TTA CCA ATC GCA AGT
8191 CTG CCT CCT CCT CCT AGT GCT AGA TAG GGA TTC CCA ATA TAT TTA CCA ATC GCA AGT
8269 CTG CCT CCT CCT CCT CCT CCT AGT GCT AGA TAG GGA TTC CCA ATA TAT TTA CCA ATC GCA AGT
8347 TCT CAT TCT ATT GCT GTT GAT TAG GAC ATA CTA CTT TGC CTT TAT GCA AGT
8425 TGT AGT GTT ATT GTT TGC TTT TTG CTT TGC TTT TGG GTT TTT TTC CGG AGG GAG GGT
8503 CTT TGC TTT GCT TTT GCT TTT GCT TGG GTT TTT TTC CGG AGG GAG GGT
```

Fig. 12, contd.

```
 8581 GGA GAA AGA ATC CTA TTA TGA AGC TCT GAC TGT CCT GGG AAC CTA TCA TAT AGA TCA GGC TTG ATT CAA CTC ATA GAG
 8659 ATC TGC CTT CTG CCT CCC AAG TGC TGG GAA GAT AGG AGA CAT ACA CCT CCA TTA CCC AAG TTT CCT TAG
 8737 CAA AAG TTT CTA GAC TTG TAT CAG AGA ATC TTA GAT AAT GGA CAT AGA CAA TTA ATA TGG ACC ATT CAA TGG CAG GAA
 8815 TCA TAC TCT ATA CTT TAT CAG GGC TTA GTC TTC AGT GCT GAA AGG CAT GCT CAG TGG GGG CAA TTT ACT TAC AGA TGA GAA
 8893 TGT TTG CCA TCA TGC AGA GAC TAC TGA ATT CAG CAG AGT GAG TAT CTG AAG GCT GAG TTT GTG GCT CAT TAC TTT AAT ATT
 8971 ACT GGG AAA GAC TAA TTT AAA TAC TGA TGA ATG TCT TTT ATA AGA AAA AAG AAA GAA TTC AAT AAA CCA
 9049 TTT AAT ACA TGG ACA AAA TCA TTC AAG AAT CAT TAG AAT CAT ACC TCA ATG GAA ATG CCA AAG GCC TTT GAT
 9127 AAT AAG ATT CAA CCT CCT GCC CTG CTC TTT TAT TAT CCA CCC ATT TCT GCT CAA TTT TGG CAT CTT GCA CAT ATG GAG ATC
 9205 AAG CCT TCC AAA CCA AGG GCC TCT CCC AAC CTC ATT GGT TGT TCC CAT GTC CAA CTT TGG CAT ATG GAG ACA
 9283 CCT TTC AAA CTC TGG GGG TTA CTG ATT AGG GGC CTA GTC AGT GAC CAT CTT GCA GTT TGT GAG AAA TCT CTG CAT CTG AGC TTG CCA TAT
 9361 TTC CAG CTC TCT AGT TCC TTC ATT AGC TCA CCT GTG AGC GAT CCC GTG TCA GTA AAG GAG CCA ATC CTG CAT CTG AGC TTG GTC
 9439 CAC CTC TCT GGT TCC TCA CGA GAA AGA GGG ATG AGA GAC TCT CTG AAG GAG ATG ATG TTC CAT ATC CAT TTC ATC AGT GAG TGC
 9517 TTC TTC AGT GCC ATA GCC GTA GTT TAT AAC GAT GGG TAT CTT TCC CAT ATG TTG CCT ACC ATT TCC AGT GCG TAC TCC AGC TTG GTC
 9595 ACT GGT TTG GTG GTT GGT GAA AAT AAG AAG GGA TAC AAA ATT TTG ACT AGA ATT GAA ATT ATC
 9673 CTG AAA CTT TGT CTT CTT CAT ATG TTG CAT GGT TAA TCC AGA TGC ATC CAT TTC TGT ATC TCT CCT AAG TCC TCC
 9751 AAA CTT TGT CTT CTT GGA TAT GTT CCC AGG ATG ATG GTG ATA TCC CTC TAA ATG AAG AAT TGT AAA CAT CAT GAC TGA
 9829 TTC CTT CTT CAT ATG TTG TGT TTA ATT GCT CAG CTT GAT TTT GAA TAC ATC AGA TGC ATC TGT ATC TCT CCT AGA
 9907 ATA TCA TGC TTT AAT GGG CAT CTG GGT TCT TTC TAG CTG TAT GCC CAG TAG AGC ATA GCG TAC CAT GTG TCC
 9985 TTC ATT GAG GGG CAT CTG GGT TCT TTC TAG CTG TAT GCC CAG TAG AGC ATA GCG TAC CAT GTG TCC
10063 GTT AAT TCA AGT TGG AAC ATC TTC TAG GTA TAT GCC CTG TAG AGC CTG GTC TTT CTG AAG TGC TAA CTC CTG TGT GAC TGA
10141 TTA TCA AGT TGG AAC ATC TTC TAG GTA TAT GCC CTG TAG AGC CTG GTC TTT CTG AAG TGC TAA CTC CTG TGT GAC TGA
10219 TTC TTA ATA AAA GCC CTA GAA CAA GGA TGA AAC GAC CAT GAG TGA AGC AGC AGC TGA CAG AGC TGC TCC AGC AGC CAT AGA
10297 ATG ACC AAT ATC GAG AAT GAA GCA TTA TCT TAT ACC ACA TCC TCT AAG ACT GTC TTT GTC CTG GAA AGG GAC CAG AGC TTT ATA TAT TTT CAT AGT
10375 CTC ATC AAT TGT TTT CAA TTG AAG ATT ATA TCT TAT ACC ACA TCC TCT AAG ACT GTC TTT GTC CTG GAA AGG GAC CAG AGC TTT ATA TAT TTT CAT AGT
10453 AAT TGT TTT CAA TTG AAG ATT ATA TCT TAT ACC ACA TCC TCT AAG ACT GTC TTT GTC CTG GAA AGG GAC CAG AGC TTT ATA TAT TTT CAT AGT
10531 AAT AAT CCT TTT CAT CCT TTC AAG GTG TTA TGA TGC ATC CTG CCA AAC CTG GAT TGA ACT TAC TCT ATA GTT GGT TGC AGA TCA
10609 CTT GTA TCT CAC AAA ACG TTC ACA GGG ACT TAG TAT CAT AGG AGT GGT CTT TTT ATA GTT GTG TAA GGT CAA TAT TTC ACA ACA GTA
10687 CTC AAG GAA ATA GAA ATG CAT CTT AGT AAT CAT AGT CCT AGC CTG GAT TGA TGA CTG ACA AGC AGC ATG GAT AAA ATG TTC CAT GCA TAG
10765 CTC CTC CAC AAG CTC AGT TTA AAT ATC AGT CTT ATA GTT GTG AGG ATG AGT GTG ACT ATA AGC CCT TTT ATA GTT GAC CAG CAT TTT CCA
10843 TAA TTA TGA GAC ACA TGG TAA GCT CAT TTT AAG AGT CAT CCA AAC TGT CCA ATA GAA AAT GCA CAG CCT TTT CCA
10921 TGA CAC AGG TTG TTA GAC CCA TGG TAA GCT CAT TTT AAG AGT CAT CCA AAC TGT CCA ATA GAA AAT GCA CAG CCT TTT CCA
10999 CAC AGG TTG TTA GAC CCA TGG TAA GCT CAT TTT AAG AGT CAT CCA AAC TGT CCA ATA GAA AAT GCA CAG CCT TTT CCA
11077 GGA AAA TTA TCT CAC AAG GAA ATA CTT CAC AGG GAC TTA GTA TCA TAG GAG TGG TCT TTT ATA GTT GTG TAA GGT CAA TAT TTC ACA ACA GTA
11155 GAA TGT TGA ACC CTG TAA GCT CAT TAT AAT AGT GAG AAC CAT GAG CAC GTG ATG AAA ATG TTC CAT GCC TAG
11233 ACA TTT GCC ATC ACC CAT CTA TAT AGA TTG ATG AGA AAG TCT ATT CCA AAC CTG AAT AAT GCA CTG TAG CAT GGG AAT ATC CTC AAC CTA
11311 CTG TCT ATC AGT GCT GAA GTT CTA TGC TGC CAT CTT CAA GTC ATC CCT AGA CAT GTG ATG ATG TTC CTT CAC CAG GCC TAG
11389 AGA CAT AGT AGC CAT TTG ATG AAA TAC AAA TAC TTC GGC AAA GAA AGG AAT TCA AAT CTG ATG GCT CCA AAC CAG GCA
11467 CCA TCT TGC AAA GCA GTT CTA CTA CAG TAA AAG ACA AGA CAC CTA AGA GCA AAA AGT CAT GCC TGA
11545 CCC CTG AAC TGT GTA CTT TGC CAT CTT GGC ATC CAA AAG CAC ATC AGA CAT TCA ATG TTC AAC AGC GCA
11623 GAT CAT GCA ACC AAT AAT GCT GAT CAC AAG GCA AAC GGA AAT ATG TTC CAT TAG GCC TAG
11701 TTG TGT ATG GTT GCT TCC GGA AGC TCC CAT AGT GAC TCC AGT AGC AAA AGA CTT GGA CTT TGA AAT CAA ATG TCT
```

Fig. 12, contd.

```
11779 CAT TTA ACA GAT TAG GAG ATG AAA CGG TAG ACT CTG TGT AGT TGT ACA CCC CTG TGA TCC CAT CGC TAG GAA GAC TGA
11857 GGC AGG AAG TCC TCG AGC TCA AAC CAG CTT TAA GAG GAA GAA AGA CAC ACT ATC AAA ATA ATT TTC ACT AAC TAC ATA
11935 GGA GAT TGG ATG TTA AGA TCT GGT CAC TAA GCA GCA TTC GAA GCC AGT GTC CAA CAG ACC TAC CTG GTA TGT TTT
12013 AAA TTG CAG GGA AAA AAA TAT CAG CCA ACA TCT TTT CAT GGT GAC TGG CCT GAG AAG GTA AGA TTC TCA GCA AGT ATC CCA
12091 TTG TTT GGA AAA CAT ACC AGA CTG GTT ATT TAG GAT CAA CTG TCA TAG CCT CAC TGG CCT CAT CAA AAA AGT AAT GCC TTA
12169 CCC ATC CCC AGA GTG TCC CAT AAC CAG GCC CTT AGG CAC ATC TGT ACC TGA TCA CCG CAT CCT CAG AAG ATT GAT GAA GAC CCT TTG CCA
12247 TTG GGA AAA CAG TCC CAT AAC CTT AGG GCC CAT CTT TGC TGC TAT ACC TGA TCA TAA AGT CCT CCA ACA GCC TGG GTG TCC CAC ACA
12325 AAC TGA GTT TCC CAC ACC CAT CTT AAA CTC AAC CAC AGC TCA CTT GAA TAA TCA GTT CAG CCC AAG TTA GTC CCC AGT CCC ATA TAC GCT TTT
12403 CCC TTT CAA GTT ATA CCC CAC AGT CCC CTA TCT ATC AAG AGT TCT GAT ATG GTC ACT GGG CAA AAA ATA GTT GTG CTA
12481 AAA ATG CAG ACC TCA AAA CTC AAC TTG TTT CAT GGG GCC CAG AGT TCT AGA AGT ACC TGA GAG TGG CAA TTG CAG GAT AGT TGT CAG
12559 GCA CAG TCA GTG GAA AAG ATC TTT AGG CTG AGA GAC TAT TCA CGA ATA TCA GCA TGG ACT ATA TTC CAT GTG TCT TCA
12637 AGA CAT AGT TTG CAC ACC CAC CAA TAA CAG AAG TAT TCT CTT TTC CAT CCA TGT AGA CTG TCT TCA
12715 AAT AGT TTG CAC ACC CAC CAA TAA CAG AAG TAT TCT CTT TTC CAT CCA TGT AGA CTG TCT TCA
12793 TAA ACA CCC CAC AGG CCC C
12871 TAT TTG TTC TAG ACG GGC C
```

VkP-IGKV1-39/J-Ck-Δ2

```
   1 GGC CGG CCC ACA TGA AAC AAT GGG CAT GTG ACA GAG CTC TTA CTA TAG CAA AAG GGA TTG TTA CTC
  79 TCC ACA CTC TCC CCT TGA GTA ACT TGA ATA CTC CCT ATA AAC AGG CCT CTC TAA ATA TTC CAT AGA TTT GTA TTA AAG ATG GTT
 157 ATA CTC TCC TGT TCA AAA TAT CTC TTG GGG GAC ATT GCC CAG CGG CCT GTG AGA GAA ATA TTA AGA CAT TCC CAG GCA AAT CTA TGC GAC
 235 TTT TTT CCT GGT GCC CTG CCC ATG CCC ATG TGC CCT TGA TTT TCA CAG CCT GTG AGC CCT TTC CAG GCC CTG GAT GAG CAC ATT GCC ATC ATG GAT TAC AGC CAT GAT TCC GAA GTG CCT TTT ATG GGC TCC
 313 GCT GCC ATG CCC ATG TGC CCT TGA TTT TCA CAG CCT GTG AGC CCT TTC CAG GCC CTG GAT GAG CAC ATT GCC ATC ATG GAT TAC AGC CAT GAT TCC GAA GTG CCT TTT ATG GGC TCC
 391 GCC CAC CCT CTG GCT GTG GAC CCT CAG AGC CAT GAT TTG AGA ACA CTA GTC AGC ATT TGT TTT TTA TGT TTC CAA TCT CAG GTG CCA GAG CCA GTG ACA
 469 TCG CAC CCT CTG GCT CCC CAG TCA GTC TGG AGA ACA CTA GTC AGC ATT TGT TTT TTA TGT TTC CAA TCT CAG GTG CCA GAG CCA GTG ACA
 547 GCT ACT CTG GCT CTC TGA AGG TAA CAT GAT TAA GAA CCA GCG TGG AGC CCC CCA ACT TCA CCT TCG ATG GTT ACA GTT GGG GCT CCT
 625 AGG GAA GTT CTC TGA AGG GCC TGA AGC AGC AGC CCA AGC ACT GGT ATC GCC CAG AGC GCT CCG GCA AGC GCT CCG GCA CCC CCA ACT TCA CCT TCG ATG GTT ACA GTT GGG GCT CCT
 703 TCC AGA TGA GCT GCG ACT GGT ATC GCC GAT ACT TCA CCA CCC CCC ACT TCA TCT CAG CCA TCA CCT CAG GCA CCG GCA GCC AGA
 781 GCA TCA GCA GCT GCG TCG ACA GCT CCT CAT TTC ATT AGT GGC TTT TAT CAG GTT TAT GGC TTG GCA CCG GCA GCC AGA
 859 TGC AGA GCG ACT TGG CCA CCT TCT TCA AGG AGG CTT TAT GGC TTT GAG AGG CTT TAT GGT GAC CGG CAA GAG CCT
 937 CCG AGG AGT CGG GGA GGA ACA AGG AGG GCT CAT CAG GCT ATG GCT CTC AGG GCC CAG TCT ACA GGT AAT CCA CGT GCG CCT AAC GAA GCC CCT AAA GTC AGT ATC AAG TGG ATC
1015 TCA AAC AAT CTT GAG GGA GAT CTT GAG GGT TAA CAT GAT TCC TTC TCT AGA AGG GCT TGG CCA GAG CCA GAG CCG CCA GCC AGG TGG AGA
1093 GAA AAT GTT TTA GGG GCA AAA ATG GAG AGG GCT TTT GAG ATC TGG AGG ACA GTT CAG GTT TAT GGC TCA GAT CAC TCT CCA CGT TTA AGA GAT TGG ATC
1171 GTG AGA TTA GCA GCG ACT TTA GGG GCA AAA AGC TTT ATT GAG GTA GTA TGG AGG AGA GGC TTT GAG ATC TGG AGG ACA GTT CAG GTT TAT GGC TCA GAT CAC TCT CCA CGT TTA AGA GAT TGG ATC
1249 AGA GAA TAA GCA TGA GAA ATA GAA ACT TGG AGA GTC CTG GAA AGT CAG AAG CAG CGC TTG AGT TTT GCA ATA AAA CAT GTG GGA TAG TGA AGG AGT TGA
1327 TTT GGA GAT GAG GAT AAC TGA GTT TCC ACA TGT CAT CCG TGT AGT ACT GTG TGC TTG GAG CTC ACG CTG GTC CTG AGT TGA
1405 GAG CAA ACT TTG AAG ATA AAC TGA GTT CCA CAT GTC ATC CGT GTA GTA CTG TGT GCT TGG AGC TCA CGC TGG TCC TGA GTT GA
1483 GAG AAG GAG ACT CAT CCG TGT TCC ACA TGT CAT CCG TGT AGT ACT GTG TGC TTG GAG CTC ACG CTG GTC CTG AGT TGA
1561 GTG AGC CGT AGC TGT AGG ACT TGC GTA TCA TCT GAC CAA AAT CAG AAG AGG GGA TAG TGC CTG AGT TGA
1639 TCA TTA AGC CGT TTG AAA TGA ACA TAA CAA GTT AAG AGA ACA TGA CTC GTT
1717 TTA TTC TAA AAT TTG TCA CAA ATG CAG GAC TCT AGA CAG CCT TGA GTT CAA GGG GTT
```

Fig. 12, contd.

```
1795 TTT TTC CTT TGT CTC ATT TCT ACA TGA AAG TAA ATT TGA AAT GAT CTT TTT TAT AAG AGT AGA AAT ACA GTT GGG
1873 TTT GAA CTA TAT GTT TTA ATG GCC ACG GTT TTG TAA GAC ACC ATT TGG TCC TTA GAC CCC GTT CCA ATT GCT CGA TTG TAA
1951 TAT ATC GCC AGC AAT GGA AAT CGG AAA CGG GTT TCC GCA ACC CCG TAG CAT GTG GGT CTG CGC GTG GAC CAC TTT CCT
2029 ATT TGG CGT TCA CCC TAG TCA GAA AGC TGC CAA GGG CAC TGT TCT GAA CCC GAG ATG GAC TAC ACT CGC AGA AAA ACA
2107 GAG GCA AAA GGG TGA GAA CTT ATT GGA GAT TTC AGA AAT AAA ATG CAG TGT TTA ATT TAG AGG TTC TAT TAG
2185 AGG AAA ATT AGA AAG GCA ATA GTC ATG GGC TTT ATC CAG TGA CTT TAT ATA AAT CCT CAC TAA ACT ATG TAA AAT
2263 GGA CTA CAG CCA GCA AAA TTA ATA TAA ATT TGT GAC ATG GGT TAG CTG GTA GGA TAT TTT TCT TTA TGC AAA AAT ATG ACT
2341 CTA GTT AAT AAT TTA GCA CTA TTT TGA AAG CTA TAT TTC CCA ATA CTT CAA CAG TAT AGA AAA ATG TTT AAC TCA GCT ATT CTT GGA ATA
2419 AAT CCA TAA TTT TGA AAA TGA AAA CTA AAG TCT CAA GTT TCT GAA TGG CAG ACT CCC AAA GAA TAG GGA ATA ACT TGT CAG
2497 GAC AGG AAC TGG GAA TGA TCT CAA TAT TGT AAG CCA GTT TCT CTG CAG AAC TTT TTT GTG TGT GCT CTG
2575 CCA TAA TTT TGA AAA TGA AAA CTA AAG TCT CAA GTT TCT GAA TGG CAG ACT CCC AAA GAA TAG GGA ATA ACT TGT CAG
2653 GAC AGG AAC TGG GAA TGA TCT CAA TAT TGT AAG CCA GTT TCT CTG CAG AAC TTT TTT GTG TGT GCT CTG
2731 ATA AAC TGT GAA TAT TGT TTT CAA AGG GTC CAT CCT AAT ACA CGT GTC CAG AGA CAT GCT GAC GCG CAG GAG GGA
2809 GCC TGA CAA CTG ATA ACA CTG TTT ACA CAT CTC ACG CGC TCC CAC CGT CCC CAG AGA CAT GCT GAC GCG CAG GAG GGA
2887 CAA CCG GAA GTA CGA CGA GGA GCA AAG CCT GGT GCA CAG CTC CAG CCC CGT GAG CCT GAC GTC CTT
2965 TAT ATA ACA TAA CTG TTT ACA CAT CTC ACG CGC TCC CAC CGT CCC CAG AGA CAT GCT GAC GCG CAG GAG GGA
3043 TTC CTC AGG GGC CGA CGC TCC CAA CTT CTA GGA CAT CTG GTG AAA AAG CAC GAC TCC AGC CAG CCT CTA
3121 CGT GGT CTG CTT CGT GGA CAA CTT CTA CCC GGA CAT GTG CAG CAT CTA CGT GAA GTG CAG CGA GCA GAG GGA
3199 CGC CGT GCT GGA GAG GCA GCA CAT CCT GCA CAG CTG GGT GCA CGC GTT TTT CTC TGT GTA ATC TGA TTC AAC CTA
3277 GGT GGT GTA CGA CGA GGT GTT GGT GTG CAT CTT CTG ATA AGC AGG CAA ACT CAA AGG CAA GAT CTG TCA AGT AGG AAA
3355 CAA CCG GAA GTA CGA CGA GGA GCA AAG CCT GGT GCA CAG CTC CAG CCC CGT GAG CCT GAC GTC CTT
3433 AGG TCT CCC TTT TCT TGG CTT TGG CCC CTT AAA ATC ACC AGT CGT GAA GCA ACC CAA GTT TCT CCC ACT ACA CTG GCT CCT
3511 CCT CCT TAC ATG ACC ACA CTT GGA CTT ATA GTA GTA TCA TGC ATC AAA GGA TAA ATA AAA TTT CTC CCT AAA GTT AAA GAA GTT AAA TGT TTA
3589 TGT GTT GCC CTG AAA TCC CTG AAA TCC AAA TTA TTT CTC TGG GCC ATG GTA ACA TGT TCT GTA ATC TGA TTC AAC CTA
3667 GTT TCC TTT CTA AGG TTC ACG AGT ACT ATT ACT AAT TTA TTT CTC TGG GCC ATG GTA ACA TGT TCT GTA ATC TGA TTC AAC CTA
3745 TCC TTT TCT CCT AAG TCG TCA AAG TCC TGA AGG GGG AAA CAT CTC CCC GAG ACC GTC TTT ACA AGC CAA CAA GAC TCT TAG GCC ATG AGG CAT ATC TGA ATC TCC AAA CCT
3823 TTT TCT AAG GCC AAG ATT GAG AGA CTC AGC TAT TTA GAA AGT TAT ATA ACA AGT TAT AAT CTA GAT AAA CTG ATA AAA ATT AAT CAA AGG AGT TAA CCT
3901 CCC AGT AAA CTT GGC GAA GTA CAC TTT GGA CTA CTT CAG CTT TTT AAC CAA AGG TAT GCA AGC AGC CTG GCT CCT
3979 ATG TGC CAT TGG GAA ACC TGT TCA GAT AAT ACA TTT TTT CAT CCA TGT TGG ATG TTT CAT ACT TTC AGG AGC CTG GCT CCT TGA GAT CTC
4057 ATC TGC CAT TGG GAA ACC TGT TCA GAT AAT ACA TTT TTT CAT CCA TGT TGG ATG TTT CAT ACT TTC AGG AGC CTG GCT CCT TGA GAT CTC
4135 AAA ATT TCT CCT AAG TCG TCA AAG TCC TGA AGC TGA GGG AAA CAT CTC CCC GAG ACC GTC TTT ACA AGC CAA CAA GAC TCT TAG GCC ATG AGG CAT ATC TGA ATC TCC AAA CCT
4213 TAA GAA GCA ACC AGT AGT TCA AAT AAG CAG CTC CTA TAC AGC TGA GAA AGT GAA GAT TAT TTA AGC ATA TTA AAA AGT TAA TCT
4291 ATT ATG ACA GAT AAT GTG AGT GCA AAC ACA TTT TTT CAT CCA TGT TGG ATG TTT CAT ACT TTC AGG AGC CTG GCT CCT TGA GAT CTC
4369 CAT AAA CAA TAA GTT TTG AGG CAG TAG CTA CAT CTT CAT GGG ATG ATG ACT CTG CAG TGC TAA CTT GTA TGT CTC AGA ATA AGC TTA TCT
4447 GAG ACA ACT ATT GTG AGT GCA ATC CCC ATT GGA TCA TAC GTC AAG AGG CTA AGC AGC CTT TCA CAG AGG GCT AAG AGC ACA AGA ATA TTA AGA
4525 GTT ACT ACT ATT GTG AGT GCA ATC CCC ATT GGA TCA TAC GTC AAG AGG CTA AGC AGC CTT TCA CAG AGG GCT AAG AGC ACA AGA ATA TTA AGA
4603 CTA ATA CCC GAT CAT GAT CAA ATC CCC CTT GGA TCA TAC GTC AAG AGG CTA AGC AGC CTT TCA CAG AGG GCT AAG AGC ACA AGA ATA TTA AGA
4681 ATC ATA CAG CAT TCA ATG GCA ATC CTC TCA TGC CTT TCT TCA AGA ATA GAG CCC CCT AAA ATG AAA AAG TAG AGG
4759 CAA ACA CCT TCA GAT CCC TTG GGG TCT ATT TAG GTA ATT TTG CAA AGT CAA ATG ACG TAT CAA TAT AGA TTA CAT TAG
4837 AGA CCT ATT GAT CAA ATC GCA TAC ATA GAG TCT CAA AGA ATA TTC AGT ATA GAG GAG GCA CAT TCG TGG AAG
4915 GGA AGG ACA ACA CTA ACA GTG ACT TTC ATT CTC CCC ATT TTC GAG GCC CCT CTG GAG ACA AGG CAT CCC TCG TGG GCT
```

```
1561 CAG AGT TGA GTG AGC CGT AGG CTG AGT TCT CTC TTT TGT CTC CTA AGT TTT TAT GAC TAC AAA AAT CAG TAA TAT GTC
1639 CTG AAA TAA TCA TTA AGC TGT AGC TTG AAA GTA TGA CTG CTT GCC ATG TAG ATA TAG GAC CTT GCT GAA ACG AGA GCT
1717 GTG TGA CTC TTA TTC TAA AAT TTG CTC ATT TCT ACA AAT GTC AGA GAC TCT GTA GGA ACG AGT CCT TGA CAG ACA AAT
1795 CAA GGG GTT TTT TTC CTT CTA TGT GTT TTA ATG GCC AAG GTT TAA GAC ATT TGA AAT CTT GTT TTC CCA TTC AGT AGA AGT ACT
1873 ACA GTT GGG TTT GAA TAT ATC GCC AAT GGA CTG AAA CGG TTT TCC ACC TCT TGG TCC TTG CAT CCC TTG GAC CTC GCG GCT
1951 CGA TTG TAA TTT CCT CGT TCA CCC TAG CGC TAA GGG CAC TGT GAA CCC CGG TAG GAT GTG ACA GAC TAC ACT AAT GTG
2029 GTG CCA GCC ATT TGG CGT CAG CAG GCA AAG TGA TCT GAA GAG AAC ATG CAT TTA TTA TCC CTT ATT TTA ATT
2107 CAC TTT CCT GAG GCA AAA ACA AGG AAA ATT AGA AAG GGC ATA AAC TGC TTT ATC AAA ATG CAT ATT AAA AGC TCA TAT ATC TTT TAG
2185 AGA AAA ACA AGG AAA ATT AGA AAG GGC ATA AAC TGC TTT ATC AAA ATG CAT ATT AAA AGC TCA TAT ATC TTT TAG
2263 TTC TAT TAG GGA ATT AGA AAG GGC ATA AAC TGC ATG GTA TAA GTC ATA ATT ATT AAA AGC TCA TAT ATC TTT TAG
2341 AGG TAA AAT CTA CAG GCA AAA GTC ATG GTA TAA ATT TGT CTG AAC TCT CAC TAA ACT CCT TTT TCT TCA TGC AAA
2419 TCA TAT TAA CTG GTT AAT AAT TTA GCA AAA ATA TTT TAG GTT ACT GGT TAG GTA GGA TAT TTT AAA ATG CAA CTA TGC GCT
2497 AAT ATG ACT ATC CCA TTA TTA TGA CAA CTA CTT TAG AGT CAT TAA CTT TGA CTG TGT TTC CCC ATA CTT GTT ATT AAC CTA TTT AAG
2575 ACT ATA CCT TTA AAA CTC TTG AAA CTA CTT TAG AGT CAT TAA AGC TTT ATT ACT AGG CAA ATG TTA AAA TGA TGT CAA
2653 GAC CCT TTT AAC TAT TTT ATT TTA AGG GGG AAG AGT TGG CTC ATA ATT CTA TTG GTA AAG AAC TCT
2731 TTC CCT TCG TTT TTA CCT CTG TCA CCC AAG CAG TTG GAC TTT TTC AGA GGC CAT CTG GCA
2809 CAG TTT GCT TAA GAT CAG AGT GTT CCT CTG CCA AAC CAG GTC GCC CAG GTC TGA ATT GCT AAT ATT TCT GGA CAC CCA
2887 GTT GCT TAA GAT TTG TCC CAT GTG AGG CCC TTA ACA CAT TAC AGT AGG GCT AGC TTC TGC ATG TGC TTG TGT TCA GAC
2965 GGC TAA AAA GAC CCT GGC TAT TCT TGG AAG AGA CCC GAG GAG AAA ATG AAA CTG GAA ATC TCT GTC AAA AGA ATG TTT CAG
3043 AAT ATA TCA GAG TAT TCT GGA GTG TCA GGA ATA AAG ACA CTG GAA ATC TCT GTC AAA GGT ATA TCA AAG GGT AGT AGC TAG
3121 TCC ACA ACA TCA GGA GTG TCA GGA ATA GAA GCA AAG CTG AGA ATC TCA AAG GGT ATA TCT ACT TGT TCC TTA TCT GTA GTT CAG
3199 GGA AGA AAG GCA AAT AAC TTA GAA ACA AGA TTG TAT ATA ACT GTT GCA TAA TAC ACT GAA ATG AAC CAT GAA CCC TTC CTT GTT GCA
3277 GAA CTA GGG CTT TTT TGT CTG TGC GAG AGC AGA CCG GGG TCT GCT TGG GCG TGG AGT ACG ACG AGA GTC GAG CTG TGG AGT GCA AGT ACA GCA TGA
3355 AGC GTG CTT TTT TGT CTG TGC GAG AGC AGA CCG GGG TCT GCT TGG GCG TGG AGT ACG ACG AGA GTC GAG CTG TGG AGT GCA AGT ACA GCA TGA
3433 TCA TAC CAT CTG GCG AGC GCA AGA AGT ACG ACG AGA GTC ACG AGC TGG AGT GCA AGT GCA GCT CCA GGT CCC ATA GCA AGT ACA AAT ACT AAA AGA CCA CCT CAT CAA TAA AGT
3511 AGC GTG CTT TTT TGT CTG TGC GAG AGC GCA AGA AGT ACG ACG AGA GTC ACG AGC TGG AGT GCA AGT GCA GCT CCA GGT CCC ATA GCA AGT ACA AAT ACT AAA AGA CCA CCT CAT CAA TAA AGT
3589 AGC TGA ACG GCA GCG AGA GGA TGC TGG AGT GTC TCC CTT TTC CCT CGG TGA CCT ACA AGA GCT CCC CAG
3667 TCG ACG GCA CCC CCG TCA AGC CCT TCA GTC CCT TCT CCT TGC CCT TCT TTC TTT TTT ATT TCT CTG CTT GGC TAC AAG GCT TCA AGT
3745 GCA GCA GCC CCG TGG TCA ATC TTC TCC TCT TCT TTG AAA AAT CAC CAC GAA CTA ACC CTC CTG CTT GTG CCT TCA CAA CCT TCA AAC AGT
3823 CCA GCC CCG TGG TCA ATC TTC TCC TCC TCT TTG AGA TCT TGC CCT TCT TTC TTA AAT CAC CAC GAA CTA ACC CTC CTG CTT GTG CCT TCA AGT
3901 CTC CAT CCC ACC TCC TTG CAC TTG AGA TGT TAG CAT CAG TTC TGA AAT GGT CAC GTC GTA ATT TGG GGC TAC AAG GCT TCA AGT
3979 CTC CCC ACC TCC TTG CAC TTG AGA TGT TAG CAT CAG TTC TGA AAT GGT CAC GTC GTA ATT TGG GGC TAC AAG GCT TCA AGT
4057 GAG TTC TAA AGA TCT TAA AGT CAC TAC ATG GCA TTT AGT TGC CCT TCT TTC GAA ATC ACA ACC CTG GAA TCT TCT CTG CTG AAT CTC TTG TGT CCC TGG
4135 TTG GCT ATG GTC GAG GCA TAC TTC ATT GCA CTA CCT ACC AAT GTT TAA CCG ACT CTG AAA GTC GCA AGA CGA CTG GGC CTT CCA AGG
4213 TTT GAG GAG GCA ATT CTG AAG CAA TAG ACA TGG CGA AGC CAT CAT TTT TCA CAG GAA GCA CAC AAA GTT ACA ATG
4291 TTC TGT AAT CTG AAG CAA TAG ACA TGG CGA AGC CAT CAT TTT TCA CAG GAA GCA CAC AAA GTT ACA ATG
4369 TAA ATG TGT AAT CTG AAG CAA TAG GAA GCC TCA AGG CTG TAA ACT TGG ACT GAA GTA GCC AAA TCA CAC AAC CTA CGT CCT TTA AGT
4447 TAA CTA GAG GCA ATT GGC TCC TAT CTG CCA GTG AGG CTG AGG CTG AGC GCA ACG GTC ACT ACC CAC AAC CTA CTT GTA CGA ATA GTG GTA GCA GTA CTA AGT
4525 TTT TAA AGT CAC ATT CAA CAC TGG CGG TTT GTT ATT ACA CCT TTA TCT CTC GGG AAG CAT CAG CCT TTA CTA TTA TCA ACA CTA CCT CTA AGT
4603 CGT GAG ATT ACA CAA ATA CAT ACC TTA AGA AGC ACT GAA CAG TAT CAT TTA TGA CAT TTA TGA CAT TTA TGA TCA ACA CTA CCT CTA AGT
4681 TAT CTC TGT ACA CCA GAA CCC TTA AGA AGC AAC AGC ACT GAA CAG TAT CAT TGA ACT CAT TTA AAG TCT AAA ACT GGA TAC AAC
```

Fig. 12, contd.

```
4759 CAA AAT GTC CAC CAA CAG TTA AAT TAT GAC ATG TTC ACA ATT GAG CTA TTA CTT AAT AAG GAG AAT TAA TAA AAT AAA
4837 ACT TAA GAG CAT AGT TTA ATC AAG AGA TAA ACA AGA TTT GCA AAA CAA AGA AAA CAA ATT TTT TCA ATG TAA GTT TAA AAG
4915 CAG GTA AAA TTT AAA ATT AAG AGA GAC ATA AGT TTT GAG ATT GGG GCA GTA AGG TGG AAT CTC AAA TGG GGC TTG GGC AAT GTT CTG
4993 TCT CTC TGT ATG GGA TGT GAA AGT TAC TAT CCT GTA ATT GGG ATC GTT CTT CCT GTA TAT ATT GTA TAC TTC ATA
5071 ATA ACT TCA CCT AAT GAA ATA TCT AAA GAC TGC AAT CAG TCA GGA TAC AGA GGA GAA TGA ATC CGT ATA CGT CAA GGC
5149 CAG AAG GAC TAC AAA ACA CAT ATA GGG AAT TCA GGA GAT TCA AAT CTC CCA CCT TGA GCC TTC TAT TCT GCC CAG AAT AGC
5227 TCA AAG GTA TAA AAT GAG GTT ACA TTA AAG GAG ACC TTC ATC AAC AGG GTC TCT CTC ATG CAT CGA AGA TGA AGA GCC
5305 CAT GTA CAC GTA TCA AAG GTT CTC GTG GGA TCA TCC ACT CAA TTT CAT CTT CCT GTC TGG GTA CCT GGA GGC CCC
5383 CAC GTA AGA ATT TAG TAA TGT GGA AAA GGA CAG CAG TGT TAG TAC ACT TCT AAT TAG CAT AAC TTT CTC AGT CCA CAT
5461 TGC ATT AAA TTT AAA CAG GGG AAA GGA CAT CTT AAA AGT CCA GTT TCC CTT AGC CTT GAG AAT GTT CTC AGT GTA CAT TAT
5539 GCA GAA TAA TGT GGG AAA GGA ACT TCT TTT CAA CAG CAC ATA TGC AGT CCA CCC CTC GCC TTC CTA CCT CTT TTA TGA CAT AGC AAC
5617 AAG GAT GAT GGT TCA ATT TGC TTT TAT AGG AGA GGG CAA GTT TCC TTT TAA ATA TAG CAT AAT GCC TCA AAA TAT CTG AGC CAT
5695 TAT CCA CTT GGA AAA ACT TCT AAT CAG CAC CAC TTA ATA TGC AGT CCA CTC CTT TTC AAA AAT AGC ATT TAT ATA CTG AAA GAG CTG
5773 CTG GGA ACC CTT ATG AAC AGA ATA AAT ATC TAA TCT AGA ATA TCT TAT AGA TAA AAA GAA TAC AGT GGT CTC TAT AGT ATA ATT ATG TGA TAA
5851 TCG AGT CTT ATC TGT GAA AAA AAG AGC CAT TTT TAA ATG AAA ATA CAT TTT TGG CTC TAA TTT TGG CTC AAG CAC TAA
5929 CTT GTG GAA AGA GGA TCT TCA TAT CTA TAT ATT GTA ATG TCA AAG GTG ATA CCA TAT AAA TGC ATT ACA CTG TTA TTG TTA GGA ACA ATA CTT AAA AAC CAT
6007 TAG AGA GGA TCT TCA TAT CTA TAT ATT GTA ATG TCA AAG GTG ATA CCA TAT AAA TGC ATT AGT GGC ACA CAG ATA AGA
6085 TCA CAA GGA TCT TCA TAT TCA TAT ATT GTA ATG TCA AAG GTG ATA CCA TAT AAA TGC ATT AGT ATA ATT ATG ATG TGA TAA
6163 AAT GTT GTT ATT TGG ACA AAG AAA ATG AAA AGC GTG TTA TCA CAT GCT TAA TTT ACA TCA AAG GTA TAT GCT AAA AAC CAT
6241 ATA AGG ATA AAG CTC TGT GAA AGC CCA CAT CCT TTT GTG TGC ATA TCA GAT ACA CCA CAT TCA ATT CGT GGA GAC GGC ATC TTT ACA AAC AAC GAG
6319 TTT GGA TAA CTA ATA AAG AAG AGC GCC CCT TGT GTG TGC ATA TCA GAT ACA CCA CAT TCA ATT CGT GGA GAC GGC ATC TTT ACA GAG
6397 CCT AAG CCT CAG CTA ATG AAA CCT CCC GCC CAA GCA CAG CAT GCC AGT GGA CCT TTG AAG CTT AGA ACT ATG AGG ACT GTG AGA GAC CAG CCC TAG CAG CTT CCT ATT GTT
6475 GCT AAG GAA CTA AGA CCT TCA AGG CAA TCA AAT GGA ACT TAG GTG TGC TGA ACT CTT CAC AAG CCA AGG ATC TGT GCT TGA TTC CCC ATG TGG AAA GCT TTA
6553 ACT GCC AAT GCC CAA AAT TAT ACA ATT GGA ATA CCA GTC TAG AAG CTT CCA AAG TCT CAC TGA CTT TTA GCA CAT CCT AAT TGC TAA AAT ATT
6631 CCT TCT CTA TGT TTT GTA TTG ATA AAC AAC TGC TTC CCT TAA TTT ACT ATA TTG TAT GCA CAT CCT AAT TGC TAA AAT ATT
6709 CCC TAC AGA CTC TTT TGC CCA AAT GTG TGC CAT GCT CTC AAC AAT ACT GGA TCC AAA CCA ATC ATG GGC ATC TTT ACA GAG
6787 ATA AGG AAT GTT TGT TGT CCA CAT GCT CTC AAG AGA CAT GCA AGT GGA GGT TTC AAT AAT TCA ATT TCA CGT GGA AGA CGC ATC TTT ACA GAG
6865 TAC AGC TAA CTA AAA ATG AAG AGA CAT TTC AAG GAC TTC CCT TTT GTT TTT GGT TTT GTT TTT AGA CTT AGG CAG CAA GAT TTT TGT AGT ATC GTT
6943 AGA AAG ACA TTA AAA AGA ATT AAG GAC TTC CCT TTT GTT TTT GGT TTT GTT TTT AGA GAG CAG CAA GAT TTT TGT AGT AGC CAG
7021 TAG TCA AAG CTA AAC AGT CCC CAG GCC CTT TGT TTT CTA CAT CTC AGA GGG TTG TCT AGA ATT GAG CAG CAA CTC AGT TTC TGT CCC CCT TAT GAC AAC TGT
7099 AGG AGA AGC CCC AGT GCC CTT TGT TTT TGG GTT TGT CCT TGG TCT GTT AGA ATT ATG GAT TCA AGT ATA GCT TCT TAT
7177 CTA GTT TTC CAG GCC CTT TGT TTT TGG GTT TGT CCT CTC TAC ACT CAG TGG CAT GAA CTC AGT CAG TTT ACA GAG
7255 GTT TTT TTT TTT CTT TTT TGT GTT TTT TGG GTT TGT AGA CTC AGA CAG CAG CAG CAG CAG CAG CTC AGT TTG TGT AGT ACA GAG
7333 TGT TTT GTT CTT CTT TGT CTA CTA CTA CTA CTG GGG TTG CAT AGA CAT GGC ATC TTT ACA GAG
7411 TTC TTC TAT ATT TAT ACA CAT ACT CAG GTT TCT AGA CTT GAT TCA CAC GAA AGG AGG CTT ACT AAT GCA CAT GAG AGA CTC AGT TTT TGT AGT TAT
7489 TCT TTA TTA AAA GGG CTA CTG TGG CAT GAA GAT TCA GAT TCA CAC GAA AGG AGG CTT CAA TTG AGA AGT CTT TGT CAC CCC CCA
7567 GCA ACT TCA ACC ATG GAG TTC CTG TGG CAT GGA CAT GAC AAT AAA CCA TCT GGG GGA CAG CTT CAT GAG ATA AGT TCT GAT
7645 GGG TCA AAT AAA GGG TCT TTT TTA AAA AAA TCC AGA ATT AGC TAT GCT TCA AAA TTG CTT GAG ATA AGT TCT TCT GAT
7723 AAT AAA AAC ATT TCT TTT TTT AAA AAA TCC AGA ATT AGC TAT GCT TCA AAA TTG CTT GAG GAA AAT CTG TTT AGA ATT
7801 AAT AAA AAC ATT TCT TTT TTT AAA AAA TCC AGA ATT AGC TAT GCT TCA AAA TTG CTT GAG GAA AAT CTG TTT AGA ATT
7879                                                                                                              AAC TTT ACA
```

Fig. 12, contd.

```
7957  AGT TAA ATA AGT TAT ATT GTA GAA AAG GTA GAG AGA ATA GTG GAA GAG AGA GAT AAG ACT TCA AAA GGA GTG
8035  GAG GGA GAT AGA GGA GAA AGC AGA TTC GCC TAT AGT CTG TTT TAA AGC TGA CAT AAC TTT GTA ACA CAG GTT CTT GGC CCC AAT TTT GTG GCC AGT CAG CTC CCG ATG CTC ACA GGC CAA GTT TGA GTA GGC TTA GGA
8113  AGC CAG GAT GGG TAT TTC GCC TAT CTG TTT CTT TGA CAT AAC TTT GTA ACA CAG GTT CTT GGC CCC AAT TTT GTG GCC AGT CAG CTC CCG ATG CTC ACA GGC CAA GTT TGA GTA GGC TTA GGA
8191  CTT CAC TTG TGC CAA CTC AGA GTC TTA TAG CTT TAA CTG GGT AAG ATT ATA AGG GAA AGG AAT CAG GCC CCC AGT GCC GCC ATG CAG GCC AAG GGA AGG AAT GTA ATG TGT ACA CTG AGA CTG AGA TGT GCT ACA
8269  CTT ATC TCC TTA TGC CAA ATT ACT AAG GAT TCT AAA ATT TTG AAG CAA TCT ATA TTG AAG GTA TAT ATG GTG AAG GGA AAT ATA ATA TGT ATA TAT ATG TGT GTG AAG GGA AAG AAT ATA ATA TGT ATA TAT ATG TGT ACA CTG AGA CTG AGA TGT GCT ACA
8347  ACT ATT TCA ACT CAA GAT AAT ACT CAA GAT AAT AAT TCT ATA TTG AAG GTA TAT ATG GTG AAG GGA AAT TAT AAT GTA CTG AGA CTT TAG ATT TTT
8425  AAT TCA ACT CAA GAT AAT AAT TCT ATA TTG AAG GTA TAT ATG GTG AAG GGA AAT TAT AAT GTA CTG AGA CTT TAG ATT TTT
8503  TAT TGT GGT TTT CGA GAC AGG TCT CGA TCT TGT GAC CTA TGC CTT GCG TAT TCT CTC TCT CTC TCT CTC
8581  AAA CTC AGA AAC CTA CCT GCC TCT GCC TCT GCC TCT GCC TCT GCC TCT GCC TCT GCC TCT GCC CCG GTG
8659  GCC TCT GCC TCT GCC TCT ATA CGC AAG TTG TAT AAG CTT TGT TTT GCT TTG CTT TTT GTT TGT CTT
8737  GCC TCT GCC TCT ATA CGC AAG TTG TAT AAG CTT TGT TTT GCT TTG CTT TTT GTT TGT CTT
8815  AAA TTT TTA AAC AGT TTG CTT TGC TTT GCT TTG CTT ATG CTC ACT ATA TCC ATG CCC
8893  GCC CTC AAA AGT TTG CTT TGC TTT GCT TTG CTT ATG CTC ACT ATA TCC ATG CCC
8971  TGC TTT GCT TTG CTT TGC TTT GCT TGC TTT ACT CTT TCC GGA ATA GTG CTG GGA ATA GTA AAG GCA TTG GGG GCA TAG ATC
9049  TTT TTT CCG GGA GAG GGA AAG CCT ACT GTT TCT ATA GAT ATC ATG AAT CTT ACT CTT GCC CAA GTG CTG CTG AAA GGC TGA GTT TGT TTT ATT AAC ATT TAT
9127  AGG CTT GAT TCA ACT CAT AGA GAT CTG AAA GTT TCT GAC ATT AAT CTT ACT TTA ACA TTT AAT ATT CTT CTA CTG ATT AGG CAT CCC AAT AGA CAA AGA
9205  AGA TAG TGA TCC GAG TTT TCA ATC TGA ATC TAT ACT TTA GCA CTT ATT AAT CGA TTA ACA TTT AAT ATT CTT CTA CTG ATT AGG CAT CCC AAT AGA CAA AGA
9283  ACT AAT GTG GAG CAT ATA CAG GTG TTT GCC ATC AGT CTT CAT AGG CTT TGA GGA GCA TTG GGG GCA TAG ATC
9361  TAG AGG CTC ATT ATA TAC AGG AAC TTT CAA TAT CTG TCA GAT CTT GCC TCA AAA GTT TGT GGC TTC TAG
9439  TTA CTC ATT TAC TTT CAA TAT CTG TCA GAT CTT GCC TCA AAA GTT TGT GGC TTC TAG
9517  AAA ATC TTT CAA TAA ACC TGA TAT ATT CAA AGA AAT CTT GGC TTT AAT TTA TAT TGA TAT TTC AAT AAC AGA GCA TAT
9595  AAG AAA AGA GCC TGA TAT TTT TCA AGT CTT TGA TTT CAA AAA TAC GAT CCT TAA GAT TTT ATT TCT CTC TGC ATT AGG CCA TCT TTT
9673  AAA GAA AAA AGC CCC AAA AGT CTT TGA TTT CAA ACC TGC CCT AAA ACC AGC TTC ACA GCT CTG TAG CTT ATA TTG TTA CCA TGT CAG ACT AGA TGA CTG TGA GCA
9751  GCT ATC CCC TAT GAT TTC CAA ACC TGC CCT AAA ACC AGC TTC ACA GCT CTG TAG CTT ATA TTG TTA CCA TGT CAG ACT AGA TGA CTG TGA GCA
9829  CTC TGT ACT AGT GCA CTT AGA TAC CTT GAG TAC TTC CTC TGT TTC ATA TTG CCA TCC AAT AGA TGA CCT GTC AGT GGA GTC TAA GAA GGA
9907  GCT ACA TAT GCA CTC TAG CTT GGA TAC TTC CTC TGT TTC ATA TTG CCA TCC AAT AGA TGA CCT GTC AGT GGA GTC TAA GAA GGA
9985  CCC CTT TAG CTT GCC AGG CAC TGG CAT AGC CTC ACG AAG AAG GCT ACG TGT ATA CTC AGT GCC CTG CCA AGT GGA GCA GTC TCC TAA GAA GGA TTA
10063 TCC ACT TCT GTA TTT GCA ATA GTA TCT CAA GGT CTT TGG CAT AGC CTC ACG AAG AAG GCT ACG TGT ATA CTC AGT GCC CCA GTC TCC TAA GAA GGA TTA
10141 TTT CTG TTC TTC CTT CCA TCT CAG CTC TTT GGT CTT CCT CTG GCA TTC TGA GTT CTA TAT TTC TCT ACT CTC CAT TGT GAT ATC TGT GGG TTA
10219 TCC GTG AAG AAT CCA ACG TAT TGA GTG CAT ATC ATG CGT ATG TTC ACT GTT TTT GGG CAT CCT ATA GTA CTC CAT TGT GAT ATC AAT GCC CTC CAG
10297 ATA TCC ACG TAT TGA GTG CAT ATC ATG CGT ATG TTC ACT GTT TTT GGG CAT CCT ATA GTA CTC CAT TGT GAT ATC AAT GCC CTC CAG
10375 ATG CAT TTT CTG GCC TAA GAA TTT CAT TGT CTC CTC TGT TGA GGG CAG TTG AAG TTG AAA AGC CCT AGA ACA AGC CCT AGA CAT TAT AAA TAA GGC TGC TAT
10453 ATG CAT TTT CTG GCC GGA CCA TCA ACA TAT CAT GAC TGT GTC CTT CAT AGC CCT AGA ACA AGC CCT AGA CAT TAT AAA TAA GGC TGC TAT
10531 CAT TTT CTG AGC GGA CCA TCA ACA TAT CAT GAC TGT GTC CTT CAT AGC CCT AGA ACA AGC CCT AGA CAT TAT AAA TAA GGC TGC TAT CTT
10609 GAG CAT AGC GGA CCA TCA ACA TAT CAT GAC TGT GTC CTT CAT AGC CCT AGA ACA AGC CCT AGA CAT TAT AAA TAA GGC TGC TAT CTT
10687 CCG GTA GTA TGA CAA ACT ACT CAT TGT CTT CAT GAC TAT CCA AAT AGA CCA CCA GAT GAG AAC GTA ATA AGC TCC ATT AAA ATC AAT
10765 AAA GGT TAT GTA TGA CAA ACT ACT CAT TGT CTT CAT GAC TAT CCA AAT AGA CCA CCA GAT GAG AAC GTA ATA AGC TCC ATT AAA ATC AAT
10843 GGA CTG CCC ACT ATC TAT AAA TAT CCT TAA TTG TCT AAA TCA GAT GAA GAT GAA AGT CTG TGA AGT GCA TCA AAT TTT GAC
10921 CAA ATG GGA AAA TAT AGA TAT CAA GTC TAT TAT CAA GAT GTT TTC CAG AGT CCT ATA AGG ATA AGG ACC ATC CTC CCC AGC TTC
10999 TAG AAA AAT TGT AGA TAT CAA TAT CAA AAT TGC CTG AGG ATA AGG ACC ATC CTC CCC AGC TTC
11077 TGC TTG CTT CTC TCT TCT TCT TCA TCC TCT CTG CTG CAA TCT CTG CTG CAA TCT CTG CTG CAA TCT CTG CTG CAA TCT CTG CTG CAA TCT CTG CTG CAA TCT CTG CTG CAA TCT CTG CTG CAA TCT CTG CTG CAA TGA GAC TGA GTG CAG
```

Fig. 12, contd.

```
11155 CGT GTA ACT CTC CTG TGA AGT ATC TCA CAA AAC GTT CTA CCT GCC AAA CCT GGA TGA GCC CTT TGT CTT TCT GAA
11233 GCT ATG AGG CTC TCT ACA TAG ACT CAA GAA TCT CAT GAC AGG GAG GAT GTA ATG AAG TGG GGA AGG CTG ACA TTA
11311 GCA TTG CTC CTG TGT GGC TCC TTA ATT TCT CAT TCA CAC TGA GAT GTT AAC TGT GAC TCA TGG GTG AAG AAG
11389 CCA GAG AGG TTC TCA AGG TTC ACA CAG GTT GCA TAT CAG ATA TCC TAA TTT TAT TAT ATT AAC TAT GGG TGA CTC CTT
11467 TAT GGG TCA AAC CCT AAC AGT AGG AAA ATG AAG ATT TTG AGA CCC TAT AGT TGT GAG AAT CAT TAT ATG TAT
11545 ATA TAT ATA TTT CAC AGT TTA GGA ATT TGC CAC ATT GTC TAT GTA AGC TCT GTA TAA ATA GAG AAT GCT ATA AAG CCC
11623 TAT TAA AGG CCA TGT GCC TTT AAC GCA TAG GAT GCT TAT GTC TAT CAC CCA TAG ACT GTA TAA CAT TGA TTC AGG GTT TGT AAT
11701 AAT GGA CTA AGG ATA CCT CAA CCT AAG ACC ATC TTG CAA ATG ACT GAT TCT ACT ACA TGG CCT GAA TAT CCC TAG TGG GAA
11779 TTT AAA TGC AAA AAT GGC TCC ACA AAT CTT CAG GAG ACC CCT GAA ATG AAC CAA TTA ACT TGG CCT AGT GCC TTT CAA CTC
11857 AAA TCT CTT GAT GTC CAA CCT AAG AGC CCT CAG GCC TTT CAA GAT ACA TTG CAA GTA ATG AGA AAT CCA TGT AGA GAC CTT CAA CTC
11935 CTG CCA TTG AAT CTT CAG AAT GGC TCC AAT TTG ACT ACA ACT TGG CCT GAT ATT GAT GAC AGA AAA GCT AAG ACT TAG
12013 AGG GAA TAA ATG CCT CTG AGA TCA TGC AAC TGC TAT AAC TGG CAA TTA TGG CAA GTA TAT CCC TAG TGG GAA
12091 AAT GTT GTT CCT GTA GCT CTC AGG AGA TTA GGA GAT CTC GAA ACG CCA AGC ACG TAG TTG TAC ACC CCT GTG
12169 AAG ACT TGG AAA TCA GAA TCG CTA CAT GTC CTG AGA GTC AGG CAG GAA GCT ACA CAG AGA AAC TAT CTA AAA
12247 ATC CCA TCG GAA AGA CTT AAT AGG AGA ATG GAT GTT AAG ATC TGG TCA TAG AGA AGC AGA ATT GAG ATT CGA AGC CAG
12325 AAT AAT TAC TAA CTA CTT ATG TTT TAA CTA GTA AGG ATC GTA AGA GGC AAT AAT TAT AAG ATT CTA TTG ATC TCT
12403 TAT TTT CTA CCT GGT AGT TGT TGT TGG AAA ATA ATA TTA TCA GCC AAC ATC TTC CAT TTC AGT ATA GCA CAG
12481 GCA ACA GAG AGT CTC CCC ACC CTT ATT GGG AGT CTC CCA TAC ACT GGT TAT TGA TTT TCA TAG CTG ATG TGG GCC ACA CTG GAT
12559 AGT ACC CCA TAA AAG TAA TGC TAC CTT ATT GGG AGT CTC CCA GTC AAG GCA ATA GCT ACC GTC ACA CTG CTT
12637 TAA AAA AAG TAA AGA AGA TAC CTT GAG GAA CTG AAA ACA CTG CAT CTG CTT CTT ACC TCC TCC AAC
12715 TGA TCA AGA AGA GGT ATC CAG AGT CTG GT GCA CAC CTT TGT GCT CTT TGT GAT CAC GTC TGT GCC CCA GCA CCT GGC CAA
12793 AGC CTG GGT ATC CAG TCC AAT AGT TGT GCT AAA CAT GTT TAG GCT CAA ACT CTT GAG GCC ATG CCC CAG GTT
12871 GGC TGT CCC CAG GCC CAT AAT AGT TGT GCT AAA CAT GTT TAG GCT GGA GCC AGA CAC GAA TTC TAG AAG TAC CTG AGA
12949 AGT CCC CAG GCC CAT AAT AGT TGT GCT AAA CAT GTT TAG GCT GGA GCC AGA CAC GAA TTC TAG AAG TAC CTG AGA
13027 CAC TGG GCC AAA ATT TGT TCA GTA TTG AAC ACC CCA CAA CAT CTT TAG ACC ATA GAA GTA TTC TCT TAT ATC
13105 GTG GCA AAA TAG TTG GTC CTA GTA AAC ACC CCA CAA CAT CTT TAG ACC ATA GAA GTA TTC TCT TAT ATC CCT TTT CCA
13183 AGC ATT GCA ATG TAG GCT GTC TTC ATA TTT GTT CTA AAC ACC CGG CC
13261 TCC ATG ATG TAG GCT GTC ATG CTA TTT GTT CTA AAC ACC CGG CC
13339
``` pSELECT-IGKV1-39/J-Ck

```
  1 GCG GCC GCA ATA AAA TAT CTT TAT TTT CAT TAC ATC TGT GTG TTT TGT AAT CGT AAC TAA CAT ACG CTC
 79 TCC ATC AAA ACA GGA TCT GCA AAA CGA AAC AGG ACA AAC TAG CAA AAT CTT CCA GTG TCC CCA GTG CCA GAA CAT TTC
157 TCT ATC GAA GGG TCG GCA ATT GCT CCG GTG CCC AGC GGT CGC CCA CAG TCC CCG AGA AGT TGG
235 GGG GAG GGT TTC TTC CCG GCA ATT GAA CGG GGG GCA TAA ACT GGG AAA GTG ATG TCG TGT ACT GGT
313 TCC GCC TTT CCG GAA CAC GTG GGA AGC AGC CTT GCA CTT GTG TAT CCT GCC TGT TTC GCA ACG GGT
391 TTG CCG CCA CAC GGT GTC TGA GCC GCG CCT CTG CCG CGG GAA CTG CTC CCT AGG TAA GTT
469 ATC CAC GCC TCA GCC GGA GCC TGC CTT GTC CGC CTT CGC CGG TCA GCC TCT AGG CGC TTT
547 TAA AGC CCC TGA GCC GGA GCC TGC CTT GTC CGC CTT CGC CGG TCA GCC TCT AGG CGC TTT
625 GCC TGA CCC TGC GTC CTC AAC TCT ACG TCT ACA GAT CCA AGC TGT GAC CGG
```

Fig. 12, contd.

```
 703 CGC CTA CCT GAG ATC ACC GGC GTG TCG ACG CCA TGG ACA TGA GAG TGC CCG CCC AGC TCC TGG GGC TCC TGC TAC
 781 TCT GGC TCC GAG GTA ACA CCC AGC ATG AGG GAG ATA GTA AAC ACT AGA TTA AAT AGC TAC CAG TGA CTT CAG GGA
 859 AGT TCT CTG ATA AGC CCC AGC CTG AGC CAG TTT ATG TTT GTT ATA AGC GGT GCT CCA AGA TGT GCC AGA ATC CAG
 937 ATG ACC CAG AGC CCC AGC TAC CTG CAG TAT CAG CCC GAC AGA GTG ACC AAG GTG GAC ATC GCC AGA TCC AGC ATC
1015 AGC GGC GTG CCC ACC AGA TAC TGC CCC AGC GCC GCC GTG AAG CCC ACC CTG AGC ACC TGC CCC AGC AGC CTG GAG
1093 AGC TTC GCC GAC GCC TAC TGC CCC ACC GTG TCC CAG CTG GAA CAG TTC ACC AAG AAG TAC ATC CCT GAG ATC CAG
1171 GAC GCC GTG AAC AGC GCT CCC AGA GAC CCC AGC CTG GTG AAG ATC AGC GCC TCT GGC GGA CAG GCC AGG GTG AAG
1249 AGA GCC GAC GCC TTC AAC ACC TAC TGC AGA GTG TCC AGC AGC CTG AGC GAG AGC AGC ACC AAG GTG GGC GTG GTG
1327 TGC TTC GTG AAC AGA GAC GTG TCC CCC AGA GAC CTG TAC ACC AAG AAG CTG AAG CTG AGC GAG CTG AAC CGG GAG
1405 CTG GAC AGC GTG CAC GAC TAC ACC GTG TTT GGA CAA ACC ACA ACT AGA ATG CAA GTT AAC
1483 TAC GAG AGG CAC AAC CTG AGC TGG TGG CCA GAC ATT TTT GAT AGA TAC TTA TTT GTA GAG
1561 AAC AAC AAT TGC TTT ATT CAT TGT GAA ATT ACA GCA TAG GCA TTC CAA ATC GAT TTA ACC CTA CCT GAA TCC TTT CTT TCA TGG
1639 AAA GAG TGT TGA GCT ATG GGT TGA ATA TTC TAA AAT AGG CAT GTA TTT AAA AAT AGG AAC CAT AGA ACT AGA
1717 AAC AAC AAT TGC TTT ATT CAT TGT GAA ATT ACA GCA TAG GCA TTC CAA ATC GAT TTA ACC CTA CCT GAA TCC TTT CTT TCA TGG
1795 GAG GAA TGA ATA GGA TTT TAA AGG CAT GTA TTT AAA AAT CAG GGG CTC CTG GGA CGA GTG CTG GGG CGT CGG
1873 AGT TTA AGA TAT AGT AGT CAA GCC CCT TCA TAA GTT TCG ACT TCC TTT GCC CTT TGT ACA CAC CTT GTA CGC CCG
1951 CAT TCC CTT TTT AAA ATA TTC TCA AGA TAG TTG TTG GAC TAC TCA TTA TGA TAC CCT CTG AAA TTG CCG TCA ACC
2029 AAT CCA GAT GCT CAA GGC CCT TCA TAA GTT CCA ACT CAT TCC GCC GCA CAG CCT GCA AGC TCC GGA TGC
2107 AAT CCA GAT GCT CAA GGC AAG CGA TCT ACT TCT ACA GCC CAG CCC TGC GCC CAA GAG CCT GCA AGC TCC GGA TGC
2185 TTT CCA CTA TCG GCG AGT ACT TCT ACA CAG ACG GTC CAT CGA TCA CCC AGA CAG CCC CAA AGG CCG CAG TCA ACC
2263 ACA GTC CCG GCT GAT GTA TTT AGT ACG ATT GCG TCG CAT GCC CAA TGC GCC ACA CCC TGA AGC TCC GGA TGC
2419 AAG GCG CCC GCT TAG CAT CCA AGA AAG CGG GCG GAT ATA GCA CAC CGG GCG CCT GCA AGC TCC GGA TGC
2497 CTC CGC TCG AAG CCG AAC GTC TGC CTC CAG ATG TCC GTC AGG ACA TTG TTG GAG
2575 TGG GAA TCC CCG TAG CGC AGG TGC TCC CGG ATC CCT GCG AGT CGG CAA ACC CGG GTT TCA ATG CCA ATG GCT CAT ACC ATG AAA TCA
2653 CCG AAA TCC GCG CTG ACG TAT TGA AGC TCC GCG ACG GGT TGC TGC AGA ACA GCG GGC AGT TCC CAA ATG CGG AGC ATC GGG GCA GCC CCC
2731 ACG GAC GCA CTG GTG AGC TCC ATG AGC CGG CAA TAG GTC AGG CTC CTG TAG AAA CCA TCG AGG GCG CAT AGA TCG GCC GCA GCG
2809 ATC GCA TCC ATG CGG CAA TGC ATG AGC TCC ATG AGC CGG CAA TAG GTC AGG CTC CTG TAG AAA CCA TCG AGG GCG CAT AGA TCG GCC GCA GCG
2887 ATC GCA TCC ATG CGG GTG TAT TGA TCC GCG ACG ATT CCT TGC GGT TGC AGA ACA GCG ACA CTG AAT TCG GTT TCA ATG CCA GTG GCA ACC
2965 TGT GCA CGG GCA AAG TGC CGG CAA TAG GTC AGG CTC CTG TAG AAA CCA TCG AGG GCG CAT AGA TCG GCC GCA GCG
3043 GCC GAT GCA ACA TGC CGA AAG ACA TGC AAA CCA TCG TTG TAG ATA TCT TTG TCG AGT GTC CGA GAC GTC TGA ATT GTC TAC AAA CAA CAA CTA TGG GTG GAG ACT TGG AAA
3121 CGC CCT CGT ATC AGA AAC TTC TCG ACA CGA GTC TGA ATT GTC TAC AAA CAA CAA CTA TGG GTG GAG ACT TGG AAA
3199 TTT TCG ATC AGA AAC TTC TCG ACA CGA GTC TGA ATT GTC TAC AAA CAA CAA CTA TGG GTG GAG ACT TGG AAA
3277 TTA TAC TAT GCC GAT ATA CTA TAT GCT ACA GAC TGC CGA TGA ATT GTC TAC AAA CAA CAA CTA TGG GTG GAG ACT TGG AAA
3355 CAC TAA ACG AGC TCT GCT TAT ATA GAC CTC ATT TAC CTC TAG CCG TCA CCA CAA CAA CAA CAT CAT CAT TGC TAA ATG GAC TTT ACC GTC GTA
3433 ACG ACA TTT TGG AAA GTC CCG TTG GTA TCC ACG AAA GTC AGG GTA CTG CCA AAA GTG GGT GAT GAT AGC GTT GTT
3511 TCC CCG TGA GTC AAA CCG CTA TCC AGT AGG CGT ACT TGT ATG TGA AAC ATA ATG GAC TTT ACC GTC GTA AAA
3589 TAC GTA GAT GTA CCG CCA AGT GTC CAT ATG TGG CAT TTG TAC CAA GTG GAG TTA CCG TAA ATA CTC
3667 ATT GAC GTC AAT GGG CGT ACT GAA ACC ATT TAC CGT CAT TAC CGT CAT TAC CGT CAT TAC CGT CAT TAC CGT CAT TAC CGT CAT TAC CGT
3745 CAC CCA TTG ACG TCA ATG GGA GTT TGT TTT GGC ACC AAA ATC AAC GGG ACT TTC CAA AAT GTC GTA ACA ACT CCG CCC CAT TGA CGC AAA TGG GCG GTA GGC GTG TAC GGT GGG AGG TCT ATA TAA GCA GAG CTG GTT TAG TGA ACC GTC AGA TCC
3823 GTC GTT GGG CGG TCA GCC AGG CGG GCC ATT TAC CGT AAG TTA TGT AAC GCG GAA CTC CAT ATA TGG GCT ATG AAC TAA TGA CCC CGT AAT TGA TTA CTA TTA ATA ACT
```

```
   1 CTT GAT TTG GGT GAT GGT TCA CGT AGT GGG CCA TCG CCC TGA TAG ACG GTT TTT CGC CCT TTG ACG TTG GAG TCC ACG
  79 TTC TTT AAT AGT GGA CTC TTG TAT TTC CAA ACT GAA ACA CTC ATC AAC TCT TTT GAT TTT TAA GGG
 157 ATT TTG CCG ATT TCG GTC TA? TGG TTA AAT CTG ATT TAA CAA TAA AAA TCG AAC GCG AAT TTT AAC AAA ATA TTA
 235 ACG TTT ACA ATT TTA TGG CTC AGT CTC AGT CGG TCT GAT ACA ATC TGC GCA TAG AGC CAG CAC CGA CCG CCA
 313 ACA CCC GCT GAC GCG CCC TGT CGG CCG TGT TCA CCG AAA ATC CTC CCG GCA TCC GCT TTA AGC CAA GTC TCC GGG AGC
 391 TGC ATG TGT CAG AGG TTT ATA ATG GTT TCA CCG GTT TCT TAG ACG GTT GGA AGA CGA TCC AGA CAA AAG GGC CTA TTT TTA TAG
 469 GTT AAT GTC ATG TCA ATA ATG TCT CGC GGA AAT GTG CGC GGA ACC CAA TAT TGA AAA
 547 TTA TTT TTC TAA ATA CAT TCA AAT CAT TTC CGT GTC CTC ATG AGA CCC CTC TGA TAA ATG CTT CAA TTT CCT TAT TGA AAA
 625 AGG AAG AGT ATG AGT ATT CAA GTA AAA GAT ATT CCG GCC TTT GCG CGA TTT TGC CTT GTT TTT GCT
 703 CAC CCA GAA ACG CTG GTG AAA CTG CCA CCG GAA GAT GCC CGA GTG GGT TAC ATC GAA CTG CAT CTC
 781 AAC AGC GGT GTA ATC CTT CGC ACA GAA AAG TTT CGC CCC CAA GAG ATG AGC ACT TTT CAG AGT GCT TTT CTG GTT
 859 GGC GCG TTA TCC GTC CCA GTG ATT CTG ACA GCC CAA ACG CGT CTC GGT CGA GAT CGC ATA CAC TTG GTT
 937 GAG TAC TCA GTC ACT GCG AAC TTA CTT CTG GGA CTG GAA GAG ATA GAA GCC CTA ACC AAC CAC AAC ATG
1015 AGT GAT CAT GTA ACT CGT ACT CGC CTT GAT CGT TGG GAA ATC CGG AAT CTG TGC ACC ATA CCA GAC GAG TCC TCA AAA ACA CCA
1093 GGG GTA GAA AAG CAT ATC GCA ATG GTT TGT TGT ACG CTT TTT ACT CTT GCT GCT AAG GGC TCC CGG CAA CAA TTA
1171 ATG CCT GTA GCA ATG GAG GTG GTT TGT TTG CCG GAT GTA ACT GGT CCA TGG TGG CCG TGG ATT GCT GAT
1249 ATA GAC TCT GGA GCC GGT GAG TCT CGC ACT GCA AAT GTA CGA GCT ATT AGA CTT AAT ATC GCT ACA CTG GTA
1327 AAA TCT ATC TAC ACG AGT CAG CAA GTT TAC TCA GAT TAT ATA GAT GAA CGA AAT CAT AGA CTT CAT TTT AAA AGG
1405 GTT AAG CAT TGG GTG TAA CTG TCA GAC CTT TTT GAT AAT CTC ATG ACC AAA ATC CCT TAA CGT GAG TTC CAC TGA GCG TCA GAC
1483 ATC TAG GTG AAG ATC CTT TTT AAA GGA TCT TCT TGA GAT CCT TTT TTT CTG CGC GTA ATC TGC TGC TTG CAA ACA AAA CCA
1561 CCC GTA GAA AAG ATC AAA GGA TCT TCA CCT AGA TCC TTT TAA ATT AAA AAT GAA GTT TTA AAT CAA TCT AAA GTA TAT ATG
1639 CCC CTA GGC GTT TGT TTG CCG GAT CAA GAG CTA CCA ACT CTT TTT CCG AAG GTA ACT GGC TTC AGC AGA GCG
1717 ATG ATG ACC ATT ACT ACA GTG TGT CCG GGC TAG CCG CCA TGT GTT GTG AGC CCT ACA CGA
1795 CAG ATA CCA AAT ACT GTT CTT CTA GTG TAG CCG TAG CGA GAC CAC TTC AAG AAC TCT GTA GCA CCG CCT ACA TAC
1873 CTC GCT CTG CTA ATC CTG TTA CCA GTG GCT GCT GCC AGT GGC GAT AAG TCG TGC TTA CCG GGT TGG AGA CGA TAG AGA CGA
1951 TAG CGG TGA GCT ATG AAG CAG ACA CTT ATC CCG AAG GGA GAA AGC GCC ACG CTT GGA GCG AAA ACC TAC CCG
2029 ACC GAA CTG AGA TAC CTA CAG CGT GAG CTA TGA GAA AGC GCC ACG CTT CCC GGA AAC GAG CCT CAC ACC TAT CCG
2107 GTA AGC GGC AGG GTC GGA ACA GGA GAG CGC ACG AGG GAG CTT CCA GGG GGA AAC GCC TGG TAT CTT TAT AGT CCT GTC
2185 GGG TTT CGC CAC CTC TGA CTT GAG CGT CGA TTT TTG TGA TGC TCG TCA GGG GGC GGA GCC TAT GGA AAA AAC GCC AGC
2263 AAC GCG GCC TTT TTA CGG TTC CTG GCC TTT TGC TGG CCT TTT GCT CAC ATG TTC TTT CCT GCG TTA TCC CCT GAT TCT
2341 GTG AGC GGC AAC GCG CGG GTC GAA ACT ATT TAC CGC AGT GGA AAT GTG CGC GGA ACC CCT ATT TGT TTA TTT TTC TAA
2419 AGC GAG GGC TTA AAC GAA GAG TTT TCG TTC CAC TGA GCG CGC GTC AGA CCC CGT AGA AAA GAT CAA AGG ATC TCT TGA GAT
2497 GAC AGG TTT CCC CGT TTC CGC AAG GGC GCT CTT CCG CGA AAT GTG CGC GGA ACC CCT ATT TGT TTA CAT TTT
2575 GCT TTA CAC TTT ATG CTT CCG GCT CGT ATG TTG TGT GGA ATT GTG AGC GGA TAA CAA TTT CAC ACA GGA AAC AGC TAT
2653 GAC CAT GAT TAC GCC AAG CTT GGC ACG ACA GGT TTC CCG ACT GGA AAG CGG GCA GTG AGC GCA ACG CAA TTA ATG TGA GTT
2731 AGT TGT TCC TTT CTA TTC ACA GGA AAC AGC TAT GAC CAT GAT TAC GCC AAG CTT GGC ACG CAG GAA CGT TCG TAC CAC ACA CAG CTC GCA
2809 CAG CCC CCG GGT AGG AAG AAA AAT ACT GCC AGC AAA CGG CAG AGC CGT TTA AGG ATC TGT GGC AGG GAT CAC GAT ATC AGG AGA CGA ACA
2887 TCT TCT CAC CAC CTC TGA CTT GAG CGT CGA TTT TAT TCG CGG AGG CGT ATT GCG AAG CGC CAA CCA ACA
2965 AGA AAA GCG GTG CTC CGG AAC CTG AAT TAA AAA GAC CTA AGC CAT CGT TTA ACG ACT GGG CTG CTG AAT CTG GAT AAT GTA ACG CGA TGT TCC ACT AAA GCG CAT CAC CAT CAC TGA CGG
3043 TCC AAC GTT GGC CTG TAC TGT CTT CGT ACC ATC CCC GCC ATC
```

Fig. 12, contd.

```
3121 TGA TGA GCA GTT GAA ATC TGG AAC TGC CTC TGT TGT GCT GAA TAA CTT CTA TCC CAG AGA GGC CAA AGT ACA
3199 GTG GAA GGT CAG GAG CCT GAC CGC CCT CCA GCT GGG CAA CTC TAA AGC AGA CAC CAA CAA GCA GGA CAG CAC CTA
3277 CAG CCT CAG CTC GCC AAA GAG CTA GAG GCT AAA CAG CCG AGA CAG CTA CGC CTG CGA TCT ATT TCA AGG AGA
3355 GGG CCT GAG TCA AAT TAT ACC TGC CTA AAT TGC CTA GGG CTG GAT TTC CCG CTT TAC CGG AGC CCC AAT CGC GCC CCC AGC CGG TGG CCA TGG GGC GGA TGC
3433 CAG TCA TAA GAA TAT AGC GTT GGA CAT GTT TGC GGA AAA TGG CCG CAG CCG CTT CAT CGA ATG GGC TGT GGC CTT CCT CGT GCT
3511 CTG CTT GCC GAA CAT CGC TCC CGA TCC CGA TAT GCC CTA TGC TGC TGA AGA GCT TGG CCG ATG GGC ATG GCT TGG CCG TGA GTT CTT AGC GGG ACT CTG
3589 CTA TCA GGA CAT CGC CGC CGA TTC CGC AGA GCG CAT CGC TTA TCG CCT CTA TGA CGA GTT CTT CGG AAT CGT TAT TGC CCG GGA CGC
3667 TTA GGG TTC GGT GCT GAT CCT CCA GCG CGG GGA TCT CAC CGG GAT CTT CGC AAG GTT CGG AAT CGT TAT TGC CCG AGC TTA TAA
3745 GGG CTG CGA TTA CAA ATA CAA TGT CCT CAC AAA TTT CTG TAT ATC TTT CAC CTA AGT CTT TAG TTG TGG TTT GTC
3823 CGG TGG TTA CAA ACT CAT AAG TGT AAA TTG CAT TCA TCC GCT ATT AAT TGC GTT CTG CTA AGG CAT CGC CAT CGT TAG AGC CTT CCA CTA AAT CTT GCC GGG
3901 TGG CAA ACT TCC CTA ATG AGT GAG CTA ACT CCT AAG GGT AAA CGC GCC AAG CTT CCA GTC TTT GGT ACG AGT CTA AAT ATG TAC
3979 CAA GTT TGC CAT TTC ATT GGT TCA TGC TAG GGT TGA CAT CCA TAT CAT AAT ATG TAC
4057 TGC CTA ATG AGT GAG CTA ACT CCT AAG GGT AAA CGC GCC AAG CTT CCA GTC TTT GGT ACG AGT CTA AAT ATG TAC
4135 TGC CTA ATG AGT GAG GAA TCT GCT AAT AAT GCG GTT TCT ACG CAT ATG CAA GTC TTT GGT ACG AGT CTA AAT ATG TAC
4213 GAA TTG CAT GAA GAA TTA TAT ATA GCA TAA ATC CCA ACA TTA TGA TTA TTG ACT AGT TAG TAA TCA ATT ACG
4291 TTA TTC ATT GGT TCA GTT CAT AGC CCA TTG ACG GAG TTC CGC GTT ACA TAA GTT CCC ATA GTA AAC CCT TTC CAT TGA CGT CAA GGG CCC
4369 ATT TAT ATT GGC TCA TGT CAT AGC CCA TTG ACG TCA ATA ATG ACG TAT GTT CCC ATA GTA ACG CCA ATA GGG ACT TTC CAT TGA CGT CAA GGG CCC
4447 GGG ACT TTA GTT CAT CAT CTA ACT GGA GGT TAT CCC ATC CAC CAT GTC CCT CAA GAG CCC
4525 AAC GAC CCC CCG TTG ACG TCA ATG GGT GTA GTC GGT CTT CCC CGA CTC ACC CTC CAA GAG CCC
4603 TGG GTG AAT GAC GGT TAT CTA ACT CAA GCG CTG CTT ACC GGT CTT CCC ATT GAC GCC CCT ATT GAC
4681 GTC AAT GAC GGT TAT CTA ACT CAA GCG CTG CTT ACC ATG GTG ATG CGG TTT TGG CAG TAC ACC AAG TCC GCC CCT ATT GAC
4759 CTC TGG GGA CCC TCT TAA ACA CTC CAT GGT GAT GCG GTT TGG CAG TAC ACT TGC AGG ATC GAC
4837 CGC CGA TTC CAC GCG GGT GGT CTT CCA TAT GGC GGT GGC CTA CTC CAG AGG ATC GAA CTA GAT ACC AGA AAA CGC ATC CCT CAA GAG CTC AGG
4915 CGT GCC CTG CAG CAG CTT GGC GGT GGC CTA CTC CAG AGG CAA GTC GGG CAG TCG GTT GTG CAA TCA GGA CAA
4993 GAA AGT TGA GCC AAA ATC TTG TGC GGC ATA GAC TGT TGA ACA TCA CCA GCC CGC AGA ACA AAA TTC ATT TAC CTC AGA
5071 AGA GGA TCT GAA TGG CAA AAC TTT AGA TCG TTA CGC TAA CTA TGA GGG CTG GAA TGC CGT GTG TAC AGG CGT TGT GGT TTG
5149 CTG GAA AGA CGA AAC TCA GTG TTT CGG TTA CAG GAG CGA AAC TCA GTG TTT CAC ACA GGA AGC ATC TTA CGC TAA CTA TGA GGG CTG GAA TGC CGT GTA ACC TAT ACC TAT TCC
5227 TAC TCG TGA CGA AAC TCA GTG TTT CGG TTA CAG GAG GGA CAG TAT GAC TGC ATC AAA TGG AAC AGG GAT TGC CAG GCT AGG CCC ATT GAC
5305 GGG CTA TAC TGG GGG CTA TGA CGG CTC TGA AAC ATG GCT AGT GCC TGT CAC ATG GCT AGT AAG ATC CAT CAT AAA TAA GTA CAG CAG
5383 GGG CTA TAC TGG GGG CTA CGG CCC TCT CGA CTG CGG CTC ACA GCC TGT GCC TAA AAT CCC TCA TCA AAG GGT GGA CAA AAT CGT TGG CGG TTC
5461 TCT GGA GTC TCA GCC TAC TGT CTG GAA GTC TCC TGA TGA CCC CGA CTG AGC CTT CAG GGT CAT CCT CAG TAT CAA TGG CAA TGT CAA CAA AGC CGG CAA AGC AAA AGC CAT
5539 TTA GTA CGC CTA CGG GAA AGG CTG TCC CGC CTG GGC CTC TCT CGT CTG CTG AAG CGC TCG CGC AAG TGG CCC TGC CCC TGG CGG CCC TGG CCA AGT TTC CTG TGC GAA TCC CTT ATT AAA AGC CAT
5617 GTA ATA GTA AGG CCA ATC GTC TCA GCT TGC GCT TGC TGC TTT CTT CCG AAA CAT ATA ATT CGT TTG TGA
5695 ATA TCA AGG CCA ATC GTC TGA GCC TAC TAT TGT CCA TCT TGC GAA AAT CTT TGA CAT AGG TTT TTA ATC CCA AAT GGC GG CGG TTC
5773 CTC TGA GGG CTT TGC GTG TAC TGA AAT CAT CAA TGG TAT GTT AAC ACT ATT TAT TAC CCA ATC CAA CGC TTC TCA TAT TGT TTT
5851 TGA GGG CGG CTC CGG CGG CTT ACA CGG CCT ACC CAA ACT GGC TAA TGC TAC AAG AGG TGT TTA TGA TTT AGA TAA ATT GAA TAC CTT CCG TTC CAT CGT AAC AGC TGT
5929 CGA TGA AAA CGG GCT ACA GTC TGC GGG TGA TGA CTC CAT AGG CAA ACT TTA ATT GAA TAC CTT CCG TTC CAT CGT AAC AGC TGT
6007 TTT CAT TGG TGA CGC TTC CGG TGC CCT TGC TTC ACC TTT GCC TAA AAT CAT ACT GCG TAA GGA
6085 TCA AGT CGG CCC TTA TGC TGG CGG CTT GAG TAA TGA ATA TGA AAT AAT CAT ACT GCG TAA GGA
6163 ATG TCG CGG CCC TTA TGC TGG CGG CTT GAG TAA TGA ATA TGA AAT AAT CAT ACT GCG TAA GGA
6241 TGT CTT TGC GTT TCT TTT ATA TGT TGC CAC CTT TAT GTA TGT GTC ATG GTT TGA TGC GAG CAT ACT GCG TAA GGA
```

```
8893  GTT CGG TGT AGG TCG TTC GCT CCA AGC TGG GCT GTG TGC ACG AAC CCC TTC AGC CCG ACC GCT GCG CCT TAT CCG
8971  GTA ACT ATC GTC TTG AGT ATG GTC CTA CGG TAA AGT TCT TGA GAA ACG TAT CGC CAG CCA CTG GTA GAA AAA GGA TTA GCA
9049  GAG CGA GGT ATG GCG TAG TGC CAG GTG CTA CAG TTA CCT TCG AGT GCT GGT GGC CTT GAT ACG CTT ACA GAA CAG TAT TTG
9127  GTA TCT GCG CTC TGA TTT GCA GCT AGT GCA AGC AAA TTA CGC GTT GAG GCT AAG AAG GAT CTC GTA GCA AAG ATC TGA CCG TCT TTT
9205  GTA GCG GTG GTT TTT CTG ACG CTC AGT AAA AAA ACT TTA GGA AGA GGA TTT TGG TCA TGA GAT AAA CTT CAA GGA TCT TCA
9283  CTA CGG GGT CTG CTG ACG CTC AGT AAA ATT AAA GTA TTA AAT GTA TAT TTC GTT AGT CAT CCA TTG CCT GAC CTG ACA GTT ACC
9361  CCT AGA TCC TTT TAA ATT AAA CAC CTA TCT CAG CGA TTC GTC CAA GTG CTG GCC CCA GTA TAC CGC GAG ACC CAC TCC CGG TCG TGT
9439  AAT GCT TAA CTA GTG AGG AGG GCT AGC AGC CCG GAA GGG CCG AGC GTC AGC GCA CAG GTG GTC CAA CTT TAT CCG CAC CCT CCA CTC
9517  AGA TAA CTA TAT CAG CAA TAA ACC GGG AAG GCC CTA GAG TAA GTA GTT CGC CAT TGC GCA AAC GAT CAA AGT TGG CCG GAG TTA CAT
9595  CAG ATT CTA TTA ATT GTT GCC TGT CAC GCT CGT CGT TTG CTT CTC TCG GTC CCT CTC TCA TGC CAT GCT TTT CTG TGA CTG TGT
9673  AGT CTA TCG GCA TCG TGG TGT TGT GCA AAA AAG CGG TTA GCT ATT CTC CTG TCA CGG GAC CGA AAC ACT CTT TTA CTT TCA CCA ATA
9751  CAG GCA TCG TGG TGT TGT GCA AAA AAG CGG TTA GCT ATT CTC CTG TCA CGG GAC CGA AAC ACT CTT TTA CTT TCA CCA GCG ATA TAC
9829  GAT CCC CCA TCG TGT GCA AAA AAG CGG TTA GCT AAT AGT GTA TGC GAC GAA AAC CCA TTG CAC ATG CCC TGA CTG GTG TAC
9907  TAT CAC TCA TGG TTA TGG CAG CAT TCT GAG AAT AGT GTA TGC TCA TCA CTC GTG CAC CCG AAC ATG CAT CTT CAA GGA TCT TAC
9985  AGT ACT CAA CCA ATA GCA GAA CTT TAA AAG TGC TCA TCA CTC GTG CAC CCG AAC GGC CGT AAC TCT CAA GGA TCT TAC
10063 CCG CGC CAC ATA GCA GAA CTT TAA AAG TGC TCA CTC GTG CAC CCG AAC GGC CGG GAA AAC CGT CAA GGA TCT TAC
10141 CGC TGT TGA GAT CCA GTT CGA GTT AAC TGT AAC CCA GTG CAC AAA ATG CAT CTT TTA CTT TCA CCA GCG TTT
10219 CTG GGT GAG CAA AAA CAG GAA CGA AAT ATG CCG CAA GGC GAA TAA GAA CAC CGA AAT GTT GAA TAC TCA
```

Fig. 13B

```
   1 atccaggcgc ggatcaataa aagatcatta ttttcaatag atctgtgtgt tggtttttg
  61 tgtgccttgg gggaggggga ggccagaatg aggcgcggcc aagggggagg gggaggccag
 121 aatgaccttg ggggaggggg aggccagaat gaccttgggg gagggggagg ccagaatgag
 181 gcgcggatcc ggagaagttc ctattccgaa gttcctattc ttcaaatagt ataggaactt
 241 cgctcgaggg atcggccatt gaacaagatg gattgcacgc aggttctccg gccgcttggg
 301 tggagaggct attcggctat gactgggcac aacagacaat cggctgctct gatgccgccg
 361 tgttccggct gtcagcgcag ggcgcccgg ttcttttgt caagaccgac ctgtccggtg
 421 ccctgaatga actgcaggac gaggcagcgc ggctatcgtg gctggccacg acgggcgttc
 481 cttgcgcagc tgtgctcgac gttgtcactg aagcgggaag ggactggctg ctattgggcg
 541 aagtgccggg gcaggatctc ctgtcatctc accttgctcc tgccgagaaa gtatccatca
 601 tggctgatgc aatgcggcgg ctgcatacgc ttgatccggc tacctgccca ttcgaccacc
 661 aagcgaaaca tcgcatcgag cgagcacgta ctcggatgga agccggtctt gtcgatcagg
 721 atgatctgga cgaagagcat caggggctcg cgccagccga actgttcgcc aggctcaagg
 781 cgcgcatgcc cgacggcgag gatctcgtcg tgacccatgg cgatgcctgc ttgccgaata
 841 tcatggtgga aaatggccgc ttttctggat tcatcgactg tggccggctg ggtgtggcgg
 901 accgctatca ggacatagcg ttggctaccc gtgatattgc tgaagagctt ggcggcgaat
 961 gggctgaccg cttcctcgtg ctttacggta tcgccgctcc cgattcgcag cgcatcgcct
1021 tctatcgcct tcttgacgag ttcttctgag gggatcgatc cgctgtaagt ctgcagaaat
1081 tgatgatcta ttaaacaata aagatgtcca ctaaaatgga agttttcct gtcatacttt
1141 gttaagaagg gtgagaacag agtacctaca ttttgaatgg aaggattgga gctacggggg
1201 tgggggtggg gtgggattag ataaatgcct gctctttact gaaggctctt tactattgct
1261 ttatgataat gtttcatagt tggatatcat aatttaaaca agcaaaacca aattaagggc
1321 cagctcattc ctcccactca tgatctatag atctatagat ctctcgtggg atcattgttt
1381 ttctcttgat tcccactttg tggttctaag tactgtggtt tccaaatgtg tcagtttcat
1441 agcctgaaga acgagatcag cagcctctgt tccacataca cttcattctc agtattgttt
1501 tgccaagttc taattccatc agaagctgac tctagatggc gcgtatgcag gttttcgaca
1561 ttgattattg actagttatt aatagtaatc aattacgggg tcattagttc atagcccata
1621 tatggagttc cgcgttacat aacttacggt aaatggcccg cctggctgac cgcccaacga
1681 cccccgccca ttgacgtcaa taatgacgta tgttcccata gtaacgccaa tagggacttt
1741 ccattgacgt caatgggtgg agtatttacg gtaaactgcc cacttggcag tacatcaagt
1801 gtatcatatg ccaagtacgc ccctattga cgtcaatgac ggtaaatggc ccgcctggca
1861 ttatgcccag tacatgacct tatgggactt tcctacttgg cagtacatct acgtattagt
1921 catcgctatt accatggtcg aggtgagccc cacgttctgc ttcactctcc ccatctcccc
1981 cccctcccca ccccaattt tgtatttatt tattttttaa ttattttgtg cagcgatggg
2041 ggcggggggg gggggggcgc gcgccaggcg ggcggggcg gggcgagggg cggggcgggg
2101 cgaggcggag aggtgcggcg gcagccaatc agagcggcgc gctccgaaag tttcctttta
2161 tggcgaggcg gcggcggcg cggccctata aaaagcgaag cgcgcggcgg gcgggagtcg
2221 ctgcgttgcc ttcgccccgt gccccgctcc gcgccgcctc gcgccgcccg ccccggctct
```

Fig. 13B, contd.

```
2281 gactgaccgc gttactccca caggtgagcg ggcgggacgg cccttctcct ccgggctgta
2341 attagcgctt ggtttaatga cggctcgttt cttttctgtg gctgcgtgaa agccttaaag
2401 ggctccggga gggccctttg tgcgggggggg agcggctcgg ggggtgcgtg cgtgtgtgtg
2461 tgcgtgggga gcgccgcgtg cggcccgcgc tgcccggcgg ctgtgagcgc tgcgggcgcg
2521 gcgcggggct ttgtgcgctc cgcgtgtgcg cgagggagc gcggccgggg gcggtgcccc
2581 gcggtgcggg ggggctgcga ggggaacaaa ggctgcgtgc ggggtgtgtg cgtgggggggg
2641 tgagcagggg gtgtgggcgc ggcggtcggg ctgtaacccc ccctgcacc cccctccccg
2701 agttgctgag cacggcccgg cttcgggtgc ggggctccgt gcggggcgtg gcgcggggct
2761 cgccgtgccg ggcgggggggt ggcggcaggt ggggggtgccg ggcgggggcgg ggccgcctcg
2821 ggccggggag ggctcggggg aggggcgcgg cggccccgga gcgccggcgg ctgtcgaggc
2881 gcggcgagcc gcagccattg ccttttatgg taatcgtgcg agagggcgca gggacttcct
2941 ttgtcccaaa tctgtgcgga gccgaaatct gggaggcgcc gccgcacccc ctctagcggg
3001 cgcggggcga agcggtgcgg cgccggcagg aaggaaatgg gcggggaggg ccttcgtgcg
3061 tcgccgcgcc gccgtccct tctccctctc cagcctcggg gctgtccgcg ggggacggc
3121 tgccttcggg ggggacgggg cagggcgggg ttcggcttct ggcgtgtgac cggcggctct
3181 agaagcgttg gggtgagtac tccctctcaa aagcgggcat gacttctgcg ctaagattgt
3241 cagtttccaa aaacgaggag gatttgatat tcacctggcc cgcggtgatg cctttgaggg
3301 tggccgcgtc catctggtca gaaaagacaa tcttttttgtt gtcaagcttg aggtgtggca
3361 ggcttgagat ctggccatac acttgagtga cattgacatc cactttgcct ttctctccac
3421 aggtgtccac tcccaggcg gcctccggag cgatcgccga tccgcctagg caattgttta
3481 aatcggccgg ccataacttc gtataatgta tgctatacga agttatggat cctcacagta
3541 ggtggcatcg ttcctttctg actgcccgcc ccccgcatgc cgtccgcga tattgagctc
3601 cgaacctctc gccctgccgc cgccggtgct ccgtcgccgc cgcgccgcca tggaatcgaa
3661 gccaccatgg atcttaccgg aaaactcgac gcaagaaaaa tcagagagat cctcataaag
3721 gtcaagaagg gcggaaagat cgccgtgtaa ttctagaccg gttcgagatc caggcgcgga
3781 tcaataaaag atcattattt tcaatagatc tgtgtgttgg ttttttgtgt gccttggggg
3841 aggggaggc cagaatgagg cgcggccaag ggggaggggg aggccagaat gaccttgggg
3901 gagggggagg ccagaatgac cttggggag ggggaggcca gaatgaggcg cgccctccgt
3961 cgacctataa cttcgtataa tgtatgctat acgaagttat ggcggccgcc accatggaca
4021 tgagagtgcc cgcccagctc ctggggctcc tgctactctg gctccgaggt aaggatggag
4081 aacactagga atttactcag ccagtgtgct cagtactgac tggaacttca gggaagttct
4141 ctgataacat gattaatagt aagaatattt gttttttatgt ttccaatctc agtgccaga
4201 tgtgacatcc agatgaccca gagcccagc agcctgagcg ccagcgtggg cgacagagtg
4261 accatcacct gcagagccag ccagagcatc agcagctacc tgaactggta tcagcagaag
4321 cccggcaagg cccccaagct gctgatctac gccgccagct ccctgcagag cggcgtgccc
4381 agcagattca gcggcagcgg ctccggcacc gacttcaccc tgaccatcag cagcctgcag
4441 cccgaggact tcgccaccta ctactgccag cagagctaca gcacccccc caccttcggc
```

Fig. 13B, contd.

```
4501 cagggcacca aggtggagat caagagagcc gacgccgctc ccaccgtgtc catcttcccc
4561 cccagcatgg aacagctgac ctctggcgga gccaccgtgg tctgcttcgt gaacaacttc
4621 taccccagag acatcagcgt gaagtggaag atcgacggca gcgagcagag ggacggcgtg
4681 ctggacagcg tgaccgacca ggacagcaag gactccacct acagcatgag cagcaccctg
4741 agcctgacca aggtggagta cgagaggcac aacctgtaca cctgcgaggt ggtgcacaag
4801 accagctcca gccccgtggt caagtccttc aaccggaacg agtgttgagc tagcttaaga
4861 tttaaatagg ccggccgcgt cgacctcgag atccaggcgc ggatcaataa aagatcatta
4921 ttttcaatag atctgtgtgt tggttttttg tgtgccttgg gggaggggga ggccagaatg
4981 aggcgcggcc aaggggaggg ggaggccag aatgaccttg ggggagggg aggccagaat
5041 gaccttgggg gaggggagg ccagaatgag gcgcgccccc gggtaccgag ctcgaattag
5101 tggatcctca cagtaggtgg catcgttcct ttctgactgc ccgccccccg catgccgtcc
5161 cgcgatattg agctccgaac ctctcgccct gccgccgccg gtgctccgtc gccgccgcgc
5221 cgccatggaa tcgcgccggt aaccgaagtt cctatacttt ctagagaata ggaacttcgg
5281 aataggaact tcaagccggt acccagcttt tgttcccttt agtgagggtt aatttcgagc
5341 ttggcgtaat catggtcata gctgtttcct gtgtgaaatt gttatccgct cacaattcca
5401 cacaacatac gagccgggag cataaagtgt aaagcctggg gtgcctaatg agtgagctaa
5461 ctcacattaa ttgcgttgcg ctcactgccc gctttccagt cgggaaacct gtcgtgccag
5521 ctgcattaat gaatcggcca acgcgcgggg agaggcggtt tgcgtattgg gcgctcttcc
5581 gcttcctcgc tcactgactc gctgcgctcg gtcgttcggc tgcggcgagc ggtatcagct
5641 cactcaaagg cggtaatacg gttatccaca gaatcagggg ataacgcagg aaagaacatg
5701 tgagcaaaag gccagcaaaa ggccaggaac cgtaaaaagg ccgcgttgct ggcgtttttc
5761 cataggctcc gcccccctga cgagcatcac aaaaatcgac gctcaagtca gaggtggcga
5821 aacccgacag gactataaag ataccaggcg tttccccctg gaagctccct cgtgcgctct
5881 cctgttccga ccctgccgct taccggatac ctgtccgcct ttctcccttc gggaagcgtg
5941 gcgctttctc atagctcacg ctgtaggtat ctcagttcgg tgtaggtcgt tcgctccaag
6001 ctgggctgtg tgcacgaacc ccccgttcag cccgaccgct gcgccttatc cggtaactat
6061 cgtcttgagt ccaacccggt aagacacgac ttatcgccac tggcagcagc cactggtaac
6121 aggattagca gagcgaggta tgtaggcggt gctacagagt tcttgaagtg gtggcctaac
6181 tacggctaca ctagaaggac agtatttggt atctgcgctc tgctgaagcc agttaccttc
6241 ggaaaaagag ttggtagctc ttgatccggc aaacaaacca ccgctggtag cggtggtttt
6301 tttgtttgca agcagcagat tacgcgcaga aaaaaggat ctcaagaaga tcctttgatc
6361 ttttctacgg ggtctgacgc tcagtggaac gaaaactcac gttaagggat tttggtcatg
6421 agattatcaa aaaggatctt cacctagatc cttttaaatt aaaaatgaag ttttaaatca
6481 atctaaagta tatatgagta aacttggtct gacagttacc aatgcttaat cagtgaggca
6541 cctatctcag cgatctgtct atttcgttca tccatagttg cctgactccc cgtcgtgtag
6601 ataactacga tacgggaggg cttaccatct ggccccagtg ctgcaatgat accgcgagac
6661 ccacgctcac cggctccaga tttatcagca ataaaccagc cagccggaag ggccgagcgc
```

Fig. 13B, contd.

```
6721 agaagtggtc ctgcaacttt atccgcctcc atccagtcta ttaattgttg ccgggaagct
6781 agagtaagta gttcgccagt taatagtttg cgcaacgttg ttgccattgc tacaggcatc
6841 gtggtgtcac gctcgtcgtt tggtatggct tcattcagct ccggttccca acgatcaagg
6901 cgagttacat gatcccccat gttgtgcaaa aaagcggtta gctccttcgg tcctccgatc
6961 gttgtcagaa gtaagttggc cgcagtgtta tcactcatgg ttatggcagc actgcataat
7021 tctcttactg tcatgccatc cgtaagatgc ttttctgtga ctggtgagta ctcaaccaag
7081 tcattctgag aatagtgtat gcggcgaccg agttgctctt gcccggcgtc aatacgggat
7141 aataccgcgc cacatagcag aactttaaaa gtgctcatca ttggaaaacg ttcttcgggg
7201 cgaaaactct caaggatctt accgctgttg agatccagtt cgatgtaacc cactcgtgca
7261 cccaactgat cttcagcatc ttttactttc accagcgttt ctgggtgagc aaaaacagga
7321 aggcaaaatg ccgcaaaaaa gggaataagg gcgacacgga atgttgaat actcatactc
7381 ttcctttttc aatattattg aagcatttat cagggttatt gtctcatgag cggatacata
7441 tttgaatgta tttagaaaaa taaacaaata ggggttccgc gcacatttcc ccgaaaagtg
7501 ccacctaaat tgtaagcgtt aatattttgt taaaattcgc gttaaatttt tgttaaatca
7561 gctcattttt taaccaatag gccgaaatcg gcaaaatccc ttataaatca aaagaataga
7621 ccgagatagg gttgagtgtt gttccagttt ggaacaagag tccactatta agaacgtgg
7681 actccaacgt caaagggcga aaaccgtct atcagggcga tggcccacta cgtgaaccat
7741 caccctaatc aagttttttg gggtcgaggt gccgtaaagc actaaatcgg aaccctaaag
7801 ggagccccg atttagagct tgacgggaa agccggcgaa cgtggcgaga aaggaaggga
7861 agaaagcgaa aggagcgggc gctagggcgc tggcaagtgt agcggtcacg ctgcgcgtaa
7921 ccaccacacc cgccgcgctt aatgccgc tacagggcgc gtcccattcg ccattcaggc
7981 tgcgcaactg ttgggaaggg cgatcggtgc gggcctcttc gctattacgc cagctggcga
8041 aagggggatg tgctgcaagg cgattaagtt gggtaacgcc agggttttcc cagtcacgac
8101 gttgtaaaac gacggccagt gagcgcgcgt aatacgactc actatagggc gaattggggg
8161 taactaagta aggatcgag
```

Fig. 15B

```
   1 atccaggcgc ggatcaataa aagatcatta ttttcaatag atctgtgtgt tggtttttg
  61 tgtgccttgg gggaggggga ggccagaatg aggcgcggcc aaggggagg gggaggccag
 121 aatgaccttg ggggagggg aggccagaat gaccttgggg gaggggagg ccagaatgag
 181 gcgcggatcc ggagaagttc ctattccgaa gttcctattc ttcaaatagt ataggaactt
 241 cgctcgaggg atcggccatt gaacaagatg gattgcacgc aggttctccg gccgcttggg
 301 tggagaggct attcggctat gactgggcac aacagacaat cggctgctct gatgccgccg
 361 tgttccggct gtcagcgcag gggcgcccgg ttcttttgt caagaccgac ctgtccggtg
 421 ccctgaatga actgcaggac gaggcagcgc ggctatcgtg gctggccacg acgggcgttc
 481 cttgcgcagc tgtgctcgac gttgtcactg aagcgggaag ggactggctg ctattgggcg
 541 aagtgccggg gcaggatctc ctgtcatctc accttgctcc tgccgagaaa gtatccatca
 601 tggctgatgc aatgcggcgg ctgcatacgc ttgatccgc tacctgccca ttcgaccacc
 661 aagcgaaaca tcgcatcgag cgagcacgta ctcggatgga agccggtctt gtcgatcagg
 721 atgatctgga cgaagagcat caggggctcg cgccagccga actgttcgcc aggctcaagg
 781 cgcgcatgcc cgacggcgag gatctcgtcg tgacccatgg cgatgcctgc ttgccgaata
 841 tcatggtgga aaatggccgc ttttctggat tcatcgactg tggccggctg ggtgtggcgg
 901 accgctatca ggacatagcg ttggctaccc gtgatattgc tgaagagctt ggcggcgaat
 961 gggctgaccg cttcctcgtg ctttacggta tcgccgctcc cgattcgcag cgcatcgcct
1021 tctatcgcct tcttgacgag ttcttctgag gggatcgatc cgctgtaagt ctgcagaaat
1081 tgatgatcta ttaaacaata aagatgtcca ctaaaatgga agtttttcct gtcatacttt
1141 gttaagaagg gtgagaacag agtacctaca ttttgaatgg aaggattgga gctacggggg
1201 tgggggtggg gtgggattag ataaatgcct gctctttact gaaggctctt tactattgct
1261 ttatgataat gtttcatagt tggatatcat aatttaaaca agcaaaacca aattaagggc
1321 cagctcattc ctcccactca tgatctatag atctatagat ctctcgtggg atcattgttt
1381 ttctcttgat tcccactttg tggttctaag tactgtggtt tccaaatgtg tcagtttcat
1441 agcctgaaga acgagatcag cagcctctgt tccacataca cttcattctc agtattgttt
1501 tgccaagttc taattccatc agaagctgac tctagatggc gcgtatgcag gttttcgaca
1561 ttgattattg actagttatt aatagtaatc aattacgggg tcattagttc atagcccata
1621 tatggagttc cgcgttacat aacttacggt aaatggcccg cctggctgac cgcccaacga
1681 cccccgccca ttgacgtcaa taatgacgta tgttcccata gtaacgccaa tagggacttt
1741 ccattgacgt caatgggtgg agtatttacg gtaaactgcc cacttggcag tacatcaagt
1801 gtatcatatg ccaagtacgc ccctattga cgtcaatgac ggtaaatggc ccgcctggca
1861 ttatgcccag tacatgacct tatgggactt tcctacttgg cagtacatct acgtattagt
1921 catcgctatt accatggtcg aggtgagccc cacgttctgc ttcactctcc ccatctcccc
1981 cccctcccca ccccaatttt gtatttatt tattttttaa ttattttgtg cagcgatggg
2041 ggcggggggg ggggggcgc gcgccaggcg gggcggggcg gggcgagggg cggggcgggg
2101 cgaggcggag aggtgcggcg gcagccaatc agagcggcgc gctccgaaag ttttcctttta
```

Fig. 15B, contd.

```
2161 tggcgaggcg gcggcggcgg cggccctata aaaagcgaag cgcgcggcgg gcgggagtcg
2221 ctgcgttgcc ttcgccccgt gccccgctcc gcgccgcctc gcgccgcccg ccccggctct
2281 gactgaccgc gttactccca caggtgagcg ggcgggacgg cccttctcct ccgggctgta
2341 attagcgctt ggtttaatga cggctcgttt cttttctgtg gctgcgtgaa agccttaaag
2401 ggctccggga gggccctttg tgcggggggg agcggctcgg ggggtgcgtg cgtgtgtgtg
2461 tgcgtgggga cgccgcgtg cggcccgcgc tgcccggcgg ctgtgagcgc tgcgggcgcg
2521 gcgcggggct ttgtgcgctc cgcgtgtgcg cgaggggagc gcggccgggg gcggtgcccc
2581 gcggtgcggg ggggctgcga ggggaacaaa ggctgcgtgc ggggtgtgtg cgtgggggg
2641 tgagcagggg gtgtgggcgc ggcggtcggg ctgtaacccc ccctgcacc ccctccccg
2701 agttgctgag cacggcccgg cttcgggtgc ggggctccgt gcggggcgtg gcgcggggct
2761 cgccgtgccg ggcgggggt ggcggcaggt ggggtgccg ggcggggcgg ggccgcctcg
2821 ggccggggag ggctcggggg aggggcgcgg cggccccgga gcgccggcgg ctgtcgaggc
2881 gcggcgagcc gcagccattg cctttatgg taatcgtgcg agagggcgca gggacttcct
2941 ttgtcccaaa tctgtgcgga gccgaaatct gggaggcgcc gccgcacccc ctctagcggg
3001 cgcggggcga agcggtgcgg cgccggcagg aaggaaatgg gcggggaggg ccttcgtgcg
3061 tcgccgcgcc gccgtcccct tctccctctc cagcctcggg gctgtccgcg gggggacggc
3121 tgccttcggg ggggacgggg cagggcgggg ttcggcttct ggcgtgtgac cggcggctct
3181 agaagcgttg gggtgagtac tccctctcaa aagcgggcat gacttctgcg ctaagattgt
3241 cagtttccaa aaacgaggag gatttgatat tcacctggcc cgcggtgatg cctttgaggg
3301 tggccgcgtc catctggtca gaaaagacaa tctttttgtt gtcaagcttg aggtgtggca
3361 ggcttgagat ctggccatac acttgagtga cattgacatc cactttgcct ttctctccac
3421 aggtgtccac tcccagggcg gcctccggag cgatcgccga tccgcctagg caattgttta
3481 aatcggccgg cataacttc gtataatgta tgctatacga agttatggat cctcacagta
3541 ggtggcatcg ttcctttctg actgcccgcc ccccgcatgc cgtcccgcga tattgagctc
3601 cgaacctctc gccctgccgc cgccggtgct ccgtcgccgc cgcgccgcca tggaatcgaa
3661 gccaccatgg atcttaccgg aaaactcgac gcaagaaaaa tcagagagat cctcataaag
3721 gtcaagaagg gcggaaagat cgccgtgtaa ttctagaccg gttcgagatc caggcgcgga
3781 tcaataaaag atcattattt tcaatagatc tgtgtgttgg ttttttgtgt gccttggggg
3841 agggggaggc cagaatgagg cgcggccaag ggggagggg aggccagaat gaccttgggg
3901 gaggggagg ccagaatgac cttggggag ggggaggcca gaatgaggcg cgccctccgt
3961 cgacctataa cttcgtataa tgtatgctat acgaagttat ggcggccgcc accatggaca
4021 tgagagtgcc cgcccagctc ctgggctcc tgctactctg gctccgaggt aaggatggag
4081 aacactagga atttactcag ccagtgtgct cagtactgac tggaacttca gggaagttct
4141 ctgataacat gattaatagt aagaatattt gttttatgt ttccaatctc agtgccaga
4201 tgtcagtctg ccctgaccca gccgcctct gtgtctggca gccctggcca gagcatcacc
4261 atcagctgca ccggcaccag cagcgacgtg ggcggctaca actacgtgtc ctggtatcag
4321 cagcaccccg gcaaggcccc caagctgatg atctacgagg tgtccaacag acccagcggc
```

Fig. 15B, contd.

```
4381 gtgagcaaca gattcagcgg cagcaagagc ggcaacaccg ccagcctgac catcagcggc
4441 ctccaggctg aggacgaggc cgactactac tgcagcagct acaccagcag ctccaccctg
4501 gtgtttggcg gcggaacaaa gctgaccgtg ctgagagccg acgccgctcc caccgtgtcc
4561 atcttccccc ccagcatgga acagctgacc tctggcggag ccaccgtggt ctgcttcgtg
4621 aacaacttct accccagaga catcagcgtg aagtggaaga tcgacggcag cgagcagagg
4681 gacggcgtgc tggacagcgt gaccgaccag acagcaagg actccaccta cagcatgagc
4741 agcaccctga gcctgaccaa ggtggagtac gagaggcaca acctgtacac ctgcgaggtg
4801 gtgcacaaga ccagctccag ccccgtggtc aagtccttca accggaacga gtgttgagct
4861 agcttaagat ttaaataggc cggccgcgtc gacctcgaga tccaggcgcg gatcaataaa
4921 agatcattat tttcaataga tctgtgtgtt ggttttttgt gtgccttggg ggaggggag
4981 gccagaatga ggcgcggcca aggggagggg ggaggccaga tgaccttggg gggaggggga
5041 ggccagaatg accttggggg aggggaggc cagaatgagg cgcgcccccg ggtaccgagc
5101 tcgaattagt ggatcctcac agtaggtggc atcgttcctt tctgactgcc cgccccccgc
5161 atgccgtccc gcgatattga gctccgaacc tctcgcctg ccgccgcgg tgctccgtcg
5221 ccgccgcgcc gccatggaat cgcgccggta accgaagttc ctatactttc tagagaatag
5281 gaacttcgga ataggaactt caagccggta cccagctttt gttccctta gtgagggtta
5341 atttcgagct tggcgtaatc atggtcatag ctgtttcctg tgtgaaattg ttatccgctc
5401 acaattccac acaacatacg agccgggagc ataaagtgta agcctgggg tgcctaatga
5461 gtgagctaac tcacattaat tgcgttgcgc tcactgcccg ctttccagtc gggaaacctg
5521 tcgtgccagc tgcattaatg aatcggccaa cgcgcgggga gaggcggttt gcgtattggg
5581 cgctcttccg cttcctcgct cactgactcg ctgcgctcgg tcgttcggct gcggcgagcg
5641 gtatcagctc actcaaaggc ggtaatacgg ttatccacag aatcagggga taacgcagga
5701 aagaacatgt gagcaaaagg ccagcaaaag gccaggaacc gtaaaaaggc cgcgttgctg
5761 gcgttttcc ataggctccg ccccctgac gagcatcaca aaatcgacg ctcaagtcag
5821 aggtggcgaa acccgacagg actataaaga taccaggcgt ttccccctgg aagctccctc
5881 gtgcgctctc ctgttccgac cctgccgctt accggatacc tgtccgcctt tctcccttcg
5941 ggaagcgtgg cgctttctca tagctcacgc tgtaggtatc tcagttcggt gtaggtcgtt
6001 cgctccaagc tgggctgtgt gcacgaaccc ccgttcagc ccgaccgctg cgccttatcc
6061 ggtaactatc gtcttgagtc aacccggta agacacgact tatcgccact ggcagcagcc
6121 actggtaaca ggattagcag agcgaggtat gtaggcggtg ctacagagtt cttgaagtgg
6181 tggcctaact acggctacac tagaaggaca gtatttggta tctgcgctct gctgaagcca
6241 gttaccttcg gaaaaagagt tggtagctct tgatccggca acaaaccac cgctggtagc
6301 ggtggttttt ttgtttgcaa gcagcagatt acgcgcagaa aaaaggatc tcaagaagat
6361 cctttgatct tttctacggg gtctgacgct cagtggaacg aaaactcacg ttaagggatt
6421 ttggtcatga gattatcaaa aaggatcttc acctagatcc ttttaaatta aaatgaagt
6481 tttaaatcaa tctaaagtat atatgagtaa acttggtctg acagttacca atgcttaatc
6541 agtgaggcac ctatctcagc gatctgtcta tttcgttcat ccatagttgc ctgactcccc
```

Fig. 15B, contd.

```
6601 gtcgtgtaga taactacgat acgggagggc ttaccatctg gccccagtgc tgcaatgata
6661 ccgcgagacc cacgctcacc ggctccagat ttatcagcaa taaaccagcc agccggaagg
6721 gccgagcgca gaagtggtcc tgcaacttta tccgcctcca tccagtctat taattgttgc
6781 cgggaagcta gagtaagtag ttcgccagtt aatagtttgc gcaacgttgt tgccattgct
6841 acaggcatcg tggtgtcacg ctcgtcgttt ggtatggctt cattcagctc cggttcccaa
6901 cgatcaaggc gagttacatg atcccccatg ttgtgcaaaa aagcggttag ctccttcggt
6961 cctccgatcg ttgtcagaag taagttggcc gcagtgttat cactcatggt tatggcagca
7021 ctgcataatt ctcttactgt catgccatcc gtaagatgct tttctgtgac tggtgagtac
7081 tcaaccaagt cattctgaga atagtgtatg cggcgaccga gttgctcttg cccggcgtca
7141 atacgggata ataccgcgcc acatagcaga actttaaaag tgctcatcat tggaaaacgt
7201 tcttcggggc gaaaactctc aaggatctta ccgctgttga gatccagttc gatgtaaccc
7261 actcgtgcac ccaactgatc ttcagcatct tttactttca ccagcgtttc tgggtgagca
7321 aaaacaggaa ggcaaaatgc cgcaaaaaag ggaataaggg cgacacggaa atgttgaata
7381 ctcatactct ccttttttca atattattga agcatttatc agggttattg tctcatgagc
7441 ggatacatat ttgaatgtat ttagaaaaat aaacaaatag gggttccgcg cacatttccc
7501 cgaaaagtgc cacctaaatt gtaagcgtta atattttgtt aaaattcgcg ttaaattttt
7561 gttaaatcag ctcattttt aaccaatagg ccgaaatcgg caaaatccct tataaatcaa
7621 aagaatagac cgagataggg ttgagtgttg ttccagtttg gaacaagagt ccactattaa
7681 agaacgtgga ctccaacgtc aaagggcgaa aaaccgtcta tcagggcgat ggcccactac
7741 gtgaaccatc accctaatca agttttttgg ggtcgaggtg ccgtaaagca ctaaatcgga
7801 accctaaagg gagcccccga tttagagctt gacggggaaa gccggcgaac gtggcgagaa
7861 aggaagggaa gaaagcgaaa ggagcgggcg ctagggcgct ggcaagtgta gcggtcacgc
7921 tgcgcgtaac caccacaccc gccgcgctta atgcgccgct acagggcgcg tcccattcgc
7981 cattcaggct gcgcaactgt tgggaagggc gatcggtgcg ggcctcttcg ctattacgcc
8041 agctggcgaa agggggatgt gctgcaaggc gattaagttg ggtaacgcca gggttttccc
8101 agtcacgacg ttgtaaaacg acggccagtg agcgcgcgta atacgactca ctatagggcg
8161 aattgggggt aactaagtaa ggatcgag
``` pVkP-O12-del2_Final(ML104)

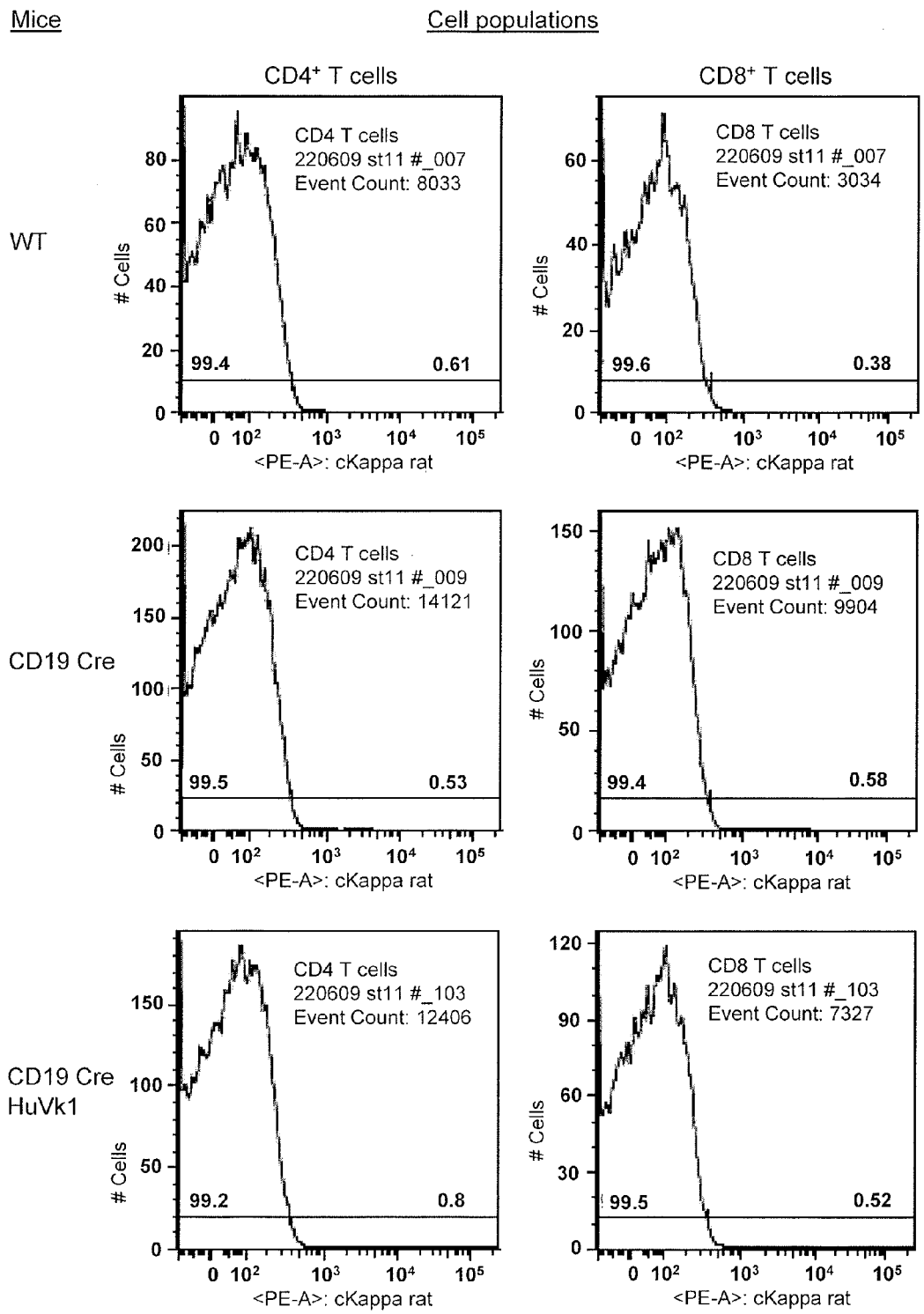
Fig. 23, contd.

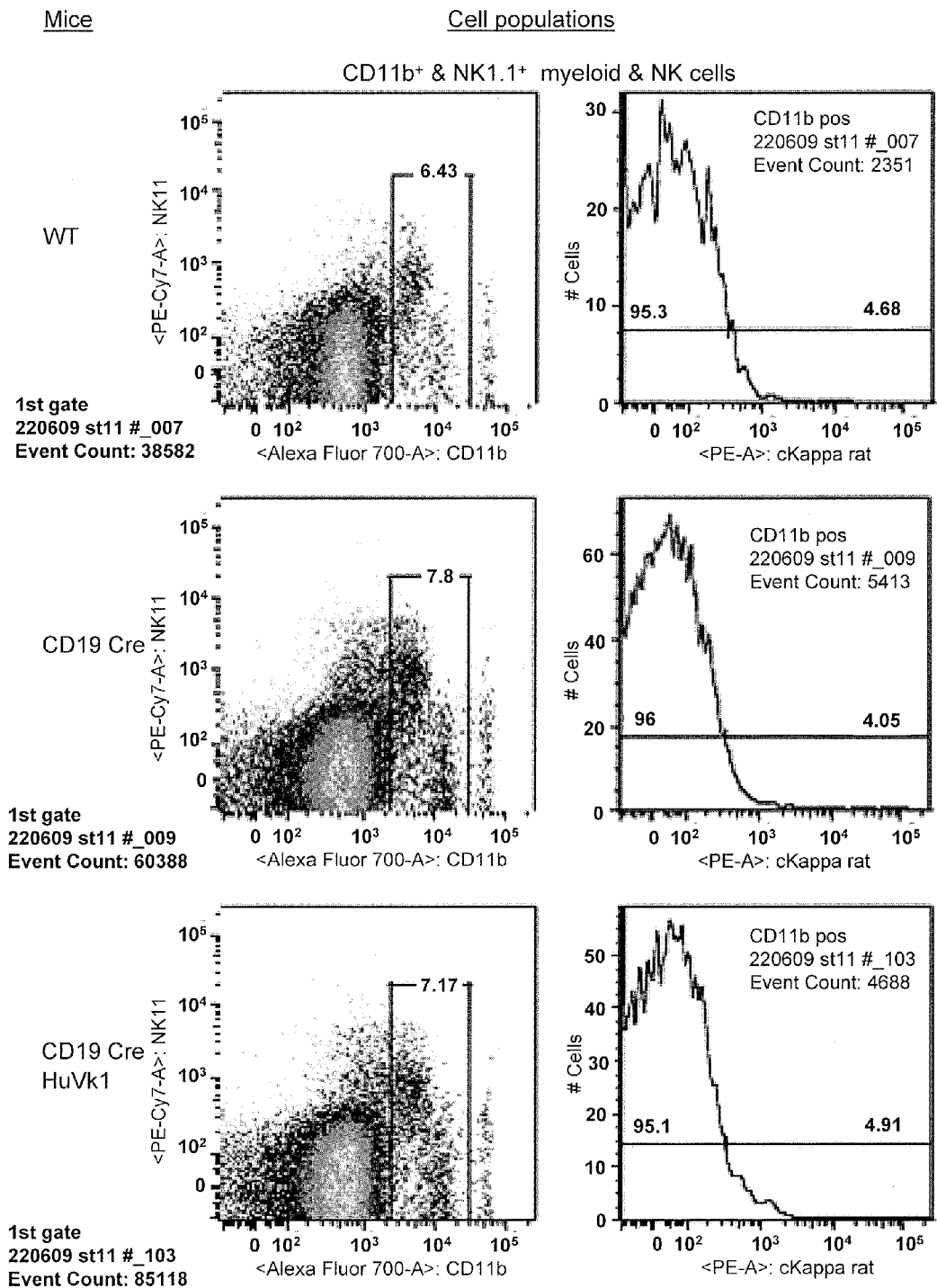
Fig. 23, contd.

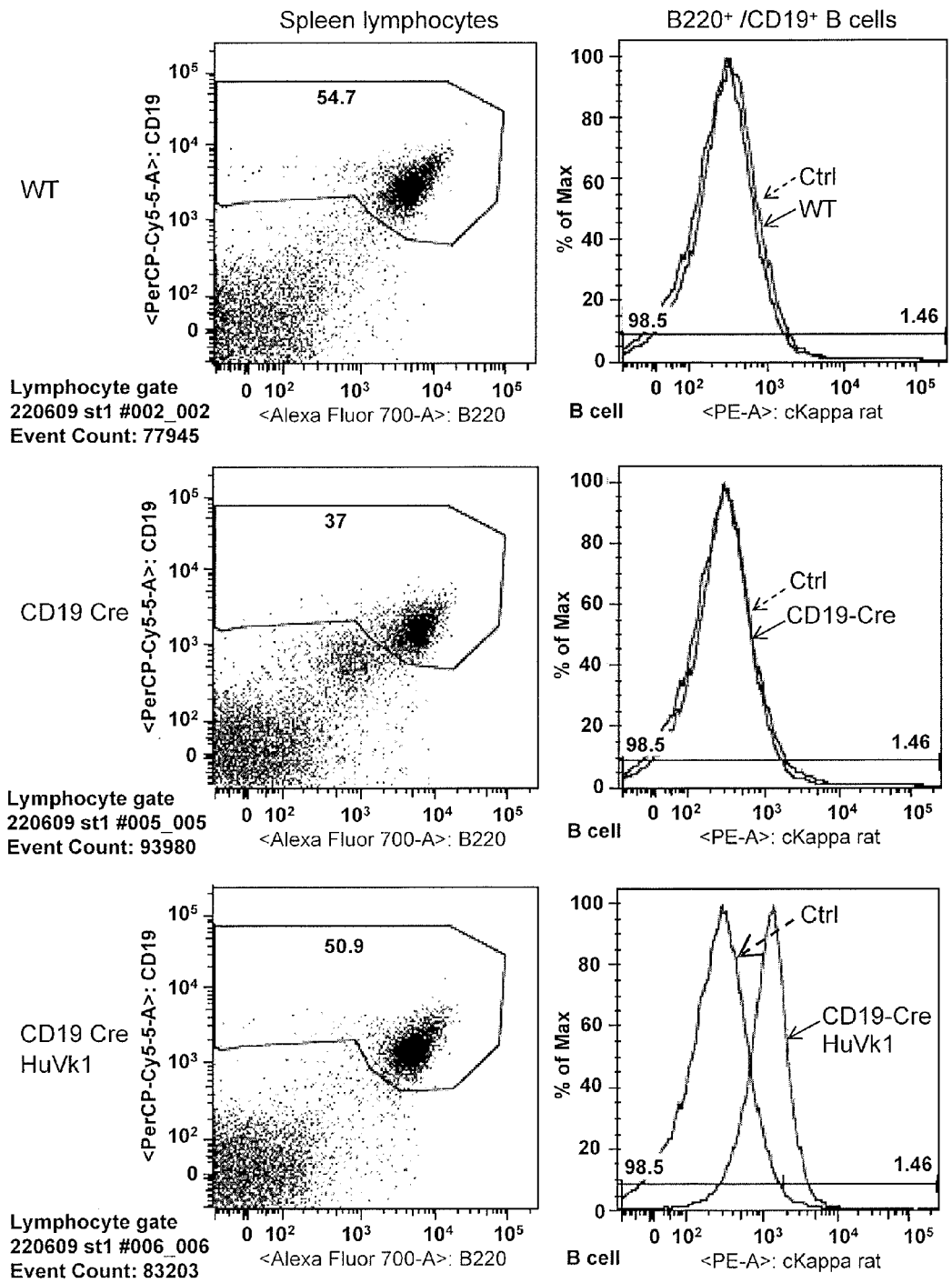
Fig. 24, contd.

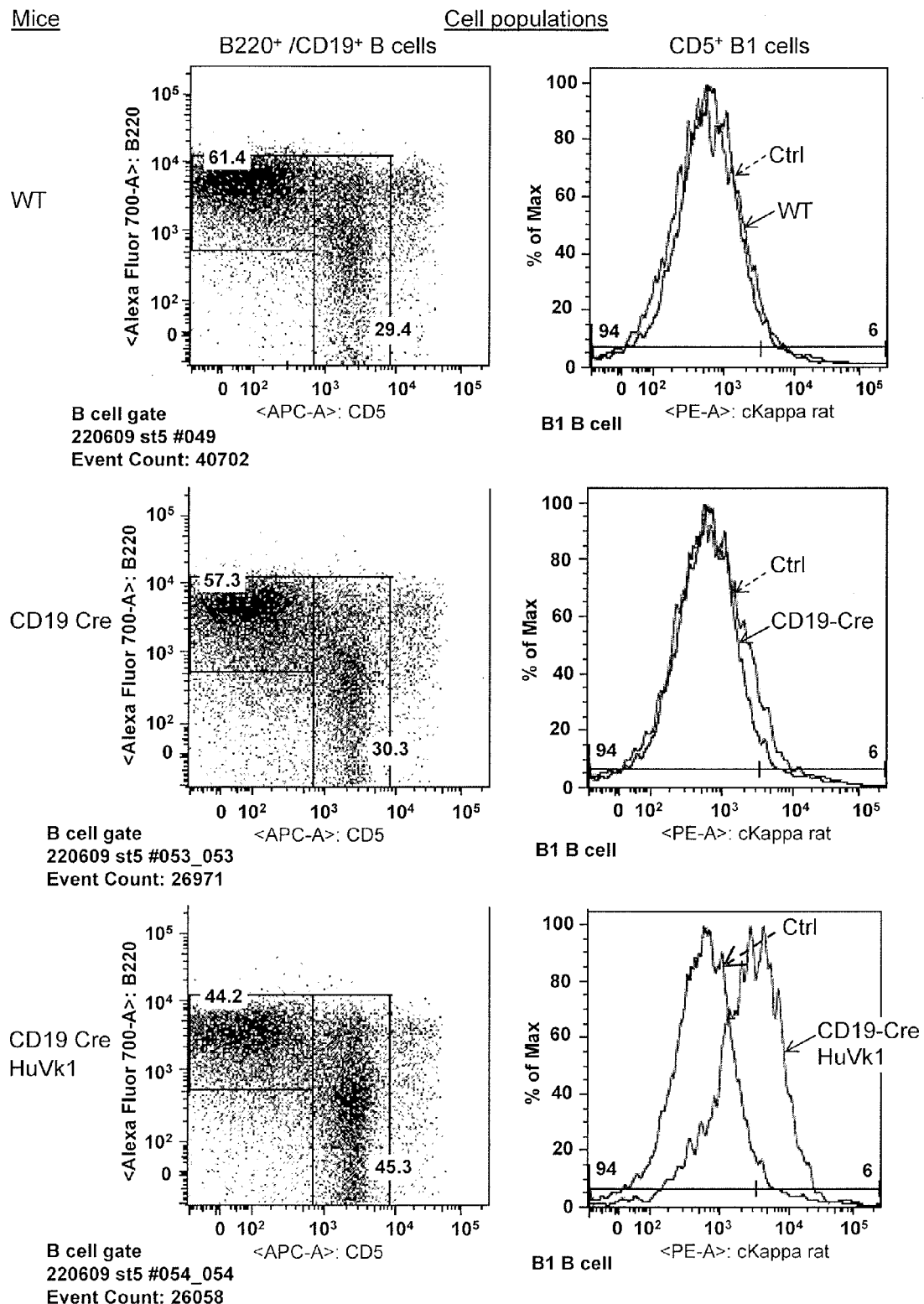
Fig. 25, contd.

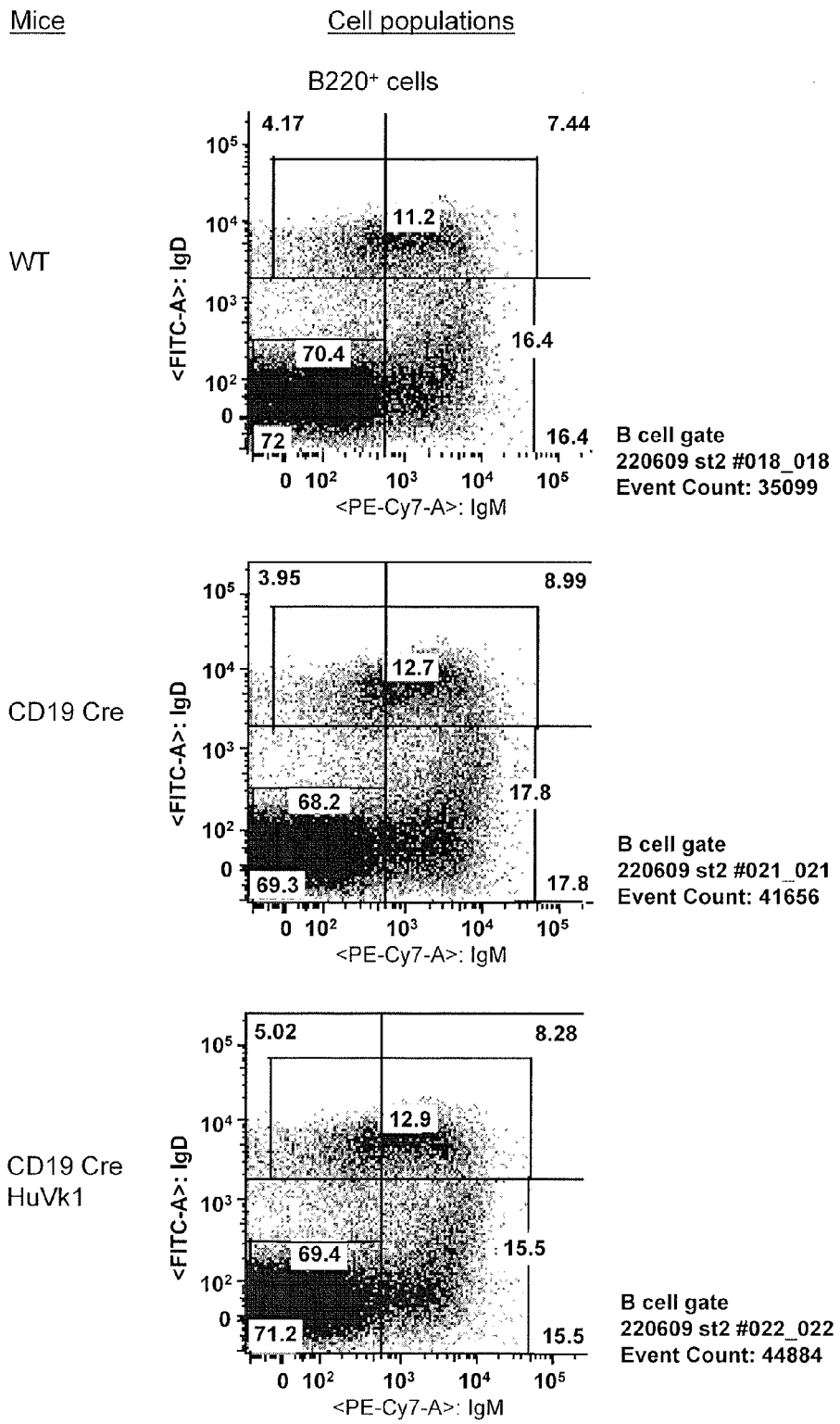
Fig. 26A, contd.

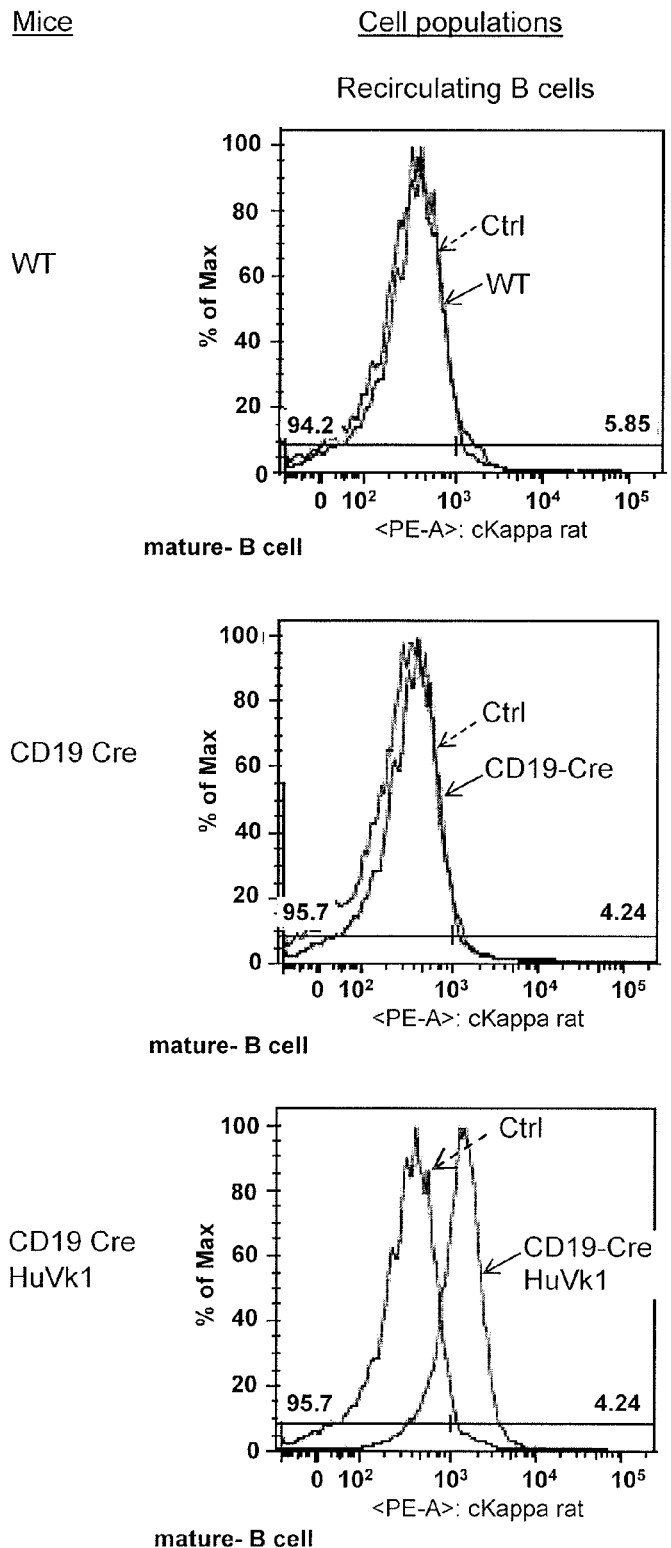
Fig. 26B, contd.

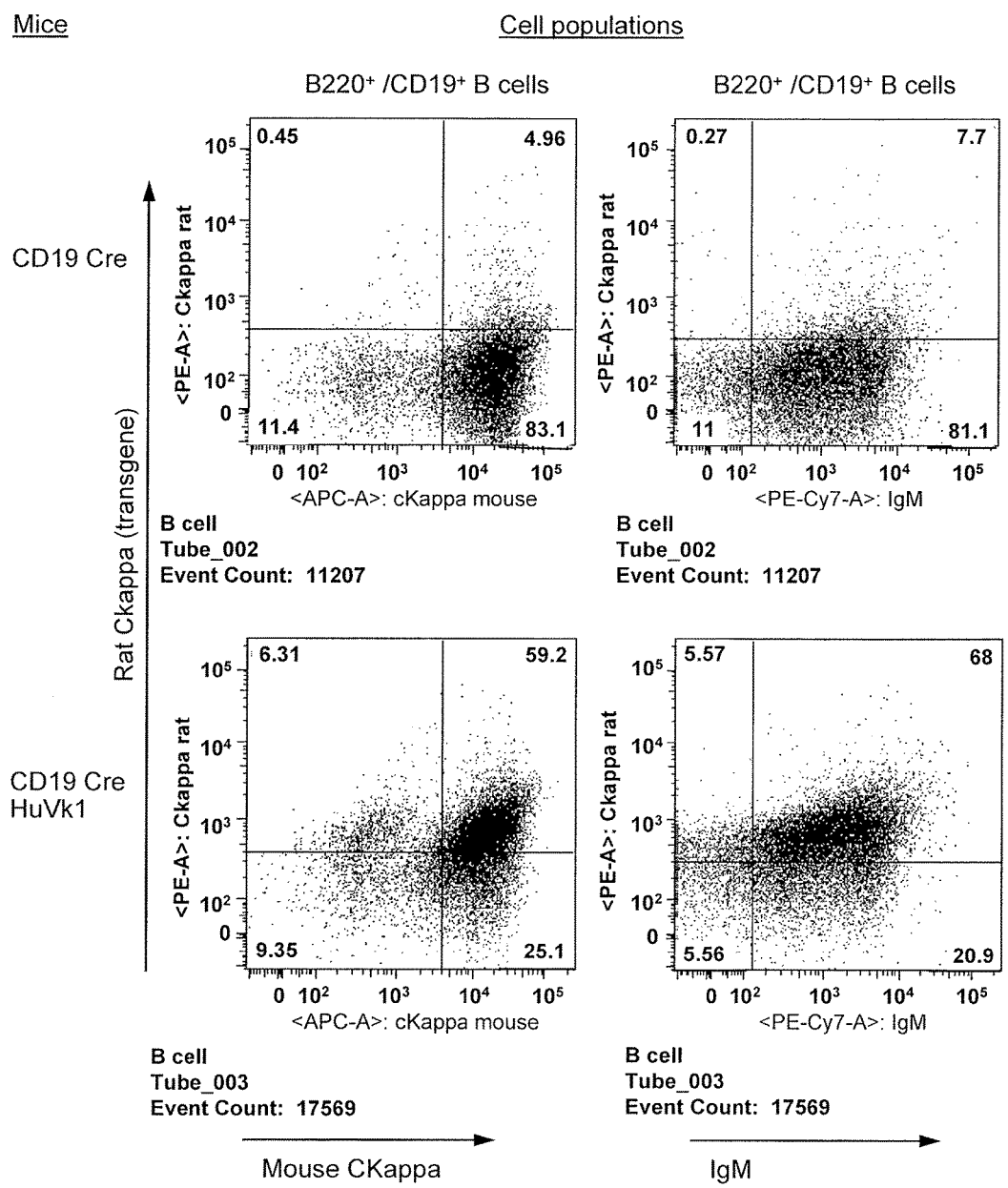
Fig. 27, contd.

FIG. 28

| | Stainings | | | | Mixtures | | | | |
|---|---|---|---|---|---|---|---|---|---|
| | # | Facs tubes # | Monoclonal | Work dilution | volume | 1st step | 2nd step | 3rd step | Final diltion |
| A | | | | | | | | | |
| Spleen | 1 | 1-8 | CD21$^{FITC}$ | 640 | 320 | | 0.50 | | |
| | | | Ckappa rat$^{PE}$ | 160 | | 2.00 | | | |
| | | | CD19$^{PerCP-Cy5.5}$ | 640 | | | 0.50 | | |
| | | | CD23$^{PE-Cy7}$ | 50 | 1:20 | | 6.40 | | 1000 |
| | | | DAPI | | | | | | |
| | | | Ckappa mouse$^{BIO-APC}$ | 100 | 1:50 | | | 3.20 APC | 5000 |
| | | | Clambda mouse$^{BIO-APC}$ | 100 | 1:30 | | | 3.20 APC | 3000 |
| | | | B220$^{Alex-700}$ | 160 | | | 2.00 | | |
| | | | FC block | 400 | | | 0.80 | | |
| Spleen | 2 | 9-16 | IgD$^{FITC}$ | 640 | 640 | | 1.00 | | |
| BM | | 17-24 | Ckappa rat$^{PE}$ | 160 | | 4.00 | | | |
| | | | CD19$^{PerCP-Cy5.5}$ | 500 | | | 1.28 | | |
| | | | IgM$^{PE-Cy7}$ | 640 | | | 1.00 | | |
| | | | DAPI | | | | | | |
| | | | Ckappa mouse$^{BIO-APC}$ | 100 | 1:50 | | | 6.40 APC | 5000 |
| | | | Clambda mouse$^{BIO-APC}$ | 100 | 1:30 | | | 6.40 APC | 3000 |
| | | | B220$^{Alex-700}$ | 160 | | | 4.00 | | |
| | | | FC block | 400 | | | 1.60 | | |
| Spleen | 3 | 25-32 | Ckappa mouse$^{FITC}$ | 400 | 320 | | 0.80 | | |
| | | | Ckappa rat$^{PE}$ | 160 | | 2.00 | | | |
| | | | CD19$^{PerCP-Cy5.5}$ | 500 | | | 0.64 | | |
| | | | IgM$^{PE-Cy7}$ | 640 | | | 0.50 | | |
| | | | DAPI | | | | | | |
| | | | Clambda mouse$^{BIO-APC}$ | 100 | 1:30 | | | 3.20 APC | 3000 |
| | | | B220$^{Alex-700}$ | 160 | | | 2.00 | | |
| | | | FC block | 400 | | | 0.80 | | |
| Spleen | 4 | 33-40 | Ckappa mouse$^{FITC}$ | 400 | 640 | | 1.60 | | |
| | | 41-48 | lambda$^{FITC}$ | 600 | | | 1.07 | | |
| PP | | | Ckappa rat$^{PE}$ | 160 | | 4.00 | | | |
| | | | CD19$^{PerCP-Cy5.5}$ | 500 | | | 1.28 | | |

FIG. 29A

| | | | | | | | | |
|---|---|---|---|---|---|---|---|---|
| | | | IgM$^{PE-Cy7}$ | 640 | | | 1.00 | |
| | | | DAPI | | | | | |
| | | | IgD$^{A647}$ | 1280 | | | 0.50 | |
| | | | B220$^{Alex-700}$ | 160 | | | 4.00 | |
| | | | PNA$^{BIO-SAV-APC-Cy7}$ | 300 | | | 2.13 | APC-Cy7 |
| | | | FC block | 400 | | | 1.60 | |
| PC | 5 | 49-56 | IgM$^{FITC}$ | 160 | | 320 | 2.00 | |
| | | | Ckappa rat$^{PE}$ | 160 | | | 2.00 | |
| | | | CD19$^{PerCP-Cy5.5}$ | 500 | | | 0.64 | |
| | | | Ckappa mouse$^{BIO-PE-Cy7}$ | 100 | 1:50 | | 3.20 | PE-Cy7 | 5000 |
| | | | Clambda mouse$^{BIO-PE-Cy7}$ | 100 | 1:30 | | 3.20 | PE-Cy7 | 3000 |
| | | | DAPI | | | | | |
| | | | CD5$^{APC}$ | 320 | | | 1.00 | |
| | | | B220$^{Alex-700}$ | 160 | | | 2.00 | |
| | | | FC block | 400 | | | 0.80 | |
| BM | 6 | 57-64 | IgM$^{FITC}$ | 160 | | 640 | 4.00 | |
| | | | Ckappa rat$^{PE}$ | 160 | | | 4.00 | |
| | | | CD19$^{PerCP-Cy5.5}$ | 500 | | | 1.28 | |
| | | | Ckappa mouse$^{BIO-PE-Cy7}$ | 100 | 1:50 | | 6.40 | PE-Cy7 | 5000 |
| | | | Clambda mouse$^{BIO-PE-Cy7}$ | 100 | 1:30 | | 6.40 | PE-Cy7 | 3000 |
| | | | DAPI | | | | | |
| | | | CD25$^{APC}$ | 80 | | | 8.00 | |
| | | | B220$^{Alex-700}$ | 160 | | | 4.00 | |
| | | | FC block | 400 | | | 1.60 | |
| RAT spleen | | | | | | | | |
| | 7 | 144 | Ckappa rat$^{PE}$ | 160 | | 80 | 0.5 | |
| | | | rat B220$^{FITC}$ | 160 | | | 0.5 | |
| Spleen | 8 | 97-104 | cyt CD3$^{FITC}$ | 320 | | 320 | 1 | |
| | | | cyt Ckappa rat$^{PE}$ | 80 | | | 4.00 | |
| | | | cyt CD11c$^{PE-TexasRED}$ | 75 | | | 4.27 | |
| | | | cyt NK1.1$^{BIO-PE-Cy7}$ | 200 | | | 1.6 | PE-Cy7 |
| | | | cyt CD19$^{PerCP-Cy5.5}$ | 320 | | | 1 | |
| | | | cyt CD4$^{APC}$ | 500 | | | 0.64 | |
| | | | cyt CD11b$^{Alex-700}$ | 50 | | | 6.40 | |

FIG. 29B

ANTIBODY PRODUCING NON-HUMAN MAMMALS

CROSS-REFERENCE TO RELATED APPLICATION

This application is a continuation of U.S. patent application Ser. No. 12/589,181, filed Oct. 19, 2009, pending, which application is a continuation of U.S. patent application Ser. No. 12/459,285, filed Jun. 29, 2009, pending, which applications claim the benefit, under 35 U.S.C. § 119(e), to U.S. Provisional Patent Application Ser. No. 61/133,274, filed Jun. 27, 2008, for "Antibody Producing Non-Human Mammals," the entire contents of each of which are hereby incorporated herein by this reference.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), files containing a TXT version and a PDF version of the Sequence Listing have been submitted concomitant with this application, the contents of which are hereby incorporated by reference.

TECHNICAL FIELD

The invention relates to the production and use of non-human animals capable of producing antibodies or derivatives thereof, which are expressed from at least partially exogenous nucleic acids (transgenes). Transgenes to produce such transgenic animals and methods to produce such heterologous antibodies; methods and vectors for producing such transgenic animals are disclosed.

BACKGROUND

B cells mediate humoral immunity by producing specific antibodies. The basic structural subunit of an antibody (Ab) is an immunoglobulin (Ig) molecule. Ig molecules consist of a complex of two identical heavy (H) and two identical light (L) polypeptide chains. At the amino terminus of each H chain and L chain is a region that varies in amino acid sequence named the variable (V) region. The remaining portion of the H and L chains is relatively constant in amino acid sequence and is named the constant (C) region. In an Ig molecule, the H and L chain V regions (VH and VL) are juxtaposed to form the potential antigen-binding site. The genes that encode H and L chain V regions are assembled somatically from segments of germline DNA during precursor B (pre-B) cell differentiation: V, D and J gene segments for the H chain and V and J gene segments for the L chain. Within Ig V regions are three regions of greatest amino acid sequence variability that interact to form the antigen-recognition site and are thus referred to as complementarity determining regions (CDRs).

The V gene segment encodes the bulk of the V region domain, including CDR1 and CDR2. Diversity in CDR1 and CDR2 derives from sequence heterogeneity among multiple different germline-encoded V segments. CDR3 is encoded by sequences that are formed by the joining of H chain V, D, and J gene segments and L chain V and J segments and by mechanisms that create nucleotide sequence heterogeneity where these segments are combined. Additional diversity may be derived from pairing of different H and L chain V regions. Collectively these processes yield a primary repertoire of antibodies encoded by germline gene segments and expressed by newly formed B cells.

An additional source of antibody diversity is imposed on top of the diversity generated by recombination of Ig gene segments. B cells are able to introduce mutations into the antibody V regions that they express, a process called somatic hypermutation. Thus, when an animal first encounters an antigen, the antigen binds to a specific B cell which happens to carry antibodies which have a V domain which binds the antigen. This primary response may activate this B cell to go on to secrete the cognate antibody. These activated B cells can also now target a somatic mutation process to their rearranged antibody gene segments and thus allow the production of daughter cells which make variants of the antibodies of the primary response. A selection process amplifies those variant B cell descendants which make an antibody of improved affinity of the antigen. In B cells, somatic hypermutations are targeted to a restricted genomic region including both the rearranged VH and VL genes. Thus somatic mutation allows affinity maturation—the production and selection of high affinity antibodies. Therefore, somatic mutation is important for the generation of high affinity antibodies.

The exquisite specificity and high affinity of antibodies and the discovery of hybridoma technology allowing the generation of monoclonal antibodies (mAbs) has generated great expectations for their utilization as targeted therapeutics for human diseases. MAbs are identical because they are produced by a single B cell and its progeny. MAbs are made by fusing the spleen cells from a mouse that has been immunized with the desired antigen with myeloma cells to generate immortalized hybridomas. One of the major impediments facing the development of in vivo applications for mAbs in humans is the intrinsic immunogenicity of non-human Igs. Patients respond to therapeutic doses of mouse mAbs by making antibodies against the mouse Ig sequences (Human Anti Mouse Antibodies; HAMA), causing acute toxicity, alter their biodistribution and accelerate clearance, thus reducing the efficacy of subsequent administrations (Mirick et al. (2004), *Q. Nucl. Med. Mol. Imaging* 48:251-257).

To circumvent the generation of HAMA, antibody humanization methods have been developed in an attempt to produce mAbs with decreased immunogenicity when applied to humans. These endeavors have yielded various recombinant DNA-based approaches aimed at increasing the content of human amino acid sequences in mAbs while retaining the specificity and affinity of the parental non-human antibody. Humanization began with the construction of mouse-human chimeric mAbs (S. L. Morrison et al. (1984), *Proc. Natl. Acad. Sci. USA* 81:6851-5), in which the Ig C regions in murine mAbs were replaced by human C regions. Chimeric mAbs contain 60-70% of human amino acid sequences and are considerably less immunogenic than their murine counterparts when injected into humans, albeit that a human anti-chimeric antibody response was still observed (W. Y. Hwang et al. (2005), *Methods* 36:3-10).

In attempts to further humanize murine mAbs, CDR grafting was developed. In CDR grafting, murine antibodies are humanized by grafting their CDRs onto the VL and VH frameworks of human Ig molecules, while retaining those murine framework residues deemed essential for specificity and affinity (P. T. Jones et al. (1986), *Nature* 321:522). Overall, CDR-grafted antibodies consist of more than 80% human amino acid sequences (C. Queen et al. (1989), *Proc. Natl. Acad. Sci. U.S.A.* 86:10029; P. Carter et al. (1992), *Proc. Natl. Acad. Sci. U.S.A.* 89:4285). Despite these efforts, CDR-grafted, humanized antibodies were shown to still evoke an antibody response against the grafted V region (W. Y. Hwang et al. (2005), *Methods* 36:3).

Subsequently to CDR grafting, humanization methods based on different paradigms such as resurfacing (E. A. Padlan et al. (1991), *Mol. Immunol.* 28:489), superhumanization (P. Tan D. A. et al. (2002), *J. Immunol.* 169:1119), human string content optimization (G. A. Lazar et al. (2007), *Mol. Immunol.* 44:1986) and humaneering have been developed in an attempt to further decrease the content of non-human sequences in therapeutic mAbs (J. C. Almagro et al. (2008), *Frontiers in Bioscience* 13:1619). As in CDR grafting approaches, these methods rely on analyses of the antibody structure and sequence comparison of the non-human and human mAbs in order to evaluate the impact of the humanization process into immunogenicity of the final product. When comparing the immunogenicity of chimeric and humanized antibodies, humanization of variable regions appears to decrease immunogenicity further (W. Y. Hwang et al. (2005), *Methods* 36:3-10).

De-immunization is another approach developed to reduce the immunogenicity of chimeric or mouse antibodies. It involves the identification of linear T-cell epitopes in the antibody of interest, using bioinformatics, and their subsequent replacement by site-directed mutagenesis to human or non-immunogenic sequences (WO 9852976 A1, the contents of which are incorporated by this reference). Although de-immunized antibodies exhibited reduced immunogenicity in primates, compared with their chimeric counterparts, some loss of binding affinity was observed (M. Jain et al. (2007). *Trends in Biotechnol.* 25:307).

The development of phage display technology complemented and extended humanization approaches in attempts to obtain less immunogenic mAbs for therapy in humans. In phage display, large collections ("libraries") of human antibody VH and VL regions are expressed on the surface of filamentous bacteriophage particles. From these libraries, rare phages are selected through binding interaction with antigen; soluble antibody fragments are expressed from infected bacteria and the affinity of binding of selected antibodies is improved by mutation (G. Winter et al. (1994), *Annu. Rev. Immunol.* 12:433). The process mimics immune selection, and antibodies with many different bindings specificities have been isolated using this approach (H. R. Hoogenboom et al. (2005), *Nat. Biotechnol.* 23:1105). Various sources of H and L chain V regions have been used to construct phage display libraries including those isolated from non-immune or immune donors. In addition, phage display libraries have been constructed of V regions that contain artificially randomized synthetic CDR regions in order to create additional diversity. Often, antibodies obtained from phage display libraries are subjected to in vitro affinity maturation to obtain high affinity antibodies (H. R. Hoogenboom et al. (2005), *Nat. Biotechnol.* 23:1105).

The creation of transgenic mouse strains producing human antibodies in the absence of mouse antibodies has provided another technology platform for the generation of specific and high affinity human mAbs for application in humans. In these transgenic animals, the endogenous mouse antibody machinery is inactivated and replaced by human Ig loci to substantially reproduce the human humoral immune system in mice (A. Jakobovits et al. (2007), *Nat. Biotechnol.* 25:1134; N. Lonberg (2005), *Nat. Biotechnol.* 23:1117). B cell development as well as Ig diversification by recombination of gene segments is faithfully reproduced in these mice, leading to a diverse repertoire of murine B cells expressing human Igs. By immunizing these mice with antigens, it was further demonstrated that these transgenic animals accumulated somatic mutations in the V regions of both heavy and light chains to produce a wide diversity of high-affinity human mAbs (N. Lonberg (2005), *Nat. Biotechnol.* 23:1117).

The question, whether "fully human" mAbs such as derived from phage display libraries or transgenic mice are less immunogenic than humanized mAbs cannot be answered yet, because full immunogenicity data are available for just two human mAbs. An anti-tumor necrosis factor mAb, developed from phage-displayed human libraries induced antibody responses in 12% of patients—at the higher end of the incidence of anti-antibody responses of the humanized antibodies (W. Y. Hwang et al. (2005), *Methods* 36:3-10).

Evaluation of the immunogenicity of the first registered human mAb generated by the transgenic approach demonstrated that mAb treatment resulted in the generation of antibodies in approximately 5.5% of treated cancer patients (A. Jakobovits et al. (2007), *Nat. Biotechnol.* 25:1134; J. A. Lofgren et al. (2007), *J. Immunol.* 178:7467).

DISCLOSURE OF THE INVENTION

Disclosed are a method and means for producing antibodies that are specific for their targets, but are less immunogenic. Described herein, the reduction of immunogenicity is at least partially achieved by providing a transgenic non-human mammal comprising, at least in its B cell lineage, a nucleic acid encoding at least an immunoglobulin light chain or heavy chain, wherein the heavy- or light chain encoding sequence is provided with a means that renders it resistant to DNA rearrangements and/or somatic hypermutations, preferably such a non-human animal is a rodent, more specifically a mouse. In certain embodiments, the nucleic acid encodes a human, human-like, or humanized immunoglobulin chain.

In the remainder of this specification, mice are typically used as examples of the non-human mammals. The transgenic, non-human, mammalian hosts are capable of mounting an immune response to an antigen, where the response produces antibodies having primate, particularly human, variable regions. Various transgenic hosts may be employed, particularly murine, lagomorpha, ovine, avine, porcine, equine, canine, feline, or the like. Mice have been used for the production of B-lymphocytes for immortalization for the production of antibodies. Since mice are easy to handle, can be bred in large numbers, and are known to have an extensive immune repertoire, mice will usually be the animal of choice. Therefore, in the following discussion, the discussion will refer to mice, but it should be understood that other animals, particularly non-primate mammals, may be readily substituted for the mice, following the same procedures.

The reason for preventing rearrangements and hypermutation is that in this manner a non-immunogenic polypeptide can be chosen beforehand knowing that this polypeptide chain will remain non-immunogenic. At least one of the chains of the resulting immunoglobulin is thus less immunogenic. The resulting antibody needs to have (usually) both a light- and a heavy chain. The non-immunogenic chain must therefore be capable of pairing with the other chain. The other chain may be an endogenous chain, an exogenous chain or a hybrid of both. For human therapy, the non-immunogenic chain should be as close to human as possible.

A means for rendering a gene encoding an immunoglobulin chain (or chains) resistant to DNA rearrangement and/or mutation is of course removal of all genetic elements responsible for the rearrangement and/or mutation. The drawback thereof is that the variability of the two chains is eliminated, whereas the invention preferably retains the variability in one chain (preferably the heavy chain) and inhibits and/or prevents the rearrangement-mutation of the other chain (preferably the light chain).

The elements for rearrangement and/or hypermutation characterized so far are located within the loci for immunoglobulins. Therefore the means for rendering the immunoglobulin encoding sequence resistant to DNA rearrangement and/or mutation is inserting the gene in a locus outside the immunoglobulin loci.

Thus, described herein, a transgenic non-human mammal is provided wherein the light/heavy chain encoding sequence is integrated in the genome of the non-human mammal in a locus outside the immunoglobulin loci. Preferably the insertion is in a locus that is resistant to gene silencing. Described herein, the integration is in the Rosa-locus or a comparable locus.

In certain embodiments, provided is an expression cassette that can be inserted into a Rosa locus or comparable locus with a means that allows expression of the immunoglobulin chain(s) essentially limited to cells of B cell lineage, preferably with a means that allows expression of the light chain encoding nucleic acid during a certain stage of the development of B cells. The term "essentially limited expression" indicates that expression is predominantly in cells of the B-cell lineage, but that lower levels of expression in other cells, as compared to the level of expression in B-cells, is possible. In certain embodiments, the term "essentially limited expression" indicates that the expression is exclusively present in cells of the B-cell lineage. Such means typically and preferably include B cell (developmental stage) specific promoters such as CD19, CD20, μHC (all V-genes), VpreB1, VpreB2, VpreB3, λ5, Igα, Igβ, κLC (all genes), λLC (all genes), BSAP (Pax5). Although it is very well possible to direct the expression of the DNA rearrangement and/or mutation resistant chain by such promoters, they are relatively weak. A strong promoter will typically be required to ensure adequate surface expression of the B cell receptor (made up of the membrane attached Ig H and L chain) and to compete with the expression and pairing of endogenous chains (if present) through allelic exclusion. Such a promoter, however is usually not tissue specific. To confer tissue specificity, an indirect system employing Cre/lox or the like is preferred. The desired chain is put under control of a strong promoter inhibited by an element that can be removed by the action of a Cre-protein, leading to activation of the desired immunoglobulin encoding gene. This system is described in detail in F. T. Wunderlich (2004), "Generation of inducible Cre systems for conditional gene inactivation in mice," Inauguraldissertation zur Erlangung des Doktorgrades der Mathematisch-Naturwissenschaftlichen Fakultät der Universität zu Köln; on the internet at deposit.ddb.de/cgi-bin/dokserv?idn=97557230x&dok_var=d1&dok_ext=pdf&filename=975572 30x.pdf.

Preferably the immunoglobulin chain produced in a manner resistant to rearrangements and hypermutation is a light chain capable of pairing with different heavy chains encoded by the non-human mammal. The light chain will then be the same (and less immunogenic) in all antibodies, but variety in specificity is retained through rearrangements and hypermutations in the heavy chains. It may in that case be preferable to silence at least one of the endogenous loci encoding a light chain, although allelic exclusion may render this unnecessary.

According to this embodiment, preferably the endogenous kappa (κ) light chain locus is functionally silenced.

If the endogenous K light chain locus is silenced, but also for other reasons, it is preferred that the resistant light chain is a κ light chain, preferably a light chain that has a germline-like sequence. Described herein such a light chain would lead to an antibody with reduced immunogenicity. The preferred germline sequence is based on the human IGKV1-39 (O12) as this light chain is very frequently observed in the human repertoire (de Wildt et al. 1999, *J. Mol. Biol.* 285(3):895) and has superior thermodynamic stability, yield and solubility (Ewert et al. 2003, *J. Mol. Biol.* 325(3):531).

The following gives more specific embodiments of the expression cassette with which the non-human animal can be provided described herein. Although this is typically advantageous for immunoglobulins, other genes of interest are also contemplated.

Thus, provided in a specific embodiment, is a transgenic non-human mammal wherein the light chain encoding nucleic acid comprises in 5'-3' direction: a B cell specific promoter, a leader, a rearranged human V gene, optionally a mouse κ-intron enhancer (MoEκi), a constant region (κ) and optionally a (truncated) mouse κ-3' enhancer (MoEκ3'). Neuberger identified and examined a novel B-cell specific enhancer located downstream of the kappa constant region (Neuberger, EP 00469025 B1, the contents of which are incorporated herein by this reference). This enhancer has been shown to play a crucial role in the expression of kappa genes as removal of the 808 bp enhancer strongly reduced expression. Deletion of the 3' kappa enhancer also strongly reduced the level of somatic hypermutations (SHM). In transgenic and cell expression studies, it has been revealed that reduced, mutated or deleted 3' kappa enhancers not only lowered expression levels, but also decreased the level of somatic hypermutations. Currently, it cannot be determined whether the 3' kappa enhancer is involved in SHM processes, expression regulation or both (review V. H. Odegard et al. (2006), *Nat. Rev. Immunol.* 6:573; M. Inlay et al. (2002), *Nat. Immunol.* 3:463).

Detailed expression studies using engineered variants of the 3' kappa enhancer indicated that a 50 nucleotide region is sufficient to drive expression. However for proper expression a reduced sequence of 145 nucleotides is preferred (EP04690251; K. B. Meyer et al. (1990), *Nucleic Acids Res.* 18(19):5609-15).

Thus, the invention in one aspect provides a nucleic acid for insertion into the genome of a non human animal that is an expression cassette for the expression of a desired proteinaceous molecule in cells developing into mature B cells during a certain stage of development, the cassette comprising means for preventing silencing of expression of the desired proteinaceous molecule after introduction into a host cell, and means for timing expression of the desired proteinaceous molecule with the desired developmental stage of the host cell.

An expression cassette is defined as a nucleic acid that has been provided with means for introduction into the genome of a host cell, such as sequences which allow for homologous recombination with a certain site in the genome. Usually the nucleic acid will be DNA, typically double stranded. Typically the expression cassette will be provided to the cell in a vector from which it is transferred to the genome of the cell. The expression cassette further comprises all elements necessary for expression of the gene in a host cell, although in certain embodiments some of such elements may be present on a second nucleic acid to be introduced, whereby these elements act in trans. Elements necessary for expression in a host cell include promoters, enhancers and other regulatory elements. Only those elements are necessary that are not provided by the host cell.

The expression of the gene of interest should not be silenced in the genome of the host cell, especially not in the development stage where expression is required. This can be done by various means, such as insertion into the endogenous locus or by providing the cassette with nucleic acid elements that prevent silencing (Kwaks et al. (2006), *Trends Biotechnol.* 24(3):137-142, which is incorporated herein by reference). It is preferred that the expression cassette is inserted in a locus that is not silenced in the host cells (EP 01439234; which is incorporated herein by reference).

The means for prevention of silencing comprise STabilizing Anti-Repression-sequences (STAR®-sequences) and Matrix Attachment Regions (MARs). A STAR sequence is a nucleic acid sequence that comprises a capacity to influence transcription of genes in cis. Typically, although not necessarily, a STAR sequence does not code by itself for a functional protein element. In one embodiment one STAR element is used. Preferably, however, more than one STAR element is used. In a particularly preferred embodiment an expression cassette described herein is provided with two STAR sequences; one STAR sequence at the 5' side of the coding sequence of the immunoglobulin gene and one STAR sequence at the 3' side of the coding sequence of the immunoglobulin gene. MARs are DNA sequences that are involved in anchoring DNA/chromatin to the nuclear matrix and they have been described in both mammalian and plant species. MARs possess a number of features that facilitate the opening and maintenance of euchromatin. MARs can increase transgene expression and limit position-effects.

Expression from the cassette should only occur during a certain period in the development of a cell, in particular a developing B cell, more in particular a B cell in a transgenic non-human animal, in particular a mouse. In this particular case the developmental period is chosen such that the expression of the gene from the cassette (typically a light- or heavy chain-like polypeptide) does not significantly interfere with the normal differentiation and/or maturation of the cell and when applicable, allows for pairing of the polypeptide chain produced with its counterpart.

This may, in one embodiment, be achieved by providing a nucleic acid described herein, wherein the means for timing expression is a promoter of which the activity is essentially limited to the certain stage of development. In a developing B cell, which, e.g., after immunization is maturing and/or differentiating, the expression of the gene of interest, when it is one of the polypeptide chains of an immunoglobulin, must not interfere (significantly) with the maturation and/or differentiation and it needs to be timed such that the resulting polypeptide can pair with its counterparts. Therefore, provided is a nucleic acid described herein wherein the certain stage starts at a stage immediately preceding or coinciding with the onset of the expression of light chain molecules by the cells at a certain stage of development into a mature B cell. This may be achieved by selecting a promoter which is active only during the suitable period. Such a promoter may be a CD19 promoter, the Ig-α promoter, the Ig-β promoter, the μhc (all genes) promoter, the Vκ promoter or analogues or homologues thereof.

In a specific embodiment, the promoter as disclosed above does not drive the expression of the gene of interest directly. Instead it drives the expression of a gene of which the product activates in trans the expression of the gene of interest. Such an activating gene may be a gene encoding a so-called Cre recombinase or Cre-like protein. The expression cassette for the gene of interest may, e.g., be provided with a sequence that inhibits expression of the gene of interest. The sequence can be removed by the action of the Cre recombinase, which is under control of the desired promoter (active during the proper stage of development). In this embodiment a set of expression cassettes is required.

Therefore, provided is a set of nucleic acids that are expression cassettes, wherein one nucleic acid comprises an expression cassette encoding a Cre-like protein under control of a promoter active during the desired stage of development of the host cell and the second nucleic acid comprises a sequence encoding a desired proteinaceous molecule under control of a constitutive promoter which can be activated by the action of a Cre-like protein. The activation is preferably achieved by removal of a stop sequence flanked by loxP sites. The Cre/lox system is described in detail in Rajewsky et al. (1996), *J. Clin. Invest.* 98:600-603, which is incorporated herein by reference. Such systems are reviewed in F. T. Wunderlich (2004), "Generation of inducible Cre systems for conditional gene inactivation in mice," Inauguraldissertation zur Erlangung des Doktorgrades der Mathematisch-Naturwissenschaftlichen Fakultät der Universität zu Köln; on the World Wide Web at deposit.ddb.de/cgi-bin/dokserv?idn=97557230x&dok_var=dl&dok_ext=pdf&filename=97557230x.pd, which is incorporated herein by reference.

Further provided is a transgenic non-human animal that has been provided with an expression cassette hereof, wherein the desired proteinaceous molecule is a polypeptide chain of an immunoglobulin. A preferred polypeptide chain is a light chain. A more preferred polypeptide is a germline or germline-like light chain. A most preferred polypeptide is encoded by the immunoglobulin kappa variable 1-39 (IGKV1-39, also known as O12) gene segment, preferably the rearranged germline kappa light chain IGKV1-39*01/IGKJ1*01 (nomenclature according to the MGT database, at [worldwideweb].imgt.org).

In certain embodiments, the polypeptide chain is rendered essentially incapable of rearrangement and/or of excluded of any sequence modification such as normally operating on Ig during the process of B cell affinity maturation. Therefore, provided is a transgenic non-human animal that has been provided with an expression cassette described herein, wherein the rearrangement and/or sequence modifications are prevented by the absence of elements at least partially responsible for somatic hypermutation such as, for example, the MoEκi enhancer.

A preferred expression cassette described herein comprises means for prevention of silencing. In one embodiment, the means for prevention of silencing are means for insertion into a locus in the genome of the host cell that is resistant to silencing. The means for insertion are preferably means for homologous recombination into the site resistant to silencing. A preferred locus when the non-human animal is a mouse is the rosa-locus.

A further preferred expression cassette described herein comprises in 5'-3' direction: a Vκ promoter, a mouse leader, a human V gene, optionally a MoEκi enhancer, a rat constant region (Cκ) and optionally a (truncated) MOEκ3' enhancer.

Yet a further preferred expression cassette described herein comprises in 5'-3' direction: a Vκ promoter, a human leader, a human V gene, optionally a MoEκi enhancer, a rat constant region (Cκ) and optionally a (truncated) MoEκ3' enhancer.

Certain antibodies produced as described herein may be be used in human therapeutics and diagnostics. Thus, provided is a method for producing a desired antibody comprising exposing a non-human mammal described herein to an antigen such that an antibody response is induced and isolating the antibodies specific for the antigen.

In certain embodiments, provided are methods for producing a desired antibody comprising exposing a non-human mammal described herein to an antigen such that an antibody response is induced and isolating cells producing such antibodies, culturing and optionally immortalizing the cells and harvesting the antibodies.

In certain embodiments, provided is a method for producing a desired antibody comprising exposing a non-human mammal described herein to an antigen such that an antibody response is induced and isolating a nucleic acid encoding at least part of such an antibody, inserting the nucleic acid or a copy or a derivative thereof in an expression cassette and expressing the antibody in a host cell.

The methods for producing antibodies from transgenic mice are known to a person skilled in the art. Particularly preferred are methods for production of mixtures of antibodies from one cell, whereby the nucleic acids encoding these antibodies have been derived from mice described herein.

These so-called oligoclonics are disclosed in WO04106375 and WO05068622, which are incorporated herein by reference.

Described herein are transgenic non-human mammals, preferably mice, capable of generating specific and high affinity hybrid mouse-human antibodies with preferably human immunoglobulin light chain variable (VL) regions in or near germline configuration and preferably murine immunoglobulin heavy chain variable (VH) regions that may have accumulated somatic mutations during the process of antigen-driven affinity maturation. It is envisaged that the murine VH regions of the hybrid antibodies may be subjected to humanization procedures to yield mAbs that have reduced immunogenicity when applied in humans based on germline or near-germline VL regions and murine VH regions that have been humanized.

In particular, we have shown that transgenic mice that harbor a DNA expression construct that encodes a rearranged human VL region under the control of cis-acting genetic elements that provide timely and regulated expression of the transgene on a significant proportion of B cells during B cell development, yet lack elements that direct the somatic hypermutation machinery to the transgene, are capable of generating specific and high affinity mouse-human hybrid antibodies with essentially unmutated L chains. It is shown that the rearranged human transgene is capable of pairing with a diversity of endogenous murine immunoglobulin H chains to form mouse-human hybrid immunoglobulins expressed on the surface of B cells and to sufficiently facilitate murine B cell development to obtain a sizeable and diverse peripheral B cell compartment.

In certain embodiments, the transgene expression construct harbors the coding sequences of a human rearranged L chain V region under the control of a human VL promoter to direct B-cell specific expression. In addition, the construct harbors the murine 3' Cκ enhancer sequence for B cell specific and inducible and high level expression of the transgene. Furthermore, the construct is designed to lack regulatory elements that facilitate the recruitment of the somatic hypermutation machinery to the transgene, such as the intron enhancer and the 3' C-kappa enhancer.

In a related embodiment, the rearranged human VL gene is inserted in the murine Rosa26 locus by site-specific integration. The Rosa26 locus is useful in the context of the "targeted transgenesis" approach for efficient generation of transgenic organisms (such as mice) with a predictable transgene expression pattern.

In certain embodiments, the rearranged human VL region is selected for its capacity to pair with many different murine VH genes so as to ensure the generation of a population of B cells with a diverse VH gene repertoire. A method of obtaining such VL regions comprises amplifying a repertoire of rearranged VH genes from the B cells of mice and a repertoire of human rearranged germline VL regions from the B cells of humans and cloning them into phagemid display vectors to prepare diverse libraries of hybrid immunoglobulins in bacteria. By nucleotide sequence analysis of collections of unselected and antigen-selected VH/VL pairs, human germline VL genes that pair with many different murine VH genes are identified. A collection of human germline VL genes with this capacity is described.

In one embodiment, it is shown that upon immunization with antigen, the B cells are capable of mounting an immune response, leading to the generation of B cells that secrete hybrid antibodies with high specificity and affinity. The V regions encoding these antibodies are characterized by the human transgenic light chain that harbors no or very few mutations and a murine heavy chain that harbors a variable number of mutations introduced by the somatic hypermutation machinery.

In a related embodiment, strategies to obtain high affinity hybrid monoclonal antibodies from the transgenic mice by hybridoma and display technologies are contemplated as well as procedures to humanize the murine VH regions to obtain less immunogenic antibodies for application in humans.

In one embodiment, provided is an immunoglobulin L chain transgene construct comprising DNA sequences that encode a human immunoglobulin VL region in combination with a light chain constant region (CL) of an animal immunoglobulin protein, which sequences are operably linked to transcription regulatory sequences that, when integrated in a non-human transgenic animal, produce an Ig VL-CL polypeptide with a human VL region that is not or marginally subject to somatic hypermutation. The Ig VL is capable of pairing with rearranged VH-CH polypeptides that are generated during B cell development in the non-human transgenic animal, with the VH-CH polypeptides retaining the capacity to undergo somatic hypermutation upon stimulation. The CL region may be of any animal species and is generally capable of pairing with the CH regions of the non-human transgenic animal.

Also included is the use of a transgene construct as above in producing a transgenic non-human animal capable of the production of hybrid antibodies consisting of VL-CL polypeptides and VH-CH polypeptides in which the VL region is of human origin and the CL, VH and CH may be of any animal species, including human. Upon immunization, these transgenic animals are capable of generating high affinity antibodies encoded by somatically hypermutated VH genes and essentially non-mutated VL genes encoded by the transgene.

In another aspect, provided is a process for the production of a transgenic non-human animal capable of the production of hybrid antibodies in response to antigenic challenge, comprising functionally disrupting the endogenous immunoglobulin light chain locus and inserting into the animal genome a transgene construct of the invention.

Included is the use of animals obtainable by this process in the production of B cells that produce immunoglobulin having human VL light chain. In another aspect of the invention there is provided a process for the production of B cells that produce immunoglobulin having human VL and binding to a selected antigen, comprising challenging an animal obtainable by a process as above with the antigen and screening for B cells from the animal that bind the antigen. Further included is B cells obtainable by this process and hybridomas obtainable by immortalizing such B cells, e.g., hybridomas obtained by fusing B cells as above with myeloma cells. Also included is a process for producing monoclonal antibody comprising cultivating such a hybridoma. In yet a further aspect, provided is the use of the above B cells in producing a hybridoma or corresponding monoclonal antibody.

Described herein is a process for the production of immunoglobulin having human VL chain and binding to a selected antigen, comprising challenging an animal obtainable as above with the antigen and obtaining immunoglobulin there from.

In one strategy, as an individual step, a rearranged VL region encoded by human germline V and J gene segments and a light chain constant region of any animal species but preferably a murine constant region is introduced into the mouse germ line. The transgene DNA may be introduced into the pronuclei of fertilized oocytes or embryonic stem cells. The integration may be random or homologous depending on the particular strategy to be employed. For example, the VL transgene may be introduced by random insertion, resulting in mice that bear one or multiple copies of the transgene in the genome. Alternatively, the human VL transgene may be targeted to a specific genomic locus using site-specific recombination as described in the art.

In certain embodiments, the VL transgene is targeted to the murine ROSA26 locus which is a suitable integration site allowing strong and predictable expression of inserted transgenes (European Patent Office document EP 1,439,234 A1, the contents of which are incorporated herein by this reference). The targeting vector allows insertion of a single copy of a gene expression cassette, thus avoiding modulation of transgene expression by the arrangement of multiple copies. By choosing the autosomal Rosa26 locus as insertion site, the expression pattern of the inserted transgene in the non-human animal is predictable. Furthermore, random X inactivation and/or modulation by chromosomal position effects are avoided. This also eliminates the need to generate and analyze multiple transgenic strains for any given transgene. Finally, the Rosa26 targeting vector for the site-specific integration can be used for multiple gene expression cassettes. Thus, it may be envisaged that two or more different rearranged germline human VL regions are inserted into the Rosa26 locus to further increase the diversity of the repertoire of hybrid or human antibodies.

In another embodiment, a rearranged human VL region may be targeted to the murine Ig kappa or lambda light chain locus so as to functionally inactivate the endogenous locus or mice containing the rearranged human VL region may be bred with mice that lack functional kappa or lambda Ig loci or both. Thus, by using transformation, using repetitive steps or in combination with breeding, transgenic animals may be obtained which are able to produce antibodies harboring the human VL transgene in the substantial absence of endogenous host immunoglobulin light chains.

In one embodiment, a human VL transgene is selected for its capacity to pair with a substantial portion of murine VH regions to form a diverse repertoire of functional mouse-human hybrid antibodies expressed on the surface of B cells. By a substantial portion of murine VH regions is meant that the human VL pairs with at least with 0.1% of the murine VH regions generated during B cell development, more preferably with at least 1% and most preferably with at least 10%. Methods to identify human VL genes with this characteristic include randomly pairing a repertoire of human VL regions with a repertoire of murine VH regions, co-expression of VH and VL regions in appropriate eukaryotic or prokaryotic expression vectors and screening for human VL regions that pair with a substantial portion of murine VH regions. In one embodiment, phagemid vectors may be used to direct expression of mouse-human antibody fragments in bacterial cells or to the surface of filamentous phage and analysis of binding capacity of antibody fragments by methods known in the art.

In another embodiment, a human VL transgene is selected for its capacity to pair with a substantial portion of human VH regions to form a diverse repertoire of human antibodies expressed on the surface of B cells. By a substantial portion of human VH regions is meant that the human VL pairs with at least with 0.1% of the human VH regions generated during B cell development, more preferably with at least 1% and most preferably with at least 10%.

In the latter embodiment, the human VL transgenic mice are crossed with mice that harbor functional rearranged or non-rearranged human H chain immunoglobulin loci and functionally inactivated endogenous H chain Ig loci as described in the art. The functional inactivation of the two copies of each of the three host Ig loci (heavy chain, kappa and lambda light chain), where the host contains the human IgH and the rearranged human VL transgene would allow for the production of purely human antibody molecules without the production of host or host human chimeric antibodies. Such a host strain, by immunization with specific antigens, would respond by the production of mouse B-cells producing specific human antibodies, which B-cells are subsequently fused with mouse myeloma cells or are immortalized in any other manner for the continuous stable production of human monoclonal antibodies. Alternatively, the population of B cells is used as a source of VH regions that can be obtained by constructing cDNA libraries or by PCR amplification using primers for human VH regions as is known in the art.

A human rearranged VL gene is reconstructed in an appropriate eukaryotic or prokaryotic microorganism and the resulting DNA fragments can be introduced into pronuclei of fertilized mouse oocytes or embryonic stem cells. Various constructs that direct B cell specific expression of VL transgenes have been described in the art and have the following general format: a leader sequence and relevant upstream sequences to direct B cell specific expression of the transgene, a coding sequence of a human VL transgene, an enhancer sequence that directs B cell specific and high level expression of the transgene and a murine constant region gene. In a preferred format, the enhancer is the C-kappa 3' enhancer because it directs high level expression in B-lineage cells, but does not recruit somatic hypermutation when used in transgene constructs.

In one embodiment, animals, preferably mice, comprising one or multiple copies of the transgene in the genome are isolated and analyzed for stable expression. Animals are selected that show stable expression of the transgene over longer periods of time, preferably in B-cells. If required, different animal lines comprising independent insertions of one or multiple copies of the transgene, preferably on different chromosomes, are crossed to obtain animals with different insertions of one or multiple copies of the transgene to increase expression of the transgene in animals, preferably in B-cells.

Further provided is progeny of a transgenic non-human animal described herein, the progeny comprising, at least in its B-cell lineage, a heavy- or light chain encoding sequence together with a means that renders the sequence resistant to DNA rearrangements and/or somatic hypermutations.

Further provided is progeny of a transgenic non-human animal described herein, the progeny comprising an expression cassette for the expression of a desired proteinaceous molecule in cells during a certain stage of development in cells developing into mature B cells.

In addition, provided is a cell that is isolated from a transgenic non-human animal described herein, the cell comprising a heavy- or light chain encoding sequence together with a means that renders the sequence resistant to DNA rearrangements and/or somatic hypermutations. In addition, provided is a cell that is isolated from a transgenic non-human animal described herein, the cell comprising an expression cassette for the expression of a desired proteinaceous molecule in cells during a certain stage of development in cells developing into mature B cells. A cell described herein, preferably an antibody-producing B-cell or a cell that is capable of differentiating or maturating into an antibody-producing B-cell, can be used for in vitro production of antibodies, as is known to the skilled person, for example, from Gascan et al. 1991, *J. Exp. Med.* 173:747-750. Methods for immortalization of a cell described herein are known in the art and include the generation of hybridomas, for example, by fusion with a myeloma cell, transformation with Epstein Barr Virus; expression of the signal transducer of activation and transcription (STAT), activation via CD40 and IL4 receptor signaling, and/or expression of Bcl6 (Shvarts et al. 2002, *Genes Dev.* 16: 681-686).

In a separate step, the mouse endogenous Kappa and Lambda light chain loci are rendered essentially non-functional such that at least the majority of B cells in the transgenic mice bear Ig receptors that contain the transgenic human VL region. Inactivation of the endogenous mouse immunoglobulin loci is achieved by targeted disruption of the appropriate loci by homologous recombination in mouse embryonic stem cells. The targeted disruption comprises alteration of the genomic sequence such that substantially no functional endogenous mouse immunoglobulin Kappa and/or Lambda light chain is produced. The term "substantially no functional endogenous mouse immunoglobulin" indicates that the endogenous Kappa and/or Lambda light chain loci are functionally silenced such that the level of functional protein expression of the endogenous Kappa and/or Lambda light chain loci, preferably the endogenous Kappa light chain locus, is reduced to about 20% of the level of expression in a reference mouse, more preferred to about 10%, more preferred to about 5%, more preferred to about 2% and more preferred to about 1%. In a most preferred embodiment, the level of functional protein expression of the endogenous Kappa and/or Lambda light chain loci is reduced to 0%. The level of functional protein expression can be determined by means known to the skilled person, including western blotting and pairing with a mouse heavy chain. The reference mouse is a mouse in which the endogenous Kappa and/or Lambda light chain loci is not disrupted. The alteration comprises mutation and/or deletion of gene sequences that are required for functional expression of the endogenous immunoglobulin genes. Alternatively, the alteration comprises insertion of a nucleic acid into the endogenous mouse immunoglobulin Kappa and/or Lambda light chain loci such that the functional expression of the endogenous immunoglobulin genes is reduced. In one embodiment, the nucleic acid comprises a silencing element resulting in transcriptional silencing of the endogenous immunoglobulin gene. In a further embodiment, or in addition, the nucleic acid comprises a sequence that disrupts splicing and/or translation of the endogenous immunoglobulin gene, for example, by introducing an exon that renders a frame shift in the coding sequence, or that comprises a premature stop codon. In each case chimeric animals are generated which are derived in part from the modified embryonic stem cells and are capable of transmitting the genetic modifications through the germ line. The mating of mouse strains with human immunoglobulin loci to strains with inactivated mouse loci yields animals which produce antibodies comprising essentially only human light chains.

A construct for homologous recombination is prepared by means known in the art and any undesirable sequences are removed, e.g., procaryotic sequences. Any convenient technique for introducing a construct for homologous recombination into a target cell may be employed. These techniques include spheroplast fusion, lipofection, electroporation, calcium phosphate-mediated DNA transfer or direct microinjection. After transformation or transfection of the target cells, target cells are selected by means of positive and/or negative markers, for example, by neomycin resistance and/or acyclovir and/or gancyclovir resistance. Those cells which show the desired phenotype may then be further analyzed by restriction analysis, electrophoresis, Southern analysis, PCR, or the like. By identifying fragments which show the presence of the lesion(s) at the target locus, cells in which homologous recombination has occurred to inactivate a copy of the target locus are identified.

Furthermore, it is shown that upon immunization, the murine and human VH regions in the afore-mentioned transgenic mice but not the VL regions are capable of undergoing somatic hypermutations to generate high affinity antibodies. Advantageously, these antibodies encoded by germline VL regions are predicted to contribute to lower immunogenicity when applied in humans and result in more stable antibodies that are less prone to aggregation and thus safer for therapeutic use in humans.

MAbs derived from the afore-mentioned non-human transgenic animals or cells all share the same identical human VL regions. It has been described that mAbs that share the same identical VL region may be co-expressed in a single clonal cell for the production of mixtures of recombinant antibodies with functional binding sites (see the incorporated WO04106375 and WO05068622). Thus, provided is a platform for the generation of specific and high affinity mAbs that constitute the basis for mixtures of mAbs produced by clonal cells.

It is preferred that mAbs derived from the afore-mentioned non-human transgenic animals or cells are directed against cellular targets. Preferred targets are human surface-expressed or soluble proteins or carbohydrate molecules. Further preferred targets are surface-expressed proteins or carbohydrate molecules that are expressed on the surface of bacteria, viruses, and other pathogens, especially of humans.

More specifically, preferred targets include cytokines and chemokines, including but not limited to InterLeukin 1beta (IL1beta), IL2, IL4, IL5, IL7, IL8, IL12, IL13, IL15, IL18, IL21, IL23 and chemokines such as, for example, CXC chemokines, CC chemokines, C chemokines (or γ chemokines) such as XCL1 (lymphotactin-α) and XCL2 (lymphotactin-β), and CX3C chemokines. Further included as preferred targets are receptor molecules of the cytokines and chemokines, including type I cytokine receptors such as, for example, the IL-2 receptor, type II cytokine receptors such as, for example, interferon receptors, immunoglobulin (Ig) superfamily receptors, tumor necrosis factor receptor family including receptors for CD40, CD27 and CD30, serine/threonine-protein kinase receptors such as TGF beta receptors, G-protein coupled receptors such as CXCR1-CXCR7, and tyrosine kinase receptors such as fibroblast growth factor receptor (FGFR) family members, EGF receptor family members including erbB1 (EGF-R; HER1), erbB2, (HER2), erbB3 (HER3), and erbB4 (HER4), insulin receptor family members including IGF-R1 and IGF-RII, PDGF receptor family members, Hepatocyte growth factor receptor family members including c-Met (HGF-R), Trk receptor family members, AXL receptor family members, LTK receptor family members, TIE receptor family members, ROR receptor family members, DDR receptor family members, KLG receptor family members, RYK receptor family members, MuSK receptor family members, and vascular endothelial growth factor receptor (VEGFR) family members.

Further preferred targets are targets that are over-expressed or selectively expressed in tumors such as, for example, VEGF, CD20, CD38, CD33, CEA, EpCAM, PSMA, CD54, Lewis Y, CD52, CD40, CD22, CD51/CD61, CD74, MUC-1, CD38, CD19, CD262 (TRAIL-R2), RANKL, CTLA4, and CD30; targets that are involved in chronic inflammation such as, for example, CD25, CD11a, TNF, CD4, CD80, CD23, CD3, CD14, IFNgamma, CD40L, CD50, CD122, TGFbeta and TGFalpha.

Preferred surface-expressed proteins or carbohydrate molecules that are expressed on the surface of bacteria, viruses, and other parasitic pathogens, especially of humans, include surface markers of influenza A and B viruses such as hemagglutinin (HA) and neuraminidase (NA), filoviruses such as Ebola virus, rabies, measles, rubella, mumps, flaviviruses such as Dengue virus types 1-4, tick-borne encephalitis virus, West Nile virus, Japanese encephalitis virus, and Yellow fever virus, Paramyxoviruses including Paramyxovirus such as Parainfluenza 1, 3, Rubulavirus such as Mumpsvirus and Parainfluenza 2, 4, Morbillivirus, and Pneumovirus such as Respiratory syncytial virus, Vaccinia, small pox, coronaviruses, including Severe Acute Respiratory Syndrome (SARS) virus, hepatitis virus A, B and C, Human Immunodeficiency Virus, Herpes viruses, including cytomegalovirus, Epstein Barr virus, Herpes simplex virus, and Varicella zoster virus, parvoviruses such as, for example, B19; *Legionella pneumophila; Listeria monocytogenes; Campylobacter jejuni; Staphylococcus aureus; E. coli* O157:H7; *Borrelia burgdorferi; Helicobacter pylori; Ehrlichia chaffeensis; Clostridium difficile; Vibrio cholera; Salmonella enterica* Serotype *Typhimurium; Bartonella henselae; Streptococcus pyogenes* (Group A Strep); *Streptococcus agalactiae* (Group B Strep); Multiple drug resistant *S. aureus* (e.g., MRSA); *Chlamydia pneumoniae; Clostridium botulinum; Vibrio vulnificus*; Parachlamydia pneumonia; *Corynebacterium amycolatum; Klebsiella pneumonia*; Linezolid-resistant enterococci (*E. faecalis* and *E. faecium*); and Multiple drug resistant *Acinetobacter baumannii*.

Most preferred targets are IL-6 and its receptor, IL-6Ralpha, glycoprotein-denominated gp130, RSV, especially the surface proteins F, G and SH and non-structural proteins such as N and M, and receptor tyrosine kinases, in particular erbB1 (EGF-R; HER1), erbB2, (HER2), erbB3 (HER3), erbB4 (HER4), IGF-R1 and IGF-RII, c-Met (HGF-R).

Therefore, provided is a platform for the generation of specific and high affinity mAbs against the above mentioned targets that constitute the basis for mixtures of mAbs produced by clonal cells. In certain embodiments, the specific and high affinity mAbs comprise mAbs that are directed against different epitopes on at least one of the targets. In a further preferred embodiment, the specific and high affinity mAbs comprise mAbs that are directed against different targets, such as, for example, one or more members of the EGF-receptor family, including erbB1 (EGF-R; HER1), erbB2, (HER2), erbB3 (HER3) and erbB4 (HER4).

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., Sambrook et al., *Molecular Cloning: A Laboratory Manual* (3rd edition, Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 12: Overview of the sequences used or referred to in this application: Human germline IGKV1-39/J DNA (SEQ ID NO:84); human germline IGKV1-39/J Protein (SEQ ID NO:85); human germline IGLV2-14/J DNA (SEQ ID NO:86); human germline IGLV2-14/J Protein (SEQ ID NO:87); Rat IGCK allele a DNA (SEQ ID NO:88); Rat IGCK allele a protein (SEQ ID NO:89); IGKV1-39/J-Ck (SEQ ID NO:90); IGLV2-14/J-Ck (SEQ ID NO:91); VkP-IGKV1-39/J-Ck (SEQ ID NO:92); VkP-IGKV1-39/J-Ck-Δ1 (SEQ ID NO:93); VkP-IGKV1-39/J-Ck-Δ2 (SEQ ID NO:94); VkP-IGLV2-14/J-Ck (SEQ ID NO:95); pSELECT-IGKV1-39/J-Ck (SEQ ID NO:96); pSelect-IGLV2-14/J-Ck (SEQ ID NO:97); MV1043 (SEQ ID NO:98); and MV1057 (SEQ ID NO:99).

FIGS. 13A-C: Generation of Rosa26-IgVk1-39 KI allele. FIG. 13A Schematic drawing of the pCAGGS-IgVK1-39 targeting vector. FIG. 13B Nucleotide sequence of the pCAGGS-IgVK1-39 targeting vector (SEQ ID NO:100). FIG. 13C Targeting strategy.

FIG. 14A Southern blot analysis of genomic DNA of ES clones comprising an insertion of the pCAGGS-IgVK1-39 targeting vector. Genomic DNA of four independent clones was digested with AseI and probed with 5e1 indicating the 5'-border of the targeting vector. All clones comprise a correct insertion of the targeting vector at the 5' end. FIG. 14B Southern blot analysis of genomic DNA of ES clones comprising an insertion of the pCAGGS-IgVK1-39 targeting vector. Genomic DNA of four independent clones was digested with MscI and probed with 3e1 indicating the 3'-border of the targeting vector. All clones comprise a correct insertion of the targeting vector at the 3' end. FIG. 14C Southern blot analysis of genomic DNA of ES clones comprising an insertion of the pCAGGS-IgVK1-39 targeting vector. Genomic DNA of four independent clones was digested with BamHI and probed with an internal Neo probe indicating the 5'-border of the targeting vector. All clones comprise a correct, single insertion of the targeting vector.

FIGS. 15A-C: Generation of Rosa26-IgV12-14 KI allele. FIG. 15A Schematic drawing of the pCAGGS-IgVL2-14 targeting vector. FIG. 15B Nucleotide sequence of the pCAGGS-IgVL2-14 targeting vector containing the CAGGS expression insert (SEQ ID NO:101) based on the rearranged germline IGLV2-14/J V lambda region (IGLV2-14/J-Ck). FIG. 15C Targeting strategy.

FIG. 16: Epibase® profile of IGKV1-39 residues 1-107 (SEQ ID NO:85).

FIG. 18A Targeting strategy. FIG. 18B Schematic drawing of the pIgKappa targeting vector.

FIG. 19A First step of the targeting strategy. FIG. 19B Second step of the targeting strategy.

FIG. 20A pVkP-O12 (VkP-IGKV1-39/J-Ck); FIG. 20B pVkP-O12-del1 (VkP-IGKV1-39/J-Ck-Δ1); FIG. 20C pVkP-O12-del2 (VkP-IGKV1-39/J-Ck-Δ2).

FIG. 21A VkP-O12 (VkP-IGKV1-39/J-Ck); FIG. 21B VkP-O12-del1 (VkP-IGKV1-39/J-Ck-Δ1); FIG. 21C VkP-O12-del2 (VkP-IGKV1-39/J-Ck-Δ2).

FIG. 26A Gating of bone marrow cells. FIG. 26B Histograms of transgene expression with overlay from one WT control.

FIG. 28: Parameters of stability for stable clones containing the germline IGKV1-39 gene.

FIG. 29A-B: Antibody mixtures used for staining of lymphocyte populations. BM=bone marrow, PC=peritoneal cavity, PP=Peyer's patches.

DETAILED DESCRIPTION OF THE INVENTION

Examples

Figure 1:
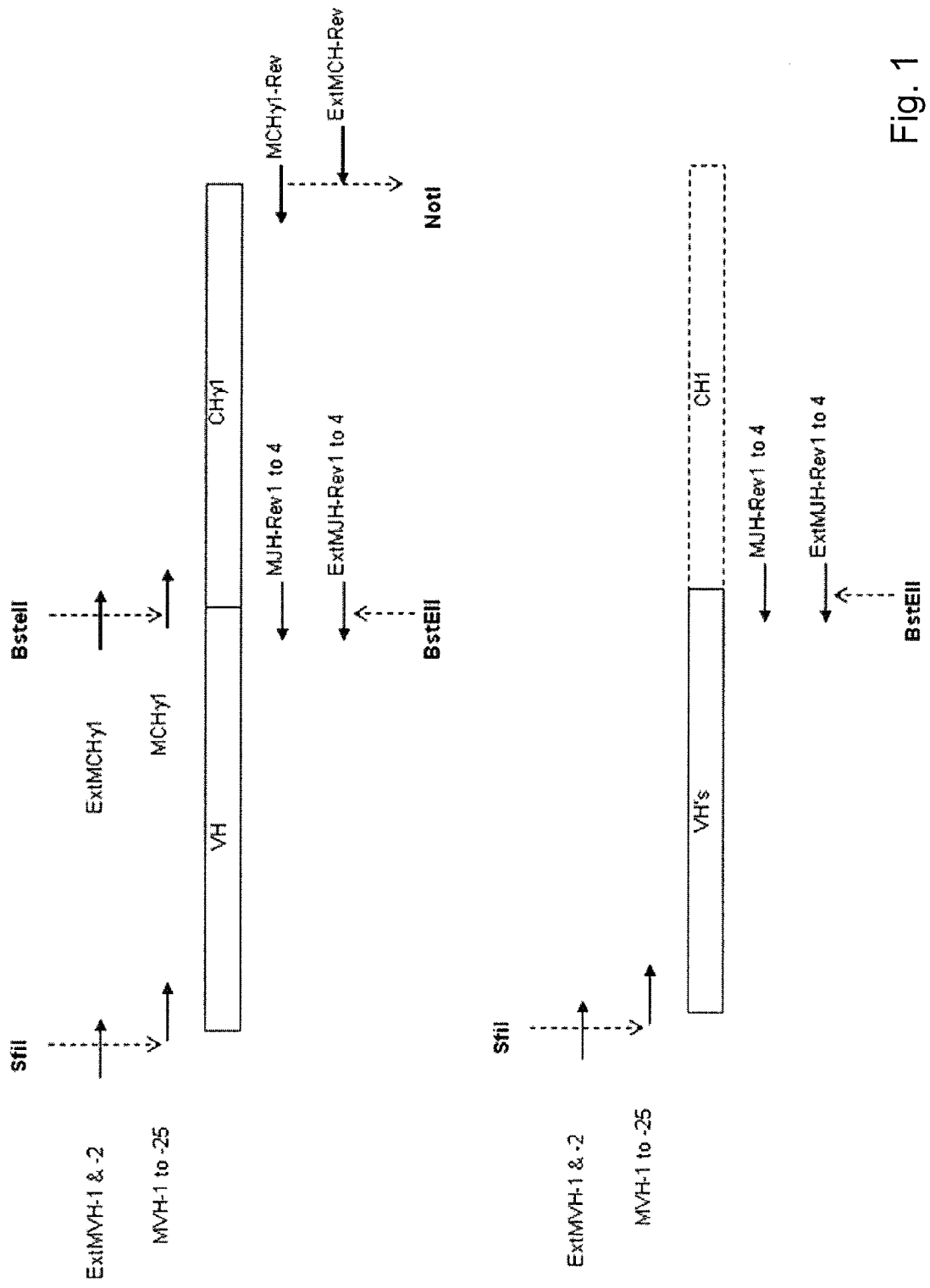
FIG. 1: A topology map of the annealing locations of mouse specific VH primers and the position of required restriction sites that are introduced by overhanging sequences at the 3' end of primers.

Example 1: Human Light Chain V-Gene Clones

This example describes the rationale behind the choice of two human light chain V-genes, one gene of the kappa type and one gene of the lambda type, that are used as a proof of concept for light chain expressing transgenic mice. De Wildt et al. 1999 (de Wildt et al. (1999), *J. Mol. Biol.* 285(3):895) analyzed the expression of human light chains in peripheral IgG-positive B-cells. Based on these data, IGKV1-39 (O12) and IGLV2-14 (2a2) were chosen as light chains as they were well represented in the B-cell repertoire. The J-segment sequence of the light chains has been chosen based upon sequences as presented in GenBank ABA26122 for IGKV1-39 (B. J. Rabquer, S. L. Smithson, A. K. Shriner and M. A. J. Westerink) and GenBank AAF20450 for IGLV2-14 (O. Ignatovich, I. M. Tomlinson, A. V. Popov, M. Bruggemann and G. J. Winter, *J. Mol. Biol.* 294 (2):457-465 (1999)).

All framework segments are converted into germline amino acid sequences to provide the lowest immunogenicity possible in potential clinical applications.

Example 2: Obtaining Mouse Heavy Chain V-Genes that Pair with Human IGKV1-39 Gene Segment to Form Functional Antibody Binding Sites This example describes the identification of mouse heavy chain V-genes that are capable of pairing with a single, rearranged human germline IGKV1-39/J region. A spleen VH repertoire from mice that were immunized with tetanus toxoid was cloned in a phage display Fab vector with a single human IGKV1-39-C kappa light chain and subjected to panning against tetanus toxoid. Clones obtained after a single round of panning were analyzed for their binding specificity. The murine VH genes encoding tetanus toxoid-specific Fab fragments were subjected to sequence analysis to identify unique clones and assign VH, DH and JH utilization.

Many of the protocols described here are standard protocols for the construction of phage display libraries and the panning of phages for binding to an antigen of interest and described in Antibody Phage Display: *Methods and Protocols* (editor(s): Philippa M. O'Brien and Robert Aitken).

Immunizations

BALB/c mice received one immunization with tetanus toxoid and were boosted after six weeks with tetanus toxoid.

Splenocyte Isolation

Preparation of spleen cell suspension. After dissection, the spleen was washed with PBS and transferred to a 60 mm Petri dish with 20 ml PBS. A syringe capped with 20 ml PBS and a G20 needle was used to repeatedly flush the spleen. After washing the flushed cells with PBS, the cells were carefully brought into suspension using 20 ml PBS and left on a bench for five minutes to separate the splenocytes from the debris and cell clusters. The splenocytes suspension was transferred on top of a Ficoll-Paque™ PLUS-filled tube and processed according to the manufacturer's procedures for lymphocyte isolation (Amersham Biosciences).

RNA Isolation and cDNA Synthesis

After isolation and pelleting of lymphocytes, the cells were suspended in TRIzol LS Reagent (Invitrogen) for the isolation of total RNA according to the accompanying manufacturer's protocol and subjected to reverse transcription reaction using 1 microgram of RNA, Superscript III RT in combination with dT20 according to manufacturer's procedures (Invitrogen).

PCR Amplification of cDNA

The cDNA was amplified in a PCR reaction using primer combinations that allow the amplification of approximately 110 different murine V-genes belonging to 15 VH families (Table 1; RefSeq NG_005838; Thiebe et al. 1999, *European Journal of Immunology* 29:2072-2081). In the first round, primer combinations that bind to the 5' end of the V-genes and 3' end of the J regions were used. In the second round, PCR products that were generated with the MJH-Rev2 primer were amplified in order to introduce modifications in the 3' region to enable efficient cloning of the products. In the last round of amplification, all PCR products were amplified using primers that introduce a SfiI restriction site at the 5' end and a BstEII restriction site at the 3' end (sec FIGS. 1 and 2, and Table 1).

Figure 2:
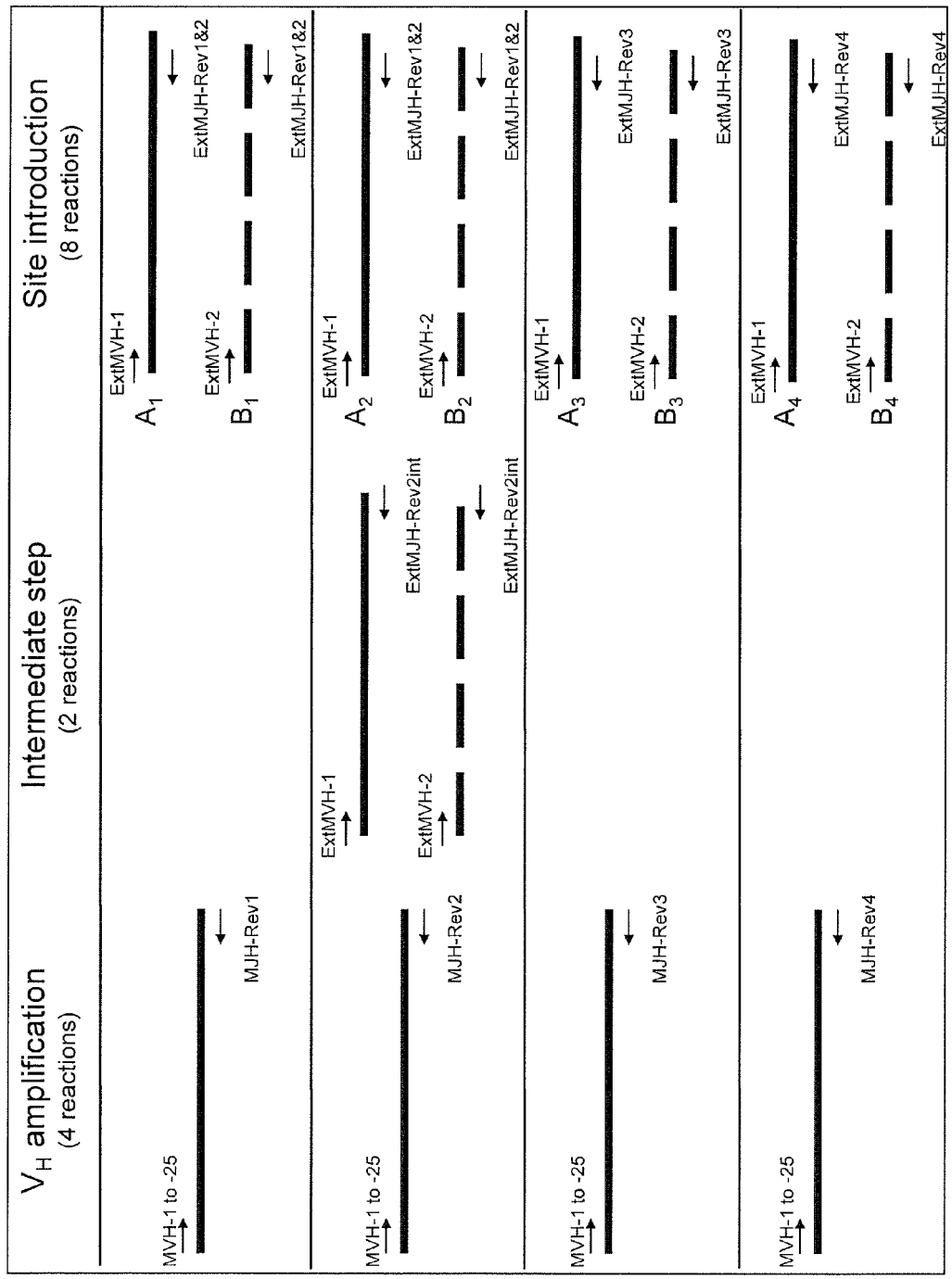
FIG. 2: PCR amplification steps (Amplification, Intermediate and Site introduction). The location and names of the mouse VH amplification primers (and mixtures of primers) are indicated per step.

Reaction conditions for 1st round PCR: four different reactions combining all 25 forward primers (MVH1 to MVH25, Table 1 and FIG. 2) and one reverse primer per reaction (MJH-Rev1, MJH-Rev2, MJH-Rev3 or MJH-Rev4; see Table 1 and FIG. 2). Fifty microliters PCR volumes were composed of 2 microliters cDNA (from RT reactions), 10 microliters 5* Phusion polymerase HF buffer, 40 nM of each of the 25 forward primers (total concentration of 1 micromolar), 1 micromolar reverse primer, 1 microliter 10 mM dNTP stock, 1.25 unit Phusion polymerase and sterile MQ water. The thermocycler program consisted of a touch down program: one cycle 98° C. for 30 seconds, 30 cycles 98° C. for ten seconds, 58° C. decreasing 0.2° C. per cycle ten seconds, 72° C. 20 seconds and one cycle 72° C. for three minutes. The second round PCR program was set up only for the products of the first PCR that contain the MJH-Rev2 primer: two different reactions combining either the ExtMVH-1 or ExtMVH-2 primers (Table 1 and FIG. 2) in combination with the reverse primer ExtMJH-Rev2int (Table 1 and FIG. 2). Fifty microliters PCR volumes were composed of 50 ng PCR product (from first PCR round), 10 microliters 5* Phusion HF buffer, 500 nM of each forward primer, 1 micromolar reverse primer, 1 microliter 10 mM dNTP stock, 1.25 unit Phusion polymerase and sterile MQ water. The thermocycler program consisted of a touch down program followed by a regular amplification step: one cycle 98° C. for 30 seconds, ten cycles 98° C. for ten seconds, 65° C. decreasing 1.5° C. per cycle ten seconds, 72° C. 20 seconds, ten cycles 98° C. for ten seconds, 55° C. ten seconds, 72° C. 20 seconds and one cycle 72° C. for three minutes. The third round PCR program was setup as described in FIG. 2. Fifty microliters PCR volumes were composed of 50 ng PCR product (from earlier PCR rounds, FIG. 2), 10 microliters 5* Phusion polymerase HF buffer, 1 micromolar forward primer (Table 1 and FIG. 2), 1 micromolar reverse primer, 1 microliter 10 mM dNTP stock, 1.25 unit Phusion polymerase and sterile MQ water. The program consists of a touch down program followed by a regular amplification step: one cycle 98° C. for 30 seconds, ten cycles 98° C. for ten seconds, 65° C. decreasing 1.5° C. per cycle ten seconds, 72° C. 20 seconds, ten cycles 98° C. for ten seconds, 55° C. ten seconds, 72° C. 20 seconds and one cycle 72° C. for three minutes. After PCR amplifications, all PCR products were gel purified using Qiaex II according to the manufacturer's protocols.

Restriction Enzyme Digestions

Figure 3:
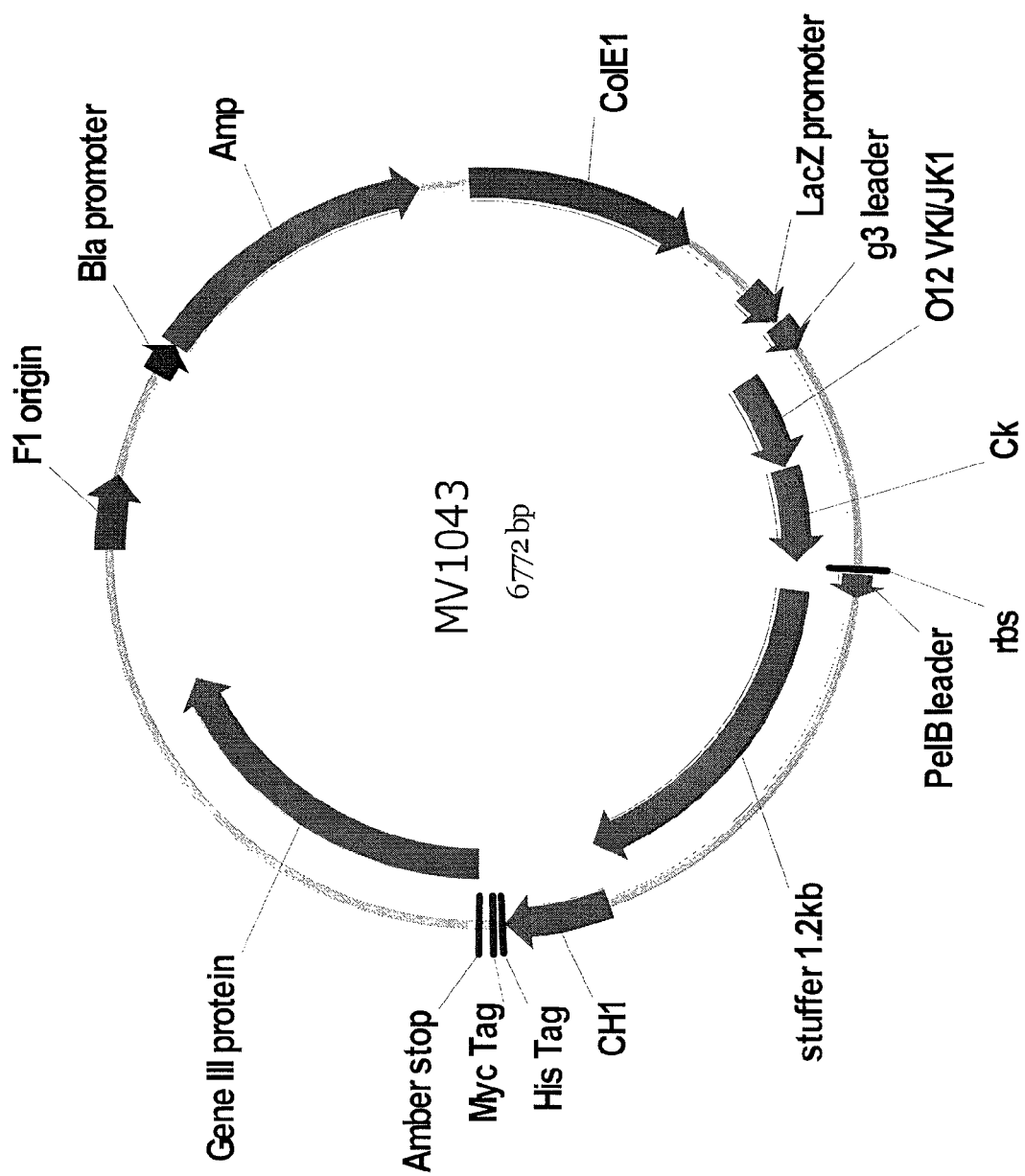
FIG. 3: Topology of the MV1043 vector. This vector is used for the cloning of human or murine VH fragments. O12 (IGKV1-39) is indicated as the VL gene. Products of this vector in combination with helper phages in *E. coli* cells allow the generation of phages that display Fab fragments on the surface of the phage particles as a fusion product to the g3 protein and presence of the vector in the phage as the genetic content (F1 ORI).
Figure 12:
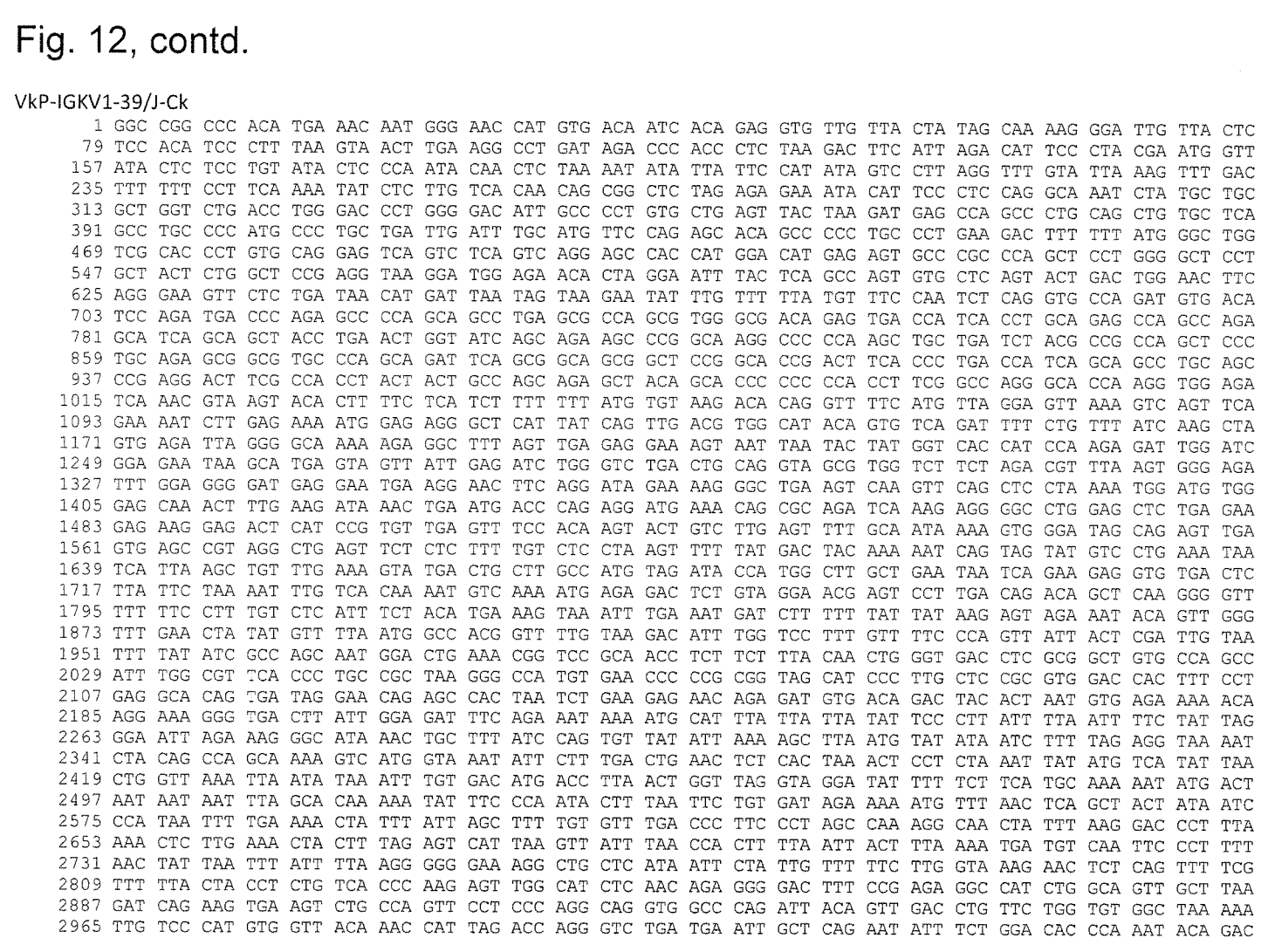
Figure 12:
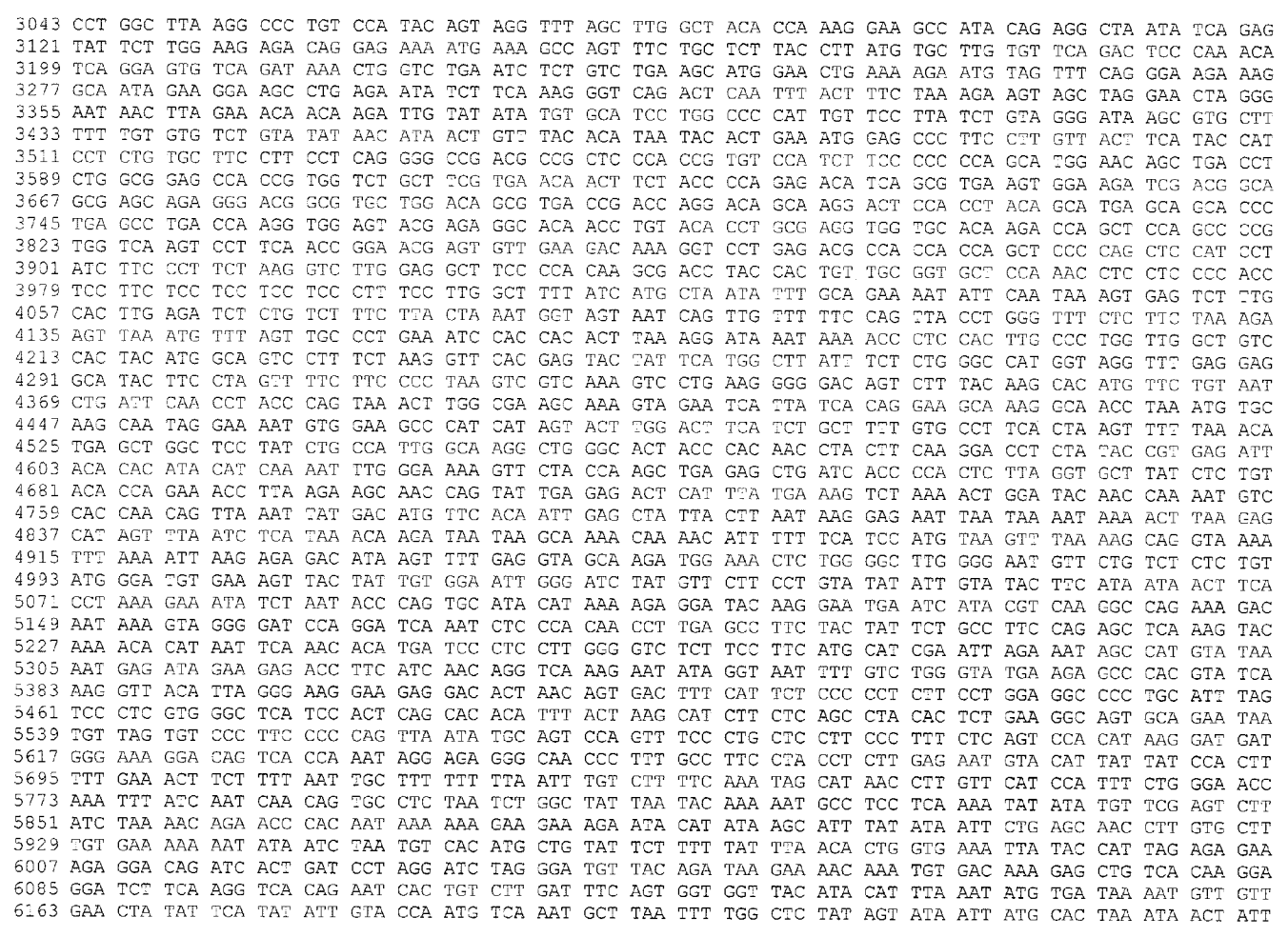
Figure 12:
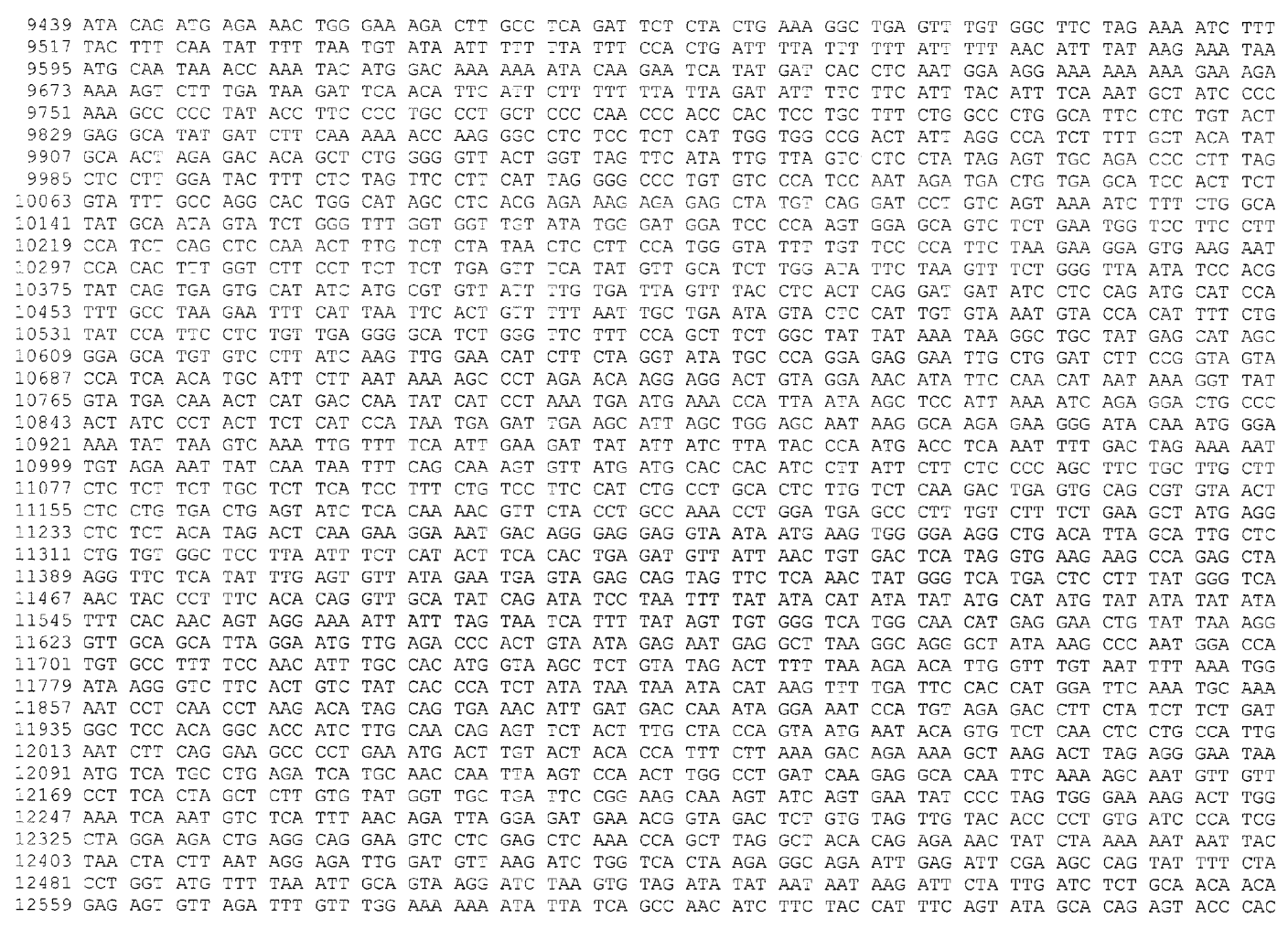
Figure 12:
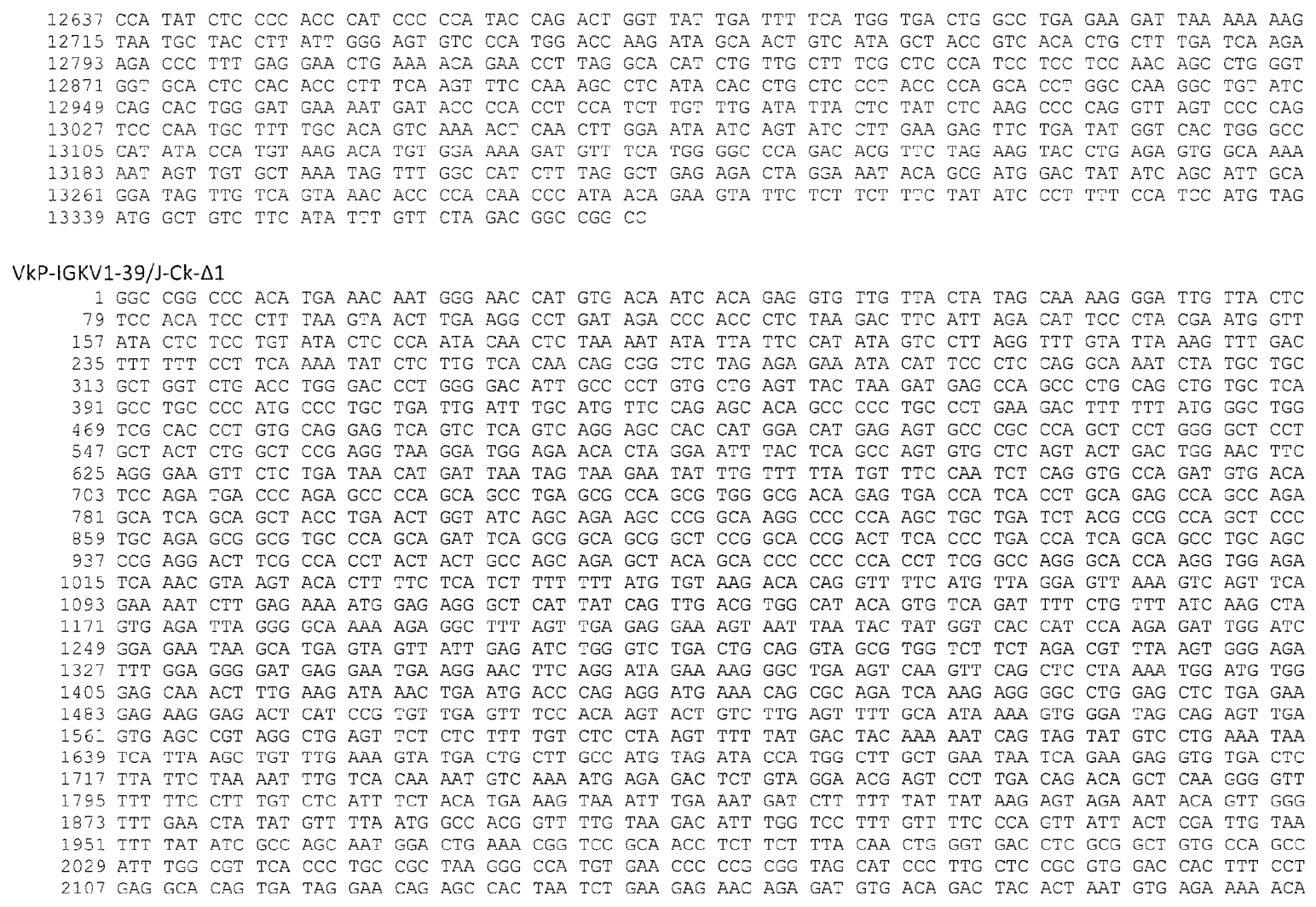
Figure 12:
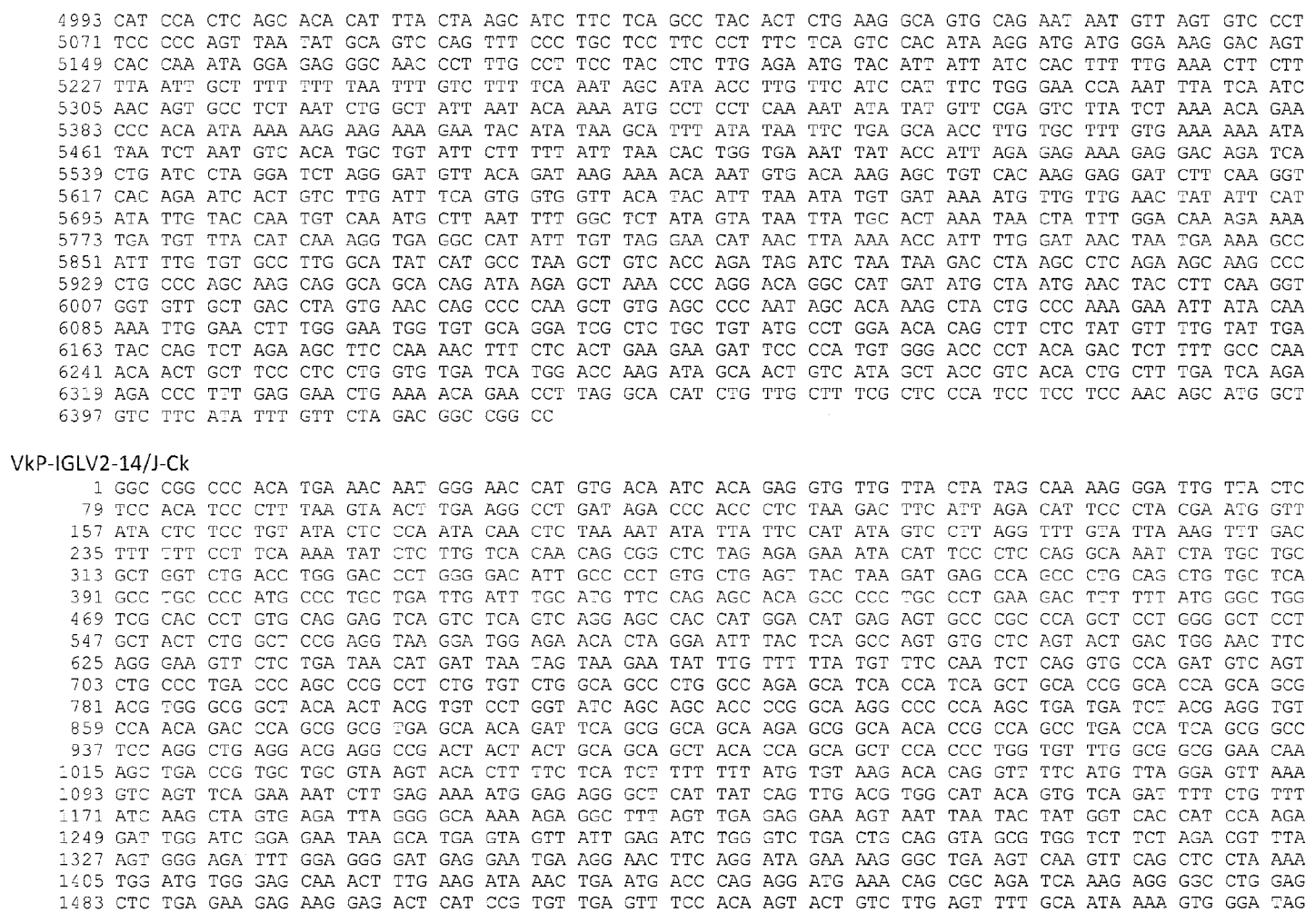
Figure 12:
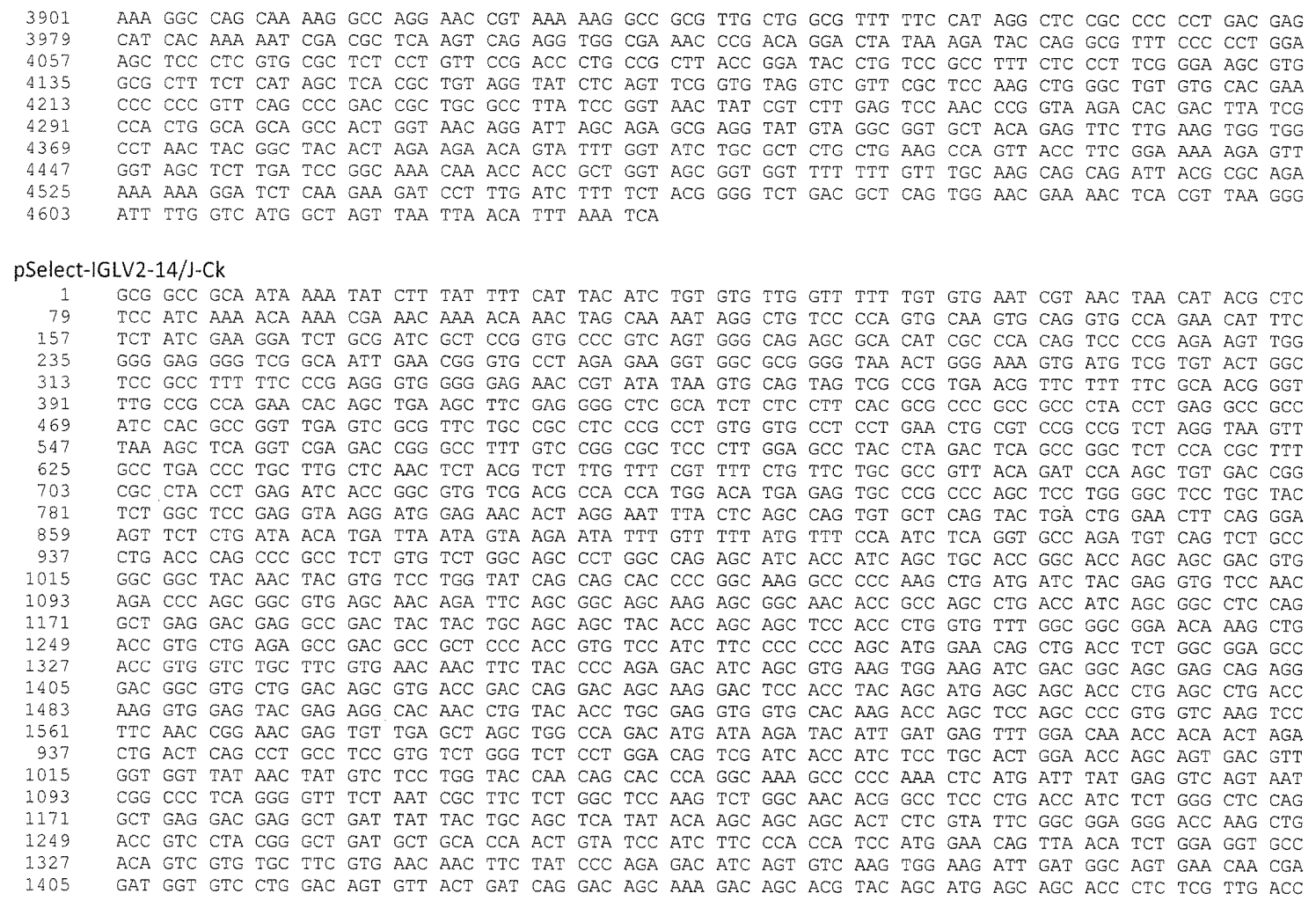
Figure 12:
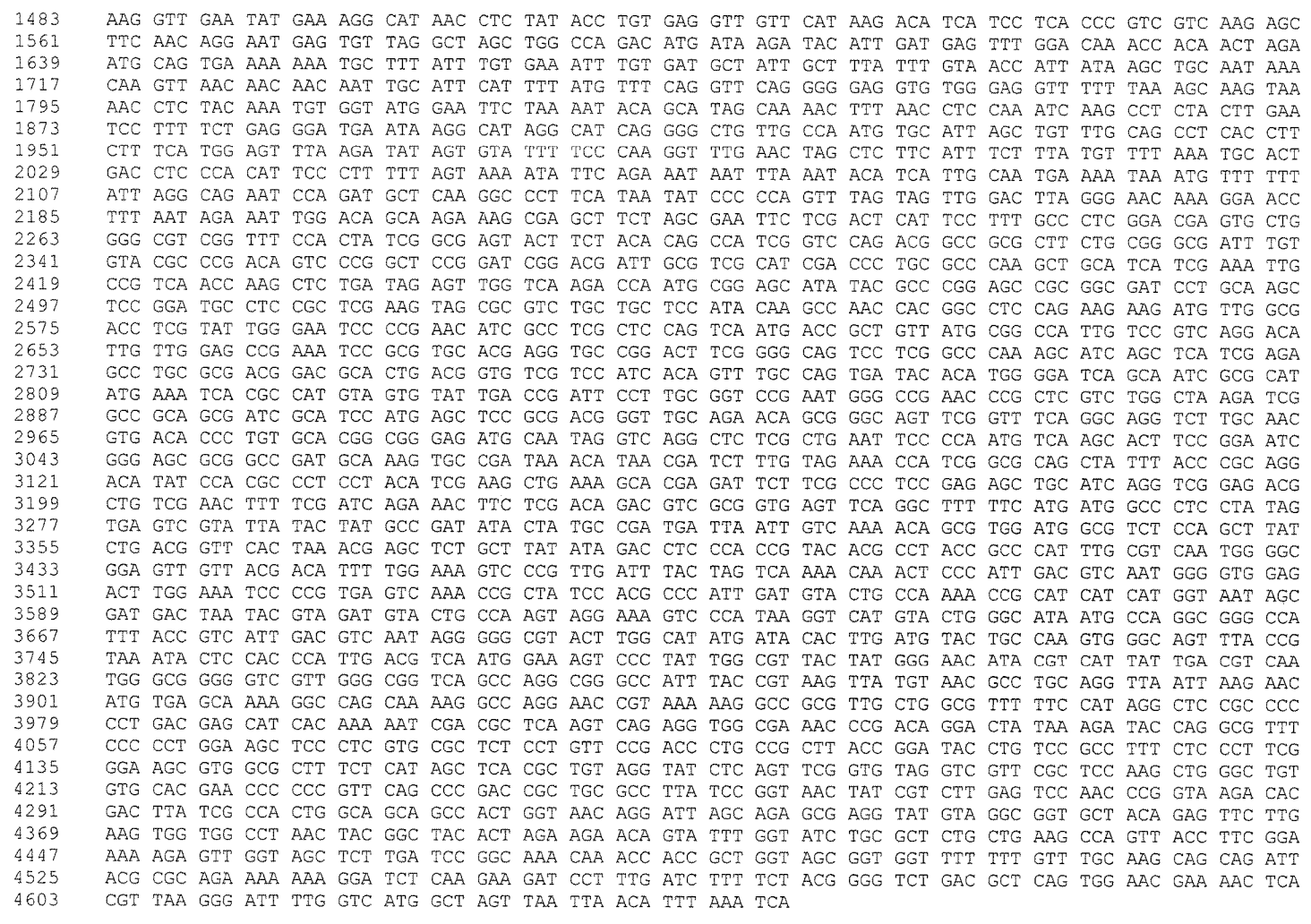
Figure 12:
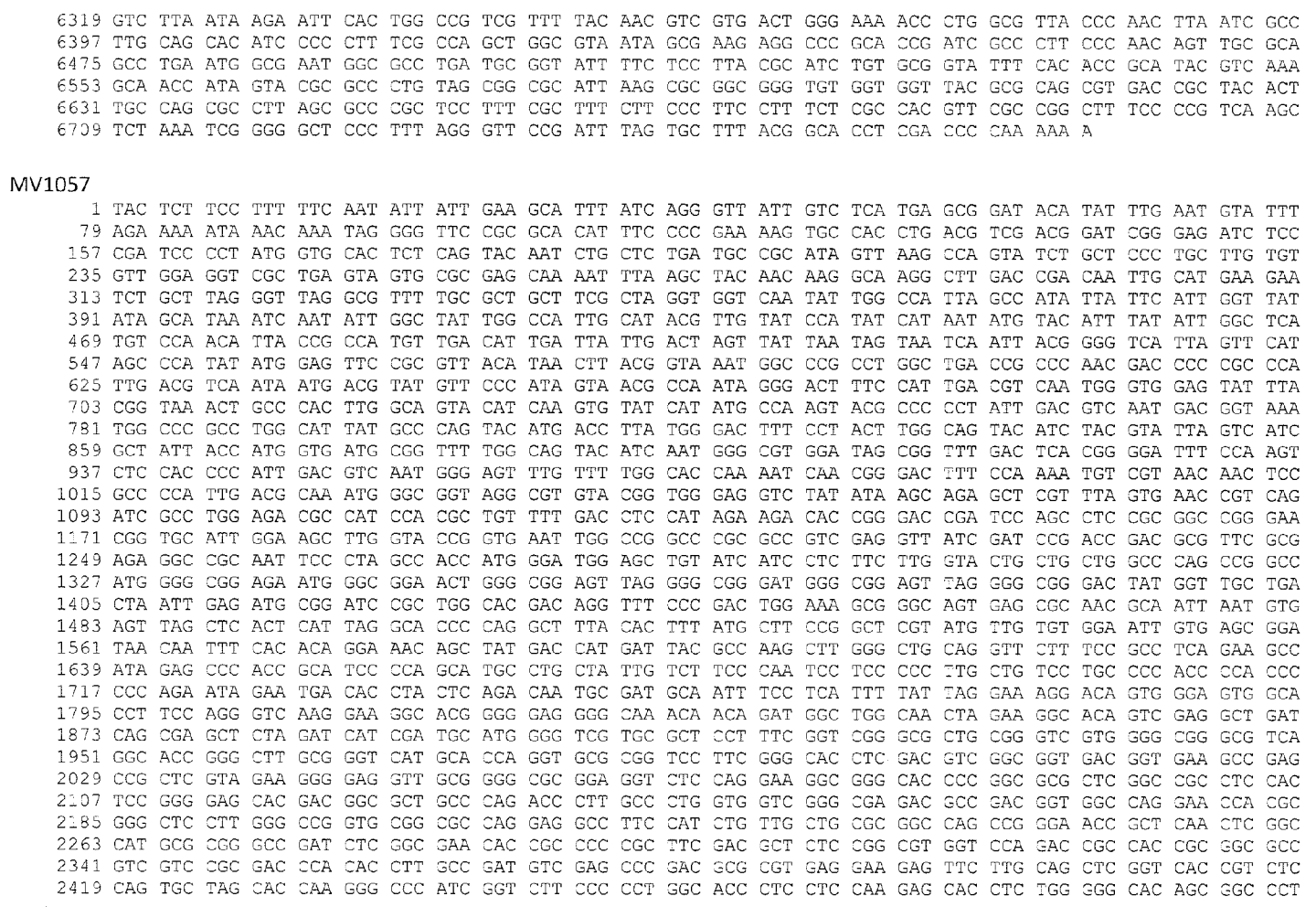
Figure 12:
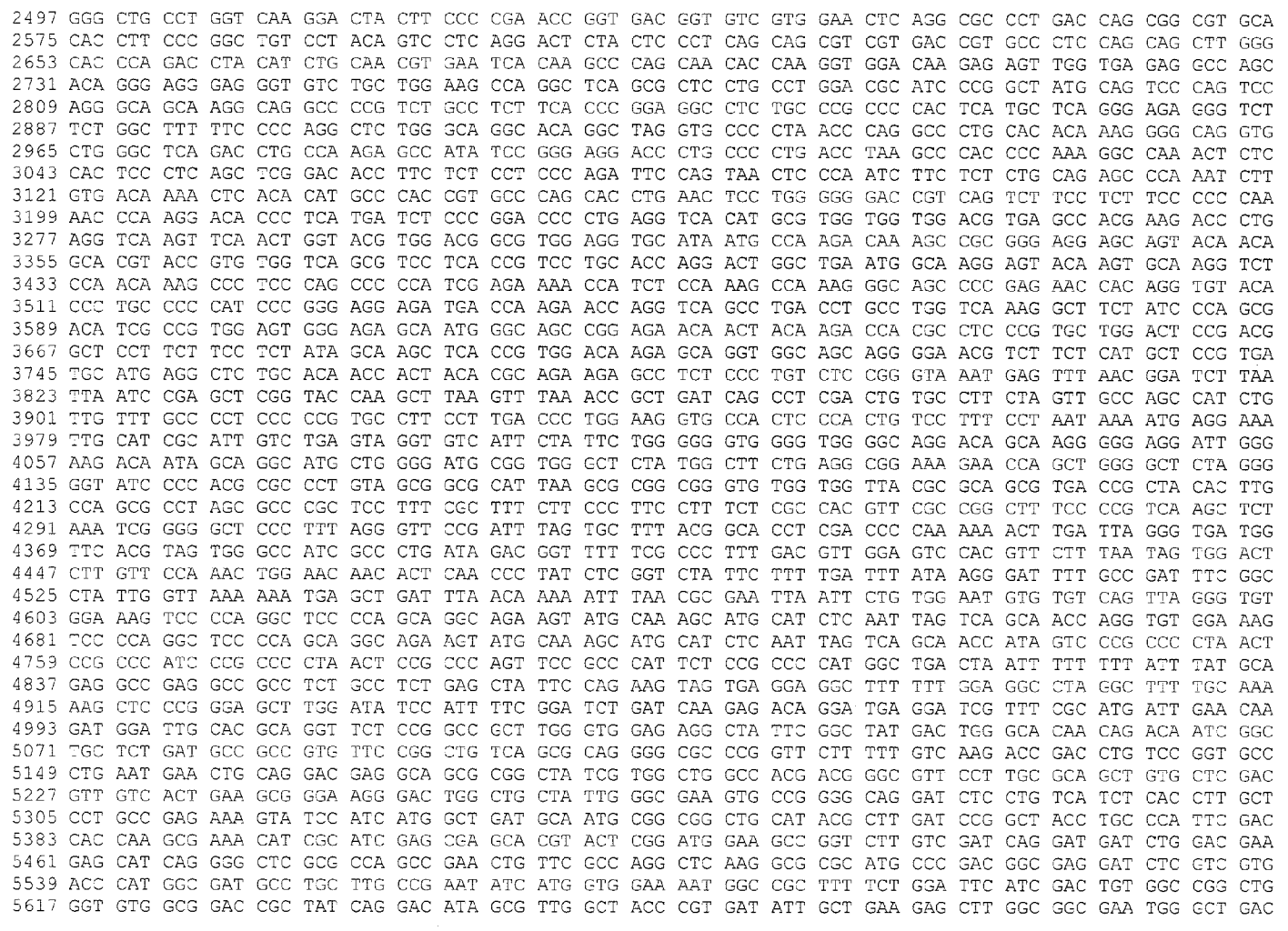
Figure 12:
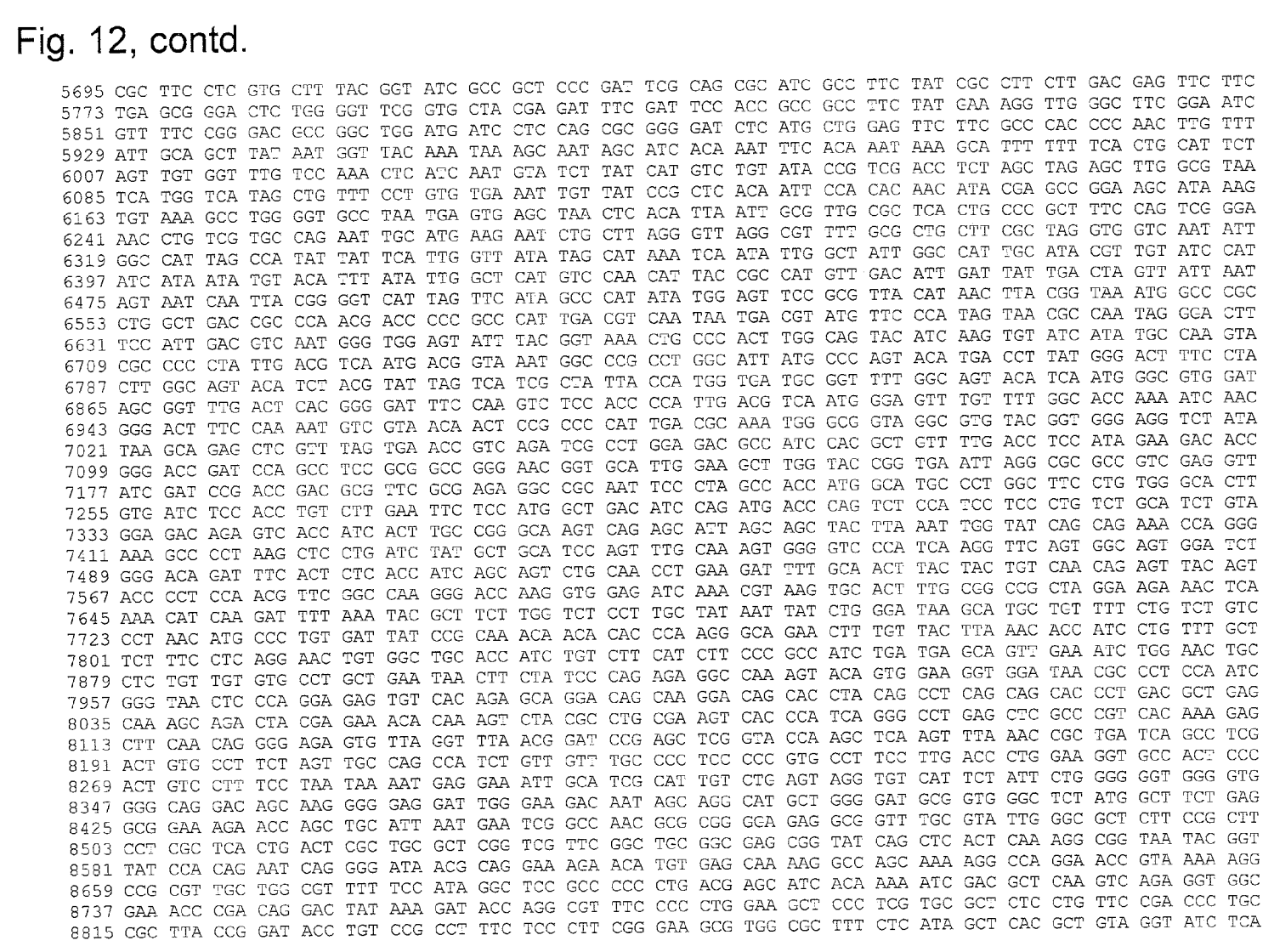

Purified products were digested with BstEII and SfiI in two steps. First 1 microgram of DNA was digested in 100 microliters reactions consisting of 10 microliters of 10* NEB buffer 3 (New England Biolabs), 1 microliter 100* BSA, 12.5 unit BstEII and sterile water for six hours at 60° C. in a stove. The products were purified using Qiaquick PCR Purification kit from Qiagen according to the manual instructions and eluted in 40 microliters water. Next all products were further digested with SfiI in 100 microliters reactions consisting of 10 microliters of 10* NEB buffer 2 (New England Biolabs), 1 microliter 100* BSA, 12.5 unit SfiI and sterile water for 12 hours at 50° C. in a stove. The digested fragments were purified by Qiaquick Gel Extraction kit following gel separation on a 20 cm 1.5% agarose TBE plus ethidium bromide gel at 80 V. 100 micrograms of the acceptor vector (MV1043, FIGS. 3 and 12) was digested with 50 units Eco91I in 600 microliters under standard conditions (Tango buffer) and next purified on a 0.9% agarose gel. After a second digestion step under prescribed conditions with 400 units SfiI in 500 microliters for 12 hours, 100 units BsrGI were added for three hours at 50° C.

Ligations

Each PCR product was ligated separately according to the following scheme: 70 ng digested PCR products, 300 ng digested acceptor vector, 100 units T4 Ligase (NEB), 1* ligase buffer in 30 microliters for 16 hours at 12° C. The ligation reactions were purified with phenol/chloroform/isoamyl alcohol extractions followed by glycogen precipitations (Sigma Aldrich #G1767) according to the manufacturer's protocol and finally dissolved in 25 microliters sterile water.

Transformations and Library Storage

The purified ligation products were transformed by electroporation using 1200 microliters TG1 electrocompetent bacteria (Stratagene #200123) per ligation batch and plated on LB carbenicillin plates containing 4% glucose. Libraries were harvested by scraping the bacteria in 50 ml LB carbenicillin. After centrifugation at 2000 g for 20 minutes at 4° C., the bacterial pellets were resuspended carefully in 2 ml ice cold 2*TY/30% glycerol on ice water and frozen on dry ice/ethanol before storage at −80° C.

Library Amplification

Libraries were grown and harvested according to procedures as described by Kramer et al. 2003 (Kramer et al. 2003, *Nucleic Acids Res.* 31(11):e59) using VCSM13 (Stratagene) as helper phage strain.

Selection of Phages on Coated Immunotubes

Tetanus toxoid was dissolved in PBS in a concentration of 2 μg/ml and coated to MAXISORP™-20 Nunc-Immuno Tube (Nunc 444474) overnight at 4° C. After discarding the coating solution, the tubes were blocked with 2% skim milk (ELK) in PBS (blocking buffer) for one hour at RT. In parallel, 0.5 ml of the phage library was mixed with 1 ml blocking buffer and incubated for 20 minutes at room temperature. After blocking the phages, the phage solution was added to the tetanus toxoid-coated tubes and incubated for two hours at RT on a slowly rotating platform to allow binding. Next, the tubes were washed ten times with PBS/0.05% TWEEN™-20 detergent followed by phage elution by an incubation with 1 ml 50 mM glycine-HCl pH 2.2 ten minutes at RT on rotating wheel and directly followed by neutralization of the harvested eluent with 0.5 ml 1 M Tris-HCl pH 7.5.

Harvesting Phage Clones

Five ml XL1-Blue MRF (Stratagene) culture at O.D. 0.4 was added to the harvested phage solution and incubated for 30 minutes at 37° C. without shaking to allow infection of the phages. Bacteria were plated on Carbenicillin/Tetracycline 4% glucose 2*TY plates and grown overnight at 37° C.

Phage Production

Phages were grown and processed as described by Kramer et al. 2003 (Kramer et al. 2003, *Nucleic Acids Res.* 31(11):e59) using VCSM13 as helper phage strain.

Phage ELISA

ELISA plates were coated with 100 microliters tetanus toxoid per well at a concentration of 2 micrograms/ml in PBS overnight at 4° C. Plates coated with 100 microliters thyroglobulin at a concentration of 2 micrograms/ml in PBS were used as a negative control. Wells were emptied, dried by tapping on a paper towel, filled completely with PBS-4% skimmed milk (ELK) and incubated for one hour at room temperature to block the wells. After discarding the block solution, phage minipreps pre-mixed with 50 μl blocking solution were added and incubated for one hour at RT. Next five washing steps with PBS-0.05% Tween-20 removed unbound phages. Bound phages were detected by incubating the wells with 100 microliters anti-M13-HRP antibody conjugate (diluted 1/5000 in blocking buffer) for one hour at room temperature. Free antibody was removed by repeating the washing steps as described above, followed by TMB substrate incubation until color development was visible. The reaction was stopped by adding 100 microliters of 2 M $H_2SO_4$ per well and analyzed on an ELISA reader at 450 nm emission wavelength (Table 2). Higher numbers indicate stronger signals and thus higher incidence of specific binding of the phage-Fab complex.

Sequencing

Clones that gave signals at least three times above the background signal (Table 2) were propagated, used for DNA miniprep procedures (see procedures Qiagen miniPrep manual) and subjected to nucleotide sequence analysis. Sequencing was performed according to the Big Dye 1.1 kit accompanying manual (Applied Biosystems) using a reverse primer (CH1_Rev1, Table 1) recognizing a 5' sequence of the CH1 region of the human IgG1 heavy chain (present in the Fab display vector MV1043, FIGS. 3 and 12). Mouse VH sequences of 28 tetanus toxoid binding clones are depicted in Table 3. The results show that the selected murine VH genes belong to different gene families, and different individual members from these gene families are able to pair with the rearranged human IGKV1-39/J VH region to form functional tetanus toxoid-specific antibody binding sites. From the sequence analyses, it was concluded that the murine VH regions utilize a diversity of DH and JH gene segments.

Example 3: Silencing of the Mouse Kappa Light Chain Locus

This example describes the silencing of the mouse endogenous kappa light chain locus. The endogenous kappa locus is modified by homologous recombination in ES cells, followed by the introduction of genetically modified ES cells in mouse embryos to obtain genetically adapted offspring.

Figure 4:
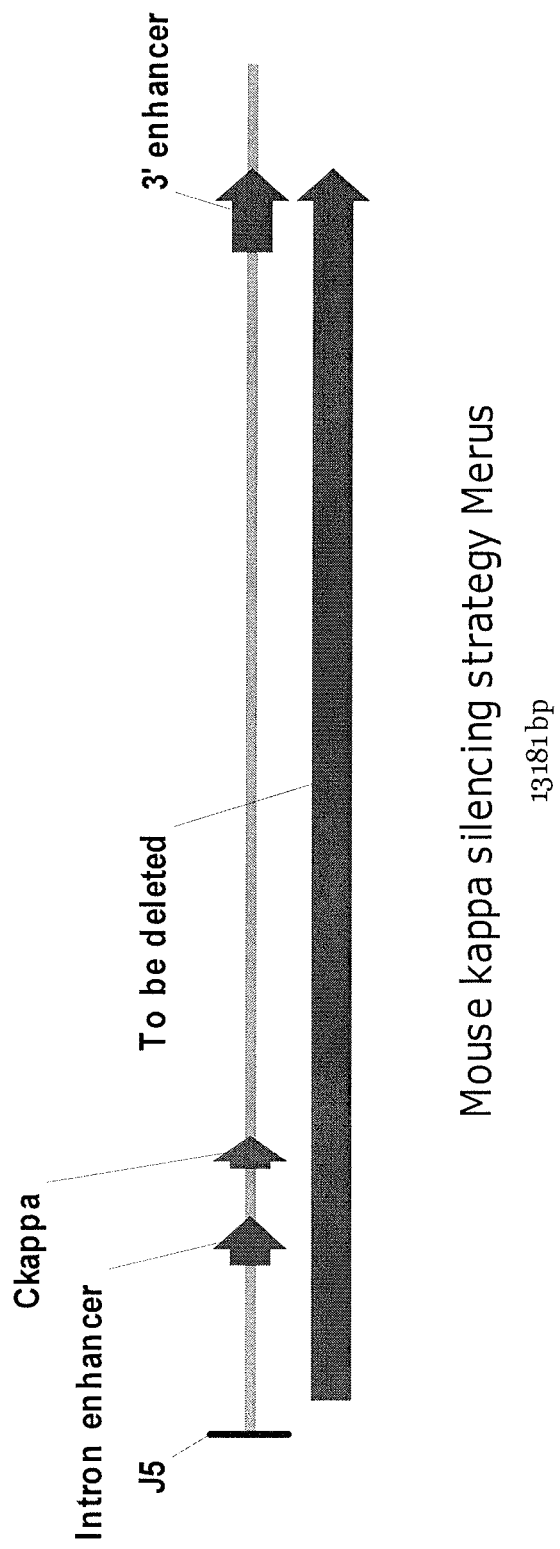
FIG. 4: The topology of the mouse Ckappa locus downstream of the J-segments. Both enhancers and Ckappa region are indicated. The lower arrow indicates the region that is removed in order to silence the locus.
Figure 18A:
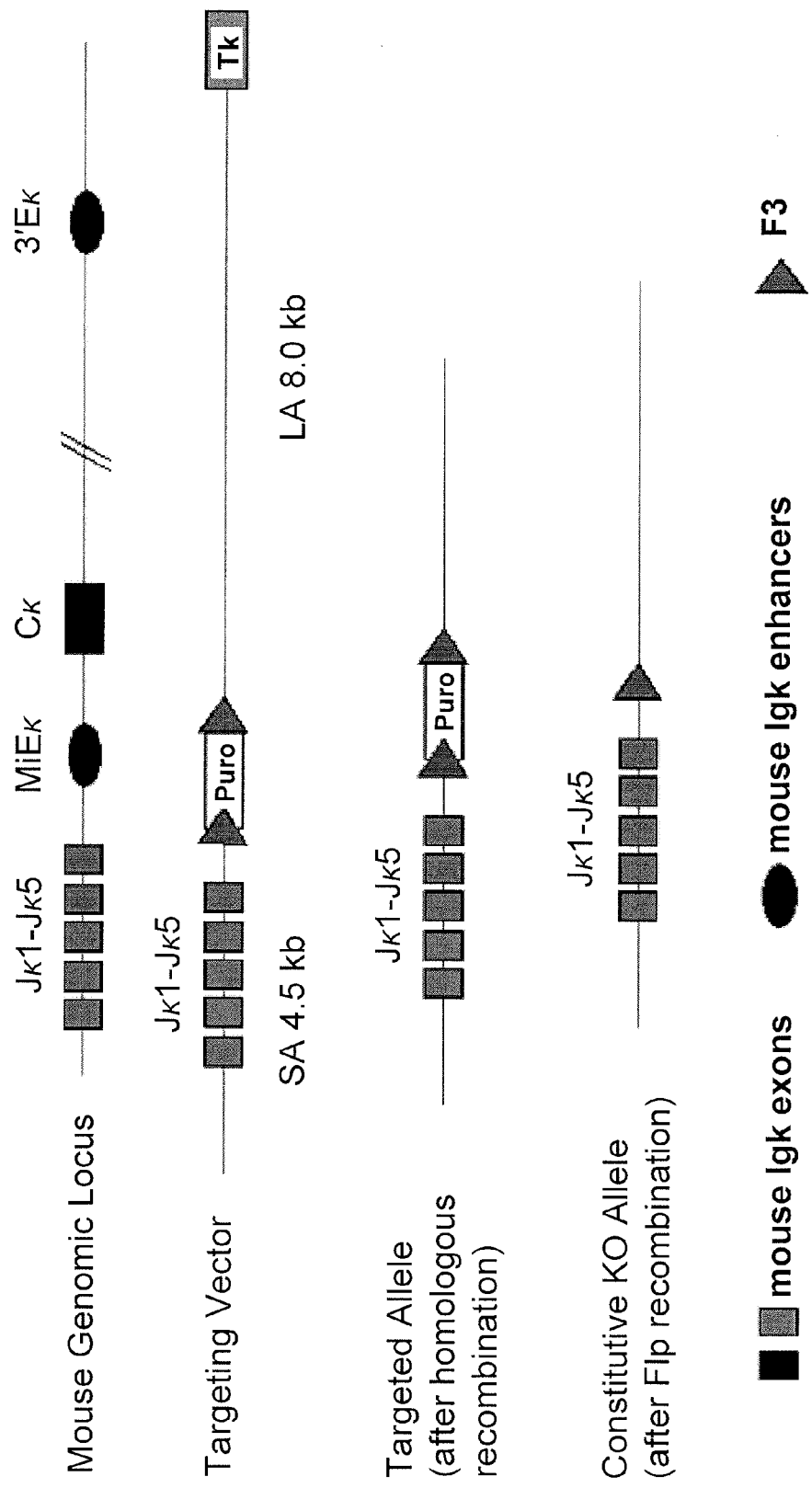
FIGS. 18A-B: Constitutive knock-out (KO) of the Ig kappa locus.
Figure 18B:
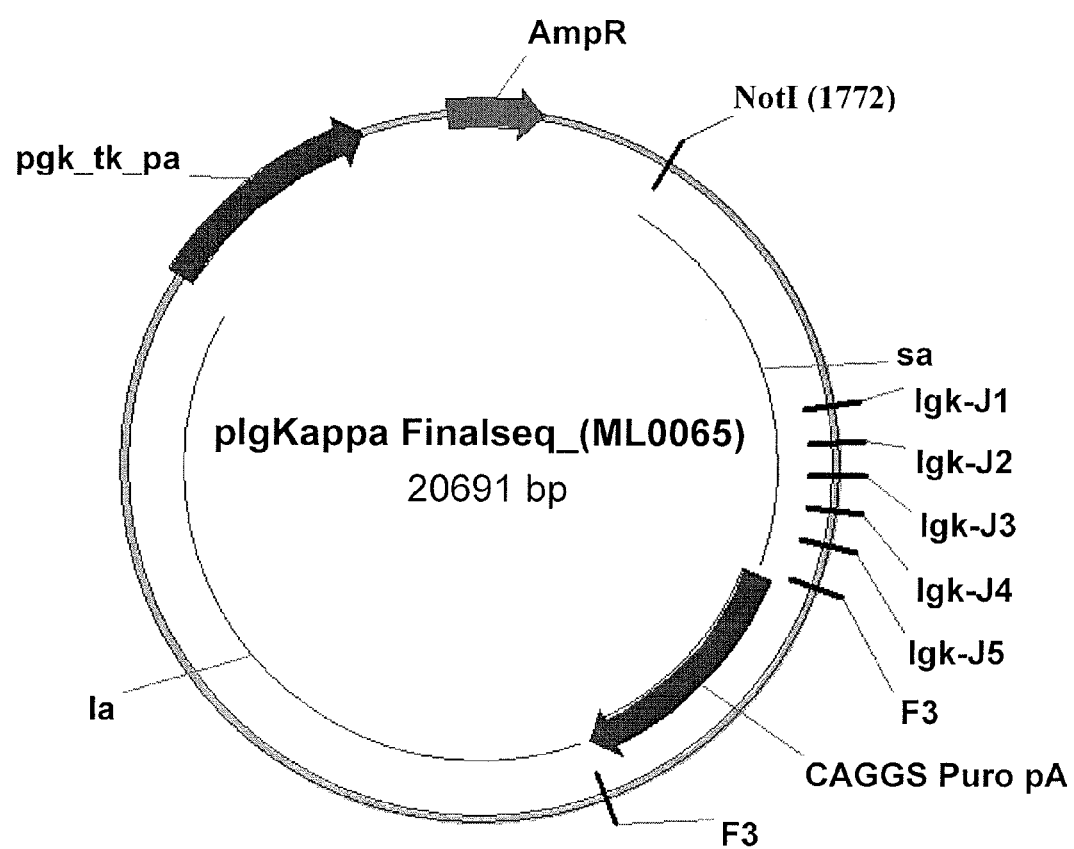

A vector that contains an assembled nucleotide sequence consisting of a part comprising the J-region to 338 bp downstream of the J5 gene segment fused to a sequence ending 3' of the 3' CK enhancer is used for homologous recombination in ES cells. The assembled sequence is used to delete a genomic DNA fragment spanning from 3' of the JK region to just 3' of the 3' CK enhancer. As a consequence of this procedure, the CK constant gene, the 3' enhancer and some intergenic regions are removed (see FIGS. 4 and 18A-B).

Construction of the Targeting Vector

A vector that received 4.5-8 kb flanking arms on the 3' and 5' end fused to the deletion segment was used for targeted homologous recombination in an ES cell line. Both arms were obtained by PCR means ensuring maximum homology. The targeting strategy allows generation of constitutive KO allele. The mouse genomic sequence encompassing the Igk intronic enhancer, Igk constant region and the Igk 3' enhancer was replaced with a PuroR cassette, which was flanked by F3 sites and inserted downstream of the Jk elements. Flp-mediated removal of the selection marker resulted in a constitutive KO allele. The replacement of the Igk MiEk-Igk C-Igk 3'E genomic region (approximately 10 kb) with a F3-Puro cassette (approx. 3 kb) was likely to decrease the efficiency of homologous recombination. Therefore, the arms of homology were extended accordingly and more ES cell colonies were analyzed after transfection in order to identify homologous recombinant clones.

Generation of ES Cells Bearing the Deleted Kappa Fragment

The generation of genetically modified ES cells was essentially performed as described (Seibler et al. (2003), *Nucleic Acids Res.* February 15; 31(4):e12). See also Example 14 for a detailed description.

Generation of ES Mice by Tetraploid Embryo Complementation

The production of mice by tetraploid embryo complementation using genetically modified ES cells was essentially performed as described (Eggan et al., *PNAS* 98:6209-6214; J. Seibler et al. (2003), *Nucleic Acids Res.* February 15; 31(4):e12; Hogan et al. (1994), Summary of mouse development, *Manipulating the Mouse Embryo*, Cold Spring Harbor Laboratory Press, Cold Spring Harbor N.Y., pp. 253-289).

Example 4: Silencing of the Mouse Lambda Light Chain Locus

This example describes the silencing of the mouse endogenous lambda light chain locus. The endogenous lambda locus is modified by homologous recombination in ES cells followed by the introduction of genetically modified ES cells in mouse embryos to obtain genetically adapted offspring.

Two regions of the murine lambda locus that together contain all functional lambda V regions are subject to deletion.

Figure 5:
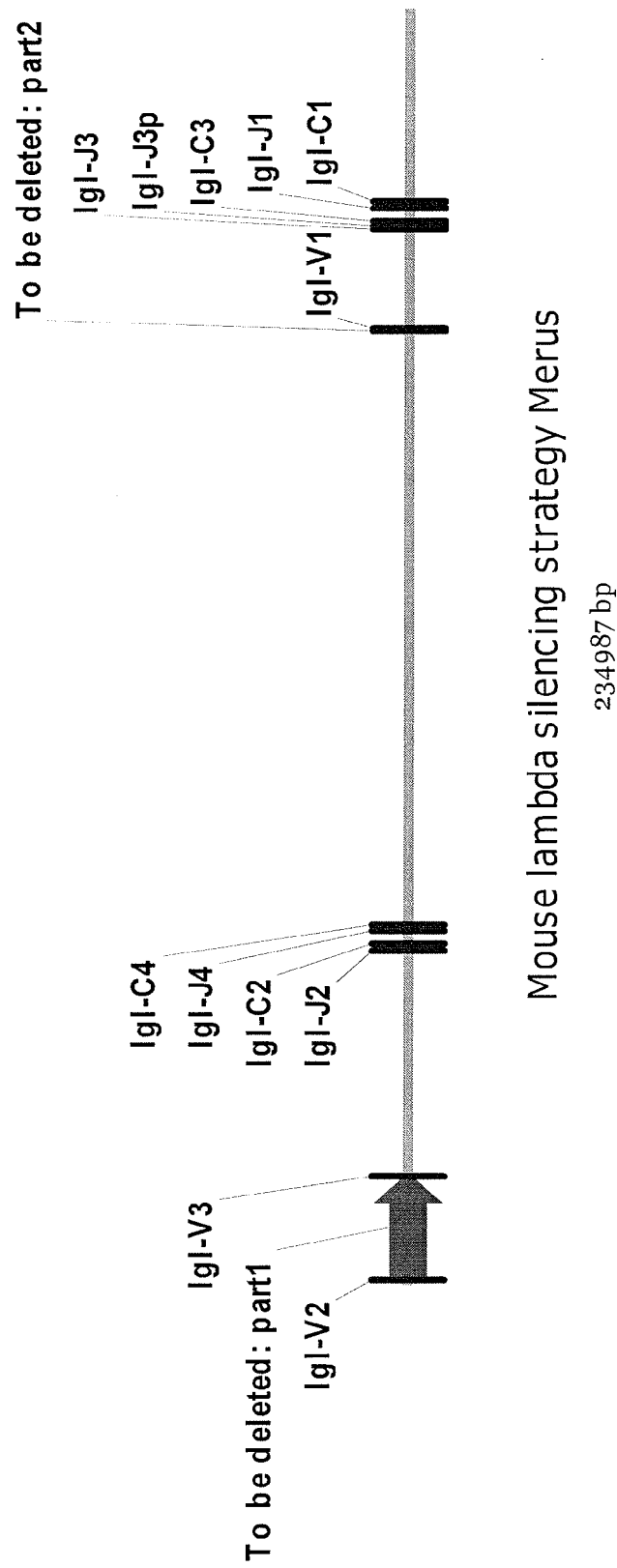
FIG. 5: The topology of the mouse C-lambda locus. All three active V-regions are indicated (Igl-V1, V2 and V3) as are the J-segments (Igl-J1, Igl-J2, Igl-J3, Igl-J4 and the pseudo segment Igl-J3p) and constant regions (Igl-C1, Igl-C2, Igl-C3 and Igl-C4). The regions that are deleted in order to silence the locus are indicated by deletion markers. These deletions include all active V genes (1, 2 and 3) and the intergenic segment between V2 and V3.
Figure 19A:
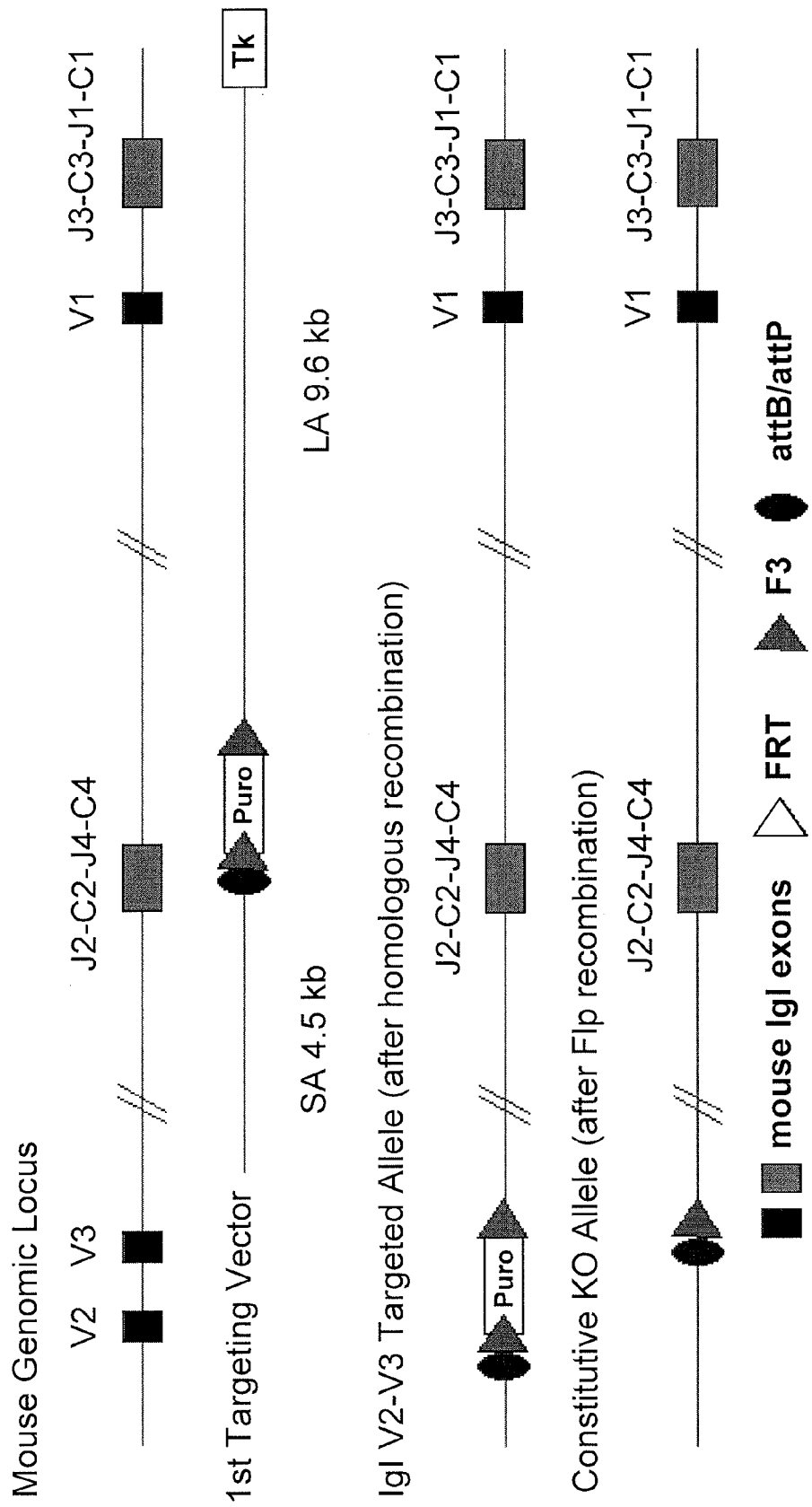
FIGS. 19A-B: Constitutive KO of the Ig lambda locus.
Figure 19B:
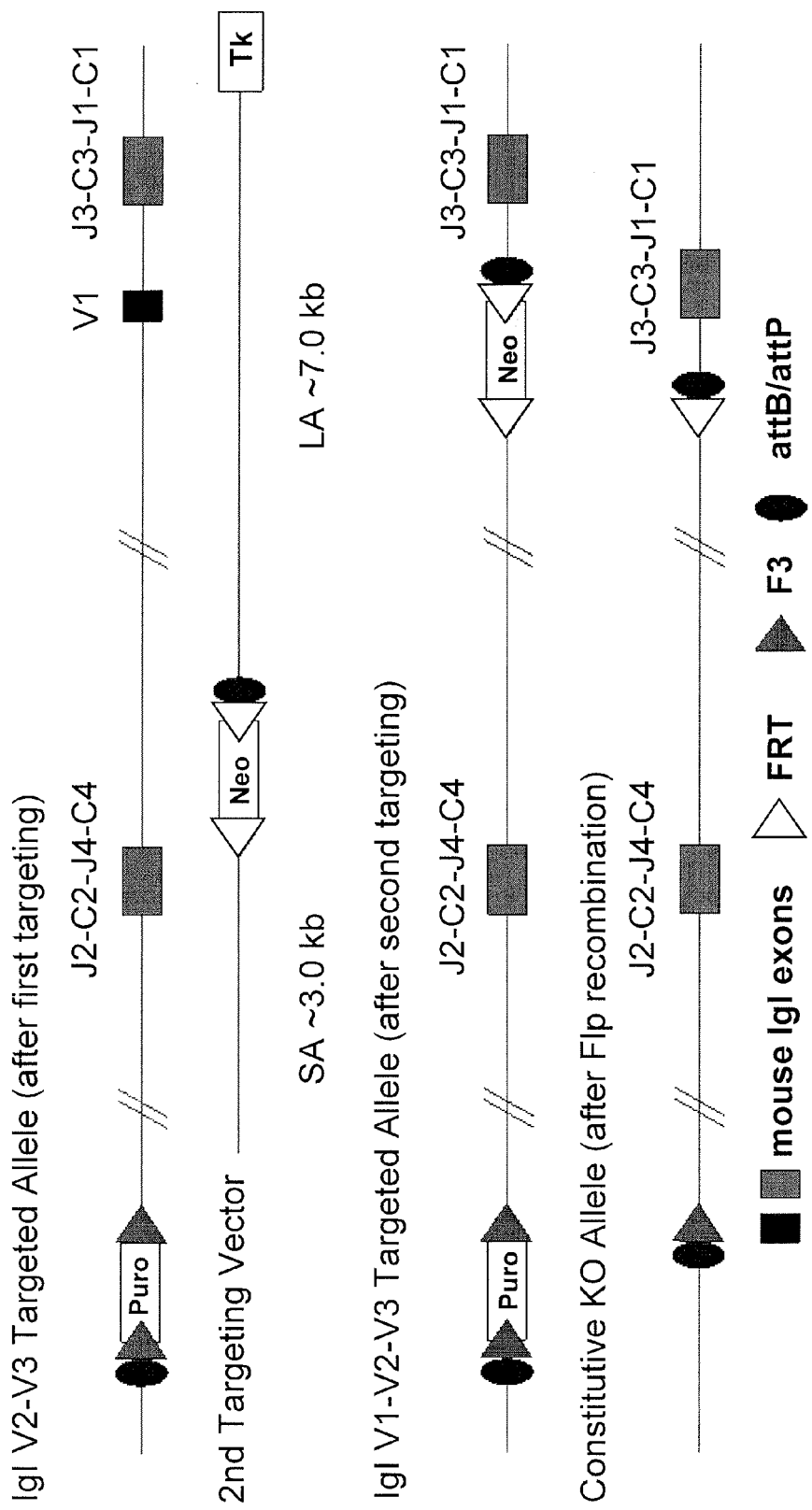

The first region targeted for homologous recombination-based deletion is a region that is located 408 bp upstream of the start site of the IGLV2 gene segment and ends 215 bp downstream of IGLV3 gene segment, including the intergenic sequence stretch between these IGLV gene segments. The second region that is subject to a deletion involves the IGLV1 gene segment consisting of a fragment spanning from 392 bp upstream to 171 bp downstream of the IGLV1 gene segment. As a consequence of these two deletion steps, all functional V-lambda genes segments are deleted, rendering the locus functionally inactive (FIGS. 5 and 19A-B).

Construction of the Targeting Vectors

Vectors that received 3-9.6 kb flanking arms on the 3' and 5' end fused to the deletion segment were used for targeted homologous recombination in an ES cell line. Both arms were obtained by PCR means ensuring maximum homology. In a first step, the mouse genomic sequence encompassing the Igl V2-V3 regions were replaced with a PuroR cassette flanked by F3 sites, which yields a constitutive KO allele after Flp-mediated removal of selection marker (see FIG. 19A). In a second step, the mouse genomic sequence encompassing the Igl V1 region was replaced with a Neo cassette in ES cell clones which already carried a deletion of the Igl V2-V3 regions (see FIG. 19B). The selection marker (NeoR) was flanked by FRT sites. A constitutive KO allele was obtained after Flp-mediated removal of selection markers.

Generation of ES Cells Bearing the Deleted Lambda Fragment

The generation of genetically modified ES cells was essentially performed as described (J. Seibler, B. Zevnik, B. KUter-Luks, S. Andreas, H. Kern, T. Hennek, A. Rode, C. Heimann, N. Faust, G. Kauselmann, M. Schoor, R. Jaenisch, K. Rajewsky, R. Kuhn, F. Schwenk (2003), *Nucleic Acids Res.*, February 15; 31(4):e12). See also, Example 14 for a detailed description. To show that both targeting events occurred on the same chromosome several double targeted clones were selected for the in vitro deletion with pCMV C31deltaCpG. The clones were expanded under antibiotic pressure on a mitotically inactivated feeder layer comprised of mouse embryonic fibroblasts in DMEM High Glucose medium containing 20% FCS (PAN) and 1200 μ/mL Leukemia Inhibitory Factor (Millipore ESG 1107). 1×10$^7$ cells from each clone were electroporated with 20 μg of circular pCMV C31deltaCpG at 240 V and 500 μF and plated on four 10 cm dishes each. Two to three days after electroporation, cells were harvested and analyzed by PCR. Primers used were:

```
                                            (SEQ ID NO: 1)
    2005_5:        CCCTTTCCAATCTTTATGGG (SEQ ID NO: 2)
    2005_7:        AGGTGGATTGGTGTCTTTTTCTC (SEQ ID NO: 3)
    2005_9:        GTCATGTCGGCGACCCTACGCC
```

PCR reactions were performed in mixtures comprising 5 μl PCR Buffer 10× (Invitrogen), 2 μl MgCl$_2$ (50 mM), 1 μl dNTPs (10 mM), 1 μl first primer (5 μM), 1 μl second primer (5 μM), 0.4 μl Taq (5 U/ul, Invitrogen), 37.6 μl H$_2$O, and 2 μl DNA. The program used was 95° C. for five minutes;

followed by 35 cycles of 95° C. for 30 seconds; 60° C. for 30 seconds; 72° C. for 1 minute; followed by 72° C. for ten minutes.

Generation of ES Mice by Tetraploid Embryo Complementation

The production of mice by tetraploid embryo complementation using genetically modified ES cells was essentially performed as described (Eggan et al., *PNAS* 98:6209-6214; J. Seibler, B. Zevnik, B. Küter-Luks, S. Andreas, H. Kern, T. Hennek, A. Rode, C. Heimann, N. Faust, G. Kauselmann, M. Schoor, R. Jaenisch, K. Rajewsky, R. Kühn, and F. Schwenk (2003), *Nucleic Acids Res.*, February 15; 31(4):e12; Hogan et al. (Cold Spring Harbor Laboratory Press, Cold Spring Harbor N.Y.), pp. 253-289).

Example 5: Construction of the CAGGS Expression Insert Based on a Rearranged Human Germline IGKV1-39/J-Ck Gene (IGKV1-39/J-Ck)

Figure 6:
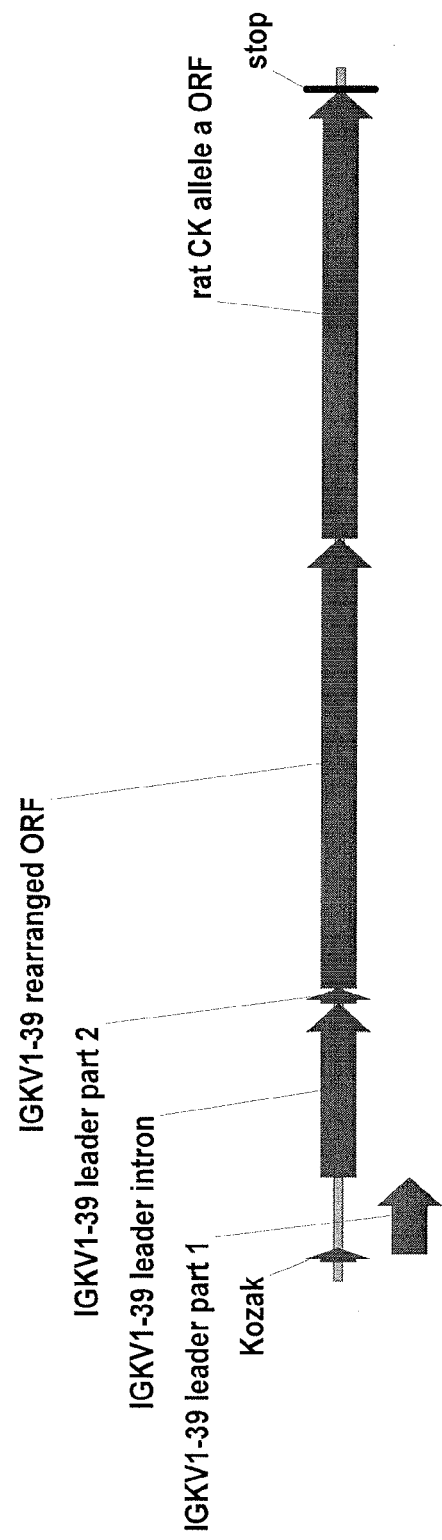
FIG. 6: Construct topology of IGKV1-39/J-Ck with an intron located in the leader open reading frame (ORF).

This example describes the construction of a CAGGS expression cassette incorporating the rearranged human germline IGKV1-39/J region. This insert expression cassette encompasses cloning sites, a Kozak sequence, a leader sequence containing an intron, an open reading frame of the rearranged IGKV1-39 region, a rat CK constant region from allele a and a translational stop sequence (IGKV1-39/J-Ck; FIG. 6). The primary construct consists of naturally occurring sequences and has been analyzed and optimized by removing undesired cis acting elements like internal TATA-boxes, poly adenylation signals, chi-sites, ribosomal entry sites, AT-rich or GC-rich sequence stretches, ARE-, INS- and CRS sequence elements, repeat sequences, RNA secondary structures, (cryptic) splice donor and acceptor sites and splice branch points (GeneArt GmbH). In addition, the codon usage in the open reading frame regions is optimized for expression in mice. The intron sequence is unchanged and thus represents the sequence identical to the coding part of the human IGKV1-39 leader intron.

Figure 13A:
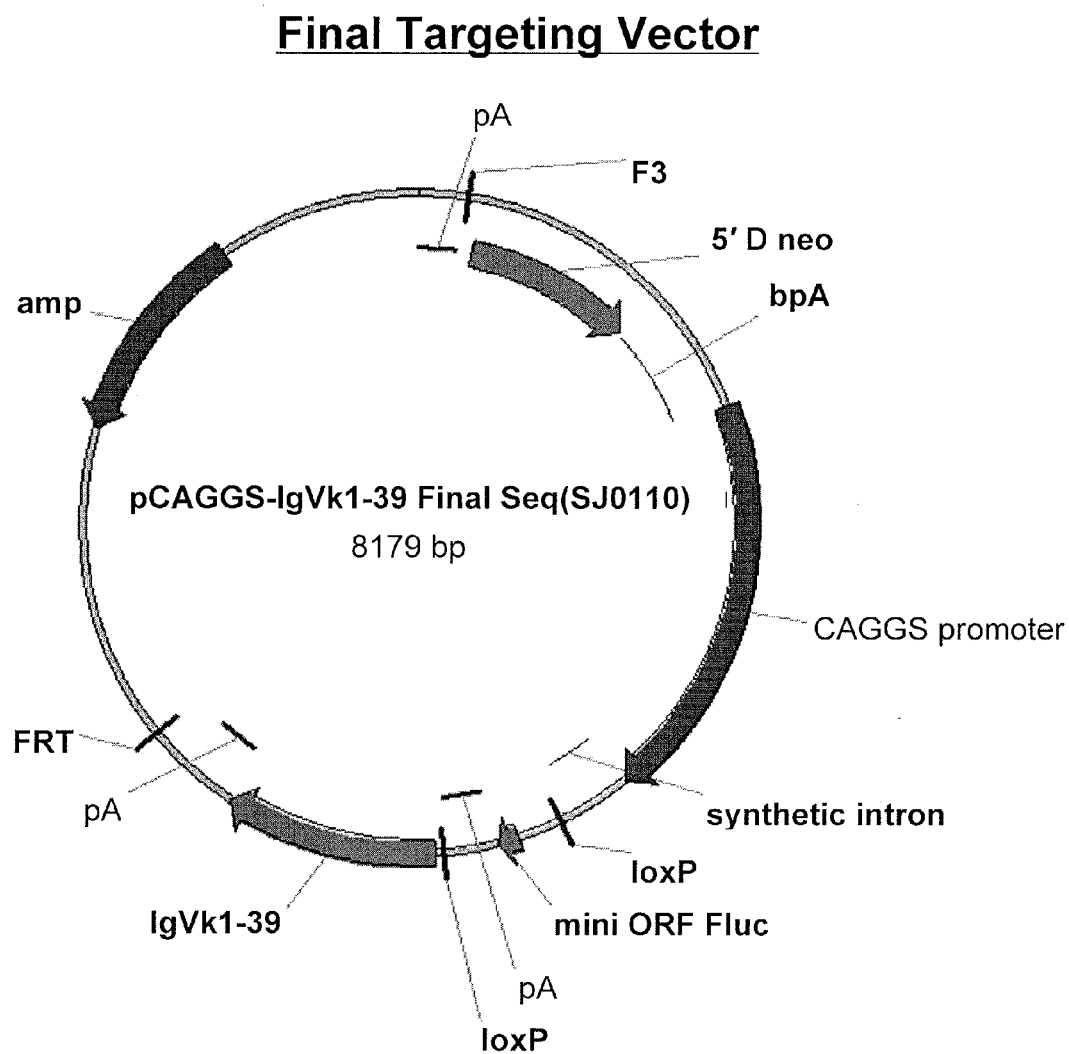
Figure 13C:
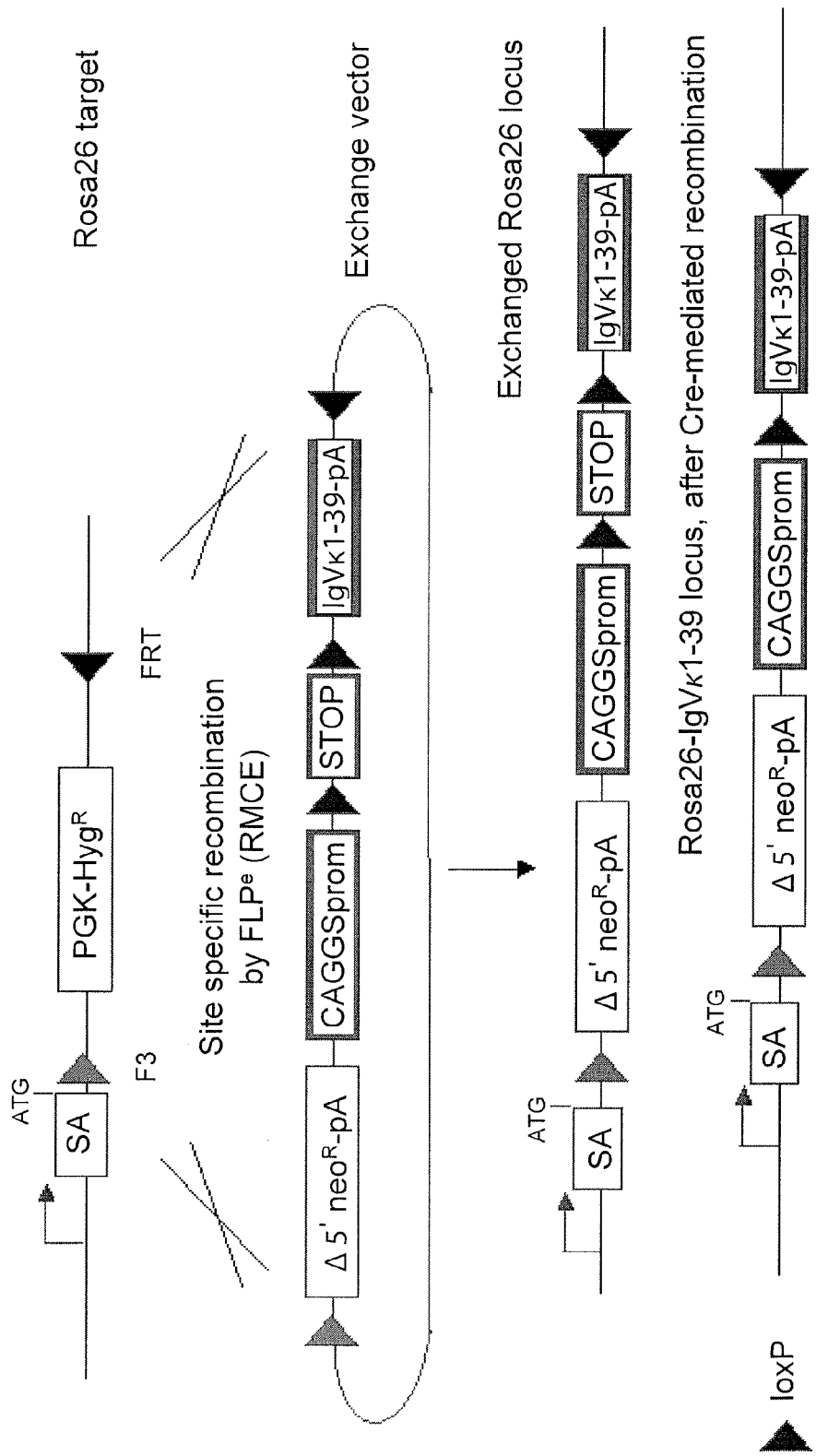

At the 5' end of the expression cassette, a NotI site was introduced and on the 3' site a NheI site. Both sites are used for cloning in the CAGGS expression module. After gene assembly according to methods used by GeneArt, the insert is digested with NotI-NheI and cloned into the expression module containing a CAGGS promoter, a stopper sequence flanked by LoxP sites ("foxed"), a polyadenylation signal sequence and, at the 5' and 3' end, sequences to facilitate homologous recombination into the Rosa26 locus of mouse ES cell lines. Promoter and/or cDNA fragments were amplified by PCR, confirmed by sequencing and/or cloned directly from delivered plasmids into an RMCE exchange vector harboring the indicated features. A schematic drawing and the confirmed sequence of the final targeting vector pCAGGS-IgVK1-39 are shown in FIGS. 13A and 13B. The targeting strategy is depicted in FIG. 13C.

Example 6: CAGGS Expression Insert Based on the Rearranged Germline IGLV2-14/J V Lambda Region (IGLV2-14/J-Ck)

Figure 7:
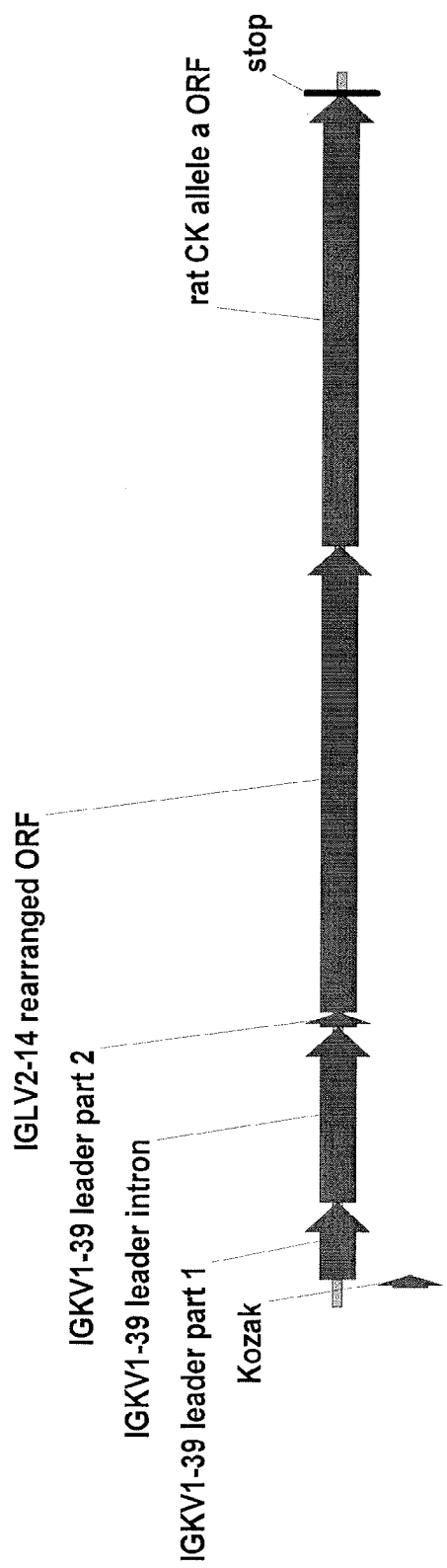
FIG. 7: Construct topology of IGLV2-14/J-Ck with an intron located in the leader open reading frame (ORF).

This example describes the sequence and insertion of an expression cassette incorporating the rearranged germline IGLV2-14/J V lambda region. This insert encompasses cloning sites, a Kozak sequence, a leader sequence containing an intron, an open reading frame of the rearranged IGLV2-14/J region, a rat CK constant region from allele a and a translational stop sequence (IGLV2-14/J-Ck; FIG. 7). The primary construct consists of naturally-occurring sequences and has been analyzed and optimized by removing undesired cis acting elements like: internal TATA-boxes, poly adenylation signals, chi-sites, ribosomal entry sites, AT-rich or GC-rich sequence stretches, ARE-, INS- and CRS sequence elements, repeat sequences, RNA secondary structures, (cryptic) splice donor and acceptor sites and splice branch points (GeneArt GmbH). In addition, the codon usage in the open reading frame regions was optimized for expression in mice. The intron sequence is unchanged and thus represents the sequence identical to the human IGKV1-39 leader intron.

Figure 15A:
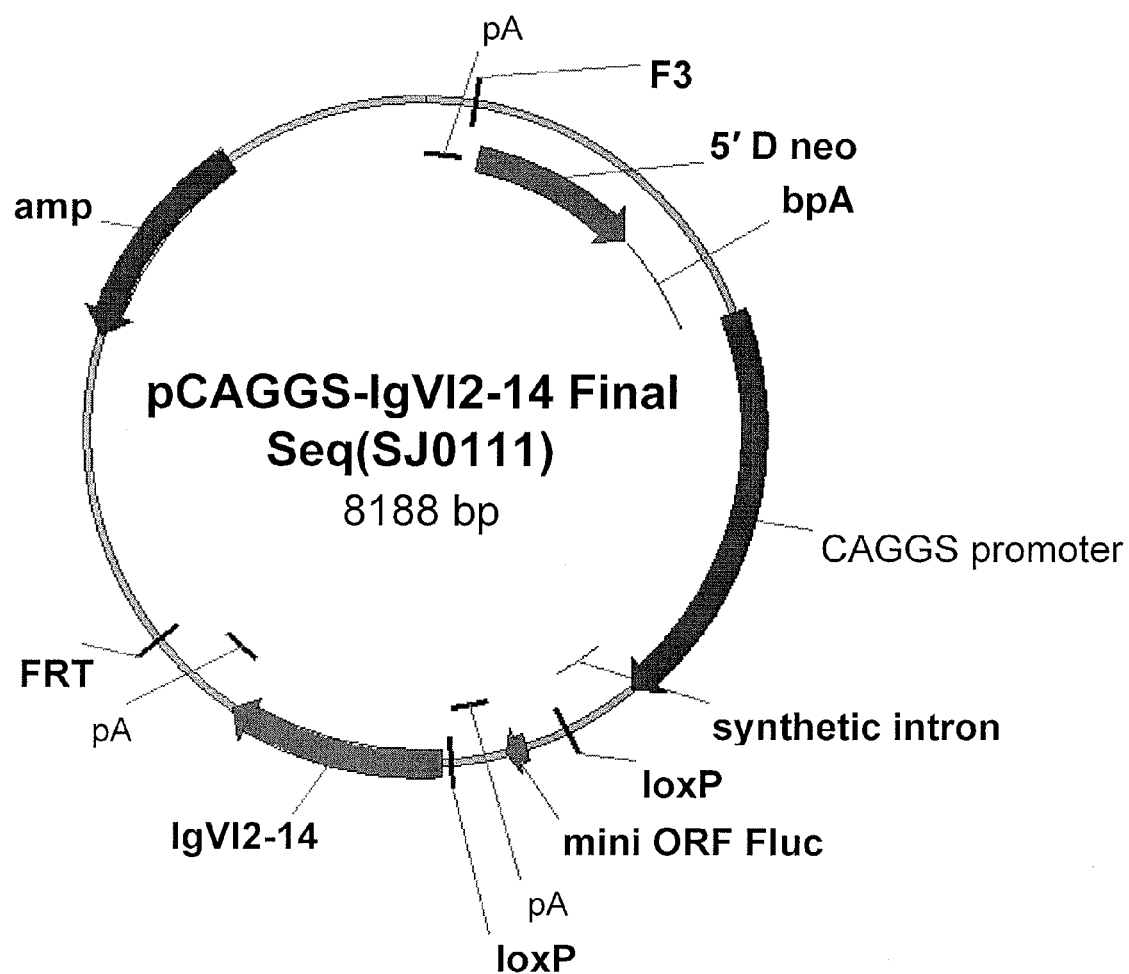
Figure 15C:
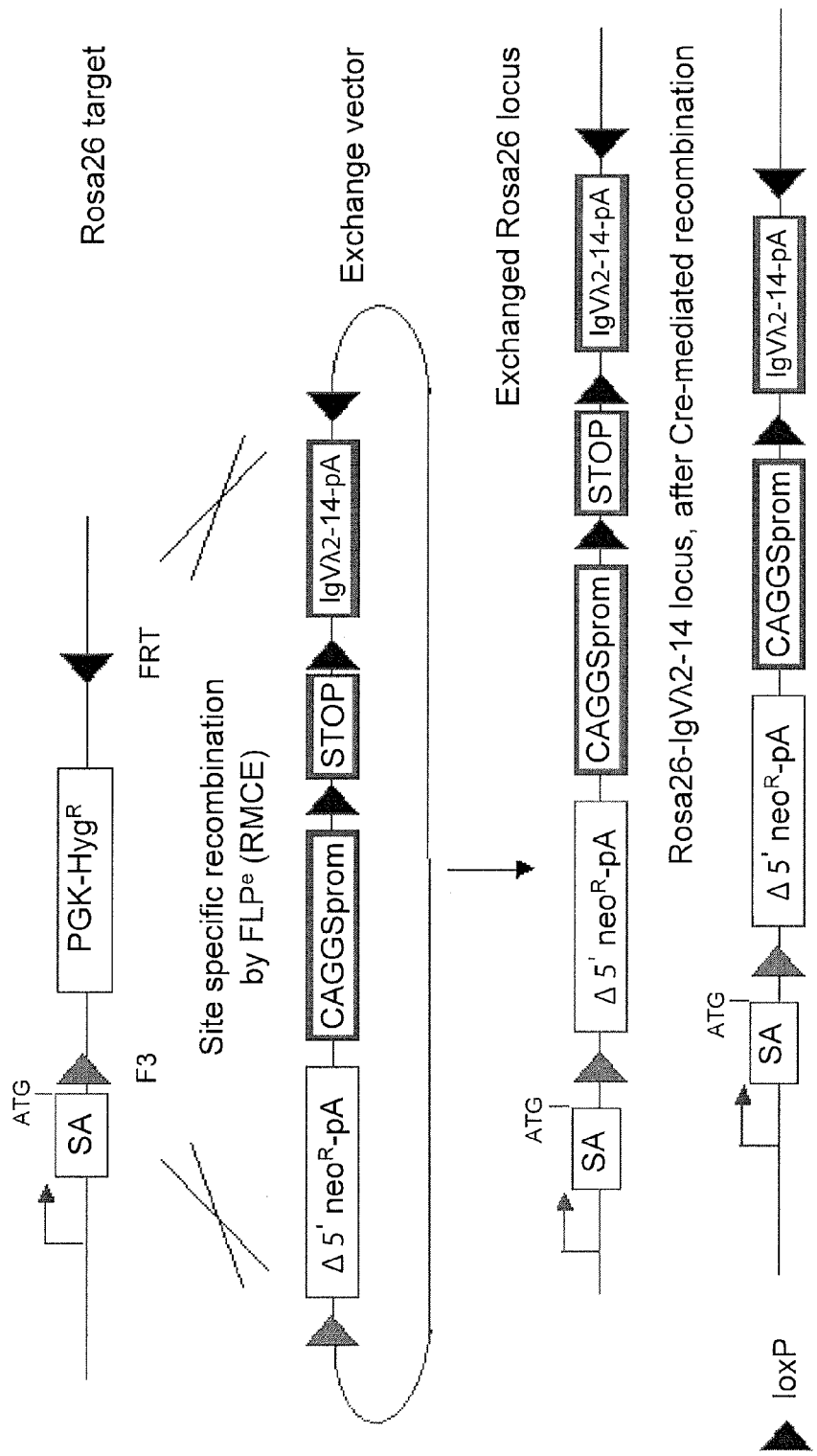
Figure 16A:
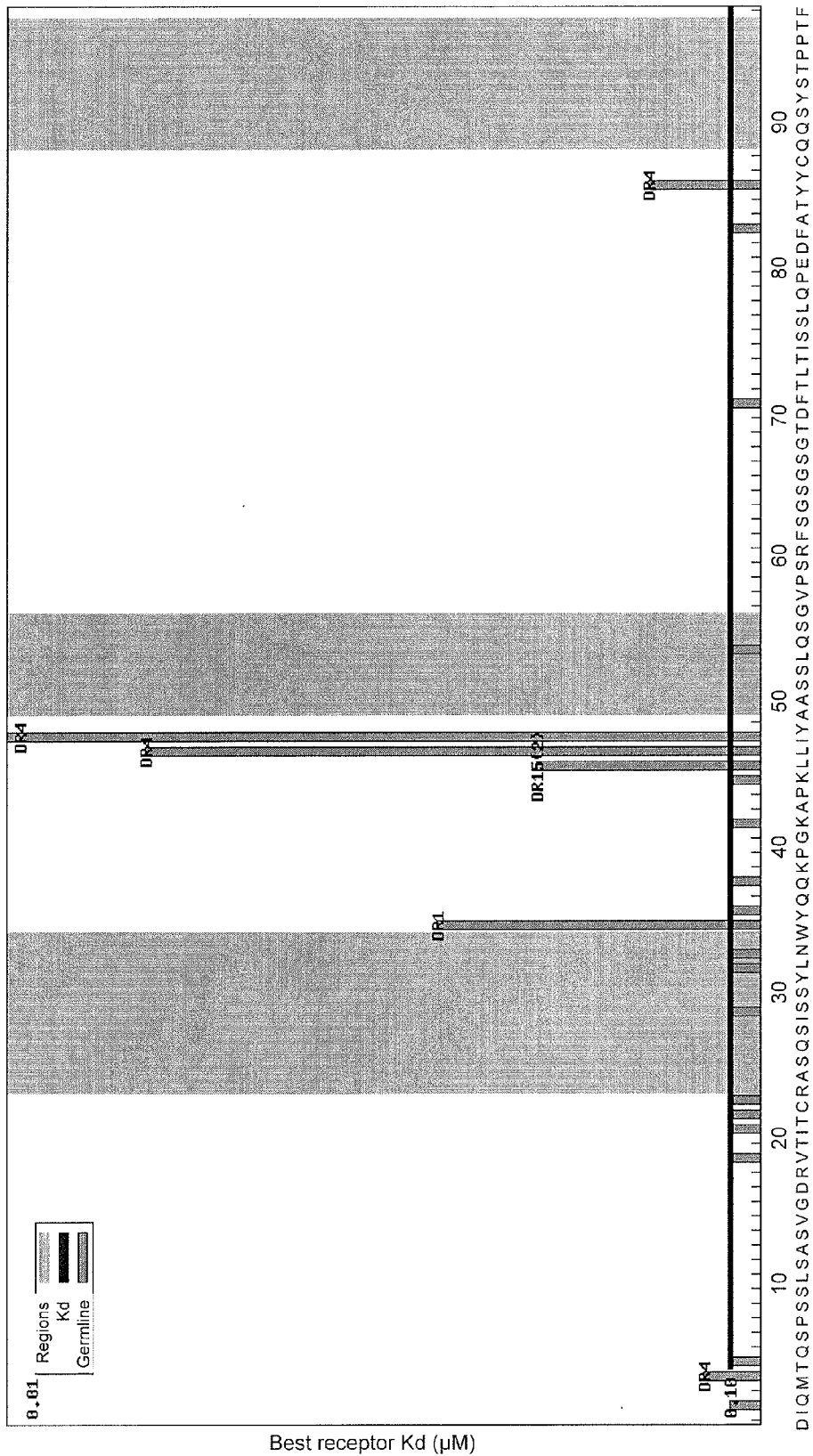
FIG. 16A displays the binding strength for DRB1 allotypes.
Figure 16B:
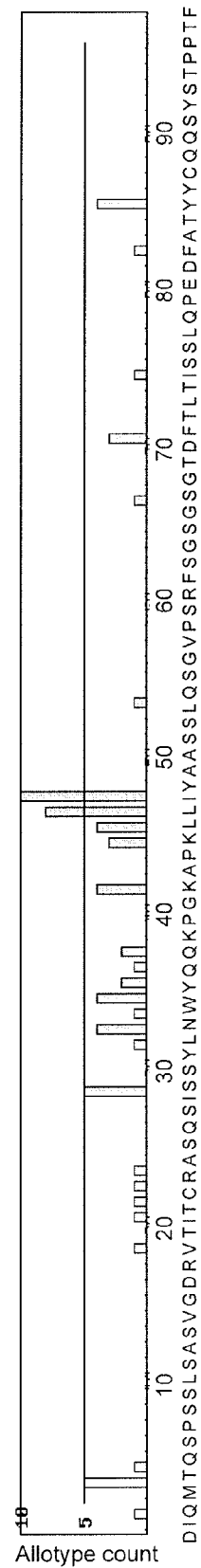
FIG. 16B shows the HLA binding promiscuity for every decameric peptide (Y-axis: the number of HLA allotypes recognizing critical epitopes in each of the peptides starting at the indicated residue shown on the X-axis). The promiscuity is measured as the number of allotypes out of the total of 47 for which the peptide is a critical binder. White columns refer to self-peptides, and black columns (absent here) to non-self peptides.
Figure 16C:
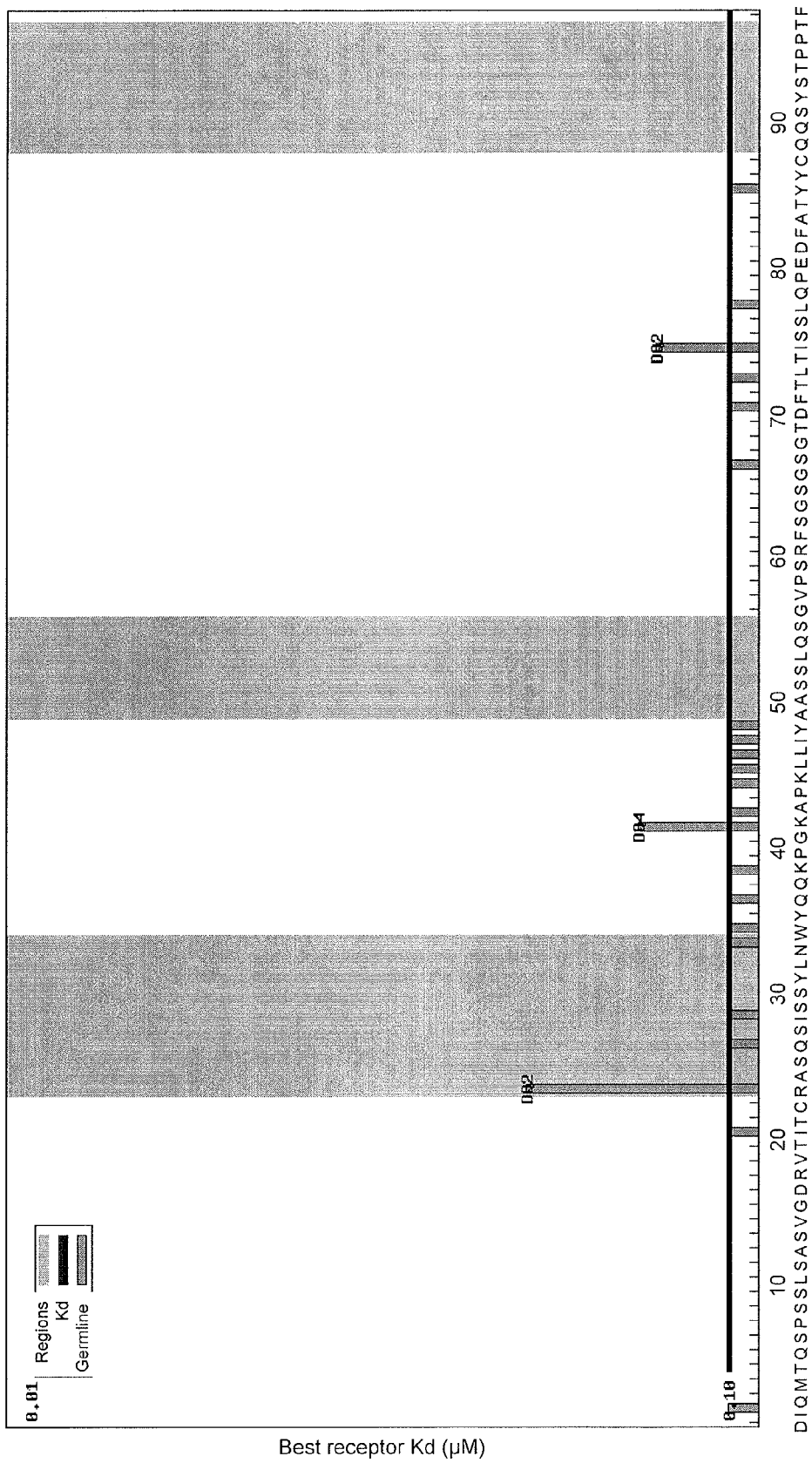
FIG. 16C displays the binding strength for DRB3/4/5, DQ and DP allotypes. The values in the figure represent dissociation constants (Kds) and are plotted on a logarithmic scale in the range 0.01 μM-0.1 μM (very strong binders may have run off the plot). For medium binding peptides, qualitative values are given only, and weak and non-binders are not shown. Values are plotted on the first residue of the peptide in the target sequence (the peptide itself extends by another nine residues). Importantly, only the strongest binding receptor for each peptide is shown: cross-reacting allotypes with lower affinity are not visible in this plot. The strongest binding receptor is indicated by its serotypic name. Finally, any germline-filtered peptides are plotted with a lighter color in the epitope map (in this case, no non-self epitopes were found).
Figure 17:
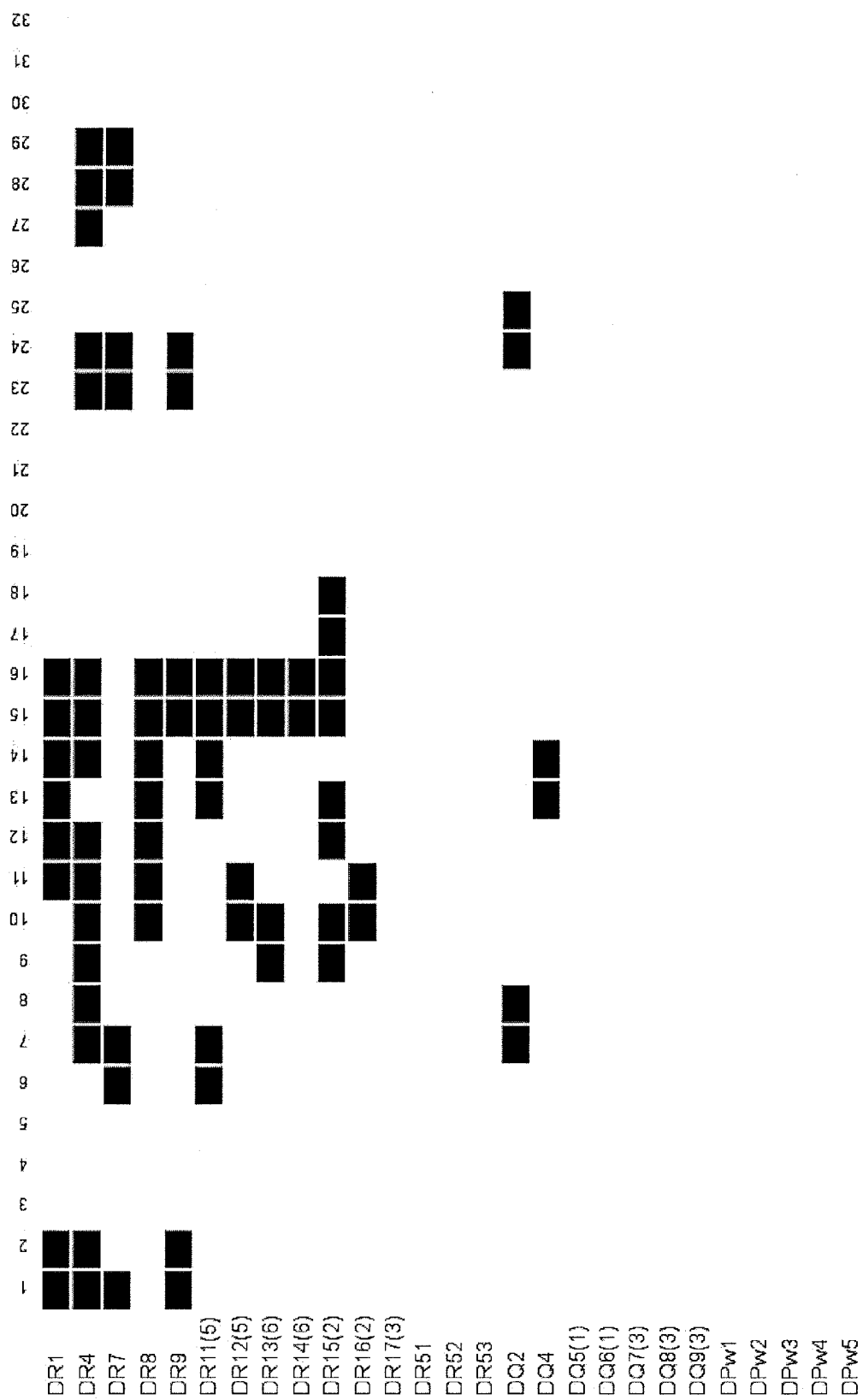
FIG. 17: Epitope map of IGKV1-39 showing the presence of peptide binders predicted in the sequence of IGKV1-39 by serotype in the 15-mer format. Each 15-mer is numbered as indicated in the top of the figure. The full sequence of the corresponding 15-mer is listed in Table 7. Black boxes indicate the presence of one or more critical self-epitopes in the 15-mer for the serotype listed on the left. Critical epitopes are operationally defined as strong or medium DRB1 binders and strong DRB3/4/5 or DP or DQ binders.

At the 5' end of the expression cassette, a NotI site was introduced and on the 3' site a NheI site. Both sites are used for cloning in the CAGGS expression module as described by TaconicArtemis. After gene assembly according to methods used by GeneArt, the insert was digested with NotI-NheI and cloned into the expression module containing a CAGGS promoter, a stopper sequence flanked by LoxP sites ("foxed"), a polyadenylation signal sequence and, at the 5' and 3' end, sequences to facilitate homologous recombination into the Rosa26 locus of mouse ES cell lines. To construct the final ROSA26 RMCE targeting vector, promoter and/or cDNA fragments were amplified by PCR. Amplified products were confirmed by sequencing and/or cloned directly from delivered plasmids into an RMCE exchange vector harboring the indicated features. A schematic drawing and the confirmed sequence of the final targeting vector pCAGGS-IgVL2-14 is shown in FIGS. 15A and 15B. The targeting strategy is depicted in FIG. 15C.

Example 7: Expression of IGKV1-39/J-Ck in HEK293 Cell Lines (pSELECT-IGKV1-39/J-Ck)

This example describes a method to verify that the IGKV1-39/J-Ck constructs described in Example 5 enable expression and detection of the IGKV1-39/J-Ck L chain in HEK293 cells. The IGKV1-39/J insert (FIG. 6) was modified at the 5' end by changing the NotI site into a SalI site. This change is required for cloning of the product into the expression cassette plasmid pSELECT-hygro (InvivoGen). The CAGGS expression insert IGKV1-39/J-Ck and pSELECT-hygro were digested with SalI and NheI, ligated and used to transform competent XL1-Blue cells using standard techniques. Colonies were picked and DNA purified using Qiagen Midi-prep columns according to the manufacturer's procedures. The resulting light chain (LC) expressing vector named 0817676_pSELECT_0815426 was used to transfect HEK293 cells with Fugene6 (Roche) according to the manufacturer's protocols. Supernatants were screened for the presence of IGKV1-39/J-Ck light chains by ELISA and western blot using anti-rat-Ck antibodies (Beckton Dickinson #550336 and 553871) and protocols used in the art.

The VH of anti-tetanus toxoid (TT) IgG MG1494 was cloned into IgG expression vector MV1056 using restriction sites SfiI and BstEII. The resulting clone was sequence verified. HEK293T cells were transfected with five different vector combinations as shown in Table 4 (see Example 8 for details of vector 0817678_pSELECT_0815427). Supernatants were harvested and IgG concentrations determined (see Table 4). No IgG could be detected for supernatants A and B containing light chain only as expected (detection antibody recognized Fc part of IgG). IgG concentration in supernatants C and D was comparable to that of positive control supernatant E, indicating correct expression of the light chain constructs.

Binding to TT was analyzed by ELISA to check functionality of the produced antibodies, using hemoglobin as negative control antigen. No TT-specific binding could be detected for supernatants A and B containing light chain only, as expected. TT-specific binding for supernatants C and D was at least as good as for positive control supernatant E, confirming correct expression of the light chain constructs and functional assembly with heavy chain. Antibodies were detected not only using an anti-human IgG secondary antibody, but also an anti-rat Ckappa light chain secondary antibody. The results confirm that the anti-rat Ckappa antibody (BD Pharmingen #553871, clone MRK-1) recognizes the light chain expressed by the pSELECT vectors.

Supernatants were analyzed by non-reducing SDS-PAGE and Western blot (not shown). Detection using an anti-human IgG heavy chain antibody did not show bands for supernatants A and B containing light chain only, as expected. Results for supernatants C and D were comparable to positive control supernatant E, with a band close to the 170 kD marker as expected for intact IgG. Additional lower molecular weight bands were observed as well for supernatants C, D and E, which might represent degradation products, IgG fragments resulting from (partial) reduction and/or irrelevant protein bands due to non-specific binding of the detection antibody.

Detection using an anti-rat Ckappa light chain antibody showed a band close to the 26 kD marker for supernatants A and B, as expected for light chain only. This band was much more intense for A compared to B, indicating that the free IGKV1-39 light chain may be better expressed and/or more stable than the free IGLV2-14 light chain. No bands were detected for control supernatant E as expected, since the expressed IgG contains a human Ckappa light chain. For supernatants C and D, expected bands close to the 170 kD marker were observed; lower molecular weight bands were also observed, but to a lesser extent than above using the anti-human IgG antibody.

In conclusion, transfection of the light chain expression constructs combined with the heavy chain of anti-tetanus toxoid (TT) IgG MG1494 resulted in IgG production comparable to the positive control construct for both the pSELECT kappa and lambda light chain constructs. Both IgG productions yielded ELISA signals in a TT ELISA that were better than or comparable to the control IgG. SDS-PAGE and Western blot analysis confirmed the presence of intact IgG. The tested anti-rat Ckappa antibody worked efficiently in both ELISA and Western blot. Culture supernatant from cells transfected with light chain constructs only did not result in detectable IgG production nor in detectable TT-specific binding, while free light chain was detected on Western blot.

Example 8: Expression of IGLV2-14/J-Ck in HEK293 Cell Lines (pSELECT-IGLV2-14/J-Ck)

This example describes a method to verify that the IGLV2-14/J constructs described in Example 6 enable expression and detection of the IGLV2-14/J-Ck L chain in HEK293 cells. The IGLV2-14/J-Ck insert (FIG. 7) was modified at the 5' end by changing the NotI site into a SalI site. This change is required for cloning of the product into the expression cassette plasmid pSELECT-hygro (InvivoGen). The CAGGS expression insert IGLV2-14/J-Ck and pSELECT-hygro were digested with SalI and NheI ligated and used to transform competentXL1-Blue cells using standard techniques. Colonies were picked and DNA purified using Qiagen Midi-prep columns according to the manufacturer's procedures. The resulting light chain (LC) expressing vector named 0817678_pSELECT_0815427 was used to transfect HEK293 cells with Fugene6 (Roche) according to the manufacturer's protocols. Supernatants were screened for the presence of IGLV2-14/J-Ck light chains by ELISA and western blot using anti-rat-Ck antibodies (Becton Dickinson #550336 and 553871) and protocols used in the art. See Example 7 for details and results.

Example 9: Construction of a VK Promoter-Driven Expression Construct Containing an IGKV1-39/J Insert and Multiple Enhancer Elements Derived from the Murine CK Locus (VkP-IGKV1-39/J-Ck; VkP-O12)

This example describes the construction of an expression cassette that contains relevant elements to enable B-cell and developmental/differentiation stage-specific expression of the rearranged human IGKV1-39 VK region, based on the IGKV1-39 VK promoter region, leader containing an intron, germline V-gene, CDR3, IGKJ segment, mouse intergenic region located between Jk and CK, rat Ck allele a open reading frame, and a mouse intergenic fragment from the 3' end of the mouse CK gene ending just 3' of the 3' CK enhancer.

Optimized open reading frames of the leader, IGKV1-39 rearranged gene, and rat CK allele a gene, as described in Example 5, was used for the construction of the expression cassette. The VK promoter region was obtained by gene synthesis procedures (GeneArt, GmbH) and is almost identical to the sequence of the human IGKV1-39 region between −500 bp and the ATG (start site) of the gene. The only deviation from the natural sequence is the introduction of a GCCACCATGG Kozak sequence (SEQ ID NO:102) at the ATG (start) site in order to promote translation. A genomic fragment from a mouse BAC clone (TaconicArtemis) is used as the basis for the introduction of individual elements. This fragment is identical to the sequence of the mouse VK locus starting with the intron donor site located directly 3' of the JK5 region and ending just 3' of the 3' CK enhancer and covers approximately 12.5 kb.

Figure 8:
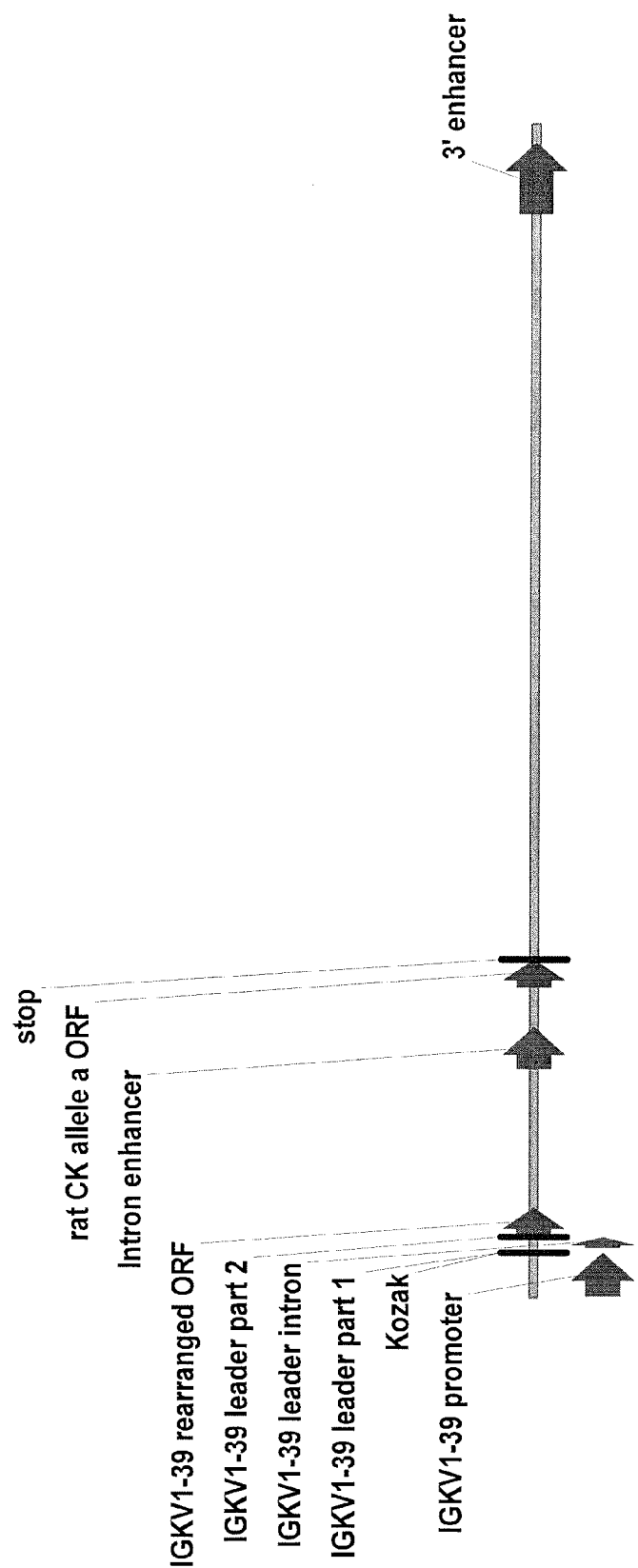
FIG. 8: Construct topology of VkP-IGKV1-39/J-Ck (VkP-O12). The promoter originates from the IGKV1-39 gene and is placed directly in front of the required elements for efficient transcription and translation. Intergenic sequences (including the enhancers) are derived from mice and obtained from BAC clones. The C-kappa sequence codes for the kappa constant region of rat.
Figure 20A:
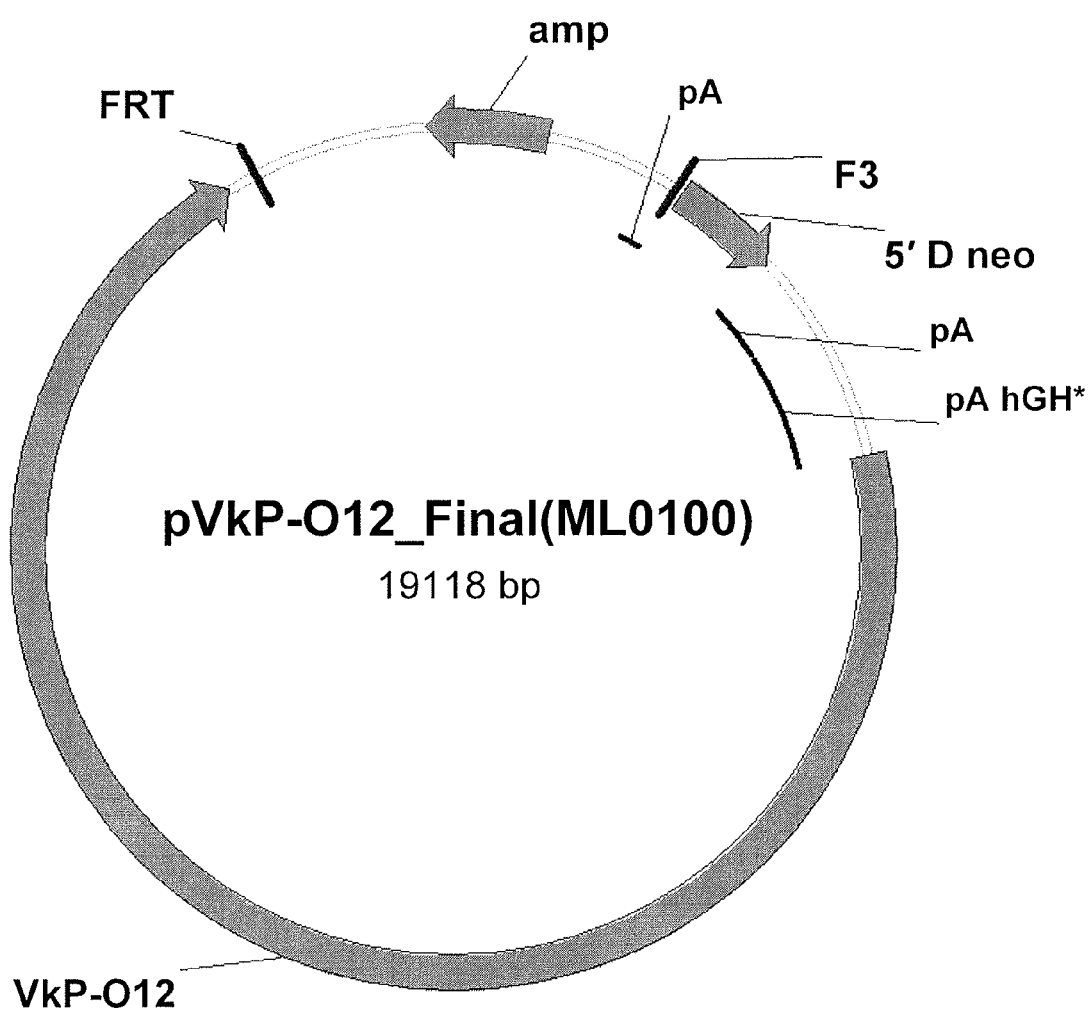
FIGS. 20A-C: Schematic drawing of targeting vectors.
Figure 21A:
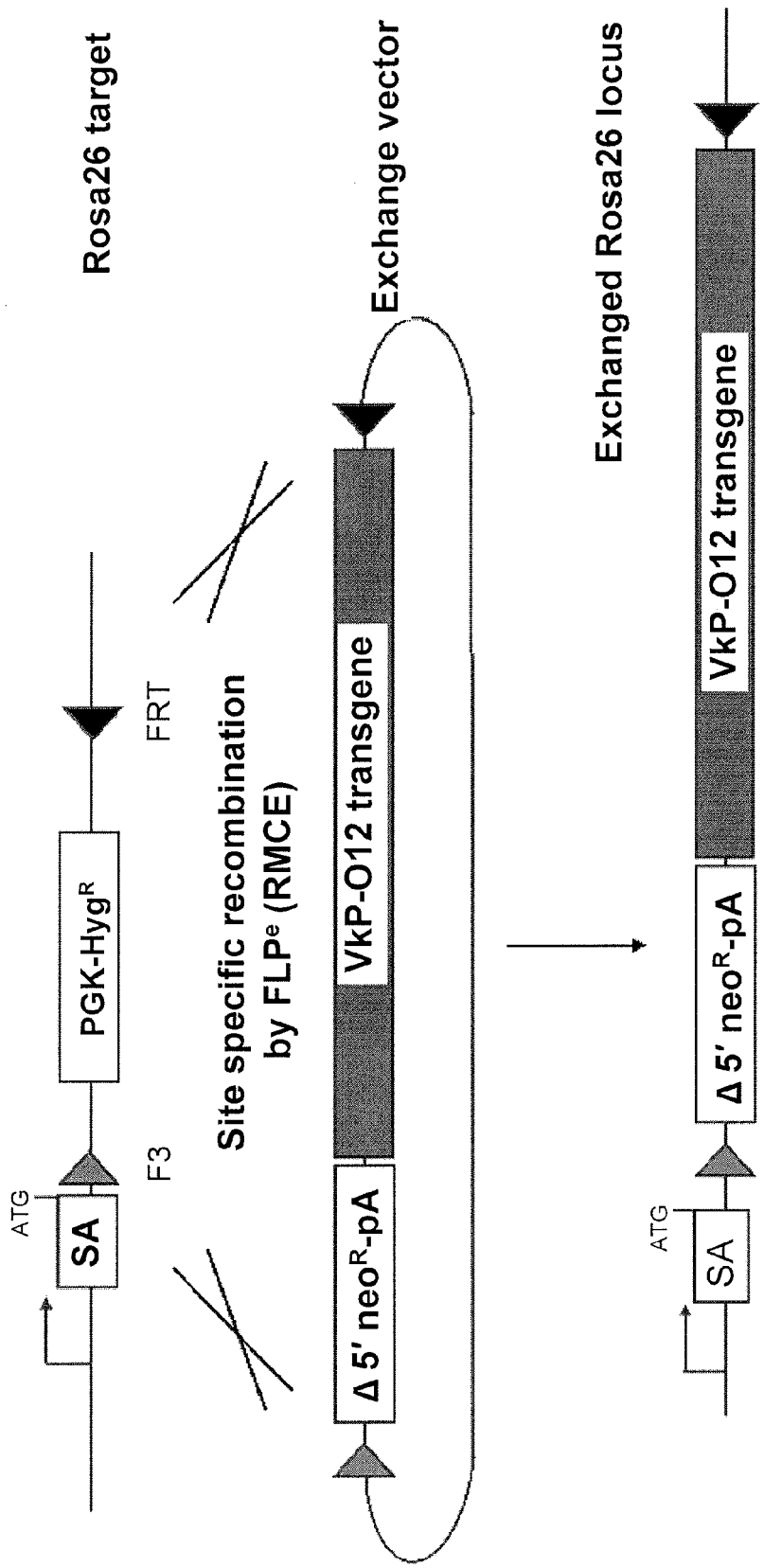
FIGS. 21A-C: Targeting strategies for insertion of transgene into the Rosa26 locus by targeted transgenesis using RMCE.

The final construct contains from 5' to 3' end the following elements: human genomic IGKV1-39 promoter (500 bp), a Kozak sequence, a human IGKV1-39 leader part 1 (optimized), a human IGKV1-39 leader intron, a human IGKV1-39 leader part 2 (optimized), a human IGKV1-39 germline gene (optimized), a human J-region (optimized), a mouse intergenic region including the intron enhancer element, a rat (*Rattus norvegicus*) kappa constant region (optimized), and a mouse intergenic region including the 3' kappa enhancer. The elements of this expression cassette are shown in FIG. 8 and named VkP-IGKV1-39/J-Ck (VkP-O12). An outline of the pVkP-O12 vector and the targeting strategy is depicted in FIGS. 20A and 21A. The vector was introduced into ES cells following standard procedures (see Example 14).

Example 10: Construction of a VK Promoter-Driven Expression Construct Containing an IGLV2-14/J Clone and Multiple CK Locus-Derived Enhancer Elements (VkP-IGLVL2-14/J-Ck; VkP-2a2)

Figure 9:
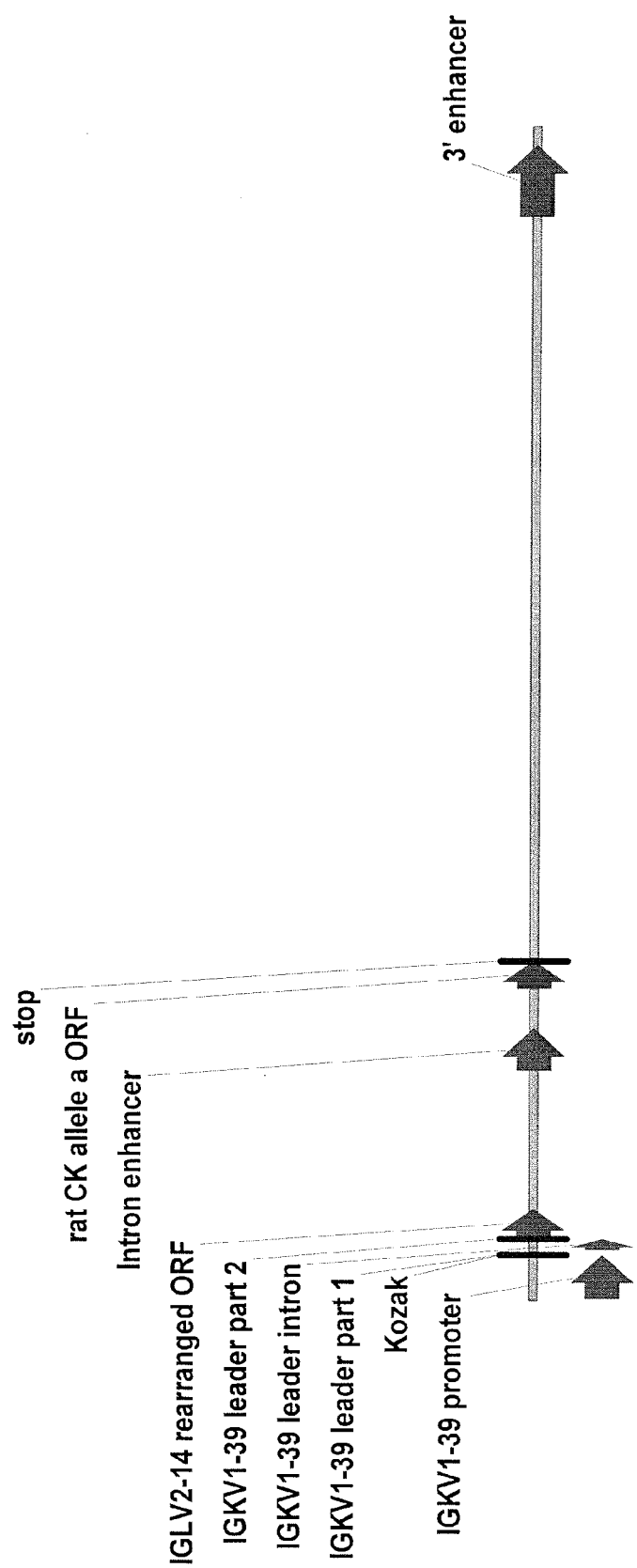
FIG. 9: Construct topology of VkP-IGLV2-14/J-Ck (VkP-2a2). The promoter originates from the IGKV1-39 gene and is placed directly in front of the required elements for efficient transcription and translation. Intergenic sequences (including the enhancers) are derived from mice and obtained from BAC clones. The C-kappa sequence codes for the kappa constant region of rat.

This example describes the same construct as described in Example 9, except that the IGKV1-39 gene and J-region are replaced by the optimized human IGLV2-14 germline gene including a unique V-J region (VkP-IGLV2-14/J-Ck; VkP-2a2; FIG. 9).

Example 11: Construction of a VK Promoter-Driven Expression Construct Containing an IGKV1-39 Clone Lacking the CK Intron Enhancer Element (VkP-IGKV1-39/J-Ck-Δ1; VkP-O12-Del1)

Figure 10:
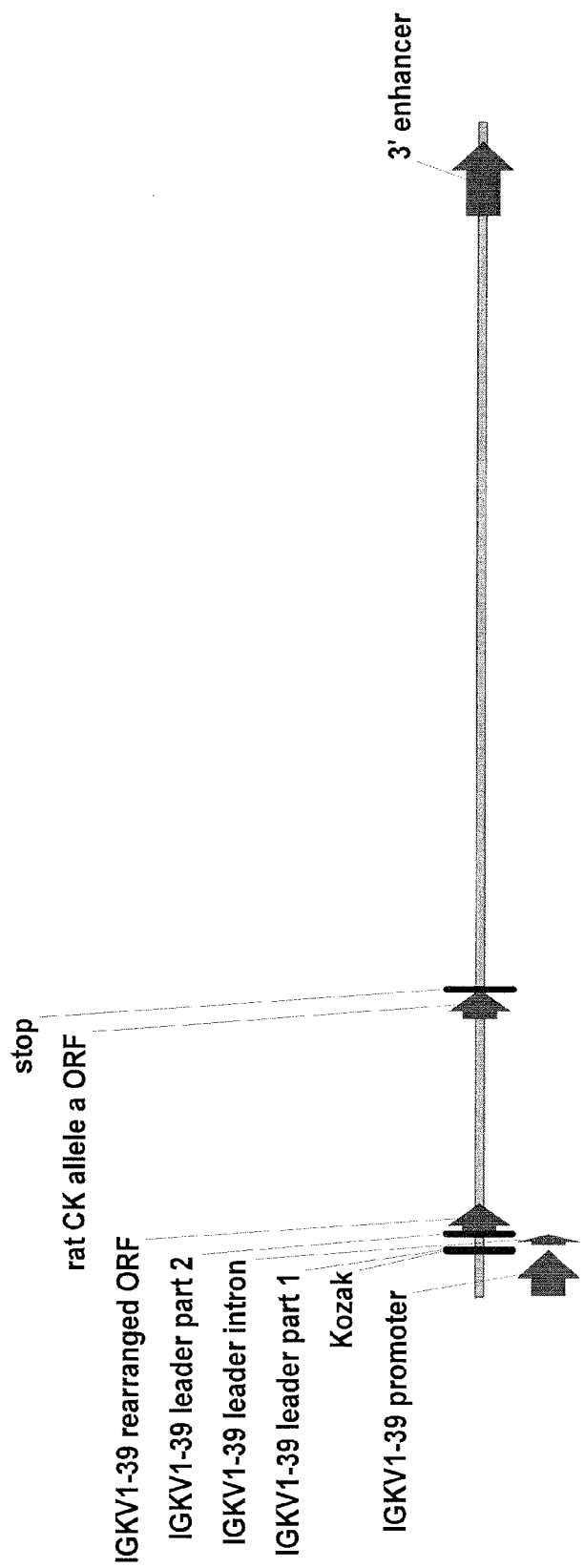
FIG. 10: Construct topology of VkP-IGKV1-39/J-Ck-Δ1 (VkP-O12-del1) is identical to VkP-IGKV1-39/J-Ck from FIG. 9 except that the intron enhancer region is removed.

The construct described in Example 9 was modified by removing the CK intron enhancer element, located in the intergenic region between the human J region and the rat CK region by standard PCR modification and DNA cloning methodologies (GeneArt, GmBH). The resulting expression cassette is shown in FIG. 10 and named VkP-IGKV1-39/J-Ck-Δ1 (VkP-O12-del1).

Figure 20B:
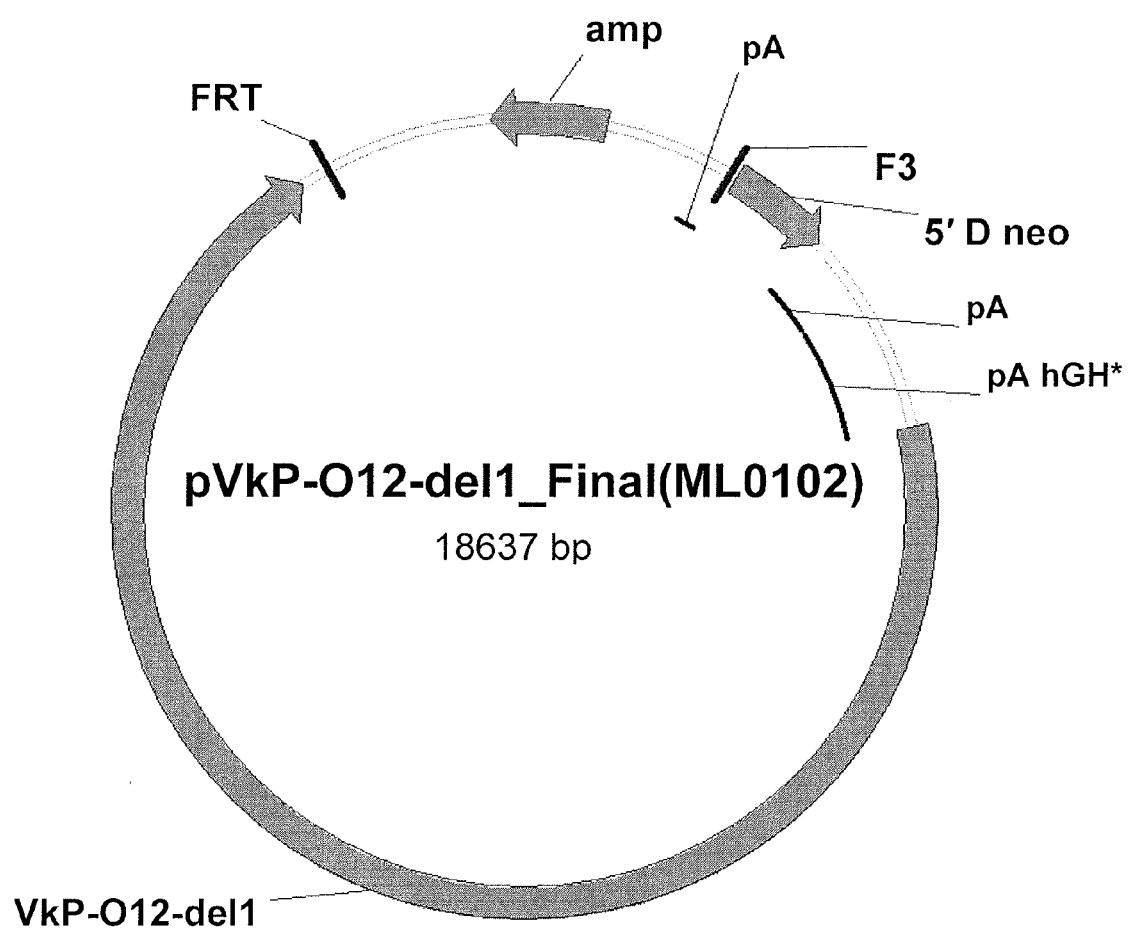
Figure 21B:
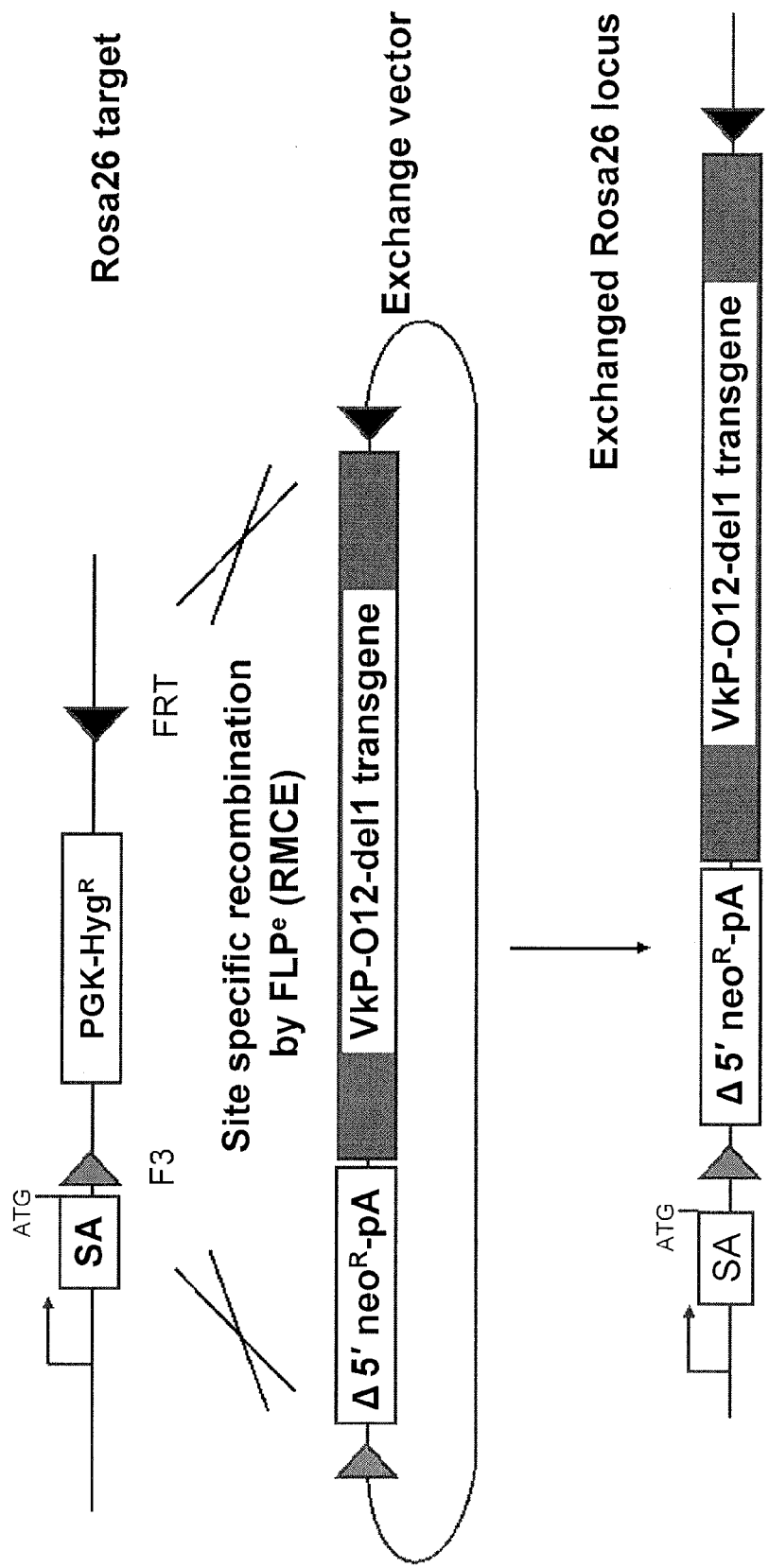

An outline of the pVkP-O12-del1 vector and the targeting strategy is depicted in FIGS. 20B and 21B. The vector was introduced into ES cells following standard procedures (see Example 14).

Example 12: Construction of a VK Promoter-Driven Expression Construct Containing an IGKV1-39 Clone Lacking the CK Intron Enhancer Element and a Truncated 3' CK Enhancer Element (VkP-IGKV1-39/J-Ck-Δ2; VkP-O12-Del2)

Figure 11:
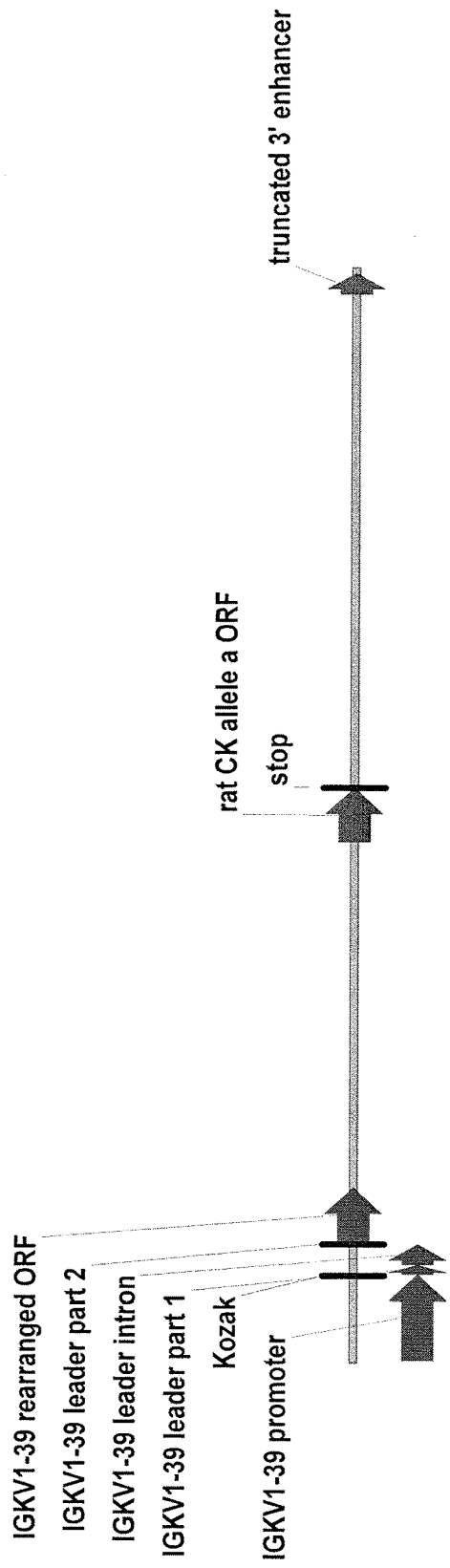
FIG. 11: Construct topology of VkP-IGKV1-39/J-Ck-Δ2 VkP-O12-del2) is identical to VkP-IGKV1-39/J-Ck-Δ1 from FIG. 10 except that a large piece of the intergenic region between the Ck gene and 3' enhancer is deleted. In addition, the 3' enhancer is reduced in size from 809 bp to 125 bp.

The construct described in Example 11 was modified by truncating the 3' CK enhancer element and deleting part of the intergenic region 3' of the rat Ck gene, to remove potential inhibitory elements. This was achieved by removing the intergenic sequence between an EcoRV site (located 3' of the rat Ck gene) and the NcoI site present in the 3' enhancer (5993 bp) and further removing the sequence between the 3' enhancer BstXI site and the BstXI site 3' of the 3' enhancer (474 bp) using standard methods. The resulting expression cassette is shown in FIG. 11 and named VkP-IGKV1-39/J-Ck-Δ2 (VkP-O12-del2).

Figure 20C:
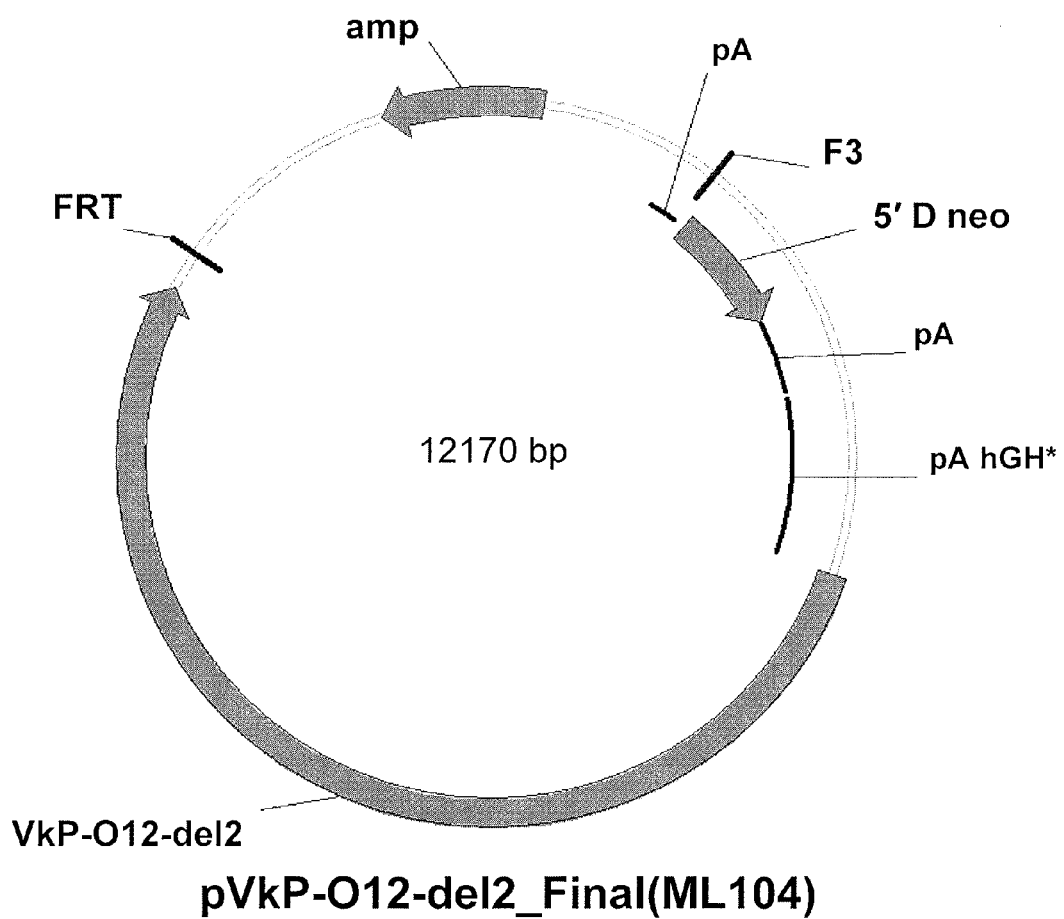
Figure 21C:
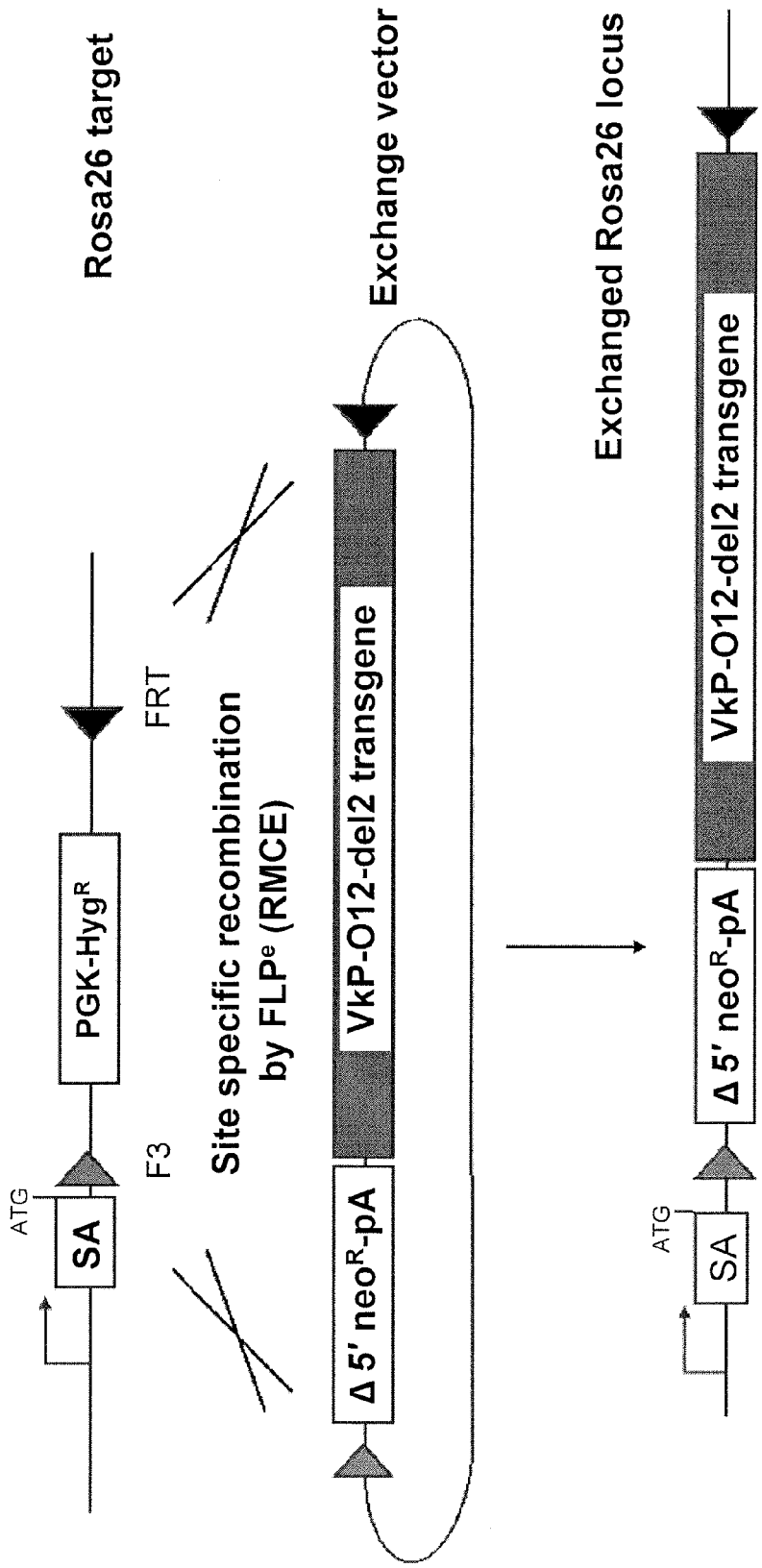

An outline of the pVkP-O12-del2 vector and the targeting strategy is depicted in FIGS. 20C and 21C. The vector was introduced into ES cells following standard procedures (see Example 14).

Example 13: Expression of Vk Constructs in Cell Lines

The constructs described in Examples 9-12 are tested for their ability to produce light chain proteins in the myeloma cell lines MPC11 (ATCC CCL167), B-cell lymphoma WEHI231 (ATCC CRL-1702), the T-cell lymphoma EL4 (ATCC TIB-39) and in HEK293 (ATCC CRL1573). The enhancer and promoter elements in the construct enable expression in the B-cell lines but not in cell lines derived from other tissues. After transfection of the cell lines using purified linearized DNA and Fugene6 (Roche) cells are cultured for transient expression. Cells and supernatant are harvested and subjected to SDS-PAGE analysis followed by western blotting using a specific anti-rat-C-kappa antibody. Supernatants are analyzed in ELISA for secreted L chains using the anti-rat CK antibody (Beckton Dickinson #550336).

Example 14: Generation of Transgenic ES Lines

All constructs as described in Examples 3, 4, 5, 6, 9, 10, 11 and 12 were used to generate individual stable transgenic ES lines by means of homologous recombination. The methods for generation of transgenic ES lines via homologous recombination are known in the field (e.g., Eggan et al., PNAS 98:6209-6214; J. Seibler, B. Zevnik, B. Küter-Luks, S. Andreas, H. Kern, T. Hennek, A. Rode, C. Heimann, N. Faust, G. Kauselmann, M. Schoor, R. Jaenisch, K. Rajewsky, R. Kühn, F. Schwenk (2003), *Nucleic Acids Res.*, February 15; 31(4):e12; Hogan et al. (Cold Spring Harbor Laboratory Press, Cold Spring Harbor N.Y.), pp. 253-289).

For all constructs described in Examples 5 and 6, and Examples 9-12, the RMCE ES cell line (derived from mouse strain 129S6B6F1-Gt(ROSA)26Sortm10Arte) was grown on a mitotically inactivated feeder layer comprised of mouse embryonic fibroblasts (MEF) in DMEM High Glucose medium containing 15% FBS (PAN 1302-P220821). Leukemia Inhibitory Factor (Chemicon ESG 1107) was added to the medium at a concentration of 900 U/mL. For manipulation, $2\times10^5$ ES-cells were plated on 3.5 cm dishes in 2 ml medium. Directly before transfection, 2 ml fresh medium was added to the cells. Three μl Fugene6 Reagent (Roche; Catalog No. 1 814 443) was mixed with 100 μl serum free medium (OptiMEM I with Glutamax I; Invitrogen; Catalog No. 51985-035) and incubated for five minutes. One hundred μl of the Fugene/OptiMEM solution was added to 2 μg circular vector and 2 μg CAGGS-Flp and incubated for 20 minutes. This transfection complex was added dropwise to the cells and mixed. Fresh medium was added to the cells the following day. From day 2 onwards, the medium was replaced daily with medium containing 250 μg/mL G418 (Geneticin; Invitrogen; Catalog No. 10131-019). Seven days after transfection, single clones were isolated, expanded, and molecular analyzed by Southern blotting according to standard procedures.

Figure 14A:
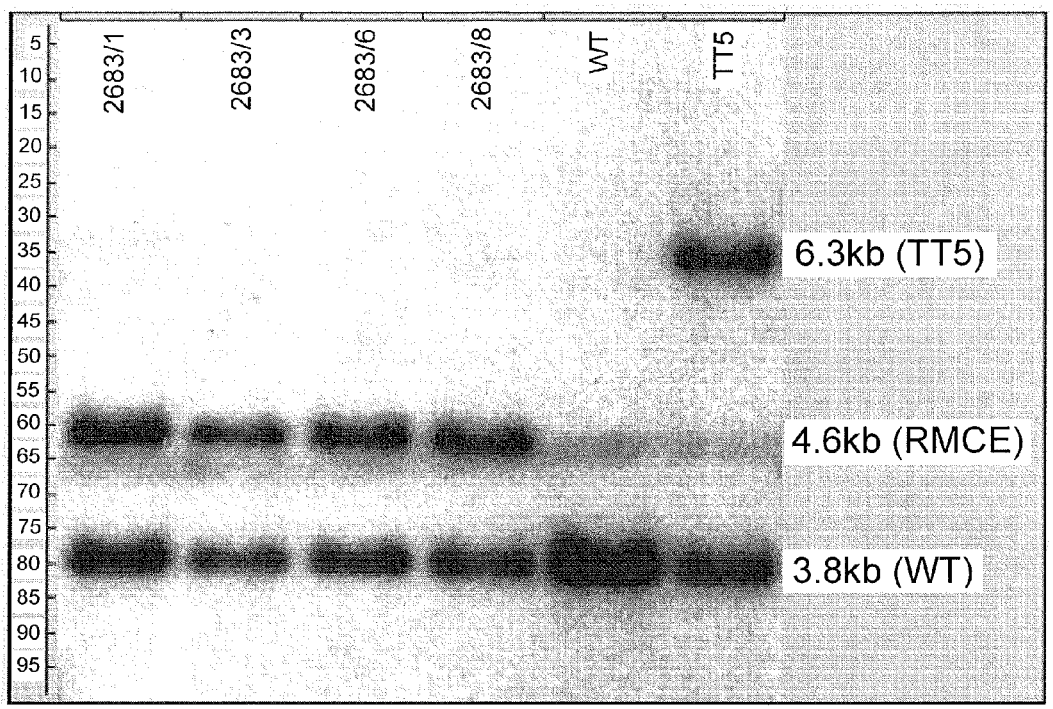
FIGS. 14A-C.
Figure 14B:
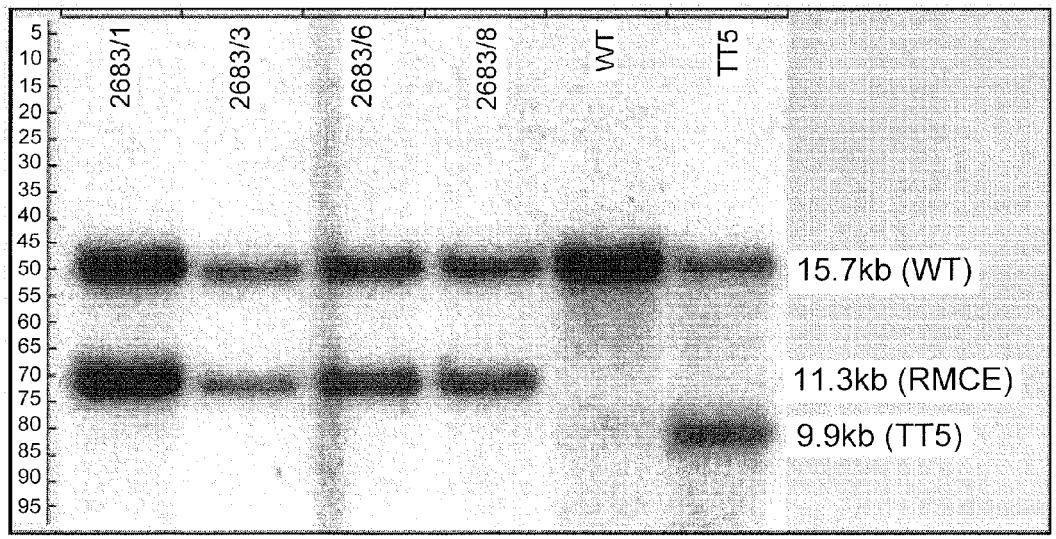
Figure 14C:
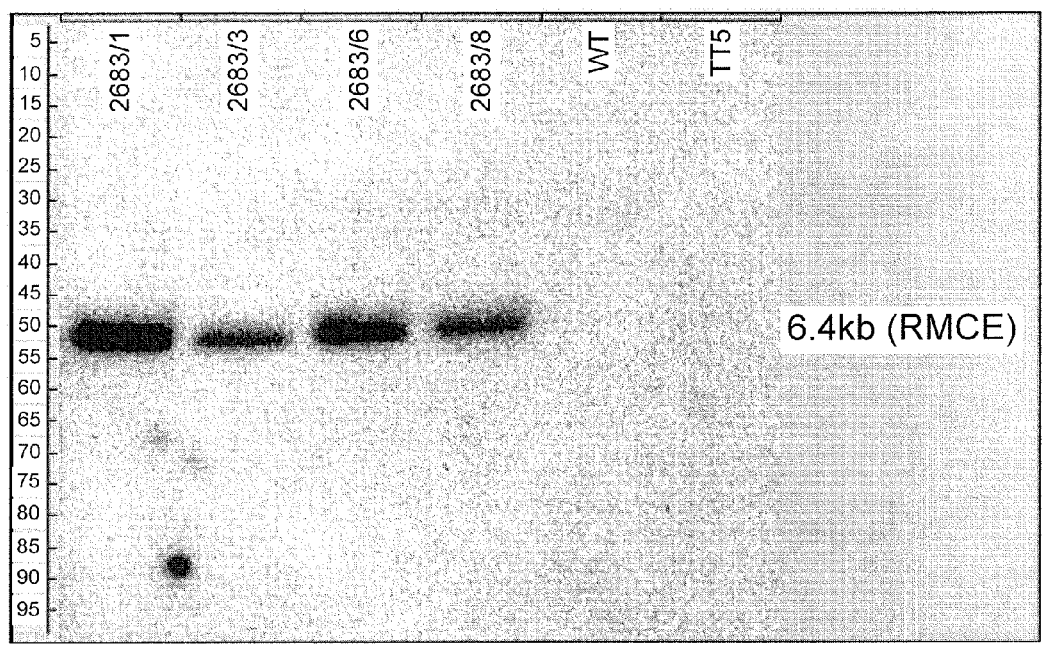

For each construct, analysis of multiple clones by restriction enzyme digestion of genomic DNA of single clones followed by hybridization with 5' probes, 3' probes, and internal probes resulted in clones that comprised a correct, single insertion at the correct position in the Rosa26 locus. An example is provided in FIGS. 14A-C.

Example 15: Generation of Transgenic Mouse Strains

All ES cell lines that were generated and verified for their modifications as described in Example 14 were used to generate stable transgenic mice by means of tetraploid recombination. The methods are known in the field. In general, after administration of hormones, superovulated Balb/c females were mated with Balb/c males. Blastocysts were isolated from the uterus at dpc 3.5. For microinjection, blastocysts were placed in a drop of DMEM with 15% FCS under mineral oil. A flat tip, piezo actuated microinjection-pipette with an internal diameter of 12-15 micrometers was used to inject 10-15 targeted C57BL/6 N.tac ES cells into each blastocyst. After recovery, injected blastocysts were transferred to each uterine horn of 2.5 days post coitum, pseudopregnant NMRI females. Chimerism was measured in chimeras (G0) by coat color contribution of ES cells to the Balb/c host (black/white). Highly chimeric mice were bred to strain C57BL/6 females. Depending on the project requirements, the C57BL/6 mating partners are non-mutant (W) or mutant for the presence of a recombinase gene (Flp-Deleter or Cre-deleter or CreER inducible deleter or combination of Flp-deleter/CreER). Germline transmission was identified by the presence of black, strain C57BL/6, offspring (G1).

For example, ESC clone IgVK1-39 2683 8 (see Examples 5 and 14) was injected in a total of 62 blastocysts in three independent experiments. Three litters were obtained with a total of six pups. All pups were chimeric. Three heterozygous offspring pups were obtained that were used for further crossing.

ESC Clone Kappa 2692 A-C10 (see Examples 3 and 14) was injected in a total of 54 blastocysts in three independent experiments. Three litters were obtained with a total of eleven pups, of which ten were chimeric. Eight heterozygous offspring pups were obtained that were used for further crossing.

ESC Clone Kappa 2692 B-C1 (see Examples 3 and 14) was injected in a total of 51 blastocysts in three independent experiments. Two litters were obtained with a total of six pups, of which four were chimeric. Three heterozygous offspring pups were obtained that were used for further crossing.

Example 16: Breeding

This example describes the breeding for obtaining mice that contain transgenic expression cassettes as described Example 14 and knock-out mice in which the endogenous lambda and kappa loci have been silenced. The localization of V-lambda on chromosome 16 and CD19 on chromosome 7 allow standard breeding procedures. The breeding of the co-localized Vk locus and Rosa26 locus on chromosome 6 with a distance of about 24 cM requires special attention during the screening as only a percentage of the offspring shows crossover in a way that both modifications are brought together on one chromosome.

All four loci have to be combined in a single mouse strain that is homo- or heterozygous for CD19-cre (not described) and modified Rosa26 transgene and homozygous for the other loci. Breeding is performed by standard breeding and screening techniques as appropriate and offered by commercial breeding companies (e.g., TaconicArtemis).

Example 17: Immunizations of Mice

Primary and booster immunization of mice are performed using standard protocols.

To validate the transgenic expression of human rearranged VK O12 (IGKV1-39)—rat Cκ light chains (see Examples 5, 14-16) in B cells from CD19-HuVκ1 mice and to assess its impact on VH repertoire size, diversity of VH family usage and V(D)J recombination after immunization, the CD19-HuVκ1 transgenic mice are immunized with tetanus toxin vaccine (TT vaccine) and VH sequence diversity of randomly picked clones from CD19-HuVκ1 mice are compared with TT-immunized wt mice and CD19-Cre HuVκ1 negative littermates. Data on the SHM frequency of the human Vκ O12 transgene in the immunized mice are obtained. A diverse collection of at least 40 TT-specific, clonally-unrelated mAbs containing the human VK O12 are recovered from CD19-HuVκ1 mice by phage display.

For this, three adult CD19-HuVκ1 mice are vaccinated with TT vaccine using standard immunization procedures. After immunization, serum titers are measured using TT specific ELISA (TT: Statens Serum Institute, Art. no. 2674) and spleen suspensions subjected to cell sorting by the FACS procedure after staining with a rat CK-specific monoclonal antibody to isolate transgenic B cells (clone RG7/9.1; BD Pharmingen#553901, Lot#06548). RNA from rat Cκ-positive B cells are extracted and the resulting cDNA material used for library building and SHM analysis.

The standard monoclonal mouse anti-rat Cκ antibody (clone RG7/9.1; BD Pharmingen#553901, Lot#06548) is used in FACS analysis of transgene expressing B cells (Meyer et al. (1996), *Int. Immunol.* 8:1561). The clone RG7/9.1 antibody reacts with a monotypic (common) kappa chain determinant. This anti-rat Cκ antibody (clone RG7/9.1 (BD Pharmingen#553901, Lot#06548) is labeled with R-phycoerythrin (PE) using the LYNX rapid conjugation kit according to the manufacturer's instructions for FACS analysis and sorting. The labeled antibody is firstly tested by flow cytometry for binding to rat Cκ-containing functional light chain proteins produced into transiently transfected HEK-293T cells; the un-conjugated antibody serves as a positive control. Two other antibodies shown to bind to rat Cκ by ELISA and Western-blot (see Example 7) are tested as well by flow cytometry.

Fab-phage display library building is carried out with a set of optimized degenerate PCR primers designed to amplify C57BL/6 VH genes; the minimal library size is $10^6$ clones, and minimal insert frequency is 80%. The vector used, MV1043 (FIGS. 3 and 12), contains the human Vκ O12 fused to a human Cκ region. The rat Cκ is therefore exchanged for the human counterpart in the library generation process.

Before selection, VH sequencing of 96 randomly picked clones is performed to validate VH repertoire diversity that is compared to diversity obtained from an unselected library previously generated using the same procedures from BALB/c mice immunized with TT. A library from C57Bl/6 wt mice that are immunized in the same way allows diversity comparison between two preselected libraries sharing the same vaccine and the same genetic background.

Several independent selections are performed on TT coated in immunotubes. Variables that may be included are selections using biotinylated antigens in solution or selections on captured TT. Based on the number and diversity of ELISA-positive clones obtained in the first selections, decisions on additional rounds of selection are made. Clones are considered positive when >3× positive over a negative control clone. Positive clones are analyzed by ELISA against a panel of negative control antigens to verify antigen specificity. The aim is to identify at least 40 unique VH regions, as based on unique CDR3 sequences and $V_HDJ_H$ rearrangements.

Amplification of the cDNA material from rat Cκ-positive sorted B cells is performed with a PCR forward primer specific to the human leader sequence and a PCR reverse primer specific to the rat Cκ sequence, in a region not redundant with the mouse Cκ sequence, as reported in a recent study (Brady et al. (2006), *JIM* 315:61). Primer combinations and annealing temperatures are firstly tested on cDNA from HEK-293T cells transfected with 0817676_pSELECT_0815426=pSELECT vector with IGKV1-39 DNA cassette (see Example 7).

The amplification products is cloned in pJET-1 vector and after XL1-blue transformation, 96 colonies are sequenced for assessing VL SHM frequency by direct comparison to the Vκ O12 (IGKV1-39) germline sequence. The R/S ratio method, as described in our study on human TT-specific antibodies (de Kruif et al. (2009), *J. Mol. Biol.* 387:548) allows discrimination between random mutations and antigen-driven mutations that occurred on VL sequences.

Example 18: Immunofluorescent Analysis of B Cell Populations in Transgenic Mouse Lines This example describes the use of antibodies and flow cytometry to analyze B cell populations in primary (bone marrow) and secondary (spleen, peritoneal) lymphoid organs and blood. Methods and reagents are described in Middendorp et al. (2002), *J. Immunol.* 168:2695; and Middendorp et al. (2004), *J. Immunol.* 172:1371. For analysis of early B cell development in bone marrow, cells were surface stained with combinations of antibodies (Becton Dickinson) specific for B220, CD19, CD25, IgM, IgD, mouse Ckappa, mouse Clambda and rat Ckappa to detect pro-B cells, pre-B cells, large pre-B cells, early and late immature B cells and recirculating B cell populations expressing the transgene on their surface. DAPI staining (Invitrogen) was included to exclude dead cells from the analysis and FC block (Becton Dickinson) to inhibit antibody interaction with Fc receptors on myeloid cells. For analysis of surface transgene expression on B cell populations in peripheral lymphoid organs and blood, cells were stained with combinations of antibodies (Becton Dickinson) specific for B220, CD5, CD19, CD21, CD23, IgM, IgD, mouse Ckappa, mouse Clambda and rat Ckappa. DAPI staining was included to exclude dead cells from the analysis and FC block to inhibit antibody interaction with Fc receptors on myeloid cells. In addition, combinations of antibodies (Becton Dickinson) specific for CD3, CD4, CD11b, CD11c and NK1.1 were included to determine if transgene expression occurred in cell types outside of the B cell compartment.

Three mice heterozygous for the human IGKV1-39/rat Ckappa transgene and heterozygous for the CD19-Cre transgene on a C57BL6 background (HuVk1/CD19-Cre) were analyzed. As controls for the FACS analysis, three littermate mice wild-type for the human IGKV1-39/rat Ckappa transgene and heterozygous for the CD19-Cre transgene on a C57BL6 background (CD19-Cre) and two C57BL6/NTac mice (Wt) were included. All animals were allowed to acclimatize in the animal facility for one week before analysis and all mice were male and six weeks of age. Lymphocytes were isolated from the femurs, spleens, peritoneal cavity and blood of mice using conventional techniques as previously described (Middendorp et al. (2002), *J. Immunol.* 168:2695; and Middendorp et al. (2004), *J. Immunol.* 172:1371). Antibodies were pre-combined as shown in FIG. 29A-B and staining was carried out in 96-well plates. Incubation with the PE-conjugated anti-rat C kappa (described above) was carried out before staining with the rat anti-murine antibodies to avoid non-specific binding. After completion of cell staining, labeled cells were analyzed on a Becton Dickinson LSR II FACS machine and the acquired data analyzed with FlowJo software (v6.4.7).

Transgenic mice were similar in weight, appearance and activity to wild-type mice. No gross anatomical alterations were observed during the harvesting of tissues. No difference was observed in the numbers of B cells in the bone marrow (BM) and spleen (Table 9) or in the numbers of B cells, T cells and myeloid cells in peripheral organs between transgenic and wild-type mice. In addition, the frequency or proportion of the cells in the different lymphocyte developmental pathways was not altered in transgenic mice when compared to wild-type mice. Thus in the double transgenic (HuVk1/CD19-Cre) and transgenic (CD19-Cre) mice lymphoid and most importantly B cell development was indistinguishable from wild-type mice.

Figure 23:
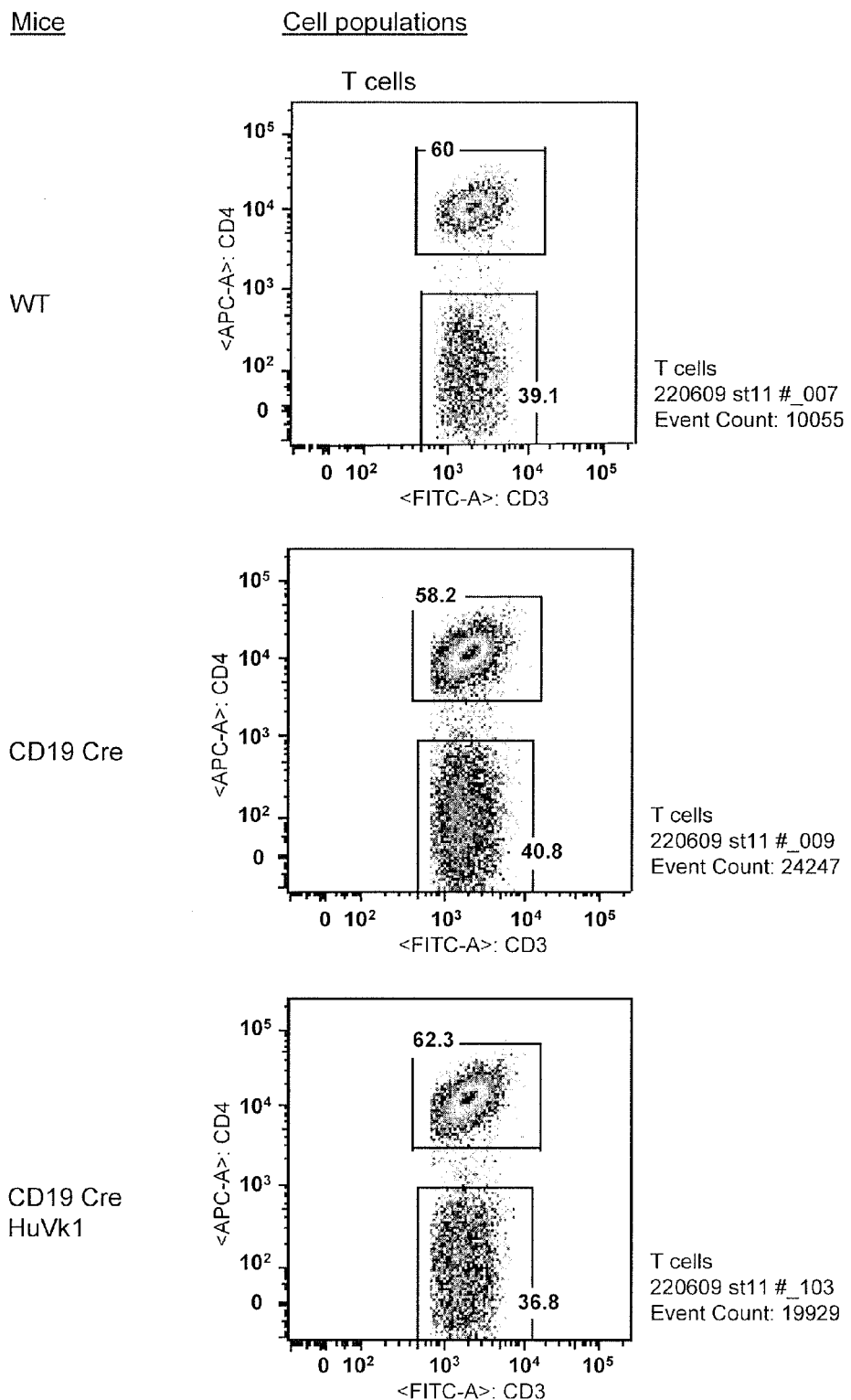
FIG. 23: Lack of transgenic human Vk1 light chain expression in non-B cell populations of the spleen.
Figure 24:
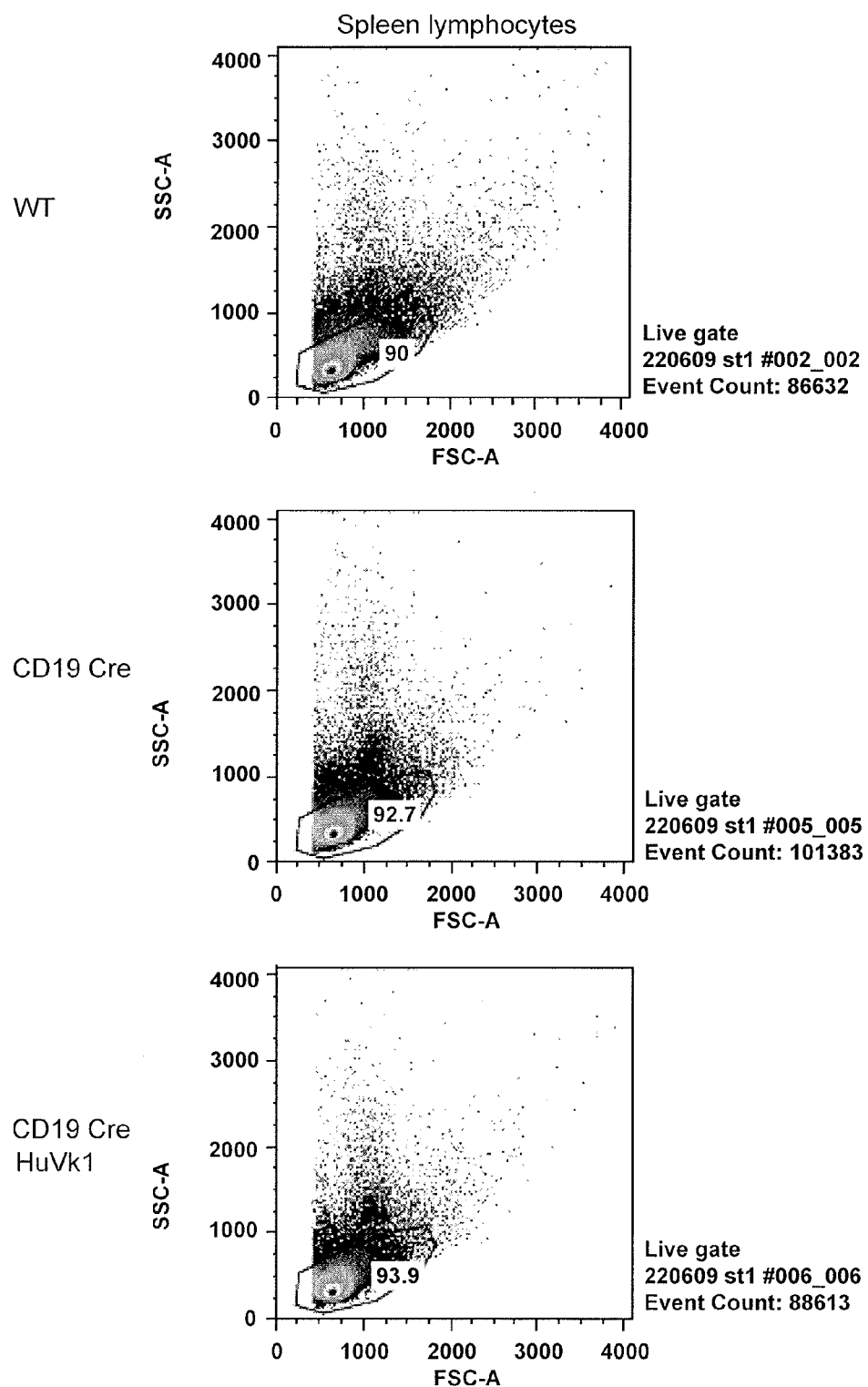
FIG. 24: Transgenic human Vk1 light chain is expressed in all B cell populations of the spleen.
Figure 25:
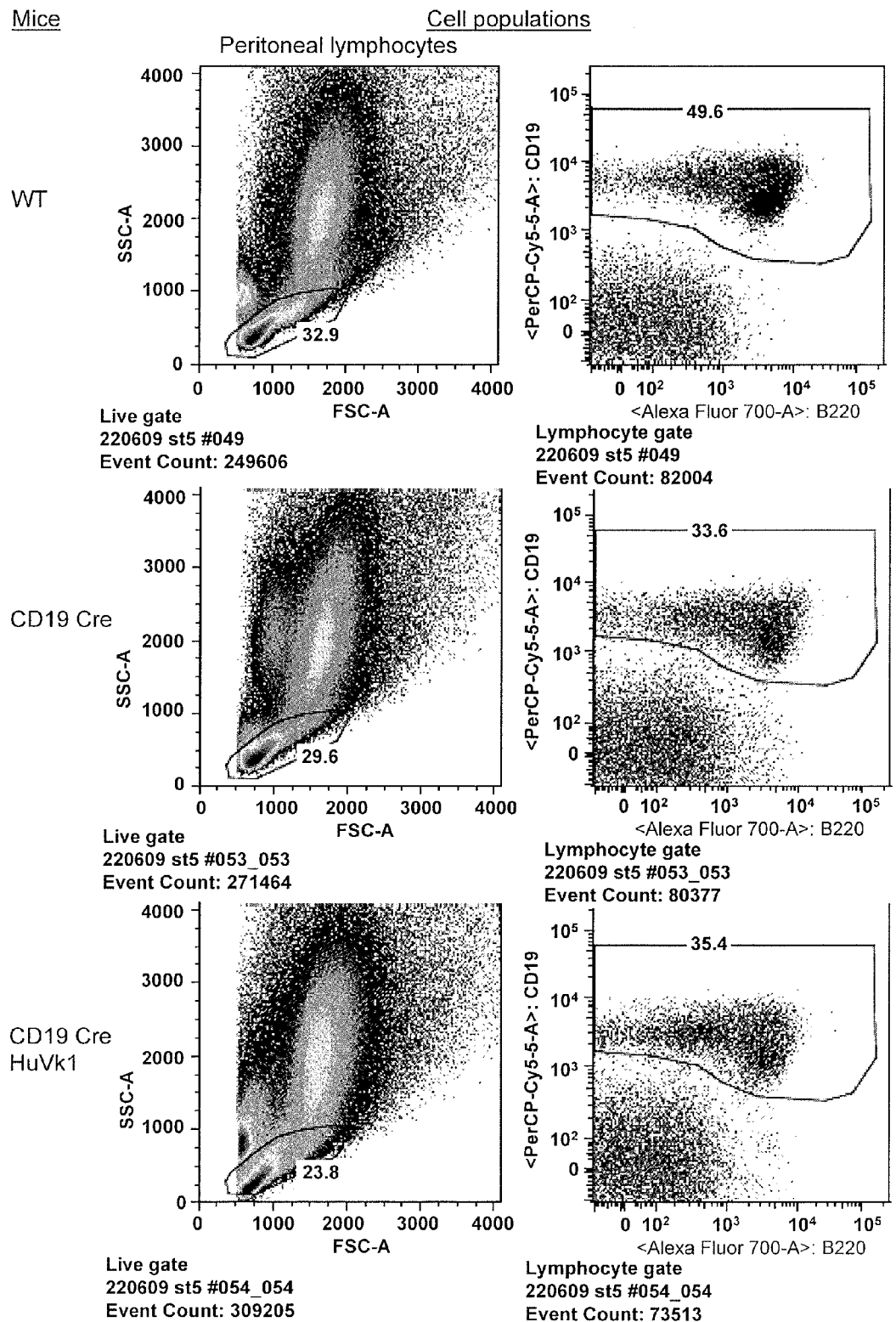
FIG. 25: Transgenic human Vk1 light chain is expressed in B1 cells of the peritoneal cavity.

In the peripheral lymphoid organs, staining with the transgene specific antibody (anti-ratCkappa-PE) was only observed in the B cell populations. T cell, myeloid cell and NK cell populations were all negative for surface expression of the transgene in the spleen (FIG. 23). In contrast, in cells stained with the pan B cell markers B220 and CD19 all cells were shifted to the right in the FACS plot indicating cell surface expression of the transgene (FIG. 24). A similar transgene-specific staining was measured in $CD5^+$ B1 cells of the peritoneum, a developmentally distinct population of B cells (FIG. 25).

Figure 26A:
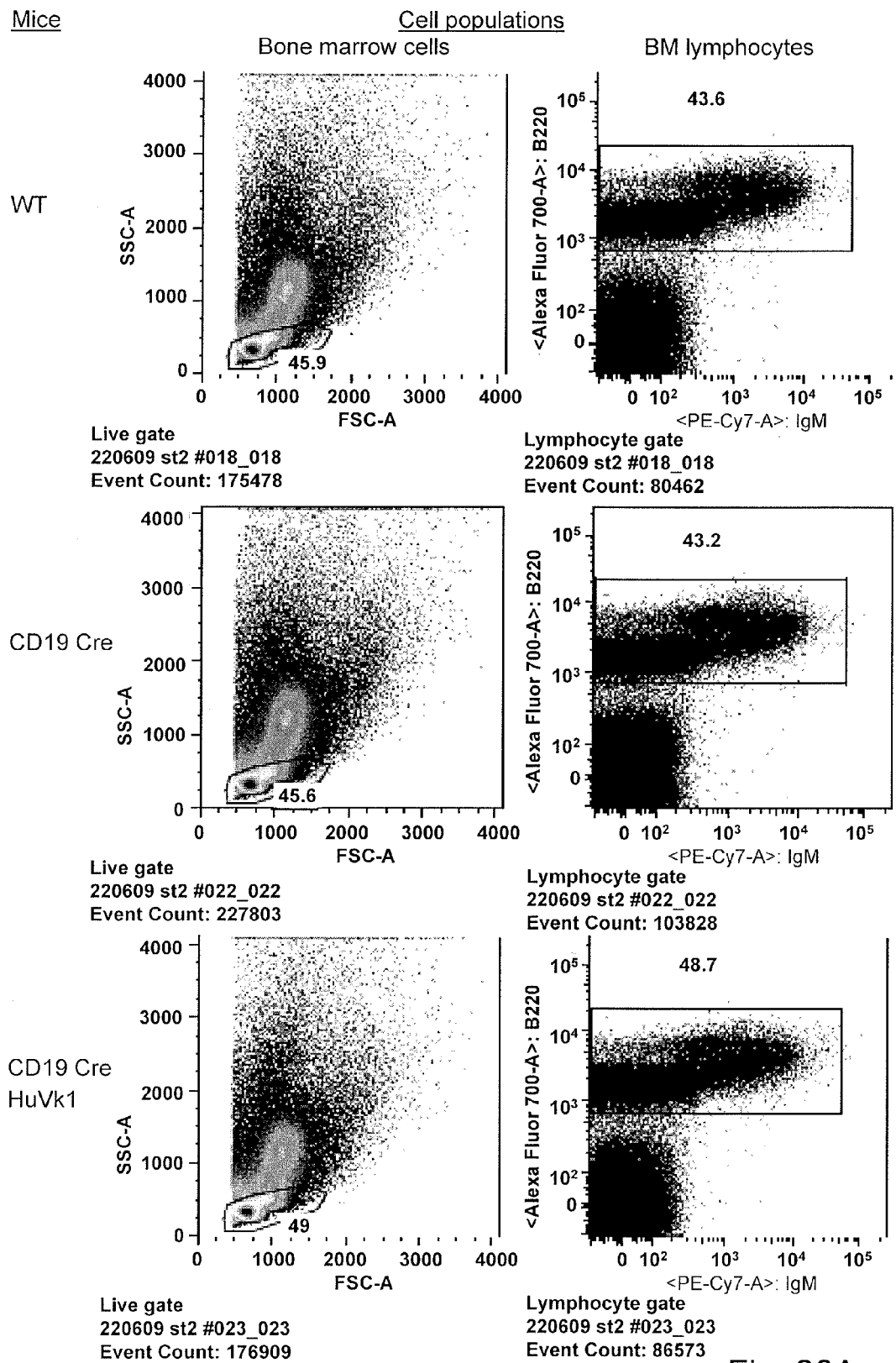
FIGS. 26A-B: Transgenic human Vk1 light chain is not expressed in pro- and pre-B cells but in the immature and recirculating populations B cells in the bone marrow.
Figure 26B:
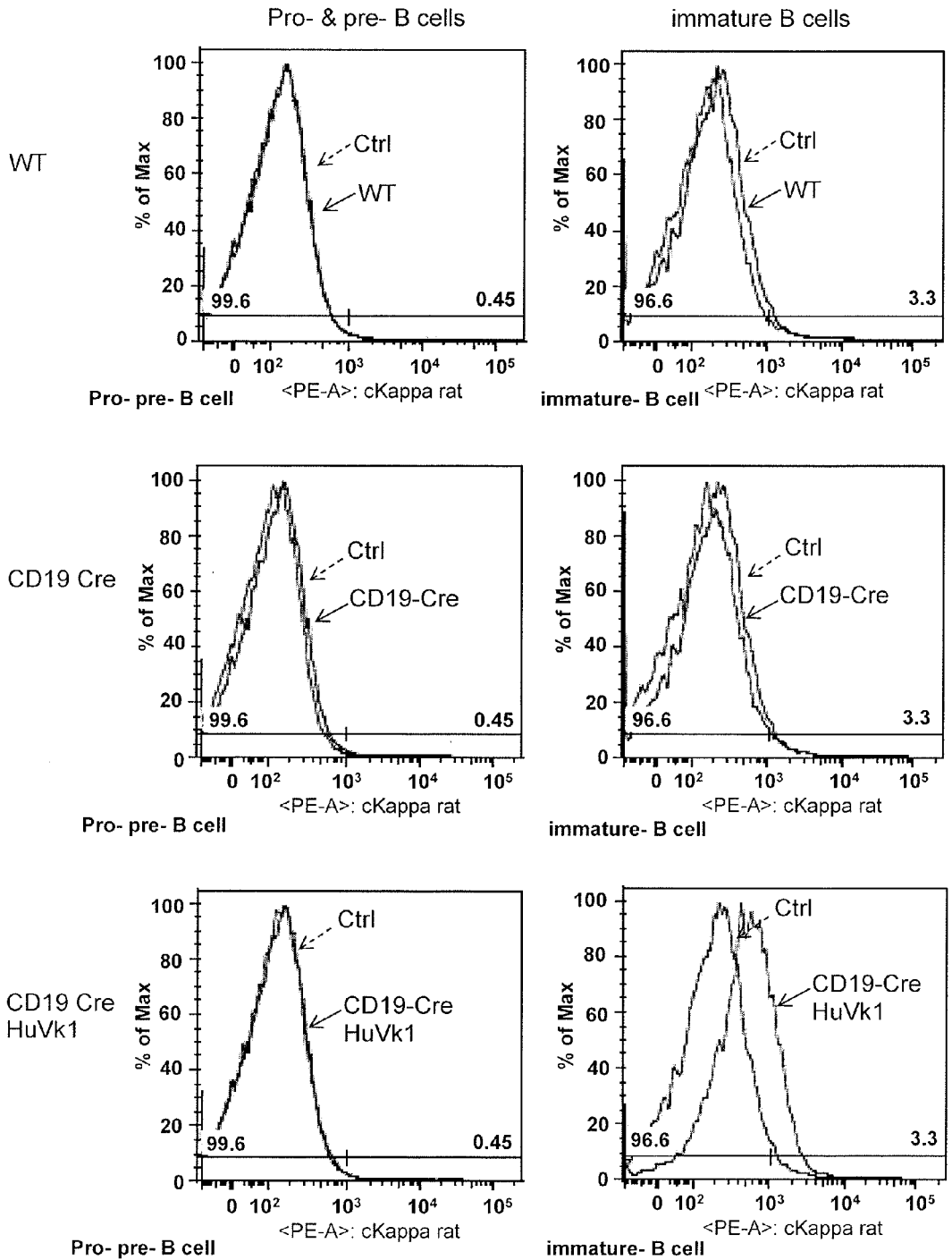
Figure 27:
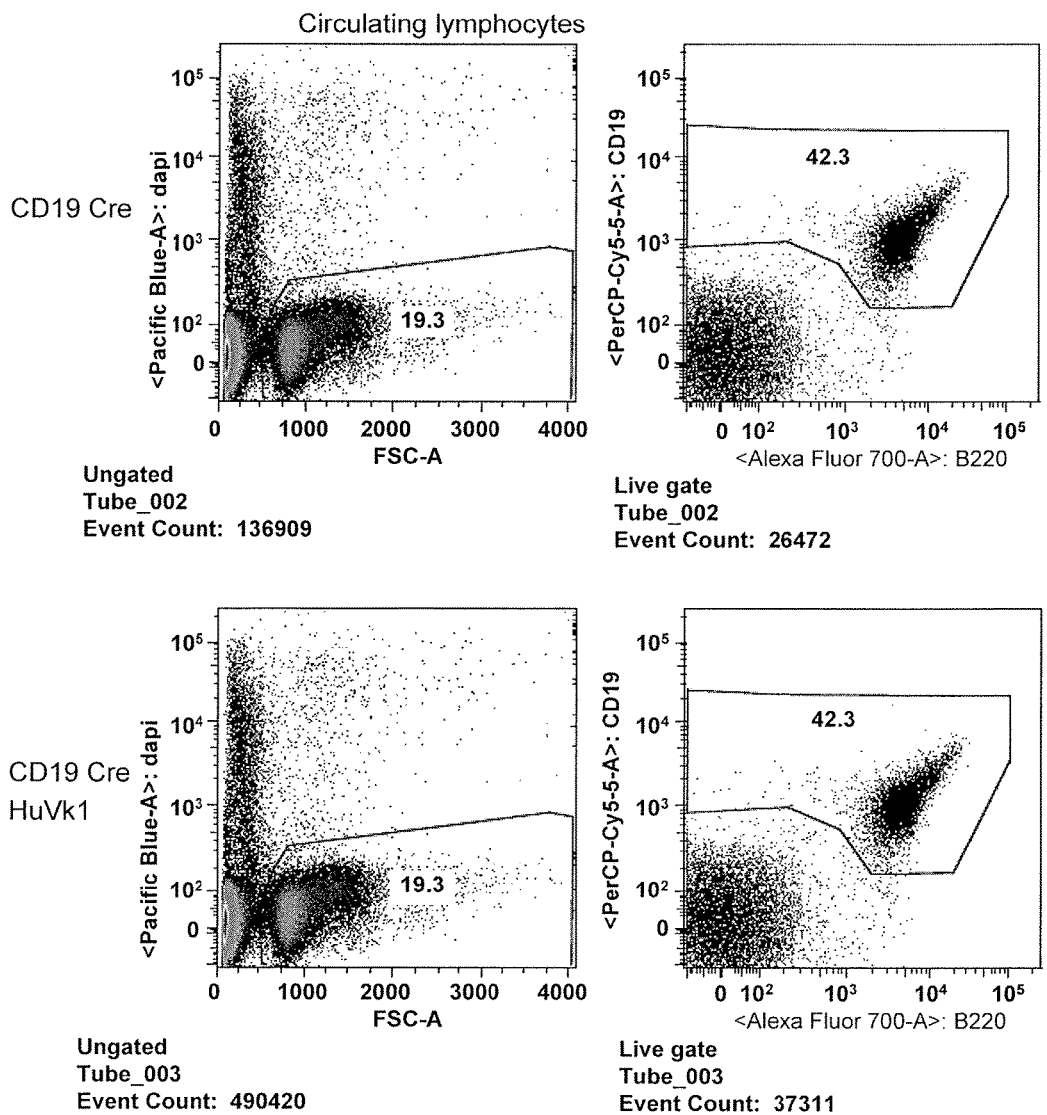
FIG. 27: Transgenic human Vk1 light chain is directly correlated with endogenous light chain and IgM expression in circulating B cells in the blood.

Differentiation of B cells from multilineage precursors to mature B cells occurs in the bone marrow. In the lymphocytes analyzed from the bone marrow, extracellular and transgene expression was not detectable in the earliest B cell progenitors the pro- and pre-B cell consistent with the pattern of normal light chain expression (FIGS. 26A-B). Transgene expression first becomes detectable in immature B cells, the developmental stage at which the germline murine light chain undergoes rearrangement and is expressed at the cell surface in the context of the preselected heavy chain (FIGS. 26A-B). Consistent with the staining in the spleen transgenic light chain expression is also detected on mature recirculating B cells (FIGS. 26A-B). Thus the CD19-Cre driven expression of the transgene is consistent with the normal pattern of light chain expression. The staining with the endogenous light chain-specific antibody is more intense than that of the transgene-specific light chain antibody. This may indicate a higher expression level of the endogenous light chain, a more sensitive staining with the endogenous light chain-specific antibody or a combination of both. Importantly, the intensity of the surface expression of the transgenic light chain is correlated with both endogenous light chain and IgM surface expression as observed in staining of circulating B cells in the blood (FIG. 27).

Thus, overall this analysis demonstrates that expression of the human IGKV1-39/Ckappa transgene is restricted to the B cell compartment and the temporal regulation of its expression is similar to the endogenous kappa and lambda light chains resulting in normal development of all B cell populations. The apparent lower level of expression of the transgene could be explained by the strength of the promoter in comparison to the promoter and enhancers present on endogenous light chain genes or by a delay in transgene expression that gives the endogenous light chains a competitive advantage in pairing with the rearranged heavy chain. This is consistent with the observation that as B cells mature the relative intensity of transgene staining increases compared to the endogenous light chains. In addition, the observation that B cells numbers are normal and that every surface Ig+ B cell co-expresses an endogenous and transgenic light chain supports the conclusion that the IGKV1-39 variable region is capable of pairing with a normal repertoire of different murine heavy chain variable regions. We conclude from this analysis that insertion of the IGKV1-39/rat Ckappa transgene driven by the CD19-Cre activated CAGGS promoter in the Rosa locus facilitates timely and B cell-specific expression of the transgene and that the transgene is capable of pairing with a normal repertoire of murine heavy chains.

Example 19: Epibase® T-Cell Epitope Profile for IGKV1-39

The protein sequence of IGKV1-39 (FIG. 12, human germline IGKV1-39/J Protein) was scanned for the presence of putative HLA class II restricted epitopes, also known as $T_H$-epitopes. For this, Algonomics' Epibase® platform was applied to IGKV1-39. In short, the platform analyzes the HLA binding specificities of all possible 10-mer peptides derived from a target sequence (Desmet et al. (1992), *Nature* 356:539-542; Desmet et al. (1997), *FASEB J.* 11:164-172; Desmet et al. (2002), *Proteins* 48:31-43; Desmet et al. (2005), *Proteins* 58:53-69). Profiling is done at the allotype level for 20 DRB1, 7 DRB3/4/5, 13 DQ and 7 DP, i.e., 47

HLA class II receptors in total (see Table 5). Epibase® calculates a quantitative estimate of the free energy of binding $\Delta G_{bind}$ of a peptide for each of the 47 HLA class II receptors. These data were then further processed as follows:

Free energies were converted into Kd-values through $\Delta G_{bind}$=RT ln(Kd).

Peptides were classified as strong (S), medium (M), weak and non (N) binders. The following cutoffs were applied:

S: strong binder: Kd<0.1 μM.

M: medium binder: 0.1 μM≤Kd<0.8 μM.

N: weak and non-binder: 0.8 μM≤Kd.

Peptides corresponding to self-peptides were treated separately. The list of self-peptides was taken from 293 antibody germline sequences. They are referred to as "germline-filtered" peptides.

S- and M-peptides are mapped onto the target sequence in so-called epitope maps; S-affinities are plotted quantitatively; M-values are presented qualitatively. As a general overview of the results, Table 6 lists the number of strong and medium binders in the analyzed proteins, for the groups of HLA class II receptors corresponding to the DRB1, DQ, DP and DRB3/4/5 genes. Counting was done separately for strong and medium affinity binders. Peptides binding to multiple allotypes of the same group were counted as one. Values between brackets refer to germline-filtered peptides. In Table 7, the sequence is shown in a format suitable for experimental work. The sequence is broken down in consecutive 15-mers overlapping by 12 residues. For each 15-mer, the promiscuity is listed (the number of allotypes out of a total of 47 for which the 15-mer contains a critical binder), as well as the implied serotypes. The Epibase® profile and epitope maps are shown in FIGS. 16A-C and 17.

It was concluded that IGKV1-39 contains no strong non-self DRB1 binders. Typically, significantly more binders were found for DRB1 than for other HLA genes. This is in agreement with experimental evidence that allotypes belonging to the DRB1 group are more potent peptide binders. Medium strength epitopes for DRB1 allotypes are expected to contribute to the population response, and cannot be disregarded. Again, no non-self DRB1 binders were found in IGKV1-39.

In the humoral response raised against an antigen, the observed $T_H$ cell activation/proliferation is generally interpreted in terms of the DRB1 specificity. However, one cannot ignore the possible contribution of the DRB3/4/5, DQ and DP genes. Given the lower expression levels of these genes as compared to DRB1, the focus was on the class of strong epitopes for DRB3/4/5, DQ and DP. "Critical epitopes" are those epitopes that are strong binders for any DRB1, DRB3/4/5, DQ or DP allotype or are medium binders for DRB1. IGKV1-39 contains no strong or medium non-self binders for DRB3/4/5, DQ, or DP.

A number of peptides are also present in germline sequences (values between brackets in Table 6). Such peptides may very well bind to HLA but they are assumed to be self and, hence, non-immunogenic. In total, six strong and 16 medium germline-filtered DRB1 binders were found in IGKV1-39. Framework region 1 up to framework region 3 is an exact match for germline V-segment VKI 2-1-(1) O12 (VBase), a.k.a. IGKV1-39*01 (IMGT). Framework region 4 is an exact match for germline J-segment JK1 (V-base) a.k.a. IGKJ1*01(IMGT). It is hardly surprising that these segments do not contain any non-self epitopes.

Example 20: Production Characteristics of IGKV1-39

Figure 28:
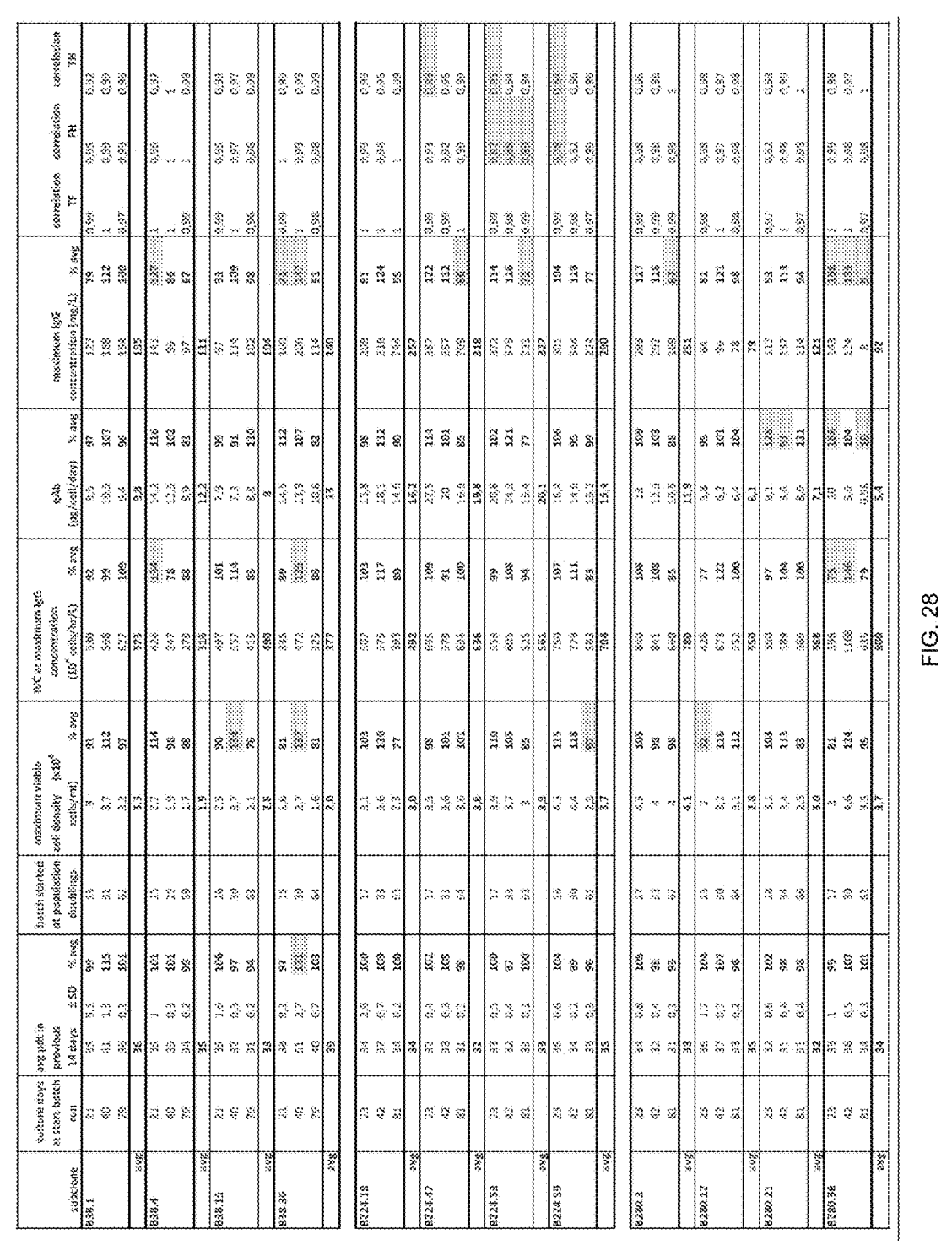

There is a great demand for antibody discovery platforms that yield therapeutic antibodies that are thermodynamically stable and give good expression yields. These characteristics are important in ensuring the stability of the drug substance during production and after injection of the drug product into the patient. In addition good expression yields impact directly on the cost of drug manufacture and thus pricing, patient access and profitability. Virtually all therapeutic antibodies in clinical use today are composed of human IgG1 and kappa constant regions but use different heavy and light chain variable regions that confer specificity. Human variable heavy and light chain domains can be divided into families that have greater than 80% sequence divergence. When rearranged examples of these families in germline configuration are combined and compared for stability and yield it is clear that the gene families are not equal in terms of biophysical properties. In particular $V_H3$, $V_H1$ and $V_H5$ have favourable stability for the heavy chains and Vk1 and Vk3 have the best stability and yield of light chains. In addition when mutations are introduced as part of the somatic hypermutation process they can interfere with $V_H/V_L$ pairing. To assess the effect that different light chain genes with different rates of mutation have on the production characteristics of a fixed $V_H$ chain, a Fab phage display library was built of light chains (kappa and lambda) from six naïve healthy donors combined with a panel of 44 TT binding heavy chains from immunized donors. After one round of selection TT binding Fab clones were isolated. Several of these shared the same $V_H$ gene as the TT clone PG1433 in combination with different light chains. The Fab light chain fragments were recloned into a kappa expression vector and transfected in combination with DNA encoding the heavy chain of PG1433 into 293 cells and specific IgG production measured by ELISA. As demonstrated in Table 8 the selected clones containing PG1433 $V_H$ combined with different light chains had between five- and ten-fold lower protein expression PG1433 $V_H$ combined with IGKV1-39. Note that all of the light chains contained amino acid mutations within their coding regions that might disrupt $V_H$ paring and reduce production stability. Thus, in addition to reducing the chances of unwanted immunogenicity, it is expected that the use of the light chain IGKV1-39 without mutations contributes to improved production stability and yields of various specificity-contributing $V_H$ genes. Indeed stable clones generated by the transfection of different $V_H$ genes all paired with IGKV1-39 are able to be passaged extensively and still retain robust production characteristics as shown in FIG. 28.

Example 21: Generation of Mice Expressing Fully Human VH and VL Regions

Transgenic mice described herein are crossed with mice that already contain a human VH locus. Examples of appropriate mice comprising a human VH locus are disclosed in Taylor et al. (1992), *Nucleic Acids Res.* 20:6287-95; Lonberg et al. (1994), *Nature* 368:856-9; Green et al. (1994), *Nat. Genet.* 7:13-21; Dechiara et al. (2009), *Methods Mol. Biol.* 530:311-24.).

After crossing and selecting for mice that are at least heterozygous for the IGKV1-39 transgene and the human VH locus, selected mice are immunized with a target. VH genes are harvested as described hereinabove. This method has the advantage that the VH genes are already fully human and thus do not require humanization.

Example 22: Isolation, Characterization, Oligoclonics Formatting and Production of Antibodies Targeting Human IL6 for Treatment of Chronic Inflammatory Diseases Such as Rheumatoid Arthritis A spleen VH repertoire from transgenic mice that are immunized with human recombinant IL6 is cloned in a phage display Fab vector with a single human IGKV1-39-C kappa light chain (identical to the mouse transgene) and subjected to panning against the immunogen human IL6. Clones that are obtained after two to four rounds of panning are analyzed for their binding specificity. VH genes encoding IL6-specific Fab fragments are subjected to sequence analysis to identify unique clones and assign VH, DH and JH utilization. The Fab fragments are reformatted as IgG1 molecules and transiently expressed. Unique clones are then grouped based on non-competition in binding assays and subjected to affinity and functional analysis. The most potent anti-IL6 IgG1 mAbs are subsequently expressed as combinations of two, three, four or five heavy chains comprising different VH-regions in the Oligoclonics format, together with one IGKV1-39-C-based kappa light chain and tested in vitro for complex formation with IL-6. The Oligoclonics are also tested in vivo for clearance of human IL-6 from mice. An Oligoclonic with the most potent clearance activity is chosen and the murine VH genes humanized according to conventional methods. The humanized IgG1 are transfected into a mammalian cell line to generate a stable clone. An optimal subclone is selected for the generation of a master cell bank and the generation of clinical trial material.

Many of the protocols described here are standard protocols for the construction of phage display libraries and the panning of phages for binding to an antigen of interest and are described, for example, in *Antibody Phage Display: Methods and Protocols* (2002), Editor(s) Philippa M. O'Brien, Robert Aitken, Humana Press, Totowa, N.J., USA.

Immunizations

Transgenic mice receive three immunizations with human IL6 every two weeks using the adjuvant Sigma titerMax according to manufacturer's instructions.

RNA Isolation and cDNA Synthesis

Three days after the last immunization, spleens and lymphnodes from the mice are removed and passed through a 70 micron filter into a tube containing PBS pH 7.4 to generate a single cell suspension. After washing and pelleting of lymphocytes, cells are suspended in TRIzol LS Reagent (Invitrogen) for the isolation of total RNA according to the manufacturer's protocol and subjected to reverse transcription reaction using 1 microgram of RNA, Superscript III RT in combination with dT20 according to manufacturer's procedures (Invitrogen).

The generation of Fab phage display libraries is carried out as described in Example 2.

Selection of Phages on Coated Immunotubes

Human recombinant IL6 is dissolved in PBS in a concentration of 5 µg/ml and coated to MAXISORP™ Nunc-Immuno Tube (Nunc 444474) overnight at 4° C. After discarding the coating solution, the tubes are blocked with 2% skim milk (ELK) in PBS (blocking buffer) for one hour at Room Temperature (RT). In parallel, 0.5 ml of the phage library is mixed with 1 ml blocking buffer and incubated for 20 minutes at room temperature. After blocking the phages, the phage solution is added to the IL6-coated tubes and incubated for two hours at RT on a slowly rotating platform to allow binding. Next, the tubes are washed ten times with PBS/0.05% TWEEN™-20 detergent followed by phage elution by incubating with 1 ml 50 mM glycine-HCl pH 2.2 ten minutes at RT on rotating wheel and directly followed by neutralization of the harvested eluent with 0.5 ml 1 M Tris-HCl pH 7.5.

Harvesting Phage Clones

A 5 ml XL1-Blue MRF (Stratagene) culture at O.D. 0.4 is added to the harvested phage solution and incubated for 30 minutes at 37° C. without shaking to allow infection of the phages. Bacteria are plated on Carbenicillin/Tetracycline 4% glucose 2*TY plates and grown overnight at 37° C.

Phage Production

Phages are grown and processed as described by Kramer et al. 2003 (Kramer et al. 2003, *Nucleic Acids Res.* 31(11): e59) using VCSM13 as helper phage strain.

Phage ELISA

ELISA plates are coated with 100 microliters human recombinant IL6 per well at a concentration of 2.5 micrograms/ml in PBS overnight at 4° C. Plates coated with 100 microliters thyroglobulin at a concentration of 2 micrograms/ml in PBS are used as a negative control. Wells are emptied, dried by tapping on a paper towel, filled completely with PBS-4% skimmed milk (ELK) and incubated for one hour at room temperature to block the wells. After discarding the block solution, phage minipreps pre-mixed with 50 µl blocking solution are added and incubated for one hour at RT. Unbound phages are subsequently removed by five washing steps with PBS-0.05% Tween-20. Bound phages are detected by incubating the wells with 100 microliters anti-M13-HRP antibody conjugate (diluted 1/5000 in blocking buffer) for one hour at room temperature. Free antibody is removed by repeating the washing steps as described above, followed by TMB substrate incubation until color development was visible. The reaction is stopped by adding 100 microliters of 2 M H2SO4 per well and analyzed on an ELISA reader at 450 nm emission wavelength.

Sequencing

Clones that give signals at least three times above the background signal are propagated, used for DNA miniprep procedures (see procedures Qiagen miniPrep manual) and subjected to nucleotide sequence analysis. Sequencing is performed according to the Big Dye 1.1 kit accompanying manual (Applied Biosystems) using a reverse primer (CH1_Rev1, Table 1) recognizing a 5' sequence of the CH1 region of the human IgG1 heavy chain (present in the Fab display vector MV1043, FIGS. 3 and 12). The sequences of the murine VH regions are analyzed for diversity of DH and JH gene segments.

Construction and Expression of Chimeric IgG1

Figure 22:
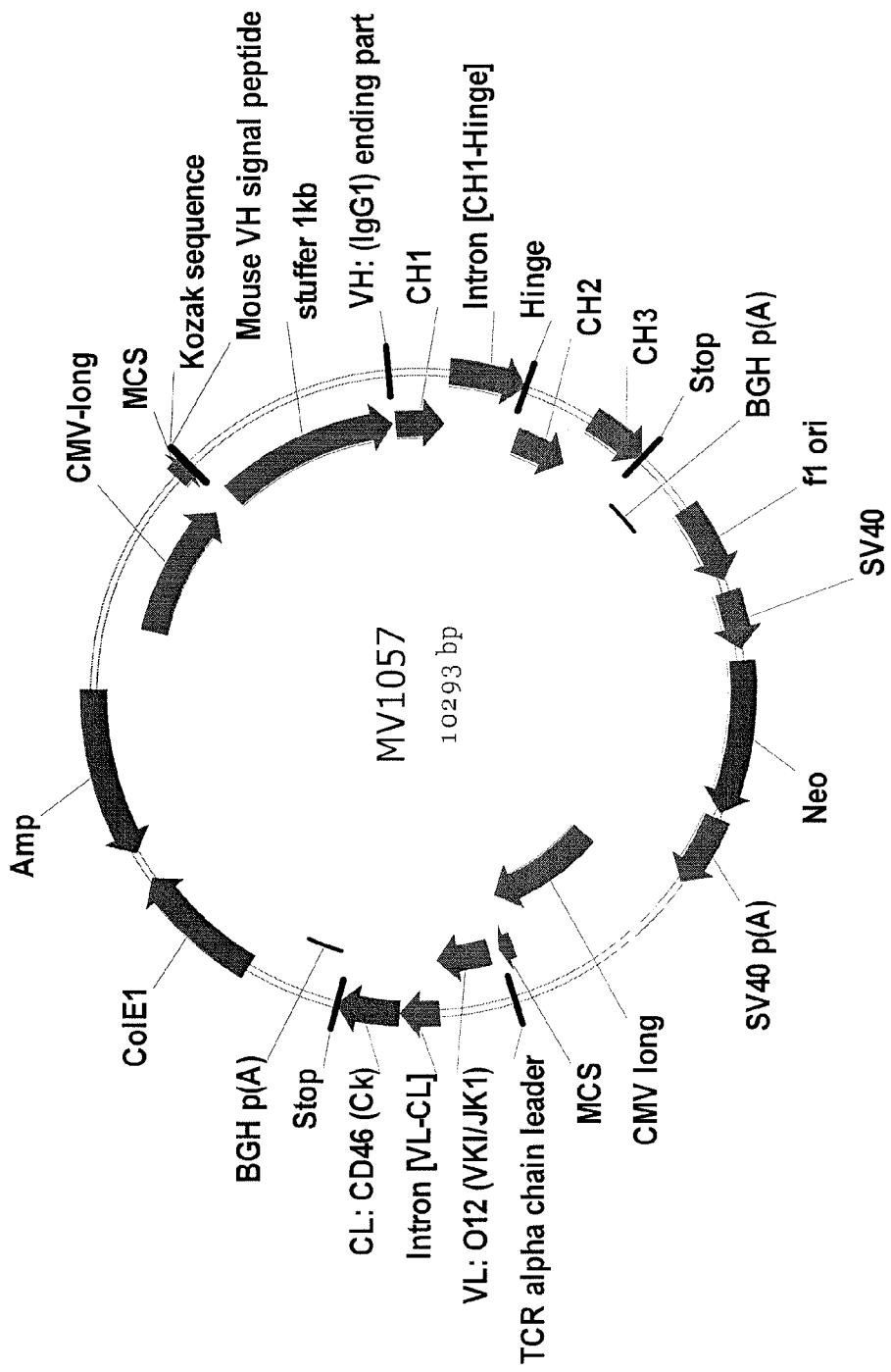
FIG. 22: Topology of the MV1057 vector. Replacing the indicated stuffer fragment with a VH fragment yields an expression vector that can be transfected to eukaryotic cells for the production of IgG1 antibodies with light chains containing an O12 (IGKV1-39) VL gene.

Vector MV1057 (FIGS. 12 and 22) was generated by cloning the transgene (IGKV1-39) L chain fragment into a derivative of vector pcDNA3000Neo (Crucell, Leiden, The Netherlands) that contains the human IgG1- and kappa constant regions. VH regions are cloned into MV1057 and nucleotide sequences for all constructs are verified according to standard techniques. The resulting constructs are transiently expressed in HEK293T cells and supernatants containing chimeric IgG1 are obtained and purified using standard procedures as described before (M. Throsby 2006, *J. Virol.* 80:6982-92).

IgG1 Binding and Competition Analysis

IgG1 antibodies are titrated in ELISA using IL6-coated plates as described above and an anti-human IgG peroxidase conjugate. Competition ELISAs to group antibodies based on epitope recognition are performed by incubating Fab phages together with IgG1 or with commercial antibodies against IL6 (e.g., Abeam cat. no. ab9324) in IL6-coated plates, followed by detection of bound Fab phage using an anti-M13 peroxidase conjugate.

IgG1 Affinity Measurements

The affinities of the antibodies to IL6 are determined with the Quantitative kinetic protocol on the Octet (ForteBio). Antibodies are captured onto an Anti-Human IgG Fc Capture biosensor and exposed to free IL6 and analyzed using proprietary software to calculate the Kd of each antibody.

Functional Activity of IL6 Antibodies

To test the ability of the selected antibodies to inhibit binding between IL6 and IL6 receptor (IL6R), an ELISA based assay is used. Various concentrations of antibody are mixed with a fixed concentration (10 ng/ml) of biotinylated IL6 as described by Naoko et al. 2007, Can. Res. 67:817-875. The IL6-antibody immune complex is added to immobilized IL6R. The binding of biotinylated IL6 to IL6R is detected with horseradish peroxidase-conjugated streptavidin. The reduction of ELISA signal is a measurement of inhibition. As positive control for inhibition of binding between IL6 and IL6R either anti-IL6R antibody (Abcam cat. no. ab34351; clone B-R6) or anti IL6 antibody (Abcam cat. no. ab9324) is used.

In vitro blocking activity of the selected anti-IL6 antibodies is measured in a proliferation assay using the IL6-dependent cell line 7TD1. Briefly, cells are incubated with different concentrations of human IL6 with or without the anti-IL6 antibody. The available amount of IL6 determines the degree of proliferation. Thus if an added antibody blocks IL6 binding the proliferation readout is reduced compared to a non binding antibody control. Proliferation is measured by the incorporation of 5-bromo-T-deoxy-uridine (BrdU) into the DNA using the BrdU proliferation kit (Roche cat. no. 11444611001) according to the manufacturer's instructions.

Generation of Anti-IL6 Oligoclonics

The most potent anti-IL6 antibodies are selected from each epitope group. The expression constructs expressing these antibodies are transfected into HEK293T cells in non-competing groups of three in different ratios (1:1:1; 3:1:1; 1:3:1; 1:1:3; 3:3:1; 1:3:3; 3:1:3; 10:1:1; 1:10:1; 1:1:10; 10:10:1; 1:10:10; 10:1:10; 3:10:1; 10:3:1; 1:10:3; 3:1:10; 10:1:3; 1:3:10). Antibody containing supernatants are harvested and purified and characterized as above.

Complex Formation and In Vivo Clearance of Anti-IL6 Oligoclonics

To measure the ability of anti-IL6 Oligoclonics to form immune complexes and to analyze these complexes Size Exclusion Chromatography (SEC) is used according to the approach disclosed by Min-Soo Kim et al. (2007), *JMB* 374:1374-1388, to characterize the immune-complexes formed with different antibodies to TNFα. Different molar ratios of the anti-IL6 Oligoclonics are mixed with human IL6 and incubated for 20 hours at 4° C. or 25° C. The mixture is analyzed on an HPLC system fitted with a size exclusion column; different elution times are correlated to molecular weight using a molecular weight standards.

The ability of antibodies to form complexes with IL6 is correlated with their ability to rapidly clear the cytokine from the circulation in vivo. This is confirmed by measuring the clearance of radiolabelled IL6 from mice. Briefly, female, six- to eight-week-old Balb/c mice are obtained and 18 hours before the experiment, the animals are injected intravenously (IV) via the lateral tail vein with different doses of purified anti-IL6 Oligoclonics. On day 0, the mice are injected IV with 50 microliters of radiolabeled IL-6 (1×10E7 cpm/mL) under the same conditions. Blood samples (approximately 50 microliters) are collected at several time intervals and stored at 4° C. The samples are centrifuged for five minutes at 4000×g and the radioactivity of the serum determined. All pharmacokinetic experiments are performed simultaneously with three animals for each treatment.

Generation of Anti-IL6 Oligoclonics Stable Clones and Preclinical Development

A lead anti-IL6 Oligoclonic is selected based on the in vitro and in vivo potency as determined above. The murine VH genes are humanized according to standard methods and combined with the fully human IGKV1-39 light chain in an expression vector as described above. Examples of humanization methods include those based on paradigms such as resurfacing (E. A. Padlan et al. (1991), *Mol. Immunol.* 28:489), superhumanization (P. Tan, D. A., et al. (2002), *J. Immunol.* 169:1119) and human string content optimization (G. A. Lazar et al. (2007), *Mol. Inzmunol.* 44:1986). The three constructs are transfected into PER.C6 cells at the predetermined optimal ratio (described above) under the selective pressure of G418 according to standard methods. A stable high producing anti-IL6 Oligoclonic clone is selected and a working and qualified master cell bank generated.

TABLE 1

List of primers

| DO- | Primer | Sequence |
|---|---|---|
| 0012 | CH1_Rev1 | TGCCAGGGGGAAGACCGATG (SEQ ID NO: 4) |
| 0656 | MVH-1 | GCCGGCCATGGCCGAGGTRMAGCTTCAGGAGTCAGGAC (SEQ ID NO: 5) |
| 0657 | MVH-2 | GCCGGCCATGGCCGAGGTSCAGCTKCAGCAGTCAGGAC (SEQ ID NO: 6) |
| 0658 | MVH-3 | GCCGGCCATGGCCCAGGTGCAGCTGAAGSASTCAGG (SEQ ID NO: 7) |
| 0659 | MVH-4 | GCCGGCCATGGCCGAGGTGCAGCTTCAGGAGTCSGGAC (SEQ ID NO: 8) |
| 0660 | MVH-5 | GCCGGCCATGGCCGARGTCCAGCTGCAACAGTCYGGAC (SEQ ID NO: 9) |
| 0661 | MVH-6 | GCCGGCCATGGCCCAGGTCCAGCTKCAGCAATCTGG (SEQ ID NO: 10) |

TABLE 1-continued

List of primers

| DO- | Primer | Sequence |
|---|---|---|
| 0662 | MVH-7 | GCCGGCCATGGCCCAGSTBCAGCTGCAGCAGTCTGG<br>(SEQ ID NO: 11) |
| 0663 | MVH-8 | GCCGGCCATGGCCCAGGTYCAGCTGCAGCAGTCTGGRC<br>(SEQ ID NO: 12) |
| 0664 | MVH-9 | GCCGGCCATGGCCCAGGTYCAGCTYCAGCAGTCTGG<br>(SEQ ID NO: 13) |
| 0665 | MVH-10 | GCCGGCCATGGCCGAGGTCCARCTGCAACAATCTGGACC<br>(SEQ ID NO: 14) |
| 0666 | MVH-11 | GCCGGCCATGGCCCAGGTCCACGTGAAGCAGTCTGGG<br>(SEQ ID NO: 15) |
| 0667 | MVH-12 | GCCGGCCATGGCCGAGGTGAASSTGGTGGAATCTG<br>(SEQ ID NO: 16) |
| 0668 | MVH-13 | GCCGGCCATGGCCGAVGTGAAGYTGGTGGAGTCTG<br>(SEQ ID NO: 17) |
| 0669 | MVH-14 | GCCGGCCATGGCCGAGGTGCAGSKGGTGGAGTCTGGGG<br>(SEQ ID NO: 18) |
| 0670 | MVH-15 | GCCGGCCATGGCCGAKGTGCAMCTGGTGGAGTCTGGG<br>(SEQ ID NO: 19) |
| 0671 | MVH-16 | GCCGGCCATGGCCGAGGTGAAGCTGATGGARTCTGG<br>(SEQ ID NO: 20) |
| 0672 | MVH-17 | GCCGGCCATGGCCGAGGTGCARCTTGTTGAGTCTGGTG<br>(SEQ ID NO: 21) |
| 0673 | MVH-18 | GCCGGCCATGGCCGARGTRAAGCTTCTCGAGTCTGGA<br>(SEQ ID NO: 22) |
| 0674 | MVH-19 | GCCGGCCATGGCCGAAGTGAARSTTGAGGAGTCTGG<br>(SEQ ID NO: 23) |
| 0675 | MVH-20 | GCCGGCCATGGCCGAAGTGATGCTGGTGGAGTCTGGG<br>(SEQ ID NO: 24) |
| 0676 | MVH-21 | GCCGGCCATGGCCCAGGTTACTCTRAAAGWGTSTGGCC<br>(SEQ ID NO: 25) |
| 0677 | MVH-22 | GCCGGCCATGGCCCAGGTCCAACTVCAGCARCCTGG<br>(SEQ ID NO: 26) |
| 0678 | MVH-23 | GCCGGCCATGGCCCAGGTYCARCTGCAGCAGTCTG<br>(SEQ ID NO: 27) |
| 0679 | MVH-24 | GCCGGCCATGGCCGATGTGAACTTGGAAGTGTCTGG<br>(SEQ ID NO: 28) |
| 0680 | MVH-25 | GCCGGCCATGGCCGAGGTGAAGGTCATCGAGTCTGG<br>(SEQ ID NO: 29) |
| 0681 | ExtMVH-1 | CAGTCACAGATCCTCGCGAATT*GGCCAGCCGGCC*ATGGCCSANG<br>(SEQ ID NO: 30) |
| 0682 | ExtMVH-2 | CAGTCACAGATCCTCGCGAATT*GGCCAGCCGGCC*ATGGCCSANC<br>(SEQ ID NO: 31) |
| 0683 | MJH-Rev1 | GGGGGTGTCGTTTTGGCTGAGGAGAC*GGTGACC*GTGG<br>(SEQ ID NO: 32) |
| 0684 | MJH-Rev2 | GGGGGTGTCGTTTTGGCTGAGGAGAC*TGTGAGA*GTGG<br>(SEQ ID NO: 33) |
| 0685 | MJH-Rev3 | GGGGGTGTCGTTTTGGCTGCAGAGAC*AGTGACC*AGAG<br>(SEQ ID NO: 34) |
| 0686 | MJH-Rev4 | GGGGGTGTCGTTTTGGCTGAGGAGAC*GGTGACT*GAGG<br>(SEQ ID NO: 35) |

TABLE 1-continued

List of primers

| DO- | Primer | Sequence |
|---|---|---|
| 0687 | ExtMJH-Rev1 & | GGGGGTGTCGTTTTGGCTGAGGAGAC*GTGACC*GTGG (SEQ ID NO: 36) |
| 0688 | ExtMJH-Rev2in | GGGGGTGTCGTTTTGGCTGAGGAGAC*GTGACA*GTGG (SEQ ID NO: 37) |
| 0690 | ExtMJH-Rev3 | GGGGGTGTCGTTTTGGCTGAGGAGAC*GTGACC*AGAG (SEQ ID NO: 38) |
| 0691 | ExtMJH-Rev4 | GGGGGTGTCGTTTTGGCTGAGGAGAC*GTGACC*GAGG (SEQ ID NO: 39) |

TABLE 2

Phage ELISA signal levels as measured at 450 nm. TT-coated plates represent plates that were coated with tetanus toxoid. Thyroglobulin-coated plates are used as negative controls. 10/10 and 15/15 indicate the number of wash steps with PBS-Tween during panning procedures. The 10/10 tetanus toxoid and 10/10 thyroglobulin plates and the 15/15 tetanus toxoid and 15/15 thyroglobulin plates are duplicates from each other except for the coating agent. OD values higher than three times the background are assumed specific.

|   | 1 | 2 | 3 | 4 | 5 | 6 | 7 | 8 | 9 | 10 | 11 | 12 |
|---|---|---|---|---|---|---|---|---|---|---|---|---|
| TT-coated plate 10/10 washings ||||||||||||||
| A | 0.139 | 0.093 | 0.089 | 0.121 | 0.117 | 0.598 | 0.146 | 0.115 | 0.18 | 0.155 | 0.543 | 0.601 |
| B | 0.136 | 0.404 | 0.159 | 0.187 | 0.489 | 0.134 | 0.216 | 0.092 | 0.222 | 0.108 | 0.181 | 0.484 |
| C | 0.197 | 0.526 | 0.09 | 0.213 | 0.395 | 0.155 | 0.108 | 0.12 | 0.183 | 0.136 | 0.092 | 0.866 |
| D | 0.143 | 0.258 | 0.101 | 0.422 | 0.088 | 0.243 | 0.485 | 0.251 | 0.304 | 0.198 | 0.478 | 0.091 |
| E | 0.445 | 0.169 | 0.526 | 0.481 | 0.206 | 0.285 | 0.111 | 0.119 | 0.128 | 0.2 | 0.118 | 0.098 |
| F | 0.237 | 0.291 | 0.594 | 0.139 | 0.206 | 0.565 | 0.543 | 0.091 | 0.136 | 0.227 | 0.228 | 0.099 |
| G | 0.459 | 0.102 | 0.152 | 0.659 | 0.203 | 0.452 | 0.152 | 0.133 | 0.094 | 0.102 | 0.375 | 0.098 |
| H | 0.341 | 0.623 | 0.745 | 0.415 | 0.682 | 0.527 | 0.655 | 0.114 | 0.258 | 0.284 | 0.685 | 0.113 |
| TT-coated plate 15/15 washings ||||||||||||||
| A | 0.247 | 0.582 | 0.421 | 0.428 | 0.133 | 0.082 | 0.262 | 0.079 | 0.343 | 0.414 | 0.095 | 0.292 |
| B | 0.065 | 0.364 | 0.073 | 0.042 | 0.049 | 0.071 | 0.046 | 0.103 | 0.078 | 0.057 | 0.048 | 0.155 |
| C | 0.081 | 0.044 | 0.066 | 0.082 | 0.225 | 0.444 | 0.203 | 0.362 | 0.122 | 0.047 | 0.052 | 0.309 |
| D | 0.092 | 0.11 | 0.59 | 0.22 | 0.33 | 0.544 | 0.058 | 0.159 | 0.047 | 0.174 | 0.086 | 0.05 |
| E | 0.469 | 0.577 | 0.206 | 0.304 | 0.13 | 0.749 | 0.431 | 0.062 | 0.167 | 0.049 | 0.056 | 0.049 |
| F | 0.846 | 0.07 | 0.561 | 0.656 | 0.882 | 0.094 | 0.383 | 0.13 | 0.152 | 0.098 | 0.134 | 0.048 |
| G | 0.537 | 0.052 | 0.49 | 0.105 | 0.337 | 0.193 | 0.514 | 0.294 | 0.068 | 0.35 | 0.525 | 0.05 |
| H | 0.061 | 0.306 | 0.157 | 0.853 | 0.054 | 0.534 | 0.102 | 0.235 | 0.441 | 0.412 | 0.565 | 0.061 |
| Thyroglobulin-coated plate 10/10 washings ||||||||||||||
| A | 0.047 | 0.051 | 0.045 | 0.043 | 0.051 | 0.044 | 0.046 | 0.042 | 0.047 | 0.048 | 0.049 | 0.05 |
| B | 0.042 | 0.042 | 0.042 | 0.042 | 0.043 | 0.041 | 0.041 | 0.042 | 0.043 | 0.045 | 0.042 | 0.046 |
| C | 0.044 | 0.043 | 0.043 | 0.044 | 0.043 | 0.044 | 0.043 | 0.042 | 0.043 | 0.041 | 0.044 | 0.046 |
| D | 0.045 | 0.044 | 0.044 | 0.044 | 0.045 | 0.046 | 0.045 | 0.056 | 0.045 | 0.049 | 0.048 | 0.73 |
| E | 0.046 | 0.045 | 0.046 | 0.044 | 0.045 | 0.044 | 0.044 | 0.044 | 0.047 | 0.046 | 0.047 | 0.926 |
| F | 0.048 | 0.045 | 0.044 | 0.046 | 0.044 | 0.043 | 0.044 | 0.046 | 0.046 | 0.046 | 0.046 | 0.792 |
| G | 0.051 | 0.048 | 0.045 | 0.045 | 0.044 | 0.043 | 0.048 | 0.045 | 0.048 | 0.051 | 0.045 | 0.053 |
| H | 0.064 | 0.05 | 0.049 | 0.047 | 0.05 | 0.051 | 0.047 | 0.046 | 0.047 | 0.047 | 0.047 | 0.056 |
| Thyroglobulin-coated plate 15/15 washings ||||||||||||||
| A | 0.036 | 0.049 | 0.045 | 0.044 | 0.046 | 0.047 | 0.046 | 0.042 | 0.042 | 0.043 | 0.042 | 0.041 |
| B | 0.045 | 0.042 | 0.041 | 0.043 | 0.043 | 0.043 | 0.045 | 0.045 | 0.047 | 0.048 | 0.044 | 0.045 |
| C | 0.049 | 0.047 | 0.047 | 0.046 | 0.046 | 0.046 | 0.045 | 0.047 | 0.046 | 0.045 | 0.045 | 0.052 |
| D | 0.047 | 0.049 | 0.048 | 0.048 | 0.048 | 0.048 | 0.047 | 0.052 | 0.048 | 0.046 | 0.048 | 0.456 |
| E | 0.049 | 0.047 | 0.047 | 0.047 | 0.047 | 0.049 | 0.047 | 0.048 | 0.047 | 0.046 | 0.048 | 0.412 |
| F | 0.05 | 0.047 | 0.046 | 0.046 | 0.046 | 0.046 | 0.046 | 0.046 | 0.046 | 0.047 | 0.048 | 0.528 |
| G | 0.05 | 0.048 | 0.045 | 0.045 | 0.046 | 0.049 | 0.048 | 0.046 | 0.053 | 0.049 | 0.05 | 0.057 |
| H | 0.057 | 0.05 | 0.046 | 0.045 | 0.047 | 0.049 | 0.047 | 0.047 | 0.046 | 0.047 | 0.053 | 0.048 |

TABLE 3

Protein sequence analysis of ELISA positive tetanus toxoid binders. CDR3 sequence, CDR3 length, VH family members and specific name, JH origin and DH origin of the clones is indicated.

| CDR3/ SEQ ID NO: | CDR3 length | VH | DH | JH | V Gene family |
|---|---|---|---|---|---|
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAYYTYDEKAWFAY (SEQ ID NO: 40) | 15 | musIGHV192 | DSP2.11 | JH3 | mouse VH7183 |
| HGAFYTYDEKPWFAY (SEQ ID NO: 41) | 15 | musIGHV192 | IGHD2-14*01 | JH3 | mouse VH7183 |
| HISYYRYDEEVSFAY (SEQ ID NO: 42) | 15 | musIGHV192 | IGHD2-14*01 | JH3 | mouse VH7183 |
| HISYYRYDEEVSFAY (SEQ ID NO: 42) | 15 | musIGHV192 | IGHD2-14*01 | JH3 | mouse VH7183 |
| GWRAFAY (SEQ ID NO: 43) | 7 | musIGHV131 | DSP2.9 | JH3 | mouse VH7183 |
| GWRAFAY (SEQ ID NO: 43) | 7 | musIGHV131 | DSP2.9 | JH3 | mouse VH7183 |
| GWRAFAY (SEQ ID NO: 43) | 7 | musIGHV131 | DSP2.9 | JH3 | mouse VH7183 |
| DRGNYYGMDY (SEQ ID NO: 44) | 10 | musIGHV178 | DSP2.1 | JH4 | mouse VH7183 |
| LGDYYVDWFFAV (SEQ ID NO: 45) | 12 | musIGHV165 | DFL16.1 | JH1 | mouse VH7183 |
| NFPAWFAF (SEQ ID NO: 46) | 8 | musIGHV547 | DST4.3inv | JH3 | mouse VJH558 |
| NFPAWFAY (SEQ ID NO: 46) | 8 | musIGHV547 | DSP2.1 | JH3 | mouse VJH558 |
| NFPAWFVY (SEQ ID NO: 46) | 8 | musIGHV547 | DSP2.1 | JH3 | mouse VJH558 |
| SFTPVPFYYGYD-WYFDV (SEQ ID NO: 47) | 17 | musIGHV532 | DSP2.3 | JH1 | mouse VJH558 |
| SFTPVPFYYGYD-WYFDV (SEQ ID NO: 47) | 17 | musIGHV532 | DSP2.3 | JH1 | mouse VJH558 |
| SDYDWYFDV (SEQ ID NO: 48) | 9 | musIGHV286 | DSP2.2 | JH1 | mouse VJH558 |
| SDYDWYFDV (SEQ ID NO: 48) | 9 | musIGHV286 | DSP2.2 | JH1 | mouse VJH558 |

TABLE 3-continued

Protein sequence analysis of ELISA positive tetanus toxoid binders. CDR3 sequence, CDR3 length, VH family members and specific name, JH origin and DH origin of the clones is indicated.

| CDR3/ SEQ ID NO: | CDR3 length | VH | DH | JH | V Gene family |
|---|---|---|---|---|---|
| DSKWAYYFDY (SEQ ID NO: 49) | 10 | | musIGHV532DST4.3 | JH2 mouse | VJH558 |
| GDYTGYGMDY (SEQ ID NO: 50) | 10 | | musIGHV125DSP2.13 | JH4 mouse | VHSM7 |
| GDYTGYGMDY (SEQ ID NO: 50) | 10 | | musIGHV125DSP2.13 | JH4 mouse | VHSM7 |
| GGYDGYWFPY (SEQ ID NO: 51) | 10 | | musIGHV125DSP2.9 | JH3 mouse | VHSM7 |

TABLE 4

Vector combinations that were transfected to HEK293T.

| Code | HC vector | LC vector | Combined vector | Prep name | Conc. (µg/ml) |
|---|---|---|---|---|---|
| A | x | 0817676_pSELECT_0815426 (IGKV1-39) | x | PIGKV1-39/P1 | — |
| B | x | 0817678_pSELECT_0815427 (IGLV2-14) | x | PIGLV2-14/P1 | — |
| C | MV1110 | 0817676_pSELECT_0815426 (IGKV1-39) | x | PMV1110/IGKV1-39/P1 | 11.0 |
| D | MV1110 | 0817678_pSELECT_0815427 (IGLV2-14) | x | PMV1110/IGLV2-14/P1 | 15.4 |
| E | x | x | MG1494 | MG1494/P2 | 16.1 |

TABLE 5

HLA allotypes considered in T$_H$-epitope profiling. The corresponding serotypes are shown, as well as allotype frequencies in the Caucasian population (Klitz et al. (2003), *Tissue Antigens* 62: 296-307; Gjertson and Terasake (eds) in: *HLA* 1997; Gjertson and Terasake (eds) in: *HLA* 1998; Castelli et al. (2002), *J. Immunol.* 169: 6928-6934). Frequencies can add up to more than 100% since each individual has two alleles for each gene. If all allele frequencies of a single gene were known, they would add up to slightly less than 200% due to homozygous individuals.

| HLA type | Serotype | Population % |
|---|---|---|
| DRB1*0101 | DR1 | 17.4 |
| DRB1*0102 | DR1 | 4.9 |
| DRB1*0301 | DR17(3) | 21.2 |
| DRB1*0401 | DR4 | 11.5 |
| DRB1*0402 | DR4 | 3.1 |
| DRB1*0404 | DR4 | 5.5 |
| DRB1*0405 | DR4 | 2.2 |
| DRB1*0407 | DR4 | <2 |
| DRB1*0701 | DR7 | 23.4 |
| DRB1*0801 | DR8 | 3.3 |
| DRB1*0802 | DR8 | <2 |
| DRB1*0901 | DR9 | <2 |
| DRB1*1101 | DR11(5) | 17 |
| DRB1*1104 | DR11(5) | 5.7 |
| DRB1*1201 | DR12(5) | 3.1 |
| DRB1*1301 | DR13(6) | 15.4 |
| DRB1*1302 | DR13(6) | 10.8 |
| DRB1*1401 | DR14(6) | 4.2 |
| DRB1*1501 | DR15(2) | 13.2 |
| DRB1*1601 | DR16(2) | 5.5 |
| DRB3*0101 | DR52 | 24.6 |
| DRB3*0202 | DR52 | 43 |
| DRB3*0301 | DR52 | 10 |
| DRB4*0101 | DR53 | 25.5 |
| DRB4*0103 | DR53 | 21 |
| DRB5*0101 | DR51 | 15.8 |
| DRB5*0202 | DR51 | 5.7 |
| DQA1*0101/DQB1*0501 | DQ5(1) | 20.5 |
| DQA1*0102/DQB1*0502 | DQ5(1) | 2.6 |
| DQA1*0102/DQB1*0602 | DQ6(1) | 26.5 |
| DQA1*0102/DQB1*0604 | DQ6(1) | 6.7 |
| DQA1*0103/DQB1*0603 | DQ6(1) | 11 |
| DQA1*0104/DQB1*0503 | DQ5(1) | 4 |
| DQA1*0201/DQB1*0202 | DQ2 | 20.9 |
| DQA1*0201/DQB1*0303 | DQ9(3) | 7.2 |
| DQA1*0301/DQB1*0301 | DQ7(3) | 12.5 |
| DQA1*0301/DQB1*0302 | DQ8(3) | 18.3 |
| DQA1*0401/DQB1*0402 | DQ4 | 4.5 |
| DQA1*0501/DQB1*0201 | DQ2 | 24.6 |
| DQA1*0501/DQB1*0301 | DQ7(3) | 20.9 |
| DPA1*0103/DPB1*0201 | DPw2 | 19.9 |
| DPA1*0103/DPB1*0401 | DPw4 | 65.1 |
| DPA1*0103/DPB1*0402 | DPw4 | 24.3 |
| DPA1*0201/DPB1*0101 | DPw1 | 6.3 |
| DPA1*0201/DPB1*0301 | DPw3 | <2 |

TABLE 5-continued

HLA allotypes considered in T$_H$-epitope profiling. The corresponding serotypes are shown, as well as allotype frequencies in the Caucasian population (Klitz et al. (2003), *Tissue Antigens* 62: 296-307; Gjertson and Terasake (eds) in: *HLA* 1997; Gjertson and Terasake (eds) in: *HLA* 1998; Castelli et al. (2002), *J. Immunol.* 169: 6928-6934). Frequencies can add up to more than 100% since each individual has two alleles for each gene. If all allele frequencies of a single gene were known, they would add up to slightly less than 200% due to homozygous individuals.

| HLA type | Serotype | Population % |
|---|---|---|
| DPA1*0201/DPB1*0501 | DPw5 | <2 |
| DPA1*0201/DPB1*0901 | — | 2.4 |

TABLE 6

T$_H$ epitope counts for IGKV1-39. Peptides binding to multiple HLAs of the same group (DRB1, DRB3/4/5, DP, DQ) are counted as one. Values between brackets refer to germline-filtered peptides.

| | DRB1 | | DRB3/4/5 | | DQ | | DP | |
|---|---|---|---|---|---|---|---|---|
| | Strong | Medium | Strong | Medium | Strong | Medium | Strong | Medium |
| Merus IGKV1-39 | 0 (+6) | 0 (+16) | 0 (+0) | 0 (+5) | 0 (+3) | 0 (+9) | 0 (+0) | 0 (+9) |

TABLE 7

Mapping of Epibase ® predictions for Merus IGKV1-39 in the classical 15-mer peptide format. This table shows the allotype count of critical epitopes (SEQ ID NOs: 52-83) and implicated serotypes for each of the 15-mers spanning the Merus IGKV1-39 sequence.

| 15mer | Start position | 15-mer sequence | Allotype count | Implicated serotypes |
|---|---|---|---|---|
| 1 | 1 | DIQMTQSPSSLSASV | 6 | DR1, DR4, DR7, DR9 |
| 2 | 4 | MTQSPSSLSASVGDR | 5 | DR1, DR4, DR9 |
| 3 | 7 | SPSSLSASVGDRVTI | 0 | |
| 4 | 10 | SLSASVGDRVTITCR | 0 | |
| 5 | 13 | ASVGDRVTITCRASQ | 0 | |
| 6 | 16 | GDRVTITCRASQSIS | 2 | DR11(5), DR7 |
| 7 | 19 | VTITCRASQSISSYL | 4 | DQ2, DR11(5), DR4, DR7 |
| 8 | 22 | TCRASQSISSYLNWY | 2 | DQ2, DR4 |
| 9 | 25 | ASQSISSYLNWYQQK | 5 | DR13(6), DR15(2), DR4 |
| 10 | 28 | SISSYLNWYQQKPGK | 8 | DR12(5), DR13(6), DR15(2), DR16(2), DR4, DR8 |
| 11 | 31 | SYLNWYQQKPGKAPK | 10 | DR1, DR12(5), DR16(2), DR4, DR51, DR8 |
| 12 | 34 | NWYQQKPGKAPKLLI | 9 | DR1, DR15(2), DR4, DR51, DR8 |
| 13 | 37 | QQKPGKAPKLLIYAA | 7 | DQ4, DR1, DR11(5), DR15(2), DR51, DR8 |
| 14 | 40 | PGKAPKLLIYAASSL | 7 | DQ4, DR1, DR11(5), DR4, DR8 |
| 15 | 43 | APKLLIYAASSLQSG | 15 | DR1, DR11(5), DR12(5), DR13(6), DR14(6), DR15(2), DR4, DR51, DR8, DR9 |
| 16 | 46 | LLIYAASSLQSGVPS | 15 | DR1, DR11(5), DR12(5), DR13(6), DR14(6), DR15(2), DR4, DR51, DR8, DR9 |
| 17 | 49 | YAASSLQSGVPSRFS | 1 | DR15(2) |
| 18 | 52 | SSLQSGVPSRFSGSG | 1 | DR15(2) |
| 19 | 55 | QSGVPSRFSGSGSGT | 0 | |

TABLE 7-continued

Mapping of Epibase ® predictions for Merus IGKV1-39 in the classical 15-mer peptide format. This table shows the allotype count of critical epitopes (SEQ ID NOs: 52-83) and implicated serotypes for each of the 15-mers spanning the Merus IGKV1-39 sequence.

| 15mer | Start position | 15-mer sequence | Allotype count | Implicated serotypes |
|---|---|---|---|---|
| 20 | 58 | VPSRFSGSGSGTDFT | 0 | |
| 21 | 61 | RFSGSGSGTDFTLTI | 0 | |
| 22 | 64 | GSGSGTDFTLTISSL | 1 | DR52 |
| 23 | 67 | SGTDFTLTISSLQPE | 4 | DR4, DR52, DR7, DR9 |
| 24 | 70 | DFTLTISSLQPEDFA | 4 | DQ2, DR4, DR7, DR9 |
| 25 | 73 | LTISSLQPEDFATYY | 1 | DQ2 |
| 26 | 76 | SSLQPEDFATYYCQQ | 0 | |
| 27 | 79 | QPEDFATYYCQQSYS | 1 | DR4 |
| 28 | 82 | DFATYYCQQSYSTPP | 5 | DR4, DR51, DR7 |
| 29 | 85 | TYYCQQSYSTPPTFG | 4 | DR4, DR51, DR7 |
| 30 | 88 | CQQSYSTPPTFGQGT | 0 | |
| 31 | 91 | SYSTPPTFGQGTKVE | 0 | |
| 32 | 94 | TPPTFGQGTKVEIK | 0 | |

TABLE 8

The $V_H$ gene from PG1433 paired with various light chain genes with differing rates of amino acid mutation were compared for production levels with the original clone containing the IGKV1-39 gene.

| IgG name | Light chain gene | Number of amino acid mutations | concentration (µg/ml) |
|---|---|---|---|
| PG1433 | 1-39 | 0 | 63, 45.5, 38.6 (avg = 49) |
| PG1631 | 1-12 | 4 | 10.5 |
| PG1632 | 1-27 | 7 | 9.3 |
| PG1634 | 1D-12 | 10 | 10.8 |
| PG1635 | 1D-33 | 6 | 10.2 |
| PG1642 | 1-5 | 8 | 7.1 |
| PG1644 | 1-9 | 3 | 7.8 |
| PG1650 | 1D-39 | 3 | 9.1 |
| PG1652 | 2D-28 | 3 | 7.1 |
| PG1653 | 3-15 | 14 | 7 |
| PG1654 | 3-20 | 2 | 5.2 |
| PG1674 | 1-40 | 7 | 8.2 |
| PG1678 | 2-11 | 2 | 8.1 |
| PG1680 | 2-14 | 15 | 10.8 |
| PG1682 | 3-1 | 13 | 9.9 |
| PG1683 | 6-57 | 6 | 13.9 |

TABLE 9

Numbers of lymphocytes harvested from the bone marrow and spleen of wild-type and transgenic mice

| | *10e6/ml cells | total vol (ml) | total cells *10⁶ |
|---|---|---|---|
| Bone Marrow | | | |
| Wt | 18.82 | 5.05 | 95.0 |
| Wt | 19.24 | 4.96 | 95.4 |
| CD19-Cre | 23.42 | 5.08 | 119.0 |
| CD19-Cre | 20.58 | 4.82 | 99.2 |
| CD19-Cre | 25.77 | 5.15 | 132.7 |
| CD19-Cre/HuVk1 | 17.71 | 5.06 | 89.6 |
| CD19-Cre/HuVk1 | 12.60 | 5.33 | 67.2 |
| CD19-Cre/HuVk1 | 18.13 | 5.27 | 95.5 |
| Spleen | | | |
| Wt | 41.70 | 5.36 | 223.5 |
| Wt | 37.85 | 4.71 | 178.3 |
| CD19-Cre | 60.19 | 3.77 | 226.9 |
| CD19-Cre | 35.06 | 3.66 | 128.3 |
| CD19-Cre | 80.69 | 4.60 | 371.2 |
| CD19-Cre/HuVk1 | 51.67 | 4.48 | 231.5 |
| CD19-Cre/HuVk1 | 58.80 | 6.24 | 366.9 |
| CD19-Cre/HuVk1 | 24.37 | 6.25 | 152.3 |

What is claimed is:

1. A transgenic mouse that has been immunized with an antigen wherein the genome of said mouse comprises a transgene comprising a single human immunoglobulin light chain germline V gene segment fused to a single human immunoglobulin light chain germline J gene segment such that there is no mutation due to said fusion, wherein said fused human V/J gene segments encode a rearranged human immunoglobulin light chain variable region, wherein the transgene is inserted by site-specific integration in the murine Rosa locus or wherein said transgene lacks the intronic light chain enhancer MoEκi or comprises a truncation of the transgene 3' kappa enhancer or combination of these; and wherein the transgene comprises a murine light chain constant region gene segment or is operatively linked to an endogenous mouse light chain constant region gene segment;

wherein if the transgene is inserted by site-specific integration in the murine Rosa locus the transgene comprises a murine light chain constant region gene segment; and wherein said transgenic mouse, in response to said antigen, has produced B cells that secrete antibodies with immunoglobulin light chains comprising said rearranged human light chain variable region and a murine light chain constant region, paired with a diversity of immunoglobulin heavy chains, which bind said antigen.

2. A method to prepare antibodies immunoreactive with a desired antigen which method comprises isolating B cells from the transgenic mouse of claim 1 and culturing said cells, optionally immortalizing said cells and harvesting the antibodies.

3. A method to prepare antibodies immunoreactive with a desired antigen which method comprises isolating nucleic acids from the B cells of the transgenic mouse of claim 1 that encode at least part of such antibodies, inserting the nucleic acids or copies or derivatives thereof into an expression cassette and expressing the antibodies in host cells.

4. A method to prepare antibodies immunoreactive with a desired antigen which method comprises recovering said antibodies from the mouse of claim 1.

* * * * *

SEQUENCE LISTING

<160> NUMBER OF SEQ ID NOS: 102

<210> SEQ ID NO 1
<211> LENGTH: 20
<212> TYPE: DNA
<213> ORGANISM: Artificial Sequence
<220> FEATURE:

<223> OTHER INFORMATION: primer

<400> SEQUENCE: 1 cccttttccaa tctttatggg                                                      20

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
aggtggattg gtgtcttttt ctc                                                   23

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gtcatgtcgg cgaccctacg cc                                                    22

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4 tgccagggggg aagaccgatg                                                      20

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
gccggccatg gccgaggtrm agcttcagga gtcaggac                                   38

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
gccggccatg gccgaggtsc agctkcagca gtcaggac                                   38

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
gccggccatg gcccaggtgc agctgaagsa stcagg                                     36

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
gccggccatg gccgaggtgc agcttcagga gtcsggac                    38

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
gccggccatg gccgargtcc agctgcaaca gtcyggac                    38

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
gccggccatg gcccaggtcc agctkcagca atctgg                      36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
gccggccatg gcccagstbc agctgcagca gtctgg                      36

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
gccggccatg gcccaggtyc agctgcagca gtctggrc                    38

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
gccggccatg gcccaggtyc agctycagca gtctgg                      36

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
gccggccatg gccgaggtcc arctgcaaca atctggacc				39

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
gccggccatg gcccaggtcc acgtgaagca gtctggg				37

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
gccggccatg gccgaggtga asstggtgga atctg				35

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17
gccggccatg gccgavgtga agytggtgga gtctg				35

<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
gccggccatg gccgaggtgc agskggtgga gtctgggg				38

<210> SEQ ID NO 19
<211> LENGTH: 37
<212> TYPE: DNA
<213> ORGANISM: Artificial Sequence
<220> FEATURE:
<223> OTHER INFORMATION: primer

<400> SEQUENCE: 19
gccggccatg gccgakgtgc amctggtgga gtctggg				37

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
gccggccatg gccgaggtga agctgatgga rtctgg				36

<210> SEQ ID NO 21
<211> LENGTH: 38

```
<212> TYPE: DNA
<213> ORGANISM: Artificial Sequence
<220> FEATURE:
<223> OTHER INFORMATION: primer

<400> SEQUENCE: 21
gccggccatg gccgaggtgc arcttgttga gtctggtg                                38

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
gccggccatg gccgargtra agcttctcga gtctgga                                 37

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
gccggccatg gccgaagtga arsttgagga gtctgg                                  36

<210> SEQ ID NO 24
<211> LENGTH: 37
<212> TYPE: DNA
<213> ORGANISM: Artificial Sequence
<220> FEATURE:
<223> OTHER INFORMATION: primer

<400> SEQUENCE: 24
gccggccatg gccgaagtga tgctggtgga gtctggg                                 37

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
gccggccatg gcccaggtta ctctraaagw gtstggcc                                38

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26
gccggccatg gcccaggtcc aactvcagca rcctgg                                  36

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27
```

```
gccggccatg gcccaggtyc arctgcagca gtctg          35
```

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28

```
gccggccatg gccgatgtga acttggaagt gtctgg         36
```

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29

```
gccggccatg gccgaggtga aggtcatcga gtctgg         36
```

<210> SEQ ID NO 30
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (44)..(44)
<223> OTHER INFORMATION: n is a, c, g, or t

<400> SEQUENCE: 30

```
cagtcacaga tcctcgcgaa ttggcccagc cggccatggc csang     45
```

<210> SEQ ID NO 31
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (44)..(44)
<223> OTHER INFORMATION: n is a, c, g, or t

<400> SEQUENCE: 31

```
cagtcacaga tcctcgcgaa ttggcccagc cggccatggc csanc     45
```

<210> SEQ ID NO 32
<211> LENGTH: 37
<212> TYPE: DNA
<213> ORGANISM: Artificial Sequence
<220> FEATURE:
<223> OTHER INFORMATION: primer

<400> SEQUENCE: 32

```
gggggtgtcg ttttggctga ggagacggtg accgtgg        37
```

<210> SEQ ID NO 33
<211> LENGTH: 37
<212> TYPE: DNA
<213> ORGANISM: Artificial Sequence
<220> FEATURE:
<223> OTHER INFORMATION: primer

<400> SEQUENCE: 33

```
gggggtgtcg ttttggctga ggagactgtg agagtgg                              37

<210> SEQ ID NO 34
<211> LENGTH: 37
<212> TYPE: DNA
<213> ORGANISM: Artificial Sequence
<220> FEATURE:
<223> OTHER INFORMATION: primer

<400> SEQUENCE: 34
gggggtgtcg ttttggctgc agagacagtg accagag                              37

<210> SEQ ID NO 35
<211> LENGTH: 37
<212> TYPE: DNA
<213> ORGANISM: Artificial Sequence
<220> FEATURE:
<223> OTHER INFORMATION: primer

<400> SEQUENCE: 35
gggggtgtcg ttttggctga ggagacggtg actgagg                              37

<210> SEQ ID NO 36
<211> LENGTH: 37
<212> TYPE: DNA
<213> ORGANISM: Artificial Sequence
<220> FEATURE:
<223> OTHER INFORMATION: primer

<400> SEQUENCE: 36
gggggtgtcg ttttggctga ggagacggtg accgtgg                              37

<210> SEQ ID NO 37
<211> LENGTH: 37
<212> TYPE: DNA
<213> ORGANISM: Artificial Sequence
<220> FEATURE:
<223> OTHER INFORMATION: primer

<400> SEQUENCE: 37
gggggtgtcg ttttggctga ggagacggtg acagtgg                              37

<210> SEQ ID NO 38
<211> LENGTH: 37
<212> TYPE: DNA
<213> ORGANISM: Artificial Sequence
<220> FEATURE:
<223> OTHER INFORMATION: primer

<400> SEQUENCE: 38
gggggtgtcg ttttggctga ggagacggtg accagag                              37

<210> SEQ ID NO 39
<211> LENGTH: 37
<212> TYPE: DNA
<213> ORGANISM: Artificial Sequence
<220> FEATURE:
<223> OTHER INFORMATION: primer

<400> SEQUENCE: 39
gggggtgtcg ttttggctga ggagacggtg accgagg                              37

<210> SEQ ID NO 40
<211> LENGTH: 15
<212> TYPE: PRT
```

```
<213> ORGANISM: Artificial Sequence
<220> FEATURE:
<223> OTHER INFORMATION: CDR3

<400> SEQUENCE: 40

His Gly Ala Tyr Tyr Thr Tyr Asp Glu Lys Ala Trp Phe Ala Tyr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: CDR3

<400> SEQUENCE: 41

His Gly Ala Phe Tyr Thr Tyr Asp Glu Lys Pro Trp Phe Ala Tyr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: CDR3

<400> SEQUENCE: 42

His Ile Ser Tyr Tyr Arg Tyr Asp Glu Glu Val Ser Phe Ala Tyr
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: CDR3

<400> SEQUENCE: 43

Gly Trp Arg Ala Phe Ala Tyr
1               5

<210> SEQ ID NO 44
<211> LENGTH: 10
<212> TYPE: PRT
<213> ORGANISM: Artificial Sequence
<220> FEATURE:
<223> OTHER INFORMATION: CDR3

<400> SEQUENCE: 44

Asp Arg Gly Asn Tyr Tyr Gly Met Asp Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: CDR3

<400> SEQUENCE: 45

Leu Gly Asp Tyr Tyr Val Asp Trp Phe Phe Ala Val
1               5                   10

<210> SEQ ID NO 46
<211> LENGTH: 8
<212> TYPE: PRT
<213> ORGANISM: Artificial Sequence
```

```
<220> FEATURE:
<223> OTHER INFORMATION: CDR3

<400> SEQUENCE: 46

Asn Phe Pro Ala Trp Phe Ala Phe
1               5

<210> SEQ ID NO 47
<211> LENGTH: 17
<212> TYPE: PRT
<213> ORGANISM: Artificial Sequence
<220> FEATURE:
<223> OTHER INFORMATION: CDR3

<400> SEQUENCE: 47

Ser Phe Thr Pro Val Pro Phe Tyr Tyr Gly Tyr Asp Trp Tyr Phe Asp
1               5                   10                  15

Val

<210> SEQ ID NO 48
<211> LENGTH: 9
<212> TYPE: PRT
<213> ORGANISM: Artificial Sequence
<220> FEATURE:
<223> OTHER INFORMATION: CDR3

<400> SEQUENCE: 48

Ser Asp Tyr Asp Trp Tyr Phe Asp Val
1               5

<210> SEQ ID NO 49
<211> LENGTH: 10
<212> TYPE: PRT
<213> ORGANISM: Artificial Sequence
<220> FEATURE:
<223> OTHER INFORMATION: CDR3

<400> SEQUENCE: 49

Asp Ser Lys Trp Ala Tyr Tyr Phe Asp Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: CDR3

<400> SEQUENCE: 50

Gly Asp Tyr Thr Gly Tyr Gly Met Asp Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: CDR3

<400> SEQUENCE: 51

Gly Gly Tyr Asp Gly Tyr Trp Phe Pro Tyr
1               5                   10

<210> SEQ ID NO 52
<211> LENGTH: 15
<212> TYPE: PRT
```

<213> ORGANISM: Artificial Sequence
<220> FEATURE:
<223> OTHER INFORMATION: epitope IGKV1-39

<400> SEQUENCE: 52

Asp Ile Gln Met Thr Gln Ser Pro Ser Ser Leu Ser Ala Ser Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 53

Met Thr Gln Ser Pro Ser Ser Leu Ser Ala Ser Val Gly Asp Arg
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 54

Ser Pro Ser Ser Leu Ser Ala Ser Val Gly Asp Arg Val Thr Ile
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 55

Ser Leu Ser Ala Ser Val Gly Asp Arg Val Thr Ile Thr Cys Arg
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 56

Ala Ser Val Gly Asp Arg Val Thr Ile Thr Cys Arg Ala Ser Gln
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 57

Gly Asp Arg Val Thr Ile Thr Cys Arg Ala Ser Gln Ser Ile Ser
1               5                   10                  15

<210> SEQ ID NO 58
<211> LENGTH: 15
<212> TYPE: PRT
<213> ORGANISM: Artificial Sequence

```
<220> FEATURE:
<223> OTHER INFORMATION: Epitope IGKV1-39

<400> SEQUENCE: 58

Val Thr Ile Thr Cys Arg Ala Ser Gln Ser Ile Ser Ser Tyr Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 59

Thr Cys Arg Ala Ser Gln Ser Ile Ser Ser Tyr Leu Asn Trp Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 60

Ala Ser Gln Ser Ile Ser Ser Tyr Leu Asn Trp Tyr Gln Gln Lys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 61

Ser Ile Ser Ser Tyr Leu Asn Trp Tyr Gln Gln Lys Pro Gly Lys
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 62

Ser Tyr Leu Asn Trp Tyr Gln Gln Lys Pro Gly Lys Ala Pro Lys
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 63

Asn Trp Tyr Gln Gln Lys Pro Gly Lys Ala Pro Lys Leu Leu Ile
1               5                   10                  15

<210> SEQ ID NO 64
<211> LENGTH: 15
<212> TYPE: PRT
<213> ORGANISM: Artificial Sequence
<220> FEATURE:
```

```
<223> OTHER INFORMATION: Epitope IGKV1-39

<400> SEQUENCE: 64

Gln Gln Lys Pro Gly Lys Ala Pro Lys Leu Leu Ile Tyr Ala Ala
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 65

Pro Gly Lys Ala Pro Lys Leu Leu Ile Tyr Ala Ala Ser Ser Leu
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 66

Ala Pro Lys Leu Leu Ile Tyr Ala Ala Ser Ser Leu Gln Ser Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 67

Leu Leu Ile Tyr Ala Ala Ser Ser Leu Gln Ser Gly Val Pro Ser
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 68

Tyr Ala Ala Ser Ser Leu Gln Ser Gly Val Pro Ser Arg Phe Ser
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 69

Ser Ser Leu Gln Ser Gly Val Pro Ser Arg Phe Ser Gly Ser Gly
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Epitope IGKV1-39
```

```
<400> SEQUENCE: 70

Gln Ser Gly Val Pro Ser Arg Phe Ser Gly Ser Gly Ser Gly Thr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 71

Val Pro Ser Arg Phe Ser Gly Ser Gly Ser Gly Thr Asp Phe Thr
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 72

Arg Phe Ser Gly Ser Gly Ser Gly Thr Asp Phe Thr Leu Thr Ile
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 73

Gly Ser Gly Ser Gly Thr Asp Phe Thr Leu Thr Ile Ser Ser Leu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 74

Ser Gly Thr Asp Phe Thr Leu Thr Ile Ser Ser Leu Gln Pro Glu
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 75

Asp Phe Thr Leu Thr Ile Ser Ser Leu Gln Pro Glu Asp Phe Ala
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Epitope IGKV1-39
```

-continued

<400> SEQUENCE: 76

Leu Thr Ile Ser Ser Leu Gln Pro Glu Asp Phe Ala Thr Tyr Tyr
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 77

Ser Ser Leu Gln Pro Glu Asp Phe Ala Thr Tyr Tyr Cys Gln Gln
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 78

Gln Pro Glu Asp Phe Ala Thr Tyr Tyr Cys Gln Gln Ser Tyr Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 79

Asp Phe Ala Thr Tyr Tyr Cys Gln Gln Ser Tyr Ser Thr Pro Pro
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 80

Thr Tyr Tyr Cys Gln Gln Ser Tyr Ser Thr Pro Pro Thr Phe Gly
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 81

Cys Gln Gln Ser Tyr Ser Thr Pro Pro Thr Phe Gly Gln Gly Thr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 82

```
Ser Tyr Ser Thr Pro Pro Thr Phe Gly Gln Gly Thr Lys Val Glu
1               5                   10                  15

<210> SEQ ID NO 83
<211> LENGTH: 14
<212> TYPE: PRT
<213> ORGANISM: Artificial Sequence
<220> FEATURE:
<223> OTHER INFORMATION: Epitope IGKV1-39

<400> SEQUENCE: 83

Thr Pro Pro Thr Phe Gly Gln Gly Thr Lys Val Glu Ile Lys
1               5                   10

<210> SEQ ID NO 84
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 84 gac atc cag atg acc cag agc ccc agc agc ctg agc gcc agc gtg ggc      48
Asp Ile Gln Met Thr Gln Ser Pro Ser Ser Leu Ser Ala Ser Val Gly
1               5                   10                  15 gac aga gtg acc atc acc tgc aga gcc agc cag agc atc agc agc tac      96
Asp Arg Val Thr Ile Thr Cys Arg Ala Ser Gln Ser Ile Ser Ser Tyr
                20                  25                  30 ctg aac tgg tat cag cag aag ccc ggc aag gcc ccc aag ctg ctg atc     144
Leu Asn Trp Tyr Gln Gln Lys Pro Gly Lys Ala Pro Lys Leu Leu Ile
            35                  40                  45 tac gcc gcc agc tcc ctg cag agc ggc gtg ccc agc aga ttc agc ggc     192
Tyr Ala Ala Ser Ser Leu Gln Ser Gly Val Pro Ser Arg Phe Ser Gly
        50                  55                  60 agc ggc tcc ggc acc gac ttc acc ctg acc atc agc agc ctg cag ccc     240
Ser Gly Ser Gly Thr Asp Phe Thr Leu Thr Ile Ser Ser Leu Gln Pro
65                  70                  75                  80 gag gac ttc gcc acc tac tac tgc cag cag agc tac agc acc ccc ccc     288
Glu Asp Phe Ala Thr Tyr Tyr Cys Gln Gln Ser Tyr Ser Thr Pro Pro
                85                  90                  95 acc ttc ggc cag ggc acc aag gtg gag atc aag                         321
Thr Phe Gly Gln Gly Thr Lys Val Glu Ile Lys
                100                 105

<210> SEQ ID NO 85
<211> LENGTH: 107
<212> TYPE: PRT
<213> ORGANISM: Homo sapiens

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105
```

<210> SEQ ID NO 86
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 86

```
cag tct gcc ctg acc cag ccc gcc tct gtg tct ggc agc cct ggc cag      48
Gln Ser Ala Leu Thr Gln Pro Ala Ser Val Ser Gly Ser Pro Gly Gln
1               5                   10                  15 agc atc acc atc agc tgc acc ggc acc agc agc gac gtg ggc ggc tac      96
Ser Ile Thr Ile Ser Cys Thr Gly Thr Ser Ser Asp Val Gly Gly Tyr
                20                  25                  30 aac tac gtg tcc tgg tat cag cag cac ccc ggc aag gcc ccc aag ctg     144
Asn Tyr Val Ser Trp Tyr Gln Gln His Pro Gly Lys Ala Pro Lys Leu
            35                  40                  45 atg atc tac gag gtg tcc aac aga ccc agc ggc gtg agc aac aga ttc     192
Met Ile Tyr Glu Val Ser Asn Arg Pro Ser Gly Val Ser Asn Arg Phe
        50                  55                  60 agc ggc agc aag agc ggc aac acc gcc agc ctg acc atc agc ggc ctc     240
Ser Gly Ser Lys Ser Gly Asn Thr Ala Ser Leu Thr Ile Ser Gly Leu
65                  70                  75                  80 cag gct gag gac gag gcc gac tac tac tgc agc agc tac acc agc agc     288
Gln Ala Glu Asp Glu Ala Asp Tyr Tyr Cys Ser Ser Tyr Thr Ser Ser
                85                  90                  95 tcc acc ctg gtg ttt ggc ggc gga aca aag ctg acc gtg ctg             330
Ser Thr Leu Val Phe Gly Gly Gly Thr Lys Leu Thr Val Leu
            100                 105                 110
```

<210> SEQ ID NO 87
<211> LENGTH: 110
<212> TYPE: PRT
<213> ORGANISM: Homo sapiens

<400> SEQUENCE: 87

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110
```

<210> SEQ ID NO 88
<211> LENGTH: 321
<212> TYPE: DNA
<213> ORGANISM: Rattus norvegicus

```
<220> FEATURE:
<221> NAME/KEY: CDS
<222> LOCATION: (1)..(321)

<400> SEQUENCE: 88 aga gcc gac gcc gct ccc acc gtg tcc atc ttc ccc ccc agc atg gaa      48
Arg Ala Asp Ala Ala Pro Thr Val Ser Ile Phe Pro Pro Ser Met Glu
1               5                   10                  15 cag ctg acc tct ggc gga gcc acc gtg gtc tgc ttc gtg aac aac ttc      96
Gln Leu Thr Ser Gly Gly Ala Thr Val Val Cys Phe Val Asn Asn Phe
            20                  25                  30 tac ccc aga gac atc agc gtg aag tgg aag atc gac ggc agc gag cag     144
Tyr Pro Arg Asp Ile Ser Val Lys Trp Lys Ile Asp Gly Ser Glu Gln
        35                  40                  45 agg gac ggc gtg ctg gac agc gtg acc gac cag gac agc aag gac tcc     192
Arg Asp Gly Val Leu Asp Ser Val Thr Asp Gln Asp Ser Lys Asp Ser
    50                  55                  60 acc tac agc atg agc agc acc ctg agc ctg acc aag gtg gag tac gag     240
Thr Tyr Ser Met Ser Ser Thr Leu Ser Leu Thr Lys Val Glu Tyr Glu
65                  70                  75                  80 agg cac aac ctg tac acc tgc gag gtg gtg cac aag acc agc tcc agc     288
Arg His Asn Leu Tyr Thr Cys Glu Val Val His Lys Thr Ser Ser Ser
                85                  90                  95 ccc gtg gtc aag tcc ttc aac cgg aac gag tgt                         321
Pro Val Val Lys Ser Phe Asn Arg Asn Glu Cys
            100                 105

<210> SEQ ID NO 89
<211> LENGTH: 107
<212> TYPE: PRT
<213> ORGANISM: Rattus norvegicus

<400> SEQUENCE: 89

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 90
<211> LENGTH: 865
<212> TYPE: DNA
<213> ORGANISM: Artificial Sequence
<220> FEATURE:
<223> OTHER INFORMATION: IGKV1-39/J-Ck

<400> SEQUENCE: 90
ggtaccgcgg ccgccaccat ggacatgaga gtgcccgccc agctcctggg gctcctgcta      60
ctctggctcc gaggtaagga tgagaacac taggaattta ctcagccagt gtgctcagta     120
ctgactggaa cttcagggaa gttctctgat aacatgatta atagtaagaa tatttgtttt     180
```

```
tatgttttcca atctcaggtg ccagatgtga catccagatg acccagagcc ccagcagcct    240
gagcgccagc gtgggcgaca gagtgaccat cacctgcaga gccagccaga gcatcagcag    300
ctacctgaac tggtatcagc agaagcccgg caaggccccc aagctgctga tctacgccgc    360
cagctccctg cagagcggcg tgcccagcag attcagcggc agcggctccg gcaccgactt    420
caccctgacc atcagcagcc tgcagcccga ggacttcgcc acctactact gccagcagag    480
ctacagcacc cccccacct tcggccaggg caccaaggtg gagatcaaga gagccgacgc    540
cgctcccacc gtgtccatct ccccccccag catggaacag ctgacctctg gcggagccac    600
cgtggtctgc ttcgtgaaca acttctaccc cagagacatc agcgtgaagt ggaagatcga    660
cggcagcgag cagagggacg gcgtgctgga cagcgtgacc gaccaggaca gcaaggactc    720
cacctacagc atgagcagca ccctgagcct gaccaaggtg gagtacgaga ggcacaacct    780
gtacacctgc gaggtggtgc acaagaccag ctccagcccc gtggtcaagt ccttcaaccg    840
gaacgagtgt tgagctagcg agctc                                          865
```

<210> SEQ ID NO 91
<211> LENGTH: 874
<212> TYPE: DNA
<213> ORGANISM: Artificial Sequence
<220> FEATURE:
<223> OTHER INFORMATION: IGLV2-14/J-Ck

<400> SEQUENCE: 91

```
ggtaccgcgg ccgccaccat ggacatgaga gtgcccgccc agctcctggg gctcctgcta    60
ctctggctcc gaggtaagga tggagaacac taggaattta ctcagccagt gtgctcagta    120
ctgactggaa cttcagggaa gttctctgat aacatgatta atagtaagaa tatttgtttt    180 tatgttttcca atctcaggtg ccagatgtca gtctgccctg acccagcccg cctctgtgtc    240
tggcagccct ggccagagca tcaccatcag ctgcaccggc accagcagcg acgtgggcgg    300
ctacaactac gtgtcctggt atcagcagca ccccggcaag gcccccaagc tgatgatcta    360
cgaggtgtcc aacagaccca gcggcgtgag caacagattc agcggcagca agagcggcaa    420
caccgccagc ctgaccatca gcggcctcca ggctgaggac gaggccgact actactgcag    480
cagctacacc agcagctcca cctggtgtt tggcggcgga acaaagctga ccgtgctgag    540
agccgacgcc gctcccaccg tgtccatctt cccccccagc atggaacagc tgacctctgg    600
cggagccacc gtggtctgct tcgtgaacaa cttctacccc agagacatca gcgtgaagtg    660
gaagatcgac ggcagcgagc agagggacgg cgtgctggac agcgtgaccg accaggacag    720
caaggactcc acctacagca tgagcagcac cctgagcctg accaaggtgg agtacgagag    780
gcacaacctg tacacctgcg aggtggtgca caagaccagc tccagccccg tggtcaagtc    840
cttcaaccgg aacgagtgtt gagctagcga gctc                                874
```

<210> SEQ ID NO 92
<211> LENGTH: 13373
<212> TYPE: DNA
<213> ORGANISM: Artificial Sequence
<220> FEATURE:
<223> OTHER INFORMATION: VkP-IGKV1-39/J-Ck

<400> SEQUENCE: 92

```
ggccggccca catgaaacaa tgggaaccat gtgacaatca cagaggtgtt gttactatag    60
caaaagggat tgttactctc cacatccctt taagtaactt gaaggcctga tagacccacc    120
ctctaagact tcattagaca ttccctacga atggttatac tctcctgtat actcccaata    180
```

```
caactctaaa atatattatt ccatatagtc cttaggtttg tattaaagtt tgactttttt    240
ccttcaaaat atctcttgtc acaacagcgg ctctagagag aaatacattc cctccaggca    300
aatctatgct gcgctggtct gacctgggac cctggggaca ttgcccctgt gctgagttac    360
taagatgagc cagccctgca gctgtgctca gcctgcccca tgccctgctg attgatttgc    420
atgttccaga gcacagcccc ctgccctgaa gactttttta tgggctggtc gcaccctgtg    480
caggagtcag tctcagtcag gagccaccat ggacatgaga gtgcccgccc agctcctggg    540
gctcctgcta ctctggctcc gaggtaagga tggagaacac taggaattta ctcagccagt    600
gtgctcagta ctgactggaa cttcagggaa gttctctgat aacatgatta atagtaagaa    660
tatttgtttt tatgtttcca atctcaggtg ccagatgtga catccagatg acccagagcc    720
ccagcagcct gagcgccagc gtgggcgaca gagtgaccat cacctgcaga gccagccaga    780
gcatcagcag ctacctgaac tggtatcagc agaagcccgg caaggccccc aagctgctga    840
tctacgccgc cagctccctg cagagcgcg tgcccagcag attcagcggc agcggctccg    900
gcaccgactt caccctgacc atcagcagcc tgcagcccga ggacttcgcc acctactact    960
gccagcagag ctacagcacc cccccccacct tcggccaggg caccaaggtg gagatcaaac   1020
gtaagtacac ttttctcatc ttttttttatg tgtaagacac aggttttcat gttaggagtt   1080
aaagtcagtt cagaaaatct tgagaaaatg gagagggctc attatcagtt gacgtggcat   1140
acagtgtcag attttctgtt tatcaagcta gtgagattag gggcaaaaag aggctttagt   1200
tgagaggaaa gtaattaata ctatggtcac catccaagag attggatcgg agaataagca   1260
tgagtagtta ttgagatctg ggtctgactg caggtagcgt ggtcttctag acgtttaagt   1320
gggagatttg gagggatgga ggaatgaagg aacttcagga tagaaaaggg ctgaagtcaa   1380
gttcagctcc taaaatggat gtgggagcaa actttgaaga taaactgaat gacccagagg   1440
atgaaacagc gcagatcaaa gaggggcctg gagctctgag aagagaagga gactcatccg   1500
tgttgagttt ccacaagtac tgtcttgagt tttgcaataa aagtgggata gcagagttga   1560
gtgagccgta ggctgagttc tctcttttgt ctcctaagtt tttatgacta caaaaatcag   1620
tagtatgtcc tgaaataatc attaagctgt ttgaaagtat gactgcttgc catgtagata   1680
ccatggcttg ctgaataatc agaagaggtg tgactcttat tctaaaattt gtcacaaaat   1740
gtcaaaatga gagactctgt aggaacgagt ccttgacaga cagctcaagg ggttttttttc  1800 ctttgtctca tttctacatg aaagtaaatt tgaaatgatc ttttttatta taagagtaga   1860
aatacagttg ggtttgaact atatgttta atggccacgg ttttgtaaga catttggtcc    1920
tttgttttcc cagttattac tcgattgtaa ttttatatcg ccagcaatgg actgaaacgg   1980
tccgcaacct cttctttaca actgggtgac ctcgcggctg tgccagccat ttggcgttca   2040
ccctgccgct aagggccatg tgaaccccccg cggtagcatc ccttgctccg cgtggaccac   2100
tttcctgagg cacagtgata ggaacagagc cactaatctg aagagaacag agatgtgaca   2160
gactacacta atgtgagaaa aacaaggaaa gggtgactta ttggagattt cagaaataaa   2220
atgcatttat tattatattc ccttatttta attttctatt agggaattag aaagggcata   2280
aactgcttta tccagtgtta tattaaaagc ttaatgtata taatcttta gaggtaaaat   2340 ctacagccag caaaagtcat ggtaaatatt ctttgactga actctcacta aactcctcta   2400
aattatatgt catattaact ggttaaatta atataaattt gtgacatgac cttaactggt   2460
taggtaggat attttttcttc atgcaaaaat atgactaata ataatttagc acaaaaatat   2520
```

```
ttcccaatac tttaattctg tgatagaaaa atgtttaact cagctactat aatcccataa      2580
ttttgaaaac tatttattag cttttgtgtt tgacccttcc ctagccaaag gcaactattt      2640
aaggacccct taaaactctt gaaactactt tagagtcatt aagttattta accacttttta    2700 attactttaa aatgatgtca attcctttt aactattaat ttatttttaag gggggaaagg     2760 ctgctcataa ttctattgtt tttcttggta aagaactctc agttttcgtt tttactacct    2820
ctgtcaccca agagttggca tctcaacaga ggggacttc cgagaggcca tctggcagtt      2880
gcttaagatc agaagtgaag tctgccagtt cctcccaggc aggtggccca gattacagtt    2940
gacctgttct ggtgtggcta aaaattgtcc catgtggtta caaaccatta gaccagggtc    3000
tgatgaattg ctcagaatat ttctggacac ccaaatacag accctggctt aaggccctgt    3060
ccatacagta ggtttagctt ggctacacca aggaagcca tacagaggct aatatcagag      3120
tattcttgga agagacagga gaaaatgaaa gccagtttct gctcttacct tatgtgcttg    3180
tgttcagact cccaaacatc aggagtgtca gataaactgg tctgaatctc tgtctgaagc    3240
atggaactga aaagaatgta gtttcaggga agaaaggcaa tagaaggaag cctgagaata    3300
tcttcaaagg gtcagactca atttactttc taaagaagta gctaggaact agggaataac    3360
ttagaaacaa caagattgta tatatgtgca tcctggcccc attgttcctt atctgtaggg    3420
ataagcgtgc ttttttgtgt gtctgtatat aacataactg tttacacata atacactgaa    3480
atggagccct tccttgttac ttcataccat cctctgtgct tccttcctca ggggccgacg    3540
ccgctcccac cgtgtccatc ttccccccca gcatggaaca gctgacctct ggcggagcca    3600
ccgtggtctg cttcgtgaac aacttctacc ccagagacat cagcgtgaag tggaagatcg    3660
acggcagcga gcagagggac ggcgtgctgg acagcgtgac cgaccaggac agcaaggact    3720
ccacctacag catgagcagc accctgagcc tgaccaaggt ggagtacgag aggcacaacc    3780
tgtacacctg cgaggtggtg cacaagacca gctccagccc cgtggtcaag tccttcaacc    3840
ggaacgagtg ttgaagacaa aggtcctgag acgccaccac cagctcccca gctccatcct    3900 atcttcccctt ctaaggtctt ggaggcttcc ccacaagcga cctaccactg ttgcggtgct    3960 ccaaaccctcc tccccacctc cttctcctcc tcctcccttt ccttggcttt tatcatgcta    4020
atatttgcag aaaatattca ataaagtgag tctttgcact tgagatctct gtctttctta    4080
ctaaatggta gtaatcagtt gttttttccag ttacctgggt ttctcttcta aagaagttaa    4140
atgtttagtt gccctgaaat ccaccacact taaaggataa ataaaaccct ccacttgccc    4200
tggttggctg tccactacat ggcagtcctt tctaaggttc acgagtacta ttcatggctt    4260
atttctctgg gccatggtag gtttgaggag gcatacttcc tagttttctt cccctaagtc    4320
gtcaaagtcc tgaaggggga cagtctttac aagcacatgt tctgtaatct gattcaacct    4380
acccagtaaa cttggcgaag caaagtagaa tcattatcac aggaagcaaa ggcaacctaa    4440
atgtgcaagc aataggaaaa tgtggaagcc catcatagta cttggacttc atctgctttt    4500
gtgccttcac taagttttta aacatgagct ggctcctatc tgccattggc aaggctgggc    4560
actacccaca acctacttca aggacctcta taccgtgaga ttacacacat acatcaaaat    4620
ttgggaaaag ttctaccaag ctgagagctg atcaccccac tcttaggtgc ttatctctgt    4680
acaccagaaa ccttaagaag caaccagtat tgagagactc atttatgaaa gtctaaaact    4740
ggatacaacc aaaatgtcca ccaacagtta aattatgaca tgttcacaat tgagctatta    4800
cttaataagg agaattaata aaataaaact taagagcata gtttaatctc ataaacaaga    4860
taataagcaa aacaaaacat tttttcatcc atgtaagttt aaaagcaggt aaaatttaaa    4920
```

```
attaagagag acataagttt tgaggtagca agatggaaac tctggggctt ggggaatgtt      4980
ctgtctctct gtatgggatg tgaaagttac tattgtggaa ttgggatcta tgttcttcct      5040
gtatatattg tatacttcat aataacttca cctaaagaaa tatctaatac ccagtgcata      5100
cataaaagag gatacaagga atgaatcata cgtcaaggcc agaaagacaa taaagtaggg      5160
gatccaggat caaatctccc acaaccttga gccttctact attctgcctt ccagagctca      5220
aagtacaaaa cacataattc aaacacatga tccctccttg gggtctcttc cttcatgcat      5280
cgaattagaa atagccatgt ataaaatgag atagaagaga ccttcatcaa caggtcaaag      5340
aatataggta attttgtctg ggtatgaaga gcccacgtat caaaggttac attagggaag      5400
gaagaggaca ctaacagtga cttcattct ccccctcttc ctggaggccc ctgcatttag       5460
tccctcgtgg gctcatccac tcagcacaca tttactaagc atcttctcag cctacactct      5520
gaaggcagtg cagaataatg ttagtgtccc ttcccccagt taatatgcag tccagtttcc      5580
ctgctccttc cctttctcag tccacataag gatgatggga aaggacagtc accaaatagg      5640
agagggcaac cctttgcctt cctacctctt gagaatgtac attattatcc acttttgaa       5700
acttctttta attgctttt tttaatttgt cttttcaaat agcataacct tgttcatcca       5760
tttctgggaa ccaaatttat caatcaacag tgcctctaat ctggctatta atacaaaaat      5820
gcctcctcaa aatatatatg ttcgagtctt atctaaaaca gaacccacaa taaaaagaa       5880
gaaagaatac atataagcat ttatataatt ctgagcaacc ttgtgctttg tgaaaaaaat      5940
ataatctaat gtcacatgct gtattctttt tatttaacac tggtgaaatt ataccattag      6000
agagaaagag gacagatcac tgatcctagg atctagggat gttacagata agaaaacaaa      6060
tgtgacaaag agctgtcaca aggaggatct tcaaggtcac agaatcactg tcttgatttc      6120
agtggtggtt acatacattt aaatatgtga taaaatgttg ttgaactata ttcatatatt      6180
gtaccaatgt caaatgctta attttggctc tatagtataa ttatgcacta ataactatt       6240
tggacaaaga aaatgatgtt tacatcaaag gtgaggccat atttgttagg aacataactt      6300
aaaaaccatt ttggataact aatgaaaagc cattttgtgt gccttggcat atcatgccta      6360
agctgtcacc agatagatct aataagacct aagcctcaga agcaagcccc tgcccagcaa      6420
gcaggcagca cagataagag ctaaacccag gacaggccat gatatgctaa tgaactacct      6480
tcaaggtggt gttgctgacc tagtgaacca gccccaagct gtgagcccca atagcacaaa      6540
gctactgccc aaagaaatta tacaaaaatt ggaactttgg gaatggtgtg caggatcgct      6600
ctgctgtatg cctggaacac agcttctcta tgttttgtat tgataccagt ctagaagctt      6660
ccaaaacttt ctcactgaag aagattcccc atgtgggacc cctacagact cttttgccca      6720
aacaactgct tccctcctgg tgtgatatct gttttgcttt tatgttagca taatattata      6780
aggaatgttt gtgtgaataa accaaacata ttttaaaagc aaatattgta tgcacatcct      6840
aattgctaaa aagtttacag ctaatagtcc catgctctcc acaatactgg atccaaataa      6900
gtcctaattt caatgttggg catctttaca gagagaaaga cattaaaaat gaagagacat      6960
gcagagagtg caccatgcca tcgtggagac agactgaagt gacacaactg ttagtcaaag      7020
aggattaagg acttccagaa gccaccaaag gaaggaggta tgaagtggtt tctccctcag      7080
agtatccaga ggagactaaa ccaaccaaca ccttttttgct taagacttct tgccttcagg      7140
actgtgagaa ggtagcttcc tattgttcta agccccagta tgtggcattt tgttaaggta      7200
gagtcaagaa accaataaaa tgcagacaga caaaaggata gctgagtttt ccaggcccctt     7260
```

```
ccttcttatt tttggttttg ttggtggtgg tggtggtggt ggtgatggtg gtggttttgt    7320
ttatgttttg tttggggagt tttttggggt tttttgggt tttgttttg ttgttgtttt       7380 ggggttttt gttgttgttg ttgtttgctt tttgttttt tgttttttgt tttttgaga       7440 cagtgtttct ctgtatagcc ctggctgtcc tggagttcct tctatctcta atgtctacat    7500
ctcagagggg atcctctaat ttcaaatgag cagtagctct ccatttttag ctcttattta    7560
ttcatttatt tacttactta cttattgtct gtagatgaaa gaattttgga gtgggaaagg    7620
gttcatgagc ccccagcaac taatgaggag ctacagacaa ttgatgtttc tggggaaagg    7680
agactcagtt tctttgagag tatagcttct gatgggtcaa ccatgttcct gtggctgatg    7740
tcacacccag gagtatgcag acaacagaaa ctggagttaa tgagttgttt taaaaataaa    7800
aaagggcatg aagcttggga tagaaattaa ggataaatac aattaaatac aggaaattct    7860
gaaagaatta ataaaaacat ttcttttttt aaaaaaaaat ccagaattag ctatgcttct    7920
tcaaaattgc ttctggagaa ctttacaagt taaataagtt atattgtaga aaaggtagag    7980
aggagaatag tggaagagag agataaggag acttcaaaag gagtggaggg agatagagga    8040
ggagaaagca gaagcaatgg ctgatagaca caggataaga gggaacagaa aggagaaaga    8100
ggaagccagg atgggtattt cttttgccta tctgtgacttg cacatggtct tggcaattat   8160
tgatgagttc aaggcttaat tcttcacttg tgccaactca acagagtctt tctttcttat    8220
aaccaggccc ccagtatgct catgtatgta tcaggtcctc ttatctcctt atagcaatcc    8280
tgtttataac tgggtaactt tgtgaaggga aggaagtgca cactgagatg tgctacaact    8340
ttttaataca aaattttgaa gagtttgtac aatgtatgta taattaataa ttaatattat    8400
gcactttaga ttttgatttc aactcaagat actaattcta tatatatggg ttaaatcaat    8460
atattaataa gtttaatttc acatgcttat ttttattgtg gttttcgaga cagggtttct    8520
ctgtatagcc ctggctgtcc tggaacccac tttgtagacc aggctggcct caaactcaga    8580
aacctacctg cctctgcctc tgcctctgcc tctgcctctg cctctgcctc tgcctctgcc    8640
tctgcctctg cctctgcctc tgcctctgcc tctgcctctg cctctgcctc tgcctctgcc    8700
tctgcctctg cctctgcctc tgcctctgcc tctgcctctg cctctgcctc tgcctctgcc    8760
tctgcctagt gctggaatta aaggtttgcg ccaccacgcc cggtgaaatt tttaaacttt    8820
atatatgtct cattctattt ctatcagata ggactgtgta gactgtgcta aactaataaa    8880
tgtgccctca aaagtaatcg caagttgtat tgttgttgtt ttgctttgct ttgcttttgct   8940 ttgctttgct ttgctttgct ttgctttgct ttgctttgct ttgctttgct ttgctttgct    9000
ttgctttgct ttgctttgct ttgcttttt gttttgggtt ttttccgggg ggagggaggg    9060
tggagaaaga atcttactat gaagctctga ctgtcctggg aactcactat atagatcagg    9120
cttgattcaa ctcatagaga tctgccttct tctgcctccc aagtgctggg aataaaggca    9180
tacacctcca tgcccagata gtgatcccaa gttttagcaa aagtttctag acttgacatt    9240
aatcgatgga gatagacatg aattacacaa agaactaatg tggagtttac ctgaatcata    9300
ctctatactt tatcagagat taaattaaca tttaataatc cagtgccagg ctagaggcac    9360
cattcaatgg cagtgtttgc catcatgcat aggcttagtc ttcagtgctg aaaggcattg    9420
ggggcaatat tactcattat acagatgaga aactgggaaa gacttgcctc agattctcta    9480
ctgaaaggct gagtttgtgg cttctagaaa atcttttact ttcaatattt ttaatgtata    9540 attttttat ttccactgat tttattttt atttttaaca tttataagaa ataaatgcaa      9600
taaaccaaat acatggacaa aaaaatacaa gaatcatatg atcacctcaa tggaaggaaa    9660
```

```
aaaaaagaaa gaaaaagtct ttgataagat tcaacattca ttcttttttt attagatatt    9720
ttcttcattt acatttcaaa tgctatcccc aaagccccct ataccttccc ctgccctgct    9780
ccccaaccca cccactcctg ctttctggcc ctggcattcc tctgtactga ggcatatgat    9840
cttcaaaaaa ccaagggcct ctcctctcat tggtggccga ctattaggcc atcttttgct    9900
acatatgcaa ctagagacac agctctgggg gttactggtt agttcatatt gttagtcctc    9960
ctatagagtt gcagacccct ttagctcctt ggatactttc tctagttcct tcattagggg   10020
ccctgtgtcc catccaatag atgactgtga gcatccactt ctgtatttgc caggcactgg   10080
catagcctca cgagaaagag agagctatgt caggatcctg tcagtaaaat ctttctggca   10140
tatgcaatag tatctgggtt tggtggttgt atatgggatg gatccccaag tggagcagtc   10200
tctgaatggt ccttccttcc atctcagctc caaactttgt ctctataact ccttccatgg   10260
gtattttgtt ccccattcta agaaggagtg aagaatccac actttggtct tccttcttct   10320
tgagtttcat atgttgcatc ttggatattc taagtttctg ggttaatatc cacgtatcag   10380
tgagtgcata tcatgcgtgt tattttgtga ttagtttacc tcactcagga tgatatcctc   10440
cagatgcatc catttgccta agaatttcat taattcactg tttttaattg ctgaatagta   10500
ctccattgtg taaatgtacc acattttctg tatccattcc tctgttgagg ggcatctggg   10560
ttctttccag cttctggcta ttataaataa ggctgctatg agcatagcgg agcatgtgtc   10620
cttatcaagt tggaacatct tctaggtata tgcccaggag aggaattgct ggatcttccg   10680
gtagtaccat caacatgcat tcttaataaa agccctagaa caaggaggac tgtaggaaac   10740
atattccaac ataataaagg ttatgtatga caaactcatg accaatatca tcctaaatga   10800
atgaaaccat taataagctc cattaaaatc agaggactgc ccactatccc tacttctcat   10860
ccataatgag attgaagcat tagctggagc aataaggcaa gagaagggat acaaatggga   10920
aaatattaag tcaaattgtt ttcaattgaa gattatatta tcttataccc aatgacctca   10980
aattttgact agaaaaattg tagaaattat caataatttc agcaaagtgt tatgatgcac   11040
cacatcctta ttcttctccc cagcttctgc ttgcttctct cttcttgctc ttcatccttt   11100
ctgtccttcc atctgcctgc actcttgtct caagactgag tgcagcgtgt aactctcctg   11160
tgactgagta tctcacaaaa cgttctacct gccaaacctg gatgagccct ttgtctttct   11220
gaagctatga ggctctctac atagactcaa gaaggaaatg acaggagga  ggtaataatg   11280 aagtggggaa ggctgacatt agcattgctc ctgtgtggct ccttaatttc tcatacttca   11340
cactgagatg ttattaactg tgactcatag gtgaagaagc cagagctaag gttctctatat  11400 ttgagtgtta tagaatgagt agagcagtag ttctcaaact atgggtcatg actcctttat   11460
gggtcaaact acccttttcac acaggttgca tatcagatat cctaatttta tatacatata   11520
tatatgcata tgtatatata tatatttcac aacagtagga aaattattta gtaatcattt   11580
tatagttgtg ggtcatggca acatgaggaa ctgtattaaa gggttgcagc attaggaatg   11640
ttgagaccca ctgtaataga gaatgaggct taaggcaggg ctataaagcc caatggacca   11700
tgtgcctttt ccaacatttg ccacatggta agctctgtat agacttttta aagaacattg   11760
gtttgtaatt ttaaatggat aagggtcttc actgtctatc acccatctat ataataaata   11820
cataagtttt gattccacca tggattcaaa tgcaaaaatc ctcaacctaa gacatagcag   11880
tgaaacattg atgaccaaat aggaaatcca tgtagagacc ttctatcttc tgatggctcc   11940
acaggcacca tcttgcaaca gagttctact ttgctaccag taatgaatac agtgtctcaa   12000
```

| | |
|---|---|
| ctcctgccat tgaatcttca ggaagcccct gaaatgactt gtactacacc atttcttaaa | 12060 |
| gacagaaaag ctaagactta gagggaataa atgtcatgcc tgagatcatg caaccaatta | 12120 |
| agtccaactt ggcctgatca agaggcacaa ttcaaaagca atgttgttcc ttcactagct | 12180 |
| cttgtgtatg gttgctgatt ccggaagcaa agtatcagtg aatatcccta gtgggaaaag | 12240 |
| acttggaaat caaatgtctc atttaacaga ttaggagatg aaacggtaga ctctgtgtag | 12300 |
| ttgtacaccc ctgtgatccc atcgctagga agactgaggc aggaagtcct cgagctcaaa | 12360 |
| ccagcttagg ctacacagag aaactatcta aaaataatt actaactact taataggaga | 12420 |
| ttggatgtta agatctggtc actaagaggc agaattgaga ttcgaagcca gtattttcta | 12480 |
| cctggtatgt tttaaattgc agtaaggatc taagtgtaga tatataataa taagattcta | 12540 |
| ttgatctctg caacaacaga gagtgttaga tttgtttgga aaaaaatatt atcagccaac | 12600 |
| atcttctacc atttcagtat agcacagagt acccacccat atctcccac ccatccccca | 12660 |
| taccagactg gttattgatt ttcatggtga ctggcctgag aagattaaaa aaagtaatgc | 12720 |
| taccttattg ggagtgtccc atggaccaag atagcaactg tcatagctac cgtcacactg | 12780 |
| ctttgatcaa gaagaccctt tgaggaactg aaaacagaac cttaggcaca tctgttgctt | 12840 |
| tcgctcccat cctcctccaa cagcctgggt ggtgcactcc acacccttc aagtttccaa | 12900 |
| agcctcatac acctgctccc taccccagca cctggccaag gctgtatcca gcactgggat | 12960 |
| gaaaatgata ccccacctcc atcttgtttg atattactct atctcaagcc ccaggttagt | 13020 |
| ccccagtccc aatgcttttg cacagtcaaa actcaacttg gaataatcag tatccttgaa | 13080 |
| gagttctgat atggtcactg gcccatata ccatgtaaga catgtggaaa agatgtttca | 13140 |
| tggggcccag acacgttcta gaagtacctg agagtggcaa aaaatagttg tgctaaatag | 13200 |
| tttggccatc tttaggctga gagactagga aatacagcga tggactatat cagcattgca | 13260 |
| ggatagttgt cagtaaacac cccacaaccc ataacagaag tattctcttc tttctatatc | 13320 |
| cctttttccat ccatgtagat ggctgtcttc atatttgttc tagacggccg gcc | 13373 |

<210> SEQ ID NO 93
<211> LENGTH: 12892
<212> TYPE: DNA
<213> ORGANISM: Artificial Sequence
<220> FEATURE:
<223> OTHER INFORMATION: VkP-IGKV1-39/J-Ck-delta1

<400> SEQUENCE: 93

| | |
|---|---|
| ggccggccca catgaaacaa tgggaaccat gtgacaatca cagaggtgtt gttactatag | 60 |
| caaaagggat tgttactctc cacatccctt taagtaactt gaaggcctga tagacccacc | 120 |
| ctctaagact tcattagaca ttccctacga atggttatac tctcctgtat actcccaata | 180 |
| caactctaaa atatattatt ccatatagtc cttaggtttg tattaaagtt tgactttttt | 240 |
| ccttcaaaat atctcttgtc acaacagcgg ctctagagag aaatacattc cctccaggca | 300 |
| aatctatgct gcgctggtct gacctgggac cctggggaca ttgcccctgt gctgagttac | 360 |
| taagatgagc cagccctgca gctgtgctca gcctgcccca tgccctgctg attgatttgc | 420 |
| atgttccaga gcacagcccc ctgccctgaa gactttttta tgggctggtc gcaccctgtg | 480 |
| caggagtcag tctcagtcag gagccaccat ggacatgaga gtgcccgccc agctcctggg | 540 |
| gctcctgcta ctctggctcc gaggtaagga tggagaacac taggaattta ctcagccagt | 600 |
| gtgctcagta ctgactggaa cttcagggaa gttctctgat aacatgatta atagtaagaa | 660 |
| tatttgtttt tatgtttcca atctcaggtg ccagatgtga catccagatg acccagagcc | 720 |

```
ccagcagcct gagcgccagc gtgggcgaca gagtgaccat cacctgcaga gccagccaga      780
gcatcagcag ctacctgaac tggtatcagc agaagcccgg caaggccccc aagctgctga      840
tctacgccgc cagctccctg cagagcggcg tgcccagcag attcagcggc agcggctccg      900
gcaccgactt caccctgacc atcagcagcc tgcagcccga ggacttcgcc acctactact      960
gccagcagag ctacagcacc ccccccacct tcggccaggg caccaaggtg gagatcaaac     1020
gtaagtacac ttttctcatc ttttttttatg tgtaagacac aggttttcat gttaggagtt     1080
aaagtcagtt cagaaaatct tgagaaaatg gagagggctc attatcagtt gacgtggcat     1140
acagtgtcag attttctgtt tatcaagcta gtgagattag gggcaaaaag aggctttagt     1200
tgagaggaaa gtaattaata ctatggtcac catccaagag attggatcgg agaataagca     1260
tgagtagtta ttgagatctg ggtctgactg caggtagcgt ggtcttctag acgtttaagt     1320
gggagatttg gaggggatga ggaatgaagg aacttcagga tagaaaaggg ctgaagtcaa     1380
gttcagctcc taaaatggat gtgggagcaa actttgaaga taaactgaat gacccagagg     1440
atgaaacagc gcagatcaaa gaggggcctg gagctctgag aagagaagga gactcatccg     1500
tgttgagttt ccacaagtac tgtcttgagt tttgcaataa aagtgggata gcagagttga     1560
gtgagccgta ggctgagttc tctcttttgt ctcctaagtt tttatgacta caaaaatcag     1620
tagtatgtcc tgaaataatc attaagctgt ttgaaagtat gactgcttgc catgtagata     1680
ccatggcttg ctgaataatc agaagaggtg tgactcttat tctaaaattt gtcacaaaat     1740
gtcaaaatga gagactctgt aggaacgagt ccttgacaga cagctcaagg ggttttttc      1800
ctttgtctca tttctacatg aaagtaaatt tgaaatgatc ttttttatta taagagtaga     1860
aatacagttg ggtttgaact atatgtttta atggccacgg ttttgtaaga catttggtcc     1920
tttgttttcc cagttattac tcgattgtaa ttttatatcg ccagcaatgg actgaaacgg     1980
tccgcaacct cttctttaca actgggtgac ctcgcggctg tgccagccat ttggcgttca     2040
ccctgccgct aagggccatg tgaaccccg  cggtagcatc ccttgctccg cgtggaccac     2100
tttcctgagg cacagtgata ggaacagagc cactaatctg aagagaacag agatgtgaca     2160
gactacacta atgtgagaaa aacaaggaaa gggtgactta ttggagattt cagaaataaa     2220
atgcatttat tattatattc ccttatttta attttctatt agggaattag aaagggcata     2280
aactgcttta tccagtgtta tattaaaagc ttaatgtata taatctttta gaggtaaaat     2340
ctacagccag caaagtcat  ggtaaatatt ctttgactga actctcacta aactcctcta     2400
aattatatgt catattaact ggttaaatta atataaattt gtgacatgac cttaactggt     2460
taggtaggat attttcttc  atgcaaaaat atgactaata ataatttagc acaaaaatat     2520
ttcccaatac tttaattctg tgatagaaaa atgtttaact cagctactat aatcccataa     2580
ttttgaaaac tatttatttg gctacaccaa aggaagccat acagaggcta atatcagagt     2640
attcttggaa gagacaggag aaaatgaaag ccagtttctg ctcttacctt atgtgcttgt     2700
gttcagactc ccaaacatca ggagtgtcag ataaactggt ctgaatctct gtctgaagca     2760
tggaactgaa aagaatgtag tttcagggaa gaaaggcaat agaaggaagc ctgagaatat     2820
cttcaaaggg tcagactcaa tttactttct aaagaagtag ctaggaacta gggataact     2880
tagaaacaac aagattgtat atatgtgcat cctggcccca ttgttcctta tctgtaggga     2940
taagcgtgct ttttttgtgtg tctgtatata acataactgt ttacacataa tacactgaaa     3000
tggagccctt ccttgttact tcataccatc ctctgtgctt ccttcctcag gggccgacgc     3060
```

```
cgctcccacc gtgtccatct tccccccccag catggaacag ctgacctctg gcggagccac    3120
cgtggtctgc ttcgtgaaca acttctaccc cagagacatc agcgtgaagt ggaagatcga    3180
cggcagcgag cagagggacg gcgtgctgga cagcgtgacc gaccaggaca gcaaggactc    3240
cacctacagc atgagcagca ccctgagcct gaccaaggtg gagtacgaga ggcacaacct    3300
gtacacctgc gaggtggtgc acaagaccag ctccagcccc gtggtcaagt ccttcaaccg    3360
gaacgagtgt tgaagacaaa ggtcctgaga cgccaccacc agctcccag ctccatccta     3420 tcttcccttc taaggtcttg gaggcttccc cacaagcgac ctaccactgt tgcggtgctc    3480
caaacctcct ccccacctcc ttctcctcct cctcccttttc cttggctttt atcatgctaa   3540
tatttgcaga aaatattcaa taaagtgagt ctttgcactt gagatctctg tcttttcttac  3600 taaatggtag taatcagttg tttttccagt tacctgggtt tctcttctaa agaagttaaa   3660
tgtttagttg ccctgaaatc caccacactt aaaggataaa taaaaccctc cacttgccct   3720
ggttggctgt ccactacatg gcagtccttt ctaaggttca cgagtactat tcatggctta   3780
tttctctggg ccatggtagg tttgaggagg catacttcct agttttcttc ccctaagtcg   3840
tcaaagtcct gaaggggac agtctttaca agcacatgtt ctgtaatctg attcaaccta    3900
cccagtaaac ttggcgaagc aaagtagaat cattatcaca ggaagcaaag gcaacctaaa   3960
tgtgcaagca ataggaaaat gtggaagccc atcatagtac ttggacttca tctgcttttg   4020
tgccttcact aagttttaa acatgagctg gctcctatct gccattggca aggctgggca    4080
ctacccacaa cctacttcaa ggacctctat accgtgagat tacacacata catcaaaatt   4140
tgggaaaagt tctaccaagc tgagagctga tcacccccact cttaggtgct tatctctgta  4200
caccagaaac cttaagaagc aaccagtatt gagagactca tttatgaaag tctaaaactg   4260
gatcaaacca aaatgtccac caacagttaa attatgacat gttcacaatt gagctattac   4320
ttaataagga gaattaataa aataaaactt aagagcatag tttaatctca taaacaagat   4380
aataagcaaa acaaaacatt ttttcatcca tgtaagttta aaagcaggta aaatttaaaa   4440
ttaagagaga cataagtttt gaggtagcaa gatggaaact ctggggcttg gggaatgttc   4500
tgtctctctg tatgggatgt gaaagttact attgtggaat tgggatctat gttcttcctg   4560
tatatattgt atacttcata ataacttcac ctaaagaaat atctaatacc cagtgcatac   4620
ataaaagagg atacaaggaa tgaatcatac gtcaaggcca gaaagacaat aaagtagggg   4680
atccaggatc aaatctccca caaccttgag ccttctacta ttctgccttc cagagctcaa   4740
agtacaaaac acataattca aacacatgat ccctccttgg ggtctcttcc ttcatgcatc    4800
gaattagaaa tagccatgta taaaatgaga tagaagagac cttcatcaac aggtcaaaga   4860
atataggtaa ttttgtctgg gtatgaagag cccacgtatc aaaggttaca ttagggaagg   4920
aagaggacac taacagtgac tttcattctc cccctcttcc tggaggcccc tgcatttagt   4980
ccctcgtggg ctcatccact cagcacacat ttactaagca tcttctcagc ctacactctg   5040
aaggcagtgc agaataatgt tagtgtccct tcccccagtt aatatgcagt ccagtttccc   5100
tgctccttcc ctttctcagt ccacataagg atgatgggaa aggacagtca ccaaatagga   5160
gagggcaacc ctttgccttc ctacctcttg agaatgtaca ttattatcca cttttttgaaa  5220 cttcttttaa ttgcttttttt ttaatttgtc ttttcaaata gcataacctt gttcatccat   5280
ttctgggaac caaatttatc aatcaacagt gcctctaatc tggctattaa tacaaaaatg   5340
cctcctcaaa atatatatgt tcgagtctta tctaaaacag aacccacaat aaaaaagaag   5400
aaagaataca tataagcatt tatataattc tgagcaacct tgtgctttgt gaaaaaaata   5460
```

```
taatctaatg tcacatgctg tattcttttt atttaacact ggtgaaatta taccattaga    5520
gagaaagagg acagatcact gatcctagga tctagggatg ttacagataa gaaaacaaat    5580
gtgacaaaga gctgtcacaa ggaggatctt caaggtcaca gaatcactgt cttgatttca    5640
gtggtggtta catacattta aatatgtgat aaaatgttgt tgaactatat tcatatattg    5700
taccaatgtc aaatgcttaa ttttggctct atagtataat tatgcactaa ataactattt    5760
ggacaaagaa aatgatgttt acatcaaagg tgaggccata tttgttagga acataactta    5820
aaaaccattt tggataacta atgaaaagcc attttgtgtg ccttggcata tcatgcctaa    5880
gctgtcacca gatagatcta ataagaccta agcctcagaa gcaagcccct gcccagcaag    5940
caggcagcac agataagagc taaacccagg acaggccatg atatgctaat gaactacctt    6000
caaggtggtt ttgctgacct agtgaaccag ccccaagctg tgagcccaa tagcacaaag     6060 ctactgccca agaaattat acaaaaattg gaactttggg aatggtgtgc aggatcgctc     6120
tgctgtatgc ctggaacaca gcttctctat gttttgtatt gataccagtc tagaagcttc    6180
caaaactttc tcactgaaga agattcccca tgtgggaccc ctacagactc ttttgcccaa    6240
acaactgctt ccctcctggt gtgatatctg ttttgctttt atgttagcat aatattataa    6300
ggaatgtttg tgtgaataaa ccaaacatat tttaaaagca aatattgtat gcacatccta    6360
attgctaaaa agtttacagc taatagtccc atgctctcca caatactgga tccaaataag    6420
tcctaatttc aatgttgggc atctttacag agagaaagac attaaaaatg aagagacatg    6480
cagagagtgc accatgccat cgtggagaca gactgaagtg acacaactgt tagtcaaaga    6540
ggattaagga cttccagaag ccaccaaagg aaggaggtat gaagtggttt ctccctcaga    6600
gtatccagag gagactaaac caaccaacac ctttttgctt aagacttctt gccttcagga    6660
ctgtgagaag gtagcttcct attgttctaa gccccagtat gtggcatttt gttaaggtag    6720
agtcaagaaa ccaataaaat gcagacagac aaaaggatag ctgagttttc caggcccttc    6780 cttcttatt ttggttttgt tggtggtggt ggtggtggtg gtgatggtgg tggttttgtt     6840
tatgttttgt ttggggagtt ttttgggtt ttttgggtt ttgttttgt tgttgttttg       6900 ggggttttg ttgttgttgt tgtttgcttt tttgttttt gttttttgtt ttttgagac       6960 agtgtttctc tgtatagccc tggctgtcct ggagttcctt ctatctctaa tgtctacatc    7020
tcagagggga tcctctaatt tcaaatgagc agtagctctc cattttagc tcttatttat     7080 tcatttattt acttacttac ttattgtctg tagatgaaag aattttggag tgggaagggg    7140
ttcatgagcc cccagcaact aatgaggagc tacagacaat tgatgtttct ggggaaagga    7200
gactcagttt ctttgagagt atagcttctg atgggtcaac catgttcctg tggctgatgt    7260
cacacccagg agtatgcaga caacagaaac tggagttaat gagttgtttt aaaaataaaa    7320
aagggcatga agcttgggat agaaattaag gataaataca attaaataca ggaaattctg    7380
aaagaattaa taaaaacatt tctttttta aaaaaaatc cagaattagc tatgcttctt      7440
caaaattgct tctggagaac tttacaagtt aaataagtta tattgtagaa aaggtagaga    7500
ggagaatagt ggaagagaga gataaggaga cttcaaaagg agtggaggga gatagaggag    7560
gagaaagcag aagcaatggc tgatagacac aggataagag ggaacagaaa ggagaaagag    7620
gaagccagga tgggtatttc tttgcctatc tgtgacttgc acatggtctt ggcaattatt    7680
gatgagttca aggcttaatt cttcacttgt gccaactcaa cagagtcttt ctttcttata    7740
accaggcccc cagtatgctc atgtatgtat caggtcctct tatctcctta tagcaatcct    7800
```

```
gtttataact gggtaacttt gtgaagggaa ggaagtgcac actgagatgt gctacaactt    7860
tttaatacaa aattttgaag agtttgtaca atgtatgtat aattaataat taatattatg    7920
cactttagat tttgatttca actcaagata ctaattctat atatatgggt taaatcaata    7980
tattaataag tttaatttca catgcttatt tttattgtgg ttttcgagac agggtttctc    8040
tgtatagccc tggctgtcct ggaacccact tgtagacca ggctggcctc aaactcagaa     8100
acctacctgc ctctgcctct gcctctgcct ctgcctctgc ctctgcctct gcctctgcct    8160
ctgcctctgc ctctgcctct gcctctgcct ctgcctctgc ctctgcctct gcctctgcct    8220
ctgcctctgc ctctgcctct gcctctgcct ctgcctctgc ctctgcctct gcctctgcct    8280
ctgcctagtg ctggaattaa aggtttgcgc caccacgccc ggtgaaattt ttaaacttta    8340
tatatgtctc attctatttc tatcagatag gactgtgtag actgtgctaa actaataaat    8400
gtgccctcaa aagtaatcgc aagttgtatt gttgttgttt tgctttgctt tgctttgctt    8460
tgctttgctt tgctttgctt tgctttgctt tgctttgctt tgctttgctt tgctttgctt    8520
tgctttgctt tgctttgctt tgctttttg ttttgggttt ttttccgggg gagggagggt     8580
ggagaaagaa tcttactatg aagctctgac tgtcctggga actcactata tagatcaggc    8640
ttgattcaac tcatagagat ctgccttctt ctgcctccca agtgctggga ataaaggcat    8700
acacctccat gcccagatag tgatcccaag ttttagcaaa agtttctaga cttgacatta    8760
atcgatggag atagacatga attacacaaa gaactaatgt ggagtttacc tgaatcatac    8820
tctatacttt atcagagatt aaattaacat ttaataatcc agtgccaggc tagaggcacc    8880
attcaatggc agtgtttgcc atcatgcata ggcttagtct tcagtgctga aaggcattgg    8940
gggcaatatt actcattata cagatgagaa actgggaaag acttgcctca gattctctac    9000
tgaaaggctg agtttgtggc ttctagaaaa tcttttactt tcaatatttt taatgtataa    9060 ttttttttatt tccactgatt ttattttta tttttaacat ttataagaaa taaatgcaat     9120
aaaccaaata catggacaaa aaaatacaag aatcatatga tcacctcaat ggaaggaaaa    9180
aaaaagaaag aaaaagtctt tgataagatt caacattcat tctttttta ttagatattt     9240 tcttcattta catttcaaat gctatcccca aagccccta taccttcccc tgccctgctc     9300
cccaacccac ccactcctgc tttctggccc tggcattcct ctgtactgag gcatatgatc    9360
ttcaaaaaac caagggcctc tcctctcatt ggtggccgac tattaggcca tcttttgcta    9420
catatgcaac tagagacaca gctctggggg ttactggtta gttcatattg ttagtcctcc    9480
tatagagttg cagaccccctt tagctccttg gatactttct ctagttcctt cattaggggc    9540
cctgtgtccc atccaataga tgactgtgag catccacttc tgtatttgcc aggcactggc    9600
atagcctcac gagaaagaga gagctatgtc aggatcctgt cagtaaaatc tttctggcat    9660
atgcaatagt atctgggttt ggtggttgta tatgggatgg atccccaagt ggagcagtct    9720
ctgaatggtc cttccttcca tctcagctcc aaactttgtc tctataactc cttccatggg    9780
tattttgttc cccattctaa gaaggagtga agaatccaca ctttggtctt ccttcttctt    9840
gagtttcata tgttgcatct tggatattct aagttctgg gttaatatcc acgtatcagt     9900
gagtgcatat catgcgtgtt attttgtgat tagtttacct cactcaggat gatatcctcc    9960
agatgcatcc atttgcctaa gaatttcatt aattcactgt ttttaattgc tgaatagtac    10020
tccattgtgt aaatgtacca cattttctgt atccattcct ctgttgaggg gcatctgggt    10080
tctttccagc ttctggctat tataaataag gctgctatga gcatagcgga gcatgtgtcc    10140
ttatcaagtt ggaacatctt ctaggtatat gcccaggaga ggaattgctg gatcttccgg    10200
```

```
tagtaccatc aacatgcatt cttaataaaa gccctagaac aaggaggact gtaggaaaca  10260
tattccaaca taataaaggt tatgtatgac aaactcatga ccaatatcat cctaaatgaa  10320
tgaaaccatt aataagctcc attaaaatca gaggactgcc cactatccct acttctcatc  10380
cataatgaga ttgaagcatt agctggagca ataaggcaag agaagggata caaatgggaa  10440
aatattaagt caaattgttt tcaattgaag attatattat cttatacccca atgacctcaa  10500 attttgacta gaaaaattgt agaaattatc aataatttca gcaaagtgtt atgatgcacc  10560
acatccttat tcttctcccc agcttctgct tgcttctctc ttcttgctct tcatcctttc  10620
tgtccttcca tctgcctgca ctcttgtctc aagactgagt gcagcgtgta actctcctgt  10680
gactgagtat ctcacaaaac gttctacctg ccaaacctgg atgagcccct tgtctttctg  10740
aagctatgag gctctctaca tagactcaag aaggaaatga cagggaggag gtaataatga  10800
agtggggaag gctgacatta gcattgctcc tgtgtggctc cttaatttct catacttcac  10860
actgagatgt tattaactgt gactcatagg tgaagaagcc agagctaagg ttctcatatt  10920
tgagtgttat agaatgagta gagcagtagt tctcaaacta tgggtcatga ctcctttatg  10980
ggtcaaacta ccctttcaca caggttgcat atcagatatc ctaattttat atacatatat  11040
atatgcatat gtatatatat atatttcaca acagtaggaa aattatttag taatcatttt  11100
atagttgtgg gtcatggcaa catgaggaac tgtattaaag ggttgcagca ttaggaatgt  11160
tgagacccac tgtaatagag aatgaggctt aaggcagggc tataaagccc aatggaccat  11220
gtgccttttc caacatttgc cacatggtaa gctctgtata gacttttttaa agaacattgg  11280 tttgtaattt taaatggata agggtcttca ctgtctatca cccatctata taataaatac  11340
ataagttttg attccaccat ggattcaaat gcaaaaatcc tcaacctaag acatagcagt  11400
gaaacattga tgaccaaata ggaaatccat gtagagacct tctatcttct gatggctcca  11460
caggcaccat cttgcaacag agttctactt tgctaccagt aatgaataca gtgtctcaac  11520
tcctgccatt gaatcttcag gaagcccctg aaatgacttg tactacacca tttcttaaag  11580
acagaaaagc taagacttag agggaataaa tgtcatgcct gagatcatgc aaccaattaa  11640
gtccaacttg gcctgatcaa gaggcacaat tcaaaagcaa tgttgttcct tcactagctc  11700
ttgtgtatgg ttgctgattc cggaagcaaa gtatcagtga atatccctag tgggaaaaga  11760
cttggaaatc aaatgtctca tttaacagat taggagatga aacggtagac tctgtgtagt  11820
tgtacacccc tgtgatccca tcgctaggaa gactgaggca ggaagtcctc gagctcaaac  11880
cagcttaggc tacacagaga aactatctaa aaaataatta ctaactactt aataggagat  11940
tggatgttaa gatctggtca ctaagaggca gaattgagat tcgaagccag tattttctac  12000
ctggtatgtt ttaaattgca gtaaggatct aagtgtagat atataataat aagattctat  12060
tgatctctgc aacaacagag agtgttagat ttgtttggaa aaaaatatta tcagccaaca  12120
tcttctacca tttcagtata gcacagagta cccaccccata tctcccccacc catccccccat  12180 accagactgg ttattgattt tcatggtgac tggcctgaga agattaaaaa aagtaatgct  12240
accttattgg gagtgtccca tggaccaaga tagcaactgt catagctacc gtcacactgc  12300
tttgatcaag aagacccttt gaggaactga aaacagaacc ttaggcacat ctgttgcttt  12360
cgctcccatc ctcctccaac agcctgggtg gtgcactcca cacccttttca agtttccaaa  12420 gcctcataca cctgctccct accccagcac ctggccaagg ctgtatccag cactgggatg  12480
aaaatgatac cccacctcca tcttgtttga tattactcta tctcaagccc caggttagtc  12540
```

| | |
|---|---|
| cccagtccca atgcttttgc acagtcaaaa ctcaacttgg aataatcagt atccttgaag | 12600 |
| agttctgata tggtcactgg gcccatatac catgtaagac atgtggaaaa gatgtttcat | 12660 |
| ggggcccaga cacgttctag aagtacctga gagtggcaaa aaatagttgt gctaaatagt | 12720 |
| ttggccatct ttaggctgag agactaggaa atacagcgat ggactatatc agcattgcag | 12780 |
| gatagttgtc agtaaacacc ccacaaccca taacagaagt attctcttct ttctatatcc | 12840 |
| cttttccatc catgtagatg gctgtcttca tatttgttct agacggccgg cc | 12892 |

<210> SEQ ID NO 94
<211> LENGTH: 6425
<212> TYPE: DNA
<213> ORGANISM: Artificial Sequence
<220> FEATURE:
<223> OTHER INFORMATION: VkP-IGKV1-39/J-Ck-delta2

<400> SEQUENCE: 94

| | |
|---|---|
| ggccggccca catgaaacaa tgggaaccat gtgacaatca cagaggtgtt gttactatag | 60 |
| caaaagggat tgttactctc cacatccctt aagtaactt gaaggcctga tagacccacc | 120 |
| ctctaagact tcattagaca ttccctacga atggttatac tctcctgtat actcccaata | 180 |
| caactctaaa atatattatt ccatatagtc cttaggtttg tattaaagtt tgactttttt | 240 |
| ccttcaaaat atctcttgtc acaacagcgg ctctagagag aaatacattc cctccaggca | 300 |
| aatctatgct gcgctggtct gacctgggac cctggggaca ttgcccctgt gctgagttac | 360 |
| taagatgagc cagccctgca gctgtgctca gcctgcccca tgcctgctg attgatttgc | 420 |
| atgttccaga gcacagcccc ctgccctgaa gactttttta tgggctggtc gcaccctgtg | 480 |
| caggagtcag tctcagtcag gagccaccat ggacatgaga gtgcccgccc agctcctggg | 540 |
| gctcctgcta ctctggctcc gaggtaagga tggagaacac taggaattta ctcagccagt | 600 |
| gtgctcagta ctgactggaa cttcagggaa gttctctgat aacatgatta atagtaagaa | 660 |
| tatttgtttt tatgtttcca atctcaggtg ccagatgtga catccagatg acccagagcc | 720 |
| ccagcagcct gagcgccagc gtgggcgaca gagtgaccat cacctgcaga gccagccaga | 780 |
| gcatcagcag ctacctgaac tggtatcagc agaagcccgg caaggccccc aagctgctga | 840 |
| tctacgccgc cagctccctg cagagcggcg tgcccagcag attcagcggc agcggctccg | 900 |
| gcaccgactt caccctgacc atcagcagcc tgcagcccga ggacttcgcc acctactact | 960 |
| gccagcagag ctacagcacc ccccccacct tcggccaggg caccaaggtg gagatcaaac | 1020 |
| gtaagtacac ttttctcatc tttttttatg tgtaagacac aggttttcat gttaggagtt | 1080 |
| aaagtcagtt cagaaaatct tgagaaaatg gagagggctc attatcagtt gacgtggcat | 1140 |
| acagtgtcag atttctgtt tatcaagcta gtgagattag gggcaaaaag aggctttagt | 1200 |
| tgagaggaaa gtaattaata ctatggtcac catccaagag attggatcgg agaataagca | 1260 |
| tgagtagtta ttgagatctg ggtctgactg caggtagcgt ggtcttctag acgtttaagt | 1320 |
| gggagatttg gagggatga ggaatgaagg aacttcagga tagaaagggg ctgaagtcaa | 1380 |
| gttcagctcc taaaatggat gtgggagcaa actttgaaga taaactgaat gacccagagg | 1440 |
| atgaaacagc gcagatcaaa gaggggcctg gagctctgag aagagaagga gactcatccg | 1500 |
| tgttgagttt ccacaagtac tgtcttgagt tttgcaataa aagtgggata gcagagttga | 1560 |
| gtgagccgta ggctgagttc tctcttttgt ctcctaagtt tttatgacta caaaaatcag | 1620 |
| tagtatgtcc tgaaataatc attaagctgt ttgaaagtat gactgcttgc catgtagata | 1680 |
| ccatggcttg ctgaataatc agaagaggtg tgactcttat tctaaaattt gtcacaaaat | 1740 |

```
gtcaaaatga gagactctgt aggaacgagt ccttgacaga cagctcaagg ggttttttc      1800 ctttgtctca tttctacatg aaagtaaatt tgaaatgatc tttttttatta taagagtaga    1860 aatacagttg ggtttgaact atatgtttta atggccacgg ttttgtaaga catttggtcc     1920
tttgttttcc cagttattac tcgattgtaa ttttatatcg ccagcaatgg actgaaacgg     1980
tccgcaacct cttctttaca actgggtgac ctcgcggctg tgccagccat ttggcgttca     2040
ccctgccgct aagggccatg tgaaccccg cggtagcatc ccttgctccg cgtgaccac       2100 tttcctgagg cacagtgata ggaacagagc cactaatctg aagagaacag agatgtgaca    2160
gactacacta atgtgagaaa aacaaggaaa gggtgactta ttggagattt cagaaataaa    2220
atgcatttat tattatattc ccttatttta attttctatt agggaattag aaagggcata    2280
aactgcttta tccagtgtta tattaaaagc ttaatgtata taatcttta gaggtaaaat     2340 ctacagccag caaaagtcat ggtaaatatt ctttgactga actctcacta aactcctcta    2400
aattatatgt catattaact ggttaaatta atataaattt gtgacatgac cttaactggt    2460
taggtaggat attttcttc atgcaaaaat atgactaata ataatttagc acaaaatat      2520 ttcccaatac tttaattctg tgatagaaaa atgtttaact cagctactat aatcccataa    2580
ttttgaaaac tatttatttg gctacaccaa aggaagccat acagaggcta atatcagagt    2640
attcttggaa gagacaggag aaaatgaaag ccagttttctg ctcttacctt atgtgcttgt   2700
gttcagactc ccaaacatca ggagtgtcag ataaactggt ctgaatctct gtctgaagca    2760
tggaactgaa aagaatgtag tttcagggaa gaaaggcaat agaaggaagc ctgagaatat   2820
cttcaaaggg tcagactcaa tttactttct aaagaagtag ctaggaacta gggaataact    2880
tagaaacaac aagattgtat atatgtgcat cctggcccca ttgttcctta tctgtaggga   2940
taagcgtgct tttttgtgtg tctgtatata acataactgt ttacacataa tacactgaaa    3000 tggagcccctt ccttgttact tcataccatc ctctgtgctt ccttcctcag ggccgacgc    3060 cgctcccacc gtgtccatct tcccccccag catggaacag ctgacctctg gcggagccac   3120
cgtggtctgc ttcgtgaaca acttctaccc cagagacatc agcgtgaagt ggaagatcga    3180
cggcagcgag cagagggacg gcgtgctgga cagcgtgacc gaccaggaca gcaaggactc    3240
cacctacagc atgagcagca ccctgagcct gaccaaggtg gagtacgaga ggcacaacct    3300
gtacacctgc gaggtggtgc acaagaccag ctccagcccc gtggtcaagt ccttcaaccg    3360
gaacgagtgt tgaagacaaa ggtcctgaga cgccaccacc agctccccag ctccatccta    3420
tcttcccttc taaggtcttg gaggcttccc cacaagcgac ctaccactgt tgcggtgctc    3480
caaacctcct ccccacctcc ttctcctcct cctcccttc cttggctttt atcatgctaa     3540
tatttgcaga aaatattcaa taaagtgagt ctttgcactt gagatctctg tctttcttac    3600
taaatggtag taatcagttg ttttccagt tacctgggtt tctcttctaa agaagttaaa    3660
tgtttagttg ccctgaaatc caccacactt aaaggataaa taaaccctc cacttgccct     3720 ggttggctgt ccactacatg gcagtccttt ctaaggttca cgagtactat tcatggctta    3780
tttctctggg ccatggtagg tttgaggagg catacttcct agtttttcttc ccctaagtcg   3840 tcaaagtcct gaagggggac agtctttaca agcacatgtt ctgtaatctg attcaaccta    3900
cccagtaaac ttggcgaagc aaagtagaat cattatcaca ggaagcaaag caacctaaa    3960 tgtgcaagca ataggaaaat gtggaagccc atcatagtac ttggacttca tctgcttttg    4020
tgccttcact aagtttttaa acatgagctg gctcctatct gccattggca aggctgggca    4080
```

```
ctacccacaa cctacttcaa ggacctctat accgtgagat tacacacata catcaaaatt     4140
tgggaaaagt tctaccaagc tgagagctga tcaccccact cttaggtgct tatctctgta     4200
caccagaaac cttaagaagc aaccagtatt gagagactca tttatgaaag tctaaaactg     4260
gatacaacca aaatgtccac caacagttaa attatgacat gttcacaatt gagctattac     4320
ttaataagga gaattaataa aataaaactt aagagcatag tttaatctca taaacaagat     4380
aataagcaaa acaaaacatt ttttcatcca tgtaagttta aaagcaggta aaatttaaaa     4440
ttaagagaga cataagttttt gaggtagcaa gatggaaact ctggggcttg gggaatgttc     4500
tgtctctctg tatgggatgt gaaagttact attgtggaat tgggatctat gttcttcctg     4560
tatatattgt atacttcata ataacttcac ctaaagaaat atctaatacc cagtgcatac     4620
ataaaagagg atacaaggaa tgaatcatac gtcaaggcca gaaagacaat aaagtagggg     4680
atccaggatc aaatctccca caaccttgag ccttctacta ttctgccttc cagagctcaa     4740
agtacaaaac acataattca aacacatgat ccctccttgg ggtctcttcc ttcatgcatc     4800
gaattagaaa tagccatgta taaaatgaga tagaagagac cttcatcaac aggtcaaaga     4860
atataggtaa ttttgtctgg gtatgaagag cccacgtatc aaaggttaca ttagggaagg     4920
aagaggacac taacagtgac tttcattctc ccctcttcc tggaggcccc tgcatttagt      4980
ccctcgtggg ctcatccact cagcacacat ttactaagca tcttctcagc ctacactctg     5040
aaggcagtgc agaataatgt tagtgtccct tcccccagtt aatatgcagt ccagtttccc     5100
tgctccttcc ctttctcagt ccacataagg atgatgggaa aggacagtca ccaaatagga     5160
gagggcaacc ctttgccttc ctacctcttg agaatgtaca ttattatcca cttttttgaaa    5220
cttcttttaa ttgcttttttt ttaatttgtc ttttcaaata gcataacctt gttcatccat    5280
ttctgggaac caaatttatc aatcaacagt gcctctaatc tggctattaa tacaaaaatg     5340
cctcctcaaa atatatatgt tcgagtctta tctaaaacag aacccacaat aaaaaagaag    5400
aaagaataca tataagcatt tatataattc tgagcaacct tgtgctttgt gaaaaaaata    5460
taatctaatg tcacatgctg tattctttttt atttaacact ggtgaaatta taccattaga    5520
gagaaagagg acagatcact gatcctagga tctagggatg ttacagataa gaaaacaaat     5580
gtgacaaaga gctgtcacaa ggaggatctt caaggtcaca gaatcactgt cttgatttca     5640
gtggtggtta catacattta aatatgtgat aaaatgttgt tgaactatat tcatatattg     5700
taccaatgtc aaatgcttaa ttttggctct atagtataat tatgcactaa ataactattt     5760
ggacaaagaa aatgatgttt acatcaaagg tgaggccata tttgttagga acataactta     5820
aaaaccattt tggataacta atgaaaagcc attttgtgtg ccttggcata tcatgcctaa     5880
gctgtcacca gatagatcta ataagaccta agcctcagaa gcaagcccct gcccagcaag     5940
caggcagcac agataagagc taaacccagg acaggccatg atatgctaat gaactacctt     6000
caaggtggtg ttgctgacct agtgaaccag ccccaagctg tgagcccccaa tagcacaaag    6060
ctactgccca agaaattat acaaaaattg gaactttggg aatggtgtgc aggatcgctc     6120
tgctgtatgc ctggaacaca gcttctctat gttttgtatt gataccagtc tagaagcttc     6180
caaaactttc tcactgaaga agattcccca tgtgggaccc ctacagactc ttttgcccaa     6240
acaactgctt ccctcctggt gtgatcatgg accaagatag caactgtcat agctaccgtc     6300
acactgcttt gatcaagaag accctttgag gaactgaaaa cagaaccctta ggcacatctg     6360
ttgctttcgc tcccatcctc ctccaacagc atggctgtct tcatatttgt tctagacggc     6420
cggcc                                                                6425
```

<210> SEQ ID NO 95
<211> LENGTH: 13382
<212> TYPE: DNA
<213> ORGANISM: Artificial Sequence
<220> FEATURE:
<223> OTHER INFORMATION: VkP-IGLV2-14/J-Ck

<400> SEQUENCE: 95

| | | | | | | |
|---|---|---|---|---|---|---|
| ggccggccca | catgaaacaa | tgggaaccat | gtgacaatca | cagaggtgtt | gttactatag | 60 |
| caaaagggat | tgttactctc | cacatcccctt | taagtaactt | gaaggcctga | tagacccacc | 120 |
| ctctaagact | tcattagaca | ttccctacga | atggttatac | tctcctgtat | actcccaata | 180 |
| caactctaaa | atatattatt | ccatatagtc | cttaggtttg | tattaaagtt | tgactttttt | 240 |
| ccttcaaaat | atctcttgtc | acaacagcgg | ctctagagag | aaatacattc | cctccaggca | 300 |
| aatctatgct | gcgctggtct | gacctgggac | cctggggaca | ttgcccctgt | gctgagttac | 360 |
| taagatgagc | cagccctgca | gctgtgctca | gcctgcccca | tgccctgctg | attgatttgc | 420 |
| atgttccaga | gcacagcccc | ctgccctgaa | gacttttta | tgggctggtc | gcaccctgtg | 480 |
| caggagtcag | tctcagtcag | gagccaccat | ggacatgaga | gtgcccgccc | agctcctggg | 540 |
| gctcctgcta | ctctggctcc | gaggtaagga | tgagaacac | taggaattta | ctcagccagt | 600 |
| gtgctcagta | ctgactggaa | cttcaggaa | gttctctgat | aacatgatta | atagtaagaa | 660 |
| tatttgtttt | tatgtttcca | atctcaggtg | ccagatgtca | gtctgccctg | acccagcccg | 720 |
| cctctgtgtc | tggcagccct | ggccagagca | tcaccatcag | ctgcaccggc | accagcagcg | 780 |
| acgtgggcgg | ctacaactac | gtgtcctggt | atcagcagca | ccccggcaag | gccccaagc | 840 |
| tgatgatcta | cgaggtgtcc | aacagaccca | gcggcgtgag | caacagattc | agcggcagca | 900 |
| agagcggcaa | caccgccagc | ctgaccatca | gcggcctcca | ggctgaggac | gaggccgact | 960 |
| actactgcag | cagctacacc | agcagctcca | ccctggtgtt | tggcggcgga | acaaagctga | 1020 |
| ccgtgctgcg | taagtacact | ttctcatct | ttttttatgt | gtaagacaca | ggttttcatg | 1080 |
| ttaggagtta | aagtcagttc | agaaaatctt | gagaaaatgg | agagggctca | ttatcagttg | 1140 |
| acgtggcata | cagtgtcaga | ttttctgttt | atcaagctag | tgagattagg | ggcaaaaaga | 1200 |
| ggctttagtt | gagaggaaag | taattaatac | tatggtcacc | atccaagaga | ttggatcgga | 1260 |
| gaataagcat | gagtagttat | tgagatctgg | gtctgactgc | aggtagcgtg | gtcttctaga | 1320 |
| cgtttaagtg | ggagatttgg | aggggatgag | gaatgaagga | acttcaggat | agaaaagggc | 1380 |
| tgaagtcaag | ttcagctcct | aaaatggatg | tgggagcaaa | ctttgaagat | aaactgaatg | 1440 |
| acccagagga | tgaaacagcg | cagatcaaag | aggggcctgg | agctctgaga | agagaaggag | 1500 |
| actcatccgt | gttgagtttc | acaagtact | gtcttgagtt | ttgcaataaa | agtgggatag | 1560 |
| cagagttgag | tgagccgtag | gctgagttct | ctctttgtc | tcctaagttt | ttatgactac | 1620 |
| aaaaatcagt | agtatgtcct | gaaataatca | ttaagctgtt | tgaaagtatg | actgcttgcc | 1680 |
| atgtagatac | catggcttgc | tgaataatca | gaagaggtgt | gactcttatt | ctaaaatttg | 1740 |
| tcacaaaatg | tcaaaatgag | agactctgta | ggaacgagtc | cttgacagac | agctcaaggg | 1800 |
| gttttttttcc | tttgtctcat | ttctacatga | aagtaaattt | gaaatgatct | tttttattat | 1860 |
| aagagtagaa | atacagttgg | gtttgaacta | tatgttttaa | tggccacggt | tttgtaagac | 1920 |
| atttggtcct | ttgttttccc | agttattact | cgattgtaat | tttatatcgc | cagcaatgga | 1980 |
| ctgaaacggt | ccgcaacctc | ttctttacaa | ctgggtgacc | tcgcggctgt | gccagccatt | 2040 |

```
tggcgttcac cctgccgcta agggccatgt gaaccccgc ggtagcatcc cttgctccgc    2100
gtggaccact ttcctgaggc acagtgatag gaacagagcc actaatctga agagaacaga    2160
gatgtgacag actacactaa tgtgagaaaa acaaggaaag ggtgacttat tggagatttc    2220
agaaataaaa tgcatttatt attatattcc cttattttaa ttttctatta gggaattaga    2280
aagggcataa actgctttat ccagtgttat attaaaagct taatgtatat aatcttttag    2340
aggtaaaatc tacagccagc aaaagtcatg gtaaatattc tttgactgaa ctctcactaa    2400
actcctctaa attatatgtc atattaactg gttaaattaa tataaatttg tgacatgacc    2460
ttaactggtt aggtaggata tttttcttca tgcaaaaata tgactaataa taatttagca    2520 caaaatatt tcccaatact ttaattctgt gatagaaaaa tgtttaactc agctactata    2580
atcccataat tttgaaaact atttattagc ttttgtgttt gacccttccc tagccaaagg    2640
caactattta aggaccccttt aaaactcttg aaactacttt agagtcatta agttatttaa    2700
ccacttttaa ttactttaaa atgatgtcaa ttcccttta actattaatt tattttaagg    2760
ggggaaaggc tgctcataat tctattgttt ttcttggtaa agaactctca gttttcgttt    2820
ttactacctc tgtcacccaa gagttggcat ctcaacagag gggactttcc gagaggccat    2880
ctggcagttg cttaagatca gaagtgaagt ctgccagttc ctcccaggca ggtggcccag    2940
attacagttg acctgttctg gtgtggctaa aaattgtccc atgtggttac aaaccattag    3000
accagggtct gatgaattgc tcagaatatt tctggacacc caaatacaga ccctggctta    3060
aggccctgtc catacagtag gtttagcttg gctacaccaa aggaagccat acagaggcta    3120
atatcagagt attcttggaa gagacaggag aaaatgaaag ccagtttctg ctcttacctt    3180
atgtgcttgt gttcagactc ccaaacatca ggagtgtcag ataaactggt ctgaatctct    3240
gtctgaagca tggaactgaa aagaatgtag tttcagggaa gaaaggcaat agaaggaagc    3300
ctgagaatat cttcaaaggg tcagactcaa tttactttct aaagaagtag ctaggaacta    3360 gggataact tagaaacaac aagattgtat atatgtgcat cctggcccca ttgttcctta    3420
tctgtaggga taagcgtgct ttttgtgtg tctgtatata acataactgt ttacacataa    3480
tacactgaaa tggagcccttt ccttgttact tcataccatc ctctgtgctt ccttcctcag    3540
gggccgacgc cgctcccacc gtgtccatct tcccccccag catggaacag ctgacctctg    3600
gcggagccac cgtggtctgc ttcgtgaaca acttctaccc cagagacatc agcgtgaagt    3660
ggaagatcga cggcagcgag cagagggacg gcgtgctgga cagcgtgacc gaccaggaca    3720
gcaaggactc cacctacagc atgagcagca ccctgagcct gaccaaggtg gagtacgaga    3780
ggcacaacct gtacacctgc gaggtggtgc acaagaccag ctccagcccc gtggtcaagt    3840
ccttcaaccg gaacgagtgt tgaagacaaa ggtcctgaga cgccaccacc agctccccag    3900
ctccatccta tcttcccttc taaggtcttg gaggcttccc cacaagcgac ctaccactgt    3960
tgcggtgctc caaacctcct ccccaccctcc ttctcctcct cctcccttttc cttggctttt    4020 atcatgctaa tatttgcaga aaatattcaa taaagtgagt ctttgcactt gagatctctg    4080
tctttcttac taaatggtag taatcagttg tttttccagt tacctgggtt tctcttctaa    4140
agaagttaaa tgtttagttg ccctgaaatc caccacactt aaaggataaa taaaaccctc    4200
cacttgccct ggttggctgt ccactacatg gcagtccttt ctaaggttca cgagtactat    4260
tcatggctta tttctctggg ccatggtagg tttgaggagg catacttcct agttttcttc    4320
ccctaagtcg tcaaagtcct gaaggggac agtcttaca agcacatgtt ctgtaatctg    4380
attcaaccta cccagtaaac ttggcgaagc aaagtagaat cattatcaca ggaagcaaag    4440
```

```
gcaacctaaa tgtgcaagca ataggaaaat gtggaagccc atcatagtac ttggacttca    4500
tctgcttttg tgccttcact aagtttttaa acatgagctg gctcctatct gccattggca    4560
aggctgggca ctacccacaa cctacttcaa ggacctctat accgtgagat tacacacata    4620
catcaaaatt tgggaaaagt tctaccaagc tgagagctga tcaccccact cttaggtgct    4680
tatctctgta caccagaaac cttaagaagc aaccagtatt gagagactca tttatgaaag    4740
tctaaaactg gatacaacca aaatgtccac caacagttaa attatgacat gttcacaatt    4800
gagctattac ttaataagga gaattaataa aataaaactt aagagcatag tttaatctca    4860
taaacaagat aataagcaaa acaaaacatt ttttcatcca tgtaagttta aaagcaggta    4920
aaatttaaaa ttaagagaga cataagtttt gaggtagcaa gatggaaact ctgggcttg    4980 gggaatgttc tgtctctctg tatgggatgt gaaagttact attgtggaat tgggatctat    5040
gttcttcctg tatatattgt atacttcata ataacttcac ctaaagaaat atctaatacc    5100
cagtgcatac ataaaagagg atacaaggaa tgaatcatac gtcaaggcca gaaagacaat    5160
aaagtagggg atccaggatc aaatctccca caaccttgag ccttctacta ttctgccttc    5220
cagagctcaa agtacaaaac acataattca aacacatgat ccctccttgg ggtctcttcc    5280
ttcatgcatc gaattagaaa tagccatgta taaaatgaga tagaagagac cttcatcaac    5340
aggtcaaaga atataggtaa ttttgtctgg gtatgaagag cccacgtatc aaaggttaca    5400
ttagggaagg aagaggacac taacagtgac tttcattctc ccctcttcc tggaggcccc    5460 tgcatttagt ccctcgtggg ctcatccact cagcacacat ttactaagca tcttctcagc    5520
ctacactctg aaggcagtgc agaataatgt tagtgtccct tcccccagtt aatatgcagt    5580
ccagtttccc tgctccttcc ctttctcagt ccacataagg atgatgggaa aggacagtca    5640
ccaaatagga gagggcaacc ctttgccttc ctacctcttg agaatgtaca ttattatcca    5700 cttttttgaaa cttcttttaa ttgcttttt ttaatttgtc ttttcaaata gcataacctt    5760
gttcatccat ttctgggaac caaatttatc aatcaacagt gcctctaatc tggctattaa    5820
tacaaaaatg cctcctcaaa atatatatgt tcgagtctta tctaaaacag aacccacaat    5880
aaaaaagaag aaagaataca tataagcatt tatataattc tgagcaacct tgtgctttgt    5940
gaaaaaaata taatctaatg tcacatgctg tattctttt atttaacact ggtgaaatta    6000
taccattaga gagaaagagg acagatcact gatcctagga tctagggatg ttacagataa    6060
gaaaacaaat gtgacaaaga gctgtcacaa ggaggatctt caaggtcaca gaatcactgt    6120
cttgatttca gtggtggtta catacattta aatatgtgat aaaatgttgt tgaactatat    6180
tcatatattg taccaatgtc aaatgcttaa ttttggctct atagtataat tatgcactaa    6240
ataactattt ggacaaagaa aatgatgttt acatcaaagg tgaggccata tttgttagga    6300
acataactta aaaaccattt tggataacta atgaaaagcc attttgtgtg ccttggcata    6360
tcatgcctaa gctgtcacca gatagatcta ataagaccta agcctcagaa gcaagccct    6420 gcccagcaag caggcagcac agataagagc taaacccagg acaggccatg atatgctaat    6480
gaactacctt caaggtggtg ttgctgacct agtgaaccag ccccaagctg tgagccccaa    6540
tagcacaaag ctactgccca aagaaattat acaaaaattg gaactttggg aatggtgtgc    6600
aggatcgctc tgctgtatgc ctggaacaca gcttctctat gttttgtatt gataccagtc    6660
tagaagcttc caaaactttc tcactgaaga agattcccca tgtgggaccc ctacagactc    6720
ttttgcccaa acaactgctt ccctcctggt gtgatatctg ttttgctttt atgttagcat    6780
```

```
aatattataa ggaatgtttg tgtgaataaa ccaaacatat tttaaaagca aatattgtat    6840
gcacatccta attgctaaaa agtttacagc taatagtccc atgctctcca caatactgga    6900
tccaaataag tcctaatttc aatgttgggc atctttacag agagaaagac attaaaaatg    6960
aagagacatg cagagagtgc accatgccat cgtggagaca gactgaagtg acacaactgt    7020
tagtcaaaga ggattaagga cttccagaag ccaccaaagg aaggaggtat gaagtggttt    7080
ctccctcaga gtatccagag gagactaaac caaccaacac cttttttgctt aagacttctt    7140 gccttcagga ctgtgagaag gtagcttcct attgttctaa gccccagtat gtggcatttt    7200
gttaaggtag agtcaagaaa ccaataaaat gcagacagac aaaaggatag ctgagttttc    7260
caggcccttc cttcttattt ttggttttgt tggtggtggt ggtggtggtg gtgatggtgg    7320
tggttttgtt tatgttttgt ttggggagtt ttttggggtt ttttttgggtt ttgtttttgt    7380 tgttgttttg ggggttttg ttgttgttgt tgtttgcttt tttgttttttt gttttttgtt    7440 tttttgagac agtgtttctc tgtatagccc tggctgtcct ggagttcctt ctatctctaa    7500
tgtctacatc tcagagggga tcctctaatt tcaaatgagc agtagctctc catttttagc    7560
tcttatttat tcatttatttt acttacttac ttattgtctg tagatgaaag aattttggag    7620
tgggaaaggg ttcatgagcc cccagcaact aatgaggagc tacagacaat tgatgtttct    7680
ggggaaagga gactcagttt ctttgagagt atagcttctg atgggtcaac catgttcctg    7740
tggctgatgt cacacccagg agtatgcaga caacagaaac tggagttaat gagttgttttt    7800 aaaaataaaa aagggcatga agcttgggat agaaattaag gataaataca attaaataca    7860
ggaaattctg aaagaattaa taaaaacatt tctttttttta aaaaaaaatc cagaattagc    7920
tatgcttctt caaaattgct tctggagaac tttacaagtt aaataagtta tattgtagaa    7980
aaggtagaga ggagaatagt ggaagagaga gataaggaga cttcaaaagg agtggaggga    8040
gatagaggag gagaaagcag aagcaatggc tgatagacac aggataagag ggaacagaaa    8100
ggagaaaagg gaagccagga tgggtattttc tttgcctatc tgtgacttgc acatggtctt    8160
ggcaattatt gatgagttca aggcttaatt cttcacttgt gccaactcaa cagagtcttt    8220 cttcttata accaggcccc cagtatgctc atgtatgtat caggtcctct tatctcctta    8280
tagcaatcct gtttataact gggtaacttt tgtgaagggaa ggaagtgcac actgagatgt    8340
gctacaactt tttaatacaa aattttgaag agtttgtaca atgtatgtat aattaataat    8400 taatatatg cactttagat tttgatttca actcaagata ctaattctat atatatgggt    8460
taaatcaata tattaataag tttaatttca catgcttatt tttattgtgg ttttcgagac    8520
agggtttctc tgtatagccc tggctgtcct ggaacccact tgtagacca ggctggcctc    8580 aaactcagaa acctacctgc ctctgcctct gcctctgcct ctgcctctgc ctctgcctct    8640
gcctctgcct ctgcctctgc ctctgcctct gcctctgcct ctgcctctgc ctctgcctct    8700
gcctctgcct ctgcctctgc ctctgcctct gcctctgcct ctgcctctgc ctctgcctct    8760
gcctctgcct ctgcctagtg ctggaattaa aggtttgcgc caccacgccc ggtgaaattt    8820
ttaaacttta tatgtctc attctatttc tatcagatag gactgtgtag actgtgctaa    8880
actaataaat gtgccctcaa aagtaatcgc aagttgtatt ttgttgtttt tgctttgctt    8940
tgctttgctt tgctttgctt tgctttgctt tgctttgctt tgctttgctt tgctttgctt    9000
tgctttgctt tgctttgctt tgctttgctt tgcttttttg ttttgggttt ttttccgggg    9060
gagggagggt ggagaaagaa tcttactatg aagctctgac tgtcctggga actcactata    9120
tagatcaggc ttgattcaac tcatagagat ctgccttctt ctgcctccca agtgctggga    9180
```

```
ataaaggcat acacctccat gcccagatag tgatcccaag ttttagcaaa agtttctaga    9240
cttgacatta atcgatggag atagacatga attacacaaa gaactaatgt ggagtttacc    9300
tgaatcatac tctatacttt atcagagatt aaattaacat ttaataatcc agtgccaggc    9360
tagaggcacc attcaatggc agtgtttgcc atcatgcata ggcttagtct tcagtgctga    9420
aaggcattgg gggcaatatt actcattata cagatgagaa actgggaaag acttgcctca    9480
gattctctac tgaaaggctg agtttgtggc ttctagaaaa tcttttactt tcaatatttt    9540
taatgtataa ttttttttatt tccactgatt ttatttttta tttttaacat ttataagaaa    9600
taaatgcaat aaaccaaata catggacaaa aaaatacaag aatcatatga tcacctcaat    9660
ggaaggaaaa aaaaagaaag aaaaagtctt tgataagatt caacattcat tctttttta    9720 ttagatattt tcttcattta catttcaaat gctatcccca aagcccccta taccttcccc    9780
tgccctgctc cccaacccac ccactcctgc tttctggccc tggcattcct ctgtactgag    9840
gcatatgatc ttcaaaaaac caagggcctc tcctctcatt ggtggccgac tattaggcca    9900
tcttttgcta catatgcaac tagagacaca gctctggggg ttactggtta gttcatattg    9960
ttagtcctcc tatagagttg cagacccctt tagctccttg gatactttct ctagttcctt   10020 cattagggc cctgtgtccc atccaataga tgactgtgag catccacttc tgtatttgcc   10080
aggcactggc atagcctcac gagaaagaga gagctatgtc aggatcctgt cagtaaaatc   10140
tttctggcat atgcaatagt atctgggttt ggtggttgta tatgggatgg atccccaagt   10200
ggagcagtct ctgaatggtc cttccttcca tctcagctcc aaactttgtc tctataactc   10260
cttccatggg tattttgttc cccattctaa gaaggagtga agaatccaca ctttggtctt   10320
ccttcttctt gagtttcata tgttgcatct tggatattct aagtttctgg gttaatatcc   10380
acgtatcagt gagtgcatat catgcgtgtt attttgtgat tagtttacct cactcaggat   10440
gatatcctcc agatgcatcc atttgcctaa gaatttcatt aattcactgt ttttaattgc   10500
tgaatagtac tccattgtgt aaatgtacca cattttctgt atccattcct ctgttgaggg   10560
gcatctgggt tctttccagc ttctggctat tataaataag gctgctatga gcatagcgga   10620
gcatgtgtcc ttatcaagtt ggaacatctt ctaggtatat gcccaggaga ggaattgctg   10680
gatcttccgg tagtaccatc aacatgcatt cttaataaaa gccctagaac aaggaggact   10740
gtaggaaaca tattccaaca taataaaggt tatgtatgac aaactcatga ccaatatcat   10800
cctaaatgaa tgaaaccatt aataagctcc attaaaatca gaggactgcc cactatccct   10860
acttctcatc cataatgaga ttgaagcatt agctggagca ataaggcaag agaagggata   10920
caaatgggaa aatattaagt caaattgttt tcaattgaag attatattat cttatacccca   10980 atgacctcaa attttgacta gaaaaattgt agaaattatc aataatttca gcaaagtgtt   11040
atgatgcacc acatccttat tcttctcccc agcttctgct tgcttctctc ttcttgctct   11100
tcatcctttc tgtccttcca tctgcctgca ctcttgtctc aagactgagt gcagcgtgta   11160
actctcctgt gactgagtat ctcacaaaac gttctacctg ccaaacctgg atgagccctt   11220
tgtctttctg aagctatgag gctctctaca tagactcaag aaggaaatga cagggaggag   11280
gtaataatga agtggggaag gctgacatta gcattgctcc tgtgtggctc cttaatttct   11340
catacttcac actgagatgt tattaactgt gactcatagg tgaagaagcc agagctaagg   11400
ttctcatatt tgagtgttat agaatgagta gagcagtagt tctcaaacta tgggtcatga   11460
ctcctttatg ggtcaaacta cccctttcaca caggttgcat atcagatatc ctaattttat   11520
```

```
atacatatat atatgcatat gtatatatat atatttcaca acagtaggaa aattatttag    11580
taatcatttt atagttgtgg gtcatggcaa catgaggaac tgtattaaag ggttgcagca    11640
ttaggaatgt tgagacccac tgtaatagag aatgaggctt aaggcagggc tataaagccc    11700
aatggaccat gtgccttttc aacatttgc cacatggtaa gctctgtata gacttttaa     11760 agaacattgg tttgtaattt taaatggata agggtcttca ctgtctatca cccatctata    11820
taataaatac ataagttttg attccaccat ggattcaaat gcaaaaatcc tcaacctaag    11880
acatagcagt gaaacattga tgaccaaata ggaaatccat gtagagacct tctatcttct    11940
gatggctcca caggcaccat cttgcaacag agttctactt tgctaccagt aatgaataca    12000
gtgtctcaac tcctgccatt gaatcttcag gaagcccctg aaatgacttg tactacacca    12060
tttcttaaag acagaaaagc taagacttag agggaataaa tgtcatgcct gagatcatgc    12120
aaccaattaa gtccaacttg gcctgatcaa gaggcacaat tcaaaagcaa tgttgttcct    12180
tcactagctc ttgtgtatgg ttgctgattc cggaagcaaa gtatcagtga atatccctag    12240
tgggaaaaga cttggaaatc aaatgtctca tttaacagat taggagatga aacggtagac    12300
tctgtgtagt tgtacacccc tgtgatccca tcgctaggaa gactgaggca ggaagtcctc    12360
gagctcaaac cagcttaggc tacacagaga aactatctaa aaaataatta ctaactactt    12420
aataggagat tggatgttaa gatctggtca ctaagaggca gaattgagat tcgaagccag    12480
tattttctac ctggtatgtt ttaaattgca gtaaggatct aagtgtagat atataataat    12540
aagattctat tgatctctgc aacaacagag agtgttagat ttgtttggaa aaaaatatta    12600
tcagccaaca tcttctacca tttcagtata gcacagagta cccacccata tctccccacc    12660 catccccat accagactgg ttattgattt tcatggtgac tggcctgaga agattaaaaa     12720
aagtaatgct accttattgg gagtgtccca tggaccaaga tagcaactgt catagctacc    12780
gtcacactgc tttgatcaag aagacccttt gaggaactga aaacagaacc ttaggcacat    12840
ctgttgcttt cgctcccatc ctcctccaac agcctgggtg gtgcactcca cacccttca    12900 agtttccaaa gcctcataca cctgctccct accccagcac ctggccaagg ctgtatccag    12960
cactgggatg aaaatgatac cccacctcca tcttgtttga tattactcta tctcaagccc    13020
caggttagtc cccagtccca atgcttttgc acagtcaaaa ctcaacttgg aataatcagt    13080
atccttgaag agttctgata tggtcactgg gcccatatac catgtaagac atgtggaaaa    13140
gatgtttcat ggggcccaga cacgttctag aagtacctga gagtggcaaa aaatagttgt    13200
gctaaatagt ttggccatct ttaggctgag agactaggaa atacagcgat ggactatatc    13260
agcattgcag gatagttgtc agtaaacacc ccacaaccca taacagaagt attctcttct    13320
ttctatatcc cttttccatc catgtagatg gctgtcttca tatttgttct agacggccgg    13380
cc                                                                  13382
```

<210> SEQ ID NO 96
<211> LENGTH: 4638
<212> TYPE: DNA
<213> ORGANISM: Artificial Sequence
<220> FEATURE:
<223> OTHER INFORMATION: pSELECT-IGKV1-39/J-Ck

<400> SEQUENCE: 96

```
gcggccgcaa taaatatct ttattttcat tacatctgtg tgttggtttt ttgtgtgaat          60
cgtaactaac atacgctctc catcaaaaca aaacgaaaca aaacaaacta gcaaaatagg         120
ctgtccccag tgcaagtgca ggtgccagaa catttctcta tcgaaggatc tgcgatcgct         180
```

```
ccggtgcccg tcagtgggca gagcgcacat cgcccacagt ccccgagaag ttggggggag    240
gggtcggcaa ttgaacgggt gcctagagaa ggtggcgcgg ggtaaactgg gaaagtgatg    300
tcgtgtactg gctccgcctt tttcccgagg gtgggggaga accgtatata agtgcagtag    360
tcgccgtgaa cgttcttttt cgcaacgggt ttgccgccag aacacagctg aagcttcgag    420
gggctcgcat ctctccttca cgcgcccgcc gccctacctg aggccgccat ccacgccggt    480
tgagtcgcgt tctgccgcct cccgcctgtg gtgcctcctg aactgcgtcc gccgtctagg    540
taagttaaaa gctcaggtcg agaccgggcc tttgtccggc gctcccttgg agcctaccta    600
gactcagccg gctctccacg ctttgcctga ccctgcttgc tcaactctac gtctttgttt    660
cgttttctgt tctgcgccgt tacagatcca agctgtgacc ggcgcctacc tgagatcacc    720
ggcgtgtcga cgccaccatg gacatgagag tgcccgccca gctcctgggg ctcctgctac    780
tctggctccg aggtaaggat ggagaacact aggaatttac tcagccagtg tgctcagtac    840
tgactggaac ttcagggaag ttctctgata acatgattaa tagtaagaat atttgttttt    900
atgtttccaa tctcaggtgc cagatgtgac atccagatga cccagagccc cagcagcctg    960
agcgccagcg tgggcgacag agtgaccatc acctgcagag ccagcagag catcagcagc   1020 tacctgaact ggtatcagca gaagcccggc aaggccccca agctgctgat ctacgccgcc   1080
agctccctgc agagcggcgt gccccagaga ttcagcggca gcggctccgg caccgacttc   1140
accctgacca tcagcagcct gcagcccgag gacttcgcca cctactactg ccagcagagc   1200
tacagcaccc cccccacctt cggccagggc accaaggtgg agatcaagag agccgacgcc   1260
gctcccaccg tgtccatctt cccccccagc atggaacagc tgacctctgg cggagccacc   1320
gtggtctgct tcgtgaacaa cttctacccc agagacatca gcgtgaagtg gaagatcgac   1380
ggcagcgagc agagggacgg cgtgctggac agcgtgaccg accaggacag caaggactcc   1440
acctacagca tgagcagcac cctgagcctg accaaggtgg agtacgagag cacaacctg   1500 tacacctgcg aggtggtgca aagaccagc tccagccccg tggtcaagtc cttcaaccgg   1560
aacgagtgtt gagctagctg gccagacatg ataagataca ttgatgagtt tggacaaacc   1620
acaactagaa tgcagtgaaa aaaatgcttt atttgtgaaa tttgtgatgc tattgcttta   1680
tttgtaacca ttataagctg caataaacaa gttaacaaca acaattgcat tcattttatg   1740
tttcaggttc agggggaggt gtgggaggtt ttttaaagca agtaaaacct ctacaaatgt   1800
ggtatggaat tctaaaatac agcatagcaa aactttaacc tccaaatcaa gcctctactt   1860 gaatccttt ctgagggatg aataaggcat aggcatcagg gctgttgcc aatgtgcatt   1920 agctgtttgc agcctcacct tctttcatgg agtttaagat atagtgtatt ttcccaaggt   1980
ttgaactagc tcttcatttc tttatgtttt aaatgcactg acctcccaca ttcccttttt   2040
agtaaaatat tcagaaataa tttaaataca tcattgcaat gaaaataaat gtttttatt    2100 aggcagaatc cagatgctca aggcccttca taatatcccc cagtttagta gttggactta   2160
gggaacaaag gaacctttaa tagaaattgg acagcaagaa agcgagcttc tagcgaattc   2220
tcgactcatt cctttgccct cggacgagtg ctggggcgtc ggtttccact atcggcgagt   2280
acttctacac agccatcggt ccagacgccg cgcttctgc gggcgatttg tgtacgcccg   2340
acagtcccgg ctccggatcg gacgattgcg tcgcatcgac cctgcgccca agctgcatca   2400
tcgaaattgc cgtcaaccaa gctctgatag agttggtcaa gaccaatgcg gagcatatac   2460
gcccggagcc gcggcgatcc tgcaagctcc ggatgcctcc gctcgaagta gcgcgtctgc   2520
```

```
tgctccatac aagccaacca cggcctccag aagaagatgt tggcgacctc gtattgggaa    2580
tccccgaaca tcgcctcgct ccagtcaatg accgctgtta tgcggccatt gtccgtcagg    2640
acattgttgg agccgaaatc cgcgtgcacg aggtgccgga cttcggggca gtcctcggcc    2700
caaagcatca gctcatcgag agcctgcgcg acggacgcac tgacggtgtc gtccatcaca    2760
gtttgccagt gatacacatg gggatcagca atcgcgcata tgaaatcacg ccatgtagtg    2820
tattgaccga ttccttgcgg tccgaatggg ccgaacccgc tcgtctggct aagatcggcc    2880
gcagcgatcg catccatgag ctccgcgacg ggttgcagaa cagcgggcag ttcggtttca    2940
ggcaggtctt gcaacgtgac accctgtgca cggcgggaga tgcaataggt caggctctcg    3000
ctgaattccc caatgtcaag cacttccgga atcgggagcg cggccgatgc aaagtgccga    3060
taaacataac gatctttgta gaaaccatcg gcgcagctat ttacccgcag gacatatcca    3120
cgccctccta catcgaagct gaaagcacga gattcttcgc cctccgagag ctgcatcagg    3180
tcggagacgc tgtcgaactt ttcgatcaga aacttctcga cagacgtcgc ggtgagttca    3240 ggcttttttca tgatggccct cctatagtga gtcgtattat actatgccga tatactatgc    3300
cgatgattaa ttgtcaaaac agcgtggatg gcgtctccag cttatctgac ggttcactaa    3360
acgagctctg cttatataga cctcccaccg tacacgccta ccgcccattt gcgtcaatgg    3420
ggcggagttg ttacgacatt ttggaaagtc ccgttgattt actagtcaaa acaaactccc    3480
attgacgtca atggggtgga gacttggaaa tccccgtgag tcaaaccgct atccacgccc    3540
attgatgtac tgccaaaacc gcatcatcat ggtaatagcg atgactaata cgtagatgta    3600
ctgccaagta ggaaagtccc ataaggtcat gtactgggca taatgccagg cgggccattt    3660
accgtcattg acgtcaatag ggggcgtact tggcatatga tacttgat gtactgccaa    3720 gtgggcagtt taccgtaaat actccaccca ttgacgtcaa tggaaagtcc ctattggcgt    3780
tactatggga acatacgtca ttattgacgt caatgggcgg gggtcgttgg gcggtcagcc    3840
aggcgggcca tttaccgtaa gttatgtaac gcctgcaggt taattaagaa catgtgagca    3900
aaaggccagc aaaaggccag gaaccgtaaa aaggccgcgt tgctggcgtt tttccatagg    3960
ctccgccccc ctgacgagca tcacaaaaat cgacgctcaa gtcagaggtg gcgaaacccg    4020
acaggactat aaagatacca ggcgtttccc cctggaagct ccctcgtgcg ctctcctgtt    4080
ccgaccctgc cgcttaccgg atacctgtcc gcctttctcc cttcgggaag cgtggcgctt    4140
tctcatagct cacgctgtag gtatctcagt tcggtgtagg tcgttcgctc caagctgggc    4200
tgtgtgcacg aaccccccgt tcagcccgac cgctgcgcct tatccggtaa ctatcgtctt    4260
gagtccaacc cggtaagaca cgacttatcg ccactggcag cagccactgg taacaggatt    4320
agcagagcga ggtatgtagg cggtgctaca gagttcttga agtggtggcc taactacggc    4380
tacactagaa gaacagtatt tggtatctgc gctctgctga gccagttac cttcggaaaa    4440 agagttggta gctcttgatc cggcaaacaa accaccgctg gtagcggtgg tttttttgtt    4500
tgcaagcagc agattacgcg cagaaaaaaa ggatctcaag aagatccttt gatcttttct    4560
acggggtctg acgctcagtg gaacgaaaac tcacgttaag ggattttggt catggctagt    4620
taattaacat ttaaatca                                                 4638
```

<210> SEQ ID NO 97
<211> LENGTH: 5349
<212> TYPE: DNA
<213> ORGANISM: Artificial Sequence
<220> FEATURE:
<223> OTHER INFORMATION: pSelect-IGVL2-14/J-Ck

<400> SEQUENCE: 97

```
gcggccgcaa taaaatatct ttattttcat tacatctgtg tgttggtttt ttgtgtgaat    60
cgtaactaac atacgctctc catcaaaaca aaacgaaaca aaacaaacta gcaaaatagg   120
ctgtccccag tgcaagtgca ggtgccagaa catttctcta tcgaaggatc tgcgatcgct   180
ccggtgcccg tcagtgggca gagcgcacat cgcccacagt ccccgagaag ttgggggag   240
gggtcggcaa ttgaacgggt gcctagaaa ggtggcgcgg ggtaaactgg gaaagtgatg   300
tcgtgtactg gctccgcctt tttcccgagg gtgggggaga accgtatata agtgcagtag   360
tcgccgtgaa cgttcttttt cgcaacgggt ttgccgccag aacacagctg aagcttcgag   420
gggctcgcat ctctccttca cgcgcccgcc gccctacctg aggccgccat ccacgccggt   480
tgagtcgcgt tctgccgcct cccgcctgtg gtgcctcctg aactgcgtcc gccgtctagg   540
taagtttaaa gctcaggtcg agaccgggcc tttgtccggc gctcccttgg agcctaccta   600
gactcagccg gctctccacg ctttgcctga ccctgcttgc tcaactctac gtctttgttt   660
cgttttctgt tctgcgccgt tacagatcca agctgtgacc ggcgcctacc tgagatcacc   720
ggcgtgtcga cgccaccatg gacatgagag tgcccgccca gctcctgggg ctcctgctac   780
tctggctccg aggtaaggat ggagaacact aggaatttac tcagccagtg tgctcagtac   840
tgactggaac ttcagggaag ttctctgata acatgattaa tagtaagaat atttgttttt   900
atgtttccaa tctcaggtgc cagatgtcag tctgccctga cccagcccgc tctgtgtct    960
ggcagccctg ccagagcat caccatcagc tgcaccggca ccagcagcga cgtgggcggc  1020
tacaactacg tgtcctggta tcagcagcac cccggcaagg cccccaagct gatgatctac  1080
gaggtgtcca acagacccag cggcgtgagc aacagattca gcggcagcaa gagcggcaac  1140
accgccagcc tgaccatcag cggcctccag gctgaggacg aggccgacta ctactgcagc  1200
agctacacca gcagctccac cctggtgttt ggcggcggaa caaagctgac cgtgctgaga  1260
gccgacgccg ctcccaccgt gtccatcttc ccccccagca tggaacagct gacctctggc  1320
ggagccaccg tggtctgctt cgtgaacaac ttctacccca gagacatcag cgtgaagtgg  1380
aagatcgacg gcagcgagca gagggacggc gtgctggaca cgtgaccga ccaggacagc  1440
aaggactcca cctacagcat gagcagcacc ctgagcctga ccaaggtgga gtacgagagg  1500
cacaacctgt acacctgcga ggtggtgcac aagaccagct ccagcccgt ggtcaagtcc  1560
ttcaaccgga acgagtgttg agctagctgg ccagacatga taagatacat tgatgagttt  1620
ggacaaacca caactagact gactcagcct gcctccgtgt ctgggtctcc tggacagtcg  1680
atcaccatct cctgcactgg aaccagcagt gacgttggtg gttataacta tgtctcctgg  1740
taccaacagc acccaggcaa agcccccaaa ctcatgattt atgaggtcag taatcggccc  1800
tcaggggttt ctaatcgctt ctctggctcc aagtctggca acacggcctc cctgaccatc  1860
tctgggctcc aggctgagga cgaggctgat tattactgca gctcatatac aagcagcagc  1920
actctcgtat tcggcggagg gaccaagctg accgtcctac gggctgatgc tgcaccaact  1980
gtatccatct cccaccatc catggaacag ttaacatctg gaggtgccac agtcgtgtgc  2040
ttcgtgaaca acttctatcc cagagacatc agtgtcaagt ggaagattga tggcagtgaa  2100
caacgagatg gtgtcctgga cagtgttact gatcaggaca gcaaagacag cacgtacagc  2160
atgagcagca ccctctcgtt gaccaaggtt gaatatgaaa ggcataacct ctatacctgt  2220
gaggttgttc ataagacatc atcctcaccc gtcgtcaaga gcttcaacag gaatgagtgt  2280
```

```
taggctagct ggccagacat gataagatac attgatgagt ttggacaaac cacaactaga    2340
atgcagtgaa aaaaatgctt tatttgtgaa atttgtgatg ctattgcttt atttgtaacc    2400
attataagct gcaataaaca agttaacaac aacaattgca ttcattttat gtttcaggtt    2460
caggggagg tgtgggaggt ttttaaagc aagtaaaacc tctacaaatg tggtatggaa      2520
ttctaaaata cagcatagca aaactttaac ctccaaatca agcctctact tgaatccttt    2580
tctgagggat gaataaggca taggcatcag gggctgttgc caatgtgcat tagctgtttg    2640
cagcctcacc ttctttcatg gagtttaaga tatagtgtat tttcccaagg tttgaactag    2700
ctcttcattt ctttatgttt taaatgcact gacctcccac attcccttt tagtaaaata     2760
ttcagaaata atttaaatac atcattgcaa tgaaaataaa tgttttttat taggcagaat    2820
ccagatgctc aaggcccttc ataatatccc ccagtttagt agttggactt agggaacaaa    2880
ggaacccttta atagaaattg gacagcaaga aagcgagctt ctagcgaatt ctcgactcat   2940
tcctttgccc tcggacgagt gctgggcgt cggtttccac tatcggcgag tacttctaca    3000
cagccatcgg tccagacggc cgcgcttctg cgggcgattt gtgtacgccc gacagtcccg    3060
gctccggatc ggacgattgc gtcgcatcga ccctgcgccc aagctgcatc atcgaaattg    3120
ccgtcaacca agctctgata gagttggtca agaccaatgc ggagcatata cgcccggagc    3180
cgcggcgatc ctgcaagctc cggatgcctc cgctcgaagt agcgcgtctg ctgctccata    3240
caagccaacc acggcctcca gaagaagatg ttggcgacct cgtattggga atccccgaac    3300
atcgcctcgc tccagtcaat gaccgctgtt atgcggccat tgtccgtcag acattgttg    3360
gagccgaaat ccgcgtgcac gaggtgccgg acttcggggc agtcctcggc ccaaagcatc    3420
agctcatcga gagcctgcgc gacggacgca ctgacggtgt cgtccatcac agtttgccag    3480
tgatacacat ggggatcagc aatcgcgcat atgaaatcac gccatgtagt gtattgaccg    3540
attccttgcg gtccgaatgg gccgaacccg ctcgtctggc taagatcggc cgcagcgatc    3600
gcatccatga gctccgcgac gggttgcaga acagcgggca gttcggtttc aggcaggtct    3660
tgcaacgtga caccctgtgc acggcgggag atgcaatagg tcaggctctc gctgaattcc    3720
ccaatgtcaa gcacttccgg aatcgggagc gcggccgatg caaagtgccg ataaacataa    3780
cgatctttgt agaaaccatc ggcgcagcta tttacccgca ggacatatcc acgccctcct    3840
acatcgaagc tgaaagcacg agattcttcg ccctccgaga gctgcatcag gtcggagacg    3900
ctgtcgaact tttcgatcag aaacttctcg acagacgtcg cggtgagttc aggcttttc    3960
atgatggccc tcctatagtg agtcgtatta tactatgccg atatactatg ccgatgatta    4020
attgtcaaaa cagcgtggat ggcgtctcca gcttatctga cggttcacta aacgagctct    4080
gcttatatag acctcccacc gtacacgcct accgcccatt tgcgtcaatg gggcggagtt    4140
gttacgacat tttggaaagt cccgttgatt tactagtcaa aacaaactcc cattgacgtc    4200
aatgggtgg agacttggaa atccccgtga gtcaaaccgc tatccacgcc cattgatgta    4260
ctgccaaaac cgcatcatca tggtaatagc gatgactaat acgtagatgt actgccaagt    4320
aggaaagtcc cataaggtca tgtactgggc ataatgccag gcgggccatt taccgtcatt    4380
gacgtcaata gggggcgtac ttggcatatg atacacttga tgtactgcca agtgggcagt    4440
ttaccgtaaa tactccaccc attgacgtca atggaaagtc cctattggcg ttactatggg    4500
aacatacgtc attattgacg tcaatggggc ggggtcgttg gcggtcagc caggcgggcc    4560
atttaccgta agttatgtaa cgcctgcagg ttaattaaga acatgtgagc aaaaggccag    4620
caaaaggcca ggaaccgtaa aaaggccgcg ttgctggcgt ttttccatag gctccgcccc    4680
```

```
cctgacgagc atcacaaaaa tcgacgctca agtcagaggt ggcgaaaccc gacaggacta    4740
taaagatacc aggcgtttcc ccctggaagc tccctcgtgc gctctcctgt tccgaccctg    4800
ccgcttaccg gatacctgtc cgcctttctc ccttcgggaa gcgtggcgct ttctcatagc    4860
tcacgctgta ggtatctcag ttcggtgtag gtcgttcgct ccaagctggg ctgtgtgcac    4920
gaaccccccg ttcagcccga ccgctgcgcc ttatccggta actatcgtct tgagtccaac    4980
ccggtaagac acgacttatc gccactggca gcagccactg gtaacaggat tagcagagcg    5040
aggtatgtag gcggtgctac agagttcttg aagtggtggc ctaactacgg ctacactaga    5100
agaacagtat ttggtatctg cgctctgctg aagccagtta ccttcggaaa aagagttggt    5160
agctcttgat ccggcaaaca aaccaccgct ggtagcggtg gttttttgt ttgcaagcag    5220 cagattacgc gcagaaaaaa aggatctcaa gaagatcctt tgatcttttc tacgggtct    5280 gacgctcagt ggaacgaaaa ctcacgttaa gggattttgg tcatggctag ttaattaaca    5340
tttaaatca                                                            5349
```

<210> SEQ ID NO 98
<211> LENGTH: 6772
<212> TYPE: DNA
<213> ORGANISM: Artificial Sequence
<220> FEATURE:
<223> OTHER INFORMATION: MV1043

<400> SEQUENCE: 98

```
cttgatttgg gtgatggttc acgtagtggg ccatcgccct gatagacggt ttttcgccct      60
ttgacgttgg agtccacgtt ctttaatagt ggactcttgt tccaaactgg aacaacactc     120
aactctatct cgggctattc ttttgattta agggatttt gccgatttc ggtctattgg      180 ttaaaaaatg agctgattta acaaaaattt aacgcgaatt ttaacaaaat attaacgttt     240 acaatttat ggtgcagtct cagtacaatc tgctctgatg ccgcatagtt aagccagccc      300
cgacacccgc caacacccgc tgacgcgccc tgacgggctt gtctgctccc ggcatccgct     360
tacagacaag ctgtgaccgt ctccgggagc tgcatgtgtc agaggttttc accgtcatca     420
ccgaaacgcg cgagacgaaa gggcctcgtg atacgcctat ttttataggt taatgtcatg     480
ataataatgg tttcttagac gtcaggtggc acttttcggg gaaatgtgcg cggaacccct     540
atttgtttat ttttctaaat acattcaaat atgtatccgc tcatgagaca ataaccctga     600
taaatgcttc aataatattg aaaaaggaag agtatgagta ttcaacattt ccgtgtcgcc     660
cttattccct tttttgcggc attttgcctt cctgtttttg ctcacccaga aacgctggtg     720
aaagtaaaag atgctgaaga tcagttgggt gcccgagtgg gttacatcga actggatctc     780
aacagcggta agatccttga gagttttcgc cccgaagaac gttttccaat gatgagcact     840
tttaaagttc tgctatgtgg cgcggtatta tcccgtattg acgccgggca agagcaactc     900
ggtcgccgca tacactattc tcagaatgac ttggttgagt actcaccagt cacagaaaag     960
catcttacgg atggcatgac agtaagagaa ttatgcagtg ctgccataac catgagtgat    1020
aacactgcgg ccaacttact tctgacaacg atcggaggac cgaaggagct aaccgctttt    1080
ttgcacaaca tgggggatca tgtaactcgc cttgatcgtt gggaaccgga gctgaatgaa    1140
gccataccaa acgacgagcg tgacaccacg atgcctgtag caatggcaac aacgttgcgc    1200
aaactattaa ctggcgaact acttactcta gcttcccggc aacaattaat agactggatg    1260
gaggcggata aagttgcagg accacttctg cgctcggccc ttccggctgg ctggtttatt    1320
```

```
gctgataaat ctggagccgg tgagcgtggg tctcgcggta tcattgcagc actggggcca    1380
gatggtaagc cctcccgtat cgtagttatc tacacgacgg ggagtcaggc aactatggat    1440
gaacgaaata gacagatcgc tgagataggt gcctcactga ttaagcattg gtaactgtca    1500
gaccaagttt actcatatat actttagatt gatttaaaac ttcattttta atttaaaagg    1560
atctaggtga agatcctttt tgataatctc atgaccaaaa tcccttaacg tgagttttcg    1620
ttccactgag cgtcagaccc cgtagaaaag atcaaaggat cttcttgaga tcctttttt    1680
ctgcgcgtaa tctgctgctt gcaaacaaaa aaaccaccgc taccagcggt ggtttgtttg    1740
ccggatcaag agctaccaac tcttttccg aaggtaactg gcttcagcag agcgcagata    1800
ccaaatactg ttcttctagt gtagccgtag ttaggccacc acttcaagaa ctctgtagca    1860
ccgcctacat acctcgctct gctaatcctg ttaccagtgg ctgctgccag tggcgataag    1920
tcgtgtctta ccgggttgga ctcaagacga tagttaccgg ataaggcgca gcggtcgggc    1980
tgaacggggg gttcgtgcat acagcccagc ttggagcgaa cgacctacac cgaactgaga    2040
tacctacagc gtgagctatg agaaagcgcc acgcttcccg aagggagaaa ggcggacagg    2100
tatccggtaa gcggcagggt cggaacagga gagcgcacga gggagcttcc agggggaaac    2160
gcctggtatc tttatagtcc tgtcgggttt cgccacctct gacttgagcg tcgatttttg    2220
tgatgctcgt caggggggcg gagcctatgg aaaaacgcca gcaacgcggc ctttttacgg    2280
ttcctggcct tttgctggcc ttttgctcac atgttcttc ctgcgttatc ccctgattct    2340
gtggataacc gtattaccgc ctttgagtga gctgataccg ctcgccgcag ccgaacgacc    2400
gagcgcagcg agtcagtgag cgaggaagcg gaagagcgcc caatacgcaa accgcctctc    2460
cccgcgcgtt ggccgattca ttaatgcagc tggcacgaca ggtttcccga ctggaaagcg    2520
ggcagtgagc gcaacgcaat taatgtgagt tagctcactc attaggcacc ccaggcttta    2580
cactttatgc ttccggctcg tatgttgtgt ggaattgtga gcggataaca atttcacaca    2640
ggaaacagct atgaccatga ttacgccaag ctttggagcc ttttttttgg agattttcaa    2700
cgtgaaaaaa ttattattcg caattccttt agttgttcct ttctattctc acagtgcaca    2760
gatccaaatg acccagtctc catcctcct gtctgcatct gtaggagaca gagtcaccat    2820
cacttgccgg gcaagtcaga gcattagcag ctacttaaat tggtatcagc agaaaccagg    2880
gaaagcccct aagctcctga tctatgctgc atccagtttg caaagtgggg tcccatcaag    2940
gttcagtggc agtggatctg ggacagattt cactctcacc atcagcagtc tgcaacctga    3000
agattttgca acttactact gtcaacagag ttacagtacc cctccaacgt tcggccaagg    3060
gaccaagctc gagatcaaac gtactgtggc tgcaccatct gtcttcatct tcccgccatc    3120
tgatgagcag ttgaaatctg gaactgcctc tgttgtgtgc ctgctgaata acttctatcc    3180
cagagaggcc aaagtacagt ggaaggtgga taacgccctc caatcgggta actcccagga    3240
gagtgtcaca gagcaggaca gcaaggacag cacctacagc ctcagcagca ccctgacgct    3300
gagcaaagca gactacgaga aacacaaagt ctacgcctgc gaagtcaccc atcagggcct    3360
gagctcgccc gtcacaaaga gcttcaacag gggagagtgt tagtaaggcg cgccaattct    3420
atttcaagga gacagtcata atgaaatacc tattgcctac ggcagccgct ggattgttat    3480
tactcgcggc ccagccggcc atggcgatgc ctgcttgccg aatatcatgg tggaaaatgg    3540
ccgcttttct ggattcatcg actgtggccg gctgggtgtg gcggaccgct atcaggacat    3600
agcgttggct acccgtgata ttgctgaaga gcttggcggc gaatgggctg accgcttcct    3660
cgtgctttac ggtatcgccg ctcccgattc gcagcgcatc gccttctatc gccttcttga    3720
```

-continued

```
cgagttcttc tgagcgggac tctggggttc ggtgctacga gatttcgatt ccaccgccgc    3780
cttctatgaa aggttgggct tcggaatcgt tttccgggac gccggctgga tgatcctcca    3840
gcgcggggat ctcatgctgg agttcttcgc ccaccccaac ttgtttattg cagcttataa    3900
tggttacaaa taaagcaata gcatcacaaa tttcacaaat aaagcatttt tttcactgca    3960
ttctagttgt ggtttgtcca aactcatcaa tgtatcttat catgtctgta taccgtcgac    4020
ctctagctag agcttggcgt aatcatggtc atagctgttt cctgtgtgaa attgttatcc    4080
gctcacaatt ccacacaaca tacgagccgg aagcataaag tgtaaagcct ggggtgccta    4140
atgagtgagc taactcacat taattgcgtt gcgctcactg cccgctttcc agtcgggaaa    4200
cctgtcgtgc cagaattgca tgaagaatct gcttagggtt aggcgttttg cgctgcttcg    4260
ctaggtggtc aatattggcc attagccata ttattcattg gttatatagc ataaatcaat    4320
attggctatt ggccattgca tacgttgtat ccatatcata atatgtacat ttatattggc    4380
tcatgtccaa cattaccgcc atgttgacat tgattattga ctagttatta atagtaatca    4440
attacggggt cattagttca tagcccatat atggagttcc gcgttacata acttacggta    4500
aatggcccgc ctggctgacc gcccaacgac ccccgcccat tgacgtcaat aatgacgtat    4560
gttcccatag taacgccaat agggactttc cattgacgtc aatgggtgga gtatttacgg    4620
taaactgccc acttggcagt acatcaagtg tatcatatgc caagtacgcc ccctattgac    4680
gtcaatgacg gtcaccgtct caagcgcctc caccaagggc ccatcggtct tcccctggc     4740
accctcctcc aagagcacct ctgggggcac agcggccctg gctgcctgg tcaaggacta     4800
cttccccgaa ccggtgacgg tgtcgtggaa ctcaggcgcc ctgaccagcg cgtccacac     4860
cttcccggct gtcctacagt cctcaggact ctactccctc agcagcgtag tgaccgtgcc    4920
ctccagcagc ttgggcaccc agacctacat ctgcaacgtg aatcacaagc ccagcaacac    4980
caaggtggac aagaaagttg agcccaaatc ttgtgcggcc gcacatcatc atcaccatca    5040
cggggccgca gaacaaaaac tcatctcaga agaggatctg aatggggccg catagactgt    5100
tgaaagttgt ttagcaaaac ctcatacaga aaattcattt actaacgtct ggaaagacga    5160
caaaacttta gatcgttacg ctaactatga gggctgtctg tggaatgcta caggcgttgt    5220
ggtttgtact ggtgacgaaa ctcagtgtta cggtacatgg ttcctattgg gcttgctat     5280
ccctgaaaat gaggggtggtg ctctgaggg tggcggttct gagggtggcg gttctgaggg    5340
tggcggtact aaacctcctg agtacggtga tacacctatt ccgggctata cttatatcaa    5400
ccctctcgac ggcacttatc cgcctggtac tgagcaaaac cccgctaatc ctaatccttc    5460
tcttgaggag tctcagcctc ttaatacttt catgtttcag aataataggt tccgaaatag    5520
gcagggtgca ttaactgttt atacgggcac tgttactcaa ggcactgacc ccgttaaaac    5580
ttattaccag tacactcctg tatcatcaaa agccatgtat gacgcttact ggaacggtaa    5640
attcagagac tgcgctttcc attctggctt taatgaggat ccattcgttt gtgaatatca    5700
aggccaatcg tctgacctgc ctcaacctcc tgtcaatgct ggcggcggct ctggtggtgg    5760
ttctggtggc ggctctgagg gtggcggctc tgagggtggc ggctctgagg gtggcggttc    5820
tgagggtggc ggctctgagg gtggcggttc cggtggcggc tccggttccg gtgatttga    5880
ttatgaaaaa atggcaaacg ctaataaggg ggctatgacc gaaaatgccg atgaaaacgc    5940
gctacagtct gacgctaaag gcaaacttga ttctgtcgct actgattacg gtgctgctat    6000
cgatggtttc attggtgacg tttccggcct tgctaatggt aatggtgcta ctggtgattt    6060
```

| | |
|---|---|
| tgctggctct aattcccaaa tggctcaagt cggtgacggt gataattcac ctttaatgaa | 6120 |
| taatttccgt caatatttac cttctttgcc tcagtcggtt gaatgtcgcc cttatgtctt | 6180 |
| tggcgctggt aaaccatatg aattttctat tgattgtgac aaaataaact tattccgtgg | 6240 |
| tgtctttgcg tttcttttat atgttgccac ctttatgtat gtattttcga cgtttgctaa | 6300 |
| catactgcgt aataaggagt cttaataaga attcactggc cgtcgtttta caacgtcgtg | 6360 |
| actgggaaaa ccctggcgtt acccaactta atcgccttgc agcacatccc ctttcgcca | 6420 |
| gctggcgtaa tagcgaagag gcccgcaccg atcgccttc ccaacagttg cgcagcctga | 6480 |
| atggcgaatg gcgcctgatg cggtattttc tccttacgca tctgtgcggt atttcacacc | 6540 |
| gcatacgtca aagcaaccat agtacgcgcc ctgtagcggc gcattaagcg cggcgggtgt | 6600 |
| ggtggttacg cgcagcgtga ccgctacact tgccagcgcc ttagcgcccg ctcctttcgc | 6660 |
| tttcttccct tcctttctcg ccacgttcgc cggctttccc cgtcaagctc taaatcgggg | 6720 |
| gctcccttta gggttccgat ttagtgcttt acggcacctc gaccccaaaa aa | 6772 |

<210> SEQ ID NO 99
<211> LENGTH: 10293
<212> TYPE: DNA
<213> ORGANISM: Artificial Sequence
<220> FEATURE:
<223> OTHER INFORMATION: MV1057

<400> SEQUENCE: 99

| | |
|---|---|
| tactcttcct ttttcaatat tattgaagca tttatcaggg ttattgtctc atgagcggat | 60 |
| acatatttga atgtatttag aaaaataaac aaatagggg tccgcgcaca tttccccgaa | 120 |
| aagtgccacc tgacgtcgac ggatcgggag atctcccgat cccctatggt gcactctcag | 180 |
| tacaatctgc tctgatgccg catagttaag ccagtatctg ctccctgctt gtgtgttgga | 240 |
| ggtcgctgag tagtgcgcga gcaaaattta agctacaaca aggcaaggct tgaccgacaa | 300 |
| ttgcatgaag aatctgctta gggttaggcg ttttgcgctg cttcgctagg tggtcaatat | 360 |
| tggccattag ccatattatt cattggttat atagcataaa tcaatattgg ctattggcca | 420 |
| ttgcatacgt tgtatccata tcataatatg tacatttata ttggctcatg tccaacatta | 480 |
| ccgccatgtt gacattgatt attgactagt tattaatagt aatcaattac ggggtcatta | 540 |
| gttcatagcc catatatgga gttccgcgtt acataactta cggtaaatgg cccgcctggc | 600 |
| tgaccgccca acgacccccg cccattgacg tcaataatga cgtatgttcc catagtaacg | 660 |
| ccaataggga ctttccattg acgtcaatgg gtggagtatt tacggtaaac tgcccacttg | 720 |
| gcagtacatc aagtgtatca tatgccaagt acgccccta ttgacgtcaa tgacggtaaa | 780 |
| tggcccgcct ggcattatgc ccagtacatg accttatggg actttcctac ttggcagtac | 840 |
| atctacgtat tagtcatcgc tattaccatg gtgatgcggt tttggcagta catcaatggg | 900 |
| cgtggatagc ggtttgactc acggggattt ccaagtctcc accccattga cgtcaatggg | 960 |
| agtttgtttt ggcaccaaaa tcaacgggac tttccaaaat gtcgtaacaa ctccgcccca | 1020 |
| ttgacgcaaa tgggcggtag gcgtgtacgg tgggaggtct atataagcag agctcgttta | 1080 |
| gtgaaccgtc agatcgcctg gagacgccat ccacgctgtt ttgacctcca tagaagacac | 1140 |
| cgggaccgat ccagcctccg cggccgggaa cggtgcattg gaagcttggt accggtgaat | 1200 |
| tggccggccc gcgccgtcga ggttatcgat ccgaccgacg cgttcgcgag aggccgcaat | 1260 |
| tccctagcca ccatgggatg gagctgtatc atcctcttct tggtactgct gctgccccag | 1320 |
| ccggccatgg ggcggagaat gggcggaact gggcggagtt aggggcggga tgggcggagt | 1380 |

```
tagggggcggg actatggttg ctgactaatt gagatgcgga tccgctggca cgacaggttt    1440
cccgactgga aagcgggcag tgagcgcaac gcaattaatg tgagttagct cactcattag    1500
gcacccagg  ctttacactt tatgcttccg gctcgtatgt tgtgtggaat tgtgagcgga    1560
taacaatttc acacaggaaa cagctatgac catgattacg ccaagcttgg gctgcaggtt    1620
ctttccgcct cagaagccat agagcccacc gcatcccag  catgcctgct attgtcttcc    1680
caatcctccc ccttgctgtc ctgccccacc ccacccccca gaatagaatg acacctactc    1740
agacaatgcg atgcaatttc ctcattttat taggaaagga cagtgggagt ggcaccttcc    1800
agggtcaagg aaggcacggg ggaggggcaa acaacagatg gctggcaact agaaggcaca    1860
gtcgaggctg atcagcgagc tctagatcat cgatgcatgg ggtcgtgcgc tcctttcggt    1920
cgggcgctgc gggtcgtggg gcgggcgtca ggcaccgggc ttgcgggtca tgcaccaggt    1980
gcgcggtcct tcgggcacct cgacgtcggc ggtgacggtg aagccgagcc gctcgtagaa    2040
ggggaggttg cggggcgcgg aggtctccag gaaggcgggc accccggcgc gctcggccgc    2100
ctccactccg gggagcacga cggcgctgcc cagacccttg ccctggtggt cgggcgagac    2160
gccgacggtg gccaggaacc acgcgggctc cttgggccgg tgcggcgcca ggaggccttc    2220
catctgttgc tgcgcggcca gccgggaacc gctcaactcg gccatgcgcg ggccgatctc    2280
ggcgaacacc gcccccgctt cgacgctctc cggcgtggtc cagaccgcca ccgcggcgcc    2340
gtcgtccgcg acccacacct tgccgatgtc gagcccgacg cgcgtgagga agagttcttg    2400
cagctcggtc accgtctcca gtgctagcac caagggccca tcggtcttcc ccctggcacc    2460
ctcctccaag agcacctctg ggggcacagc ggccctgggc tgcctggtca aggactactt    2520
ccccgaaccg gtgacggtgt cgtggaactc aggcgccctg accagcggcg tgcacacctt    2580
cccggctgtc ctacagtcct caggactcta ctccctcagc agcgtcgtga ccgtgccctc    2640
cagcagcttg gcacccagag cctacatctg caacgtgaat cacaagccca gcaacaccaa    2700
ggtggacaag agagttggtg agaggccagc acagggaggg agggtgtctg ctggaagcca    2760
ggctcagcgc tcctgcctgg acgcatcccg gctatgcagt cccagtccag ggcagcaagg    2820
caggccccgt ctgcctcttc acccggaggc ctctgcccgc ccactcatg  ctcagggaga    2880
gggtcttctg gcttttttcc caggctctgg gcaggcacag gctaggtgcc cctaacccag    2940
gccctgcaca caaggggca  ggtgctgggc tcagacctgc caagagccat atccgggagg    3000
accctgcccc tgacctaagc ccaccccaaa ggccaaactc tccactccct cagctcggac    3060
accttctctc ctcccagatt ccagtaactc ccaatcttct ctctgcagag cccaaatctt    3120
gtgacaaaac tcacacatgc ccaccgtgcc cagcacctga actcctgggg gaccgtcag   3180
tcttcctctt ccccccaaaa cccaaggaca ccctcatgat ctcccggacc cctgaggtca    3240
catgcgtggt ggtggacgtg agccacgaag accctgaggt caagttcaac tggtacgtgg    3300
acggcgtgga ggtgcataat gccaagacaa agccgcggga ggagcagtac aacagcacgt    3360
accgtgtggt cagcgtcctc accgtcctgc accaggactg gctgaatggc aaggagtaca    3420
agtgcaaggt ctccaacaaa gccctcccag cccccatcga gaaaaccatc tccaaagcca    3480
aagggcagcc ccgagaacca caggtgtaca ccctgccccc atcccgggag gagatgacca    3540
agaaccaggt cagcctgacc tgcctggtca aaggcttcta tcccagcgac atcgccgtgg    3600
agtgggagag caatgggcag ccggagaaca actacaagac cacgcctccc gtgctggact    3660
ccgacggctc cttcttcctc tatagcaagc tcaccgtgga caagagcagg tggcagcagg    3720
```

```
ggaacgtctt ctcatgctcc gtgatgcatg aggctctgca caaccactac acgcagaaga    3780
gcctctccct gtctccgggt aaatgagttt aacggatctt aattaatccg agctcggtac    3840
caagcttaag tttaaaccgc tgatcagcct cgactgtgcc ttctagttgc cagccatctg    3900
ttgtttgccc ctcccccgtg ccttccttga ccctggaagg tgccactccc actgtccttt    3960
cctaataaaa tgaggaaatt gcatcgcatt gtctgagtag gtgtcattct attctggggg    4020
gtggggtggg gcaggacagc aaggggagg attgggaaga caatagcagg catgctgggg    4080
atgcggtggg ctctatggct tctgaggcgg aaagaaccag ctgggctct aggggtatc      4140 cccacgcgcc ctgtagcggc gcattaagcg cggcgggtgt ggtggttacg cgcagcgtga    4200
ccgctacact tgccagcgcc tagcgcccgc tcctttcgct ttcttccctt cctttctcgc    4260
cacgttcgcc ggctttcccc gtcaagctct aaatcggggg ctccctttag ggttccgatt    4320
tagtgcttta cggcacctcg accccaaaaa acttgattag ggtgatggtt cacgtagtgg    4380
gccatcgccc tgatagacgg ttttcgccc tttgacgttg gagtccacgt tctttaatag    4440
tggactcttg ttccaaactg gaacaacact caacccctatc tcggtctatt cttttgattt    4500 ataaggatt ttgccgattt cggcctattg gttaaaaaat gagctgattt aacaaaaatt     4560
taacgcgaat taattctgtg aatgtgtgt cagttagggt gtggaaagtc cccaggctcc     4620
ccagcaggca gaagtatgca aagcatgcat ctcaattagt cagcaaccag gtgtggaaag   4680
tccccaggct ccccagcagg cagaagtatg caaagcatgc atctcaatta gtcagcaacc   4740
atagtcccgc ccctaactcc gcccatcccg cccctaactc cgcccagttc cgcccattct    4800 ccgcccatg gctgactaat ttttttattt tatgcagagg ccgaggccgc ctctgcctct     4860
gagctattcc agaagtagtg aggaggcttt tttggaggcc taggcttttg caaaaagctc    4920
ccgggagctt ggatatccat tttcggatct gatcaagaga caggatgagg atcgtttcgc   4980
atgattgaac aagatggatt gcacgcaggt tctccggccg cttgggtgga gaggctattc    5040
ggctatgact gggcacaaca gacaatcggc tgctctgatg ccgccgtgtt ccggctgtca    5100 gcgcagggc gcccggttct ttttgtcaag accgacctgt ccggtgccct gaatgaactg    5160
caggacgagg cagcgcggct atcgtggctg gccacgacgg gcgttccttg cgcagctgtg   5220
ctcgacgttg tcactgaagc gggaagggac tggctgctat tgggcgaagt gccggggcag    5280
gatctcctgt catctcacct tgctcctgcc gagaaagtat ccatcatggc tgatgcaatg    5340
cggcggctgc atacgcttga tccggctacc tgcccattcg accaccaagc gaaacatcgc    5400
atcgagcgag cacgtactcg gatggaagcc ggtcttgtcg atcaggatga tctggacgaa    5460
gagcatcagg ggctcgcgcc agccgaactg ttcgccaggc tcaaggcgcg catgcccgac    5520
ggcgaggatc tcgtcgtgac ccatggcgat gcctgcttgc cgaatatcat ggtggaaaat    5580
ggccgctttt ctggattcat cgactgtggc cggctgggtg tggcggaccg ctatcaggac    5640
atagcgttgg ctacccgtga tattgctgaa gagcttggcg gcgaatgggc tgaccgcttc    5700
ctcgtgcttt acggtatcgc cgctcccgat tcgcagcgca tcgccttcta tcgccttctt    5760
gacgagttct tctgagcggg actctggggt tcggtgctac gagatttcga ttccaccgcc    5820
gccttctatg aaaggttggg cttcggaatc gttttccggg acgccggctg atgatcctc    5880 cagcgcgggg atctcatgct ggagttcttc gcccacccca acttgtttat tgcagcttat    5940
aatggttaca ataaagcaa tagcatcaca aatttcacaa ataaagcatt ttttcactg     6000 cattctagtt gtggtttgtc caaactcatc aatgtatctt atcatgtctg tataccgtcg    6060
acctctagct agagcttggc gtaatcatgg tcatagctgt ttcctgtgtg aaattgttat    6120
```

```
ccgctcacaa ttccacacaa catacgagcc ggaagcataa agtgtaaagc ctggggtgcc   6180
taatgagtga gctaactcac attaattgcg ttgcgctcac tgcccgcttt ccagtcggga   6240
aacctgtcgt gccagaattg catgaagaat ctgcttaggg ttaggcgttt tgcgctgctt   6300
cgctaggtgg tcaatattgg ccattagcca tattattcat tggttatata gcataaatca   6360
atattggcta ttggccattg catacgttgt atccatatca taatatgtac atttatattg   6420
gctcatgtcc aacattaccg ccatgttgac attgattatt gactagttat taatagtaat   6480
caattacggg gtcattagtt catagcccat atggagtt ccgcgttaca taacttacgg      6540
taaatggccc gcctggctga ccgcccaacg accccccgccc attgacgtca ataatgacgt   6600
atgttcccat agtaacgcca tagggactt tccattgacg tcaatgggtg gagtatttac     6660
ggtaaactgc ccacttggca gtacatcaag tgtatcatat gccaagtacg ccccctattg   6720
acgtcaatga cggtaaatgg cccgcctggc attatgccca gtacatgacc ttatgggact   6780
ttcctacttg gcagtacatc tacgtattag tcatcgctat taccatggtg atgcggtttt   6840
ggcagtacat caatgggcgt ggatagcggt ttgactcacg gggatttcca gtctccacc   6900 ccattgacgt caatgggagt ttgttttggc accaaaatca acgggacttt ccaaaatgtc   6960
gtaacaactc cgccccattg acgcaaatgg gcggtaggcg tgtacggtgg gaggtctata   7020
taagcagagc tcgtttagtg aaccgtcaga tcgcctggag acgccatcca cgctgttttg   7080
acctccatag aagacaccgg gaccgatcca gcctccgcgg ccgggaacgg tgcattggaa   7140
gcttggtacc ggtgaattag gcgcgccgtc gaggttatcg atccgaccga cgcgttcgcg   7200
agaggccgca attccctagc caccatggca tgccctggct tcctgtgggc acttgtgatc   7260
tccacctgtc ttgaattctc catggctgac atccagatga cccagtctcc atcctccctg   7320
tctgcatctg taggagacag agtcaccatc acttgccggg caagtcagag cattagcagc   7380
tacttaaatt ggtatcagca gaaaccaggg aaagccccta agctcctgat ctatgctgca   7440
tccagtttgc aaagtggggt cccatcaagg ttcagtggca gtggatctgg gacagatttc   7500
actctcacca tcagcagtct gcaacctgaa gattttgcaa cttactactg tcaacagagt   7560
tacagtaccc ctccaacgtt cggccaaggg accaaggtgg agatcaaacg taagtgcact   7620
ttgcggccgc taggaagaaa ctcaaaacat caagatttta aatacgcttc ttggtctcct   7680
tgctataatt atctgggata agcatgctgt tttctgtctg tccctaacat gccctgtgat   7740
tatccgcaaa caacacaccc aagggcagaa cttttgttact taaacaccat cctgtttgct   7800
tctttcctca ggaactgtgg ctgcaccatc tgtcttcatc ttcccgccat ctgatgagca   7860
gttgaaatct ggaactgcct ctgttgtgtg cctgctgaat aacttctatc ccagagaggc   7920
caaagtacag tggaaggtgg ataacgccct ccaatcgggt aactcccagg agagtgtcac   7980
agagcaggac agcaaggaca gcacctacag cctcagcagc accctgacgc tgagcaaagc   8040
agactacgag aaacacaaag tctacgcctg cgaagtcacc catcagggcc tgagctcgcc   8100
cgtcacaaag agcttcaaca ggggagagtg ttaggtttaa cggatccgag ctcggtacca   8160
agctcaagtt taaaccgctg atcagcctcg actgtgcctt ctagttgcca gccatctgtt   8220
gtttgcccct cccccgtgcc ttccttgacc ctggaaggtg ccactcccac tgtccttcc    8280 taataaaatg aggaaattgc atcgcattgt ctgagtaggt gtcattctat tctggggggt   8340
ggggtggggc aggacagcaa ggggaggat tggaagaca atagcaggca tgctgggat     8400 gcggtgggct ctatggcttc tgaggcggaa agaaccagct gcattaatga atcggccaac   8460
```

| | | | | |
|---|---|---|---|---|
| gcgcggggag | aggcggtttg | cgtattgggc | gctcttccgc | ttcctcgctc actgactcgc | 8520 |
| tgcgctcggt | cgttcggctg | cggcgagcgg | tatcagctca | ctcaaaggcg gtaatacggt | 8580 |
| tatccacaga | atcagggat | aacgcaggaa | agaacatgtg | agcaaaaggc cagcaaaagg | 8640 |
| ccaggaaccg | taaaaaggcc | gcgttgctgg | cgttttttcca | taggctccgc ccccctgacg | 8700 |
| agcatcacaa | aaatcgacgc | tcaagtcaga | ggtggcgaaa | cccgacagga ctataaagat | 8760 |
| accaggcgtt | tccccctgga | agctccctcg | tgcgctctcc | tgttccgacc ctgccgctta | 8820 |
| ccggatacct | gtccgccttt | ctcccttcgg | gaagcgtggc | gctttctcat agctcacgct | 8880 |
| gtaggtatct | cagttcggtg | taggtcgttc | gctccaagct | gggctgtgtg cacgaacccc | 8940 |
| ccgttcagcc | cgaccgctgc | gccttatccg | gtaactatcg | tcttgagtcc aacccggtaa | 9000 |
| gacacgactt | atcgccactg | gcagcagcca | ctggtaacag | gattagcaga gcgaggtatg | 9060 |
| taggcggtgc | tacagagttc | ttgaagtggt | ggcctaacta | cggctacact agaagaacag | 9120 |
| tatttggtat | ctgcgctctg | ctgaagccag | ttaccttcgg | aaaaagagtt ggtagctctt | 9180 |
| gatccggcaa | acaaaccacc | gctggtagcg | gtggtttttt | tgtttgcaag cagcagatta | 9240 |
| cgcgcagaaa | aaaaggatct | caagaagatc | ctttgatctt | ttctacgggg tctgacgctc | 9300 |
| agtggaacga | aaactcacgt | taagggattt | tggtcatgag | attatcaaaa aggatcttca | 9360 |
| cctagatcct | tttaaattaa | aaatgaagtt | ttaaatcaat | ctaaagtata tatgagtaaa | 9420 |
| cttggtctga | cagttaccaa | tgcttaatca | gtgaggcacc | tatctcagcg atctgtctat | 9480 |
| ttcgttcatc | catagttgcc | tgactccccg | tcgtgtagat | aactacgata cgggagggct | 9540 |
| taccatctgg | ccccagtgct | gcaatgatac | cgcgagaccc | acgctcaccg gctccagatt | 9600 |
| tatcagcaat | aaaccagcca | gccggaaggg | ccgagcgcag | aagtggtcct gcaactttat | 9660 |
| ccgcctccat | ccagtctatt | aattgttgcc | gggaagctag | agtaagtagt tcgccagtta | 9720 |
| atagtttgcg | caacgttgtt | gccattgcta | caggcatcgt | ggtgtcacgc tcgtcgtttg | 9780 |
| gtatggcttc | attcagctcc | ggttcccaac | gatcaaggcg | agttacatga tcccccatgt | 9840 |
| tgtgcaaaaa | agcggttagc | tccttcggtc | ctccgatcgt | tgtcagaagt aagttggccg | 9900 |
| cagtgttatc | actcatggtt | atggcagcac | tgcataattc | tcttactgtc atgccatccg | 9960 |
| taagatgctt | ttctgtgact | ggtgagtact | caaccaagtc | attctgagaa tagtgtatgc | 10020 |
| ggcgaccgag | ttgctcttgc | ccggcgtcaa | tacgggataa | taccgcgcca catagcagaa | 10080 |
| ctttaaaagt | gctcatcatt | ggaaaacgtt | cttcggggcg | aaaactctca aggatcttac | 10140 |
| cgctgttgag | atccagttcg | atgtaaccca | ctcgtgcacc | caactgatct tcagcatctt | 10200 |
| ttactttcac | cagcgtttct | gggtgagcaa | aaacaggaag | gcaaaatgcc gcaaaaaagg | 10260 |
| gaataagggc | gacacggaaa | tgttgaatac | tca | | 10293 |

<210> SEQ ID NO 100
<211> LENGTH: 8179
<212> TYPE: DNA
<213> ORGANISM: Artificial Sequence
<220> FEATURE:
<223> OTHER INFORMATION: pCAGGS-IgVK1-39 targeting vector

<400> SEQUENCE: 100

| | | | | |
|---|---|---|---|---|
| atccaggcgc | ggatcaataa | aagatcatta | ttttcaatag | atctgtgtgt tggttttttg | 60 |
| tgtgccttgg | gggagggggga | ggccagaatg | aggcgcggcc | aaggggagg gggaggccag | 120 |
| aatgaccttg | ggggaggggg | aggccagaat | gaccttgggg | gaggggggagg ccagaatgag | 180 |
| gcgcggatcc | ggagaagttc | ctattccgaa | gttcctattc | ttcaaatagt ataggaactt | 240 |

```
cgctcgaggg atcggccatt gaacaagatg gattgcacgc aggttctccg gccgcttggg    300
tggagaggct attcggctat gactgggcac aacagacaat cggctgctct gatgccgccg    360
tgttccggct gtcagcgcag gggcgcccgg ttcttttttgt caagaccgac ctgtccggtg    420
ccctgaatga actgcaggac gaggcagcgc ggctatcgtg gctggccacg acgggcgttc    480
cttgcgcagc tgtgctcgac gttgtcactg aagcgggaag ggactggctg ctattgggcg    540
aagtgccggg gcaggatctc ctgtcatctc accttgctcc tgccgagaaa gtatccatca    600
tggctgatgc aatgcggcgg ctgcatacgc ttgatccggc tacctgccca ttcgaccacc    660
aagcgaaaca tcgcatcgag cgagcacgta ctcggatgga agccggtctt gtcgatcagg    720
atgatctgga cgaagagcat caggggctcg cgccagccga actgttcgcc aggctcaagg    780
cgcgcatgcc cgacgcgag gatctcgtcg tgacccatgg cgatgcctgc ttgccgaata    840
tcatggtgga aaatggccgc ttttctggat tcatcgactg tggccggctg ggtgtggcgg    900
accgctatca ggacatagcg ttggctaccc gtgatattgc tgaagagctt ggcggcgaat    960
gggctgaccg cttcctcgtg ctttacggta tcgccgctcc cgattcgcag cgcatcgcct   1020
tctatcgcct tcttgacgag ttcttctgag gggatcgatc cgctgtaagt ctgcagaaat   1080
tgatgatcta ttaaacaata aagatgtcca ctaaaatgga agttttttcct gtcatacttt   1140 gttaagaagg gtgagaacag agtacctaca ttttgaatgg aaggattgga gctacggggg   1200
tgggggtggg gtgggattag ataaatgcct gctctttact gaaggctctt tactattgct   1260
ttatgataat gtttcatagt tggatatcat aatttaaaca agcaaaacca aattaagggc   1320
cagctcattc ctcccactca tgatctatag atctatagat ctctcgtggg atcattgttt   1380
ttctcttgat tcccactttg tggttctaag tactgtggtt tccaaatgtg tcagtttcat   1440
agcctgaaga acgagatcag cagcctctgt tccacataca cttcattctc agtattgttt   1500
tgccaagttc taattccatc agaagctgac tctagatggc gcgtatgcag gttttcgaca   1560
ttgattattg actagttatt aatagtaatc aattacgggg tcattagttc atagcccata   1620
tatggagttc cgcgttacat aacttacggt aaatggcccg cctggctgac cgcccaacga   1680
cccccgccca ttgacgtcaa taatgacgta tgttcccata gtaacgccaa tagggacttt   1740
ccattgacgt caatgggtgg agtatttacg gtaaactgcc cacttggcag tacatcaagt   1800
gtatcatatg ccaagtacgc cccctattga cgtcaatgac ggtaaatggc ccgcctggca   1860
ttatgcccag tacatgacct tatgggactt tcctacttgg cagtacatct acgtattagt   1920
catcgctatt accatggtcg aggtgagccc cacgttctgc ttcactctcc ccatctcccc   1980
cccctcccca cccccaattt tgtatttatt tattttttaa ttattttgtg cagcgatggg   2040 ggcgggggg ggggggcgc gcgccaggcg gggcggggcg gggcgagggg cggggcgggg   2100
cgaggcggag aggtgcggcg gcagccaatc agagcggcgc gctccgaaag tttccttttta   2160 tggcgaggcg gcggcggcgg cggccctata aaaagcgaag cgcgcggcgg gcgggagtcg   2220
ctgcgttgcc ttcgccccgt gccccgctcc gcgccgcctc gcgccgcccg cccggctct   2280 gactgaccgc gttactccca caggtgagcg ggcgggacgg cccttctcct ccgggctgta   2340
attagcgctt ggtttaatga cggctcgttt cttttctgtg gctgcgtgaa agccttaaag   2400
ggctccggga gggccctttg tgcggggggg agcggctcgg ggggtgcgtg cgtgtgtgtg   2460
tgcgtgggga gcgccgcgtg cggcccgcgc tgcccgcgg ctgtgagcgc tgcgggcgcg   2520
gcgcggggct ttgtgcgctc cgcgtgtgcg cgaggggagc gcggccgggg gcggtgcccc   2580
```

```
gcggtgcggg ggggctgcga ggggaacaaa ggctgcgtgc ggggtgtgtg cgtgggggg      2640 tgagcagggg gtgtgggcgc ggcggtcggg ctgtaacccc ccctgcacc ccctccccg       2700 agttgctgag cacggcccgg cttcgggtgc ggggctccgt gcggggcgtg gcgcggggct    2760
cgccgtgccg ggcgggggt ggcggcaggt gggggtgccg ggcggggcgg ggccgcctcg     2820
ggccggggag ggctcggggg aggggcgcgg cggccccgga gcgccggcgg ctgtcgaggc    2880
gcggcgagcc gcagccattg ccttttatgg taatcgtgcg agaggcgca gggacttcct     2940 ttgtcccaaa tctgtgcgga gccgaaatct gggaggcgcc gccgcacccc ctctagcggg    3000
cgcggggcga gcggtgcgg cgccggcagg aaggaaatgg gcggggaggg ccttcgtgcg     3060
tcgccgcgcc gccgtcccct tctccctctc cagcctcggg gctgtccgcg ggggacggc     3120 tgccttcggg ggggacgggg cagggcgggg ttcggcttct ggcgtgtgac cggcggctct    3180
agaagcgttg gggtgagtac tccctctcaa aagcgggcat gacttctgcg ctaagattgt    3240
cagtttccaa aaacgaggag gatttgatat tcacctggcc cgcggtgatg cctttgaggg    3300
tggccgcgtc catctggtca gaaaagacaa tctttttgtt gtcaagcttg aggtgtggca    3360
ggcttgagat ctggccatac acttgagtga cattgacatc cactttgcct ttctctccac    3420
aggtgtccac tccagggcg gcctccggag cgatcgccga tccgcctagg caattgttta    3480
aatcggccgg ccataacttc gtataatgta tgctatacga agttatggat cctcacagta    3540
ggtggcatcg ttccttctg actgcccgcc ccccgcatgc cgtcccgcga tattgagctc     3600
cgaacctctc gccctgccgc cgccggtgct ccgtcgccgc cgcgccgcca tggaatcgaa    3660
gccaccatgg atcttaccgg aaaactcgac gcaagaaaaa tcagagagat cctcataaag    3720
gtcaagaagg gcggaaagat cgccgtgtaa ttctagaccg gttcgagatc caggcgcgga   3780
tcaataaaag atcattattt tcaatagatc tgtgtgttgg ttttttgtgt gccttggggg    3840 aggggaggc cagaatgagg cgcggccaag ggggaggggg aggccagaat gaccttgggg    3900 gaggggagg ccagaatgac cttggggag ggggaggcca gaatgaggcg cgccctccgt     3960
cgacctataa cttcgtataa tgtatgctat acgaagttat ggcggccgcc accatggaca    4020
tgagagtgcc cgcccagctc ctggggctcc tgctactctg gctccgaggt aaggatggag    4080
aacactagga atttactcag ccagtgtgct cagtactgac tggaacttca gggaagttct    4140
ctgataacat gattaatagt aagaatattt gttttatgt ttccaatctc aggtgccaga    4200
tgtgacatcc agatgaccca gagccccagc agcctgagcg ccagcgtggg cgacagagtg    4260
accatcacct gcagagccag ccagagcatc agcagctacc tgaactggta tcagcagaag   4320
cccggcaagg cccccaagct gctgatctac gccgccagct ccctgcagag cggcgtgccc    4380
agcagattca gcggcagcgg ctccggcacc gacttccccc tgaccatcag cagcctgcag    4440
cccgaggact tcgccaccta ctactgccag cagagctaca gcaccccccc cacccttcggc    4500 cagggcacca aggtggagat caagagagcc gacgccgctc ccaccgtgtc catcttcccc    4560
cccagcatgg aacagctgac ctctggcgga gccaccgtgg tctgcttcgt gaacaacttc    4620
taccccagag acatcagcgt gaagtggaag atcgacggca gcgagcagag ggacggcgtg    4680
ctggacagcg tgaccgacca ggacagcaag gactccacct acagcatgag cagcaccctg    4740
agcctgacca aggtggagta cgagaggcac aacctgtaca cctgcgaggt ggtgcacaag    4800
accagctcca gccccgtggt caagtccttc aaccggaacg agtgttgagc tagcttaaga    4860
tttaaatagg ccgccgcgt cgacctcgag atccaggcgc ggatcaataa aagatcatta    4920
ttttcaatag atctgtgtgt tggttttttg tgtgccttgg gggagggga ggccagaatg     4980
```

```
aggcgcggcc aaggggagg gggaggccag aatgaccttg ggggaggggg aggccagaat    5040
gaccttgggg gaggggagg ccagaatgag gcgcgccccc gggtaccgag ctcgaattag    5100
tggatcctca cagtaggtgg catcgttcct ttctgactgc ccgcccccg catgccgtcc    5160
cgcgatattg agctccgaac ctctcgccct gccgccgccg gtgctccgtc gccgccgcgc    5220
cgccatggaa tcgcgccggt aaccgaagtt cctatacttt ctagagaata ggaacttcgg    5280
aataggaact tcaagccggt acccagcttt tgttcccttt agtgagggtt aatttcgagc    5340
ttggcgtaat catggtcata gctgtttcct gtgtgaaatt gttatccgct cacaattcca    5400
cacaacatac gagccgggag cataaagtgt aaagcctggg gtgcctaatg agtgagctaa    5460
ctcacattaa ttgcgttgcg ctcactgccc gctttccagt cgggaaacct gtcgtgccag    5520
ctgcattaat gaatcggcca acgcgcgggg agaggcggtt tgcgtattgg gcgctcttcc    5580
gcttcctcgc tcactgactc gctgcgctcg gtcgttcggc tgcggcgagc ggtatcagct    5640
cactcaaagg cggtaatacg gttatccaca gaatcagggg ataacgcagg aaagaacatg    5700
tgagcaaaag gccagcaaaa ggccaggaac cgtaaaaagg ccgcgttgct ggcgtttttc    5760
cataggctcc gccccctga cgagcatcac aaaaatcgac gctcaagtca gaggtggcga    5820
aacccgacag gactataaag ataccaggcg tttccccctg gaagctccct cgtgcgctct    5880
cctgttccga ccctgccgct taccggatac ctgtccgcct ttctcccttc gggaagcgtg    5940
gcgctttctc atagctcacg ctgtaggtat ctcagttcgg tgtaggtcgt tcgctccaag    6000
ctgggctgtg tgcacgaacc ccccgttcag cccgaccgct gcgccttatc cggtaactat    6060
cgtcttgagt ccaacccggt aagacacgac ttatcgccac tggcagcagc cactggtaac    6120
aggattagca gagcgaggta tgtaggcggt gctacagagt tcttgaagtg gtggcctaac    6180
tacggctaca ctagaaggac agtatttggt atctgcgctc tgctgaagcc agttaccttc    6240
ggaaaaagag ttggtagctc ttgatccggc aaacaaacca ccgctggtag cggtggtttt    6300
tttgtttgca agcagcagat tacgcgcaga aaaaaaggat ctcaagaaga tcctttgatc    6360
ttttctacgg ggtctgacgc tcagtggaac gaaaactcac gttaagggat tttggtcatg    6420
agattatcaa aaaggatctt cacctagatc cttttaaatt aaaaatgaag ttttaaatca    6480
atctaaagta tatatgagta aacttggtct gacagttacc aatgcttaat cagtgaggca    6540
cctatctcag cgatctgtct atttcgttca tccatagttg cctgactccc cgtcgtgtag    6600
ataactacga tacgggaggg cttaccatct ggccccagtg ctgcaatgat accgcgagac    6660
ccacgctcac cggctccaga tttatcagca ataaaccagc cagccggaag ggccgagcgc    6720
agaagtggtc ctgcaacttt atccgcctcc atccagtcta ttaattgttg ccgggaagct    6780
agagtaagta gttcgccagt taatagtttg cgcaacgttg ttgccattgc tacaggcatc    6840
gtggtgtcac gctcgtcgtt tggtatggct tcattcagct ccggttccca acgatcaagg    6900
cgagttacat gatcccccat gttgtgcaaa aaagcggtta gctccttcgg tcctccgatc    6960
gttgtcagaa gtaagttggc cgcagtgtta tcactcatgg ttatggcagc actgcataat    7020
tctcttactg tcatgccatc cgtaagatgc ttttctgtga ctggtgagta ctcaaccaag    7080
tcattctgag aatagtgtat gcggcgaccg agttgctctt gcccggcgtc aatacgggat    7140
aataccgcgc cacatagcag aactttaaaa gtgctcatca ttggaaaacg ttcttcgggg    7200
cgaaaactct caaggatctt accgctgttg agatccagtt cgatgtaacc cactcgtgca    7260
cccaactgat cttcagcatc ttttactttc accagcgttt ctgggtgagc aaaaacagga    7320
```

| | |
|---|---:|
| aggcaaaatg ccgcaaaaaa gggaataagg gcgacacgga aatgttgaat actcatactc | 7380 |
| ttccttttc aatattattg aagcatttat cagggttatt gtctcatgag cggatacata | 7440 |
| tttgaatgta tttagaaaaa taaacaaata ggggttccgc gcacatttcc ccgaaaagtg | 7500 |
| ccacctaaat tgtaagcgtt aatattttgt taaaattcgc gttaaatttt tgttaaatca | 7560 |
| gctcattttt taaccaatag gccgaaatcg gcaaaatccc ttataaatca aagaataga | 7620 |
| ccgagatagg gttgagtgtt gttccagttt ggaacaagag tccactatta agaacgtgg | 7680 |
| actccaacgt caaagggcga aaaccgtct atcagggcga tggcccacta cgtgaaccat | 7740 |
| caccctaatc aagtttttg gggtcgaggt gccgtaaagc actaaatcgg aaccctaaag | 7800 |
| ggagccccg atttagagct tgacggggaa agccggcgaa cgtggcgaga aaggaaggga | 7860 |
| agaaagcgaa aggagcgggc gctagggcgc tggcaagtgt agcggtcacg ctgcgcgtaa | 7920 |
| ccaccacacc cgccgcgctt aatgcgccgc tacagggcgc gtcccattcg ccattcaggc | 7980 |
| tgcgcaactg ttgggaaggg cgatcggtgc gggcctcttc gctattacgc cagctggcga | 8040 |
| aagggggatg tgctgcaagg cgattaagtt gggtaacgcc agggttttcc cagtcacgac | 8100 |
| gttgtaaaac gacggccagt gagcgcgcgt aatacgactc actataggc gaattggggg | 8160 |
| taactaagta aggatcgag | 8179 |

<210> SEQ ID NO 101
<211> LENGTH: 8188
<212> TYPE: DNA
<213> ORGANISM: Artificial Sequence
<220> FEATURE:
<223> OTHER INFORMATION: pCAGGS-IgVL2-14 targeting vector

<400> SEQUENCE: 101

| | |
|---|---:|
| atccaggcgc ggatcaataa aagatcatta ttttcaatag atctgtgtgt tggtttttg | 60 |
| tgtgccttgg gggagggga ggccagaatg aggcgcggcc aaggggagg gggaggccag | 120 |
| aatgaccttg ggggagggg aggccagaat gaccttgggg gaggggagg ccagaatgag | 180 |
| gcgcggatcc ggagaagttc ctattccgaa gttcctattc tcaaatagt ataggaactt | 240 |
| cgctcgaggg atcggccatt gaacaagatg gattgcacgc aggttctccg gccgcttggg | 300 |
| tggagaggct attcggctat gactgggcac aacagacaat cggctgctct gatgccgccg | 360 |
| tgttccggct gtcagcgcag gggcgcccgg ttctttttgt caagaccgac ctgtccggtg | 420 |
| ccctgaatga actgcaggac gaggcagcgc ggctatcgtg gctggccacg acgggcgttc | 480 |
| cttgcgcagc tgtgctcgac gttgtcactg aagcgggaag ggactggctg ctattgggcg | 540 |
| aagtgccggg gcaggatctc ctgtcatctc accttgctcc tgccgagaaa gtatccatca | 600 |
| tggctgatgc aatgcggcgg ctgcatacgc ttgatccggc tacctgccca ttcgaccacc | 660 |
| aagcgaaaca tcgcatcgag cgagcacgta ctcggatgga agccggtctt gtcgatcagg | 720 |
| atgatctgga cgaagagcat caggggctcg cgccagccga actgttcgcc aggctcaagg | 780 |
| cgcgcatgcc cgacggcgag gatctcgtcg tgacccatgg cgatgcctgc ttgccgaata | 840 |
| tcatggtgga aaatggccgc ttttctggat tcatcgactg tggccggctg ggtgtggcgg | 900 |
| accgctatca ggacatagcg ttggctaccc gtgatattgc tgaagagctt ggcggcgaat | 960 |
| gggctgaccg cttcctcgtg ctttacggta tcgccgctcc cgattcgcag cgcatcgcct | 1020 |
| tctatcgcct tcttgacgag ttcttctgag gggatcgatc cgctgtaagt ctgcagaaat | 1080 |
| tgatgatcta ttaaacaata aagatgtcca ctaaaatgaa gtttttcct gtcatacttt | 1140 |
| gttaagaagg gtgagaacag agtacctaca ttttgaatgg aaggattgga gctacggggg | 1200 |

-continued

```
tgggggtggg gtgggattag ataaatgcct gctctttact gaaggctctt tactattgct      1260
ttatgataat gtttcatagt tggatatcat aatttaaaca agcaaaacca aattaagggc      1320
cagctcattc ctcccactca tgatctatag atctatagat ctctcgtggg atcattgttt      1380
ttctcttgat tcccactttg tggttctaag tactgtggtt tccaaatgtg tcagtttcat      1440
agcctgaaga acgagatcag cagcctctgt tccacataca cttcattctc agtattgttt      1500
tgccaagttc taattccatc agaagctgac tctagatggc gcgtatgcag gttttcgaca      1560
ttgattattg actagttatt aatagtaatc aattacgggg tcattagttc atagcccata      1620
tatggagttc cgcgttacat aacttacggt aaatggcccg cctggctgac cgcccaacga      1680
ccccccgccca ttgacgtcaa taatgacgta tgttcccata gtaacgccaa tagggacttt      1740
ccattgacgt caatgggtgg agtatttacg gtaaactgcc cacttggcag tacatcaagt      1800
gtatcatatg ccaagtacgc ccctattga cgtcaatgac ggtaaatggc ccgcctggca       1860
ttatgcccag tacatgacct tatgggactt tcctacttgg cagtacatct acgtattagt      1920
catcgctatt accatggtcg aggtgagccc cacgttctgc ttcactctcc ccatctcccc      1980
ccctccccca cccccaattt tgtatttatt tattttttaa ttattttgtg cagcgatggg      2040
ggcgggggg gggggggcgc gcgccaggcg gggcggggcg gggcgagggg cggggcgggg      2100
cgaggcggag aggtgcggcg gcagccaatc agagcggcgc gctccgaaag tttccttta     2160
tggcgaggcg gcggcggcgg cggccctata aaaagcgaag cgcgcggcgg cgggagtcg      2220
ctgcgttgcc ttcgcccgt gccccgctcc gcgccgcctc gcgccgcccg ccccggctct      2280
gactgaccgc gttactccca caggtgagcg ggcgggacgg cccttctcct ccgggctgta     2340
attagcgctt ggtttaatga cggctcgttt cttttctgtg gctgcgtgaa agccttaaag      2400
ggctccggga gggccctttg tgcggggggg agcggctcgg ggggtgcgtg cgtgtgtgtg      2460
tgcgtggga gcgccgcgtg cggcccgcgc tgcccggcgg ctgtgagcgc tgcgggcgcg      2520
gcgcggggct ttgtgcgctc cgcgtgtgcg cgaggggagc gcggccgggg gcggtgcccc      2580
gcggtgcggg ggggctgcga ggggaacaaa ggctgcgtgc ggggtgtgtg cgtgggggg      2640
tgagcagggg gtgtgggcgc ggcggtcggg ctgtaacccc cccctgcacc cccctccccg      2700
agttgctgag cacggcccgg cttcgggtgc ggggctccgt gcggggcgtg gcgcggggct      2760
cgccgtgccg ggcggggggt ggcggcaggt ggggtgccg ggcggggcgg ggccgcctcg      2820
ggccggggag ggctcggggg aggggcgcgg cggccccgga gcgccggcgg ctgtcgaggc      2880
gcggcgagcc gcagccattg cctttatgg taatcgtgcg agagggcgca gggacttcct      2940
ttgtcccaaa tctgtgcgga gccgaaatct gggaggcgcc gccgcacccc ctctagcggg      3000
cgcggggcga agcggtgcgg cgccggcagg aaggaaatgg gcgggagggg ccttcgtgcg      3060
tcgccgcgcc gccgtcccct tctccctctc cagcctcggg gctgtccgcg ggggacggc      3120
tgccttcggg gggacgggg cagggcgggg ttcggcttct ggcgtgtgac cggcggctct      3180
agaagcgttg gggtgagtac tccctctcaa aagcgggcat gacttctgcg ctaagattgt      3240
cagtttccaa aaacgaggag gatttgatat tcacctggcc cgcggtgatg cctttgaggg      3300
tggccgcgtc catctggtca gaaaagacaa tcttttttgtt gtcaagcttg aggtgtggca      3360
ggcttgagat ctggccatac acttgagtga cattgacatc cactttgcct ttctctccac      3420
aggtgtccac tcccagggcg gcctccggag cgatcgccga tccgcctagg caattgttta      3480
aatcggccgg ccataacttc gtataatgta tgctatacga agttatggat cctcacagta      3540
```

```
ggtggcatcg ttcctttctg actgcccgcc cccgcatgc cgtcccgcga tattgagctc    3600
cgaacctctc gccctgccgc cgccggtgct ccgtcgccgc cgcgccgcca tggaatcgaa    3660
gccaccatgg atcttaccgg aaaactcgac gcaagaaaaa tcagagagat cctcataaag    3720
gtcaagaagg gcggaaagat cgccgtgtaa ttctagaccg gttcgagatc caggcgcgga    3780
tcaataaaag atcattattt tcaatagatc tgtgtgttgg ttttttgtgt gccttggggg    3840
agggggaggc cagaatgagg cgcggccaag ggggagggg aggccagaat gaccttgggg     3900
gaggggagg ccagaatgac cttggggag ggggaggcca gaatgaggcg cgccctccgt      3960
cgacctataa cttcgtataa tgtatgctat acgaagttat ggcggccgcc accatggaca    4020
tgagagtgcc cgcccagctc ctggggctcc tgctactctg gctccgaggt aaggatggag    4080
aacactagga atttactcag ccagtgtgct cagtactgac tggaacttca gggaagttct    4140
ctgataacat gattaatagt aagaatattt gtttttatgt ttccaatctc aggtgccaga    4200
tgtcagtctg ccctgaccca gcccgcctct gtgtctggca gccctggcca gagcatcacc    4260
atcagctgca ccggcaccag cagcgacgtg ggcggctaca actacgtgtc ctggtatcag    4320
cagcaccccg gcaaggcccc caagctgatg atctacgagg tgtccaacag acccagcggc    4380
gtgagcaaca gattcagcgg cagcaagagc ggcaacaccg ccagcctgac catcagcggc    4440
ctccaggctg aggacgaggc cgactactac tgcagcagct acaccagcag ctccaccctg    4500
gtgtttggcg gcggaacaaa gctgaccgtg ctgagagccg acgccgctcc caccgtgtcc    4560
atcttccccc ccagcatgga acagctgacc tctggcggag ccaccgtggt ctgcttcgtg    4620
aacaacttct accccagaga catcagcgtg aagtggaaga tcgacggcag cgagcagagg    4680
gacggcgtgc tggacagcgt gaccgaccag gacagcaagg actccaccta cagcatgagc    4740
agcaccctga gcctgaccaa ggtggagtac gagaggcaca acctgtacac ctgcgaggtg    4800
gtgcacaaga ccagctccag ccccgtggtc aagtccttca accggaacga gtgttgagct    4860
agcttaagat ttaaataggc cggccgcgtc gacctcgaga tccaggcgcg gatcaataaa    4920
agatcattat tttcaataga tctgtgtgtt ggttttttgt gtgccttggg ggagggggag    4980
gccagaatga ggcgcggcca aggggagggg ggaggccaga atgaccttgg gggagggga    5040
ggccagaatg accttggggg aggggaggc cagaatgagg cgcgcccccg ggtaccgagc     5100
tcgaattagt ggatcctcac agtaggtggc atcgttcctt tctgactgcc cgccccccgc    5160
atgccgtccc gcgatattga gctccgaacc tctcgccctg ccgccgccgg tgctccgtcg    5220
ccgccgcgcc gccatggaat cgcgccggta accgaagttc ctatactttc tagagaatag    5280
gaacttcgga ataggaactt caagccggta cccagctttt gttcccttta gtgagggtta    5340
atttcgagct tggcgtaatc atggtcatag ctgtttcctg tgtgaaattg ttatccgctc    5400
acaattccac acaacatacg agccgggagc ataaagtgta aagcctgggg tgcctaatga    5460
gtgagctaac tcacattaat tgcgttgcgc tcactgcccg ctttccagtc gggaaacctg    5520
tcgtgccagc tgcattaatg aatcggccaa cgcgcgggga gaggcggttt gcgtattggg    5580
cgctcttccg cttcctcgct cactgactcg ctgcgctcgg tcgttcggct gcggcgagcg    5640
gtatcagctc actcaaaggc ggtaatacgg ttatccacag aatcagggga taacgcagga    5700
aagaacatgt gagcaaaagg ccagcaaaag gccaggaacc gtaaaaaggc cgcgttgctg    5760
gcgtttttcc ataggctccg ccccccctgac gagcatcaca aaaatcgacg ctcaagtcag    5820
aggtggcgaa acccgacagg actataaaga taccaggcgt ttccccctgg aagctccctc    5880
gtgcgctctc ctgttccgac cctgccgctt accggatacc tgtccgcctt tctcccttcg    5940
```

```
ggaagcgtgg cgctttctca tagctcacgc tgtaggtatc tcagttcggt gtaggtcgtt    6000
cgctccaagc tgggctgtgt gcacgaaccc cccgttcagc ccgaccgctg cgccttatcc    6060
ggtaactatc gtcttgagtc caacccggta agacacgact tatcgccact ggcagcagcc    6120
actggtaaca ggattagcag agcgaggtat gtaggcggtg ctacagagtt cttgaagtgg    6180
tggcctaact acggctacac tagaaggaca gtatttggta tctgcgctct gctgaagcca    6240
gttaccttcg gaaaaagagt tggtagctct tgatccggca acaaaccac cgctggtagc     6300 ggtggttttt ttgtttgcaa gcagcagatt acgcgcagaa aaaaggatc tcaagaagat     6360 cctttgatct tttctacggg gtctgacgct cagtggaacg aaaactcacg ttaagggatt    6420
ttggtcatga gattatcaaa aaggatcttc acctagatcc ttttaaatta aaaatgaagt    6480
tttaaatcaa tctaaagtat atatgagtaa acttggtctg acagttacca atgcttaatc    6540
agtgaggcac ctatctcagc gatctgtcta tttcgttcat ccatagttgc ctgactcccc    6600
gtcgtgtaga taactacgat acgggagggc ttaccatctg gccccagtgc tgcaatgata    6660
ccgcgagacc cacgctcacc ggctccagat ttatcagcaa taaaccagcc agccggaagg    6720
gccgagcgca gaagtggtcc tgcaacttta tccgcctcca tccagtctat taattgttgc    6780
cgggaagcta gagtaagtag ttcgccagtt aatagtttgc gcaacgttgt tgccattgct    6840
acaggcatcg tggtgtcacg ctcgtcgttt ggtatggctt cattcagctc cggttcccaa    6900
cgatcaaggc gagttacatg atcccccatg ttgtgcaaaa aagcggttag ctccttcggt    6960
cctccgatcg ttgtcagaag taagttggcc gcagtgttat cactcatggt tatggcagca    7020
ctgcataatt ctcttactgt catgccatcc gtaagatgct tttctgtgac tggtgagtac    7080
tcaaccaagt cattctgaga atagtgtatg cggcgaccga gttgctcttg cccggcgtca    7140
atacgggata ataccgcgcc acatagcaga actttaaaag tgctcatcat tggaaaacgt    7200 tcttcgggc gaaaactctc aaggatctta ccgctgttga tccagttc gatgtaaccc       7260 actcgtgcac ccaactgatc ttcagcatct tttactttca ccagcgtttc tgggtgagca    7320
aaaacaggaa ggcaaaatgc cgcaaaaaag ggaataaggg cgacacggaa atgttgaata    7380
ctcatactct tcctttttca atattattga agcatttatc agggttattg tctcatgagc    7440
ggatacatat ttgaatgtat ttagaaaaat aaacaaatag gggttccgcg cacatttccc    7500
cgaaaagtgc cacctaaatt gtaagcgtta atattttgtt aaaattcgcg ttaaattttt    7560
gttaaatcag ctcattttt aaccaatagg ccgaaatcgg caaaatccct tataaatcaa    7620
aagaatagac cgagataggg ttgagtgttg ttccagtttg gaacaagagt ccactattaa    7680
agaacgtgga ctccaacgtc aaagggcgaa aaaccgtcta tcaggcgat ggcccactac     7740 gtgaaccatc accctaatca agttttttgg ggtcgaggtg ccgtaaagca ctaaatcgga    7800
accctaaagg gagccccga tttagagctt gacggggaaa gccggcgaac gtggcgagaa     7860
aggaagggaa gaaagcgaaa ggagcgggcg ctagggcgct ggcaagtgta gcggtcacgc    7920
tgcgcgtaac caccacaccc gccgcgctta atgcgccgct acagggcgcg tcccattcgc    7980
cattcaggct gcgcaactgt tgggaagggc gatcggtgcg ggcctcttcg ctattacgcc    8040
agctggcgaa aggggatgt gctgcaaggc gattaagttg gtaacgcca gggttttccc     8100 agtcacgacg ttgtaaaacg acggccagtg agcgcgcgta atacgactca ctatagggcg    8160
aattgggggt aactaagtaa ggatcgag                                       8188
```

<210> SEQ ID NO 102

```
<211> LENGTH: 10
<212> TYPE: DNA
<213> ORGANISM: Artificial Sequence
<220> FEATURE:
<223> OTHER INFORMATION: Kozak sequence

<400> SEQUENCE: 102
gccaccatgg                                                          10
```